(12) United States Patent
Szymaniak et al.

(10) Patent No.: US 12,358,921 B2
(45) Date of Patent: *Jul. 15, 2025

(54) ANTIVIRAL HETEROCYCLIC COMPOUNDS

(71) Applicant: ENANTA PHARMACEUTICALS, INC., Watertown, MA (US)

(72) Inventors: Adam Szymaniak, Boston, MA (US); Robert Leon, Sharon, MA (US); Kevin McGrath, Brighton, MA (US); Xiben Li, Lexington, MA (US); Tyler J. Mann, Brighton, MA (US); Jianming Yu, Plainsboro, NJ (US); In Jong Kim, Lexington, MA (US); Scott Mitchell, Woburn, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 8 days.

This patent is subject to a terminal disclaimer.

(21) Appl. No.: 18/131,405

(22) Filed: Apr. 6, 2023

(65) Prior Publication Data
US 2023/0357258 A1 Nov. 9, 2023

Related U.S. Application Data

(60) Provisional application No. 63/328,400, filed on Apr. 7, 2022.

(51) Int. Cl.
| | |
|---|---|
| *C07D 491/048* | (2006.01) |
| *A61K 45/06* | (2006.01) |
| *A61P 31/14* | (2006.01) |
| *C07D 519/00* | (2006.01) |

(52) U.S. Cl.
CPC ......... *C07D 491/048* (2013.01); *A61K 45/06* (2013.01); *A61P 31/14* (2018.01); *C07D 519/00* (2013.01); *C07B 2200/05* (2013.01)

(58) Field of Classification Search
CPC .. C07D 401/12; C07D 401/14; C07D 405/14; C07D 409/14; C07D 413/14; C07D 417/12; C07D 417/14; C07D 471/04; C07D 491/048; C07D 519/00; C07B 2200/05; A61P 31/14; A61K 45/06
See application file for complete search history.

(56) References Cited

U.S. PATENT DOCUMENTS

| | | |
|---|---|---|
| 4,010,153 A | 3/1977 | Kajfez et al. |
| 4,511,510 A | 4/1985 | Mauri |
| 4,835,168 A | 5/1989 | Paget et al. |
| 4,988,692 A | 1/1991 | Gasc et al. |
| 5,571,809 A | 11/1996 | Hargrave et al. |
| 5,637,697 A | 6/1997 | Finch et al. |
| 5,646,140 A | 7/1997 | Sugg et al. |
| 5,681,833 A | 10/1997 | Castro et al. |
| 7,041,662 B2 | 5/2006 | Sattlegger et al. |
| 7,582,624 B2 | 9/2009 | Carter et al. |
| 8,999,969 B2 | 4/2015 | Mackman et al. |
| 9,617,289 B2 | 4/2017 | Tahri et al. |
| 9,732,098 B2 | 8/2017 | Hunt et al. |
| 9,957,281 B2 | 5/2018 | Shook et al. |
| 10,358,441 B2 | 7/2019 | Kim et al. |
| 10,398,706 B2 | 9/2019 | Shook et al. |
| 10,570,153 B2 | 2/2020 | Shook et al. |

(Continued)

FOREIGN PATENT DOCUMENTS

| | | |
|---|---|---|
| EP | 0167919 A2 | 1/1986 |
| WO | 9308175 A1 | 4/1993 |

(Continued)

OTHER PUBLICATIONS

Pubchem, SID 311324621, Available Date: Feb. 23, 2016 [retrieved on Jul. 14, 2023]. Retrieved from the Internet: <URL: https://pubchem.ncbi.nlm.nih.gov/substance/311324621.

(Continued)

*Primary Examiner* — Kortney L. Klinkel
*Assistant Examiner* — Sophia Reilly
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, esters, or prodrugs thereof:

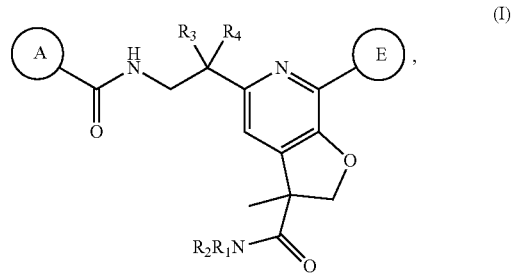

which inhibit Human Respiratory Syncytial Virus (HRSV) or Human Metapneumovirus (HMPV) inhibitors. The present invention further relates to pharmaceutical compositions comprising the aforementioned compounds for administration to a subject suffering from HRSV or HMPV infection. The invention also relates to methods of treating an HRSV or HMPV infection in a subject by administering a pharmaceutical composition comprising the compounds of the present invention.

16 Claims, No Drawings

(56) References Cited

U.S. PATENT DOCUMENTS

| | | | |
|---|---|---|---|
| 10,865,215 B2 | 12/2020 | Shook et al. | |
| 11,254,664 B2 | 2/2022 | Zhu et al. | |
| 11,390,631 B1 | 7/2022 | Shook et al. | |
| 11,420,976 B2 | 8/2022 | He et al. | |
| 11,505,558 B1 | 11/2022 | Szymaniak et al. | |
| 11,572,367 B2 | 2/2023 | Szymaniak et al. | |
| 11,912,695 B2 | 2/2024 | Zhu et al. | |
| 11,945,830 B2* | 4/2024 | Szymaniak | A61K 31/444 |
| 12,006,326 B2 | 6/2024 | Szymaniak et al. | |
| 12,162,857 B2 | 12/2024 | Yu et al. | |
| 2005/0261339 A1 | 11/2005 | Ohi et al. | |
| 2006/0040923 A1 | 2/2006 | Carter et al. | |
| 2006/0083741 A1 | 4/2006 | Hoffman et al. | |
| 2007/0142403 A1 | 6/2007 | Powell et al. | |
| 2007/0185094 A1 | 8/2007 | Lattmann et al. | |
| 2007/0185096 A1 | 8/2007 | Powell et al. | |
| 2007/0293482 A1 | 12/2007 | Dowdell et al. | |
| 2008/0139536 A1 | 6/2008 | Dowdell et al. | |
| 2009/0274655 A1 | 11/2009 | Grimes et al. | |
| 2010/0015063 A1 | 1/2010 | Carter et al. | |
| 2010/0168384 A1 | 7/2010 | Mdcaniel et al. | |
| 2011/0274654 A1 | 11/2011 | Bahadoor et al. | |
| 2012/0196846 A1 | 8/2012 | Mackman et al. | |
| 2012/0245151 A1 | 9/2012 | Gavai et al. | |
| 2014/0038947 A1 | 2/2014 | Glick et al. | |
| 2014/0100365 A1 | 4/2014 | Gavai et al. | |
| 2014/0148573 A1 | 5/2014 | Ku et al. | |
| 2014/0328796 A1 | 11/2014 | Phadke et al. | |
| 2015/0038514 A1 | 2/2015 | Grunenberg et al. | |
| 2015/0065504 A1 | 3/2015 | Wang et al. | |
| 2015/0218111 A1 | 8/2015 | Gavai et al. | |
| 2015/0231152 A1 | 8/2015 | Zhao et al. | |
| 2015/0299210 A1 | 10/2015 | Bailey et al. | |
| 2016/0244460 A1 | 8/2016 | Wang et al. | |
| 2017/0022221 A1 | 1/2017 | Blaisdell et al. | |
| 2017/0226127 A1 | 8/2017 | Estrada et al. | |
| 2017/0226129 A1 | 8/2017 | Yu et al. | |
| 2017/0305935 A1 | 10/2017 | Hunt et al. | |
| 2017/0355717 A1 | 12/2017 | Hunt et al. | |
| 2018/0065932 A1 | 3/2018 | Wang et al. | |
| 2018/0193352 A1 | 7/2018 | Shook et al. | |
| 2018/0237425 A1 | 8/2018 | Kim et al. | |
| 2018/0258102 A1 | 9/2018 | Shook et al. | |
| 2018/0354912 A1 | 12/2018 | Or et al. | |
| 2019/0002478 A1 | 1/2019 | Kim et al. | |
| 2019/0002479 A1 | 1/2019 | Kim et al. | |
| 2019/0023692 A1 | 1/2019 | Tahri et al. | |
| 2019/0040084 A1 | 2/2019 | Yu et al. | |
| 2019/0092791 A1 | 3/2019 | Hunt et al. | |
| 2019/0152968 A1 | 5/2019 | Blaisdell et al. | |
| 2019/0177283 A1 | 6/2019 | Hague | |
| 2019/0192535 A1 | 6/2019 | Shook et al. | |
| 2019/0202841 A1 | 7/2019 | Hunt et al. | |
| 2019/0315766 A1 | 10/2019 | Yu et al. | |
| 2020/0377519 A1 | 12/2020 | Qiu et al. | |
| 2021/0238188 A1 | 8/2021 | He et al. | |
| 2022/0119398 A1 | 4/2022 | Or et al. | |
| 2022/0356189 A1 | 11/2022 | Szymaniak et al. | |
| 2023/0087410 A1 | 3/2023 | Shook et al. | |
| 2023/0108803 A1 | 4/2023 | Szymaniak et al. | |
| 2023/0115580 A1 | 4/2023 | Szymaniak et al. | |
| 2023/0125803 A1 | 4/2023 | Szymaniak et al. | |
| 2023/0357258 A1 | 11/2023 | Szymaniak et al. | |
| 2023/0365525 A1 | 11/2023 | Yu et al. | |
| 2024/0368174 A1* | 11/2024 | Szymaniak | A61K 31/4375 |
| 2024/0368176 A1 | 11/2024 | Szymaniak et al. | |

FOREIGN PATENT DOCUMENTS

| | | | |
|---|---|---|---|
| WO | 2004026843 A1 | 4/2004 | |
| WO | 2004052348 A2 | 6/2004 | |
| WO | 2005042530 A1 | 5/2005 | |
| WO | 2005089769 A1 | 9/2005 | |
| WO | 2005090319 A1 | 9/2005 | |
| WO | 2006081389 A1 | 8/2006 | |
| WO | 2010103306 A1 | 9/2010 | |
| WO | 2011005842 A1 | 1/2011 | |
| WO | 2011112186 A1 | 9/2011 | |
| WO | 2011151651 A1 | 12/2011 | |
| WO | 2012012776 A1 | 1/2012 | |
| WO | 2012068622 A1 | 5/2012 | |
| WO | 2012080446 A1 | 6/2012 | |
| WO | 2012080447 A1 | 6/2012 | |
| WO | 2012080449 A1 | 6/2012 | |
| WO | 2012080450 A1 | 6/2012 | |
| WO | 2012080451 A1 | 6/2012 | |
| WO | 2013096681 A1 | 6/2013 | |
| WO | 2013186332 A1 | 12/2013 | |
| WO | 2013186334 A1 | 12/2013 | |
| WO | 2014031784 A1 | 2/2014 | |
| WO | 2014047369 A1 | 3/2014 | |
| WO | 2014047397 A1 | 3/2014 | |
| WO | 2014060411 A1 | 4/2014 | |
| WO | 2014125444 A1 | 8/2014 | |
| WO | 2014184350 A1 | 11/2014 | |
| WO | 2014186035 A1 | 11/2014 | |
| WO | 2014209983 A1 | 12/2014 | |
| WO | 2015026792 A1 | 2/2015 | |
| WO | 2015110446 A1 | 7/2015 | |
| WO | 2016018697 A1 | 2/2016 | |
| WO | 2016022464 A1 | 2/2016 | |
| WO | 2016055791 A1 | 4/2016 | |
| WO | 2016055792 A1 | 4/2016 | |
| WO | 2016097761 A1 | 6/2016 | |
| WO | 2016138158 A1 | 9/2016 | |
| WO | 2016166546 A1 | 10/2016 | |
| WO | 2017015449 A1 | 1/2017 | |
| WO | 2017123864 A1 | 7/2017 | |
| WO | 2017123884 A1 | 7/2017 | |
| WO | 2017175000 A1 | 10/2017 | |
| WO | 2018152413 A1 | 8/2018 | |
| WO | 2019067864 A1 | 4/2019 | |
| WO | 2021066922 A1 | 4/2021 | |
| WO | 2021198981 A1 | 10/2021 | |
| WO | 2021214136 A1 | 10/2021 | |
| WO | WO-2022182861 A1* | 9/2022 | A61K 31/4355 |
| WO | 2022211812 A1 | 10/2022 | |

OTHER PUBLICATIONS

Pubchem, SID 74832 [retrieved on Jun. 12, 2023], Retrieved from the Internet <URL: https://pubchem.ncbi.nlm.nih.gov/substance/74832>.
STN Registry database entry: CAS RN 1348594-72-8 (Entered STN: Dec. 4, 2011).
STN Registry database entry: CAS RN 1348849-53-5 (Entered STN: Dec. 5, 2011).
STN Registry database entry: CAS RN 1348924-24-2 (Entered STN: Dec. 5, 2011).
STN Registry database entry: CAS RN 1349463-13-3 (Entered STN: Dec. 6, 2011).
STN Registry database entry: CAS RN 1349533-81-8 (Entered STN: Dec. 6, 2011).
STN Registry database entry: CAS RN 1349749-23-0 (Entered STN: Dec. 6, 2011).
STN Registry database entry: CAS RN 1350148-32-1 (Entered STN: Dec. 7, 2011).
Pubchem-CID: 10595203pg 3, Fig, Oct. 25, 2006.
"4-(2-Hydroxyethoxy)-3-methoxy-N-[3,3,3-1-22 trifluoro-2-[7-(4-fluorophenyl)-3-[2-(methylamino )ethyl]-2,3-dihydrofuro[2,3-c]pyridin-5-yl]-2-methylpropyl]benzamide", Pubmed Compound Record for CID 139332032, U.S. National Library of Medicine, Nov. 2, 2019, https:l/pubchem.ncbi.nlm.nih.gov/compound/139332032).
"N-[(2R)-2-[3-(Aminomethyl)-7-(4-fluorophenyl)- 1-22 3-methyl-2H-furo[2,3-c]pyridin-5-yl]-3,3,3-trifluoro-2-hydroxypropyl]-4-(2-hydroxyethoxy)-3-methoxybenzamide", Pubmed Compound Record for CID 117924934, U.S. National Library of Medicine, Feb. 23, 2016, https://pubchem.ncbi.nlm.nih.gov/compound/117924934.
Aquino, C. J., et al., "Discovery of 1,5-Benzodiazepines with Peripheral Cholecystokinin (CCK-A) Receptor Agonist Activity. 1. Optimization of the Agonist "Trigger"", J. Med. Chem., 39, 1996, 562-569, 1st page only.

(56) References Cited

OTHER PUBLICATIONS

Bond, S., et al., "1,2,3,9b-Tetrahydro-5H-imidazo[2,1-a]isoindol-5-ones as a new class of respiratory syncytial virus (RSV) fusion inhibitors. Part 2: Identification of BTA9881 as a preclinical candidate", Bioorg & Med Chem Lett, 25, 976-981.

Carter, M. C, et al., "1,4-Benzodiazepines as Inhibitors of Respiratory Syncytial Virus", J. Med. Chem., 49DOI: http://dx.doi.org/10.1021/jm051185t, Mar. 9, 2006, 2311-2319.

Chapman, J., et al., "RSV604, a Novel Inhibitor of Respiratory Syncytial Virus Replication", Antimicrobial Agents and Chemotherapy, 51(9), 3346-3353.

Fordyce, et al., "Discovery of novel benzothienoazepine derivatives as potent inhibitors of respiratory syncytial virus", Bioorganic & Medicinal Chemistry Letters, 27, 2017, 2201-2206.

Henderson, E. A, et al., "1,4-Benzodiazepines as Inhibitors of Respiratory Syncytial Virus. The Identification of a Clinical Candidate", Journal of Medicinal Chemistry, 50(7)DOI: http://dx.doi.org/10.1021/jm0607471, Apr. 2007, 1685-1692.

Lee, et al., "", (Document No. 140:69941) retrieved from STN; entered in STN on Jul. 8, 2003.

Mackman, R. L., et al., "Discovery of an Oral Respiratory Syncytial Virus (RSV) Fusion Inhibitor (GS-5806) and Clinical Proof of Concept in a Human RSV Challenge Study", J. Med. Chem., 58, 2015, 1630-1643.

Mayo Clinic Staff, Respiratory syncytial virus (RSV) [online], retrieved from internet on Jun. 25, 2017.; URL http://www.mayoclinic.org/diseases-condiitons/respiratory-syncytial-virus/basics/prevention.

Olszewska, W., et al., "Emerging drugs for respiratory syncytial virus infection", Expert Opin. Emerg. Drugs, 14(2), 207-217.

Perron, M., et al., "GS-5806 Inhibits a Broad Range of Respiratory Syncytial Virus Clinical Isolates by Blocking the Virus-Cell Fusion Process", Antimicrobial Agents and Chemotherapy, 60(3)https://www.ncbi.nlm.nih.gov/pmc/articles/PMC4776015/, 1264-1273.

Stein, D. S, et al., "Oral ribavirin treatment of influenza A and B", Antimicrobial Agents and Chemotherapy, 31(8)URL:http://dx.doi.org/10.1128/AAC.31.8.1285>, Aug. 1987, 1285-1287.

Sudo, K., et al., "YM-53403, a unique anti-respiratory syncytial virus agent with a novel mechanism of action", Antiviral Research, 65, 125-131.

Wang, G., et al., "Discovery of 4'-Chloromethyl-2'-deoxy-3',5'-di-O-isobutyryl-2'-fluorocytidine (ALS-8176), a First-in-Class RSV Polymerase Inhibitor for Treatment of Human Respiratory Syncytial Virus Infection", J. Med. Chem., 58, 1862-1878.

Xiong, H., "Discovery of a Potent Respiratory Syncytial Virus RNA Polymerase Inhibitor", Bioorganic & Medicinal Chemistry Letters, 23, 6789-6793.

Pubchem, SID 471385789, Modify Date: Sep. 27, 2022 [retrieved on Jun. 15, 2024]., Retrieved from the Internet <URL: https://pubchem.ncbi.nlm.nih.gov/substance/471385789> entire document.

* cited by examiner

ANTIVIRAL HETEROCYCLIC COMPOUNDS

RELATED APPLICATION

This application claims the benefit of U.S. Provisional Application No. 63/328,400, filed on Apr. 7, 2022. The entire teachings of the above application are incorporated herein by reference.

TECHNICAL FIELD

The present invention relates generally to compounds and pharmaceutical compositions useful as Respiratory Syncytial Virus (RSV) inhibitors and Human Metapneumovirus (HMPV) inhibitors.

BACKGROUND OF THE INVENTION

Human respiratory syncytial virus (HRSV) is a negative sense virus, containing a non-segmented, single-stranded linear RNA genome. As a Paramyxovirus of two serotypes in the genus *Pneumoviridae*, HRSV contains 10 genes that encode for 11 proteins. The nucleocapsid protein (N), the RNA polymerase protein (L), the phosphoprotein (P) and the transcription anti-termination factor (M2-1) along with the RNA genome make up the ribonucleoprotein (RNP) complex. Several small-molecule compounds have been shown to target the RNP complex. Additionally, the fusion protein (F), paramount for viral attachment to the host, has been extensively studied. High resolution structures of the F protein interacting with inhibitors have been attained, while structural studies with the N protein are earlier in development. A direct result of the HRSV protein studies and research, the F protein, L protein and N protein have been the major focus of drug discovery efforts.

The increased effort in HRSV drug discovery is a result of HRSV being the leading cause of acute lower respiratory infections (ALRI) in patients of all ages. In addition to respiratory infections, patient populations at high risk during HRSV infections include the elderly, immunocompromised, children up to the age of two and patients with chronic obstructive pulmonary disorder (COPD) or chronic heart failure (CHF). HRSV was found over four years to cause 177,500 hospital admissions and 14,000 deaths in the U.S. elderly population. It is well-known that almost all children will be infected with HRSV in the first 3 years after birth and HRSV infection is more severe in premature infants. In fact, HRSV is the most common cause of bronchiolitis and pneumonia in infants under the age of one in the U.S. It is estimated that approximately 3.2 million hospitalizations and 66,000 deaths worldwide in children less than 5 years old are due to HRSV. HRSV has been associated with more deaths of infants below one year old and more infant hospitalizations than influenza.

HRSV infection can also affect healthy individuals and repeated HRSV infections even over the course of two months can occur. Symptoms are similar to colds in healthy individuals, however fever, wheezing, rapid and difficult breathing, and cyanosis occur in more severe cases. Currently, the treatment options for HRSV infection are quite limited and there is no vaccine due to unsuccessful attempts to date. Palivizumab is a monoclonal antibody that is approved for prophylactic use, but its use is limited due to its high price. Palivizumab is generally only used for high risk infants, such as premature infants or those with cardiac/lung disease, but has been only 60% effective in reducing hospitalizations. Ribavirin is approved as an inhalation treatment option, but its effectiveness is limited and there are safety concerns associated with it. Taking into account the treatment options, and the consistent seasonality of the HRSV epidemic, the development of new therapeutic agents for the treatment of HRSV is desirable.

There have been several RSV fusion inhibitors that have been disclosed in the following publications: WO2010103306, WO2012068622, WO2013096681, WO2014060411, WO2013186995, WO2013186334, WO2013186332, WO2012080451, WO2012080450, WO2012080449, WO2012080447, WO2012080446, WO2015110446, WO2017009316, *J. Med Chem.* 2015, 58, 1630-1643, *Bioorg. Med Chem. Lett.*, 2015, 25, 976-981 and *Nat. Commun.*, 2017, 8, 167. Examples of other N-protein inhibitors for treatment of HRSV have been disclosed in the following publications: WO2004026843, *J. Med. Chem.* 2006, 49, 2311-2319, and *J. Med Chem.* 2007, 50, 1685-1692. Examples of L-protein inhibitors for HRSV have been disclosed in the following publications: WO2011005842, WO2005042530, Antiviral Res. 2005, 65, 125-131, and *Bioorg. Med Chem. Lett.* 2013, 23, 6789-6793. Examples of nucleosides/polymerase inhibitors have been disclosed in the following publications: WO2011005842, WO2013242525, WO2014031784, WO2015026792, WO20160055791, WO2016138158 and *J. Med. Chem.* 2015, 58, 1862-1878.

Likewise, human metapneumovirus (HMPV), a negative-sense, single-stranded RNA enveloped virus, that belongs to the *Pneumoviridae* family and Metapneumovirus genus discovered by van Den Hoogen in 2001, is also a common cause of acute lower respiratory tract infections (ALRTIs). Although often mild, this virus can be serious and life-threatening in high-risk groups, such as children under the age of 5 years, elderly adults over the age of 65 years, and adults with underlying disease (e.g., Chronic Obstructive Pulmonary Disease (COPD), asthma, congestive heart failure, or diabetes). In healthy adults over the age of 65 years, the annual incidence rate of HMPV infection is 1.2/1,000, and 38% of disease (e.g., COPD), and individuals are twice as likely to have symptomatic disease and requirement for medical care. In immunocompromised individuals, HMPV is responsible for 6% of total respiratory infections in lung transplants and 3% of lower respiratory infections associated with stem cell transplant. HMPV infection is also thought to be associated with acute graft rejection.

Like HRSV, infection is thought to attach to the target cell via the glycoprotein (G) protein interactions and followed by fusion via the F protein. HMPV L protein sequence is homologous to HRSV L protein.

HMPV infection is the second most common cause of lower respiratory tract infection in children (behind HRSV) and also problematic for the elderly population. There are 4 subtypes of HMPV found in clinical isolates (A1, A2, B1 and B2). Reinfection occurs throughout childhood following initial infection. No therapeutics are currently available for HMPV infection.

Taking into account the seasonality and predictability of the HRSV and HMPV epidemics, HRSV epidemics in elderly institutions, and the severity of infection in high risk infants, the need for a potent and effective treatment for HRSV and HMPV is clear. The present invention has identified compounds that are heterocyclic molecules that are potent against HRSV-A/B and HMPV. The invention includes methods to prepare these molecules, methods for the RSV cell-based assay, the HMPV-TN/94-49 A2 cell-based assay, and small-molecules that have potential to treat HRSV/HEMPV infection.

SUMMARY OF THE INVENTION

The present invention provides compounds represented by Formula (I), and pharmaceutically acceptable salts, esters, and prodrugs thereof that can be used to treat or prevent viral (particularly HRSV or HMPV) infection:

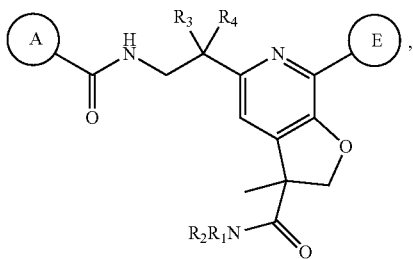

or a pharmaceutically acceptable salt, ester or prodrug thereof, wherein:
A is selected from the group consisting of:
  1) optionally substituted aryl; and
  2) optionally substituted heteroaryl;
E is selected from the group consisting of:
  1) optionally substituted aryl; and
  2) optionally substituted heteroaryl;
$R_1$ and $R_2$ are each independently selected from the group consisting of:
  1) hydrogen;
  2) optionally substituted —$C_1$-$C_8$ alkyl;
  3) optionally substituted —$C_3$-$C_8$ cycloalkyl;
  4) optionally substituted 3- to 8-membered heterocycloalkyl;
  5) optionally substituted aryl;
  6) optionally substituted arylalkyl;
  7) optionally substituted heteroaryl; and
  8) optionally substituted heteroarylalkyl;
alternatively, $R_1$ and $R_2$ are taken together with the nitrogen atom to which they are attached to form an optionally substituted 3- to 8-membered heterocyclic ring;
$R_3$ is hydroxy or fluorine; and
$R_4$ is selected from the group consisting of:
  1) hydrogen;
  2) optionally substituted —$C_1$-$C_6$ alkyl;
  3) optionally substituted —$C_3$-$C_8$ cycloalkyl;
  4) optionally substituted 3- to 8-membered heterocyclic;
  5) optionally substituted aryl;
  6) optionally substituted arylalkyl;
  7) optionally substituted heteroaryl; and
  8) optionally substituted heteroarylalkyl;
Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), $R_1$ is hydrogen.

In certain embodiments of the compounds of Formula (I), $R_1$ is hydrogen, and $R_2$ is hydrogen.

In certain embodiments of the compounds of Formula (I), $R_3$ is —OH.

In certain embodiments of the compounds of Formula (I), $R_4$ is optionally substituted methyl or optionally substituted cyclopropyl.

In certain embodiments of the compounds of Formula (I), $R_4$ is selected from one of the following:

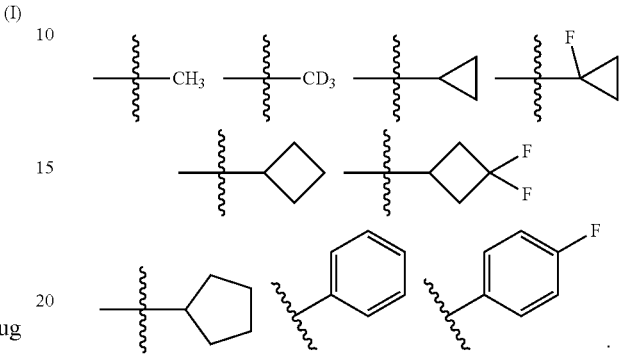

In certain embodiments of the compounds of Formula (I), $R_3$ is OH, and $R_4$ is $CF_3$, $CD_3$, or cyclopropyl.

In certain embodiments of the compounds of Formula (I), $R_1$ is hydrogen, $R_2$ is hydrogen, $R_3$ is OH, and $R_4$ is $CF_3$, $CD_3$, or cyclopropyl.

In certain embodiments of the compounds of Formula (I), A is selected from one of the following by removal of a hydrogen atom:

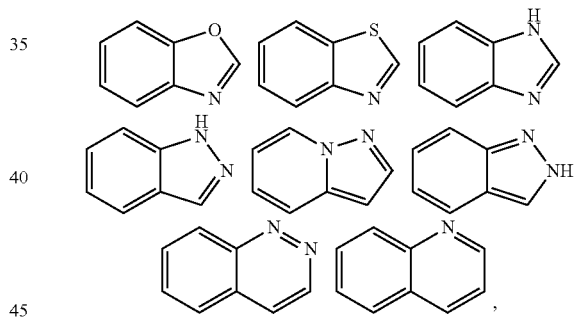

wherein each of these groups is optionally substituted.

In certain embodiments of the compounds of Formula (I), A is selected from the groups set forth below,

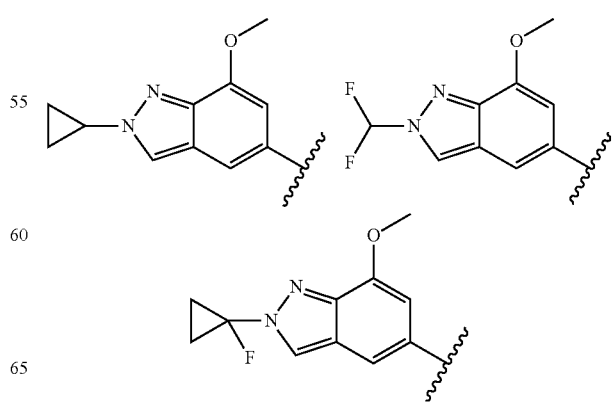

-continued
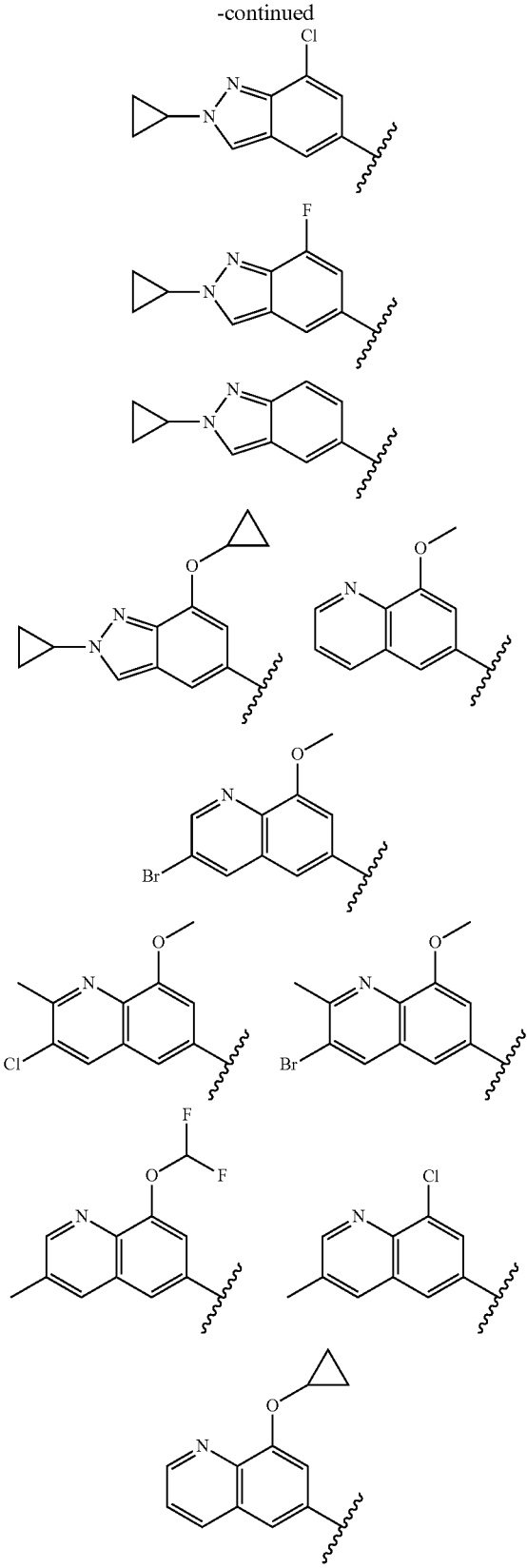
In certain embodiments of the compounds of Formula (I), E is optionally substituted aryl, preferably optionally substituted phenyl.
In certain embodiments of the compounds of Formula (I), E is selected from the groups set forth below,
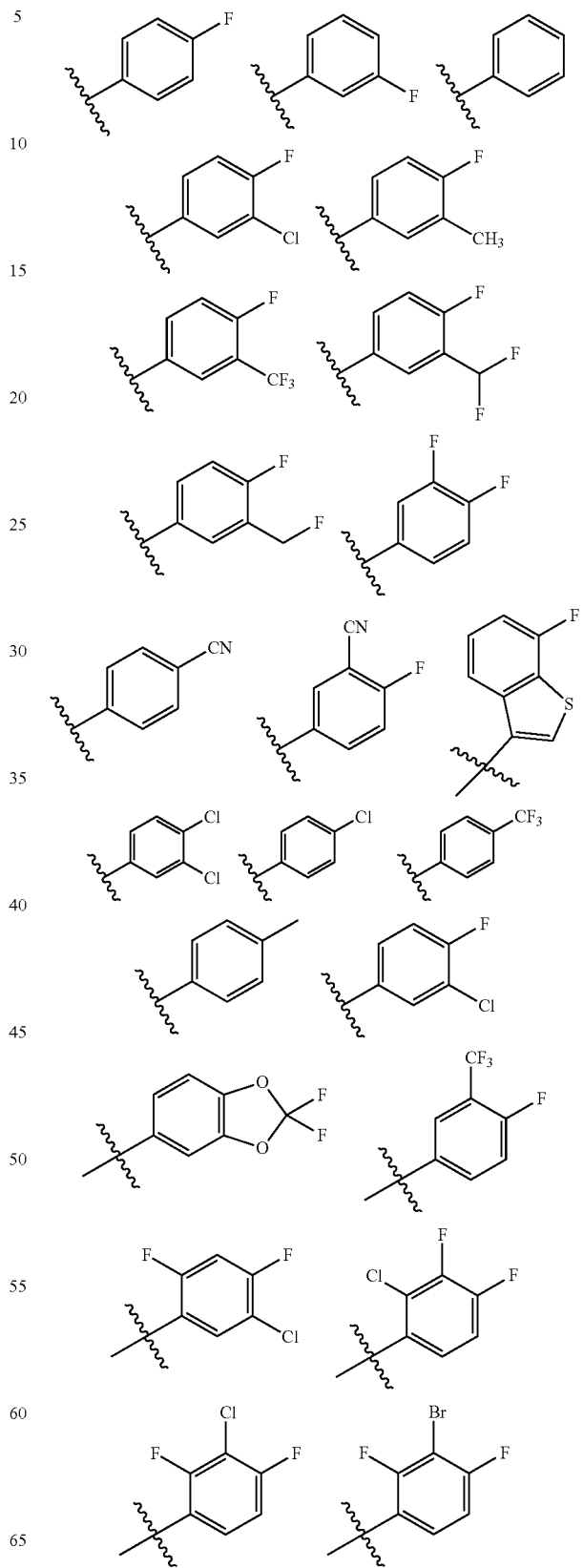

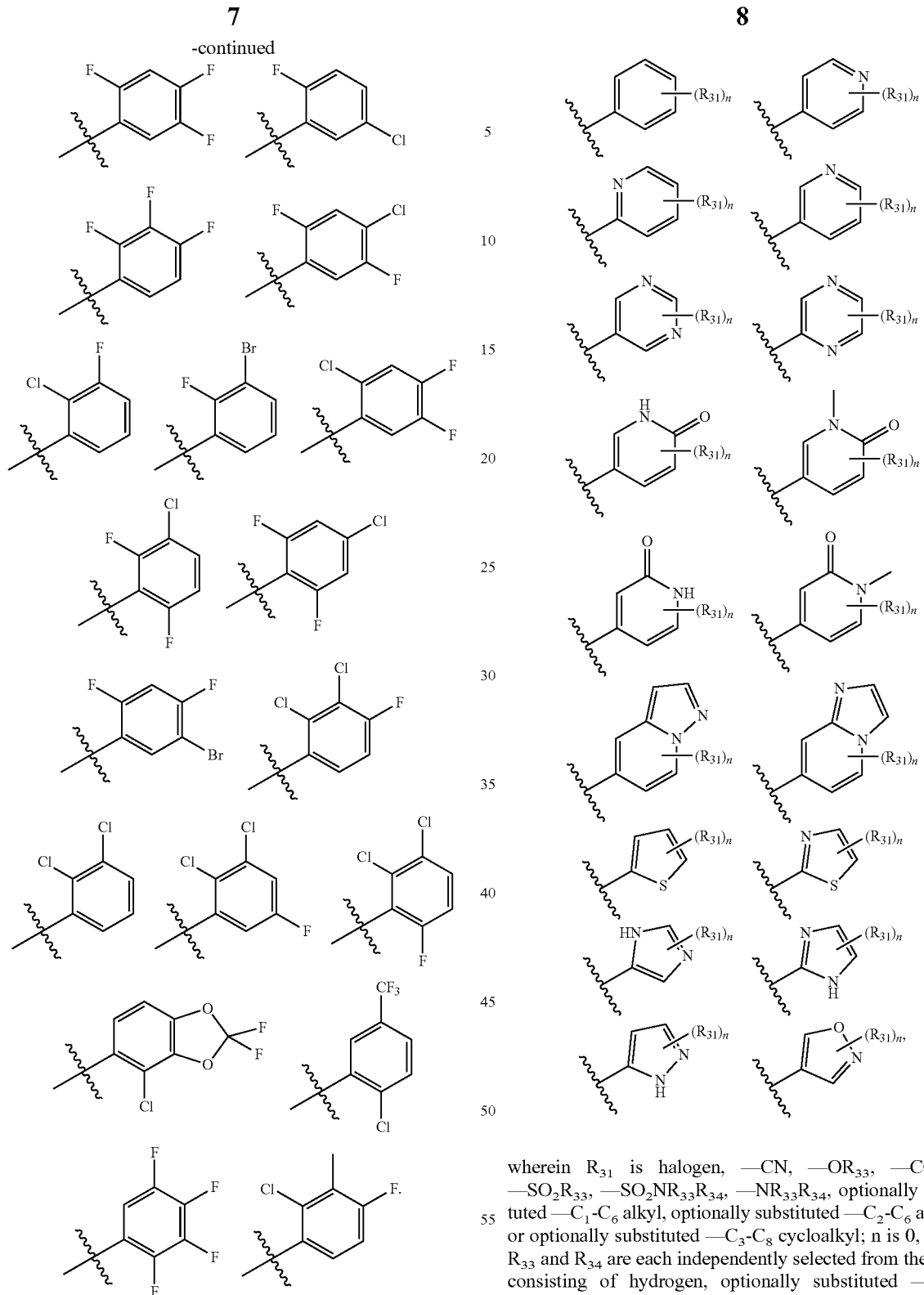

In certain embodiments of the compounds of Formula (I), $R_4$ is optionally substituted phenyl.

In certain embodiments of the compounds of Formula (I), $R_4$ is optionally substituted heteroaryl.

In certain embodiments of the compounds of Formula (I), $R_4$ is selected from one of the following:

wherein $R_{31}$ is halogen, —CN, —OR$_{33}$, —CO$_2$R$_{33}$, —SO$_2$R$_{33}$, —SO$_2$NR$_{33}$R$_{34}$, —NR$_{33}$R$_{34}$, optionally substituted —C$_1$-C$_6$ alkyl, optionally substituted —C$_2$-C$_6$ alkenyl, or optionally substituted —C$_3$-C$_8$ cycloalkyl; n is 0, 1 or 2; $R_{33}$ and $R_{34}$ are each independently selected from the group consisting of hydrogen, optionally substituted —C$_1$-C$_6$ alkyl, optionally substituted —C$_2$-C$_6$ alkenyl, optionally substituted —C$_3$-C$_8$ cycloalkyl, optionally substituted 3- to 8-membered heterocycloalkyl, optionally substituted aryl, and optionally substituted heteroaryl. Preferably, $R_{31}$ is selected from halogen, optionally substituted methyl, and optionally substituted methoxyl. More preferably, $R_{31}$ is —F, —Cl, —CH$_3$, —CHF$_2$, —CF$_3$, or —OCH$_3$.

In certain embodiments of the compounds of Formula (I), $R_3$ is OH, and $R_4$ is optionally substituted phenyl.

In certain embodiments of the compounds of Formula (I), A is selected from one of the following by removal of a hydrogen atom:

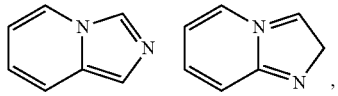

wherein each of these groups is optionally substituted.

In certain embodiments of the compounds of Formula (I), A is selected from the groups set forth below,

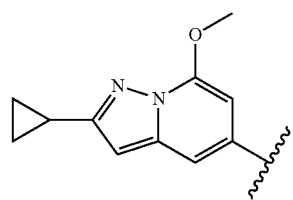

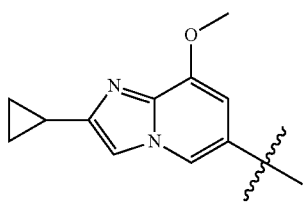

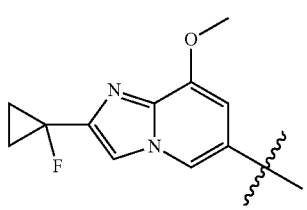

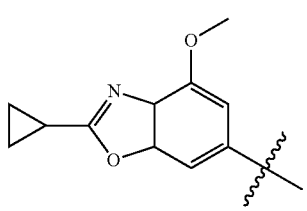

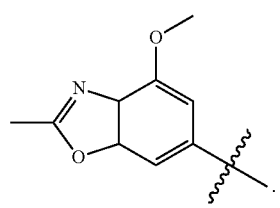

In one embodiment of the present invention, the compound of Formula (I) is represented by Formula (Ia) or Formula (Ib),

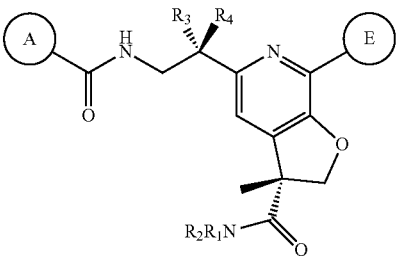

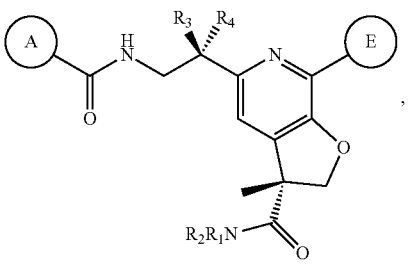

wherein A, E, $R_1$, $R_2$, $R_3$ and $R_4$ are as previously defined. Preferably, the compound of Formula (I) is represented by Formula (Ia).

In one embodiment of the present invention, the compound of Formula (I) is represented by Formula (II),

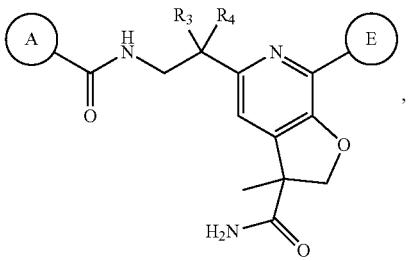

wherein A, E, $R_3$, and $R_4$ are as previously defined.

In one embodiment of the present invention, the compound of Formula (I) is represented by Formula (IIa),

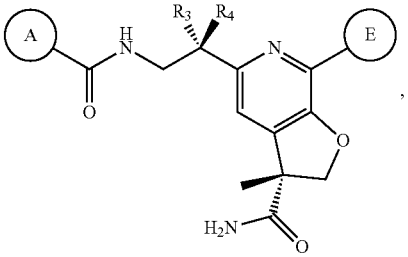

wherein A, E, $R_3$, and $R_4$ are as previously defined.

In one embodiment of the present invention, the compound of Formula (I) is represented by one of Formulae (III-1)~(III-7), (III-1)
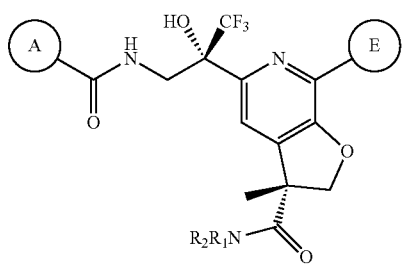
(III-2)
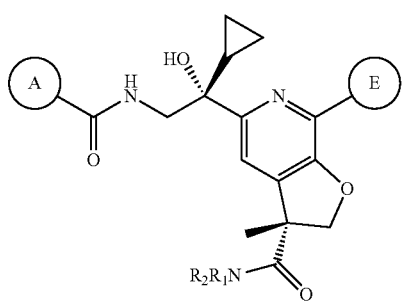
(III-3)
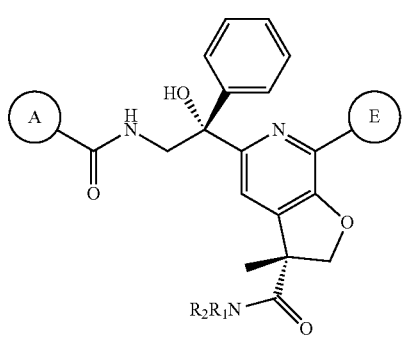
(III-4)
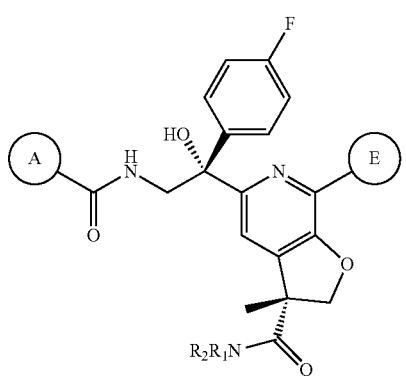
(III-5)
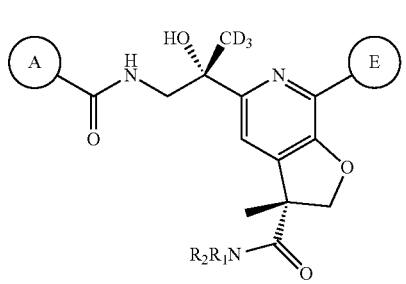
(III-6)
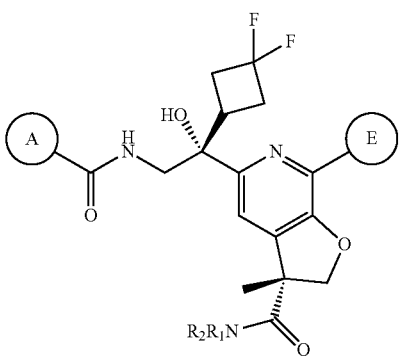
(III-7)
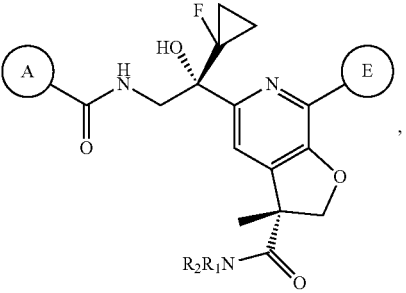
wherein A, E, $R_1$ and $R_2$ are as previously defined.
In one embodiment of the present invention, the compound of Formula (I) is represented by one of Formulae (IV-1)~(IV-7),
(IV-1)
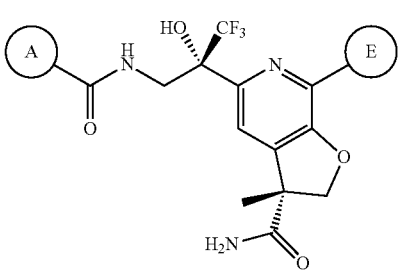
(IV-2)
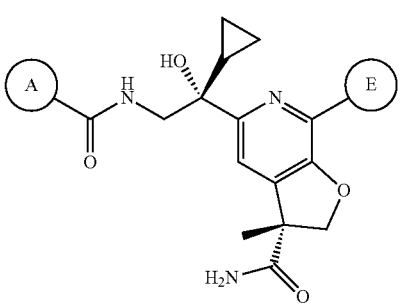

-continued
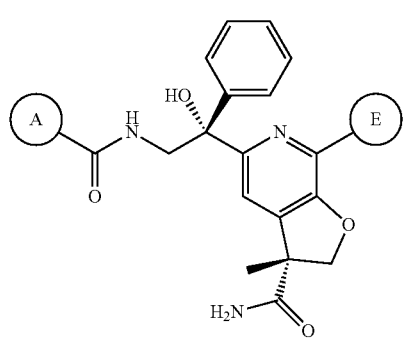
(IV-3)
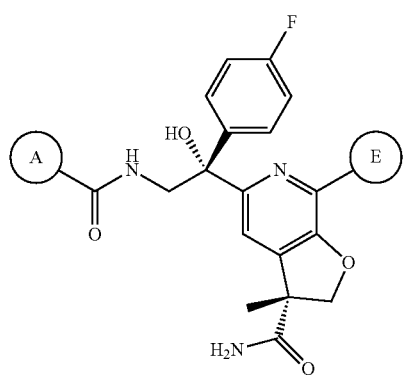
(IV-4)
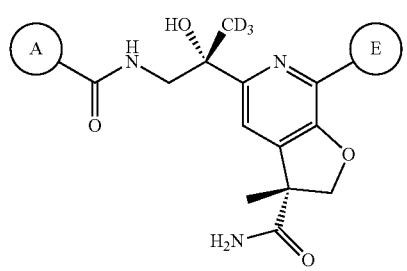
(IV-5)
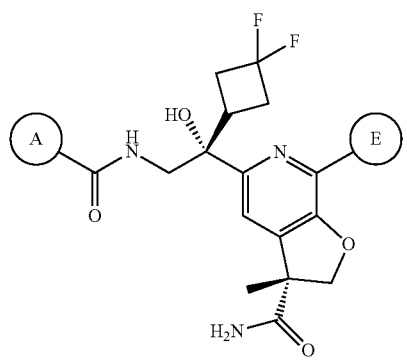
(IV-6)
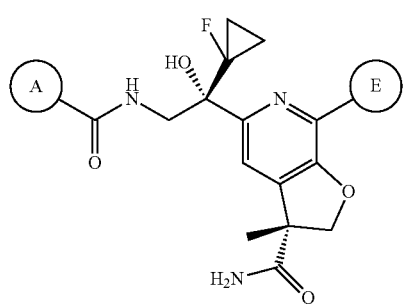
(IV-7)
wherein A and E are as previously defined.
In one embodiment of the present invention, the compound of Formula (I) is represented by one of Formulae (IV-1) (IV-7), A is selected from the groups set forth below,
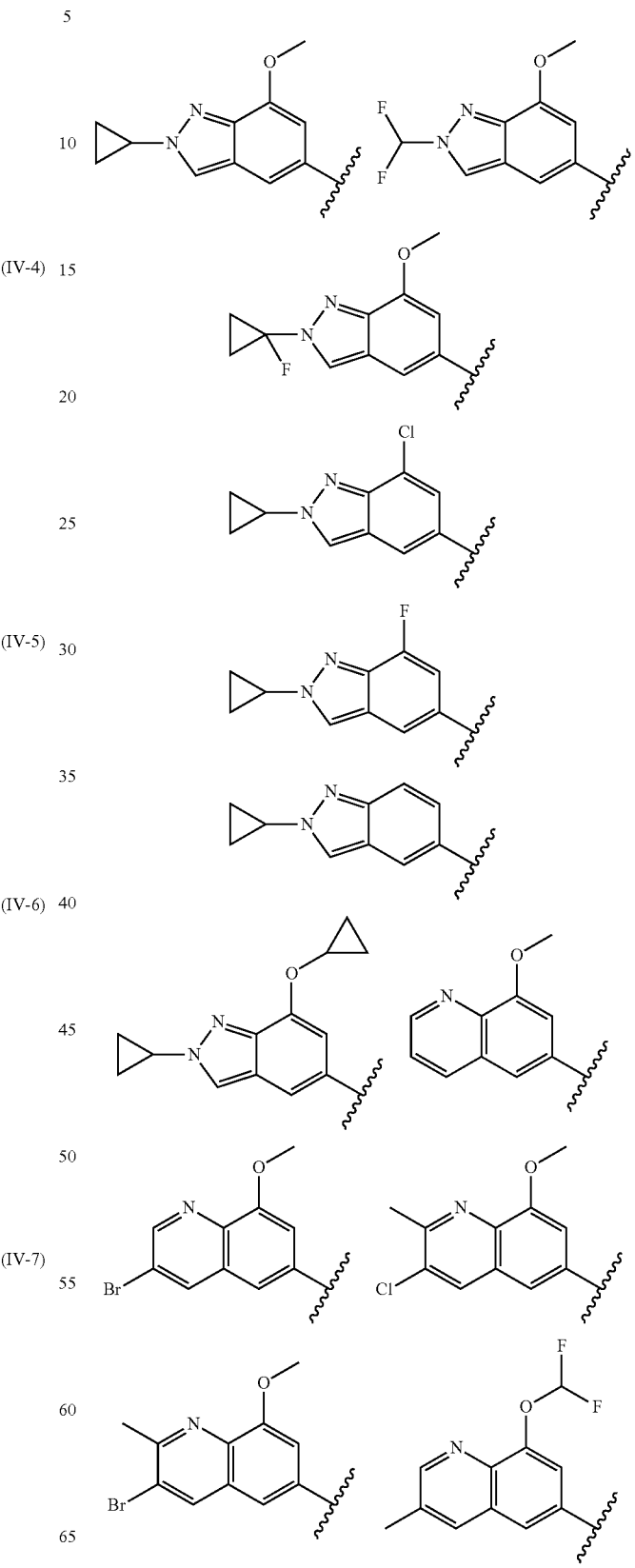

-continued
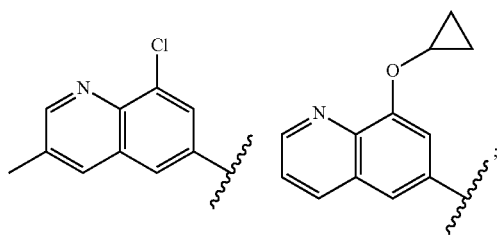
and E is selected from the groups set forth below,
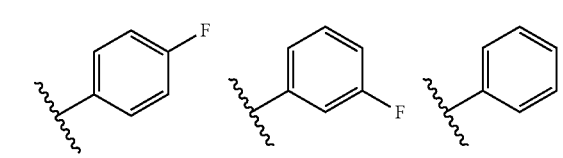
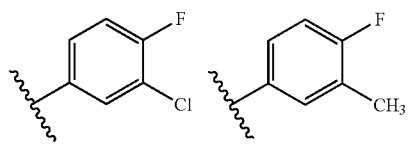
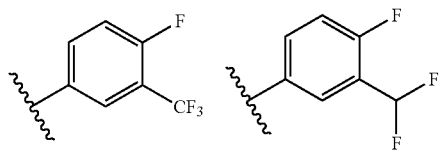
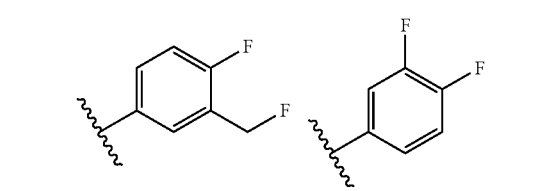
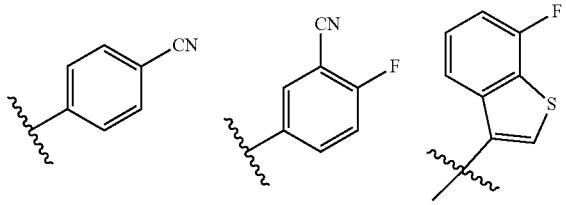
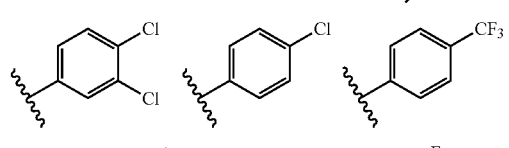
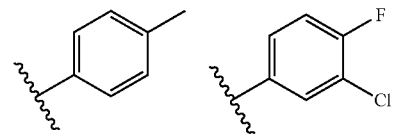
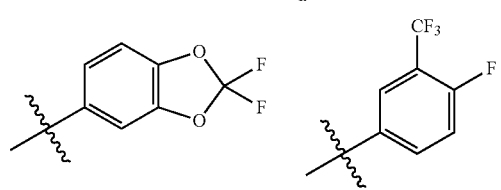
-continued
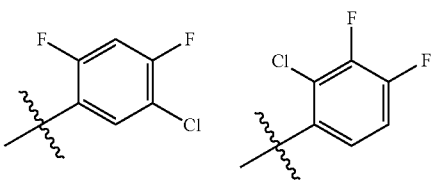
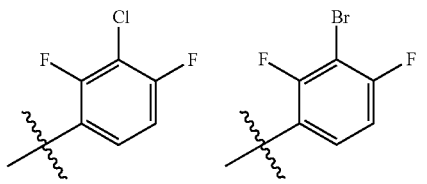
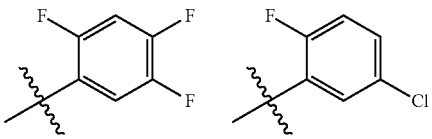
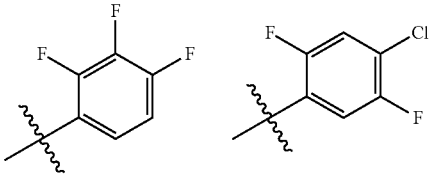
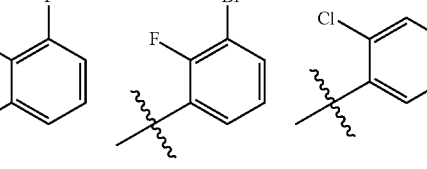
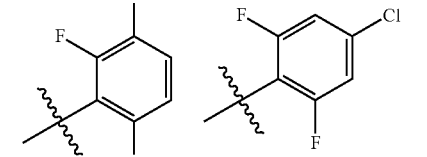
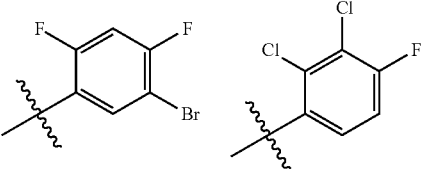
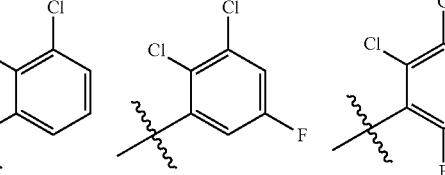
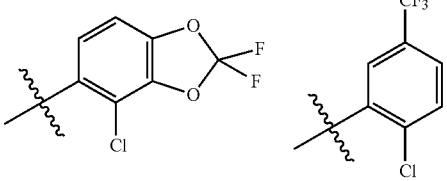

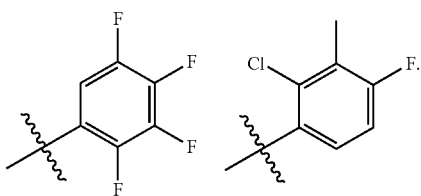
In one embodiment of the present invention, the compound of Formula (I) is represented by one of Formulae (IV-1)~(IV-7), A is selected from one of the following by removal of a hydrogen atom, and each of these groups is optionally substituted:
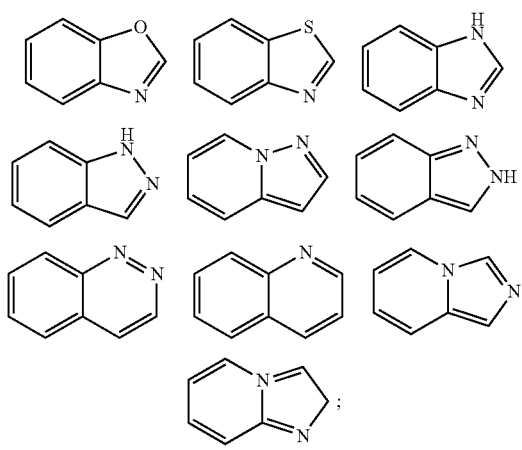
and E is selected from the groups set forth below,
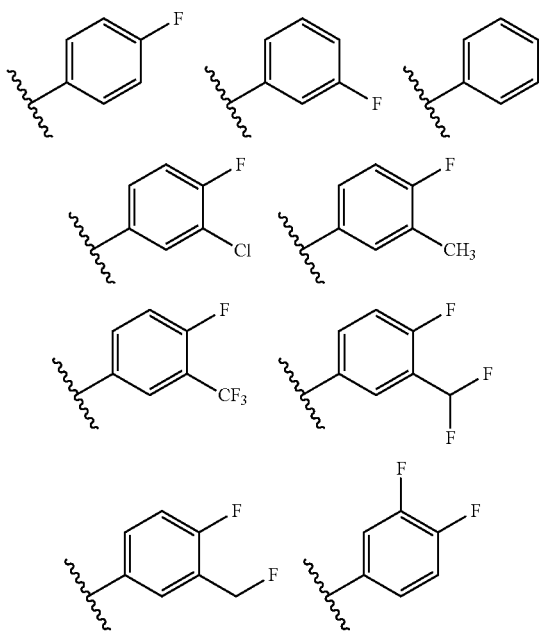
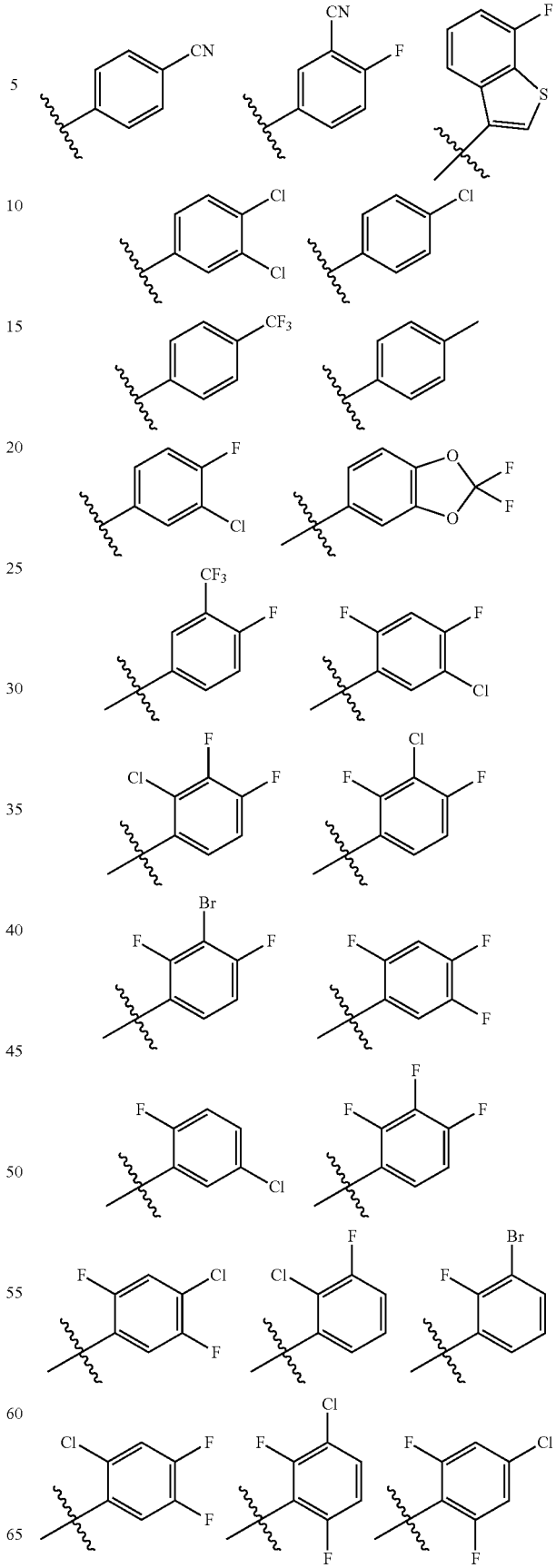

-continued

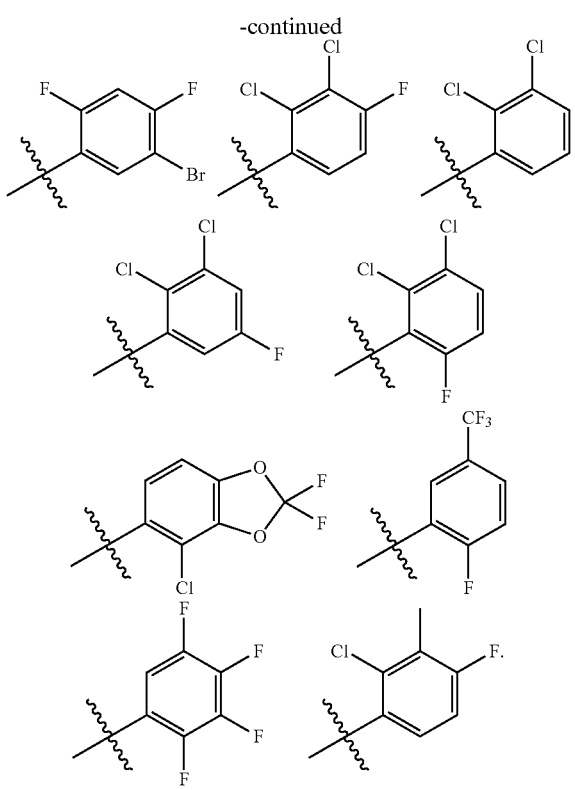

In one embodiment of the present invention, the compound of Formula (I) is represented by Formula (V-1), or Formula (V-2),

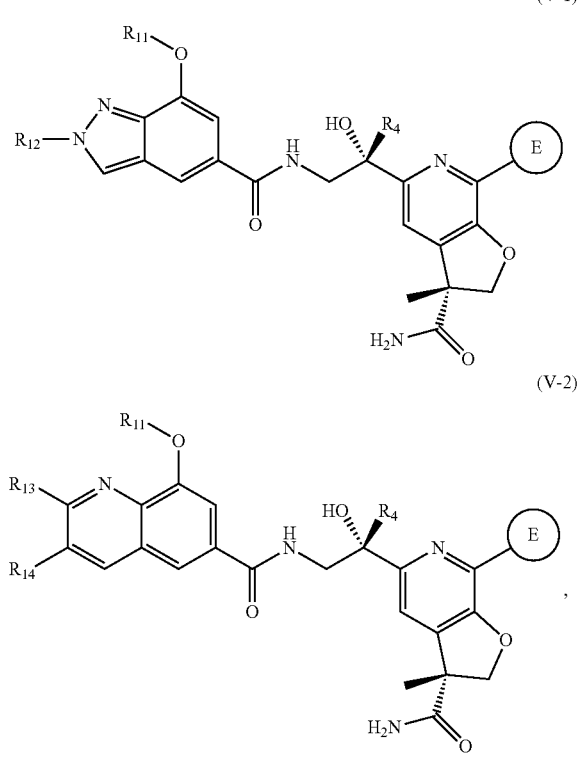

wherein E and $R_4$ are as previously defined, and $R_{11}$ is selected from optionally substituted —$C_1$-$C_6$ alkyl, optionally substituted —$C_3$-$C_8$ cycloalkyl, optionally substituted 3- to 8-membered heterocyclic, optionally substituted aryl, optionally substituted arylalkyl, optionally substituted heteroaryl, and optionally substituted heteroarylalkyl. Preferably, $R_1$ is optionally substituted methyl or optionally substituted cyclopropyl. Preferably, $R_{11}$ is methyl or cyclopropyl.

$R_{12}$ is selected from hydrogen, optionally substituted —$C_1$-$C_6$ alkyl, optionally substituted —$C_3$-$C_8$ cycloalkyl, optionally substituted 3- to 8-membered heterocyclic, optionally substituted aryl, optionally substituted arylalkyl, optionally substituted heteroaryl, and optionally substituted heteroarylalkyl. Preferably, $R_{12}$ is optionally substituted methyl or optionally substituted cyclopropyl. More Preferably, $R_{12}$ is —$CH_3$, —$CHF_2$, —$CD_3$, cyclopropyl,

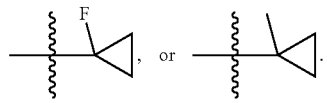

$R_{13}$ and $R_{14}$ are each independently selected from hydrogen, halogen, —$OR_{11}$, —$NH_2$, optionally substituted —$C_1$-$C_6$-alkyl, optionally substituted —$C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl. Alternatively, $R_{13}$ and $R_{14}$ are taken together with the carbon atoms to which they are attached to form a 4- to 7-membered ring fused with the phenyl ring. Preferably, $R_{13}$ and $R_{14}$ are each independently selected from halogen, optionally substituted methyl, and optionally substituted methoxyl.

In one embodiment of the present invention, the compound of Formula (I) is represented by Formula (V-1), or Formula (V-2), wherein E is substituted phenyl, and $R_4$ is selected from one of the following:

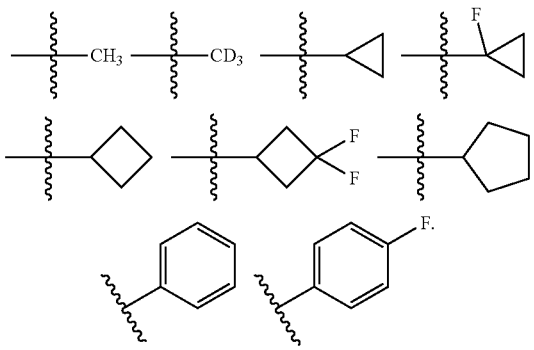

In one embodiment of the present invention, the compound of Formula (I) is represented by Formula (V-1), or Formula (V-2), wherein E is selected from the groups set forth below,

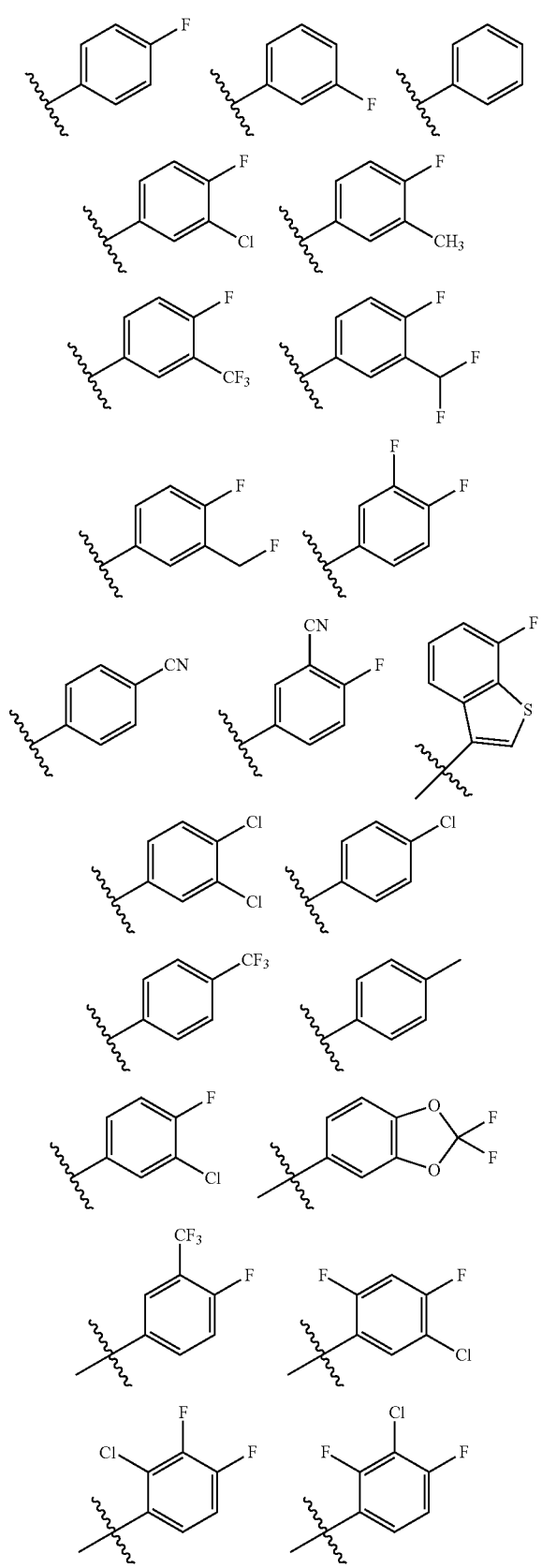
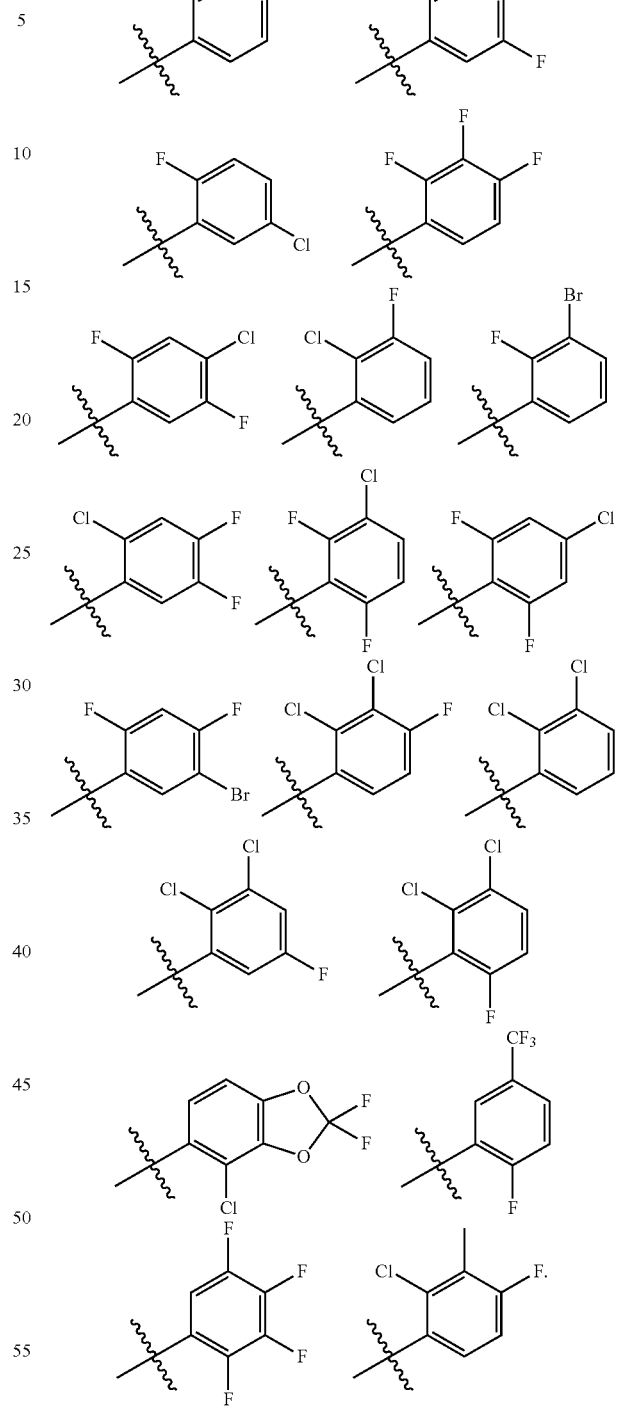

In one embodiment of the present invention, the compound of Formula (I) is represented by Formula (V-1), or Formula (V-2), wherein E is substituted phenyl; Ru is optionally substituted methyl or optionally substituted cyclopropyl; $R_{12}$ is optionally substituted methyl or optionally substituted cyclopropyl; $R_{13}$ and $R_{14}$ are each independently selected from halogen, optionally substituted methyl, and optionally substituted methoxyl; and $R_4$ is selected from one of the following.

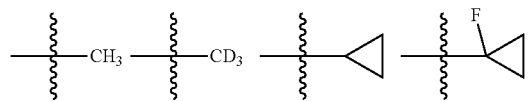

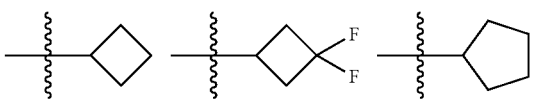

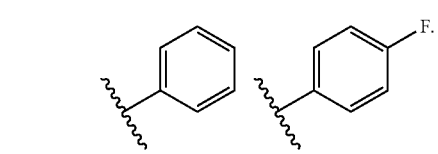

In one embodiment of the present invention, the compound of Formula (I) is represented by Formula (VI-1), or Formula (VI-2), (VI-1)

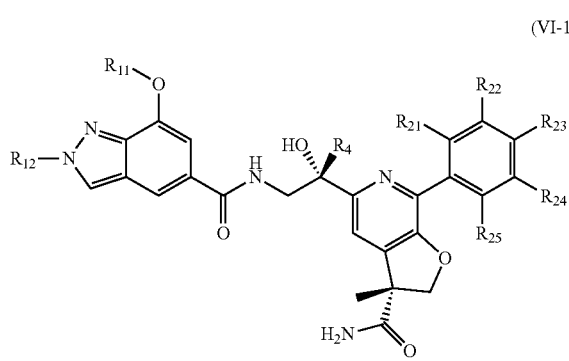

(VI-2)

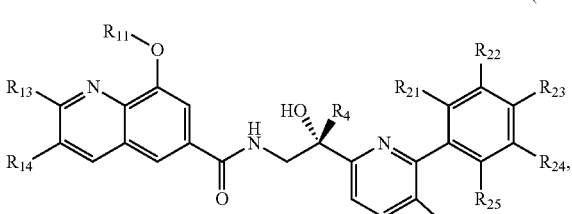

wherein $R_4$, $R_{11}$, $R_{12}$, $R_{13}$, and $R_{14}$, are as previously defined, and each $R_{21}$, $R_{22}$, $R_{23}$, $R_{24}$, and $R_{25}$ are independently selected from hydrogen, halogen, optionally substituted methyl, and optionally substituted methoxyl.

In one embodiment of the present invention, the compound of Formula (I) is represented by one of Formulae (VII-1)~(VII-6), (VII-1)

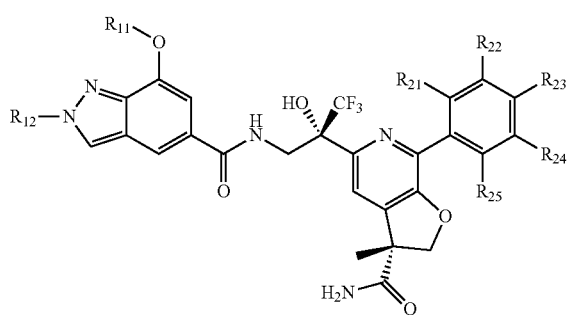

(VII-2)

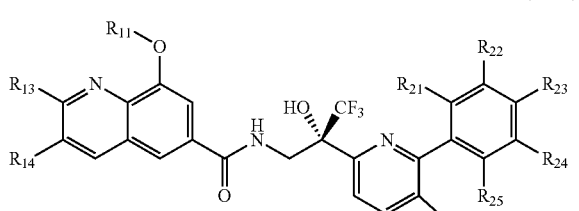

(VII-3)

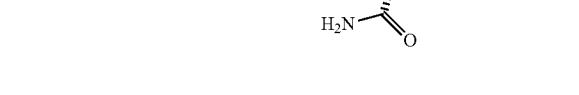

(VII-4)

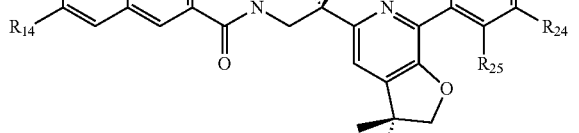

(VII-5)

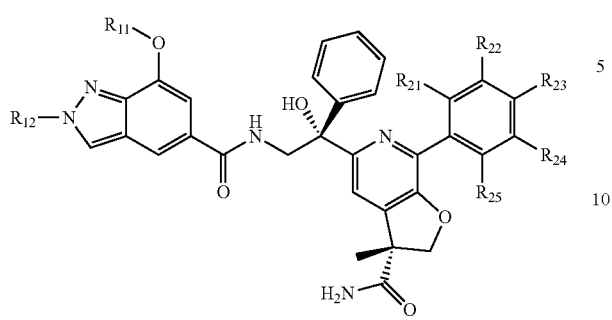

(VII-6)

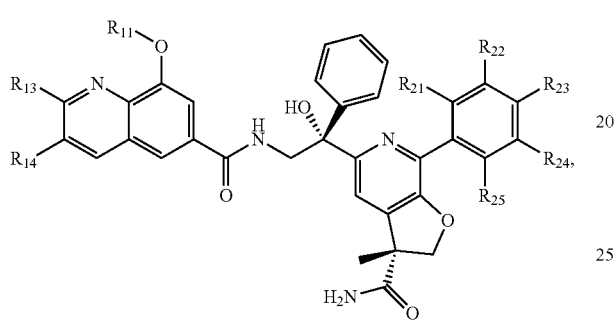

wherein $R_{11}$, $R_{12}$, $R_{13}$, $R_{14}$, $R_{21}$, $R_{22}$, $R_{23}$, $R_{24}$, and $R_{25}$ are as previously defined.

In one embodiment of the present invention, the compound of Formula (I) is represented by one of Formulae (VIII-1)~(VIII-2), (VIII-1)

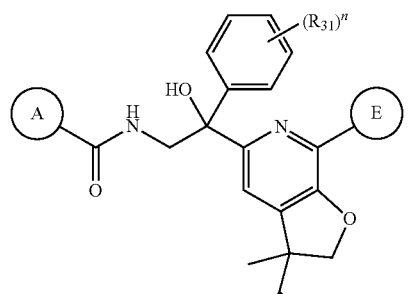

(VIII-2)

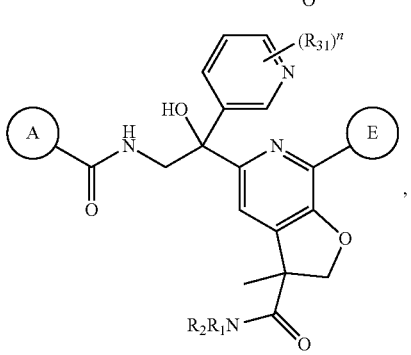

wherein A, E, $R_1$, $R_2$, $R_{31}$, and n are as previously defined.

In one embodiment of the present invention, the compound of Formula (I) is represented by one of Formulae (VIII-1a)~(VIII-2a), (VIII-1a)

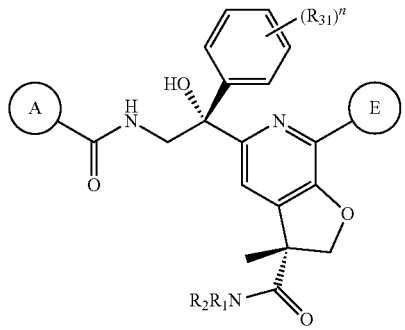

(VIII-2a)

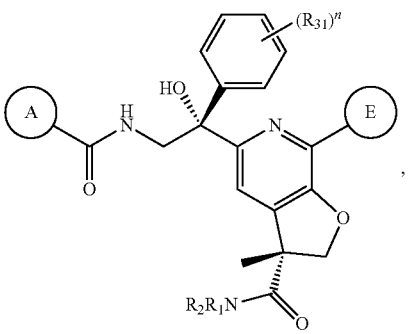

wherein A, E, $R_1$, $R_-$, $R_{31}$, and n are as previously defined.

In one embodiment of the present invention, the compound of Formula (I) is represented by one of Formulae (VIII-1a)~(VIII-2a), A is selected from one of the following by removal of a hydrogen atom, and each of these groups is optionally substituted:

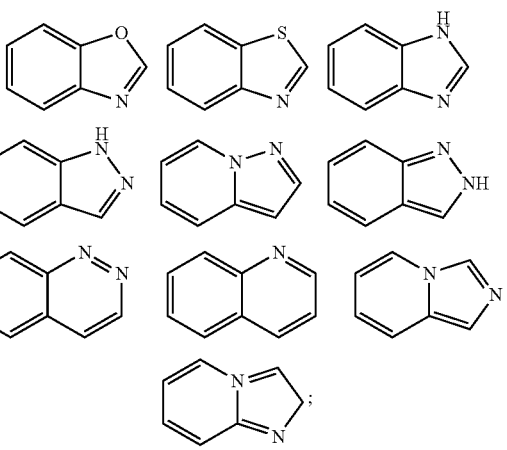

and E is selected from the groups set forth below,

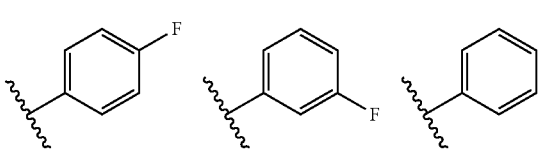

-continued
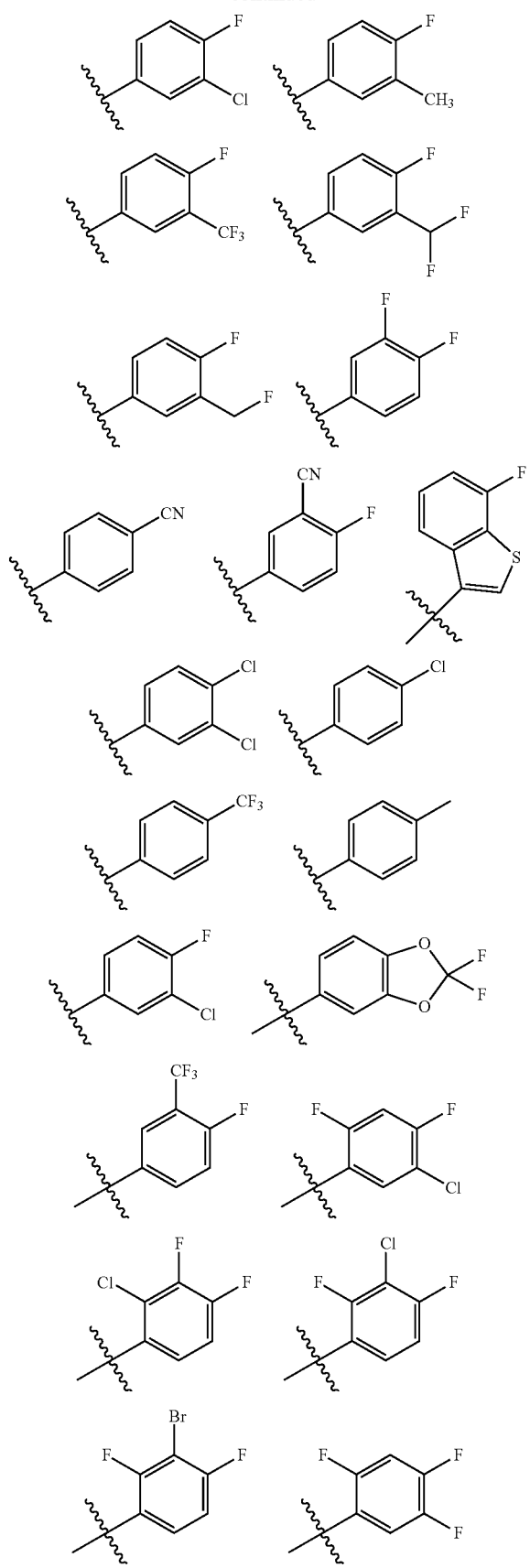
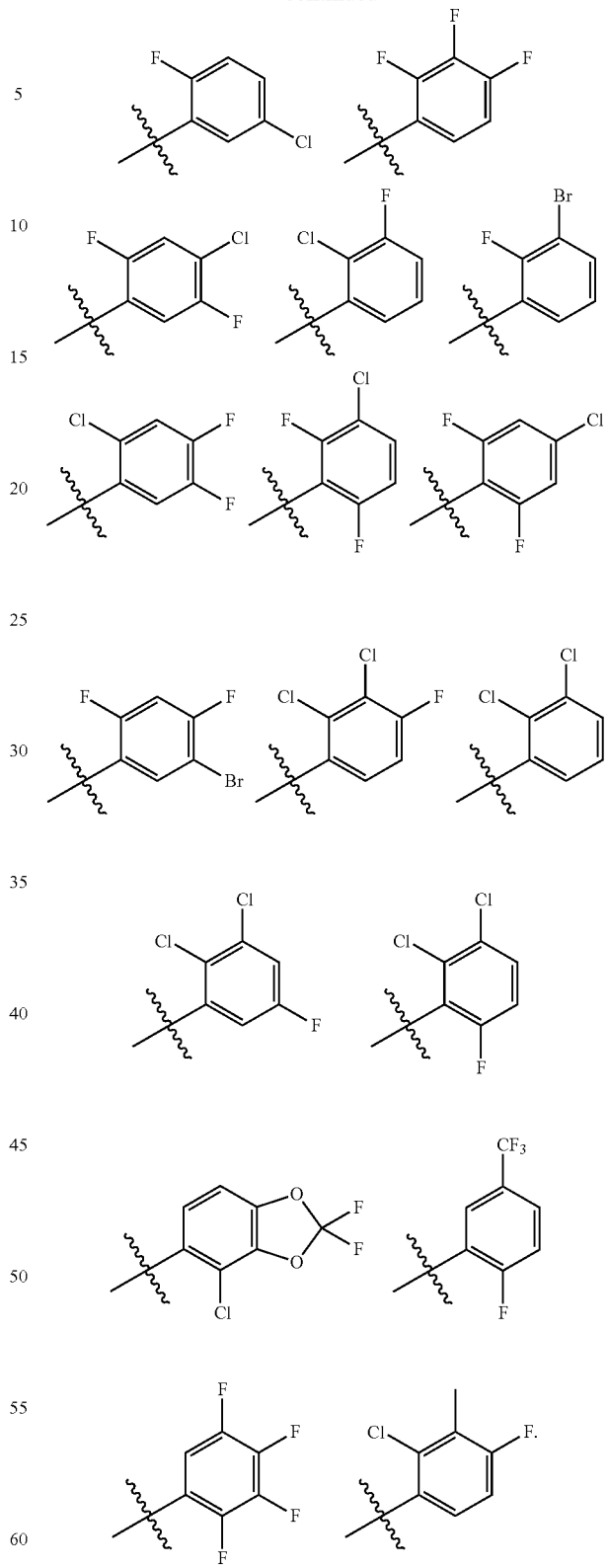
Preferably, $R_1$ is hydrogen, and $R_2$ is hydrogen.
In one embodiment of the present invention, the compound of Formula (I) is represented by one of Formulae (IX-1)~(IX-8),

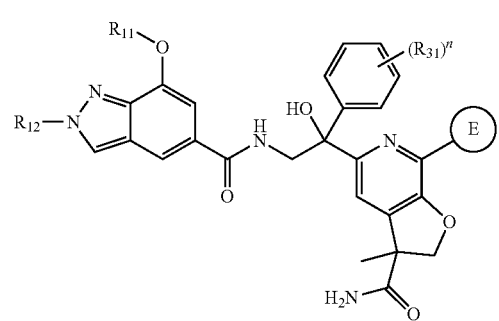
(IX-1)
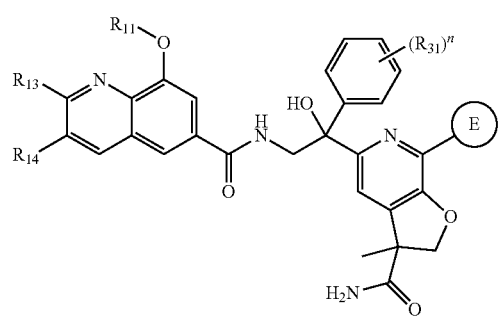
(IX-2)
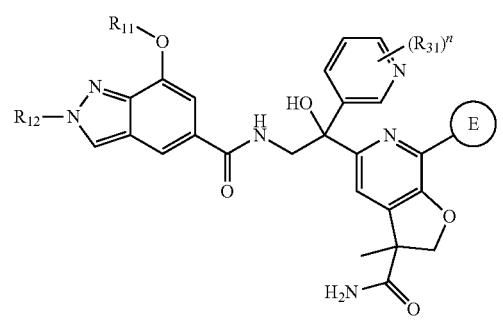
(IX-3)
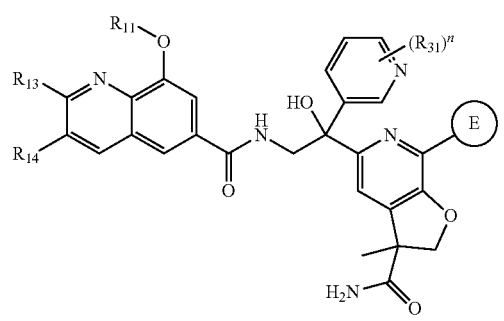
(IX-4)
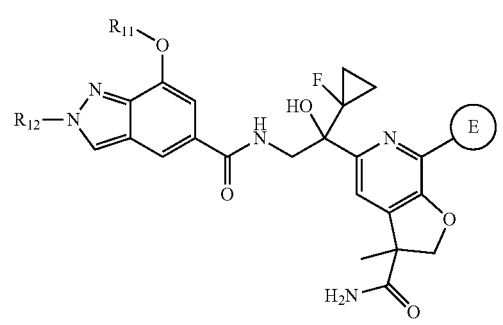
(IX-5)
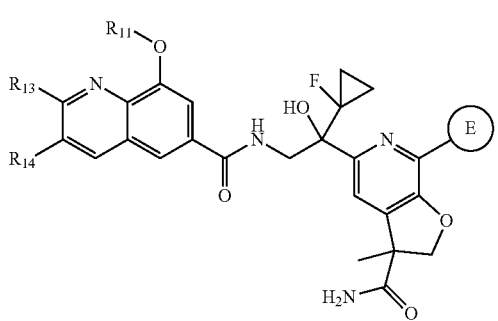
(IX-6)
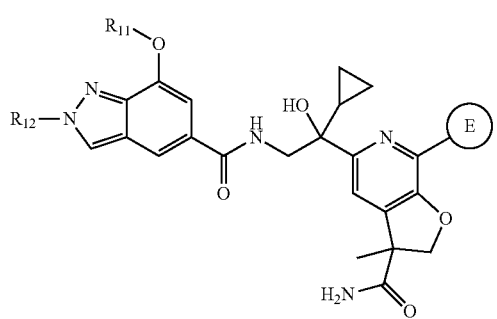
(IX-7)
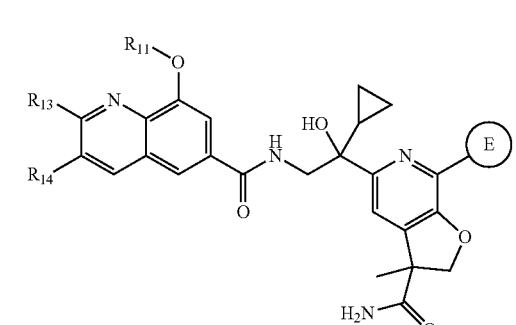
(IX-8)
wherein E, $R_{11}$, $R_{12}$, $R_{13}$, $R_{14}$, $R_{31}$, and n are as previously defined.
In one embodiment of the present invention, the compound of Formula (I) is represented by one of Formulae (IX-1a)~(IX-8a),
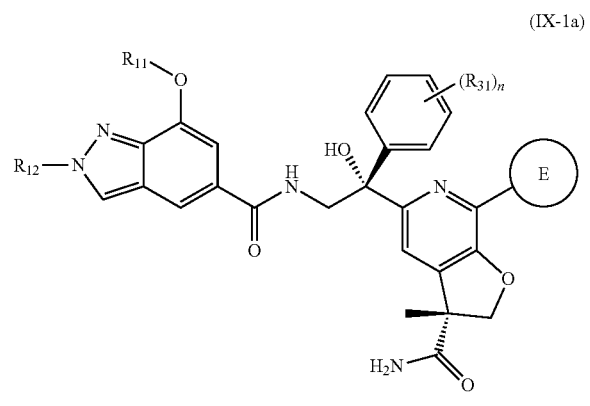
(IX-1a)

(IX-2a)
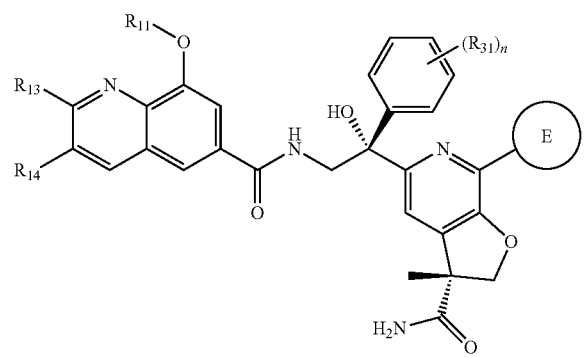
(IX-3a)
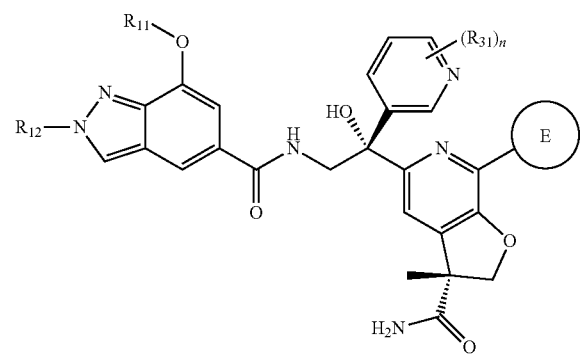
(IX-4a)
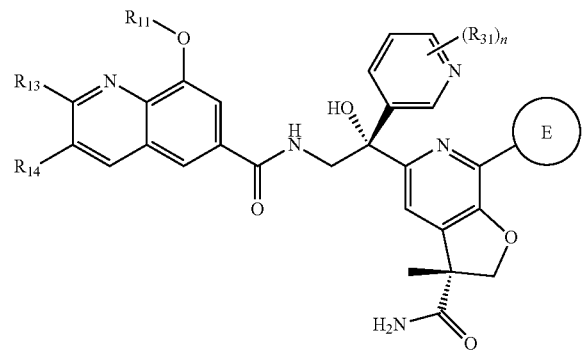
(IX-5a)
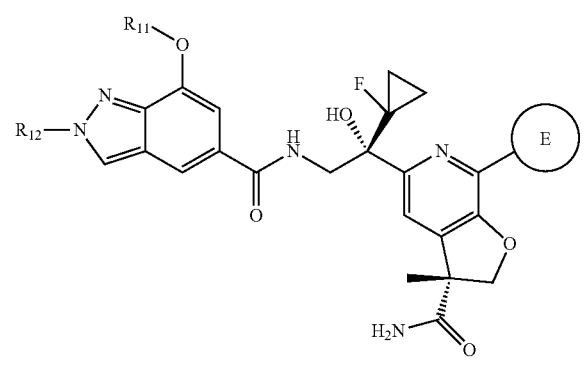
(IX-6a)
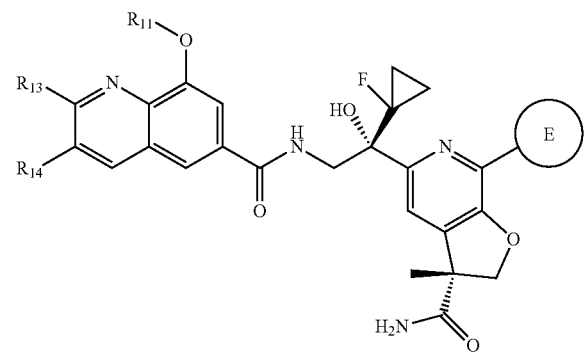
(IX-7a)
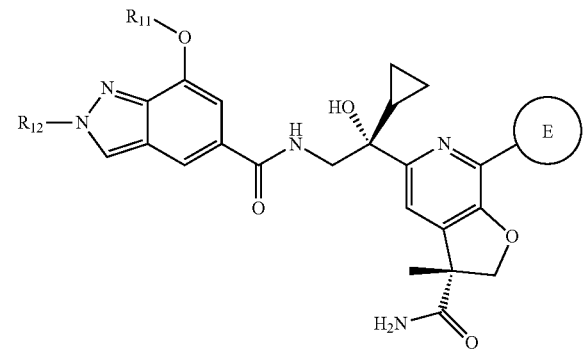
(IX-8a)
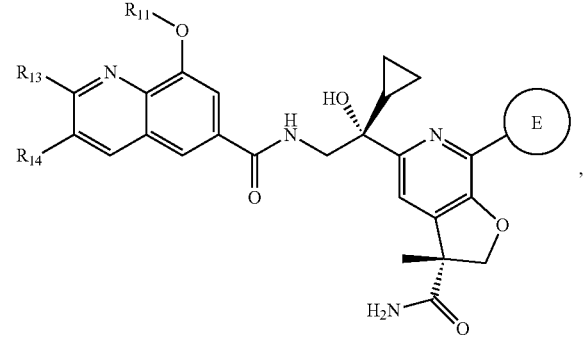
wherein E, $R_{11}$, $R_{12}$, $R_{13}$, $R_{14}$, $R_{31}$, and n are as previously defined.
In one embodiment of the present invention, the compound of Formula (I) is represented by one of Formulae (TX-1a)~(LX-8a), E is selected from the groups set forth below,
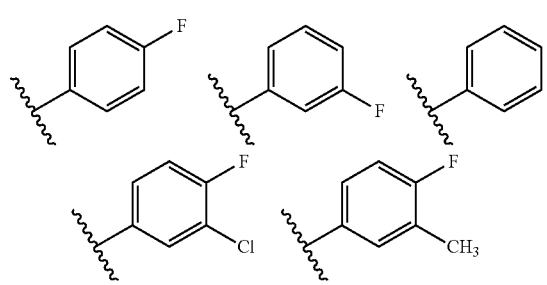

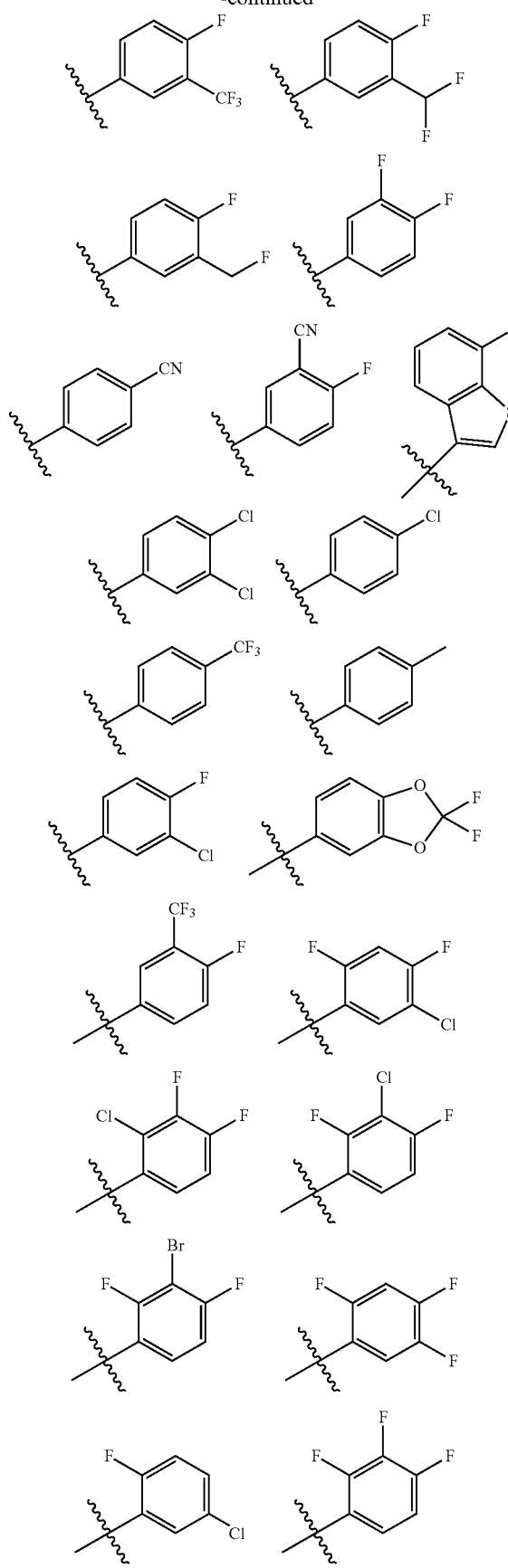
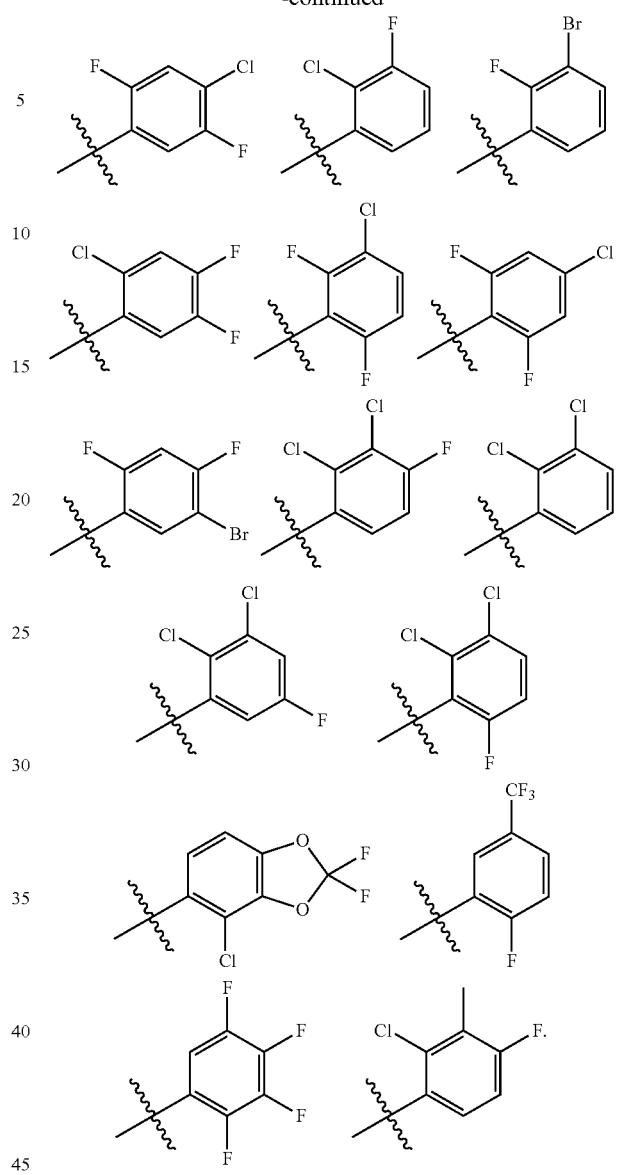
In one embodiment of the present invention, the compound of Formula (I) is represented by one of Formulae (X-1)~(X-12),
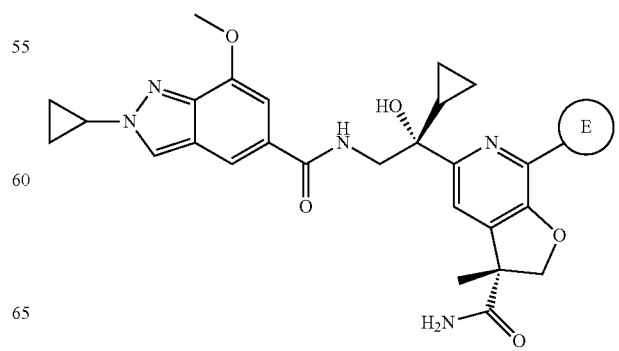

(X-2)
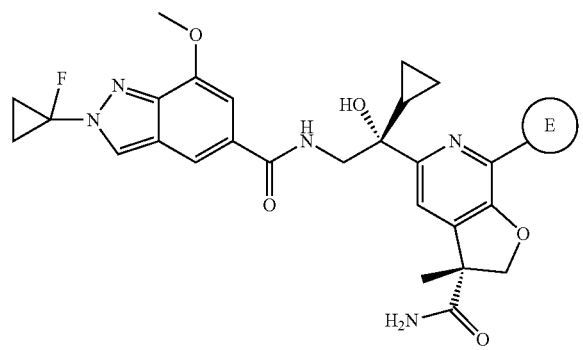
(X-3)
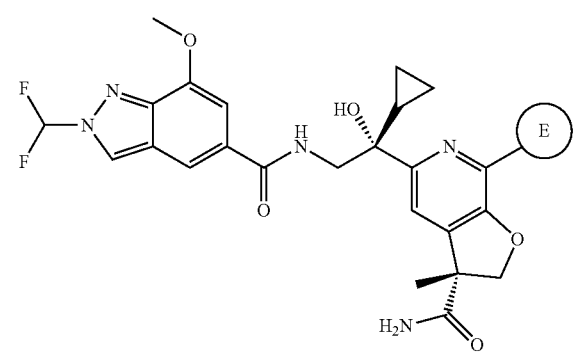
(X-4)
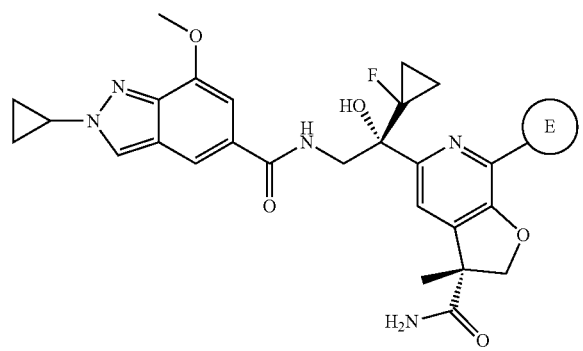
(X-5)
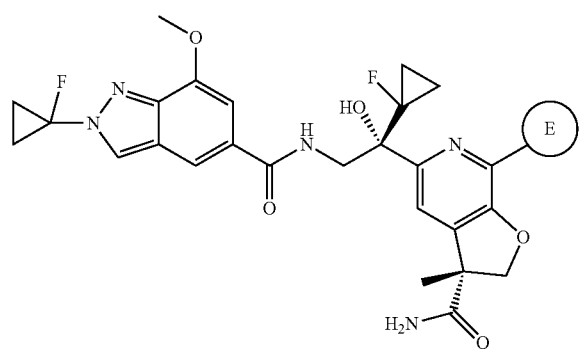
(X-6)
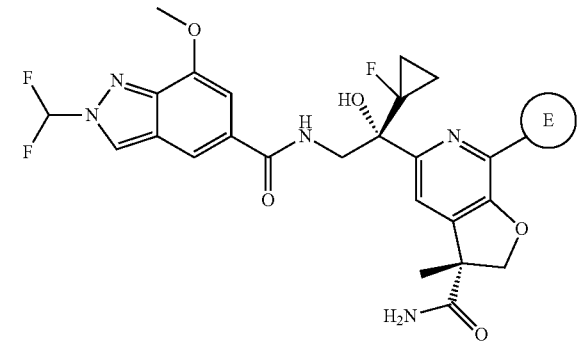
(X-7)
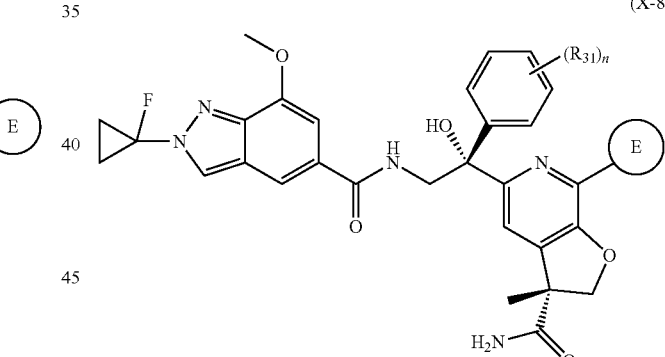
(X-8)
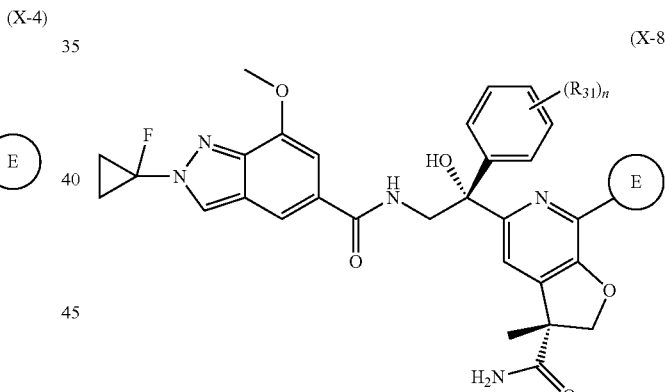
(X-9)
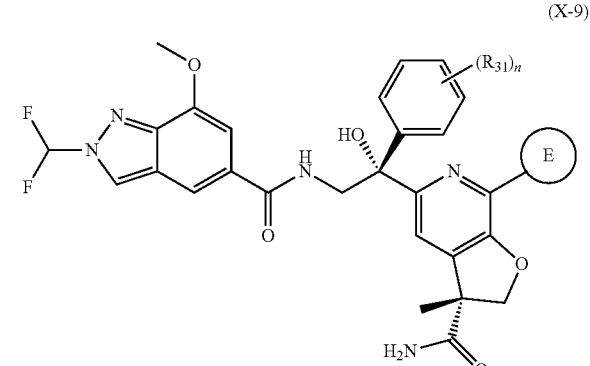

(X-10)
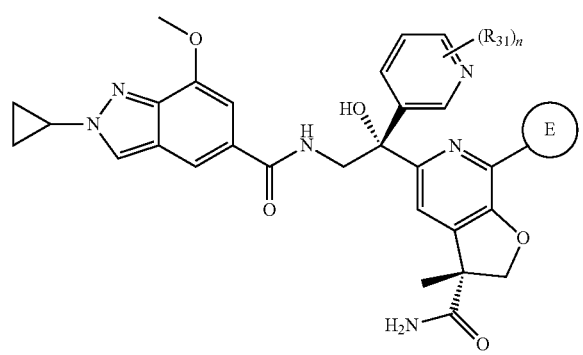
(X-11)
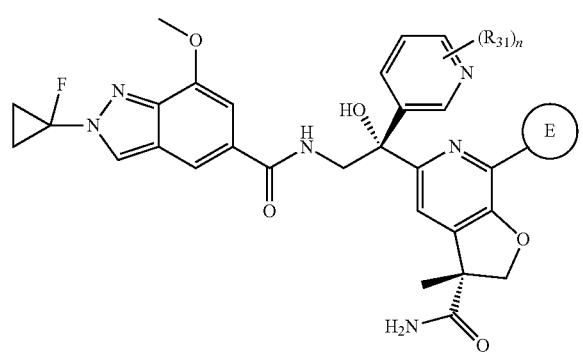
(X-12)
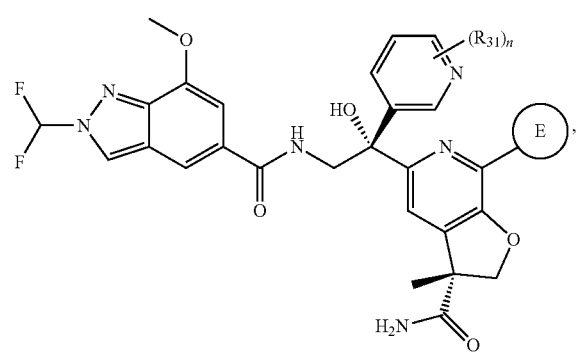
wherein E, R<sub>31</sub>, and n are as previously defined.
In one embodiment of the present invention, the compound of Formula (I) is represented by one of Formulae (X-1)~(X-12), and E is selected from the groups set forth below,
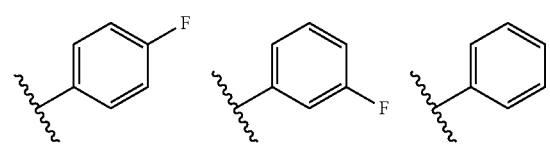
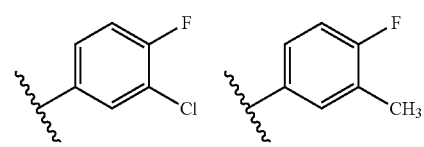
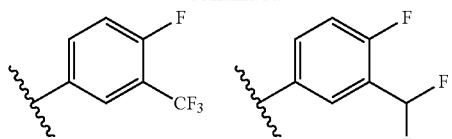
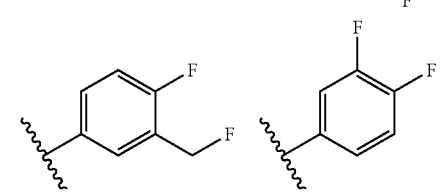
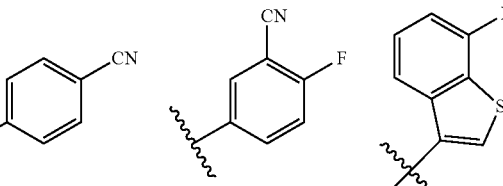
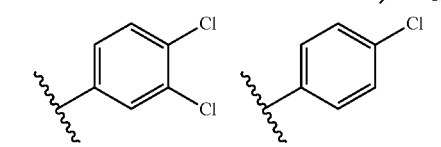
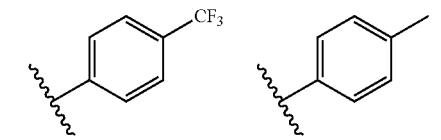
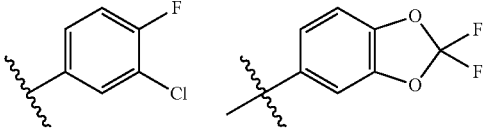
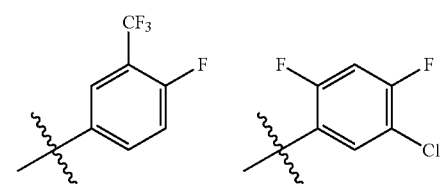
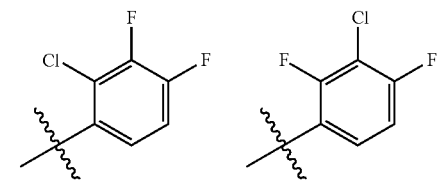
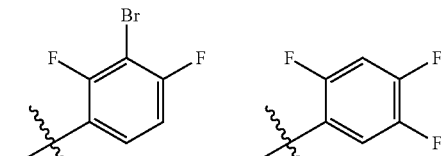
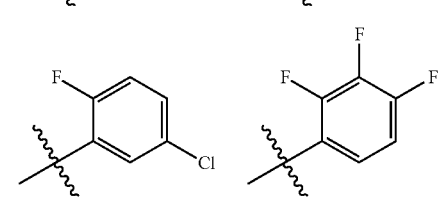

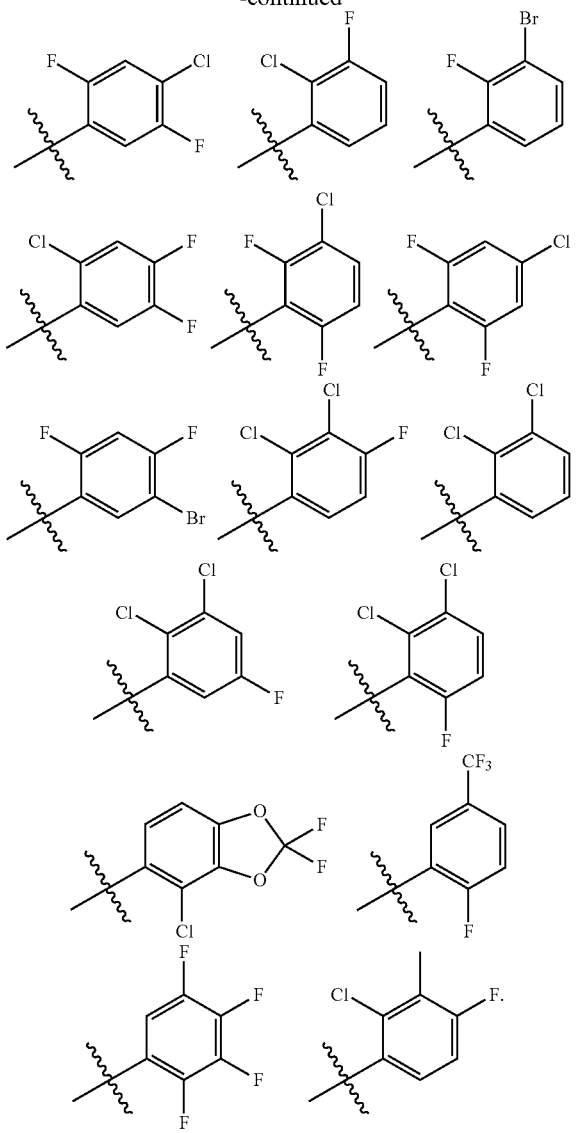

It will be appreciated that the description of the present invention herein should be construed in congruity with the laws and principles of chemical bonding. In some instances, it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebulizer containing a medicament which comprises (a) a derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents; e.g., starches, arabic gums, gelatin, methylcellulose, carboxymethylcellulose or polyvinyl pyrrolidone; disaggregating agents, e.g., starch, alginic acid, alginates or sodium starch glycolate; effervescing mixtures; dyestuffs; sweeteners; wetting agents, such as lecithin, polysorbates, laurylsulphates; and, in general, nontoxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluant or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral center include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono-, bi-, or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl", "$C_1$-$C_6$ alkyl," "$C_1$-$C_{10}$ alkyl" $C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl"

means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$)alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O) C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "carbocycle" or "carbocyclic" refers to a saturated, partially unsaturated or aromatic cyclic group in which each atom within the ring is carbon. Examples of cabocyclics include cycloalkyl, cycloalkenyl and aryl groups.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo [2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, —$C_1$-$C_{12}$-alkyl; —$C_2$-$C_{12}$-alkenyl, —$C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$CO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$— $C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S) NH—$C_3$-$C_{12}$-cycloalkyl, —NHC(S)NH-aryl, —NHC(S) NH-heteroaryl, —NHC(S)NH-heterocycloalkyl, —NHC (NH)$NH_2$, —NHC(NH)NH—$C_1$-$C_{12}$-alkyl, —NHC(NH) NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC (NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH) NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_3$-$C_{12}$-cycloalkyl, —$NHSO_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. In certain embodiments, the substituents are independently selected from halo, preferably Cl and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy, —CN; —OH; NH$_2$; C$_1$-C$_4$-alkylamino; di(C$_1$-C$_4$-alkyl)amino; and N$_{02}$. It is understood that the aryls, heteroaryls, alkyls, and the like can be further substituted. In some cases, each substituent in a substituted moiety is additionally optionally substituted when possible with one or more groups, each group being independently selected from C$_1$-C$_4$-alkyl; —CF$_3$, —OCH$_3$, —OCF$_3$, —F, —Cl, —Br, —I, —OH, —NO$_2$, —CN, and —NH$_2$.

In certain embodiments, a substituted alkyl, alkenyl or alkoxy group is substituted with one or more halogen atoms, preferably fluorine or chlorine atoms. Such substituted alkyl groups include fluoromethyl, difluoromethyl and trifluoromethyl. Such substituted alkoxy groups include fluoromethoxy, difluoromethoxy and trifluoromethoxy.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but are not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-*2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art.

Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2$^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis,* John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention.

Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of *Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound.

The term "treating", as used herein, means relieving, lessening, reducing, eliminating, modulating, or ameliorating, i.e., causing regression of the disease state or condition. Treating can also include inhibiting, i.e., arresting the development, of an existing disease state or condition, and relieving or ameliorating, i.e., causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or nonstoichiometric amounts of solvent. Some compounds have a tendency to trap a fixed molar ratio of solvent molecules in the crystalline solid state, thus forming a solvate. If the solvent is water, the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. *Fieser and M. Fieser, Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
AD-mix-β for (9S)-(9"S)-9,9"-[1,4-Phthalazinediylbis(oxy)]bis[10,11-dihydro-6'-methoxycinchonan];
Bn for benzyl;
BOP for (Benzotriazol-1-yloxy)tris(dimethylamino)phosphonium hexafluorophosphate;
BzCl for benzoyl chloride;
mCPBA for meta-chloroperbenzoic acid;
Cbz for benzyloxycarbonyl;
CDI for carbonyldiimidazole;
DAST for diethylaminosulfur trifluoride;
DBU for 1,8-Diazabicycloundec-7-ene;
DCE for dichloroethane;
DCM for dichloromethane;
Dess-Martin periodinane for 1,1,1-tris(acetyloxy)-1,1-dihydro-1,2-benziodoxol-3-(1H)-one;
DIAD for diisopropyl azodicarboxylate;
DIBAL-H for diisobutylaluminum hydride;
DMAP for N,N-dimethylaminopyridine;
DME for 1,2-dimethoxyethane;
DMF for N,N-dimethyl formamide;
DMSO for dimethylsulfoxide;
DPPA for diphenylphosphoryl azide or diphenyl phosphorylazidate;
dppf for 1,1'-Bis(diphenylphosphino)ferrocene;
EDCI or EDC for 1-(3-diethylaminopropyl)-3-ethylcarbodiimide hydrochloride;
EA or EtOAc for ethyl acetate;
Ghosez's reagent for 1-Chloro-N,N,2-trimethyl-1-propenylamine;
HATU for O (7-Azabenzotriazole-1-yl)-N,N,N',N'-tetramethyluronium hexafluorophosphate;
HCl for hydrochloric acid;
Hunig's base for diisopropylethylamine;
PyBOP for (Benzotriazol-1-yloxy)tripyrrolidinophosphonium hexafluorophosphate;
LDA for Lithium diisopropylamine;
Pd—C for palladium carbon;
PE for petroleum ether;

Ph for phenyl;
RT for reverse transcription;
RT-PCR for reverse transcription-polymerase chain reaction;
TBME for tert-butyl methyl ether;
TEA for triethylamine;
Tf$_2$O for trifluoromethanesulfonic anhydride;
TFA for trifluoroacetic acid;
THF for tetrahydrofuran;
(TMS)$_2$NH for hexamethyldisilazane;
TBS for tert-Butyldimethylsilyl;
TBDPS for tert-Butyldiphenylsilyl;
TMS for trimethylsilyl;
TPAP tetrapropylammonium perruthenate;
TPP or PPh$_3$ for triphenylphosphine;
Ts or tosyl for p-CH$_3$C$_6$H$_4$SO$_2$—;
tBOC or Boc for tert-butyloxy carbonyl; and
Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1 illustrates methods to prepare a compound of formula 11 from compounds 1 and 2, wherein n=1, 2 or 3; P is hydroxy protecting group; Ar is E; and E is as previously defined. Alkylation of the hydroxy pyridine 1 with hydroxy epoxide using Mitsunobu reaction conditions affords epoxide 4. Alternatively, hydroxy epoxide is converted to 3 which has a leaving group such as but not limited to, tosyl and methanlsulfonyl followed by alkylation in the presence of base such as but not limited to, K$_2$CO$_3$ and Cs$_2$CO$_3$, provides 4. Intramolecular epoxide opening mediated by base such as but not limited to, LDA, produces compound 5. Hydroxy group compound 5 is protected with proper protecting group such as but not limited to, TBDPS and TBS, affords compound 6. Trifluomethyl ketone 7 is obtained from iodine-magnesium exchange of compound 6 followed by addition of ester such as but not limited to, ethyl 2,2,2-trifluoroacetate. Trifluoromethyl ketone 7 in cross-coupled with various metal coupling partners 8, but not limited to, boronic acids, boronic esters, organotin reagents, organozinc reagents, organomagnesium reagents, organo silicon reagents or the like catalyzed by appropriate Pd, Ni, Cu or the like catalyst to afford compound 9. Nitromethane addition in the presence of base such as but not limited to, K$_2$CO$_3$ and Cs$_2$CO$_3$, to compound 9 affords compound 10. Reduction of nitro group with reducing reagents such as but not limited to, zinc and acetic acid, produces key intermediate 11.

Scheme 1

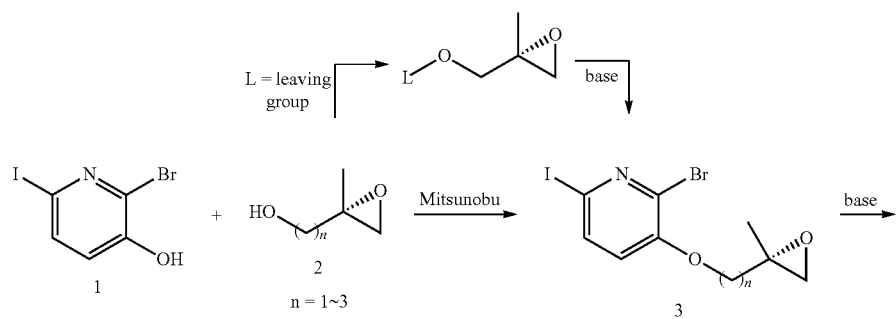

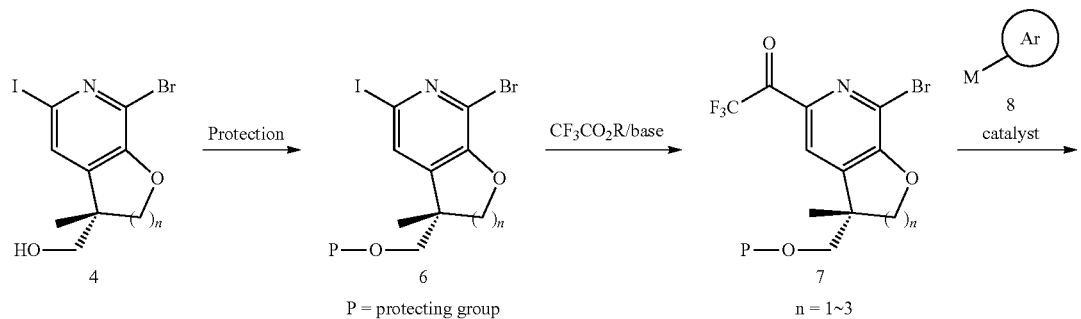

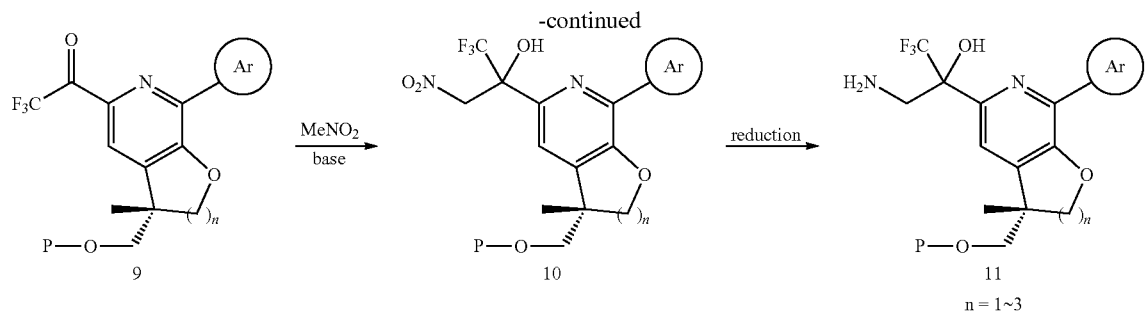

As seen in scheme 2, wherein $Ar_1$ is A; Ar is E; R is $R_{11}$; n is 1, 2 or 3; and A, E, $R_{11}$ are as previously defined. Key intermediate 11 is coupled with various carboxylic acids to afford amide 14. Amide 14 is then reacted with a variety of electrophiles to produce various ethers, esters and carbamates of formula 15. Amide 14 is also oxidized to an aldehyde 16, and then reductive amination provides a variety of amines 17. The hydroxyl of —CH$_2$OH in amide 14 is converted to cyanomethyl 18 via activation followed by cyanation. Compound 14-1 is further transformed to acetamide 19 in the presence of a catalyst such as, but not limited to, Parkin's catalyst.

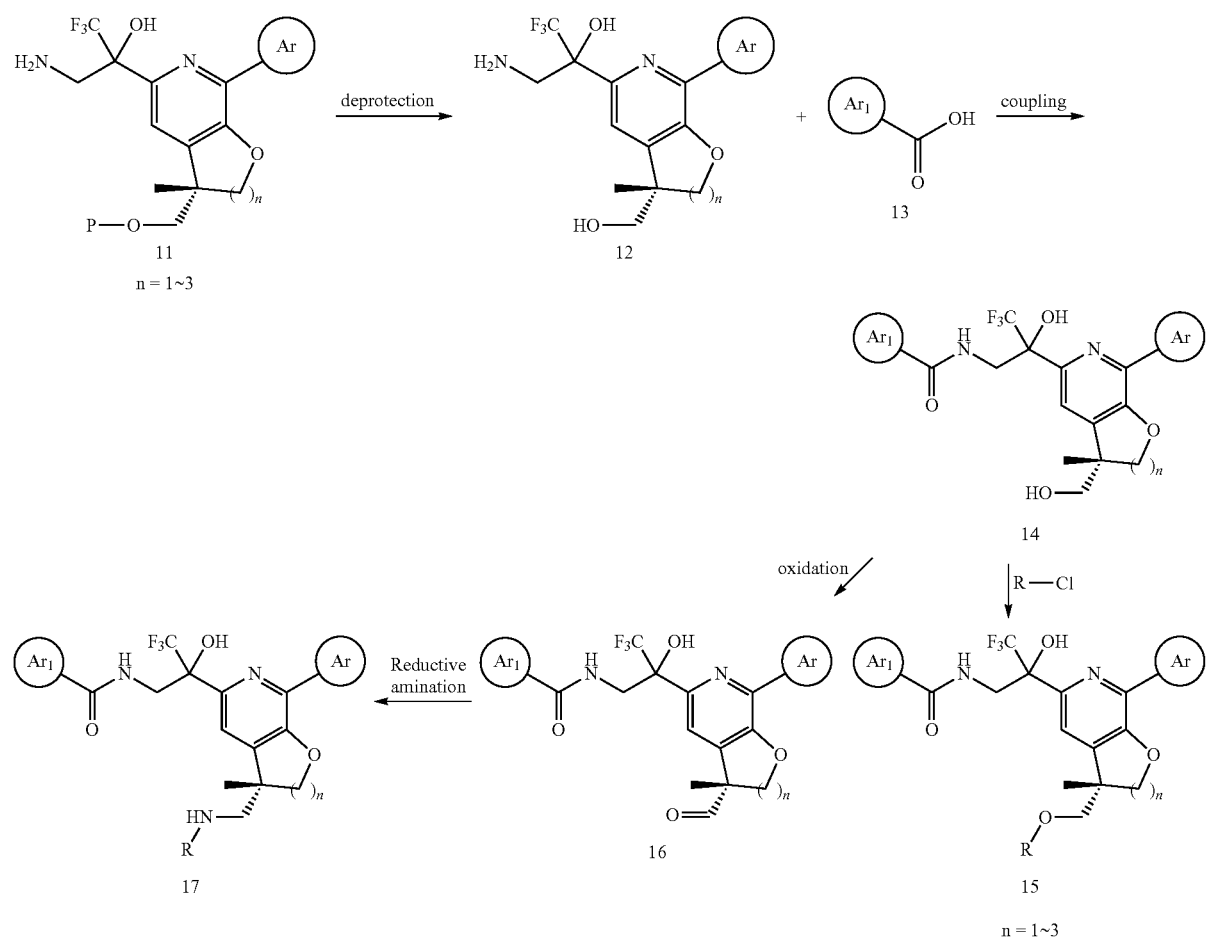

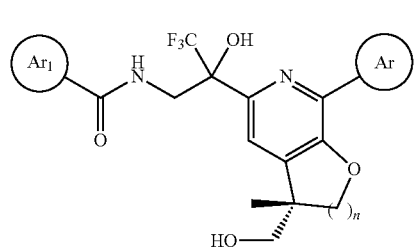

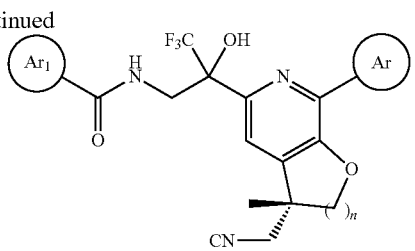

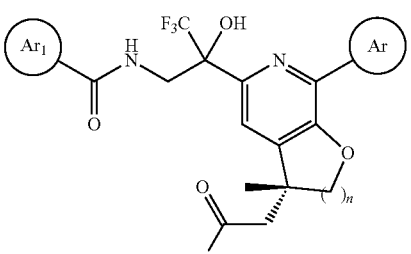

As seen in scheme 3, wherein $Ar_1$ is A; Ar is E; R is $R_{11}$; and A, E, $R_{11}$ are as previously defined. An aldehyde 16 is converted to the benzyl protected amine through reductive amination. Hydrogenolysis affords the free amine 20. Lastly, displacement with a variety of electrophiles gives N-substituted compounds 21.

Scheme 3

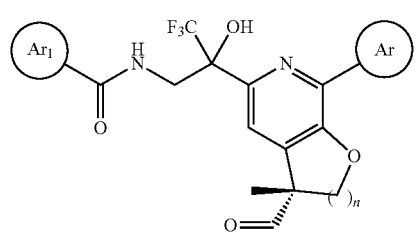

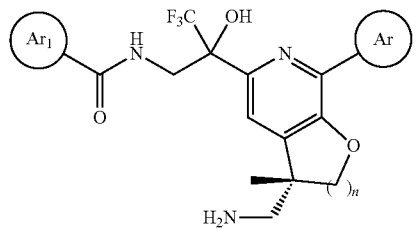

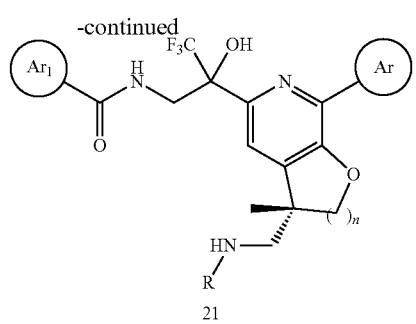

As seen in Scheme 4, wherein $Ar_1$ is A; Ar is E; R' is —$C_1$-$C_6$ alkyl, —$C_3$-$C_6$ cycloalkyl, aryl, or heteroaryl; n is 1, 2 or 3; and A and E are as previously defined. After oxidation of aldehyde 16 to acid 22, which is further converted to amides 23 and sulfonamides 24 using common methods such as but not limited to, HATU and DIPEA. From there diversification to a variety of esters and amides is conducted.

Scheme 4

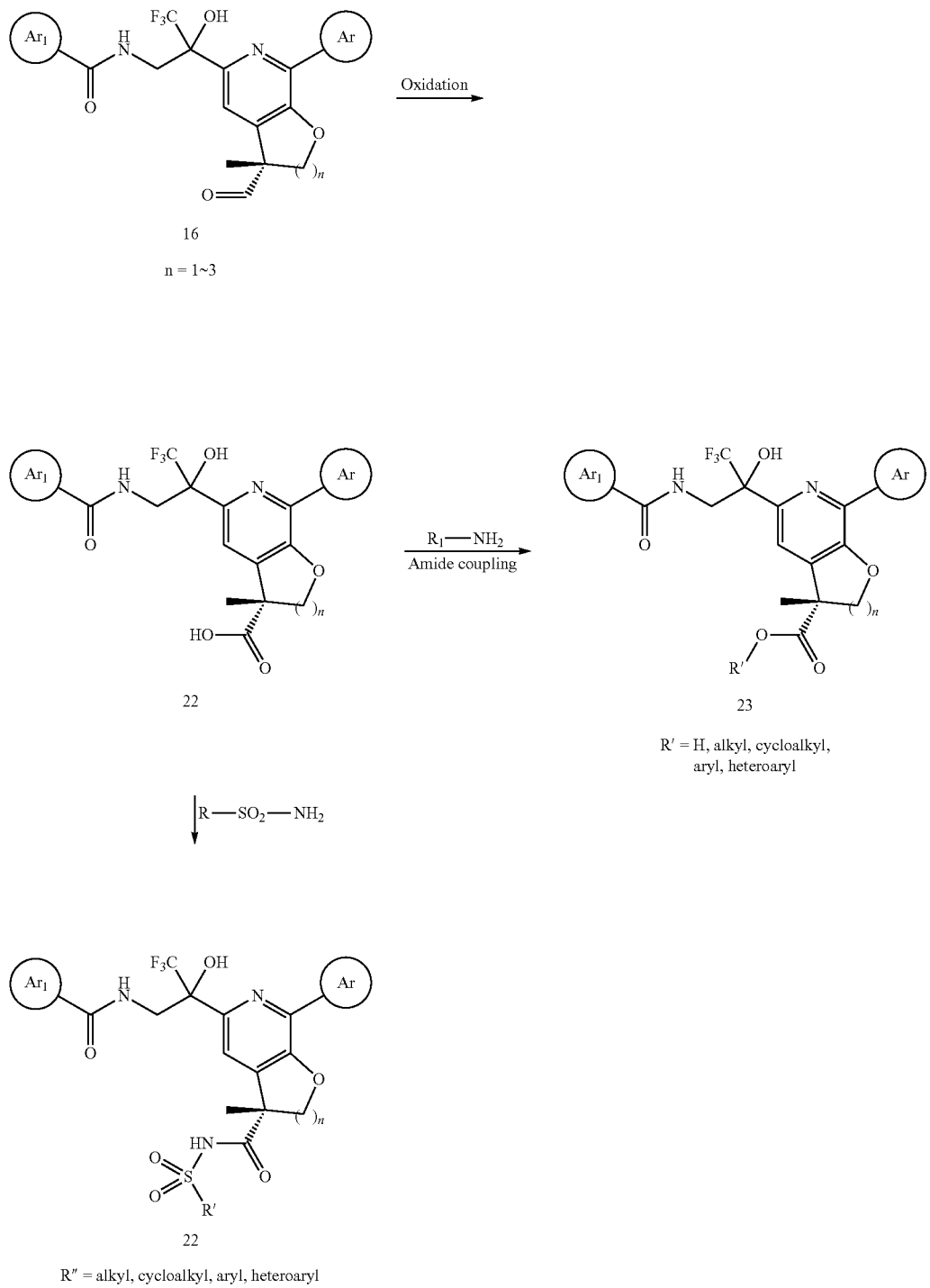

Scheme 5 illustrates another method to prepare a compound of formula 11, wherein Ar is E; P is a hydroxy protecting group; n is 1, 2 or 3; and E is as previously defined. Ketone 9 is converted to compound of formula 26 via olefination. Alternatively, 26 is obtained from; 1) 6 via cross-coupling with metal coupling partner 6-1, which can be, but is not limited to, a boronic acid, a boronic ester, an organotin reagent, an organozinc reagent, an organomagnesium reagent, an organosilicon reagent or the like catalyzed by appropriate Pd, Ni, Cu or the like catalyst to afford compound 25; 2) compound 25 is converted to compound 26 as previously described method in scheme 1. With 26 in hand, Compounds of formula 27 are prepared by dihydroxylation followed by epoxide formation. Epoxide opening of compound 27 with amine equivalent such as but not limited to, $NH_4OH$ and $NH_3$, provides compounds of formula 11.

Scheme 5

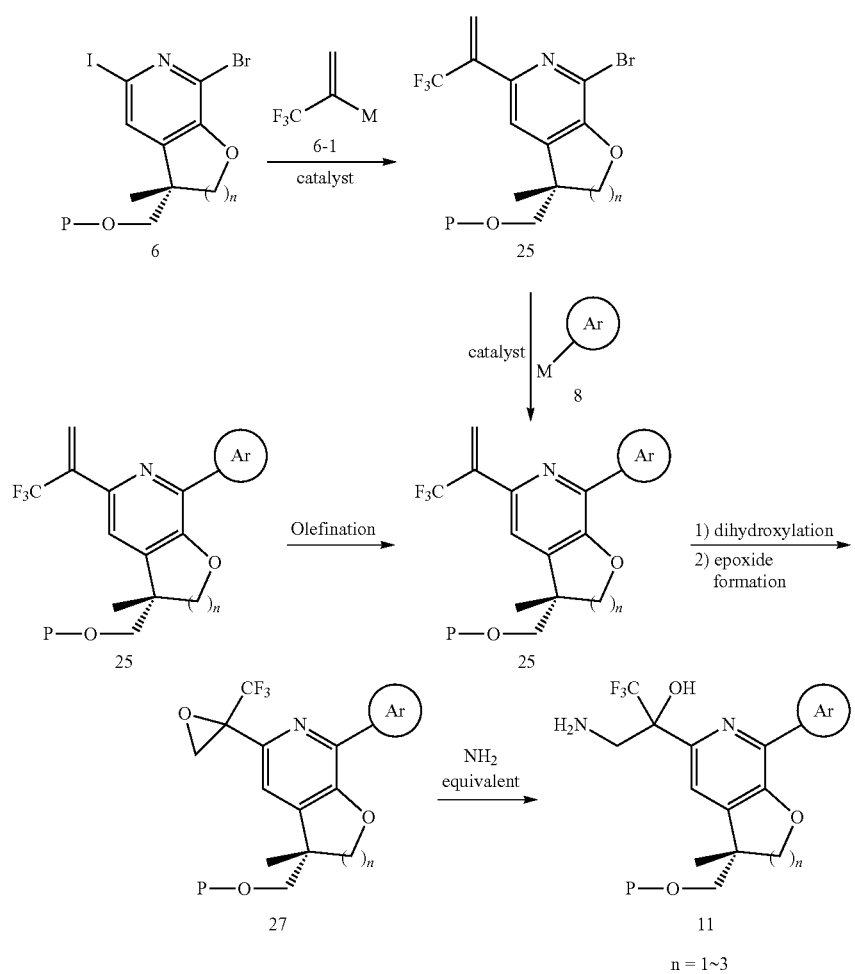

Scheme 6 illustrates another method to prepare a compound of formula 23, wherein $Ar_1$ is A; Ar is E; R' is —$C_1$-$C_6$ alkyl, —$C_3$-$C_6$ cycloalkyl, aryl, or heteroaryl; n is 1, 2 or 3; and A and E are as previously defined. Amine 11 is protected with a protecting group such as but not limited to, Boc and Cbz. After deprotection of hydroxy protecting group, subsequent oxidations provide acid 30. Compound 30 is coupled with various amines to provide amide 31. Deprotection of amine protecting group followed by subsequent amide formation affords compounds of formula 23.

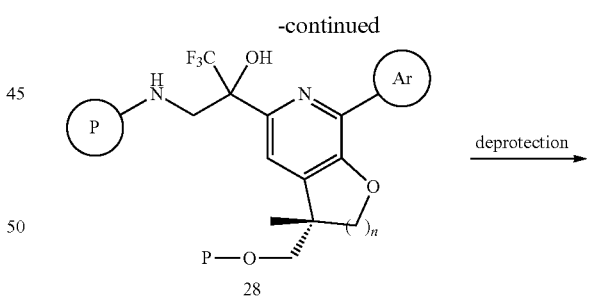

Scheme 6

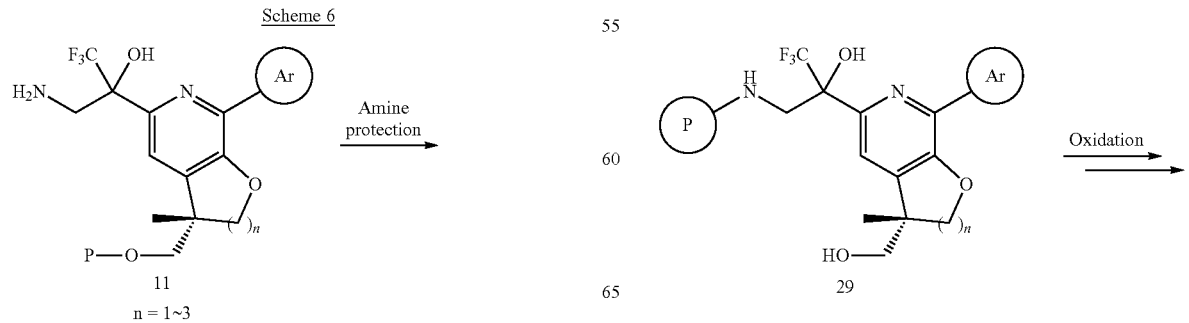

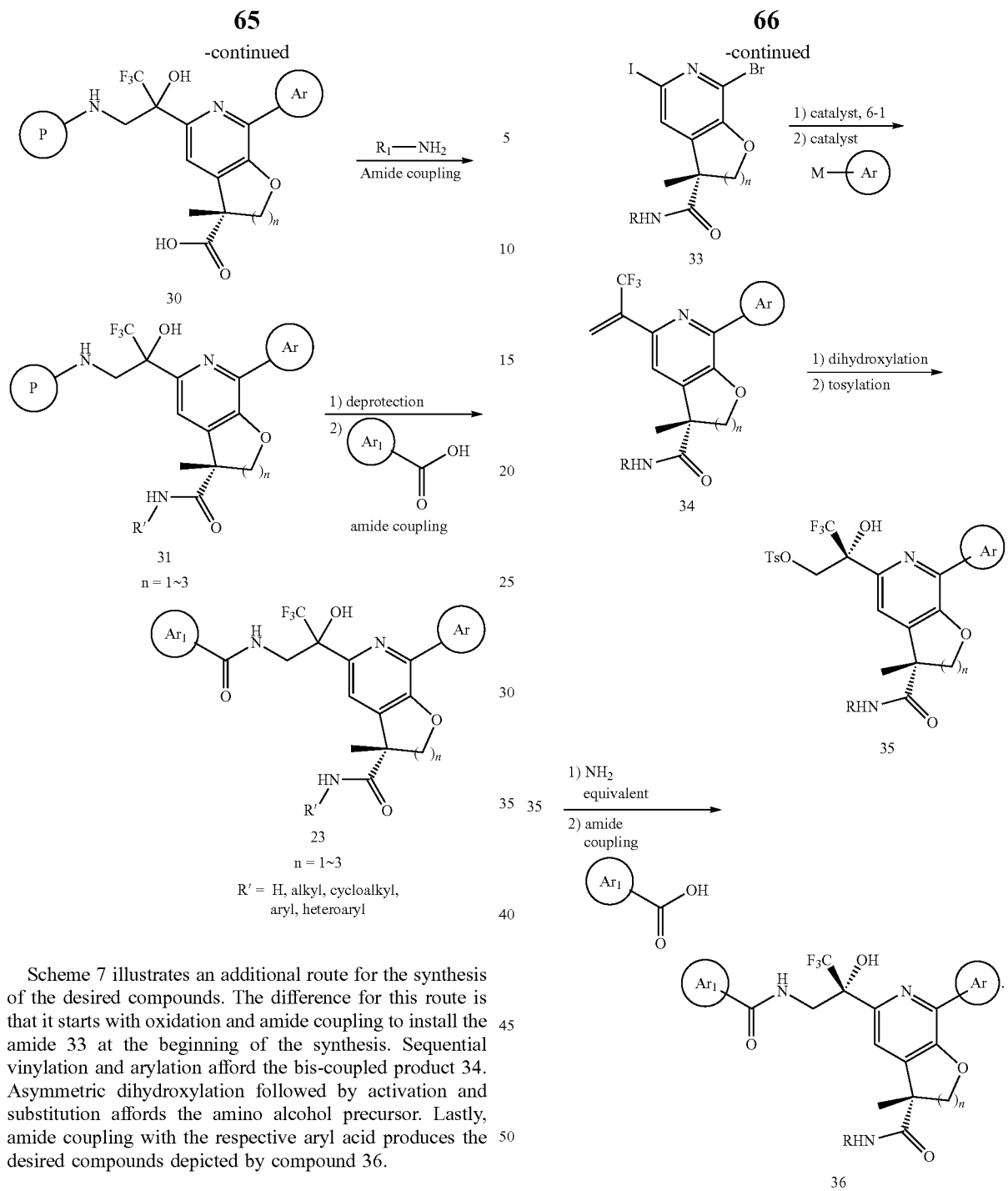

Scheme 7 illustrates an additional route for the synthesis of the desired compounds. The difference for this route is that it starts with oxidation and amide coupling to install the amide 33 at the beginning of the synthesis. Sequential vinylation and arylation afford the bis-coupled product 34. Asymmetric dihydroxylation followed by activation and substitution affords the amino alcohol precursor. Lastly, amide coupling with the respective aryl acid produces the desired compounds depicted by compound 36.

Scheme 7

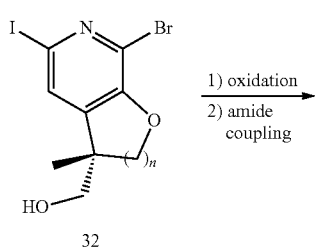

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art, and such changes and modifications including, without limitation, those relating to the chemical structures, substituents, derivatives, formulations and/or methods of the invention may be made without departing from the spirit of the invention and the scope of the appended claims.

Certain synthetic procedures useful in the preparation of compounds of the invention are disclosed in US 2022/0356189, the contents of which are incorporated by reference herein in their entirety.

Intermediate 1

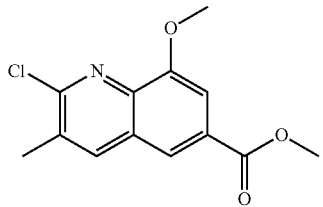 [SMILES: COC(=O)c1cc(OC)c2nc(Cl)c(C)cc2c1]

Intermediate 1 Steps a and b

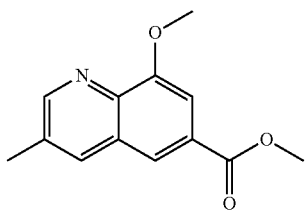

A solution of methyl 4-amino-3-methoxybenzoate (10 g, 55.19 mmol) in HCl (80 mL) was treated with methacrolein (9.67 g, 137.97 mmol) for 5 hours at 100° C. The reaction was monitored by LCMS. The resulting mixture was concentrated under reduced pressure. The crude product was used in the next step directly without further purification. ESI-MS m/z: 217.95 [M+H]$^+$.

A solution of the compound from step a (10 g, 46.03 mmol) in MeOH (100 mL) was treated with SOCl$_2$ (10 mL, 137.86 mmol) at 0° C. The final reaction mixture was reacted for 40 min at 80° C. The reaction was monitored by LCMS. The resulting mixture was concentrated under reduced pressure. The reaction was adjusted to pH=8 with NaHCO$_3$ at room temperature. The resulting mixture was extracted with EA. The combined organic layers were washed with brine, dried over anhydrous Na$_2$SO$_4$. After filtration, the filtrate was concentrated under reduced pressure. The residue was purified by silica gel column chromatography, eluted with PE/EA (1:1) to afford the desired product (4.386 g, 41%) as a brown solid. ESI-MS m/z: 232.00 [M+H]$^+$.

Intermediate 1 Steps c and d

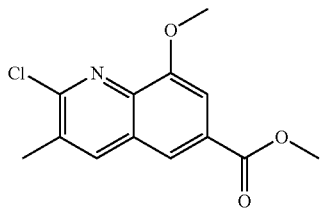 [SMILES: COC(=O)c1cc(OC)c2nc(Cl)c(C)cc2c1]

A mixture of methyl the compound from step b (3.9 g, 16.86 mmol) and m-CPBA (8.73 g, 50.59 mmol) in DCM (20 mL) was stirred for overnight at room temperature. The reaction was quenched with sat. sodium hyposulfite (aq.) at room temperature. The resulting mixture was extracted with CH$_2$Cl$_2$. The combined organic layers were concentrated under reduced pressure. The residue was purified by silica gel column chromatography, eluted with CH$_2$Cl$_2$/MeOH (15:1) to afford the desired product (2.6 g, 62%) as a yellow solid. ESI-MS m/z: 248.05 [M+H]$^+$. A solution of the compound from step c (2.6 g, 10.51 mmol) and POCl$_3$ (20.96 g, 136.70 mmol) was stirred for 1 hour at 95° C. The reaction was monitored by LCMS. The resulting mixture was concentrated under reduced pressure, quenched with Water/Ice. The aqueous layer was extracted with EA. The combined organic layers were concentrated under reduced pressure. The residue was purified by silica gel column chromatography, eluted with PE/EA (5:1) to afford the desired product (1.5 g, 53%) as a yellow solid. ESI-MS m/z: 266.00 [M+H]$^+$.

Intermediate 2

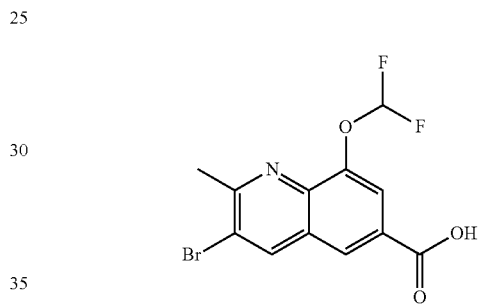

Intermediate 2 Steps a and b

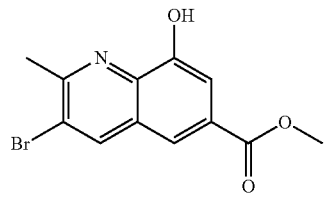

A solution of (2Z)-2-bromobut-2-enal (5 g) and methyl 4-amino-3-hydroxybenzoate (10 g) in HCl (20 mL) and AcOH (30 mL) was stirred for 1 hr at 100° C. under N$_2$ atmosphere. The resulting solution was concentrated to afford desired product (crude) as a brown solid. ESI-MS m/z: 282.00 [M+H]$^+$.

A solution of the compound from step a (10 g, 35.45 mmol) and H$_2$SO$_4$ (10 mL) in MeOH (30 mL) was stirred for 2 hr at 80° C. The mixture/residue was neutralized to pH 7-8 with NaHCO$_3$. The resulting mixture was extracted with EA (×3). The combined organic layers were washed with water, dried over anhydrous Na$_2$SO$_4$. After filtration, the filtrate was concentrated under reduced pressure. The residue was purified by silica gel column chromatography, eluted with PE/EA to afford the desired product (1 g, 9.5%) as a yellow solid. ESI-MS m/z: 296.00 [M+H]$^+$.

Intermediate 2 Steps c and d

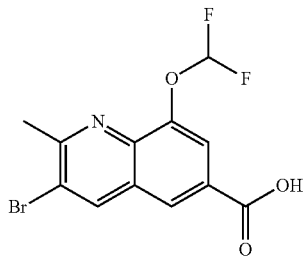 [SMILES: Cc1nc2c(OC(F)F)cc(C(=O)O)cc2cc1Br]

A solution of the compound from step b (1 g, 3.38 mmol), sodium 2-chloro-2,2-difluoroacetate (1 g, 6.56 mmol) and Cs$_2$CO$_3$ (2.20 g, 6.75 mmol) in DMF (10 mL) was stirred for 2 hr at 80° C. The residue was purified by silica gel column chromatography, eluted with PE/EA to afford the desired product (800 mg, 68%) as a yellow solid. ESI-MS m/z: 346.00 [M+H]$^+$.

A solution/mixture of the compound from step c (800 mg, 2.31 mmol) and LiOH (553 mg, 23.11 mmol) in MeOH (10 mL) and H$_2$O (10 mL) was stirred for 6 hr at room temperature under N$_2$ atmosphere. The crude product was recrystallized from MeOH/H$_2$O to afford the desired product (500 mg, 65%) as a yellow solid. ESI-MS m/z: 332.00 [M+H]$^+$.

Intermediate 3

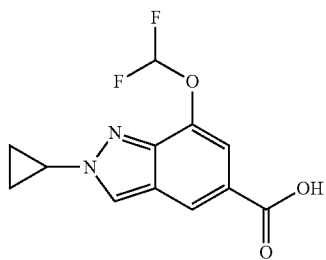 [SMILES: O=C(O)c1cc(OC(F)F)c2nn(C3CC3)cc2c1]

Intermediate 3 Step a

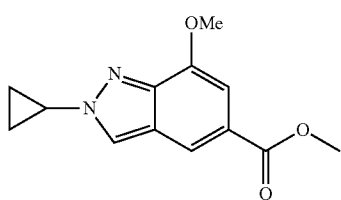 [SMILES: COC(=O)c1cc(OC)c2nn(C3CC3)cc2c1]

A 100 mL rbf was charged with 2-cyclopropyl-7-methoxy-2H-indazole-5-carboxylic acid (500 mg, 2.153 mmol), toluene (4.98 ml) and MeOH (2.99 ml) then cooled to 0° C. in an ice bath. TMS-diazomethane (2.8 mL, 5.60 mmol) dropwise by hand over 10 min. The mixture allowed to stir for 1 h then the diazo reagent was quenched by the additon of AcOH, until the yellow color of the diazo reagent had faded. The mixture was then concentrated and carried foraward to the next step directly ESI-MS m/z: 247.213 [M+H]$^+$.

Intermediate 3 Step b

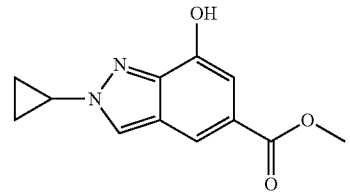 [SMILES: COC(=O)c1cc(O)c2nn(C3CC3)cc2c1]

A 100 mL rbf with stirbar was charged with methyl 2-cyclopropyl-7-hydroxy-2H-indazole-5-carboxylate (529 mg, 2.15 mmol), tetrabutylammonium iodide (1.032 g, 2.80 mmol) and CH$_2$Cl$_2$ (21.5 ml). The mixture was cooled to −78° C. and trichloroborane (5.38 ml, 5.38 mmol) was added dropwise over 10 min. The mixture was stirred at −78° C. for 1 h then allowed to warm to 0° C. in an ice bath with stirring for 1 h. The mixture was then diluted with water (50 mL) and ethyl acetate (50 mL) the layers were separated and the aqeuous layer was washed with EtOAc (4×50 mL) The combined organics were washed with brine, dried over Na$_2$SO$_4$ filtered and concentrated to afford a red oil which was purified by silica gel chromatography to afford the desired product as white solid (489 mg, 98% yield). ESI-MS m/z: 233.201 [M+H]$^+$.

Intermediate 3 Step c

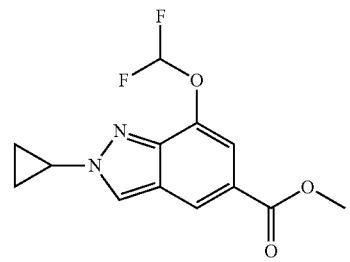 [SMILES: COC(=O)c1cc(OC(F)F)c2nn(C3CC3)cc2c1]

A 100 mL round bottom flask was charged with 2-cyclopropyl-7-hydroxy-2H-indazole-5-carboxylic acid (0.499 g, 2.15 mmol), cesium carbonate (1.401 g, 4.30 mmol), DMF (21.50 ml) then sodium chlorodifluoroacetate (0.656 g, 4.30 mmol). The mixture was heated to 105° C. for 6 h, then cooled to room temperature and purified by silica gel chromatography (0 to 30% EtOAc in cyclohexane) to afford the desired compound as a white solid (176.4 mg, 29% yield). ESI-MS m/z: 283.160 [M+H]$^+$.

Intermediate 3 Step d

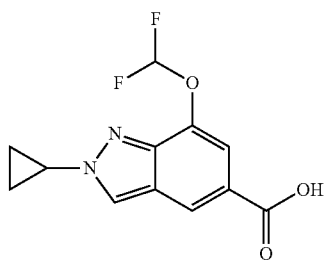 [SMILES: O=C(O)c1cc(OC(F)F)c2nn(C3CC3)cc2c1]

A 20 mL vial was charged with methyl 2-cyclopropyl-7-(difluoromethoxy)-2H-indazole-5-carboxylate (174 mg, 0.616 mmol) which was dissolved in MeOH (2.055 ml), THF (2.055 ml) and water (2.055 ml). Lithium hydroxide (78 mg, 1.849 mmol) was freshly crushed and added. The reaction mixture was allowed to stir for 2 h. The reaction mixture was then carefully acidified by the addition of 1 M HCl. The mixture was diluted with water and EtOAc. The aqueous layer was washed with EtOAc (3×5 mL) the combined organic layers were washed with brine, then concentrated to afford the desired product as a white solid (147.6 mg, 89% yield). ESI-MS m/z: 269.145 [M+H]$^+$.

Intermediate 4

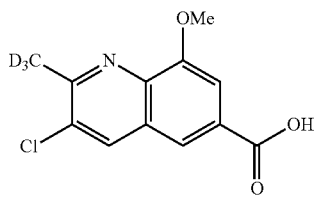 [SMILES: [2H]C([2H])([2H])c1nc2c(OC)cc(C(=O)O)cc2cc1Cl]

Intermediate 4 Step a

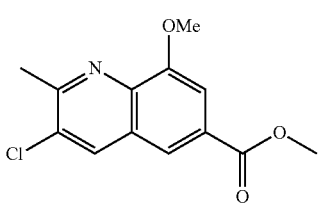

A 20 mL vial was charged with 3-chloro-8-methoxy-2-methylquinoline-6-carboxylic acid (200 mg, 0.795 mmol), toluene (1.84 ml), and MeOH (1.104 ml) then cooled to 0° C. in an ice bath, TMS-diazomethane (1.0 mL, 2.07 mmol) was added dropwise by hand over 10 min. The mixture was allowed to stir for 1 h, then the diazo reagent was quenched by the addition of AcOH until the yellow color of the diazo reagent disappeared, the mixture was concentrated to afford the desired product (48 mg, 95%) as a yellow solid. ESI-MS m/z: 266.091 [M+H]$^+$.

Intermediate 4 Step b

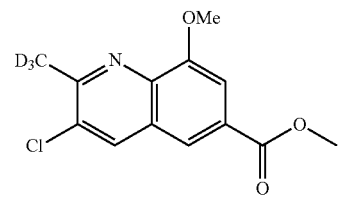 [SMILES: [2H]C([2H])([2H])c1nc2c(OC)cc(C(=O)OC)cc2cc1Cl]

An 8 mL vial was charged with methyl 3-chloro-8-methoxy-2-methylquinoline-6-carboxylate (0.211 g, 0.795 mmol) then D2O (1.125 was added and the mixture was heated to 100° C. for 18 h. The mixture was then cooled to room temperature and diluted with EtOAc. The phases were separated and the organic layer was washed 3×1 mL with NaHCO$_3$. The organic layer was dired over Na$_2$SO$_4$, filtered, concentrated and purified by combiflash to afford the desired product as a yellow solid (105 mg, 34% yield) ESI-MS m/z: 269.156/271.135 [M+H]$^+$.

Intermediate 4 Step c

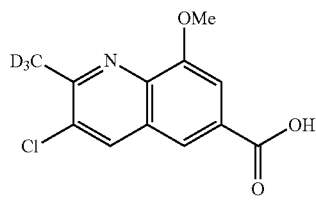 [SMILES: [2H]C([2H])([2H])c1nc2c(OC)cc(C(=O)O)cc2cc1Cl]

A 20 mL via was charged with methyl 3-chloro-8-methoxy-2-(methyl-d3)quinoline-6-carboxylate (100 mg, 0.372 mmol) which was dissolved in water (1.240 ml) THF (1.240 ml) methanol (1.240 ml) then lithium hydroxide (26.7 mg, 1.116 mmol) was freshly crushed and added. The mixture was allowed to stir for 1 h then was diluted with 10% MeOH in DCM then carefully acidified by addition of 1 M HCl, the phases were separated and the aqueous layer was washed with 10% MeOH in DCM. The combined organic phases were concentrated to afford the desired product as a white solid (87 mg, 92% yield) ESI-MS m/z: 255.163/257.175 [M+H]$^+$.

Intermediate 5

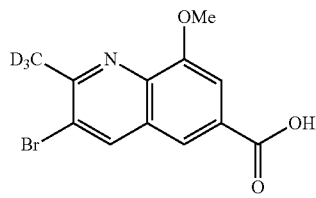 [SMILES: [2H]C([2H])([2H])c1nc2c(OC)cc(C(=O)O)cc2cc1Br]

An 8 mL vial was charged with 3-bromo-8-methoxy-2-methylquinoline-6-carboxylic acid which was suspended in 0.7 mL of D2O, then heated to 100° C. for 18 h. The crude material was lyophilized and used without further purification (48 mg, 95%) as a yellow solid. ESI-MS m/z: 299.033/300.961 [M+H]$^+$.

Intermediate 6

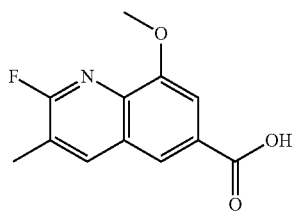 [SMILES: COc1cc(C(=O)O)cc2cc(C)c(F)nc12]

Intermediate 6 Step a

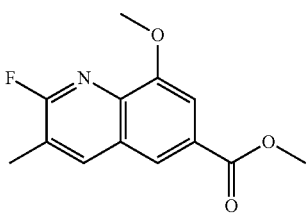 [SMILES: COC(=O)c1cc(OC)c2nc(F)c(C)cc2c1]

In an oven dried vial with a stirbar, methyl 2-chloro-8-methoxy-3-methylquinoline-6-carboxylate (250 mg, 0.941 mmol) was dissolved in DMF (1.9 mL), and anhydrous Me$_4$NF (175 mg, 2.0 equiv.) was added. The vial was sealed and heated to 80° C. overnight. The reaction mixture was then cooled to room temperature, diluted with DCM, and washed twice with water, and once with brine. The organic phase was then dried over sodium sulfate, filtered, and concentrated. The crude residue was purified by automated column chromatography (silica gel) to afford the fluoride as a white solid, which was contaminated with some chloride starting material (48 mg, 20%). ESI-MS m/z: 250.134 [M+H]$^+$.

Intermediate 6 Step b

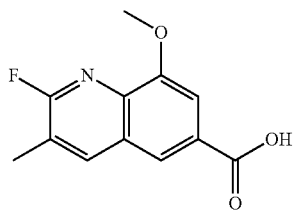 [SMILES: COc1cc(C(=O)O)cc2cc(C)c(F)nc12]

In a one dram vial, methyl-2-fluoro-8-methoxy-3-methylquinoline-6-carboxylate (48 mg, 0.18 mmol 1.0 equiv.) was dissolved in THF (0.3 mL), and water (0.15 mL), and the mixture cooled to 0° C. LiOH (8.7 mg, 0.36 mmol, 2.0 equiv.) was added, and the mixture stirred for 15 minutes before the cooling bath was removed. After 2 hours at room temperature, the mixture was acidified to pH ~5 with AcOH, and the mixture concentrated directly. The crude residue was purified by prep-HPLC (ACN/H$_2$O, 20-90%, 25 min) to afford the product carboxylic acid (13 mg, 31%). ESI-MS m/z: 236.16 [M+H]$^+$.

Intermediate 7

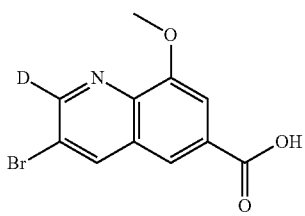 [SMILES: [2H]c1nc2c(OC)cc(C(=O)O)cc2cc1Br]

Intermediate 7 Step a

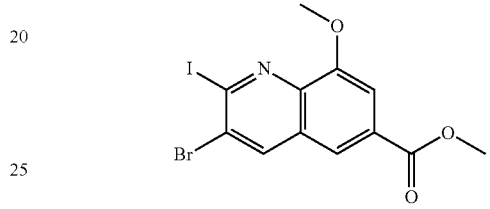

The above compound was prepared from methyl-3-bromo-2-chloro-8-methoxyquinoline-6-carboxylate according to the following procedure: To a suspension of methyl-3-bromo-2-chloro-8-methoxyquinoline-6-carboxylate (443 mg, 1.34 mmol, 1.0 equiv) in DCM (5 mL) was added HCl (4M in 1,4-dioxane, 0.34 mL, 1.34 mmol, 1.0 equiv) and the mixture stirred at room temperature for 5 minutes. The solvent was then removed in vacuo and the residue suspended in MeCN (6.7 mL). NaI (1.0 g, 6.7 mmol, 5.0 equiv.) was then added, the vial sealed, and heated to 80° C. for 3 hours. Cooled the mixture to room temperature, and removed the solvent in vacuo. Redissolved the residue in DCM, abd the organic solution was washed sequentially with 10% aqueous K$_2$CO$_3$ solution and water, dried over sodium sulfate, filtered, and concentrated. The crude residue was purified by automated column chromatography (silica gel) to afford the iodide as a white solid (434 mg, 77%). ESI-MS m/z: 423.93 [M+H]$^+$.

Intermediate 7 Step b

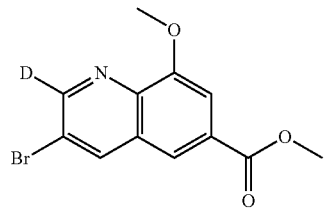 [SMILES: [2H]c1nc2c(OC)cc(C(=O)OC)cc2cc1Br]

In an oven dried vial with a stirbar methyl 3-bromo-2-iodo-8-methoxyquinoline-6-carboxylate (75 mg, 0.18 mmol, 1.0 equiv.) was suspended in THF (0.5 mL) and Et$_2$O (0.5 mL) and the mixture was cooled to 0° C. Isopropylmagnesium chloride (0.11 mL, 0.22 mmol, 1.2 equiv) was added, and the reaction mixture was stirred for 1 hour at that temperature, before being quenched by dropwise addition of CD₃OD (0.6 mL, 14.8 mmol, 15 equiv.). The mixture was stirred for an additional 15 minutes at room temperature before being poured into saturated aqueous ammonium chloride. The quenched reaction mixture was diluted with water and DCM, the layers, were separated, and the aqueous layer extracted 3 times with DCM. Combined organic extracts were dried over sodium sulfate, filtered, and concentrated. The crude material was purified by automated column chromatography (silica gel) to afford the deuterated product methyl-3-bromo-8-methoxyquinoline-6-carboxylate-2-D as a white solid (9.0 mg, 17%). ESI-MS m/z: 297.06 [M+H]⁺.

Intermediate 7 Step c

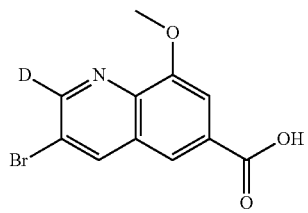

In a one dram vial with a stirbar, methyl-3-bromo-8-methoxyquinoline-6-carboxylate-2-D as a white solid (9.0 mg, 1.0 equiv, 0.032 mmol) was dissolved in THF (0.1 mL), MeOH (0.1 mL) and water (0.1 mL). LiOH (7 mg, 0.30 mmol, 10 equiv.) was added and the reaction mixture stirred at room temperature overnight. The mixture was then acidified to pH ~2 with 2M HCl, and concentrated directly to obtain the carboxylic acid, which was used without further purification (8.0 mg, 93%). ESI-MS m/z: 283.05 [M+H]⁺.

Intermediate 8

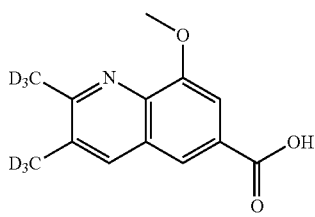 [SMILES: [2H]C([2H])([2H])c1cc2cc(C(=O)O)cc(OC)c2nc1C([2H])([2H])[2H]]

The above compound was prepared from 8-methoxy-2-methyl-3-(methyl-d3)quinoline-6-carboxylic acid with the similar method to example X step X, to afford the hexadeutero compound as an orange solid (27 mg, 96%). ESI-MS m/z: 238.16 [M+H]⁺.

Intermediate 9

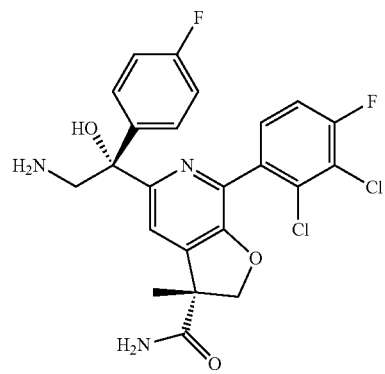 [SMILES: C[C@]1(C(N)=O)COc2c1cc([C@@](O)(CN)c1ccc(F)cc1)nc2-c1ccc(F)c(Cl)c1Cl]

Intermediate 9 Step a

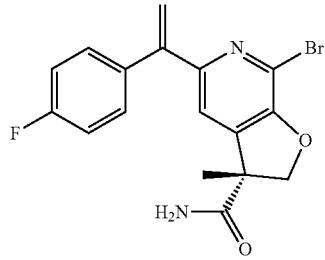 [SMILES: C=C(c1ccc(F)cc1)c1cc2c(c(Br)n1)OC[C@]2(C)C(N)=O]

A mixture of (R)-7-bromo-5-iodo-3-methyl-2,3-dihydrofuro[2,3-c]pyridine-3-carboxamide (2 g, 5.22 mmol), 2-(1-(4-fluorophenyl)vinyl)-4,4,5,5-tetramethyl-1,3,2-dioxaborolane (1.57 g, 6.32 mmol), Pd(dppf)Cl₂ (0.382 g, 0.52 mmol), K₂CO₃ (2.17 g, 15.67 mmol) in dioxane (21 mL) and H₂O (5 mL) was stirred for 2 hours at 90° C. under nitrogen atmosphere. The reaction was monitored by LCMS. The resulting mixture was filtered, the filter cake was washed with EA. The filtrate was concentrated under reduced pressure. The residue was purified by silica gel column chromatography (eluted 50% ethyl acetate in hexanes) to afford the desired product (1.97 g, 75 wt %, 75%) as a red oil. ESI-MS m/z: 377.06 [M+H]⁺.

Intermediate 9 Step b

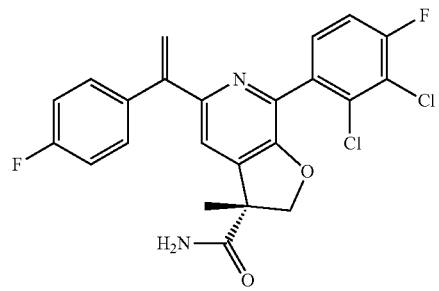 [SMILES: C=C(c1ccc(F)cc1)c1cc2c(c(-c3ccc(F)c(Cl)c3Cl)n1)OC[C@]2(C)C(N)=O]

A mixture of the compound from step a (1 g, 2.25 mmol), 2-(2,3-dichloro-4-fluorophenyl)-4,4,5,5-tetramethyl-1,3,2- dioxaborolane (0.82 g, 2.82 mmol), Pd(dppf)Cl$_2$(0.165 g, 0.225 mmol), and K$_2$CO$_3$ (0.70 g, 5.07 mmol) in dioxane (9 mL) and H$_2$O (2.25 mL) was stirred for 2 h at 90° C. under nitrogen atmosphere. The reaction was cooled to r.t. and the mixture was diluted with EtOAc and sat. ammonium chloride. The aqueous was extracted with EtOAc, combined, dried over sodium sulfate, filtered and concentrated. The crude material was purified by automated column chromatography (silica, 0-100% ethyl acetate in cyclohexane) to afford the desired product (1.50 g, 80% wt, 87%) as a red oil. ESI-MS m/z: 461.12 [M+H]$^+$.

Intermediate 9 Step c

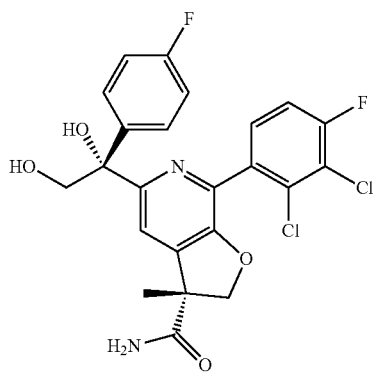 [SMILES: C[C@]1(C(N)=O)COc2c1cc([C@@](O)(CO)c1ccc(F)cc1)nc2-c1ccc(F)c(Cl)c1Cl]

A solution of the compound from step b (1.5 g, 3.38 mmol) in t-BuOH (17 mL) and H$_2$O (17 mL) was cooled to 0° C. Methanesulfonamide (0.64 g, 6.77 mmol) and AD-mix-β (13.18 g, 16.92 mmol) were added and the reaction was stirred overnight at room temperature and monitored by LCMS. The reaction was cooled to r.t. and the mixture was diluted with EtOAc and quenched with sodium sulfite. The aqueous was extracted with EtOAc, combined, dried over sodium sulfate, filtered and concentrated. The crude material was purified by automated column chromatography (silica, 0-100% ethyl acetate in cyclohexane) to afford the desired product (1.0 g, 60%) as a yellow solid. ESI-MS m/z: 495.09 [M+H]$^+$.

Intermediate 9 Step d

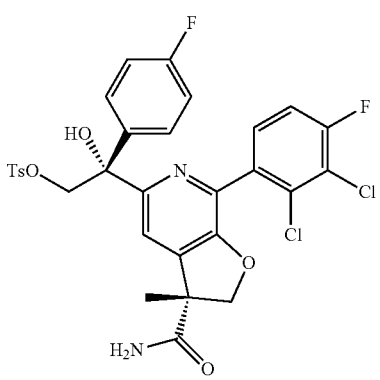 [SMILES: Cc1ccc(S(=O)(=O)OC[C@@](O)(c2ccc(F)cc2)c2cc3c(c(-c4ccc(F)c(Cl)c4Cl)n2)OC[C@]3(C)C(N)=O)cc1]

A solution of the compound from step c (1.0 g, 2.01 mmol) in DCM (11 mL) was cooled to 0 C°. TsCl(0.654 g, 3.43 mmol), TEA (0.84 mL, 6.06 mmol) and DMAP (0.24 g, 2.01 mmol) were added, and the reaction stirred for 90 min at room temperature. The crude reaction was concentrated, and the material was purified by automated column chromatography (silica, 0-100% ethyl acetate in cyclohexane) to afford the desired product (1.6 g, 70% wt, 85%) as a yellow solid. ESI-MS m/z: 649.10 [M+H]$^+$.

Intermediate 9 Step e

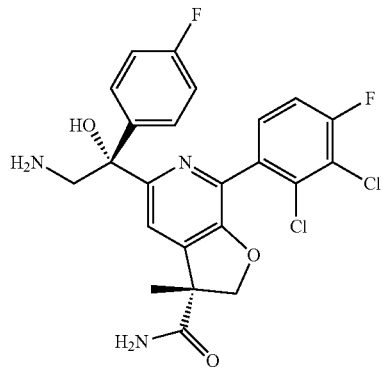 [SMILES: C[C@]1(C(N)=O)COc2c1cc([C@@](O)(CN)c1ccc(F)cc1)nc2-c1ccc(F)c(Cl)c1Cl]

Into a 250 mL round-bottom flask containing step d (1.6 g, 3.04 mmol) were added NH$_3$ (55 mL, 156 eq, 7N in MeOH) at room temperature. The resulting mixture was stirred for 20 hr at room temperature and monitored by LCMS. The solvent was removed, and the crude mixture was dissolved in EtOAc. The organics were washed 3× with sat. sodium bicarbonate, and the organics were concentrated. The crude material was triturated with DCM to afford the desired product (425 mg, 35%) as an off-white solid. ESI-MS m/z: 494.11 [M+H]$^+$.

Intermediate 10

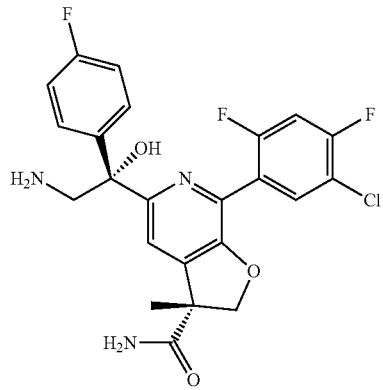 [SMILES: C[C@]1(C(N)=O)COc2c1cc([C@@](O)(CN)c1ccc(F)cc1)nc2-c1cc(Cl)c(F)cc1F]

The above compound was prepared in an analogous fashion to Intermediate 9. ESI-MS m/z: 478.17 [M+H]$^+$.

Intermediate 11

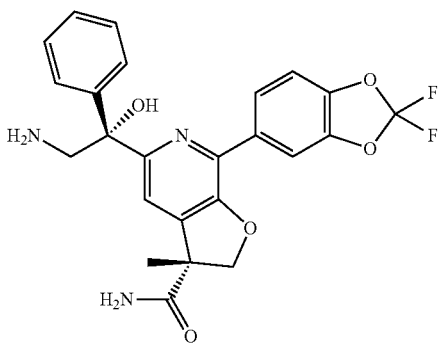 [SMILES: C[C@]1(C(N)=O)COc2c1cc([C@@](O)(CN)c1ccccc1)nc2-c1ccc2c(c1)OC(F)(F)O2]

The above compound was prepared in an analogous fashion to Intermediate 9. ESI-MS m/z: 470.17 [M+H]+.

Intermediate 12

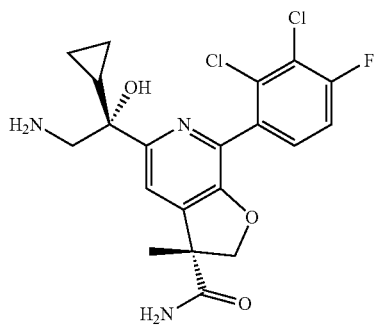 [SMILES: C[C@]1(C(N)=O)COc2c1cc([C@@](O)(CN)C1CC1)nc2-c1ccc(F)c(Cl)c1Cl]

The above compound was prepared with the similar method to Intermediate 9, to afford the amino alcohol. (133 mg, quant. yield). ESI-MS m/z: 440.13 [M+H]+.

Intermediate 13

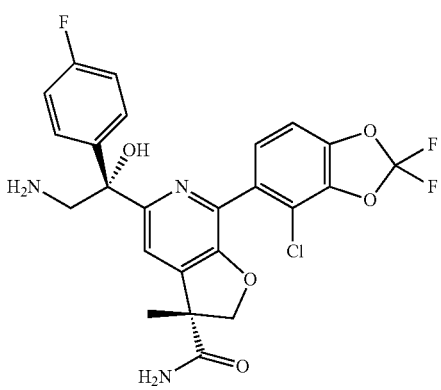 [SMILES: C[C@]1(C(N)=O)COc2c1cc([C@@](O)(CN)c1ccc(F)cc1)nc2-c1ccc2c(c1Cl)OC(F)(F)O2]

The above compound was prepared with the similar method to Intermediate 9, to afford the amino alcohol. (158 mg, quant. yield). ESI-MS m/z: 522.18 [M+H]+.

Intermediate 14

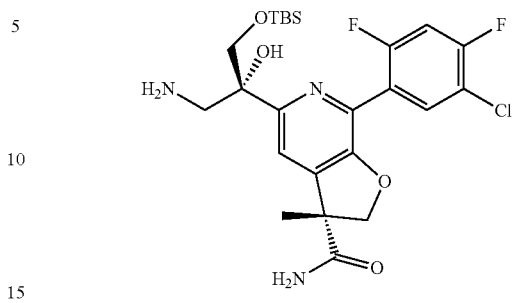

The above compound was prepared with the similar method to Intermediate 9, to afford the amino alcohol. (170 mg, quant. yield). ESI-MS m/z: 528.27 [M+H]+.

Example 1

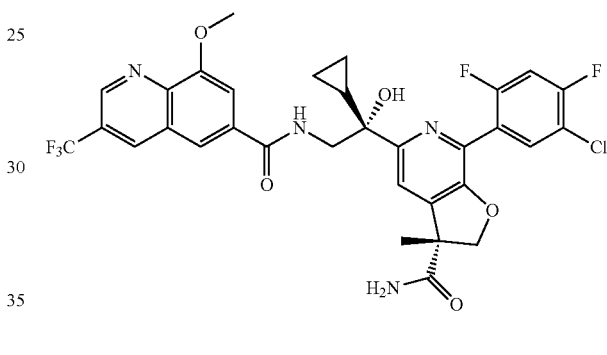

To a 20 mL vial equipped with a stir bar was added (R)-5-((S)-2-amino-1-cyclopropyl-1-hydroxyethyl)-7-(5-chloro-2,4-difluorophenyl)-3-methyl-2,3-dihydrofuro[2,3-c]pyridine-3-carboxamide (15 mg, 0.035 mmol) and 8-methoxy-3-(trifluoromethyl)quinoline-6-carboxylic acid (10.56 mg, 0.039 mmol). The solids were dissolved in DMF (0.20 mL), and DIPEA (18.54 μl, 0.106 mmol) was added. The vial was cooled to 0° C., and PyBOP (22.10 mg, 0.042 mmol) was added. The reaction was stirred for 10 minutes, warmed to room temperature, and monitored by LCMS (1 hr). Upon the completion the reaction was diluted with EtOAc and quenched with sat. ammonium chloride. The aqueous was extracted with EtOAc, collected with a phase separator cartridge and concentrated. The crude material was purified by prep-HPLC (ACN/H$_2$O, 20-90%, 25 min), fractions concentrated with a Biotage V10 evaporator, and the material lyophilized to afford a fluffy, white solid (13 mg, 53%) as the desired product. ESI-MS m/z: 677.20 [M+H]+.

The following Table 1 contains examples that were prepared with the similar method to Example 1. The majority of compounds were purified by prep-HPLC (ACN/H$_2$O, 20-90%, 25 min), and some were purified by automated column chromatography (silica gel). The aryl acid coupling partners were prepared according to Intermediates 1-14, or by analogous procedures with slight modifications and also prepared according to procedures found in U.S. patent application Ser. No. 17/679,746.

TABLE 1

| Example | Structure | MS+ m/z |
|---|---|---|
| 2 | 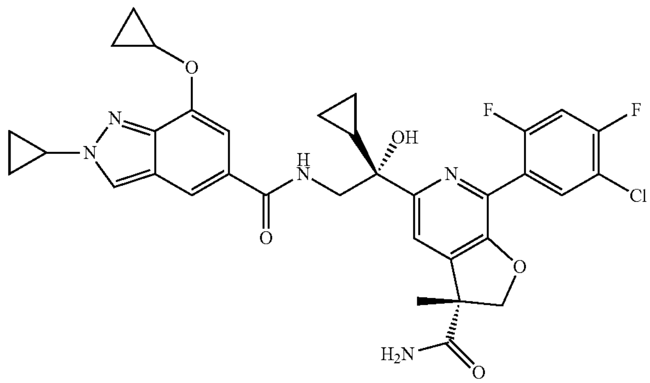 [SMILES: C[C@]1(C(N)=O)COc2c1cc([C@@](O)(CNC(=O)c1cc(OC3CC3)c3nn(C4CC4)cc3c1)C1CC1)nc2-c1cc(Cl)c(F)cc1F] | 664.25 |
| 3 | 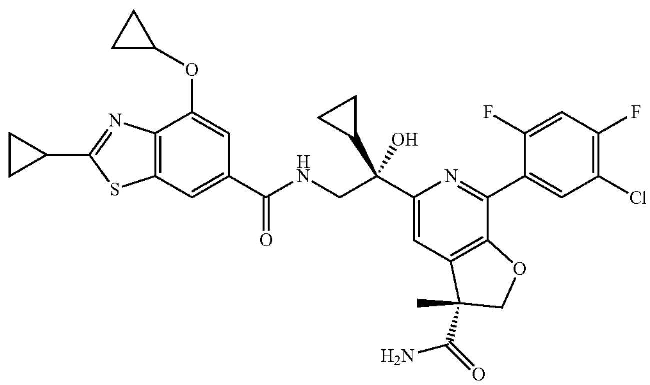 [SMILES: C[C@]1(C(N)=O)COc2c1cc([C@@](O)(CNC(=O)c1cc(OC3CC3)c3nc(C4CC4)sc3c1)C1CC1)nc2-c1cc(Cl)c(F)cc1F] | 681.24 |
| 4 | 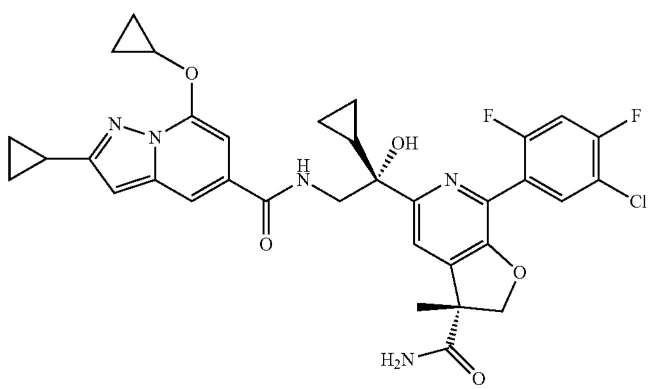 [SMILES: C[C@]1(C(N)=O)COc2c1cc([C@@](O)(CNC(=O)c1cc(OC3CC3)n3nc(C4CC4)cc3c1)C1CC1)nc2-c1cc(Cl)c(F)cc1F] | 664.31 |
| 5 | 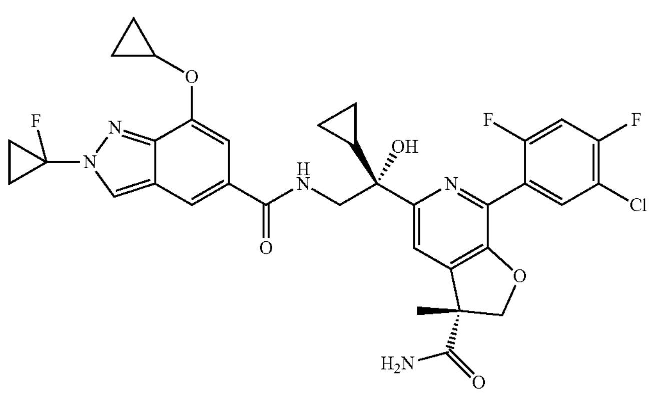 [SMILES: C[C@]1(C(N)=O)COc2c1cc([C@@](O)(CNC(=O)c1cc(OC3CC3)c3nn(C4(F)CC4)cc3c1)C1CC1)nc2-c1cc(Cl)c(F)cc1F] | 682.25 |

TABLE 1-continued

| Example | Structure | MS⁺ m/z |
|---------|-----------|---------|
| 6 | 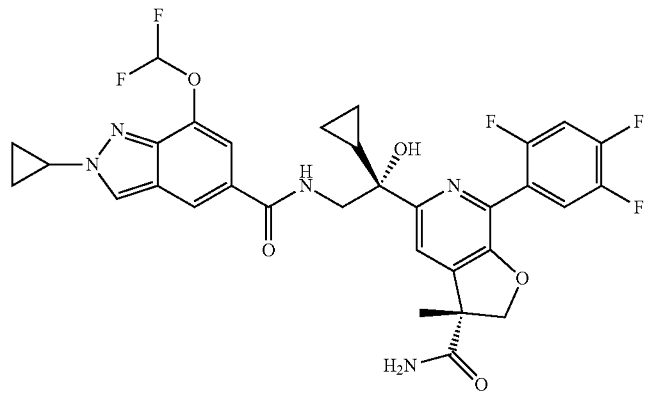 [SMILES: C[C@]1(C(N)=O)COc2c1cc([C@@](O)(CNC(=O)c1cc(OC(F)F)c3nn(C4CC4)cc3c1)C1CC1)nc2-c1cc(F)c(F)cc1F] | 658.23 |
| 7 | 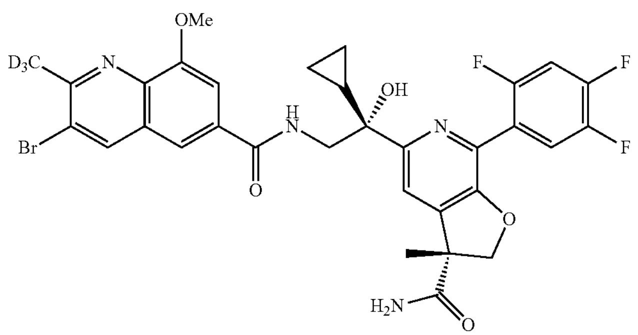 [SMILES: [2H]C([2H])([2H])c1nc2c(OC)cc(C(=O)NC[C@](O)(c3cc4c(c(-c5cc(F)c(F)cc5F)n3)OC[C@]4(C)C(N)=O)C3CC3)cc2cc1Br] | 688.10 |
| 9 | 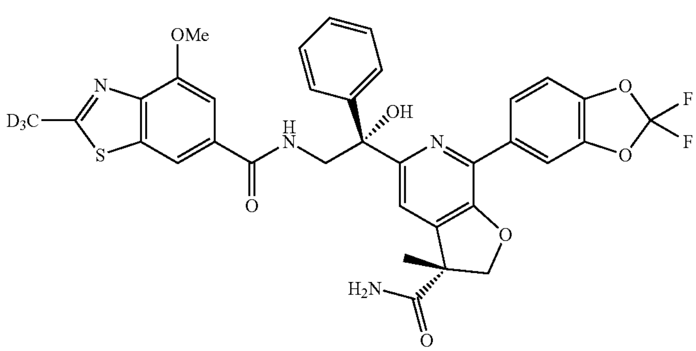 [SMILES: [2H]C([2H])([2H])c1nc2c(OC)cc(C(=O)NC[C@@](O)(c3ccccc3)c3cc4c(c(-c5ccc6c(c5)OC(F)(F)O6)n3)OC[C@]4(C)C(N)=O)cc2s1] | 678.21 |
| 10 | 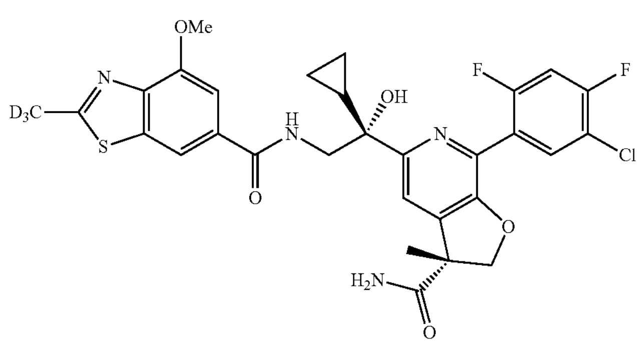 [SMILES: [2H]C([2H])([2H])c1nc2c(OC)cc(C(=O)NC[C@](O)(c3cc4c(c(-c5cc(Cl)c(F)cc5F)n3)OC[C@]4(C)C(N)=O)C3CC3)cc2s1] | 632.09 |

TABLE 1-continued

| Example | Structure | MS+ m/z |
|---|---|---|
| 11 | 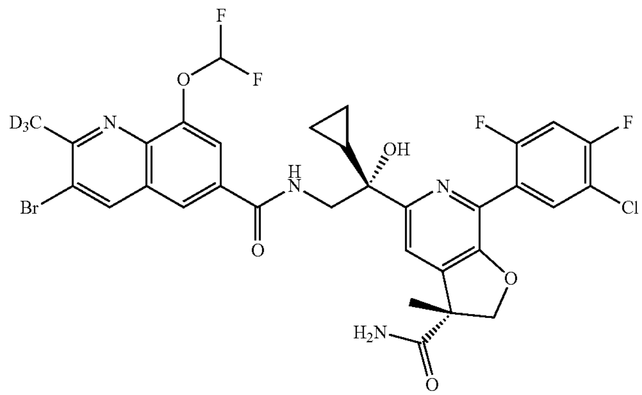 [SMILES: [2H]C([2H])([2H])c1nc2c(OC(F)F)cc(C(=O)NC[C@](O)(c3cc4c(c(-c5cc(Cl)c(F)cc5F)n3)OC[C@]4(C)C(N)=O)C3CC3)cc2cc1Br] | 741.87 |
| 12 | 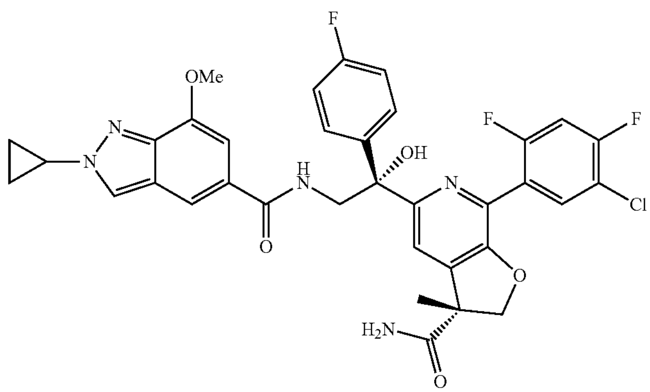 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cn(C3CC3)nc12] | 692.19 |
| 13 | 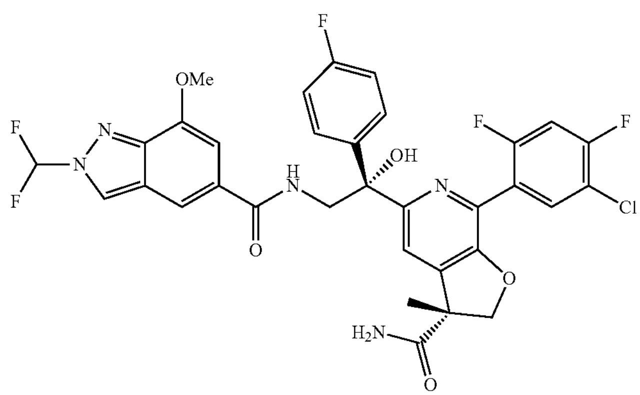 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cn(C(F)F)nc12] | 702.25 |
| 14 | 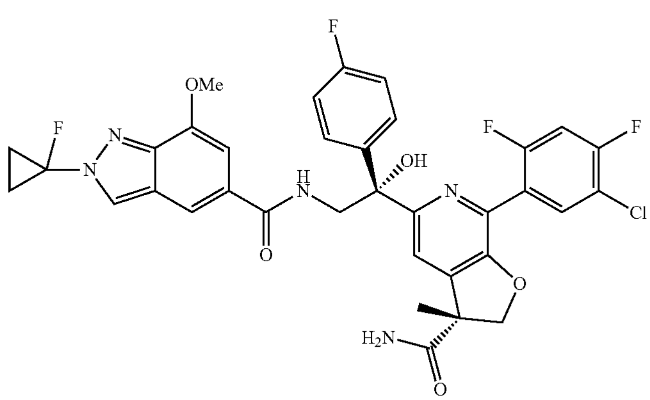 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cn(C3(F)CC3)nc12] | 710.25 |

TABLE 1-continued

| Example | Structure | MS+ m/z |
|---|---|---|
| 15 | 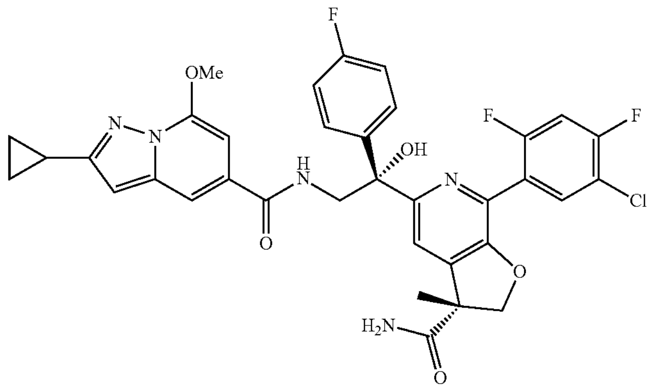 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cc(C3CC3)nn12] | 692.28 |
| 16 | 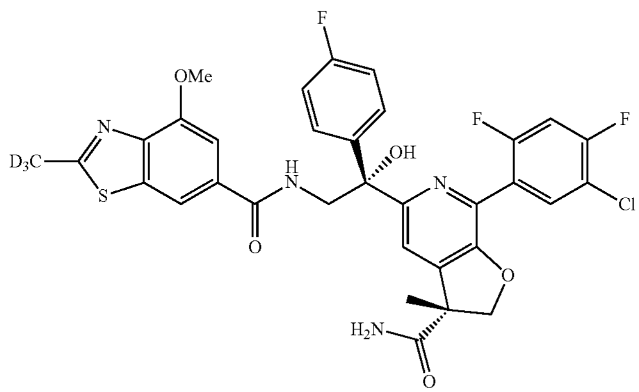 [SMILES: [2H]C([2H])([2H])c1nc2c(OC)cc(C(=O)NC[C@@](O)(c3ccc(F)cc3)c3cc4c(c(-c5cc(Cl)c(F)cc5F)n3)OC[C@]4(C)C(N)=O)cc2s1] | 686.20 |
| 17 | 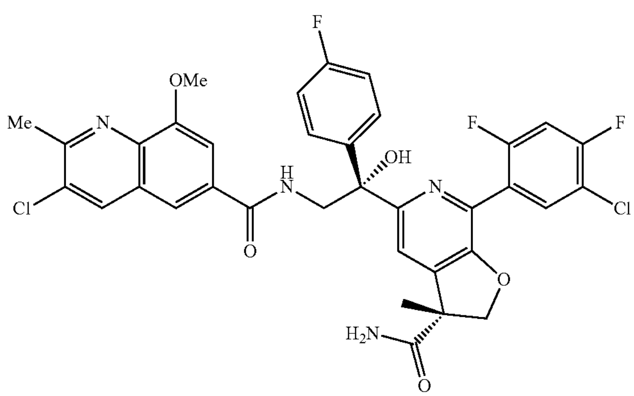 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cc(Cl)c(C)nc12] | 711.18 |
| 18 | 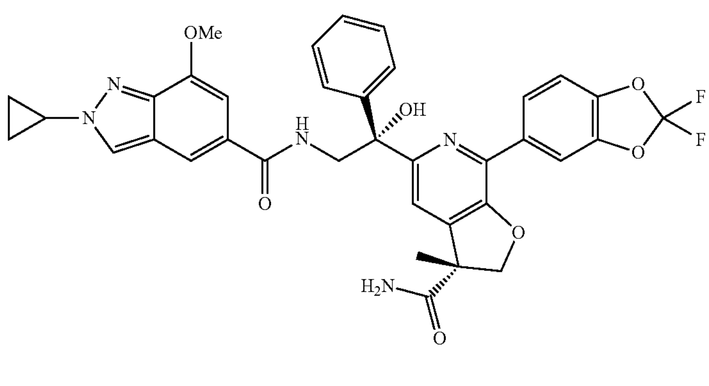 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2cn(C3CC3)nc12] | 684.25 |

TABLE 1-continued

| Example | Structure | MS+ m/z |
|---------|-----------|---------|
| 19 | 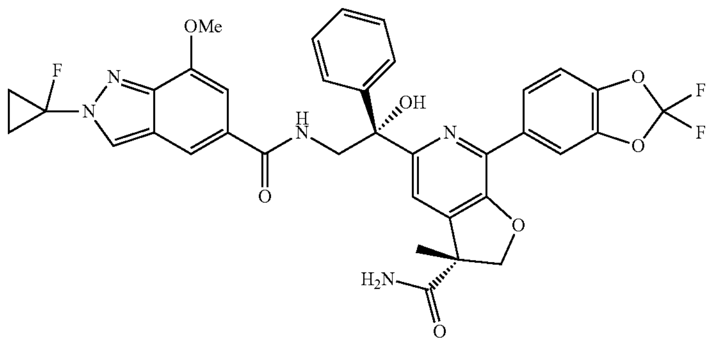 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2cn(C3(F)CC3)nc12] | 702.24 |
| 20 | 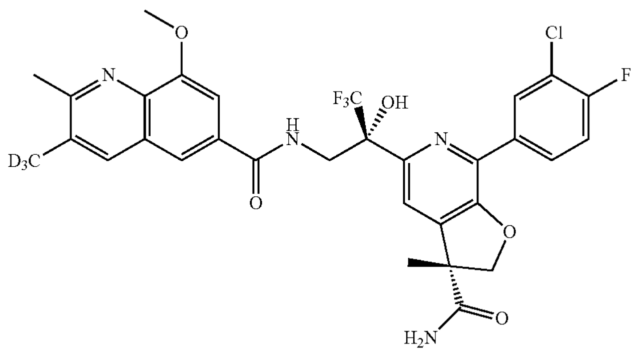 [SMILES: [2H]C([2H])([2H])c1cc2cc(C(=O)NC[C@](O)(c3cc4c(c(-c5ccc(F)c(Cl)c5)n3)OC[C@]4(C)C(N)=O)C(F)(F)F)cc(OC)c2nc1C] | 650.17 |
| 21 | 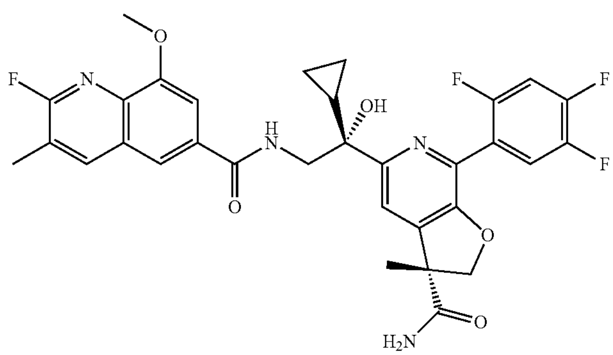 [SMILES: COc1cc(C(=O)NC[C@](O)(c2cc3c(c(-c4cc(F)c(F)cc4F)n2)OC[C@]3(C)C(N)=O)C2CC2)cc2cc(C)c(F)nc12] | 625.32 |
| 22 | 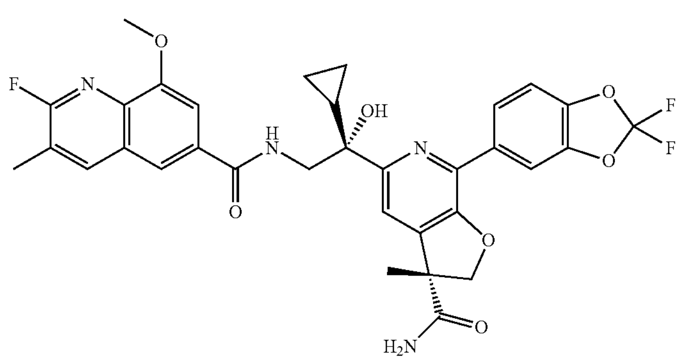 [SMILES: COc1cc(C(=O)NC[C@](O)(c2cc3c(c(-c4ccc5c(c4)OC(F)(F)O5)n2)OC[C@]3(C)C(N)=O)C2CC2)cc2cc(C)c(F)nc12] | 651.38 |

TABLE 1-continued

| Example | Structure | MS+ m/z |
|---------|-----------|---------|
| 23 | 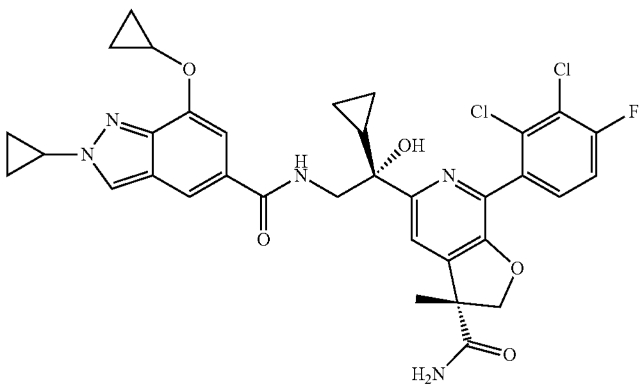 [SMILES: C[C@]1(C(N)=O)COc2c1cc([C@@](O)(CNC(=O)c1cc(OC3CC3)c3nn(C4CC4)cc3c1)C1CC1)nc2-c1ccc(F)c(Cl)c1Cl] | 680.25 |
| 24 | 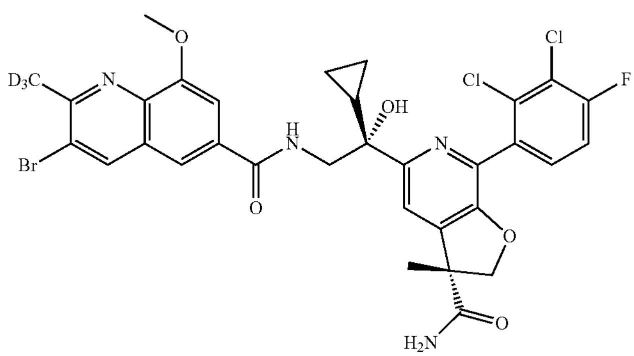 [SMILES: [2H]C([2H])([2H])c1nc2c(OC)cc(C(=O)NC[C@](O)(c3cc4c(c(-c5ccc(F)c(Cl)c5Cl)n3)OC[C@]4(C)C(N)=O)C3CC3)cc2cc1Br] | 721.88 |
| 25 | 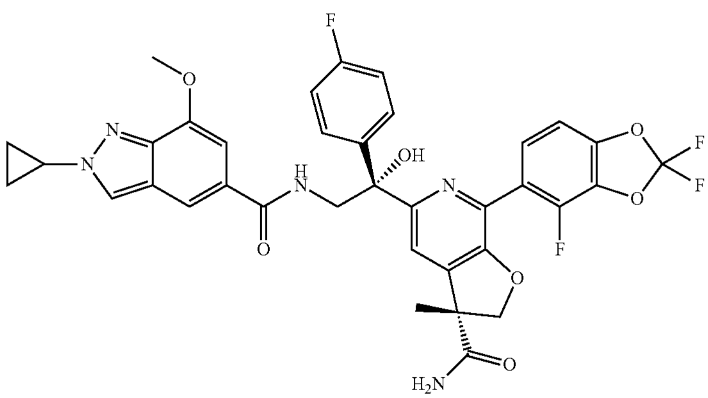 [SMILES: COc1cc(C(=O)NC[C@@](O)(c2ccc(F)cc2)c2cc3c(c(-c4ccc5c(c4F)OC(F)(F)O5)n2)OC[C@]3(C)C(N)=O)cc2cn(C3CC3)nc12] | 736.29 |
| 26 | 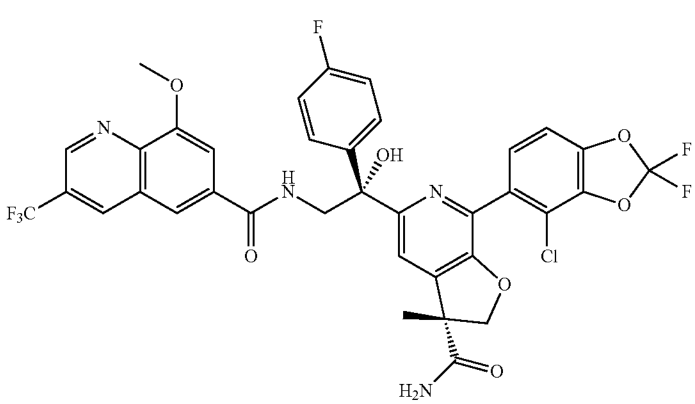 [SMILES: COc1cc(C(=O)NC[C@@](O)(c2ccc(F)cc2)c2cc3c(c(-c4ccc5c(c4Cl)OC(F)(F)O5)n2)OC[C@]3(C)C(N)=O)cc2cc(C(F)(F)F)cnc12] | 775.28 |

TABLE 1-continued
| Example | Structure | MS+ m/z |
|---|---|---|
| 27 | 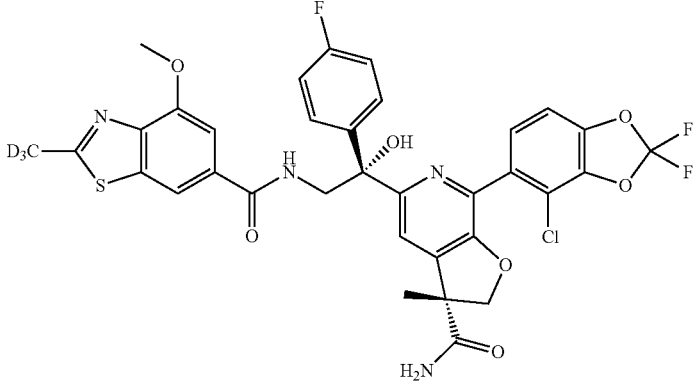 [SMILES: [2H]C([2H])([2H])c1nc2c(OC)cc(C(=O)NC[C@@](O)(c3ccc(F)cc3)c3cc4c(c(-c5ccc6c(c5Cl)OC(F)(F)O6)n3)OC[C@]4(C)C(N)=O)cc2s1] | 730.21 |
| 28 | 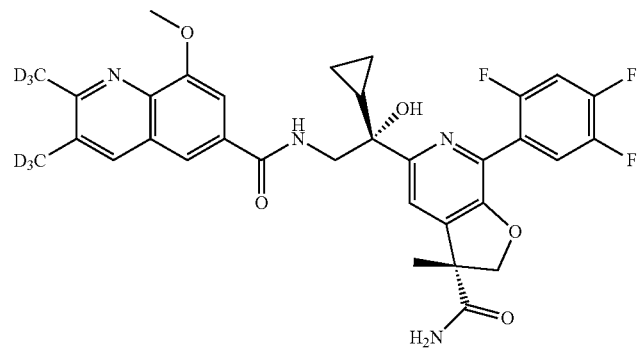 [SMILES: [2H]C([2H])([2H])c1cc2cc(C(=O)NC[C@](O)(c3cc4c(c(-c5cc(F)c(F)cc5F)n3)OC[C@]4(C)C(N)=O)C3CC3)cc(OC)c2nc1C([2H])([2H])[2H]] | 627.34 |
| 29 | 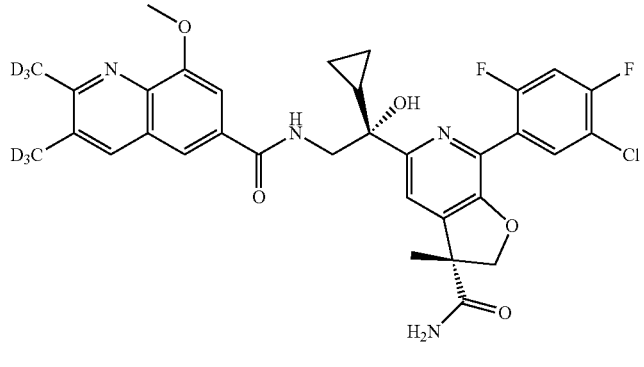 [SMILES: [2H]C([2H])([2H])c1cc2cc(C(=O)NC[C@](O)(c3cc4c(c(-c5cc(Cl)c(F)cc5F)n3)OC[C@]4(C)C(N)=O)C3CC3)cc(OC)c2nc1C([2H])([2H])[2H]] | 643.22 |
| 30 | 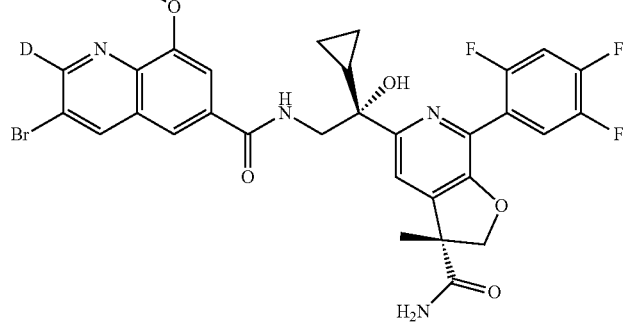 | 673.84 |

TABLE 1-continued

| Example | Structure | MS+ m/z |
|---|---|---|
| 31 | 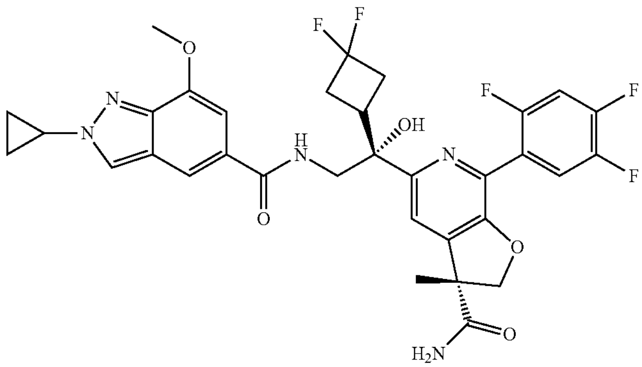 [SMILES: COc1cc(C(=O)NC[C@](O)(c2cc3c(c(-c4cc(F)c(F)cc4F)n2)OC[C@]3(C)C(N)=O)C2CC(F)(F)C2)cc2cn(C3CC3)nc12] | 672.26 |
| 32 | 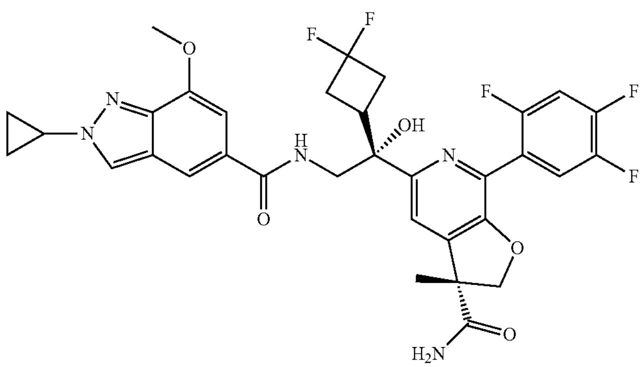 [SMILES: COc1cc(C(=O)NC[C@](O)(c2cc3c(c(-c4cc(F)c(F)cc4F)n2)OC[C@]3(C)C(N)=O)C2CC(F)(F)C2)cc2cn(C3CC3)nc12] | 697.66 |
| 33 | 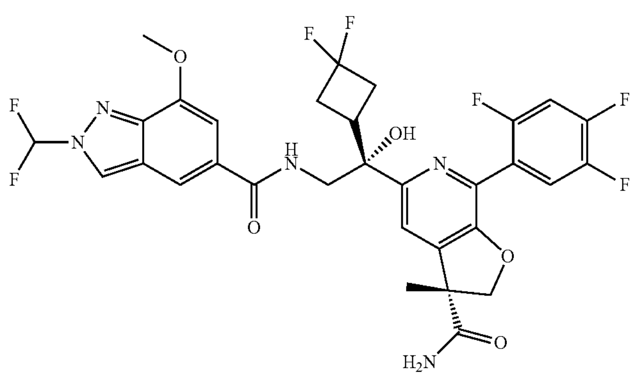 [SMILES: COc1cc(C(=O)NC[C@](O)(c2cc3c(c(-c4cc(F)c(F)cc4F)n2)OC[C@]3(C)C(N)=O)C2CC(F)(F)C2)cc2cn(C(F)F)nc12] | 682.15 |
| 34 | 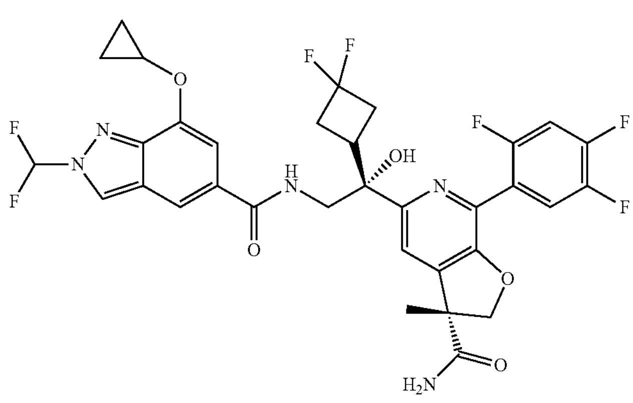 [SMILES: C[C@]1(C(N)=O)COc2c1cc([C@@](O)(CNC(=O)c1cc(OC3CC3)c3nn(C(F)F)cc3c1)C1CC(F)(F)C1)nc2-c1cc(F)c(F)cc1F] | 707.61 |

TABLE 1-continued

| Example | Structure | MS+ m/z |
|---|---|---|
| 35 | 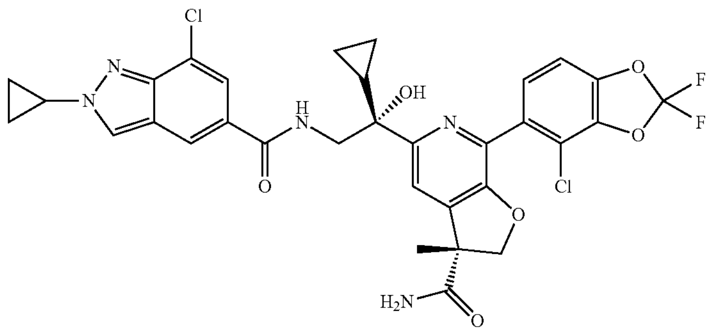 [SMILES: C[C@]1(C(N)=O)COc2c1cc([C@@](O)(CNC(=O)c1cc(Cl)c3nn(C4CC4)cc3c1)C1CC1)nc2-c1ccc2c(c1Cl)OC(F)(F)O2] | 686.10 |
| 36 | 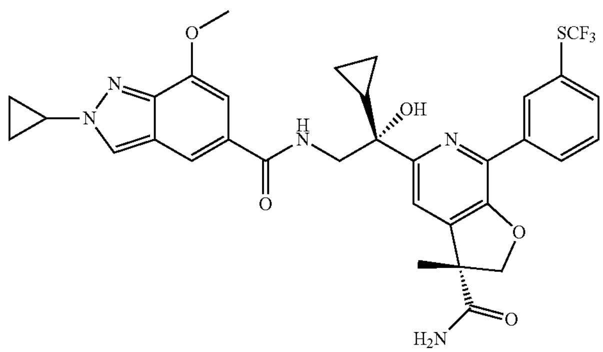 | 668.27 |
| 37 | 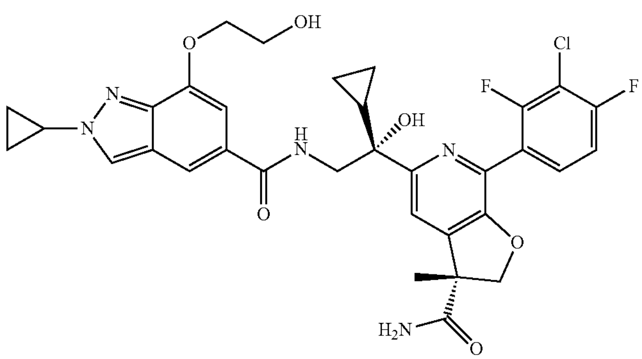 [SMILES: C[C@]1(C(N)=O)COc2c1cc([C@@](O)(CNC(=O)c1cc(OCCO)c3nn(C4CC4)cc3c1)C1CC1)nc2-c1ccc(F)c(Cl)c1F] | 668.21 |
| 38 | 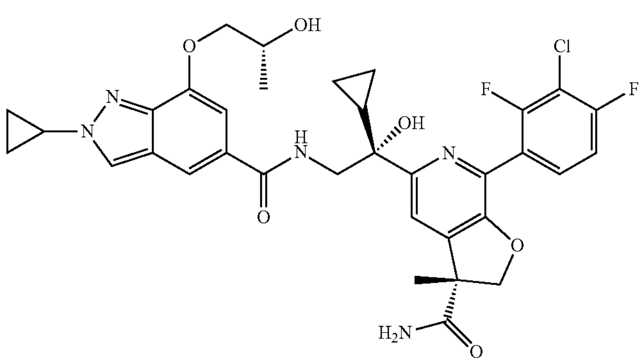 [SMILES: C[C@@H](O)COc1cc(C(=O)NC[C@](O)(c2cc3c(c(-c4ccc(F)c(Cl)c4F)n2)OC[C@]3(C)C(N)=O)C2CC2)cc2cn(C3CC3)nc12] | 682.26 |

TABLE 1-continued

| Example | Structure | MS+ m/z |
|---------|-----------|---------|
| 39 | 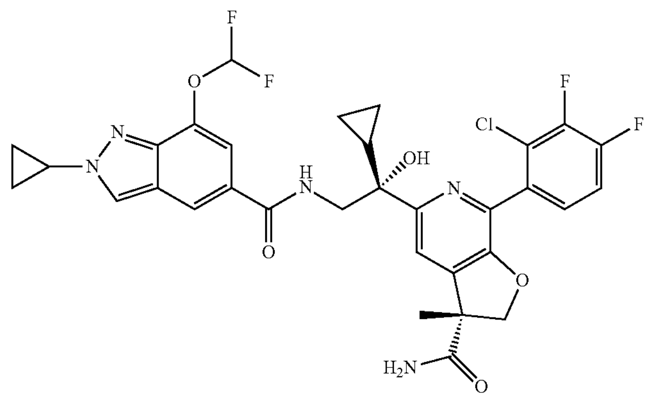 [SMILES: C[C@]1(C(N)=O)COc2c1cc([C@@](O)(CNC(=O)c1cc(OC(F)F)c3nn(C4CC4)cc3c1)C1CC1)nc2-c1ccc(F)c(F)c1Cl] | 674.17 |
| 40 | 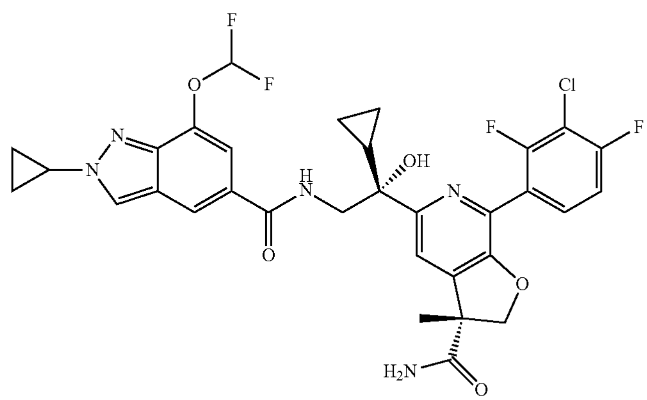 [SMILES: C[C@]1(C(N)=O)COc2c1cc([C@@](O)(CNC(=O)c1cc(OC(F)F)c3nn(C4CC4)cc3c1)C1CC1)nc2-c1ccc(F)c(Cl)c1F] | 674.19 |
| 41 | 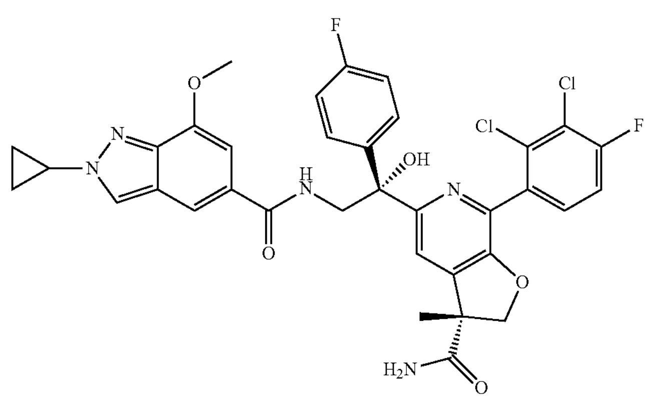 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cn(C3CC3)nc12] | 708.17 |
| 42 | 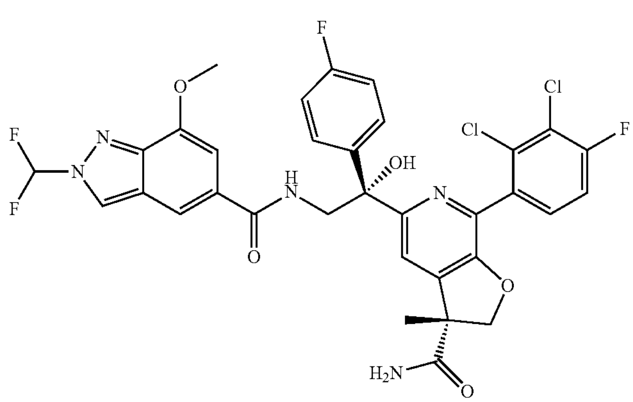 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cn(C(F)F)nc12] | 718.14 |

TABLE 1-continued

| Example | Structure | MS+ m/z |
|---|---|---|
| 43 | 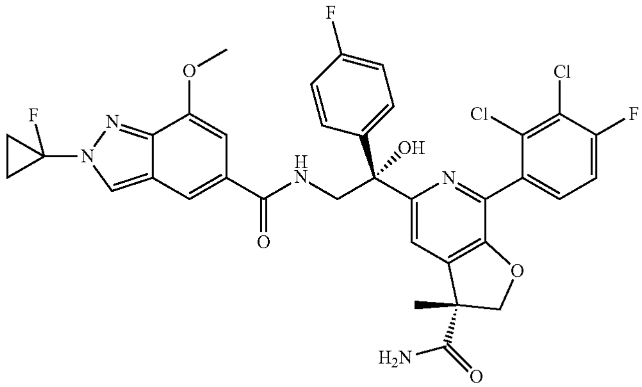 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cn(C3(F)CC3)nc12] | 726.16 |
| 44 | 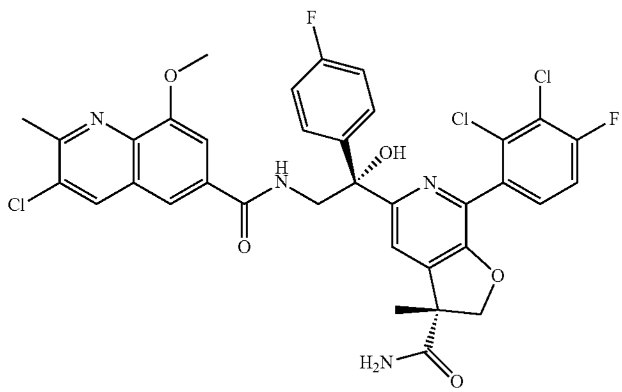 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cc(Cl)c(C)nc12] | 727.12 |
| 45 | 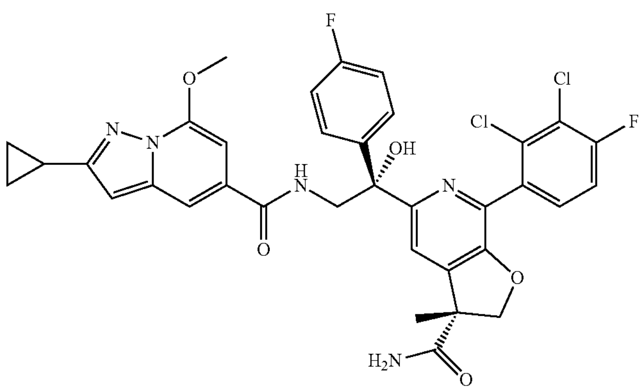 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cc(C3CC3)nn12] | 708.23 |
| 46 | 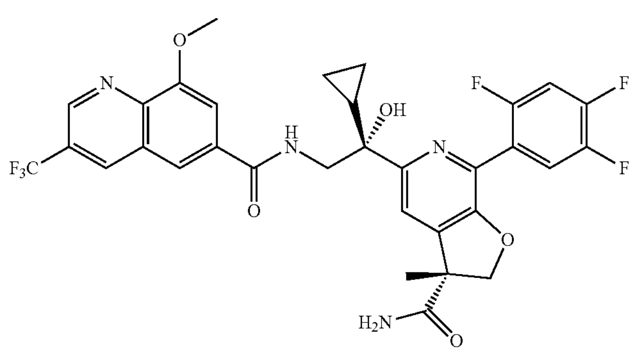 [SMILES: COc1cc(C(=O)NC[C@](O)(c2cc3c(c(-c4cc(F)c(F)cc4F)n2)OC[C@]3(C)C(N)=O)C2CC2)cc2cc(C(F)(F)F)cnc12] | 661.24 |

Intermediate 15

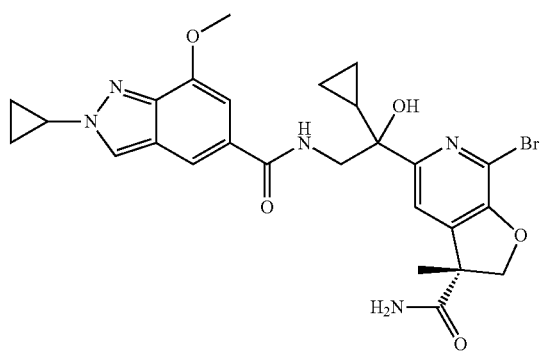 [SMILES: COc1cc(C(=O)NCC(O)(c2cc3c(c(Br)n2)OC[C@]3(C)C(N)=O)C2CC2)cc2cn(C3CC3)nc12]

Intermediate 15 Steps a and b

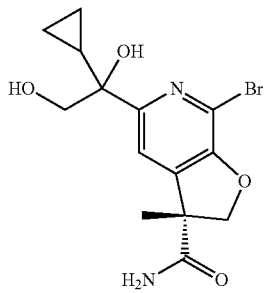 [SMILES: C[C@]1(C(N)=O)COc2c1cc(C(O)(CO)C1CC1)nc2Br]

To a 250 mL rbf flask was added 2-(1-cyclopropylvinyl)-4,4,5,5-tetramethyl-1,3,2-dioxaborolane (6.33 g, 32.6 mmol) and the oil was dissolved in 1,4-Dioxane (104 mL). (R)-7-bromo-5-iodo-3-methyl-2,3-dihydrofuro[2,3-c]pyridine-3-carboxamide (10 g, 26.1 mmol) was added followed by PdCl$_2$(dppf) (1.91 g, 2.61 mmol) and Water (26.1 mL). Potassium carbonate (10.83 g, 78 mmol) was then added, the rbf equipped with a condenser, the system purged with N$_2$ and the reaction heated to 90° C. for 2 hrs. The reaction was cooled to r.t. and the mixture was diluted with EtOAc and sat. ammonium chloride. The aqueous was extracted with EtOAc, combined, dried over sodium sulfate, filtered and concentrated. The crude material was purified by automated column chromatography (silica, 0-100% ethyl acetate in cyclohexane) to afford the desired product (10.38 g, 70% wt, 86%) as a red oil. ESI-MS m/z: 323.20 [M+H]$^+$.

(R)-7-bromo-5-(1-cyclopropylvinyl)-3-methyl-2,3-dihydrofuro[2,3-c]pyridine-3-carboxamide (3.90 g, 12.07 mmol), K$_2$OsO$_4$·2H$_2$O (0.19 g, 0.52 mmol) and NMO (3.96 g, 33.79 mmol) in THF (10 mL), H$_2$O (10 mL) and acetone (10 mL) was stirred for overnight at room temperature. The reaction was quenched by the addition of Na$_2$S$_2$O$_3$ (20 mL) at room temperature. The aqueous layer was extracted with EA (3×200 mL). The residue was purified by silica gel column chromatography, eluted with PE/EA to afford the desired product (2.60 g) as a yellow solid. ESI-MS m/z: 356.90 [M+H]$^+$.

Intermediate 15 Steps c and d

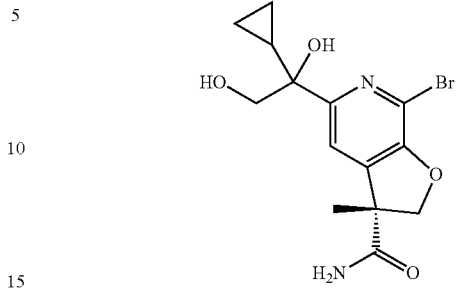

A solution of the compound from step b (2.80 g, 7.84 mmol), TsCl(1.79 g, 9.41 mmol), DMAP (48 mg, 0.39 mmol) and TEA (2.38 g, 23.52 mmol) in DCM (50 mL) was stirred for 2 hr at 0° C. The mixture was acidified to pH 7-8 with HCl. The resulting mixture was extracted with EA (3×200 mL). The combined organic layers were washed with water (3×200 mL), dried over anhydrous Na$_2$SO$_4$. After filtration, the filtrate was concentrated under reduced pressure. The residue was purified by silica gel column chromatography, eluted with PE/EA to afford the desired product (2 g, 50%) as a yellow solid. ESI-MS m/z: 510.90 [M+H]$^+$.

To a stirred solution of NH$_3$(g) in MeOH (200 mL) were added the compound from step c (3 g, 5.87 mmol) in MeOH (3 mL) dropwise at room temperature. The mixture was stirred for 20 hours at room temperature. The resulting mixture was concentrated under reduced pressure. The residue was dissolved in EtOAc, washed with sat aq. NaHCO$_3$ and concentrated to afford the desired product (2 g, 96%) as a white solid. ESI-MS m/z: 355.95 [M+H]$^+$.

Intermediate 15 Step e

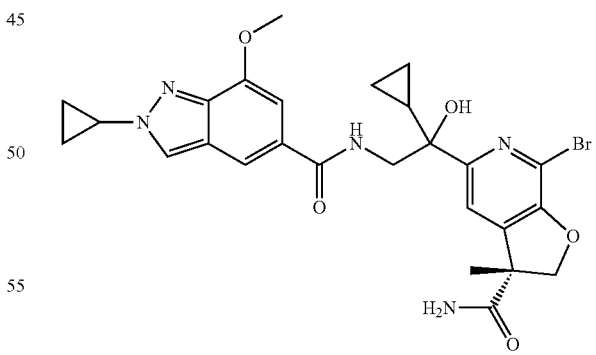

A solution of the compound from step d (700 mg, 1.97 mmol) in DMF (5 mL) was treated with 2-cyclopropyl-7-methoxy-2H-indazole-5-carboxylic acid (391 mg, 1.68 mmol), PyBOP (877 mg, 1.69 mmol) and DIPEA (363 mg, 2.81 mmol) for 1 hr at room temperature. The reaction was monitored by LCMS. The residue was purified by reverse flash chromatography to afford the titled compound (1 g, 86%) as a white solid. ESI-MS m/z: 570.30 [M+H]$^+$.

Intermediate 16

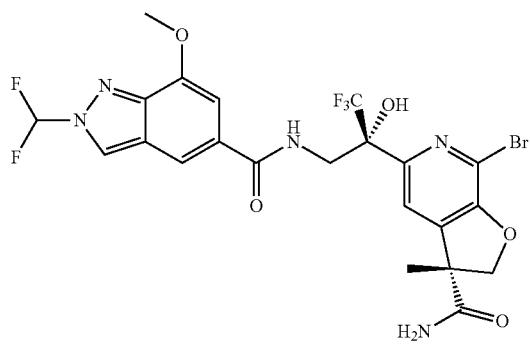 [SMILES: COc1cc(C(=O)NC[C@](O)(c2cc3c(c(Br)n2)OC[C@]3(C)C(N)=O)C(F)(F)F)cc2cn(C(F)F)nc12]

The above compound was prepared with the similar method to Intermediate 15 and was purified by automated column chromatography (silica gel) to afford the pyridyl bromide as a white solid (812 mg, 85%). ESI-MS m/z: 610.02 [M+H]+.

Example 47

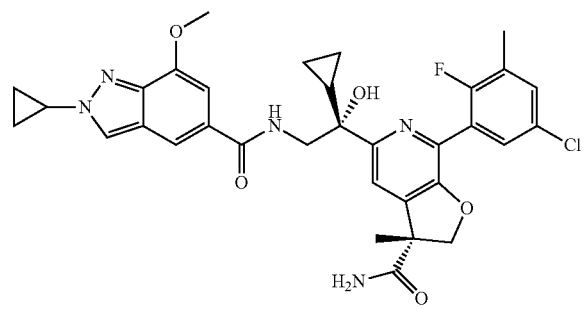 [SMILES: COc1cc(C(=O)NC[C@](O)(c2cc3c(c(-c4cc(Cl)cc(C)c4F)n2)OC[C@]3(C)C(N)=O)C2CC2)cc2cn(C3CC3)nc12]

To a 2 dram vial equipped with a stir bar was added Pd(PPh$_3$)Cl$_2$ (7.38 mg, 10.52 μmol), sodium carbonate (22.30 mg, 0.210 mmol), (5-chloro-2-fluoro-3-methylphenyl)boronic acid (19.82 mg, 0.105 mmol) and (3R)-7-bromo-5-(1-cyclopropyl-2-(2-cyclopropyl-7-methoxy-2H-indazole-5-carboxamido)-1-hydroxyethyl)-3-methyl-2,3-dihydrofuro[2,3-c]pyridine-3-carboxamide (40 mg, 0.070 mmol). The vial was purged with N$_2$ and the solids dissolved in 1,4-Dioxane (0.28 mL) and Water (0.07 mL). The reaction was heated to 90° C. and monitored by LCMS (1 hr). The reaction was cooled to r.t., filtered over a pad of silica gel with EtOAc and concentrated. The crude material was purified by and diastereomers separated by prep-HPLC (ACN/H$_2$O, 20-90%, 25 min), fractions concentrated with a Biotage V10 evaporator, and the material lyophilized to afford a fluffy, white solid (6 mg, 13%) as the desired product. ESI-MS m/z: 634.31 [M+H]+.

The following Table 2 contains examples that were prepared with a similar method to Example 47 using intermediates 15-16 or analogs thereof. If necessary to push conversion, more palladium and boronic acid were added. The majority of compounds were purified and the diastereomers were separated by prep-HPLC (ACN/H$_2$O, 20-90%, 25 min). If reported as a mixture of diastereomers, they were likely not separable by HPLC.

TABLE 2

| Example | Structure | MS+ m/z |
|---|---|---|
| 48 | 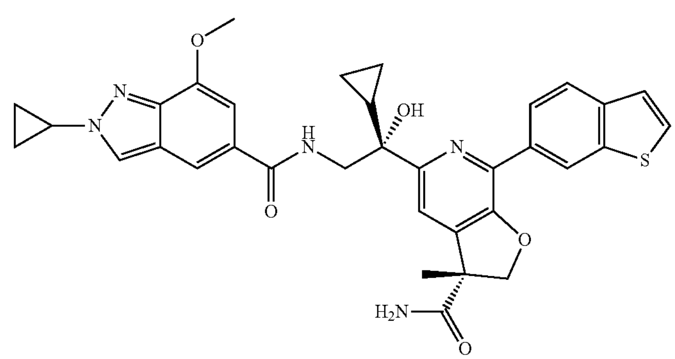 [SMILES: COc1cc(C(=O)NC[C@](O)(c2cc3c(c(-c4ccc5ccsc5c4)n2)OC[C@]3(C)C(N)=O)C2CC2)cc2cn(C3CC3)nc12] | 624.15 |

TABLE 2-continued
| Example | Structure | MS+ m/z |
|---|---|---|
| 49 | 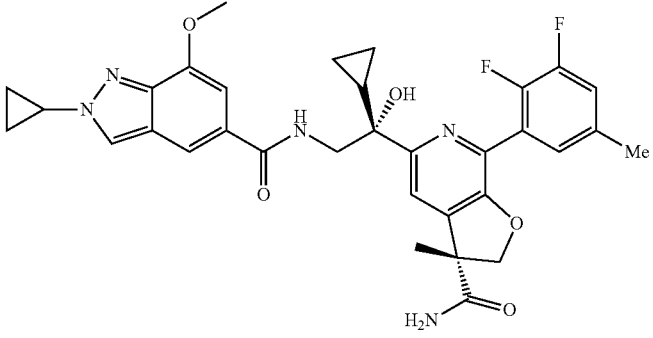 [SMILES: COc1cc(C(=O)NC[C@](O)(c2cc3c(c(-c4cc(C)cc(F)c4F)n2)OC[C@]3(C)C(N)=O)C2CC2)cc2cn(C3CC3)nc12] | 618.33 |
| 50 | 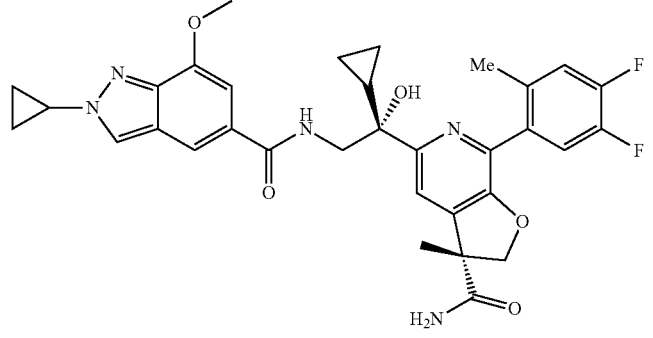 [SMILES: COc1cc(C(=O)NC[C@](O)(c2cc3c(c(-c4cc(F)c(F)cc4C)n2)OC[C@]3(C)C(N)=O)C2CC2)cc2cn(C3CC3)nc12] | 618.25 |
| 51 | 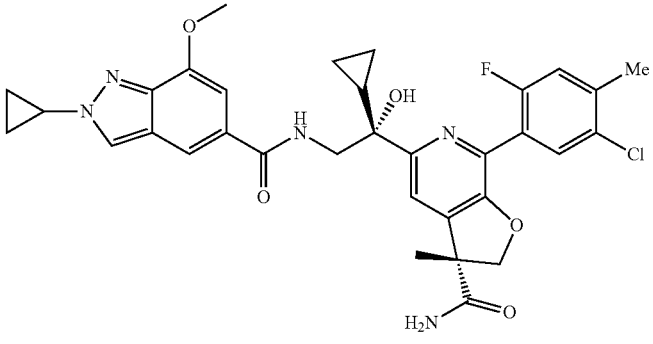 [SMILES: COc1cc(C(=O)NC[C@](O)(c2cc3c(c(-c4cc(Cl)c(C)cc4F)n2)OC[C@]3(C)C(N)=O)C2CC2)cc2cn(C3CC3)nc12] | 634.24 |
| 52 | 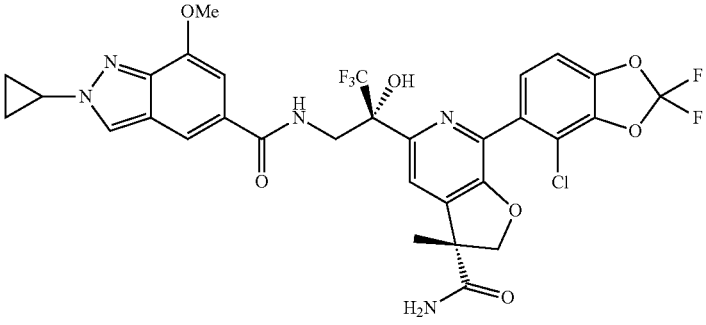 [SMILES: COc1cc(C(=O)NC[C@](O)(c2cc3c(c(-c4ccc5c(c4Cl)OC(F)(F)O5)n2)OC[C@]3(C)C(N)=O)C(F)(F)F)cc2cn(C3CC3)nc12] | 710.18 |

TABLE 2-continued

| Example | Structure | MS+ m/z |
|---------|-----------|---------|
| 53 | 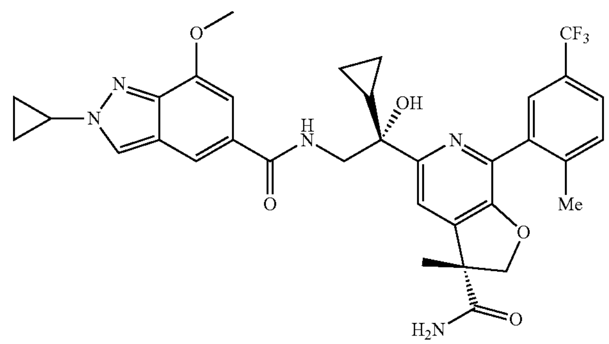 [SMILES: COc1cc(C(=O)NC[C@](O)(c2cc3c(c(-c4cc(C(F)(F)F)ccc4C)n2)OC[C@]3(C)C(N)=O)C2CC2)cc2cn(C3CC3)nc12] | 650.30 |
| 54 | 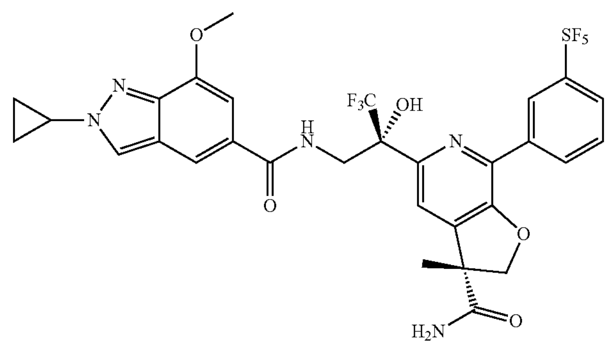 | 722.15 |
| 55 | 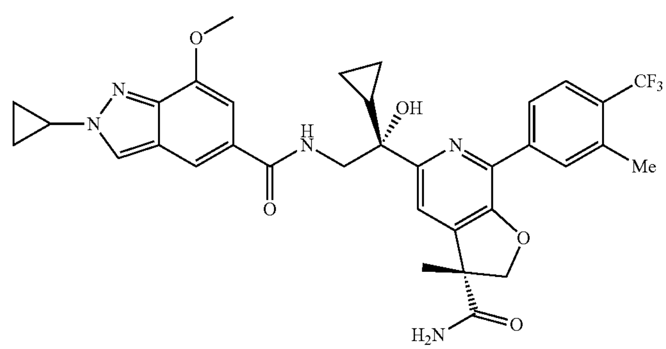 [SMILES: COc1cc(C(=O)NC[C@](O)(c2cc3c(c(-c4ccc(C(F)(F)F)c(C)c4)n2)OC[C@]3(C)C(N)=O)C2CC2)cc2cn(C3CC3)nc12] | 650.34 |
| 56 | 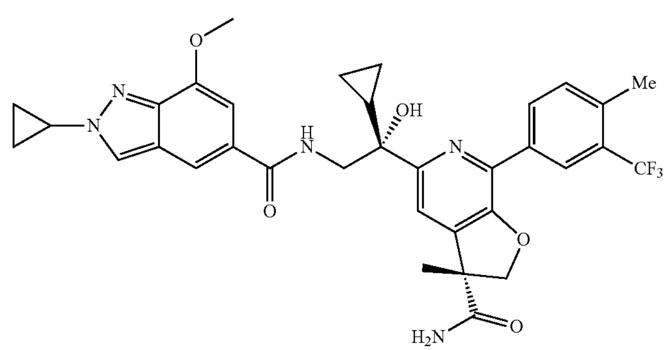 | 650.33 |

TABLE 2-continued
| Example | Structure | MS+ m/z |
|---|---|---|
| 57 | 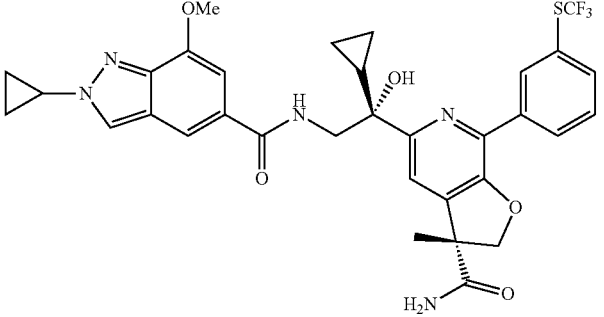 | 668.24 |
| 58 | 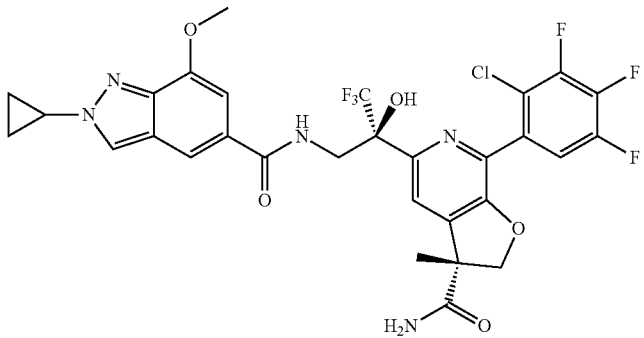 [SMILES: COc1cc(C(=O)NC[C@@](O)(c2cc3c(c(-c4cc(F)c(F)c(F)c4Cl)n2)OC[C@]3(C)C(N)=O)C(F)(F)F)cc2cn(C3CC3)nc12] | 684.99 |
| 59 | 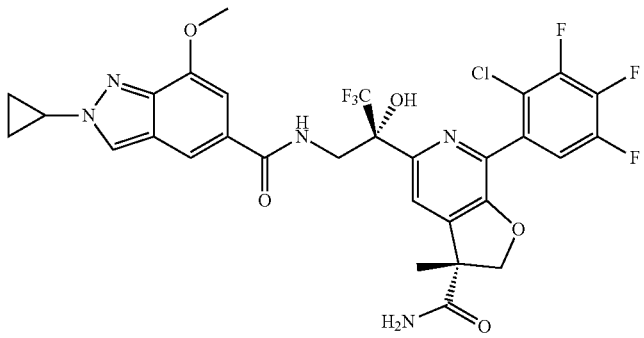 [SMILES: COc1cc(C(=O)NC[C@](O)(c2cc3c(c(-c4cc(F)c(F)c(F)c4Cl)n2)OC[C@]3(C)C(N)=O)C(F)(F)F)cc2cn(C3CC3)nc12] | 683.99 |
| 60 | 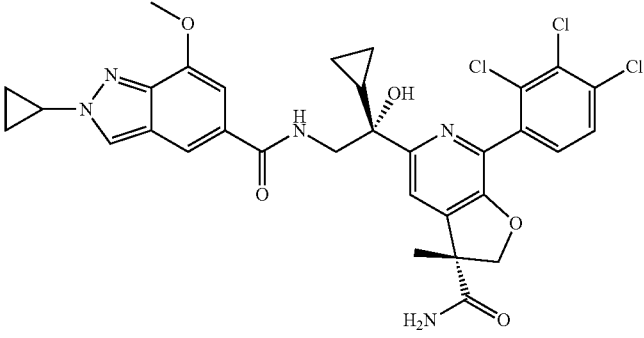 [SMILES: COc1cc(C(=O)NC[C@](O)(c2cc3c(c(-c4ccc(Cl)c(Cl)c4Cl)n2)OC[C@]3(C)C(N)=O)C2CC2)cc2cn(C3CC3)nc12] | 672.10 |

TABLE 2-continued
| Example | Structure | MS+ m/z |
|---|---|---|
| 61 | 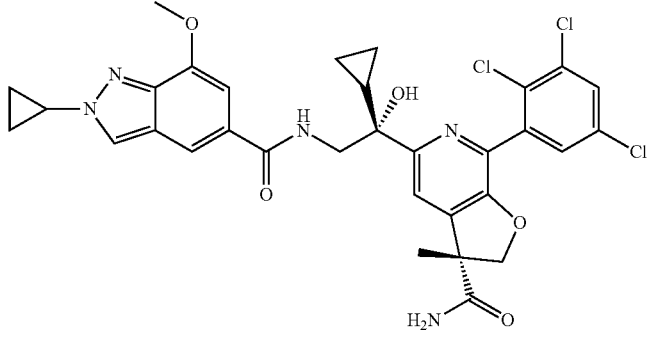 [SMILES: COc1cc(C(=O)NC[C@](O)(c2cc3c(c(-c4cc(Cl)cc(Cl)c4Cl)n2)OC[C@]3(C)C(N)=O)C2CC2)cc2cn(C3CC3)nc12] | 672.17 |
| 62 | 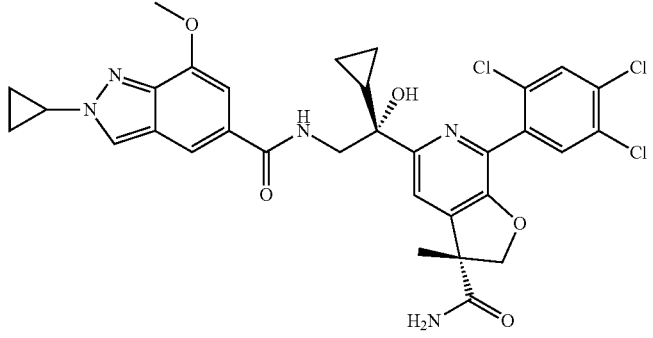 [SMILES: COc1cc(C(=O)NC[C@](O)(c2cc3c(c(-c4cc(Cl)c(Cl)cc4Cl)n2)OC[C@]3(C)C(N)=O)C2CC2)cc2cn(C3CC3)nc12] | 672.05 |
| 63 | 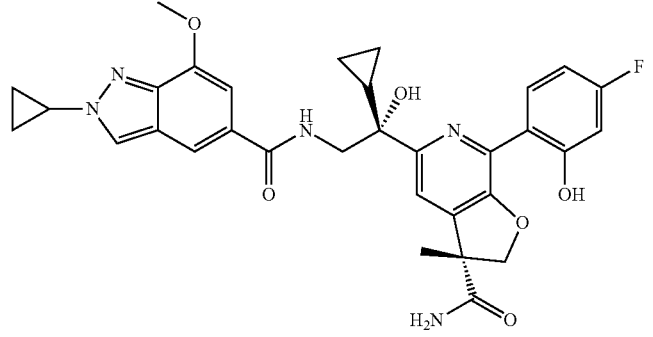 [SMILES: COc1cc(C(=O)NC[C@](O)(c2cc3c(c(-c4ccc(F)cc4O)n2)OC[C@]3(C)C(N)=O)C2CC2)cc2cn(C3CC3)nc12] | 602.30 |
| 64 | 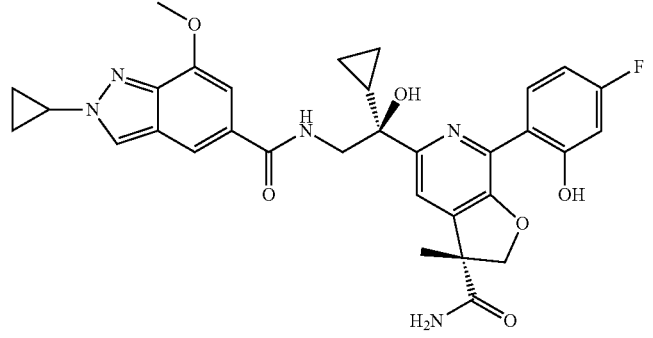 [SMILES: COc1cc(C(=O)NC[C@@](O)(c2cc3c(c(-c4ccc(F)cc4O)n2)OC[C@]3(C)C(N)=O)C2CC2)cc2cn(C3CC3)nc12] | 602.30 |

TABLE 2-continued

| Example | Structure | MS+ m/z |
|---|---|---|
| 65 | 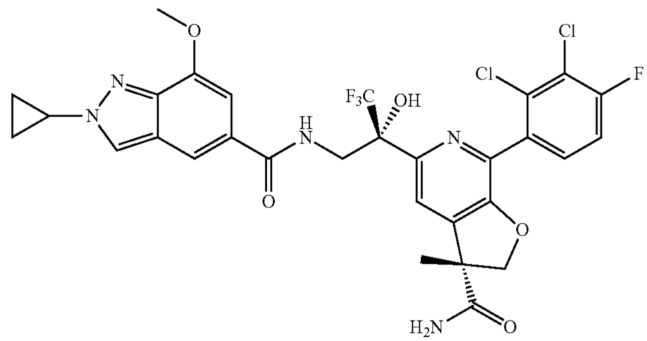 [SMILES: COc1cc(C(=O)NC[C@](O)(c2cc3c(c(-c4ccc(F)c(Cl)c4Cl)n2)OC[C@]3(C)C(N)=O)C(F)(F)F)cc2cn(C3CC3)nc12] | 682.10 |
| 66 | 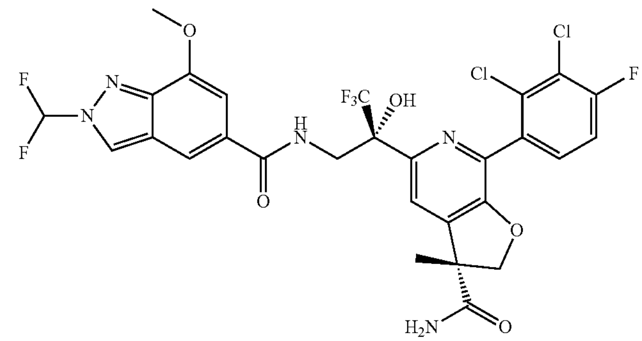 [SMILES: COc1cc(C(=O)NC[C@](O)(c2cc3c(c(-c4ccc(F)c(Cl)c4Cl)n2)OC[C@]3(C)C(N)=O)C(F)(F)F)cc2cn(C(F)F)nc12] | 692.05 |
| 67 | 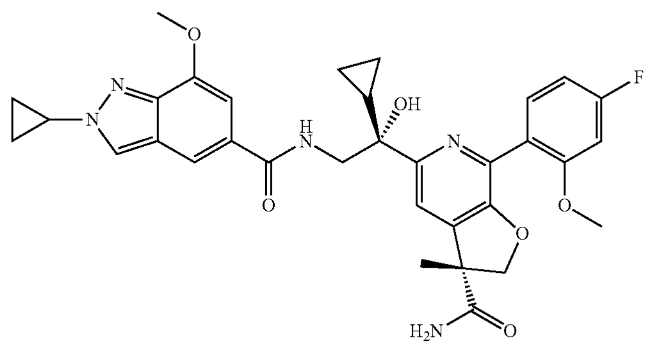 [SMILES: COc1cc(F)ccc1-c1nc([C@@](O)(CNC(=O)c2cc(OC)c3nn(C4CC4)cc3c2)C2CC2)cc2c1OC[C@]2(C)C(N)=O] | 616.35 |
| 68 | 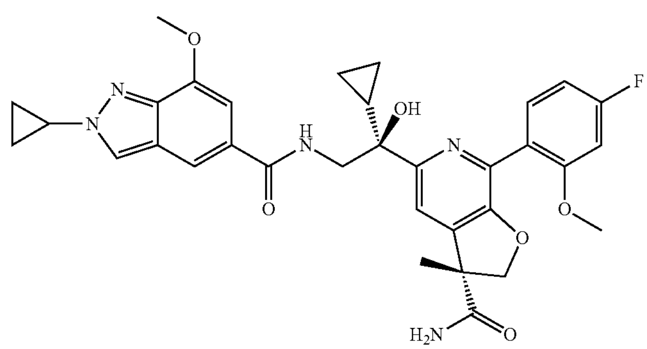 [SMILES: COc1cc(F)ccc1-c1nc([C@](O)(CNC(=O)c2cc(OC)c3nn(C4CC4)cc3c2)C2CC2)cc2c1OC[C@]2(C)C(N)=O] | 616.35 |

TABLE 2-continued
| Example | Structure | MS+ m/z |
|---|---|---|
| 69 | 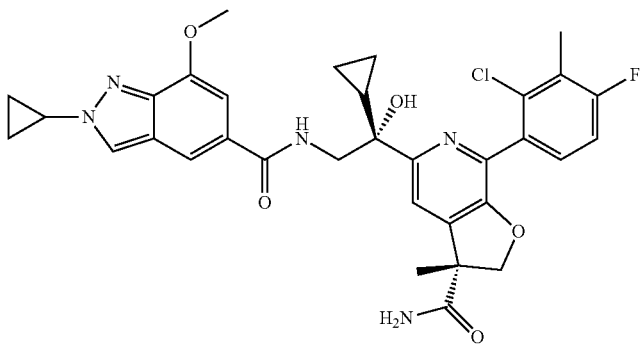 [SMILES: COc1cc(C(=O)NC[C@](O)(c2cc3c(c(-c4ccc(F)c(C)c4Cl)n2)OC[C@]3(C)C(N)=O)C2CC2)cc2cn(C3CC3)nc12] | 634.23 |
| 70 | 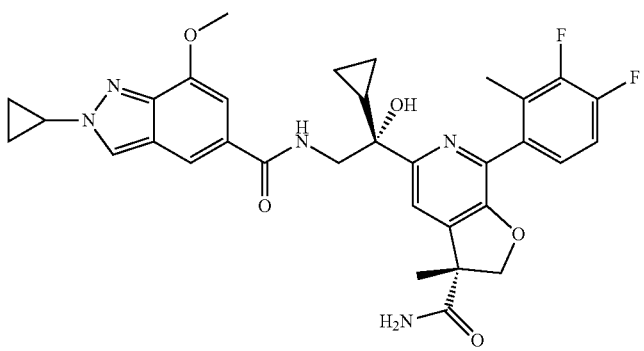 [SMILES: COc1cc(C(=O)NC[C@](O)(c2cc3c(c(-c4ccc(F)c(F)c4C)n2)OC[C@]3(C)C(N)=O)C2CC2)cc2cn(C3CC3)nc12] | 618.34 |
| 71 | 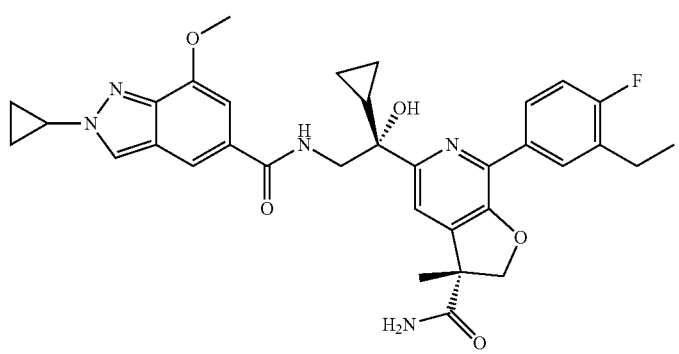 [SMILES: CCc1cc(-c2nc([C@@](O)(CNC(=O)c3cc(OC)c4nn(C5CC5)cc4c3)C3CC3)cc3c2OC[C@]3(C)C(N)=O)ccc1F] | 614.32 |
| 72 | 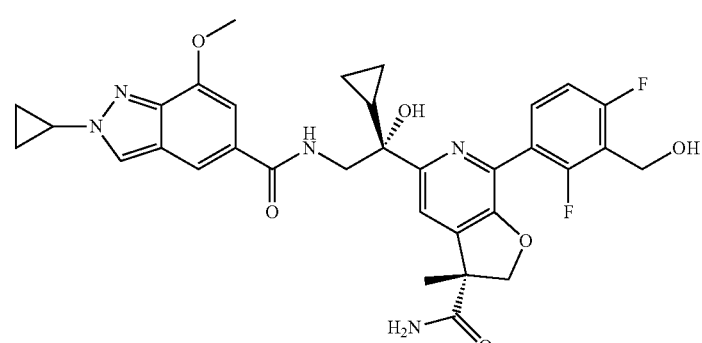 | 634.32 |

Intermediate 17

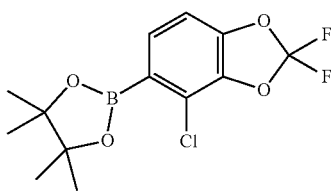 [SMILES: CC1(C)OB(c2ccc3c(c2Cl)OC(F)(F)O3)OC1(C)C]

Intermediate 17 Step a

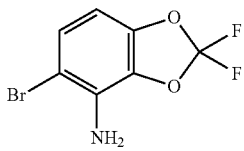 [SMILES: Nc1c(Br)ccc2c1OC(F)(F)O2]

A solution of 2,2-difluoro-1,3-benzodioxol-4-amine (5.00 g, 28.88 mmol) in CHCl$_3$ (10 mL) was treated with NBS (5.66 g, 31.80 mmol) for 1 h at room temperature. The reaction was monitored by LCMS. The resulting mixture was extracted with CH$_2$Cl$_2$. The combined organic layers were washed with brine, dried over anhydrous Na$_2$SO$_4$. After filtration, the filtrate was concentrated under reduced pressure. The residue was purified by silica gel column chromatography, eluted with PE/EA (2:1) to afford the compound (5.66 g, 78%) as a yellow oil. ESI-MS m/z: 253.80 [M+H]$^+$.

Intermediate 17 Step b

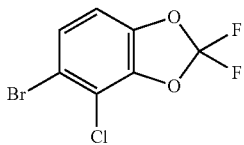 [SMILES: FC1(F)Oc2ccc(Br)c(Cl)c2O1]

A solution of CuCl$_2$ (3.20 g, 23.81 mmol) in MeCN (10 mL) was treated with t-BuNO$_2$ (3.07 g, 29.76 mmol) for 10 min at 55° C. under nitrogen atmosphere followed by the addition of the compound from step a (3 g, 11.90 mmol) dropwise at 55° C. The final reaction mixture was heated for 30 min at 55° C. The reaction was monitored by LCMS. The mixture was acidified to pH 3 with conc. HCl. The resulting mixture was extracted with EtOAc. The combined organic layers were washed with brine. After filtration, the filtrate was concentrated under reduced pressure. The residue was purified by prep-TLC (PE/EA 10:1) to afford the titled compound (396.6 mg, 7%) as a white oil. $^1$H NMR (400 MHz, CDCl$_3$) δ 6.92 (d, J=8.6 Hz, 1H), 7.40 (d, J=8.6 Hz, 1H).

Intermediate 17 Step c

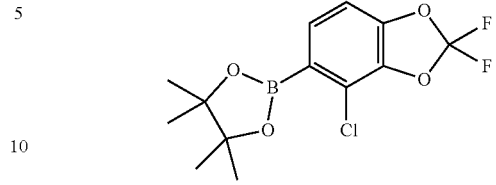

A solution of the compound from step b (2.87 g, 10.57 mmol) in THF (10 mL) was treated with iPrMgCl—LiCl (1.3 M in THF, 8 mL, 10.57 mmol) for 30 min at −20° C. under nitrogen atmosphere followed by the addition of 2-isopropoxy-4,4,5,5-tetramethyl-1,3,2-dioxaborolane (2.36 g, 12.69 mmol) dropwise at −20° C. The final reaction mixture was reacted for 1 h at room temperature. The reaction was monitored by H-NMR. The resulting mixture was extracted with CH$_2$Cl$_2$. The combined organic layers dried over anhydrous Na$_2$SO$_4$. After filtration, the filtrate was concentrated under reduced pressure. The residue was purified by silica gel column chromatography, eluted with PE/EA (4:1) to afford the titled compound (2.25 g, 67%) as a yellow oil. $^1$H NMR (400 MHz, CDCl$_3$) δ 1.36 (s, 12H), 6.96 (d, J=8.1 Hz, 1H), 7.52 (d, J=8.1 Hz, 1H).

Intermediate 18

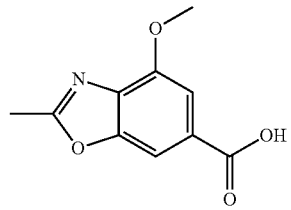

Intermediate 18 Steps a & b

A solution of 5-bromo-1-fluoro-3-methoxy-2-nitrobenzene (10 g, 40.00 mmol) in DMF (70 mL) was treated with Cs$_2$CO$_3$ (13.03 g, 40.00 mmol) and phenylmethanol (8.65 g, 80.00 mmol) for overnight at 70° C. The reaction was monitored by LCMS. The resulting mixture was filtered, the filter cake was washed with ethyl acetate. The filtrate was extracted with EtOAc. The combined organic layers were washed with brine and concentrated under reduced pressure. The residue was purified by silica gel column chromatography, eluted with PE/EA (9:1) to afford the crude compound (15 g) as a yellow oil.

A solution of the compound from step a (15 g, 44.65 mmol) in EtOH (100 mL) was treated with NH$_4$Cl(47.77 g, 893.08 mmol) in H₂O (100 mL) and Fe (7.48 g, 133.96 mmol) for 30 min at 80° C. The reaction was monitored by LCMS. The resulting mixture was filtered, the filter cake was washed with ethyl acetate. The filtrate was concentrated under reduced pressure. The resulting mixture was extracted with EtOAc. The combined organic layers were concentrated under reduced pressure. The residue was purified by silica gel column chromatography, eluted with PE/EA (9:1) to afford the desired compound (8.9 g, 65%) as a brown oil. ESI-MS m/z: 307.95 [M+H]⁺.

Intermediate 18 Steps c & d

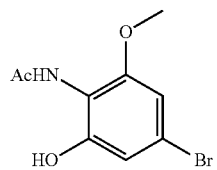

A solution of the compound from step b (6 g, 19.47 mmol) in THF (150 mL) was treated with Ac₂O (4.97 g, 48.67 mmol) and Et₃N (9.85 g, 97.35 mmol) for overnight at 0° C. to room temperature. The reaction was monitored by LCMS. The resulting mixture was extracted with EtOAc. The combined organic layers were concentrated under reduced pressure. The residue was purified by trituration with PE to afford the desired compound (6.24 g, 92%) as a white solid. ESI-MS m/z: 350.05 [M+H]⁺.

A solution of the compound from step c (6.21 g, 17.73 mmol) in CH₂Cl₂ (200 mL) was treated with boron trichloride (88.66 mL, 88.66 mmol) at 0° C. The reaction was stirred for 2 h at room temperature. The reaction was monitored by LCMS. The reaction was quenched with water at room temperature. The resulting mixture was extracted with EtOAc. The combined organic layers were concentrated under reduced pressure. The residue was purified by reversed-phase flash chromatography to afford the desired compound (1.5 g, 33%) as a white solid. ESI-MS m/z: 259.95 [M+H]⁺.

Intermediate 18 Steps e, f & g

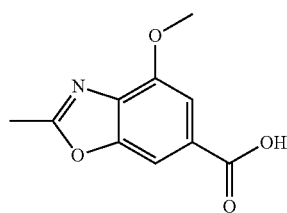

A solution of the compound from step d (1.5 g, 5.77 mmol) in CHCl₃ (10 mL) was treated with POCl₃ (1.33 g, 8.65 mmol) for overnight at 65° C. The reaction was monitored by LCMS. The reaction was quenched with water at room temperature. The resulting mixture was extracted with EtOAc. The combined organic layers were concentrated under reduced pressure. The residue was purified by silica gel column chromatography, eluted with PE/EA (5:1) to afford the desired compound (980 mg, 70%) as a white solid. ESI-MS m/z: 241.95 [M+H]⁺.

To a solution of the compound from step e (1.25 g, 5.16 mmol) in DMF (6 mL), MeOH (6 mL) and TEA (1.5 mL) was added DPPP (852 mg, 2.07 mmol), Pd(OAc)₂ (232 mg, 1.03 mmol) in a pressure tank. The mixture was purged with carbon monoxide and then was pressurized to 20 atm with carbon monoxide at 100° C. overnight. The reaction was monitored by LCMS. The resulting mixture was extracted with EtOAc. The combined organic layers were concentrated under reduced pressure. The residue was purified by silica gel column chromatography, eluted with PE/EA (3:1) to afford the titled compound (730 mg, 64%) as a white solid. ESI-MS m/z: 222.10 [M+H]⁺.

A solution of step f (400 mg, 1.81 mmol) in THF (8 mL) and MeOH (2 mL) was treated with a solution of LiOH (433 mg, 18.08 mmol) in H₂O (2 mL) for 2 h at room temperature. The reaction was monitored by LCMS. The product was precipitated by the addition of HCl. The precipitated solids were collected by filtration and washed with water to afford the titled compound (249.8 mg, 66%) as a white solid. ESI-MS m/z: 208.10 [M+H]⁺.

Intermediate 19

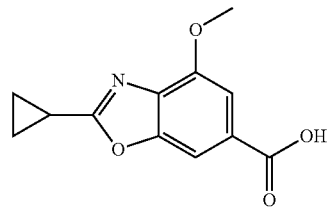 [SMILES: COc1cc(C(=O)O)cc2oc(C3CC3)nc12]

Intermediate 19 Step a

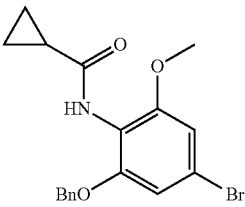 [SMILES: COc1cc(Br)cc(OCc2ccccc2)c1NC(=O)C1CC1]

A solution of the compound from Intermediate 18 step b (2.7 g, 8.76 mmol) in dioxane (20 mL) was treated with cyclopropanecarbonyl chloride (1.1 g, 10.52 mmol) for 5 hours at 100° C. The reaction was monitored by LCMS. The resulting mixture was concentrated under reduced pressure. The residue was purified by trituration with diethyl ether. The precipitated solids were collected by filtration and washed with diethyl ether to afford the desired compound (2.78 g, 88%) as a white solid. ESI-MS m/z: 376.05 [M+H]⁺.

Intermediate 19 Steps b, c, d & e

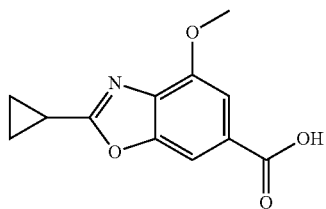 [SMILES: COc1cc(C(=O)O)cc2oc(C3CC3)nc12]

The following compound was prepared in an analogous sequence to Intermediate 18 above and purified by reversed-phase flash chromatography to afford the title compound (416.4 mg, 58%) as a white solid. ESI-MS m/z: 234.10 [M+H]$^+$.

Intermediate 20

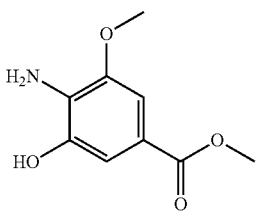

Intermediate 20 Step a

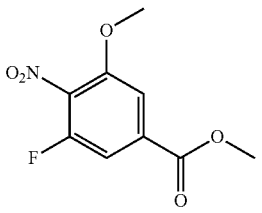 [SMILES: COC(=O)c1cc(F)c([N+](=O)[O-])c(OC)c1]

A solution of methyl 3,5-difluoro-4-nitrobenzoate (3 g, 13.82 mmol) in MeOH (50 mL) was treated with KOH (853 mg, 15.20 mmol) for 3 hours at 70° C. The reaction was monitored by TLC. The resulting mixture was extracted with EtOAc. The combined organic layers were concentrated under reduced pressure. The crude product was used in the next step directly without further purification.

Intermediate 20 Steps b & c

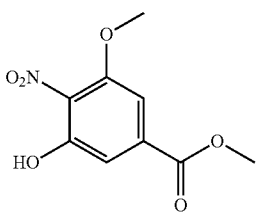 [SMILES: COC(=O)c1cc(O)c([N+](=O)[O-])c(OC)c1]

To a flask containing the compound from step a (2.50 g, 10.91 mmol) and 2-methanesulfonylethanol (1.42 g, 11.45 mmol) under N$_2$ was added DMSO (50 mL) and t-BuOK (1.29 g, 11.45 mmol). The reaction was stirred under N$_2$ at RT for 20 hours. An additional portion of 2-methanesulfonylethanol (1.42 g, 11.45 mmol) and t-BuOK (1.29 g, 11.45 mmol) was added, and the reaction was stirred for an additional 3.5 hours. The reaction was monitored by LCMS. The mixture/residue was acidified to pH<1 with conc. HCl. The resulting mixture was extracted with EtOAc. The aqueous layer was concentrated under reduced pressure. The resulting mixture was used in the next step directly without further purification. ESI-MS m/z: 211.95 [M−H]$^−$.

A solution of the compound from step b (400 mg, 1.88 mmol) in MeOH (10 mL) was treated with H$_2$SO$_4$ (1 mL) for 2 hours at 70° C. The reaction was monitored by LCMS. The resulting mixture was extracted with EtOAc. The combined organic layers were concentrated under reduced pressure. The crude product was used in the next step directly without further purification. ESI-MS m/z: 225.95 [M−H]$^−$.

Intermediate 20 Step d

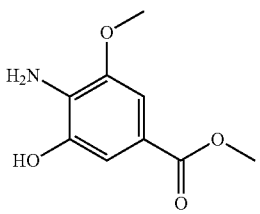

A solution of methyl the compound from step c (1.4 g, 6.16 mmol) in EtOH (50 mL) was treated with NH$_4$Cl (6.5 g, 123.26 mmol) in H$_2$O (50 mL) and Fe (1.03 g, 18.49 mmol) for 30 mins at 80° C. The reaction was monitored by LCMS. The resulting mixture was filtered, the filter cake was washed with EtOAc. The filtrate was concentrated under reduced pressure. The resulting mixture was extracted with EtOAc. The combined organic layers were concentrated under reduced pressure. The residue was purified by silica gel column chromatography, eluted with PE/EA (1:1) to afford the titled compound (428 mg, 35%) as a white solid. ESI-MS m/z: 198.10 [M+H]$^+$. $^1$H NMR (400 MHz, DMSO-d6) δ 3.75 (s, 3H), 3.79 (s, 3H), 7.00 (d, J=1.8 Hz, 1H), 7.09 (dd, J=1.8, 0.8 Hz, 1H), 9.45 (s, 1H).

Intermediate 21

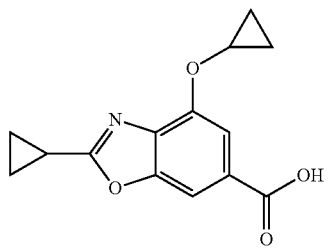 [SMILES: O=C(O)c1cc(OC2CC2)c2nc(C3CC3)oc2c1]

Intermediate 21 Steps a & b

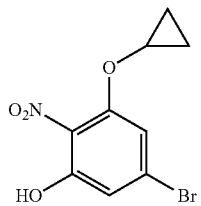 [SMILES: O=[N+]([O-])c1c(O)cc(Br)cc1OC1CC1]

A solution of 5-bromo-1,3-difluoro-2-nitrobenzene (5 g, 21.00 mmol), cyclopropanol (1.22 g, 21.00 mmol) and $Cs_2CO_3$ (13.69 g, 42.00 mmol) in DMF (50 mL) was stirred for overnight at 60° C. The resulting mixture was extracted, concentrated and purified by silica gel column chromatography to afford the desired compound (4.4 g, 75%) as a yellow oil. $^1$H NMR (400 MHz, DMSO-d6) δ 0.70-0.94 (m, 4H), 4.17-4.26 (m, 1H), 7.60-7.65 (m, 1H), 7.68 (t, J=1.8 Hz, 1H).

A solution of the compound from step a (4 g, 14.50 mmol), 2-methanesulfonylethanol (1.89 g, 15.20 mmol) and t-BuOK (1.71 g, 15.20 mmol) in DMSO (40 mL) was stirred for overnight at room temperature. 2-methanesulfonylethanol (1.89 g, 15.20 mmol) and t-BuOK (1.71 g, 15.20 mmol) were added, and the mixture was stirred for additional 3 h at room temperature. The mixture was acidified, extracted, concentrated and purified by silica gel column chromatography to afford the desired compound (2.6 g, 65%) as a yellow solid. ESI-MS m/z: 271.95 [M−H]$^-$.

Intermediate 21 Steps c & d

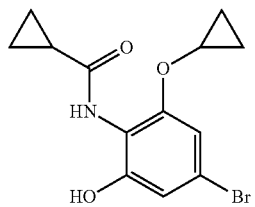 [SMILES: O=C(Nc1c(O)cc(Br)cc1OC1CC1)C1CC1]

A solution of the compound from step b (2.6 g, 9.50 mmol), $NH_4Cl$ (5.07 g, 95.00 mmol), Fe (5.30 g, 95.00 mmol), $H_2O$ (10 mL) in EtOH (20 mL) was stirred for 30 mins at 80° C. The resulting mixture was filtered, concentrated and purified by silica gel column chromatography to afford the desired compound (2 g, 86%) as a brown solid. ESI-MS m/z: 245.90 [M+H]$^+$.

A solution of the compound from step c (1.5 g, 6.10 mmol), cyclopropanecarbonyl chloride (0.58 g, 5.50 mmol) and TEA (0.93 g, 9.20 mmol) in THF (20 mL) was stirred for 1 h at 0° C. The resulting mixture was extracted, concentrated and purified by silica gel column chromatography to afford the desired compound (1.2 g, 62%) as a brown solid. ESI-MS m/z: 313.90 [M+H]$^+$.

Intermediate 21 Steps e & f

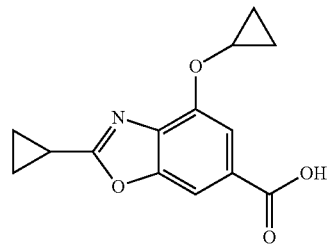 [SMILES: O=C(O)c1cc(OC2CC2)c2nc(C3CC3)oc2c1]

A solution of the compound from step d (1.2 g, 3.80 mmol) and $POCl_3$ (884 mg, 5.70 mmol) in $CHCl_3$ (20 mL) was stirred for 24 hours at 65° C. The resulting mixture was extracted, concentrated and purified by silica gel column chromatography to afford the desired compound (1 g, 88%) as a yellow oil. ESI-MS m/z: 293.90 [M+H]$^+$.

A solution of the compound from step e (660 mg, 2.20 mmol), $Ac_2O$ (458 mg, 4.49 mmol), DIPEA (254 mg, 1.97 mmol), XantPhos (57 mg, 0.10 mmol), oxalic acid (404 mg, 4.49 mmol) and $Pd(AcO)_2$ (50 mg, 0.22 mmol) in DMF (5 mL) was stirred for 6 h at 100° C. under nitrogen atmosphere. The resulting mixture was filtered and purified by reversed-phase flash chromatography to afford the desired compound (235.5 mg, 40%) as a white solid. ESI-MS m/z: 260.10 [M+H]$^+$. $^1$H NMR (400 MHz, DMSO-d6) δ 0.72-0.79 (m, 2H), 0.79-0.91 (m, 2H), 1.11-1.27 (m, 4H), 2.23-2.34 (m, 1H), 4.06-4.15 (m, 1H), 7.73 (d, J=1.3 Hz, 1H), 7.77 (d, J=1.3 Hz, 1H), 13.12 (s, 1H).

Intermediate 22

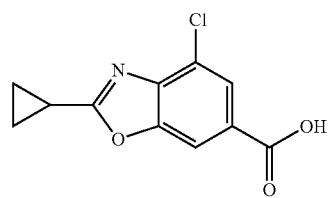 [SMILES: O=C(O)c1cc(Cl)c2nc(C3CC3)oc2c1]

Intermediate 22 Steps a & b

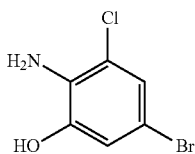

A solution of 5-bromo-1-chloro-3-fluoro-2-nitrobenzene (4 g, 15.70 mmol), 2-methanesulfonylethanol (2.05 g, 16.50 mmol) and t-BuOK (1.85 g, 16.50 mmol) in DMSO (40 mL) was stirred for overnight at room temperature under nitrogen atmosphere. 2-methanesulfonylethanol (2.05 g, 16.50 mmol) and t-BuOK (1.85 g, 16.50 mmol) was added and the resulting mixture was stirred for additional 3 hours at room temperature. The resulting mixture was extracted, concentrated and purified by silica gel column chromatography to afford the desired compound (2.2 g, 55%) as a yellow solid. ESI-MS m/z: 251.85 [M−H]⁻.

A solution of the compound from step a (2.2 g, 8.70 mmol), Fe (4.87 g, 87.10 mmol), NH₄Cl (4.66 g, 87.10 mmol), H₂O (10 mL) in EtOH (20 mL) was stirred for 30 mins at 80° C. The resulting mixture was concentrated and purified by silica gel column chromatography to afford the desired compound (1.2 g, 61%) as a brown solid. ESI-MS m/z: 223.85 [M+H]⁺.

Intermediate 22 Steps c, d & e

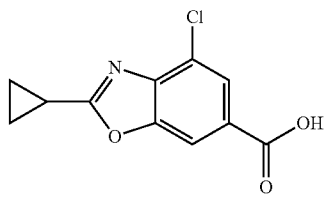 [SMILES: O=C(O)c1cc(Cl)c2nc(C3CC3)oc2c1]

A solution of the compound from step b (1.3 g, 5.80 mmol), cyclopropanecarbonyl chloride (0.61 g, 5.80 mmol) and TEA (0.89 g, 8.70 mmol) in THF (10 mL) was stirred for 1 h at 0° C. The resulting mixture was extracted, concentrated and purified by silica gel column chromatography to afford the desired compound (1 g, 58%) as a yellow solid. ESI-MS m/z: 291.85 [M+H]⁺.

A solution of the compound from step c (1 g, 3.44 mmol) and POCl₃ (791 mg, 5.16 mmol) in CHCl₃ (10 mL) was stirred for overnight at 65° C. The resulting mixture was extracted, concentrated and purified by silica gel column chromatography to afford the desired compound (800 mg, 85%) as a yellow oil. ESI-MS m/z: 273.85 [M+H]⁺.

A solution of the compound from step d (1 g, 3.67 mmol), XantPhos (212 mg, 0.36 mmol), Ac₂O (749 mg, 7.34 mmol), DIPEA (948 mg, 7.34 mmol), oxalic acid (660 mg, 7.34 mmol) and Pd(AcO)₂ (82 mg, 0.367 mmol) in DMF (20 mL) was stirred for 6 hours at 100° C. under nitrogen atmosphere. The residue was purified by reversed-phase flash chromatography to afford the desired compound (587.7 mg, 61%) as a white solid. ESI-MS m/z: 238.05 [M+H]⁺¹H NMR (400 MHz, DMSO-d6) δ 1.16-1.35 (m, 4H), 2.31-2.42 (m, 1H), 7.91 (t, J=1.6 Hz, 1H), 8.07-8.13 (m, 1H), 13.39 (s, 1H).

Intermediate 23

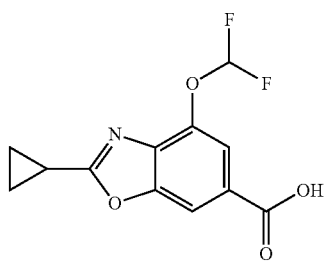 [SMILES: O=C(O)c1cc(OC(F)F)c2nc(C3CC3)oc2c1]

Intermediate 23 Steps a & b

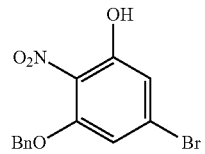

A solution of 5-bromo-1,3-difluoro-2-nitrobenzene (2 g, 8.40 mmol), benzyl alcohol (4.54 g, 42.02 mmol) and Cs₂CO₃ (13.7 g, 42.02 mmol) in DMF (10 mL) was stirred for overnight at 70° C. under N₂ atmosphere. The aqueous layer was extracted with EA (3×20 mL). The combined organic layers were concentrated under reduced pressure to afford the crude for next step directly.

A solution of the compound from step a (2 g, 4.83 mmol) and boron trichloride (20 mL) in CH₂Cl₂ (40 mL) was stirred for 2 hours at 0° C. The resulting mixture was extracted with EA. The combined organic layers were washed with water. The residue product was purified by reverse phase flash to afford the desired product (1.5 g, 96%) as a yellow solid. ESI-MS m/z: 322.00 [M−H]⁻.

Intermediate 23 Steps c & d

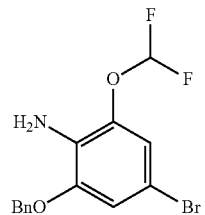

A solution of the compound from step b (1.5 g, 4.63 mmol), sodium 2-chloro-2,2-difluoroacetate (1.4 g, 9.26 mmol) and Cs₂CO₃ (3.02 g, 9.26 mmol) in DMF (15 mL) was stirred for 2 hr at 80° C. under N₂ atmosphere. The residue was purified by prep-TLC to afford the desired product (1.2 g, 69%) as a yellow solid.

A solution of the compound from step c (1.2 g, 3.21 mmol), Fe (1.79 g, 32.07 mmol) and NH₄Cl (1.72 g, 32.07 mmol) in EtOH (20 mL) and H₂O (10 mL) was stirred for 2 hours at 80° C. under N₂ atmosphere. The resulting mixture was filtered. The resulting mixture was extracted with EA.

The combined organic layers were washed with water, organic layers were concentrated under reduced pressure to afford the desired product (1 g, 91%) as a yellow oil. ESI-MS m/z: 344.00 [M+H]⁺.

129
Intermediate 23 Steps e & f

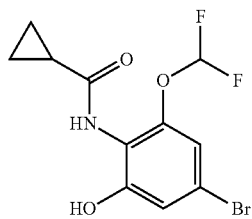 [SMILES: O=C(Nc1c(O)cc(Br)cc1OC(F)F)C1CC1]

A solution of the compound from step d (1 g, 2.91 mmol) and cyclopropanecarbonyl chloride (607 mg, 5.81 mmol) in dioxane (20 mL) was stirred for 2 hours at 100° C. under N₂ atmosphere. The resulting mixture was extracted with EA (3×2 mL). The combined organic layers were washed with water and concentrated under reduced pressure to afford the desired product (900 mg, 75%) as a yellow solid. ESI-MS m/z: 412.00 [M+H]⁺.

A solution of the compound from step e (900 mg, 2.18 mmol) and boron trichloride (11.25 mL) in DCM (30 mL) was stirred for 2 hours at 0° C. The resulting mixture was extracted with EA. The combined organic layers were washed with water. The residue product was purified by reverse phase flash to afford the desired product (600 mg, 85%) as a yellow oil. ESI-MS m/z: 322.00 [M+H]⁺.

Intermediate 23 Steps g & h

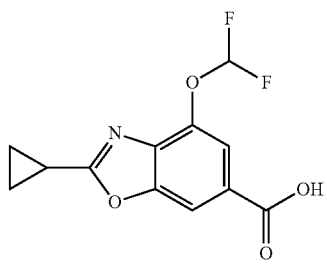 [SMILES: O=C(O)c1cc(OC(F)F)c2nc(C3CC3)oc2c1]

A solution of the compound from step f (600 mg, 1.86 mmol) and POCl₃ (428 mg, 2.80 mmol) in CHCl₃ (10 mL) was stirred for overnight at 65° C. under N₂ atmosphere. The residue was purified by silica gel column chromatography, eluted with PE/EA to afford the desired product (400 mg, 71%) as a yellow oil. ESI-MS m/z: 304.00 [M+H]⁺.

A solution of the compound from step g (400 mg, 1.32 mmol), Pd(OAc)₂ (59 mg, 0.26 mmol), Ac₂O (269 mg, 2.63 mmol), XantPhos (76 mg, 0.13 mmol) and DIEA (340 mg, 2.63 mmol) in DMF (10 mL) was stirred for overnight at 100° C. under N₂ atmosphere. The crude product was purified by reverse phase flash to afford the desired product (200 mg, 56%) as a white solid. ESI-MS m/z: 270.00 [M+H]⁺. ¹H NMR (400 MHz, DMSO-d6) δ 1.15-1.31 (m, 4H), 2.34 (tdt, J=13.4, 10.0, 5.0 Hz, 1H), 7.32-7.77 (m, 2H), 8.01 (d, J=3.0 Hz, 1H), 13.41 (s, 1H).

130
Intermediate 24

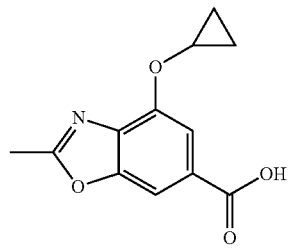 [SMILES: Cc1nc2c(OC3CC3)cc(C(=O)O)cc2o1]

Intermediate 24 Step a

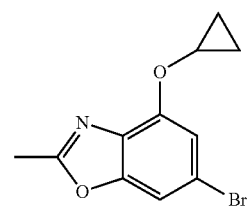

A solution of 2-amino-5-bromo-3-cyclopropoxyphenol (1 g, 4.09 mmol), acetyl chloride (289 mg, 3.68 mmol) and TEA (621 mg, 6.14 mmol) in THF (10 mL) was stirred for 2 hours at 0° C. The resulting mixture was extracted, concentrated and purified by silica gel column chromatography to afford the desired compound (600 mg, 51%) as a brown oil. ESI-MS m/z: 285.95 [M+H]⁺.

Intermediate 24 Step b

A solution of the compound from step a (1.2 g, 4.19 mmol), POCl₃ (1.29 g, 8.38 mmol) in CHCl₃ (5 mL) was stirred for 24 hours at 65° C. The resulting mixture was extracted, concentrated and purified by silica gel column chromatography to afford the desired compound (1 g, 88%) as a brown solid. ESI-MS m/z: 267.90 [M+H]⁺.

Intermediate 24 Step c

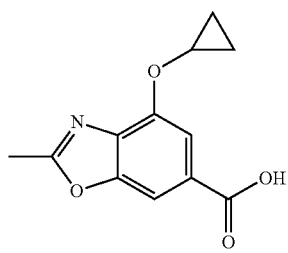

A solution of the compound from step b (420 mg, 1.57 mmol), Pd(OAc)$_2$ (35 mg, 0.157 mmol), Ac$_2$O (319 mg, 3.13 mmol), XantPhos (90 mg, 0.157 mmol), oxalic acid (282 mg, 3.13 mmol) and DIPEA (404 mg, 3.13 mmol) in DMF (5 mL) was stirred for 6 hours at 100° C. under nitrogen atmosphere. The residue was purified by reversed-phase flash chromatography to afford the desired compound (207.3 mg, 52%) as a white solid. ESI-MS m/z: 245.90 [M+H]$^+$. $^1$H NMR (400 MHz, DMSO-d6) δ 0.72-0.84 (m, 2H), 0.84-0.92 (m, 2H), 2.62 (s, 3H), 4.10-4.20 (m, 1H), 7.73 (d, J=1.3 Hz, 1H), 7.80 (d, J=1.3 Hz, 1H), 13.18 (s, 1H).

Intermediate 25

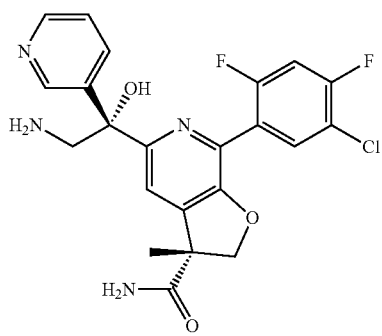 [SMILES: C[C@]1(C(N)=O)COc2c1cc([C@@](O)(CN)c1cccnc1)nc2-c1cc(Cl)c(F)cc1F]

Intermediate 25 Step a

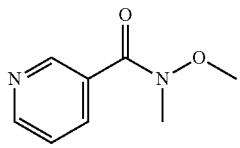

A mixture of niacin (5 g, 40.61 mmol), methoxy(methyl)amine hydrochloride (5.94 g, 60.92 mmol), HATU (15.44 g, 40.61 mmol) and DIEA (10.50 g, 81.23 mmol) in DCM (50 mL) was stirred for 2 hours at room temperature. The reaction was monitored by LCMS. The resulting mixture was washed with water. The aqueous layer was extracted with EA. The combined organic layers were concentrated under reduced pressure. The residue was purified by silica gel column chromatography, eluted with PE/EA (1:1) to afford the desired product (3.9 g, 57%) as a light-yellow liquid. ESI-MS m/z: 167.05 [M+H]$^+$.

Intermediate 25 Step b

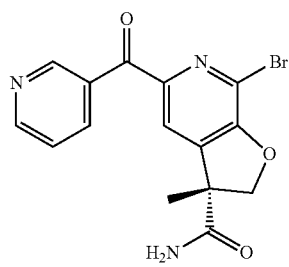 [SMILES: C[C@]1(C(N)=O)COc2c1cc(C(=O)c1cccnc1)nc2Br]

Into a 250 mL 3-necked round-bottom flask were added (R)-7-bromo-5-iodo-3-methyl-2,3-dihydrofuro[2,3-c]pyridine-3-carboxamide (2 g, 5.22 mmol), the compound from step a (1.30 g, 7.83 mmol) and THF (15 mL) at room temperature. The mixture was allowed to cool down to 0° C. iPrMgCl (1.07 g, 10.44 mmol) was added dropwise under nitrogen atmosphere at 0° C. The resulting mixture was stirred for 2 hours at room temperature under nitrogen atmosphere. The reaction was quenched with sat. NH$_4$Cl (aq.) at room temperature. The resulting mixture was extracted with EA. The combined organic layers were concentrated under reduced pressure. The residue was purified by silica gel column chromatography, eluted with EA to afford the desired product (970 mg, 51%) as a yellow solid. ESI-MS m/z: 361.95 [M+H]$^+$.

Intermediate 25 Step c

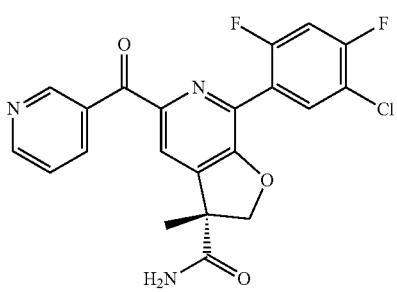 [SMILES: C[C@]1(C(N)=O)COc2c1cc(C(=O)c1cccnc1)nc2-c1cc(Cl)c(F)cc1F]

A mixture of the compound from step b (800 mg, 2.21 mmol), 2-(5-chloro-2,4-difluorophenyl)-4,4,5,5-tetramethyl-1,3,2-dioxaborolane (606 mg, 2.21 mmol), K$_2$CO$_3$ (610 mg, 4.42 mmol) and Pd(dppf)Cl$_2$ (161 mg, 0.22 mmol) in Dioxane (9 mL), H$_2$O (1 mL) was stirred for 1 h at 80° C. under nitrogen atmosphere. The resulting mixture was filtered, the filter cake was washed with EA. The filtrate was concentrated under reduced pressure. The residue was purified by silica gel column chromatography, eluted with PE/EA (1:1) to afford the desired product (820 mg, 86%) as a yellow solid. ESI-MS m/z: 430.05 [M+H]$^+$.

Intermediate 25 Step d

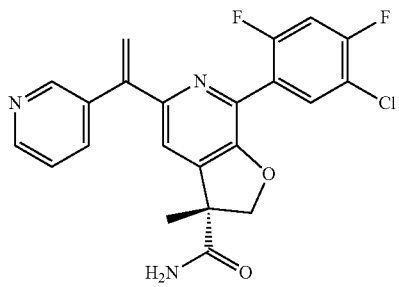 [SMILES: C=C(c1cccnc1)c1cc2c(c(-c3cc(Cl)c(F)cc3F)n1)OC[C@]2(C)C(N)=O]

To a stirred solution of methyltriphenylphosphonium bromide (1.70 g, 4.77 mmol) in THF (50 mL) was added 1 M t-BuOK in THF (428 mg, 3.81 mmol) dropwise at 0° C. under nitrogen atmosphere. The resulting mixture was stirred for 30 min at 0° C. under nitrogen atmosphere. The compound from step c (820 mg, 1.90 mmol) in THF was added and stirred for 2 hours at 50° C. The resulting mixture was poured into water, extracted with EA. The combined organic layers were concentrated under reduced pressure. The residue was purified by silica gel column chromatography, eluted with EA to afford the crude product (430 mg) as a yellow solid. ESI-MS m/z: 428.15 [M+H]⁺.

Intermediate 25 Step e

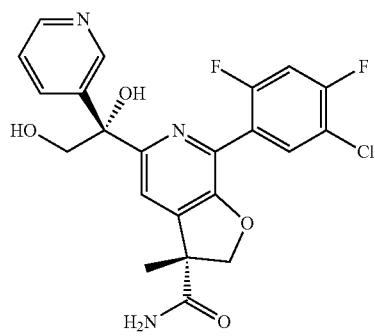 [SMILES: C[C@]1(C(N)=O)COc2c1cc([C@@](O)(CO)c1cccnc1)nc2-c1cc(Cl)c(F)cc1F]

A mixture of the compound from step d (400 mg, 0.93 mmol), methanesulfonamide (89 mg, 0.93 mmol) and ADMIX-β (2.18 g, 2.80 mmol) in t-BuOH (5 mL), H₂O (5 mL) was stirred for overnight at room temperature. The resulting mixture was extracted with EA. The combined organic layers were concentrated under reduced pressure. The residue was purified by Prep-TLC (CH₂Cl₂/MeOH 10:1) to afford the desired product (30 mg) as an off-white solid. ESI-MS m/z: 462.10 [M+H]⁺.

Intermediate 25 Step f

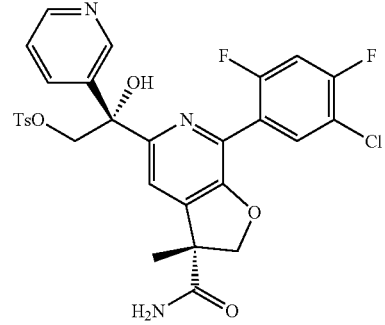 [SMILES: Cc1ccc(S(=O)(=O)OC[C@@](O)(c2cccnc2)c2cc3c(c(-c4cc(Cl)c(F)cc4F)n2)OC[C@]3(C)C(N)=O)cc1]

A mixture of the compound from step e (30 mg, 0.06 mmol), TsCl (18 mg, 0.09 mmol), TEA (19 mg, 0.19 mmol) and DMAP (8 mg, 0.06 mmol) in DCM (2 mL) was stirred for 1 h at room temperature. The mixture was acidified to pH 5 with HCl (2 M aq.). The resulting mixture was extracted with CH₂Cl₂. The combined organic layers were concentrated under reduced pressure.

The residue was purified by prep-TLC (EA) to afford the desired product (30 mg, 74%) as a yellow solid. ESI-MS m/z: 616.15 [M+H]⁺.

Intermediate 25 Step g

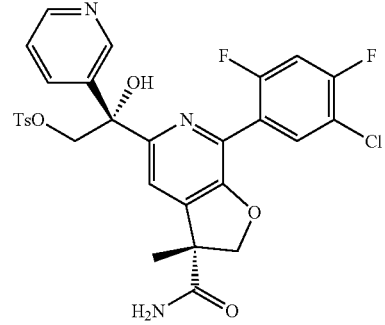 [SMILES: Cc1ccc(S(=O)(=O)OC[C@@](O)(c2cccnc2)c2cc3c(c(-c4cc(Cl)c(F)cc4F)n2)OC[C@]3(C)C(N)=O)cc1]

A solution of the compound from step f (30 mg, 0.05 mmol) and NH₃(g) in MeOH (5 mL) was stirred for overnight at 40° C. The resulting mixture was concentrated under reduced pressure. The residue was purified by Prep-TLC (CH₂Cl₂/MeOH (7 M NH₃) 10:1) to afford the desired product (10 mg, 44%) as an off-white solid. ESI-MS m/z: 461.25 [M+H]⁺.

Intermediate 26

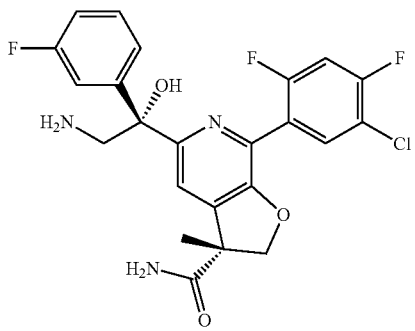 [SMILES: C[C@]1(C(N)=O)COc2c1cc([C@@](O)(CN)c1cccc(F)c1)nc2-c1cc(Cl)c(F)cc1F]

The above compound was prepared with the similar method to Intermediate 9, to afford the amino alcohol. (100 mg). ESI-MS m/z: 478.50 [M+H]+.

Intermediate 27

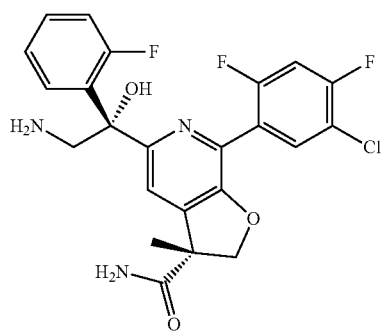 [SMILES: C[C@]1(C(N)=O)COc2c1cc([C@@](O)(CN)c1ccccc1F)nc2-c1cc(Cl)c(F)cc1F]

The above compound was prepared with the similar method to Intermediate 9, to afford the amino alcohol. (60 mg, 53%). ESI-MS m/z: 478.20 [M+H]+.

Intermediate 28

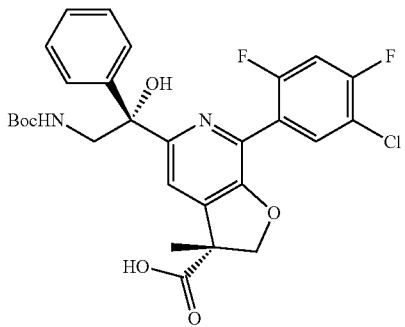 [SMILES: CC(C)(C)OC(=O)NC[C@@](O)(c1ccccc1)c1cc2c(c(-c3cc(Cl)c(F)cc3F)n1)OC[C@]2(C)C(=O)O]

Intermediate 28 Step a

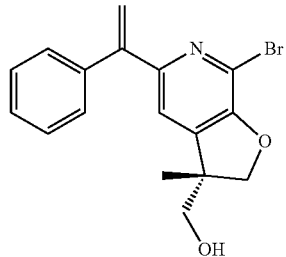 [SMILES: C=C(c1ccccc1)c1cc2c(c(Br)n1)OC[C@]2(C)CO]

A solution of (S)-(7-bromo-5-iodo-3-methyl-2,3-dihydrofuro[2,3-c]pyridin-3-yl)methanol (3 g, 7.83 mmol), 4,4,5,5-tetramethyl-2-(1-phenylethenyl)-1,3,2-dioxaborolane (1.8 g, 7.83 mmol), Pd(dppf)Cl₂ (573 mg, 0.78 mmol) and K₂CO₃ (2.1 g, 15.66 mmol) in dioxane (40 mL) and H₂O (4 mL) was stirred for 2 hours at 80° C. under N₂ atmosphere. The residue was purified by silica gel column chromatography, eluted with PE/EA to afford the desired product (2.8 g, 99%) as a brown oil. ESI-MS m/z: 346.05 [M+H]+.

Intermediate 28 Step b

A mixture of the compound from step a (2 g, 5.78 mmol), 1-(5-chloro-2,4-difluorophenyl)-3,3,4,4-tetramethylborolane (1.6 g, 5.78 mmol), Pd(dppf)Cl₂ (422 mg, 0.58 mmol) and K₂CO₃ (1.6 g, 11.55 mmol) in dioxane (20 mL) and H₂O (2 mL) was stirred for 2 hours at 80° C. under N₂ atmosphere. The residue was purified by silica gel column chromatography, eluted with PE/EA to afford the desired product (1.6 g, 66%) as a yellow solid. ESI-MS m/z: 414.20 [M+H]+.

Intermediate 28 Steps c & d

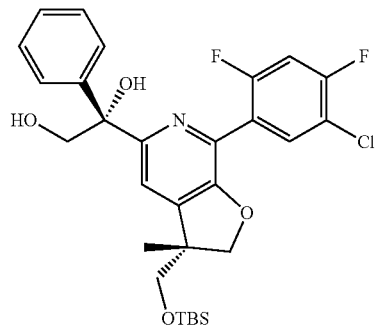 [SMILES: CC(C)(C)[Si](C)(C)OC[C@@]1(C)COc2c1cc([C@@](O)(CO)c1ccccc1)nc2-c1cc(Cl)c(F)cc1F]

A solution of the compound from step b (1.6 g, 3.88 mmol), TBSCl (870 mg, 5.79 mmol) and imidazole (0.39 g, 5.80 mmol) in DCM (10 mL) was stirred for 2 hours at r.t. The resulting mixture was extracted with DCM (3×100 mL). The combined organic layers were washed with water (3×200 mL). The organic layer was concentrated under reduced pressure. The residue was purified by reverse flash chromatography to afford the desired product (1.9 g, 93%) as a white solid. ESI-MS m/z: 528.30 [M+H]$^+$.

A solution of the compound from step c (2 g, 3.78 mmol), ADMIX-0 (8.85 g, 11.36 mmol) and methanesulfonamide (0.36 g, 3.78 mmol) in t-BuOH (10 mL) and H$_2$O (10 mL) was stirred for overnight at 0° C. The resulting mixture was extracted with EA (3×200 mL). The combined organic layers were washed with water (3×200 mL). The organic layer was concentrated under reduced pressure. The residue was purified by reverse flash chromatography to afford the desired product (1.5 g, 70%) as a white solid. ESI-MS m/z: 562.40 [M+H]$^+$.

Intermediate 28 Steps e & f

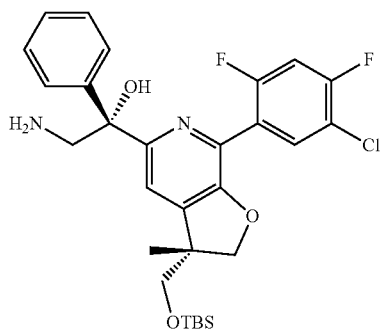 [SMILES: CC(C)(C)[Si](C)(C)OC[C@@]1(C)COc2c1cc([C@@](O)(CN)c1ccccc1)nc2-c1cc(Cl)c(F)cc1F]

A solution of the compound from step d (1.5 g, 2.66 mmol), TsCl (763 mg, 4.00 mmol), TEA (810 mg, 8.00 mmol) and DMAP (232 mg, 2.66 mmol) in DCM (20 mL) was stirred for 2 hours at 0° C. The resulting mixture was extracted with EA (3×200 mL). The combined organic layers were washed with water (3×200 mL). The organic layer was concentrated under reduced pressure. The residue was purified by silica gel column chromatography, eluted with PE/EA to afford the desired product (1.5 g, 78%) as a white solid. ESI-MS m/z: 716.50 [M+H]$^+$.

A solution of the compound from step e (1.5 g, 2.66 mmol) in MeOH (5 mL) was added into the solution of N$_{13}$(g) in MeOH (30 mL) and stirred for overnight at 40° C. The residue was purified by prep-TLC (DCM/NH$_3$ in MeOH=15/1) to afford the desired product (1.1 g, 93%) as a white solid. ESI-MS m/z: 561.40 [M+H]$^+$.

Intermediate 28 Steps g & h

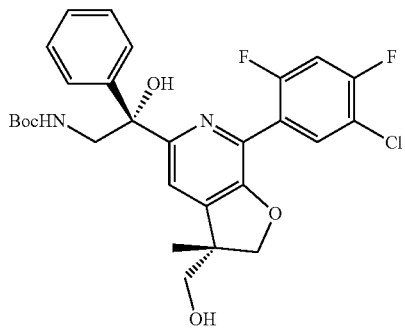 [SMILES: CC(C)(C)OC(=O)NC[C@@](O)(c1ccccc1)c1cc2c(c(-c3cc(Cl)c(F)cc3F)n1)OC[C@]2(C)CO]

A solution of the compound from step f (900 mg, 1.60 mmol), (Boc)$_2$O (525 mg, 2.40 mmol) and TEA (486 mg, 4.81 mmol) in DCM (10 mL) was stirred for 2 hours at r.t. The resulting mixture was extracted with DCM (3×100 mL). The combined organic layers were washed with water (3×100 mL). The organic layer was concentrated under reduced pressure. The residue was purified by reverse flash chromatography to afford the desired product (600 mg, 56%) as a white solid. ESI-MS m/z: 661.20 [M+H]$^+$.

A solution of the compound from step g (900 mg, 1.36 mmol) and TBAF (355 mg, 1.36 mmol) in THF (10 mL) was stirred for 1 h at r.t. The resulting mixture was extracted with EA (3×200 mL). The combined organic layers were washed with water (3×200 mL). The organic layer was concentrated under reduced pressure. The residue was purified by reverse flash chromatography to afford the desired product (430 mg, 57%) as a white solid. ESI-MS m/z: 547.15 [M+H]$^+$.

Intermediate 28 Steps i & j

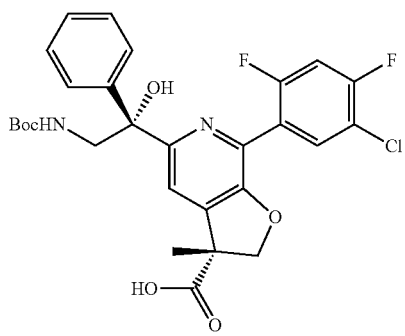 [SMILES: CC(C)(C)OC(=O)NC[C@@](O)(c1ccccc1)c1cc2c(c(-c3cc(Cl)c(F)cc3F)n1)OC[C@]2(C)C(=O)O]

A solution of the compound from step h (140 mg, 0.25 mmol), and DMP (271 mg, 0.64 mmol) in DCM (10 mL) was stirred for 12 hours at r.t. The resulting mixture was extracted with DCM (3×20 mL). The combined organic layers were washed with water (3×20 mL). The organic layer was concentrated under reduced pressure to afford the desired crude product as a white oil. ESI-MS m/z: 545.30 [M+H]$^+$.

A solution of the compound from step i (230 mg, 0.42 mmol), 2-methyl-2-butene (354 mg, 5.04 mmol) in t-BuOH: H$_2$O (2:1) was added NaClO$_2$ (380 mg, 4.20 mmol) and NaH$_2$PO$_4$ (504 mg, 4.20 mmol) in water dropwise at room temperature and stirred for 2 hours. The aqueous layer was extracted with EtOAc (3×10 mL), The resulting mixture was concentrated under reduced pressure. The crude product was used in the next step directly without further purification. ESI-MS m/z: 561.30 [M+H]⁺.

Intermediate 29

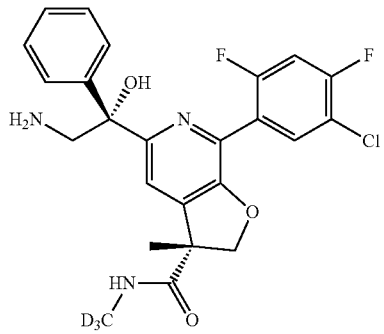 [SMILES: [2H]C([2H])([2H])NC(=O)[C@@]1(C)COc2c1cc([C@@](O)(CN)c1ccccc1)nc2-c1cc(Cl)c(F)cc1F]

Intermediate 29 Steps a and b

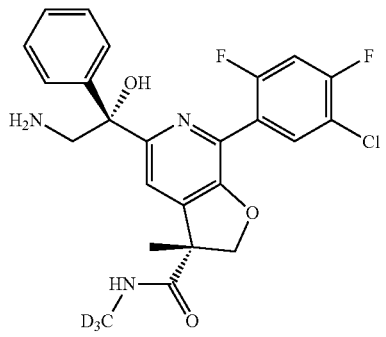 [SMILES: [2H]C([2H])([2H])NC(=O)[C@@]1(C)COc2c1cc([C@@](O)(CN)c1ccccc1)nc2-c1cc(Cl)c(F)cc1F]

A solution of Intermediate 28 above (120 mg, 0.21 mmol), deuteromethyl amine (8 mg, 0.21 mmol), HATU (81 mg, 0.21 mmol) and DIEA (83 mg, 0.64 mmol) in DMF (1 mL) was stirred for 2 hours at room temperature. The residue was purified by prep-TLC (PE/EA 1:1) to afford the desired product (80 mg, 64%) as a white solid. ESI-MS m/z: 577.15 [M+H]⁺. A solution of the compound from step a (120 mg, 2.66 mmol) in HCl in 1,4-dioxane (2 mL) stirred for 1 h at r.t. The residue was purified by prep-TLC (DCM/NH₃ in MeOH=15/1) to afford the desired product (36.8 mg, 54%) as a white solid. ESI-MS m/z: 477.15 [M+H]⁺.

Intermediate 30

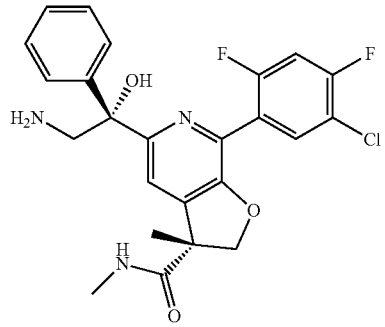 [SMILES: CNC(=O)[C@@]1(C)COc2c1cc([C@@](O)(CN)c1ccccc1)nc2-c1cc(Cl)c(F)cc1F]

The above compound was prepared with the similar method to Intermediate 29 above, to afford the amino alcohol. (23 mg). ESI-MS m/z: 474.15 [M+H]⁺.

Intermediate 31

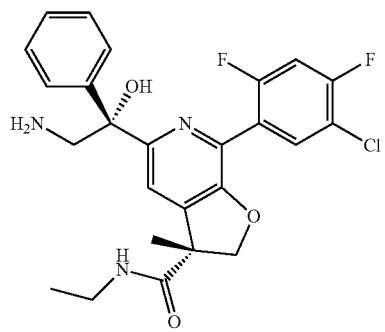 [SMILES: CCNC(=O)[C@@]1(C)COc2c1cc([C@@](O)(CN)c1ccccc1)nc2-c1cc(Cl)c(F)cc1F]

The above compound was prepared with the similar method Intermediate 29 above, to afford the amino alcohol.

Intermediate 32

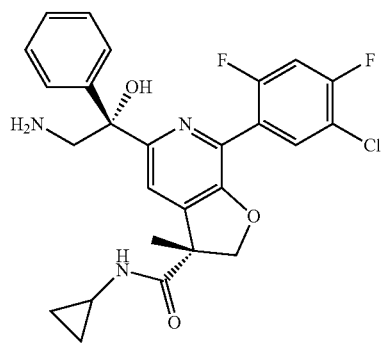 [SMILES: C[C@]1(C(=O)NC2CC2)COc2c1cc([C@@](O)(CN)c1ccccc1)nc2-c1cc(Cl)c(F)cc1F]

The above compound was prepared with the similar method to Intermediate 29 above, to afford the amino alcohol.

Intermediate 33

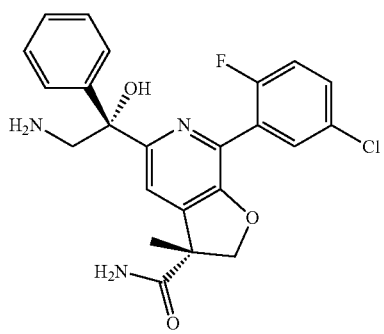 [SMILES: C[C@]1(C(N)=O)COc2c1cc([C@@](O)(CN)c1ccccc1)nc2-c1cc(Cl)ccc1F]

The above compound was prepared with the similar method to Intermediate 9, to afford the amino alcohol. (150 mg, 68%). ESI-MS m/z: 442.00 [M+H]$^+$.

Intermediate 34

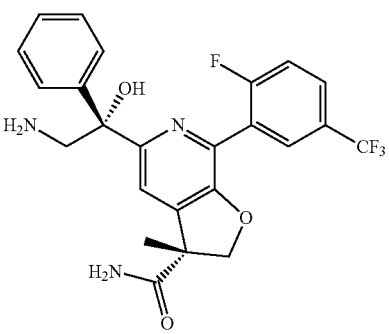 [SMILES: C[C@]1(C(N)=O)COc2c1cc([C@@](O)(CN)c1ccccc1)nc2-c1cc(C(F)(F)F)ccc1F]

The above compound was prepared with the similar method to Intermediate 9, to afford the amino alcohol. (46.1 mg, 19%). ESI-MS m/z: 476.25 [M+H]$^+$.

Intermediate 35

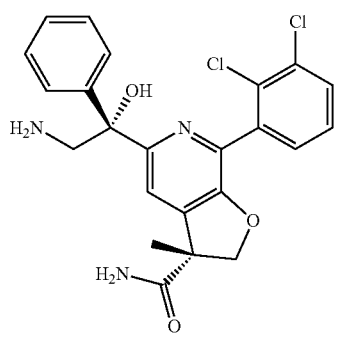 [SMILES: C[C@]1(C(N)=O)COc2c1cc([C@@](O)(CN)c1ccccc1)nc2-c1cccc(Cl)c1Cl]

The above compound was prepared with the similar method to Intermediate 9, to afford the amino alcohol (113.6 mg, 48%). ESI-MS m/z: 458.10 [M+H]$^+$.

Intermediate 36

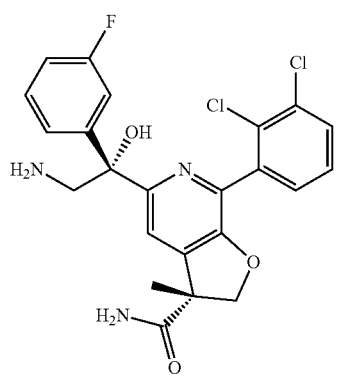 [SMILES: C[C@]1(C(N)=O)COc2c1cc([C@@](O)(CN)c1cccc(F)c1)nc2-c1cccc(Cl)c1Cl]

The above compound was prepared with the similar method to Intermediate 9, to afford the amino alcohol (89.5 mg, 60%). ESI-MS m/z: 476.00 [M+H]$^+$.

Intermediate 37

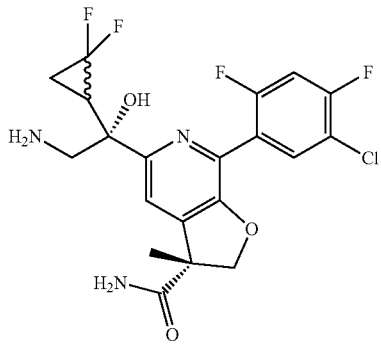 [SMILES: C[C@]1(C(N)=O)COc2c1cc([C@@](O)(CN)C1CC1(F)F)nc2-c1cc(Cl)c(F)cc1F]

The above compound was prepared with the similar method to Intermediate 9, to afford the amino alcohol as a mixture of diastereomers. Diastereomers were separated after subsequent amide coupling and the stereochemistry was arbitrarily assigned (370 mg, 78%). ESI-MS m/z: 460.05 [M+H]$^+$.

Intermediate 38

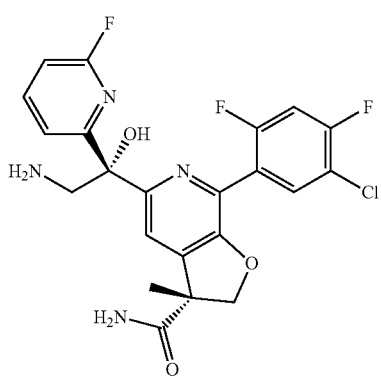 [SMILES: C[C@]1(C(N)=O)COc2c1cc([C@@](O)(CN)c1cccc(F)n1)nc2-c1cc(Cl)c(F)cc1F]

Intermediate 38 Step a

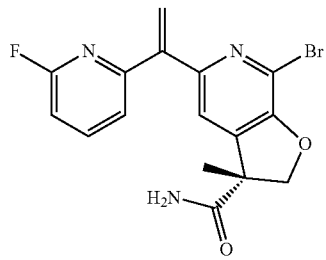 [SMILES: C=C(c1cccc(F)n1)c1cc2c(c(Br)n1)OC[C@]2(C)C(N)=O]

(1-(6-fluoropyridin-2-yl)vinyl)diisobutylaluminum was prepared according to literature procedure in Gao, F. et. al. *J. Am. Chem. Soc.* 2010, 132, 32, 10961-10963. In a vial, (R)-7-bromo-5-iodo-3-methyl-2,3-dihydrofuro[2,3-c]pyridine-3-carboxamide (1.1 g, 2.87 mmol), xantphos (0.332 g, 0.574 mmol), and palladium(II) chloride (0.051 g, 0.287 mmol) were dissolved in DCE (3.59 ml). (1-(6-fluoropyridin-2-yl)vinyl)diisobutylaluminum (5.22 ml, 5.74 mmol) was added as a solution in THF. The vial was heated to 80° C. and monitored by LCMS. Water added and aqueous layer washed with EtOAc. Combined organic layer dried over MgSO4 and concentrated. Purified by silica gel chromatography, 0-70% EtOAc/cHex to afford the title compound (603 mg, 55.5%). ESI-MS m/z: 378.00/380.00 [M+H]⁺.

Intermediate 38 Steps b-e

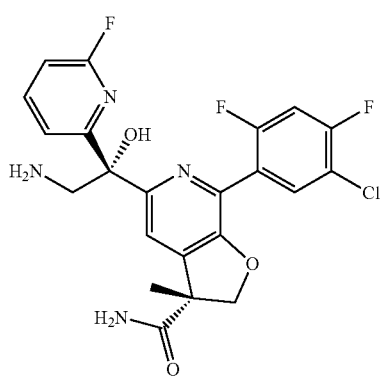 [SMILES: C[C@]1(C(N)=O)COc2c1cc([C@@](O)(CN)c1cccc(F)n1)nc2-c1cc(Cl)c(F)cc1F]

The above compound was prepared with the similar method to Intermediate 9, and the crude material was purified by prep-TLC (silica gel, MeOH in DCM with NH₃) to afford the desired product (200 mg, 81%) as a white solid. ESI-MS m/z: 479.00 [M+H]⁺.

Intermediate 39

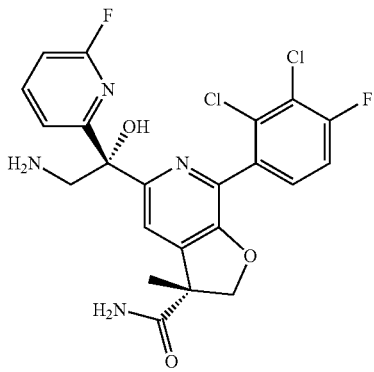 [SMILES: C[C@]1(C(N)=O)COc2c1cc([C@@](O)(CN)c1cccc(F)n1)nc2-c1ccc(F)c(Cl)c1Cl]

The above compound was prepared with the similar method to Intermediate 38 to afford the desired product (13 mg, 62%) as a white solid. ESI-MS m/z: 495.09 [M+H]⁺.

Intermediate 40

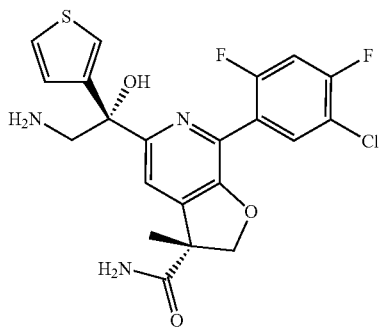 [SMILES: C[C@]1(C(N)=O)COc2c1cc([C@@](O)(CN)c1ccsc1)nc2-c1cc(Cl)c(F)cc1F]

The above compound was prepared with the similar method to Intermediate 9, and the crude material was purified by prep-TLC (silica gel, MeOH in DCM with NH₃) to afford the desired product (475 mg, 71%) as a white solid. ESI-MS m/z: 466.31 [M+H]⁺.

Intermediate 41

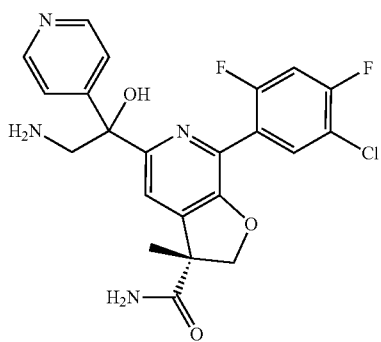 [SMILES: C[C@]1(C(N)=O)COc2c1cc(C(O)(CN)c1ccncc1)nc2-c1cc(Cl)c(F)cc1F]

Intermediate 41 Step a

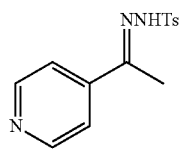

A solution of 4-acetylpyridine (2 g, 16.50 mmol) and 4-toluenesulfonyl hydrazide (4.61 g, 24.70 mmol) in $CH_3OH$ (20 mL) was stirred for 2 hours at 70° C. The mixture was filtered and washed to afford the desired precipitated solids (2 g, 41%) as a white solid. ESI-MS m/z: 290.00 [M+H]$^+$.

Intermediate 41 Step b

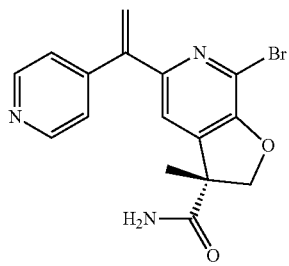 [SMILES: C=C(c1ccncc1)c1cc2c(c(Br)n1)OC[C@]2(C)C(N)=O]

A solution of the compound from step a (566 mg, 1.96 mmol), Pd(PPh$_3$)$_2$Cl$_2$ (91 mg, 0.13 mmol), LiO$^t$Bu (309 mg, 4.83 mmol) and (R)-7-bromo-5-iodo-3-methyl-2,3-dihydro-furo[2,3-c]pyridine-3-carboxamide (500 mg, 1.30 mmol) in dioxane (5 mL) was stirred for overnight at 90° C. under nitrogen atmosphere. The resulting mixture was extracted, concentrated and purified by silica gel column chromatography to afford the desired compound (450 mg crude) as a yellow solid. ESI-MS m/z: 360.00 [M+H]$^+$.

Intermediate 41 Steps c, d, e & f

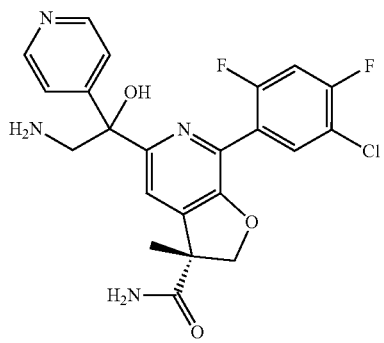 [SMILES: C[C@]1(C(N)=O)COc2c1cc(C(O)(CN)c1ccncc1)nc2-c1cc(Cl)c(F)cc1F]

The amino alcohol was synthesize in four analogous steps (cross-coupling, dihydroxylation, tosylation, amination) to Intermediate 9 to afford the title compound (50 mg, 74%) as a white solid. ESI-MS m/z: 460.95 [M+H]$^+$.

The diastereomers were separated after subsequent amide coupling using prep-HPLC.

Intermediate 42

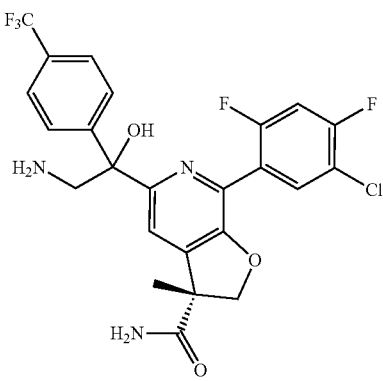 [SMILES: C[C@]1(C(N)=O)COc2c1cc(C(O)(CN)c1ccc(C(F)(F)F)cc1)nc2-c1cc(Cl)c(F)cc1F]

Intermediate 42 Step a

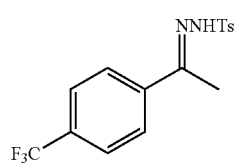

A mixture of p-(trifluoromethyl)acetophenone (1 g, 5.32 mmol) and TsNHNH$_2$ (1.48 g, 8.00 mmol) in MeOH (18 mL) was stirred for 5 hours at 70° C. The reaction was monitored by TLC. The resulting mixture was concentrated under reduced pressure. The residue was purified by silica gel column chromatography, eluted with PE/EA (1:1) to afford the desired compound (1.75 g, 92%) as a white solid. ESI-MS m/z: 357.05 [M+H]$^+$.

Intermediate 42 Step b

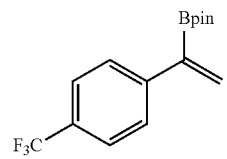

Into a 40 mL vial were added the compound from step a (1.29 g, 3.62 mmol), TMBQ (1.63 g, 10.86 mmol), bis (pinacolato)diboron (1.38 g, 5.43 mmol), Pd(OAc)$_2$ (41 mg, 0.18 mmol), PPh$_3$ (95 mg, 0.36 mmol) and NaH (261 mg, 10.86 mmol) at room temperature. After degassed and filled with N$_2$, toluene (40 mL) was added to the vial. The reaction mixture was reacted for overnight at 90° C. The reaction was monitored by LCMS. The resulting mixture was filtered, the filter cake was washed with ethyl acetate. The filtrate was concentrated under reduced pressure. The residue was purified by silica gel column chromatography, eluted with PE/EA (1:1) to afford the desired compound (2.4 g) as a brown solid. $^1$H NMR (400 MHz, CDCl$_3$) δ 1.33 (s, 12H), 6.13 (s, 1H), 6.17 (d, J=2.7 Hz, 1H), 7.57 (s, 4H).

Intermediate 42 Step c

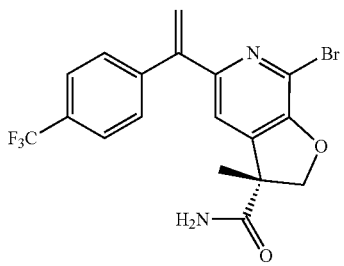 [SMILES: C=C(c1ccc(C(F)(F)F)cc1)c1cc2c(c(Br)n1)OC[C@]2(C)C(N)=O]

A solution of the compound from step b (778 mg, 2.61 mmol) in dioxane (8 mL) and H₂O (2 mL) was treated with (R)-7-bromo-5-iodo-3-methyl-2,3-dihydrofuro[2,3-c]pyridine-3-carboxamide (500 mg, 1.31 mmol), K₂CO₃ (361 mg, 2.61 mmol) and Pd(dppf)Cl₂CH₂Cl₂ (106 mg, 0.13 mmol) for 1 hr at 80° C. under nitrogen atmosphere. The reaction was monitored by LCMS. The resulting mixture was extracted with EtOAc. The combined organic layers were concentrated under reduced pressure. The residue was purified by reversed-phase flash chromatography to afford the desired compound (443 mg, 79%) as a brown oil. ESI-MS m/z: 427.00 [M+H]⁺.

Intermediate 42 Steps d, e, f & g

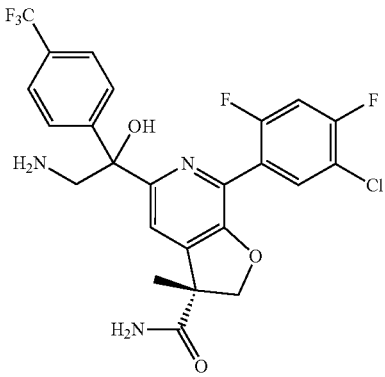 [SMILES: C[C@]1(C(N)=O)COc2c1cc(C(O)(CN)c1ccc(C(F)(F)F)cc1)nc2-c1cc(Cl)c(F)cc1F]

The amino alcohol was synthesized in four analogous steps (cross-coupling, racemic dihydroxylation, tosylation, amination) to Intermediate 9 to afford the title compound (208 mg, 90%) as a white solid. ESI-MS m/z: 528.10 [M+H]⁺.

The diastereomers were separated after subsequent amide coupling using prep-TLC.

Intermediate 43

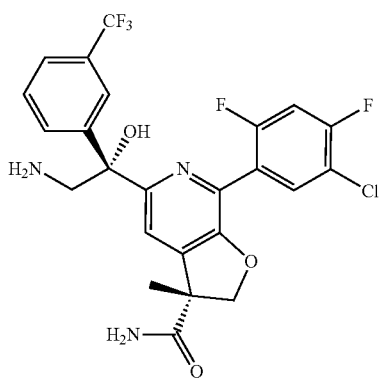 [SMILES: C[C@]1(C(N)=O)COc2c1cc([C@@](O)(CN)c1cccc(C(F)(F)F)c1)nc2-c1cc(Cl)c(F)cc1F]

The amino alcohol was synthesized in an analogous sequence to Intermediate 42 using ADMIX-β for a selective dihydroxylation to afford the title compound (181.4 mg, 66%) as a white solid. ESI-MS m/z: 528.10 [M+H]⁺.

Intermediate 44

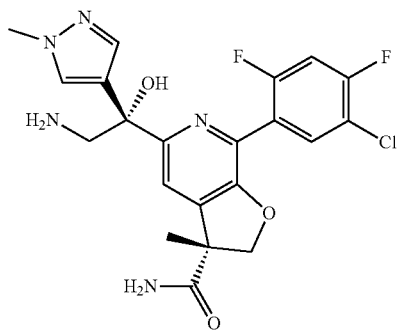 [SMILES: Cn1cc([C@](O)(CN)c2cc3c(c(-c4cc(Cl)c(F)cc4F)n2)OC[C@]3(C)C(N)=O)cn1]

The amino alcohol was synthesized in an analogous sequence to Intermediate 42 using ADMIX-β for a selective dihydroxylation to afford the title compound (10 mg, 23%) as a white solid. ESI-MS m/z: 464.30 [M+H]⁺.

Intermediate 45

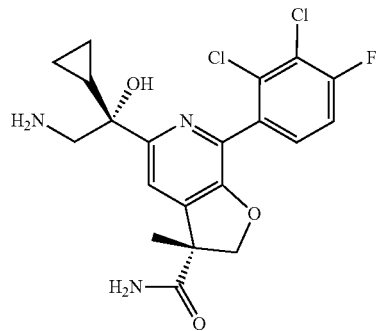 [SMILES: C[C@]1(C(N)=O)COc2c1cc([C@@](O)(CN)C1CC1)nc2-c1ccc(F)c(Cl)c1Cl]

Intermediate 45 Step a

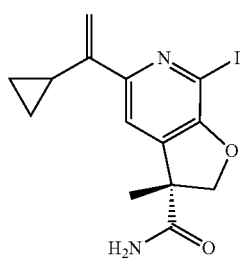 [SMILES: C=C(c1cc2c(c(I)n1)OC[C@]2(C)C(N)=O)C1CC1]

Dissolved (R)-7-bromo-5-(1-cyclopropylvinyl)-3-methyl-2,3-dihydrofuro[2,3-c]pyridine-3-carboxamide (1.42 g, 4.39 mmol, 1.00 equiv.) in 1,4-dioxane (22 mL) and sodium iodide (2.31 g, 15.4 mmol, 3.50 equiv.) was added. Began sparging the suspension with nitrogen gas, and added copper (I) iodide (167 mg, 0.879 mmol, 0.2 equiv.) and N,N'-dimethylethylenediamine (0.208 mL, 1.93 mmol, 0.4 equiv.). Continued sparging for an additional 5 minutes before affixing a reflux condenser to the flask and heating to 100° C. with stirring. After stirring for 2 hours at this temperature, the reaction mixture was cooled to room temperature and diluted with saturated aqueous sodium bicarbonate, water, and EtOAc. The layers were separated and the aqueous layer extracted with EtOAc (3×50 mL). The combined organic extracts were dried over sodium sulfate, filtered, and the filtrate was concentrated to a crude oil. This crude material was purified by automated flash chromatography on silica gel (0-100% EtOAc in cyclohexane) to afford the pure iodide product as a yellow foam (1.03 g, 63%). ESI-MS m/z: 371.178 [M+H]$^+$.

Intermediate 45 Step b

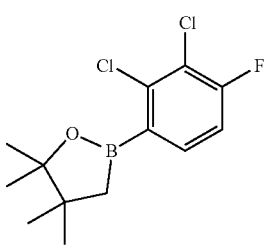

1-bromo-2,3-dichloro-4-fluorobenzene (4.74 g, 19.4 mmol) was dissolved in THF (97 ml) and the solution was cooled to −40° C. in a dry ice/acetone bath. Isopropylmagnesium chloride (2 M in THF, 10.7 ml, 21.4 mmol, 1.1 equiv.) was added and the resultant mixture was allowed to stir for one hour at that temperature. After that time, i-PrOB (pin) (4.76 ml, 23.3 mmol, 1.2 equiv.) was added. The reaction mixture was then warmed up to room temperature and allowed to stir. During this time, some solid began to precipitate. After 1 hour, the reaction was quenched with saturated aqueous sodium bicarbonate. The layers were separated, and the aqueous layer was extracted with EtOAc (3×50 mL). The combined organic extracts were washed with brine (1×50 mL), dried over sodium sulfate, filtered, and concentrated to afford the crude boronic ester as a crystalline white solid (5.65 g, 89%). The crude product contained ~8% pinacol by weight and was used without further purification (no m z for boronic ester detected).

Intermediate 45 Step c

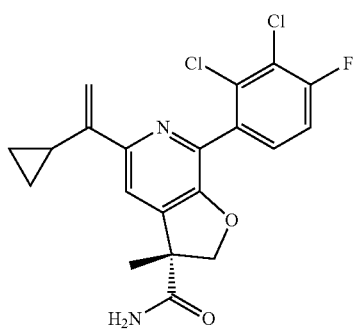 [SMILES: C=C(c1cc2c(c(-c3ccc(F)c(Cl)c3Cl)n1)OC[C@]2(C)C(N)=O)C1CC1]

Compound from step a (1.04 g, 2.81 mmol, 1.0 equiv.) was dissolved in 1,4-dioxane (11.2 mL) and K$_2$CO$_3$ (1.17 g, 8.43 mmol, 3.0 equiv.), Pd(dppf)Cl$_2$ (123 mg, 0.169 mmol, 0.06 equiv.) and boronic ester from step b (1.10 g, 3.79 mmol, 1.35 equiv.) were added. Water (2.8 mL) was added and the resultant biphasic suspension was sparged with nitrogen for 5 minutes. The vial was sealed and heated to 90° C. with stirring for one hour before being cooled to room temperature. The reaction mixture was diluted with water and EtOAc. The layers were separated and the aqueous layer extracted with EtOAc (3×50 mL). The combined organic extracts were dried over sodium sulfate, filtered, and the filtrate was concentrated to a crude oil. This crude material was purified by automated flash chromatography on silica gel (0-100% EtOAc in cyclohexane) to afford the pure product 5 as a yellow foam (940 mg, 82%). ESI-MS m/z: 407.156 [M+H]$^+$.

Intermediate 45 Steps d, e & f

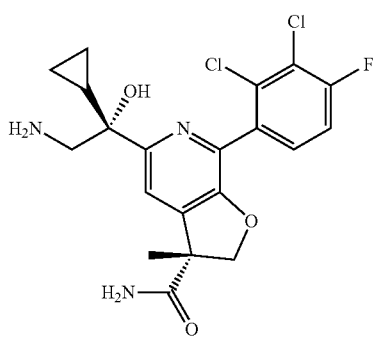 [SMILES: C[C@]1(C(N)=O)COc2c1cc([C@@](O)(CN)C1CC1)nc2-c1ccc(F)c(Cl)c1Cl]

The above compound was prepared with the similar steps to Intermediate 9 to afford the desired product (700 mg, 99%) as a white solid. ESI-MS m/z: 440.08 [M+H]$^+$.

Intermediate 46

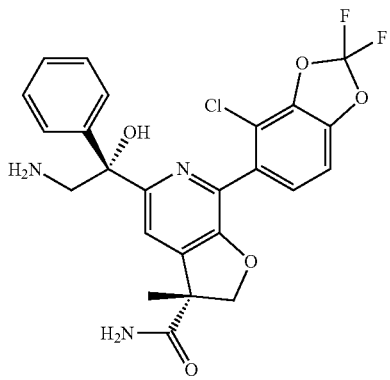 [SMILES: C[C@]1(C(N)=O)COc2c1cc([C@@](O)(CN)c1ccccc1)nc2-c1ccc2c(c1Cl)OC(F)(F)O2]

The above compound was prepared with the similar method to Intermediate 45 to afford the desired product (138 mg, 90%) as a white solid. ESI-MS m/z: 504.14 [M+H]$^+$.

Intermediate 47

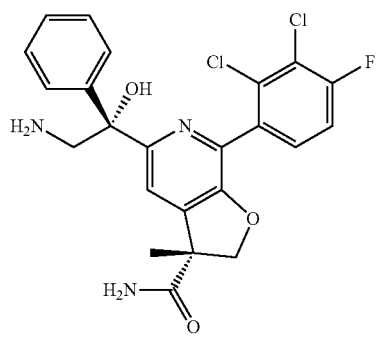 [SMILES: C[C@]1(C(N)=O)COc2c1cc([C@@](O)(CN)c1ccccc1)nc2-c1ccc(F)c(Cl)c1Cl]

The above compound was prepared with the similar method to Intermediate 45 to afford the desired product (417 mg, 99%) as a white solid. ESI-MS m/z: 476.17 [M+H]$^+$.

Intermediate 48

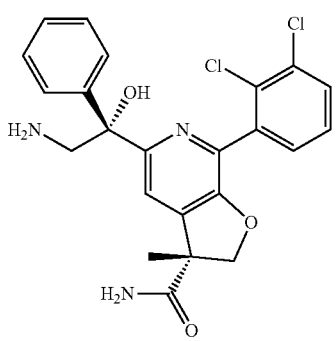 [SMILES: C[C@]1(C(N)=O)COc2c1cc([C@@](O)(CN)c1ccccc1)nc2-c1cccc(Cl)c1Cl]

The above compound was prepared with the similar method to Intermediate 45 to afford the desired product (222 mg, 93%) as a white solid. ESI-MS m/z: 458.22 [M+H]$^+$.

Intermediate 49

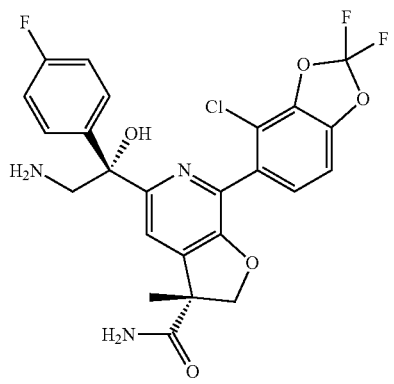 [SMILES: C[C@]1(C(N)=O)COc2c1cc([C@@](O)(CN)c1ccc(F)cc1)nc2-c1ccc2c(c1Cl)OC(F)(F)O2]

The above compound was prepared with the similar method to Intermediate 45 to afford the desired product (158 mg, 100%) as a white solid. ESI-MS m/z: 522.18 [M+H]$^+$.

Intermediate 50

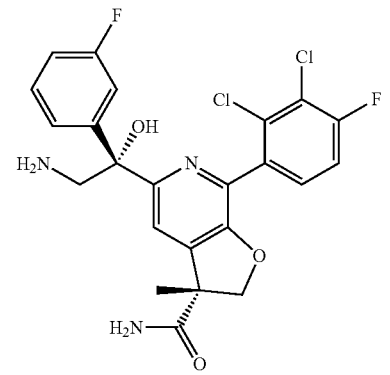 [SMILES: C[C@]1(C(N)=O)COc2c1cc([C@@](O)(CN)c1cccc(F)c1)nc2-c1ccc(F)c(Cl)c1Cl]

The above compound was prepared with the similar method to Intermediate 45 to afford the desired product (291 mg, 76%) as a white solid. ESI-MS m/z: 494.24 [M+H]$^+$.

Intermediate 51

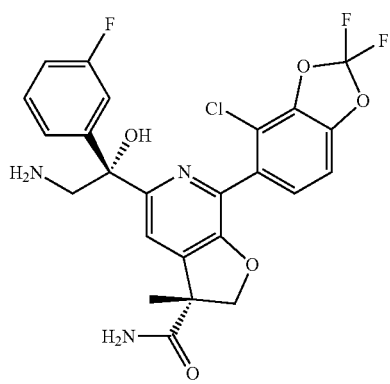 [SMILES: C[C@]1(C(N)=O)COc2c1cc([C@@](O)(CN)c1cccc(F)c1)nc2-c1ccc2c(c1Cl)OC(F)(F)O2]

The above compound was prepared with the similar method to Intermediate 45 to afford the desired product (158 mg, 100%) as a white solid. ESI-MS m/z: 522.18 [M+H]⁺.

Intermediate 52

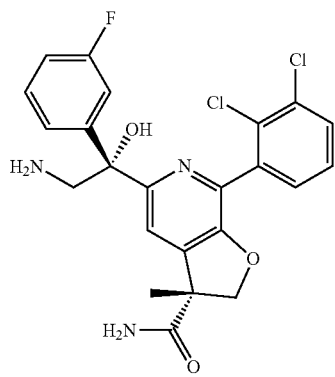 [SMILES: C[C@]1(C(N)=O)COc2c1cc([C@@](O)(CN)c1cccc(F)c1)nc2-c1cccc(Cl)c1Cl]

The above compound was prepared with the similar method to Intermediate 45 to afford the desired product (800 mg, 96%) as a white solid. ESI-MS m/z: 476.17 [M+H]⁺.

Intermediate 53

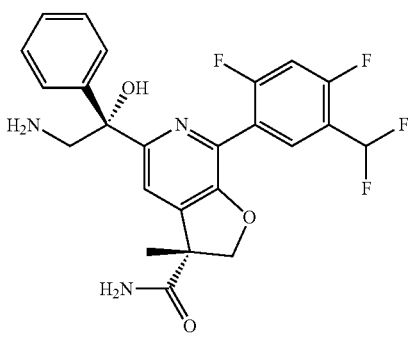 [SMILES: C[C@]1(C(N)=O)COc2c1cc([C@@](O)(CN)c1ccccc1)nc2-c1cc(C(F)F)c(F)cc1F]

The above compound was prepared with the similar steps to Intermediate 9 to afford the desired product (421 mg, 90%) as a white solid. ESI-MS m/z: 440.08 [M+H]⁺.

Intermediate 54

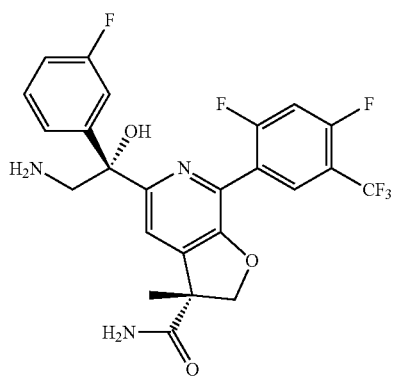 [SMILES: C[C@]1(C(N)=O)COc2c1cc([C@@](O)(CN)c1cccc(F)c1)nc2-c1cc(C(F)(F)F)c(F)cc1F]

The above compound was prepared with the similar steps to Intermediate 9 to afford the desired product (608 mg, 97%) as a white solid. ESI-MS m/z: 440.08 [M+H]⁺.

Intermediate 55

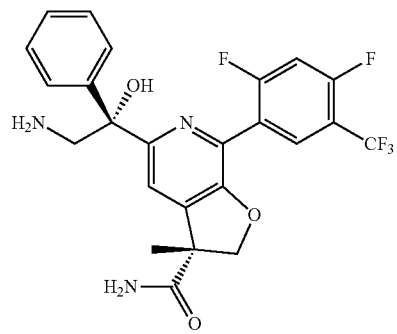 [SMILES: C[C@]1(C(N)=O)COc2c1cc([C@@](O)(CN)c1ccccc1)nc2-c1cc(C(F)(F)F)c(F)cc1F]

The above compound was prepared with the similar steps to Intermediate 9 to afford the desired product (560 mg, 93%) as a white solid. ESI-MS m/z: 495.45 [M+H]⁺.

Intermediate 56

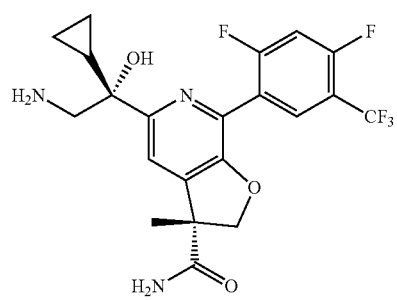 [SMILES: C[C@]1(C(N)=O)COc2c1cc([C@@](O)(CN)C1CC1)nc2-c1cc(C(F)(F)F)c(F)cc1F]

The above compound was prepared in an analogous fashion to Intermediate 9 to afford the desired amino alcohol as an off-white solid (689 mg, 94%) ESI-MS m/z: 459.44 [M+H]⁺.

Intermediate 58

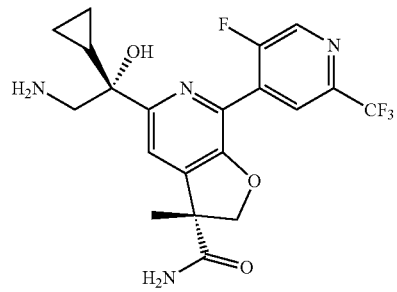 [SMILES: C[C@]1(C(N)=O)COc2c1cc([C@@](O)(CN)C1CC1)nc2-c1cc(C(F)(F)F)ncc1F]

The above compound was prepared in an analogous fashion to Intermediate 9 to afford the desired amino alcohol as an off-white solid (293 mg, 100%) ESI-MS m/z: 441.34 [M+H]⁺.

The following Table 3 contains examples that were prepared with the similar method to Example 1. The majority of compounds were purified by prep-HPLC (ACN/H₂O, 20-90%, 25 min), and some were purified by automated column chromatography (silica gel). The aryl boronic ester starting materials and aryl acid amide coupling partners were prepared according to Intermediates 1-58, or by analogous procedures with slight modifications and also prepared according to procedures found in U.S. Pat. No. 11,572,367.

TABLE 3

| Example | Structure | MS+ m/z |
|---|---|---|
| 79 | 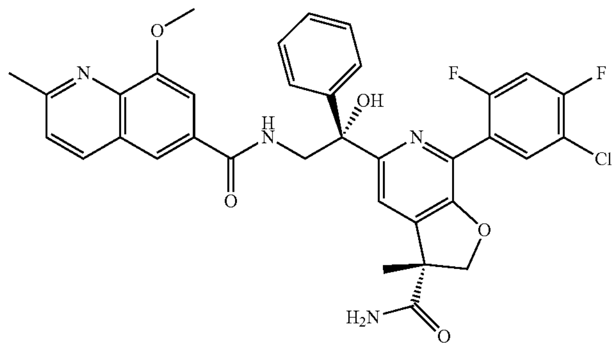 [SMILES: COc1cc(C(=O)NC[C@@](O)(c2ccccc2)c2cc3c(c(-c4cc(Cl)c(F)cc4F)n2)OC[C@]3(C)C(N)=O)cc2ccc(C)nc12] | 659.13 |
| 80 | 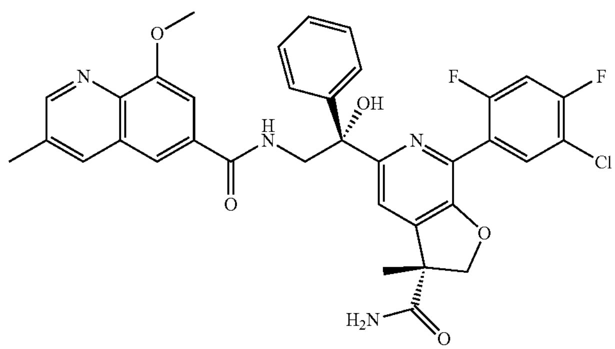 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C)cnc12] | 659.19 |
| 81 | 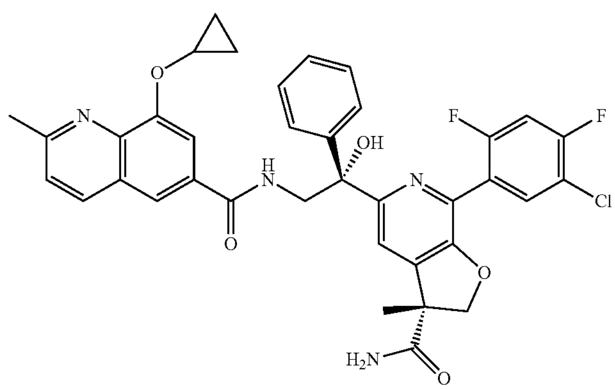 [SMILES: Cc1ccc2cc(C(=O)NC[C@@](O)(c3ccccc3)c3cc4c(c(-c5cc(Cl)c(F)cc5F)n3)OC[C@]4(C)C(N)=O)cc(OC3CC3)c2n1] | 680.45 |
| 82 | 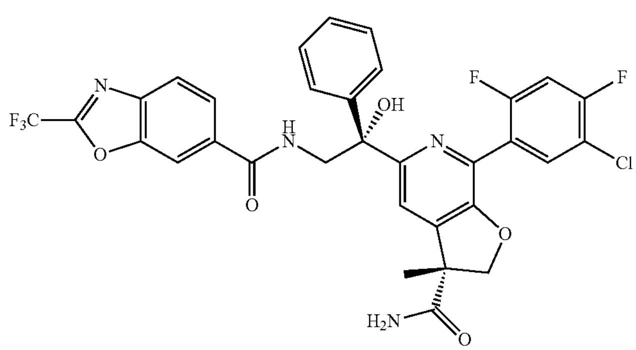 [SMILES: C[C@]1(C(N)=O)COc2c1cc([C@@](O)(CNC(=O)c1ccc3nc(C(F)(F)F)oc3c1)c1ccccc1)nc2-c1cc(Cl)c(F)cc1F] | 673.46 |

TABLE 3-continued

| Example | Structure | MS+ m/z |
|---|---|---|
| 83 | 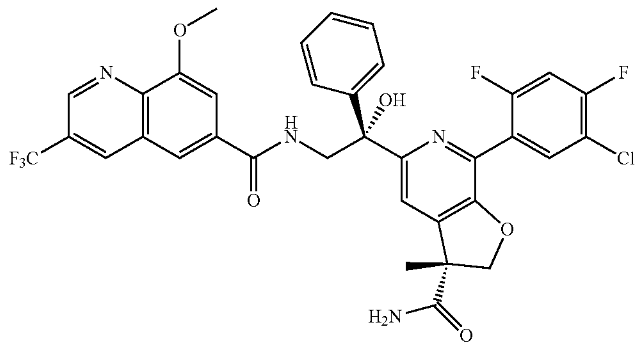 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C(F)(F)F)cnc12] | 713.49 |
| 84 | 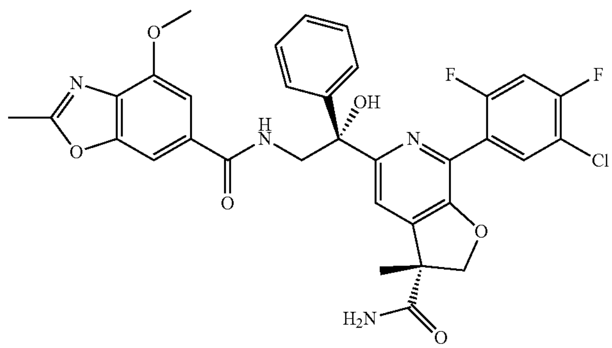 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C)nc12] | 649.47 |
| 85 | 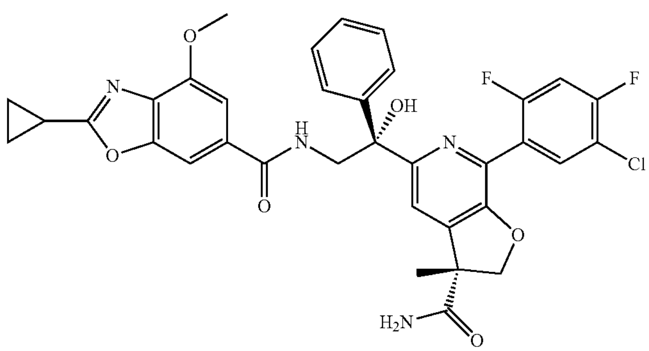 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C3CC3)nc12] | 675.54 |
| 86 | 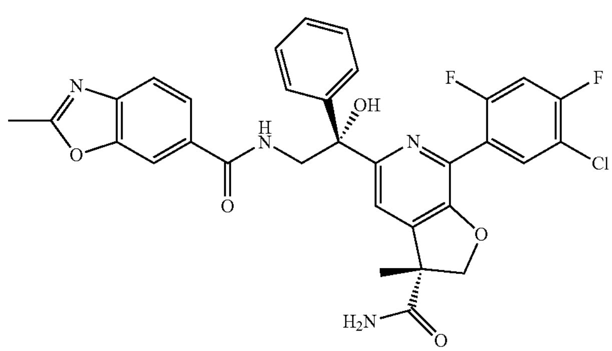 [SMILES: Cc1nc2ccc(C(=O)NC[C@@](O)(c3ccccc3)c3cc4c(c(-c5cc(Cl)c(F)cc5F)n3)OC[C@]4(C)C(N)=O)cc2o1] | 619.42 |

TABLE 3-continued

| Example | Structure | MS+ m/z |
|---|---|---|
| 87 | 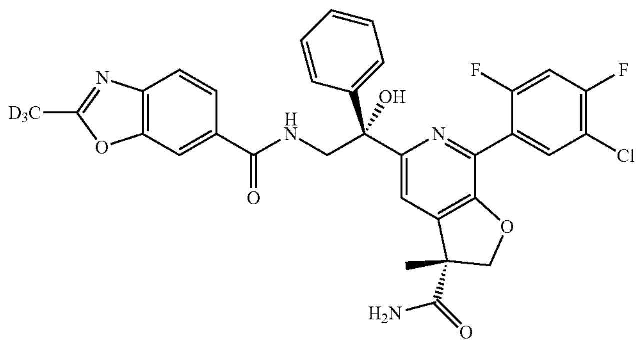 [SMILES: [2H]C([2H])([2H])c1nc2ccc(C(=O)NC[C@@](O)(c3ccccc3)c3cc4c(c(-c5cc(Cl)c(F)cc5F)n3)OC[C@]4(C)C(N)=O)cc2o1] | 622.44 |
| 88 | 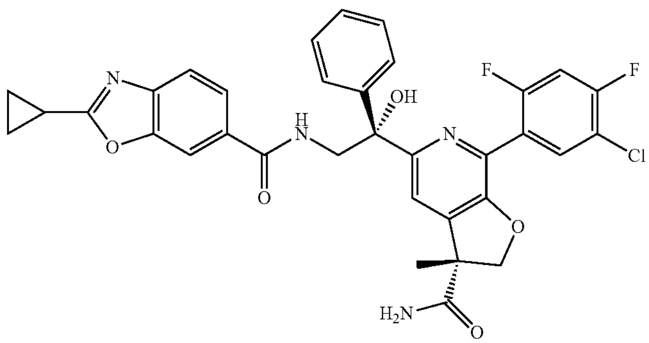 [SMILES: C[C@]1(C(N)=O)COc2c1cc([C@@](O)(CNC(=O)c1ccc3nc(C4CC4)oc3c1)c1ccccc1)nc2-c1cc(Cl)c(F)cc1F] | 645.42 |
| 89 | 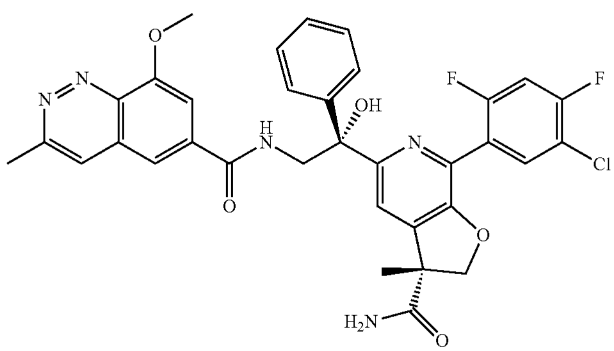 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C)nnc12] | 660.44 |
| 90 | 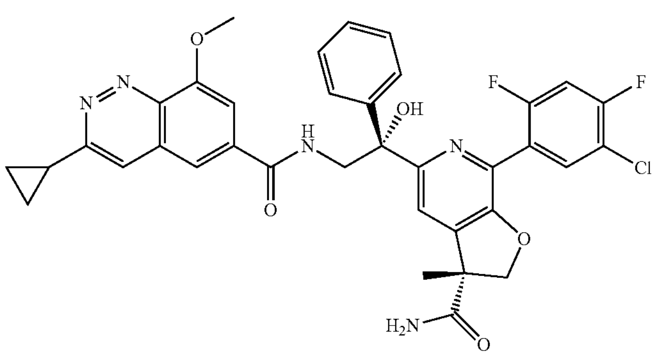 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C3CC3)nnc12] | 686.50 |

TABLE 3-continued

| Example | Structure | MS+ m/z |
|---|---|---|
| 93 | 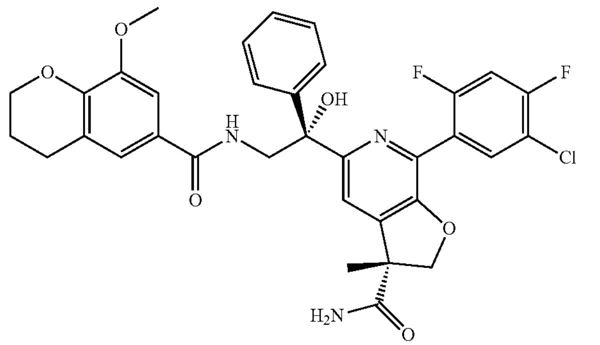 [SMILES: COc1cc(C(=O)NC[C@@](O)(c2ccccc2)c2cc3c(c(-c4cc(Cl)c(F)cc4F)n2)OC[C@]3(C)C(N)=O)cc2c1OCCC2] | 650.40 |
| 94 | 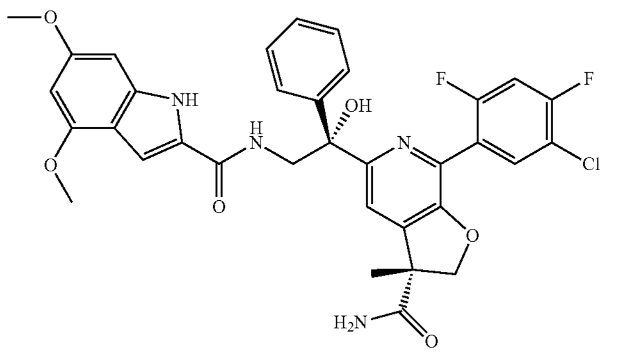 [SMILES: COc1cc(OC)c2cc(C(=O)NC[C@@](O)(c3ccccc3)c3cc4c(c(-c5cc(Cl)c(F)cc5F)n3)OC[C@]4(C)C(N)=O)[nH]c2c1] | 663.35 |
| 95 | 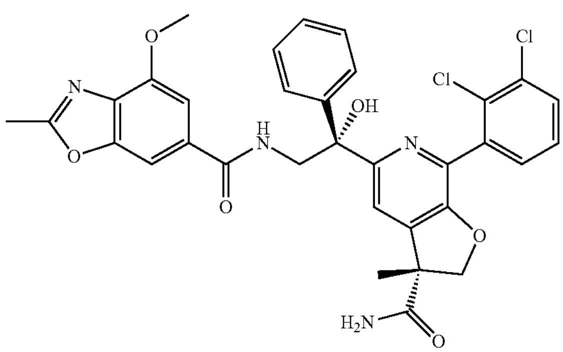 [SMILES: COc1cc(C(=O)NC[C@@](O)(c2ccccc2)c2cc3c(c(-c4cccc(Cl)c4Cl)n2)OC[C@]3(C)C(N)=O)cc2oc(C)nc12] | 647.30 |
| 96 | 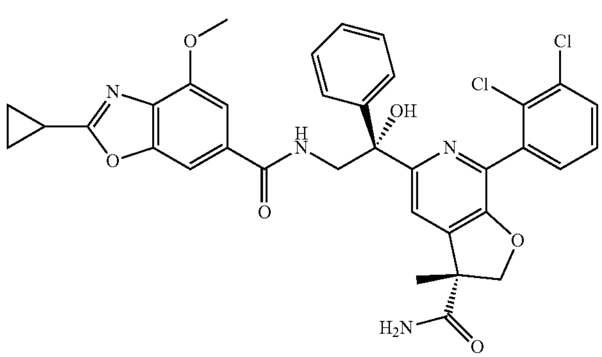 [SMILES: COc1cc(C(=O)NC[C@@](O)(c2ccccc2)c2cc3c(c(-c4cccc(Cl)c4Cl)n2)OC[C@]3(C)C(N)=O)cc2oc(C3CC3)nc12] | 673.28 |

TABLE 3-continued

| Example | Structure | MS+ m/z |
|---|---|---|
| 97 | 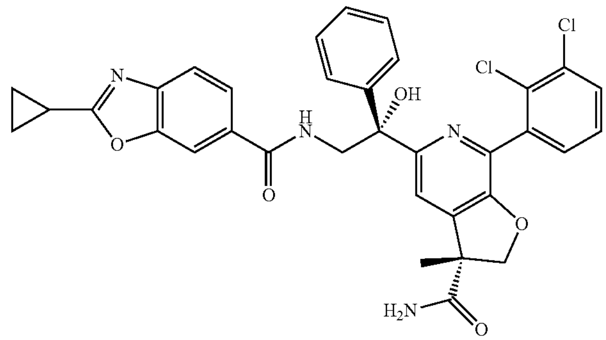 [SMILES: C[C@]1(C(N)=O)COc2c1cc([C@@](O)(CNC(=O)c1ccc3nc(C4CC4)oc3c1)c1ccccc1)nc2-c1cccc(Cl)c1Cl] | 643.20 |
| 98 | 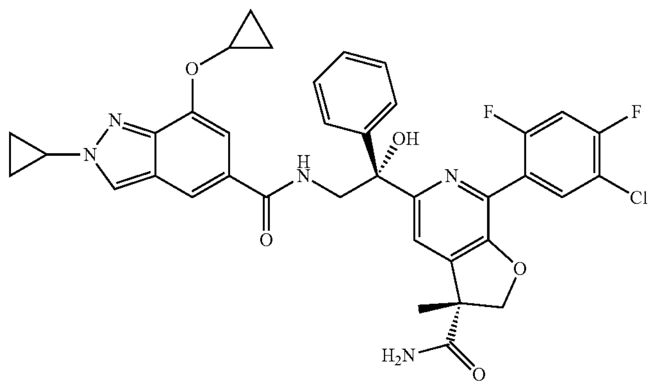 [SMILES: C[C@]1(C(N)=O)COc2c1cc([C@@](O)(CNC(=O)c1cc(OC3CC3)c3nn(C4CC4)cc3c1)c1ccccc1)nc2-c1cc(Cl)c(F)cc1F] | 700.39 |
| 99 | 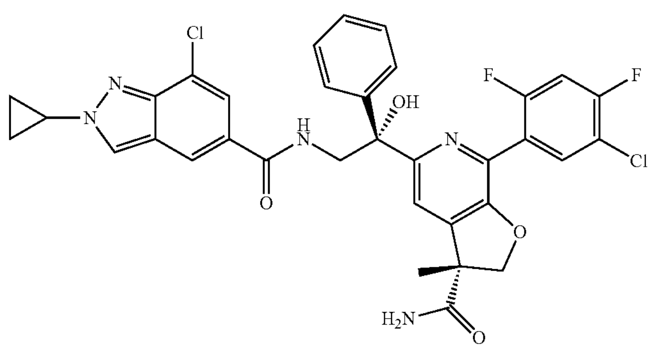 [SMILES: C[C@]1(C(N)=O)COc2c1cc([C@@](O)(CNC(=O)c1cc(Cl)c3nn(C4CC4)cc3c1)c1ccccc1)nc2-c1cc(Cl)c(F)cc1F] | 678.18 |
| 100 | 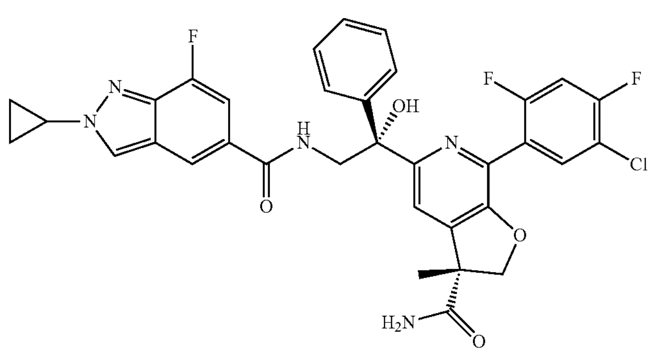 [SMILES: C[C@]1(C(N)=O)COc2c1cc([C@@](O)(CNC(=O)c1cc(F)c3nn(C4CC4)cc3c1)c1ccccc1)nc2-c1cc(Cl)c(F)cc1F] | 662.33 |

TABLE 3-continued

| Example | Structure | MS+ m/z |
|---------|-----------|---------|
| 101 | 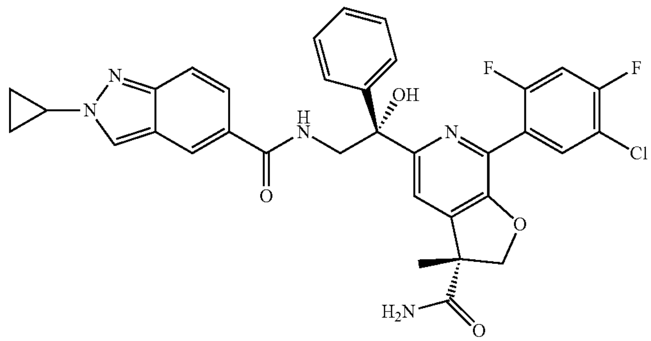 [SMILES: C[C@]1(C(N)=O)COc2c1cc([C@@](O)(CNC(=O)c1ccc3nn(C4CC4)cc3c1)c1ccccc1)nc2-c1cc(Cl)c(F)cc1F] | 644.38 |
| 102 | 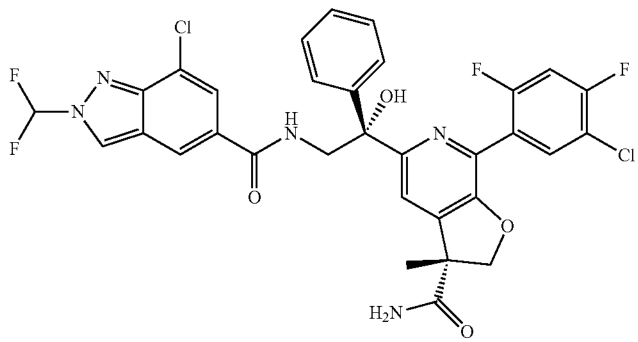 [SMILES: C[C@]1(C(N)=O)COc2c1cc([C@@](O)(CNC(=O)c1cc(Cl)c3nn(C(F)F)cc3c1)c1ccccc1)nc2-c1cc(Cl)c(F)cc1F] | 688.20 |
| 109 | 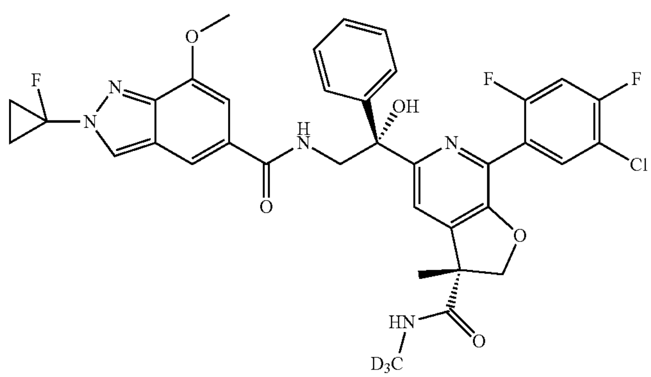 [SMILES: [2H]C([2H])([2H])NC(=O)[C@@]1(C)COc2c1cc([C@@](O)(CNC(=O)c1cc(OC)c3nn(C4(F)CC4)cc3c1)c1ccccc1)nc2-c1cc(Cl)c(F)cc1F] | 709.53 |
| 110 | 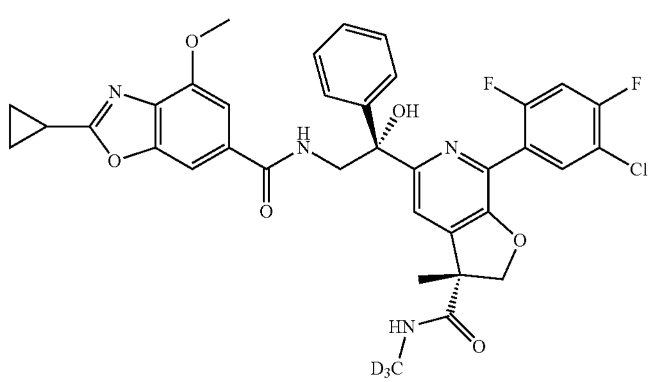 [SMILES: [2H]C([2H])([2H])NC(=O)[C@@]1(C)COc2c1cc([C@@](O)(CNC(=O)c1cc(OC)c3nc(C4CC4)oc3c1)c1ccccc1)nc2-c1cc(Cl)c(F)cc1F] | 692.53 |

TABLE 3-continued

| Example | Structure | MS+ m/z |
|---|---|---|
| 113 | 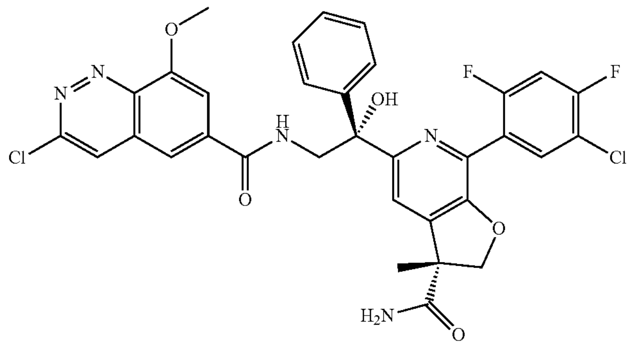 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)nnc12] | 680.20 |
| 115 | 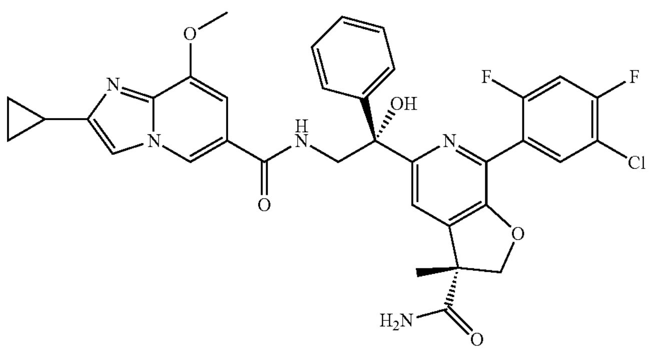 [SMILES: COc1cc(C(=O)NC[C@@](O)(c2ccccc2)c2cc3c(c(-c4cc(Cl)c(F)cc4F)n2)OC[C@]3(C)C(N)=O)cn2cc(C3CC3)nc12] | 674.42 |
| 117 | 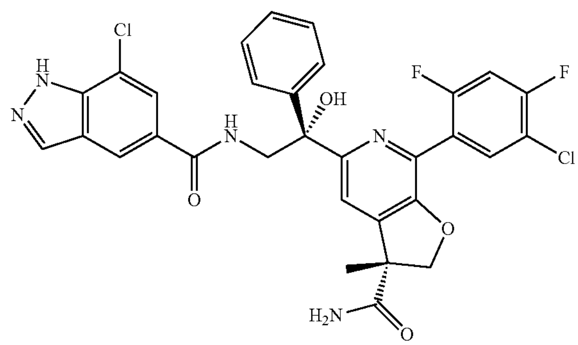 [SMILES: C[C@]1(C(N)=O)COc2c1cc([C@@](O)(CNC(=O)c1cc(Cl)c3[nH]ncc3c1)c1ccccc1)nc2-c1cc(Cl)c(F)cc1F] | 638.11 |
| 118 | 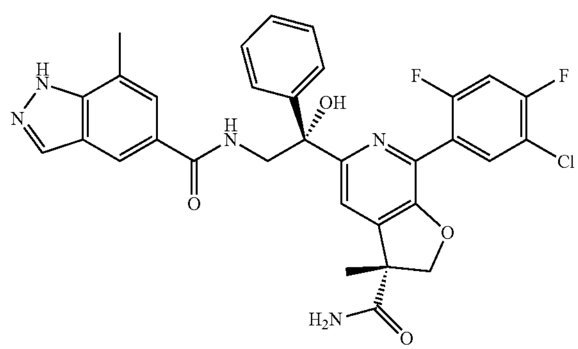 [SMILES: Cc1cc(C(=O)NC[C@@](O)(c2ccccc2)c2cc3c(c(-c4cc(Cl)c(F)cc4F)n2)OC[C@]3(C)C(N)=O)cc2cn[nH]c12] | 618.17 |

TABLE 3-continued

| Example | Structure | MS+ m/z |
|---------|-----------|---------|
| 130 | 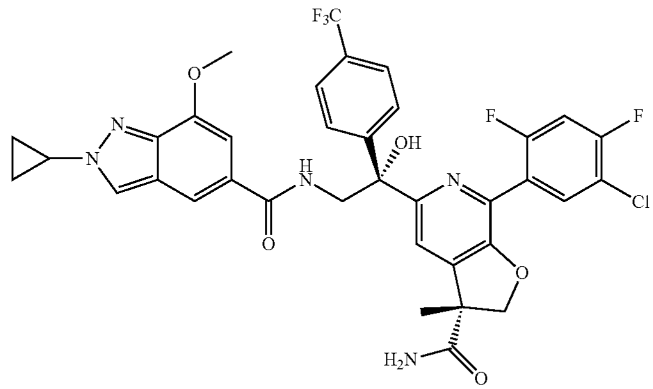 [SMILES: COc1cc(C(=O)NC[C@@](O)(c2ccc(C(F)(F)F)cc2)c2cc3c(c(-c4cc(Cl)c(F)cc4F)n2)OC[C@]3(C)C(N)=O)cc2cn(C3CC3)nc12] | 741.95 |
| 131 | 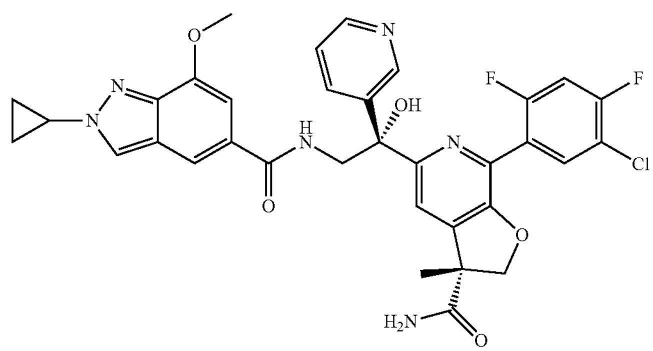 [SMILES: COc1cc(C(=O)NC[C@@](O)(c2cccnc2)c2cc3c(c(-c4cc(Cl)c(F)cc4F)n2)OC[C@]3(C)C(N)=O)cc2cn(C3CC3)nc12] | 675.15 |
| 132 | 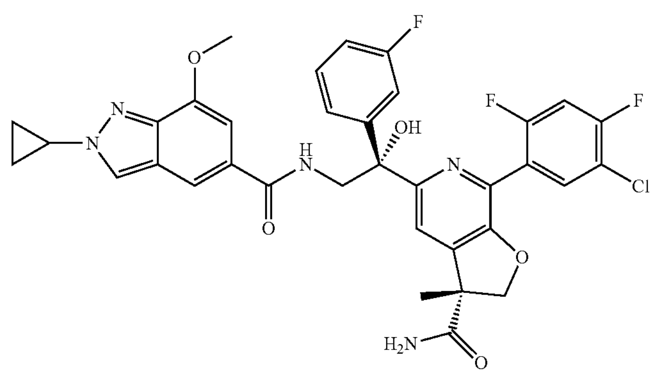 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cn(C3CC3)nc12] | 692.40 |
| 133 | 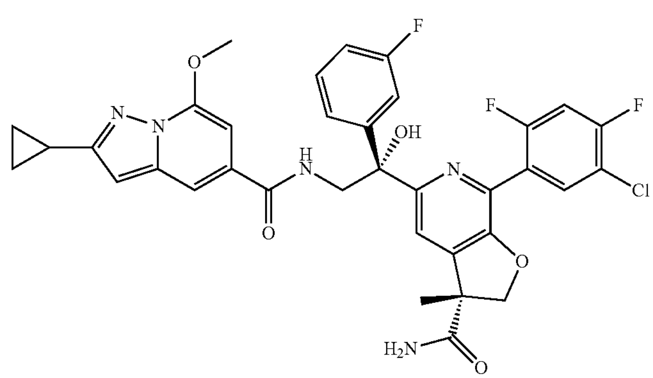 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cc(C3CC3)nn12] | 692.40 |

TABLE 3-continued

| Example | Structure | MS+ m/z |
|---|---|---|
| 134 | 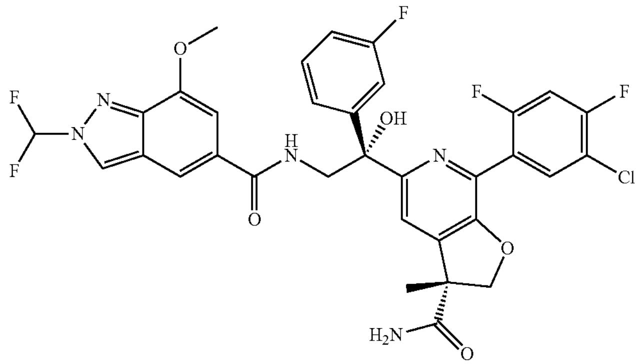 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cn(C(F)F)nc12] | 702.40 |
| 135 | 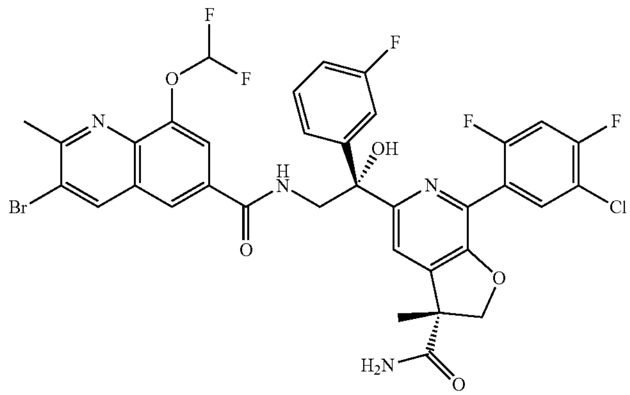 [SMILES: Cc1nc2c(OC(F)F)cc(C(=O)NC[C@@](O)(c3cccc(F)c3)c3cc4c(c(-c5cc(Cl)c(F)cc5F)n3)OC[C@]4(C)C(N)=O)cc2cc1Br] | 793.35 |
| 136 | 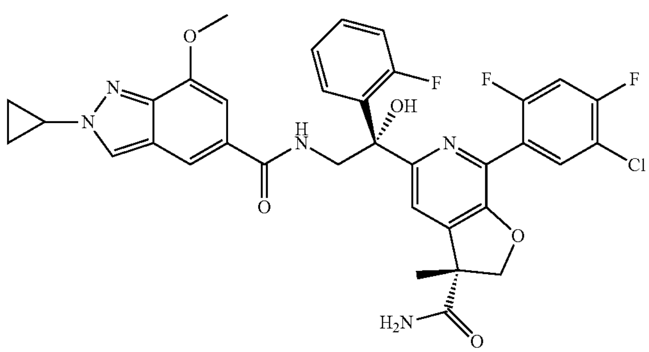 [SMILES: COc1cc(C(=O)NC[C@](O)(c2cc3c(c(-c4cc(Cl)c(F)cc4F)n2)OC[C@]3(C)C(N)=O)c2ccccc2F)cc2cn(C3CC3)nc12] | 692.10 |
| 137 | 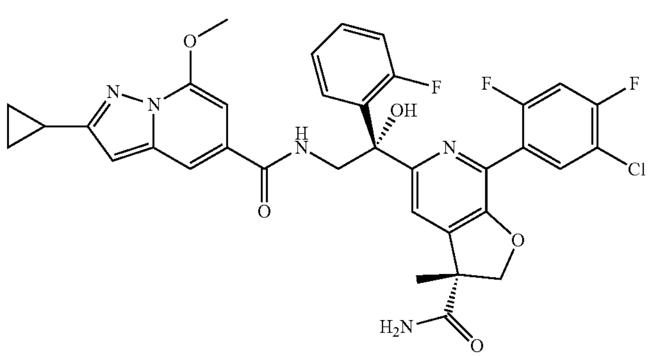 [SMILES: COc1cc(C(=O)NC[C@](O)(c2cc3c(c(-c4cc(Cl)c(F)cc4F)n2)OC[C@]3(C)C(N)=O)c2ccccc2F)cc2cc(C3CC3)nn12] | 692.40 |

TABLE 3-continued

| Example | Structure | MS+ m/z |
|---|---|---|
| 138 | 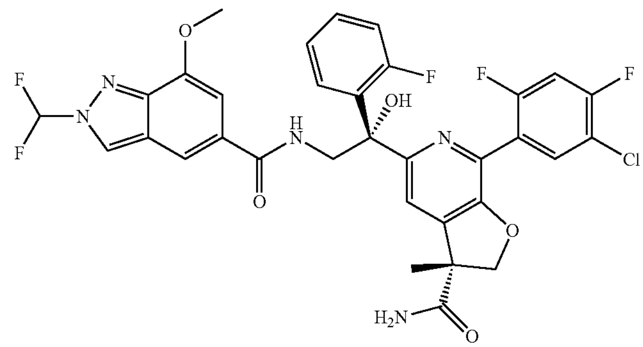 [SMILES: COc1cc(C(=O)NC[C@](O)(c2cc3c(c(-c4cc(Cl)c(F)cc4F)n2)OC[C@]3(C)C(N)=O)c2ccccc2F)cc2cn(C(F)F)nc12] | 702.40 |
| 139 | 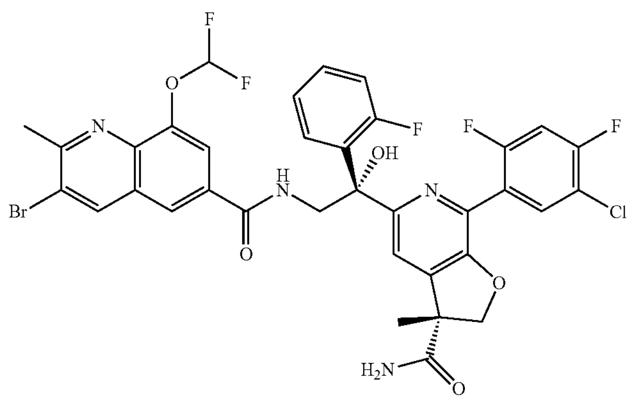 [SMILES: Cc1nc2c(OC(F)F)cc(C(=O)NC[C@](O)(c3cc4c(c(-c5cc(Cl)c(F)cc5F)n3)OC[C@]4(C)C(N)=O)c3ccccc3F)cc2cc1Br] | 793.35 |
| 140 | 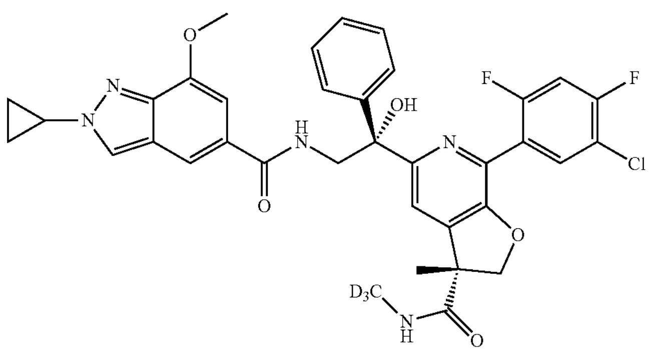 [SMILES: [2H]C([2H])([2H])NC(=O)[C@@]1(C)COc2c1cc([C@@](O)(CNC(=O)c1cc(OC)c3nn(C4CC4)cc3c1)c1ccccc1)nc2-c1cc(Cl)c(F)cc1F] | 691.30 |
| 141 | 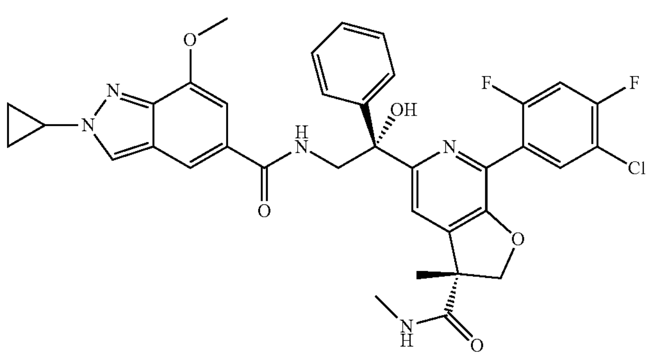 [SMILES: CNC(=O)[C@@]1(C)COc2c1cc([C@@](O)(CNC(=O)c1cc(OC)c3nn(C4CC4)cc3c1)c1ccccc1)nc2-c1cc(Cl)c(F)cc1F] | 688.20 |

TABLE 3-continued

| Example | Structure | MS+ m/z |
|---|---|---|
| 142 | 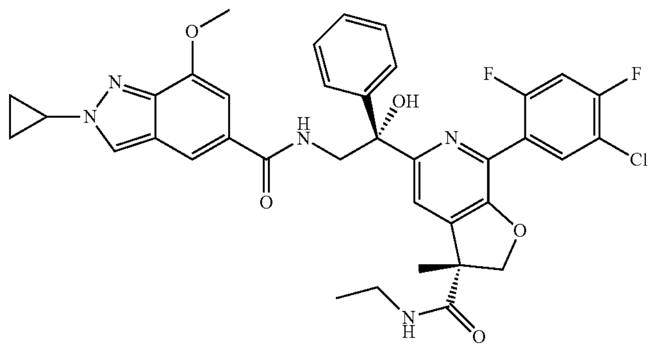 [SMILES: CCNC(=O)[C@@]1(C)COc2c1cc([C@@](O)(CNC(=O)c1cc(OC)c3nn(C4CC4)cc3c1)c1ccccc1)nc2-c1cc(Cl)c(F)cc1F] | 702.50 |
| 143 | 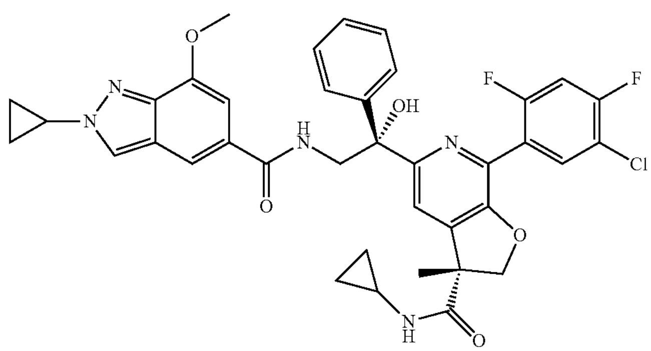 [SMILES: COc1cc(C(=O)NC[C@@](O)(c2ccccc2)c2cc3c(c(-c4cc(Cl)c(F)cc4F)n2)OC[C@]3(C)C(=O)NC2CC2)cc2cn(C3CC3)nc12] | 714.50 |
| 144 | 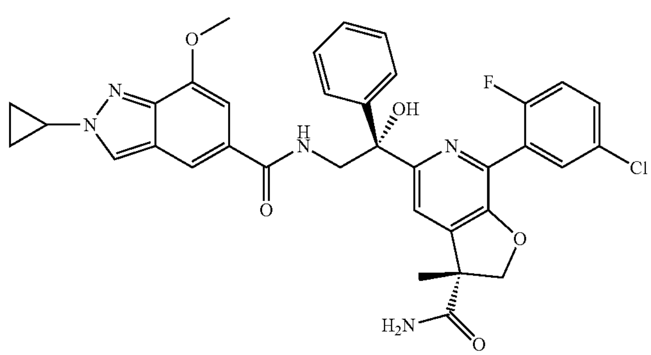 [SMILES: COc1cc(C(=O)NC[C@@](O)(c2ccccc2)c2cc3c(c(-c4cc(Cl)ccc4F)n2)OC[C@]3(C)C(N)=O)cc2cn(C3CC3)nc12] | 656.00 |
| 145 | 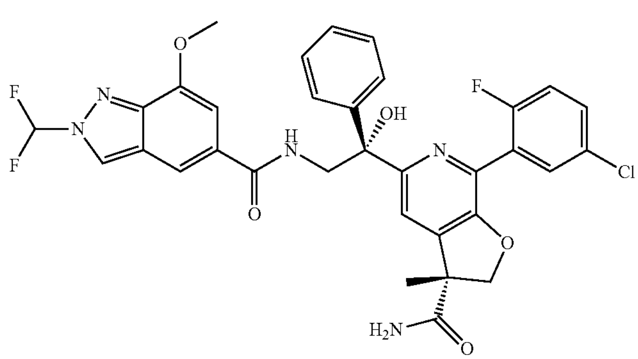 [SMILES: COc1cc(C(=O)NC[C@@](O)(c2ccccc2)c2cc3c(c(-c4cc(Cl)ccc4F)n2)OC[C@]3(C)C(N)=O)cc2cn(C(F)F)nc12] | 666.40 |

TABLE 3-continued

| Example | Structure | MS+ m/z |
|---|---|---|
| 146 | 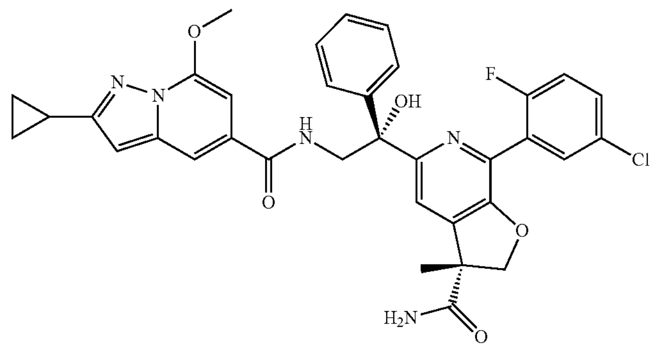 [SMILES: COc1cc(C(=O)NC[C@@](O)(c2ccccc2)c2cc3c(c(-c4cc(Cl)ccc4F)n2)OC[C@]3(C)C(N)=O)cc2cc(C3CC3)nn12] | 656.45 |
| 147 | 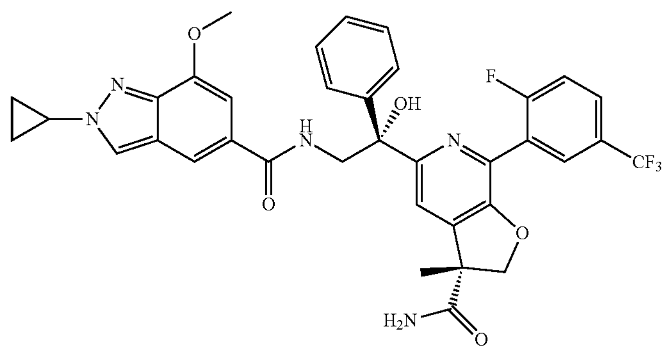 [SMILES: COc1cc(C(=O)NC[C@@](O)(c2ccccc2)c2cc3c(c(-c4cc(C(F)(F)F)ccc4F)n2)OC[C@]3(C)C(N)=O)cc2cn(C3CC3)nc12] | 690.50 |
| 148 | 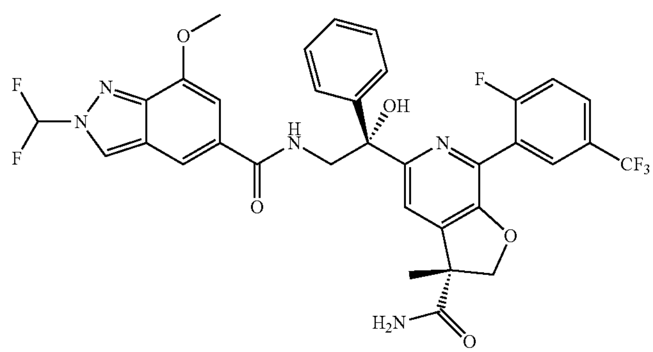 [SMILES: COc1cc(C(=O)NC[C@@](O)(c2ccccc2)c2cc3c(c(-c4cc(C(F)(F)F)ccc4F)n2)OC[C@]3(C)C(N)=O)cc2cn(C(F)F)nc12] | 700.45 |
| 149 | 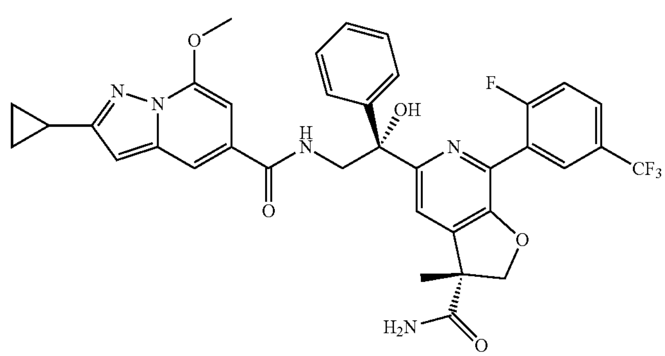 [SMILES: COc1cc(C(=O)NC[C@@](O)(c2ccccc2)c2cc3c(c(-c4cc(C(F)(F)F)ccc4F)n2)OC[C@]3(C)C(N)=O)cc2cc(C3CC3)nn12] | 690.50 |

TABLE 3-continued

| Example | Structure | MS+ m/z |
|---|---|---|
| 152 | 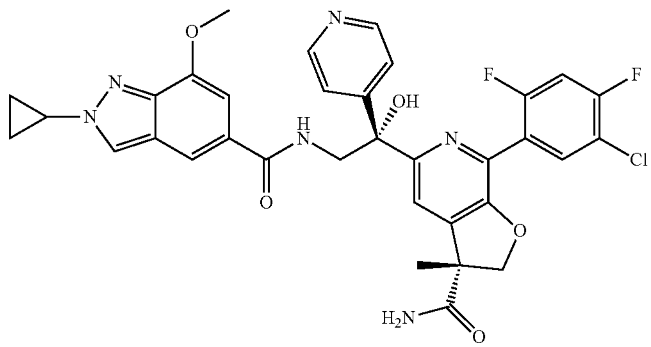 [SMILES: COc1cc(C(=O)NC[C@@](O)(c2ccncc2)c2cc3c(c(-c4cc(Cl)c(F)cc4F)n2)OC[C@]3(C)C(N)=O)cc2cn(C3CC3)nc12] | 675.35 |
| 153 | 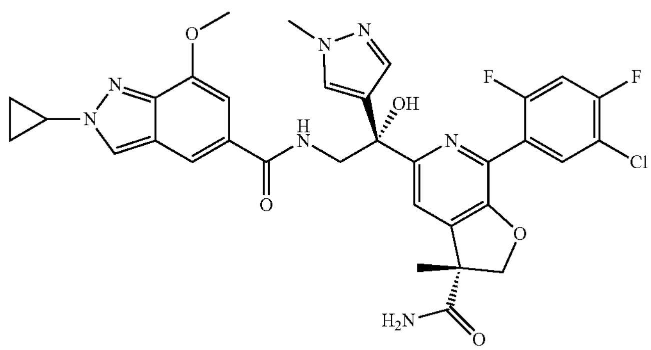 [SMILES: COc1cc(C(=O)NC[C@@](O)(c2cnn(C)c2)c2cc3c(c(-c4cc(Cl)c(F)cc4F)n2)OC[C@]3(C)C(N)=O)cc2cn(C3CC3)nc12] | 678.20 |
| 154 | 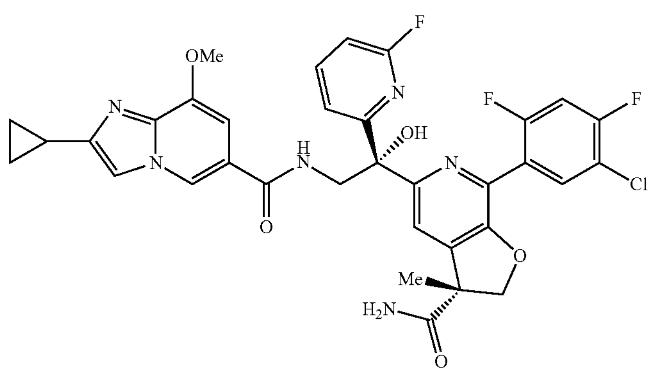 [SMILES: COc1cc(C(=O)NC[C@@](O)(c2cccc(F)n2)c2cc3c(c(-c4cc(Cl)c(F)cc4F)n2)OC[C@]3(C)C(N)=O)cn2cc(C3CC3)nc12] | 693.20 |
| 155 | 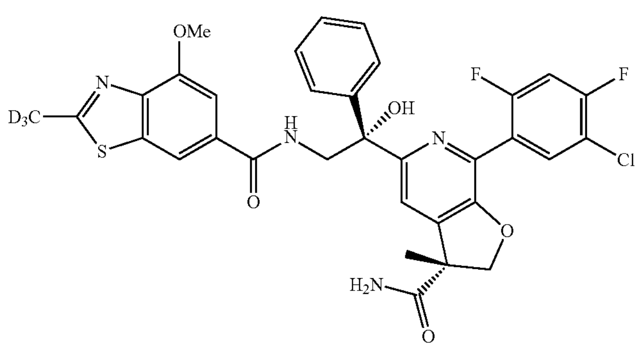 [SMILES: [2H]C([2H])([2H])c1nc2c(OC)cc(C(=O)NC[C@@](O)(c3ccccc3)c3cc4c(c(-c5cc(Cl)c(F)cc5F)n3)OC[C@]4(C)C(N)=O)cc2s1] | 668.21 |

TABLE 3-continued
| Example | Structure | MS+ m/z |
|---|---|---|
| 156 | 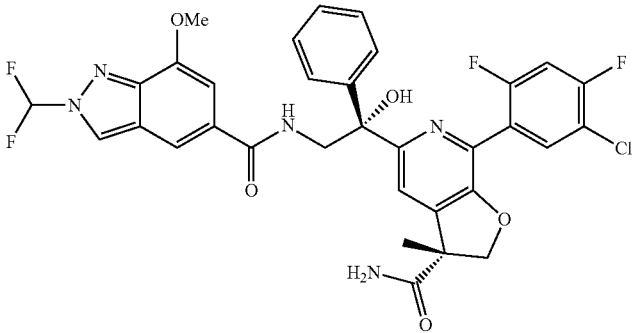 [SMILES: COc1cc(C(=O)NC[C@@](O)(c2ccccc2)c2cc3c(c(-c4cc(Cl)c(F)cc4F)n2)OC[C@]3(C)C(N)=O)cc2cn(C(F)F)nc12] | 684.24 |
| 157 | 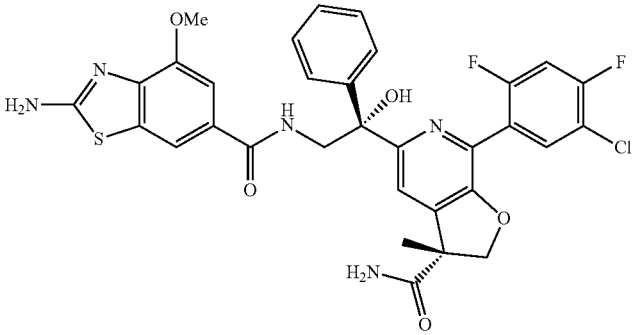 [SMILES: COc1cc(C(=O)NC[C@@](O)(c2ccccc2)c2cc3c(c(-c4cc(Cl)c(F)cc4F)n2)OC[C@]3(C)C(N)=O)cc2sc(N)nc12] | 666.21 |
| 158 | 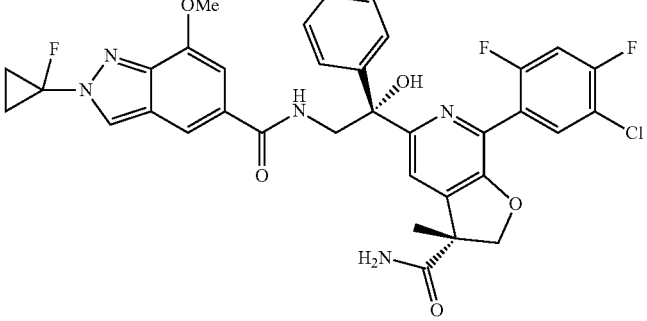 | 692.30 |
| 159 | 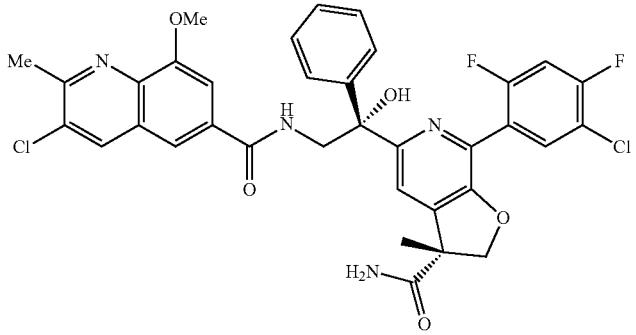 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)c(C)nc12] | 693.23 |

TABLE 3-continued

| Example | Structure | MS+ m/z |
|---|---|---|
| 160 | 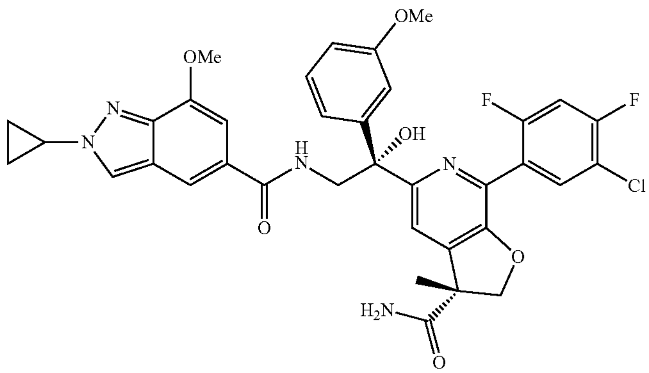 [SMILES: COc1cccc([C@](O)(CNC(=O)c2cc(OC)c3nn(C4CC4)cc3c2)c2cc3c(c(-c4cc(Cl)c(F)cc4F)n2)OC[C@]3(C)C(N)=O)c1] | 704.33 |
| 161 | 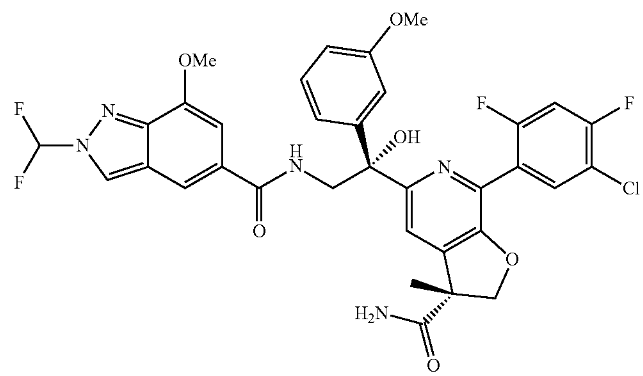 [SMILES: COc1cccc([C@](O)(CNC(=O)c2cc(OC)c3nn(C(F)F)cc3c2)c2cc3c(c(-c4cc(Cl)c(F)cc4F)n2)OC[C@]3(C)C(N)=O)c1] | 714.27 |
| 162 | 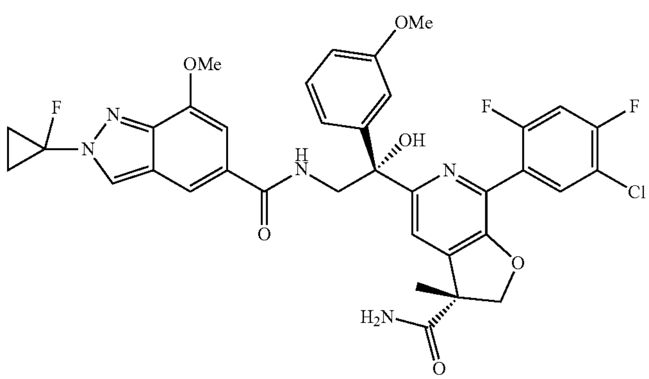 [SMILES: COc1cccc([C@](O)(CNC(=O)c2cc(OC)c3nn(C4(F)CC4)cc3c2)c2cc3c(c(-c4cc(Cl)c(F)cc4F)n2)OC[C@]3(C)C(N)=O)c1] | 722.23 |
| 163 | 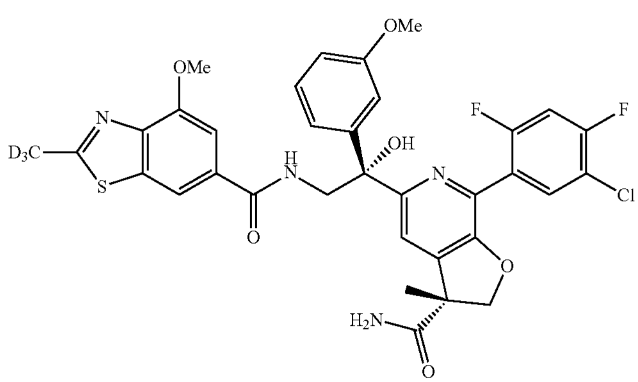 [SMILES: [2H]C([2H])([2H])c1nc2c(OC)cc(C(=O)NC[C@@](O)(c3cccc(OC)c3)c3cc4c(c(-c5cc(Cl)c(F)cc5F)n3)OC[C@]4(C)C(N)=O)cc2s1] | 698.18 |

TABLE 3-continued

| Example | Structure | MS+ m/z |
|---|---|---|
| 164 | 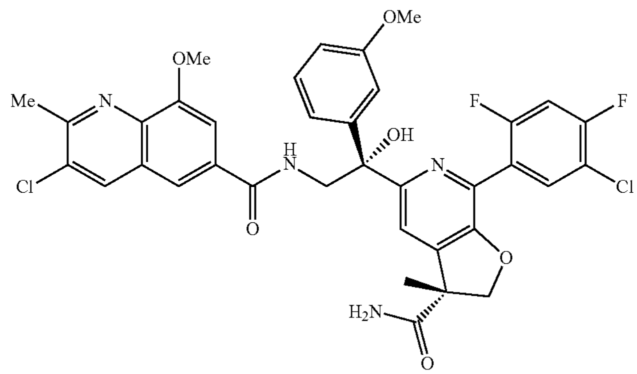 [SMILES: COc1cccc([C@](O)(CNC(=O)c2cc(OC)c3nc(C)c(Cl)cc3c2)c2cc3c(c(-c4cc(Cl)c(F)cc4F)n2)OC[C@]3(C)C(N)=O)c1] | 724.16 |
| 165 | 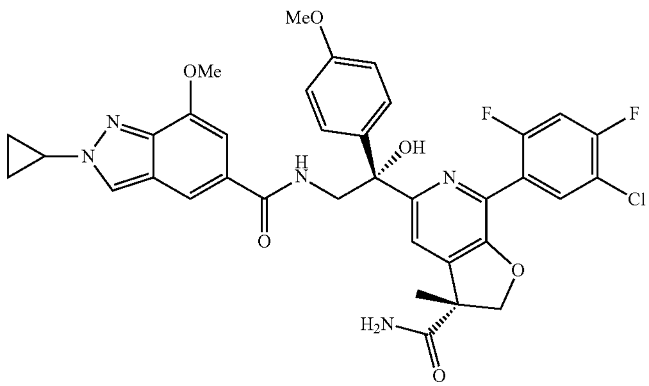 [SMILES: COc1ccc([C@](O)(CNC(=O)c2cc(OC)c3nn(C4CC4)cc3c2)c2cc3c(c(-c4cc(Cl)c(F)cc4F)n2)OC[C@]3(C)C(N)=O)cc1] | 704.26 |
| 166 | 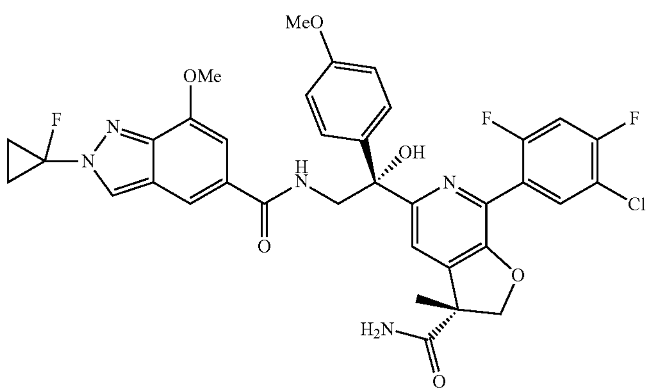 [SMILES: COc1ccc([C@](O)(CNC(=O)c2cc(OC)c3nn(C4(F)CC4)cc3c2)c2cc3c(c(-c4cc(Cl)c(F)cc4F)n2)OC[C@]3(C)C(N)=O)cc1] | 722.36 |
| 167 | 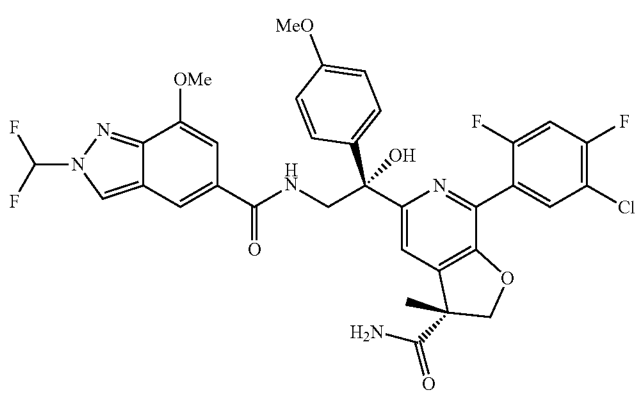 [SMILES: COc1ccc([C@](O)(CNC(=O)c2cc(OC)c3nn(C(F)F)cc3c2)c2cc3c(c(-c4cc(Cl)c(F)cc4F)n2)OC[C@]3(C)C(N)=O)cc1] | 714.39 |

TABLE 3-continued
| Example | Structure | MS+ m/z |
|---|---|---|
| 168 | 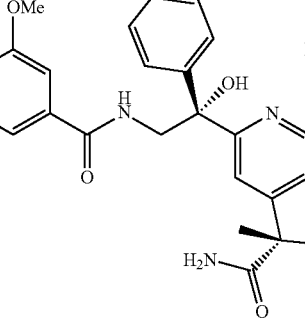 | 698.37 |
| 169 | 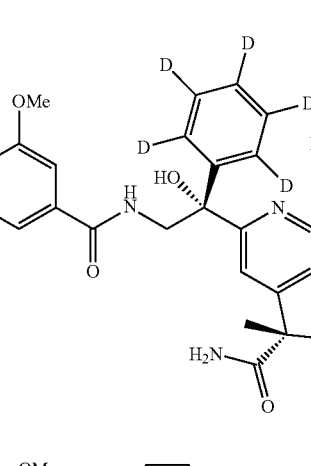 | 679.31 |
| 170 | 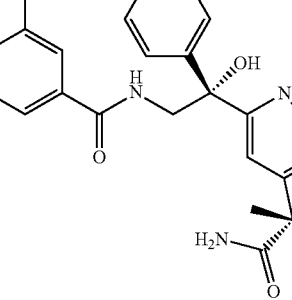 | 676.36 |
| 171 | 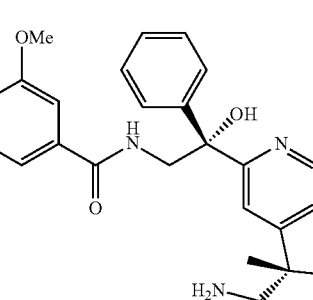 | 659.08 |

TABLE 3-continued

| Example | Structure | MS+ m/z |
|---------|-----------|---------|
| 172 | 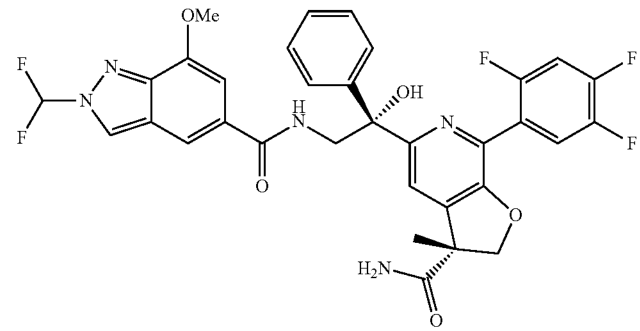 [SMILES: COc1cc(C(=O)NC[C@@](O)(c2ccccc2)c2cc3c(c(-c4cc(F)c(F)cc4F)n2)OC[C@]3(C)C(N)=O)cc2cn(C(F)F)nc12] | 668.20 |
| 173 | 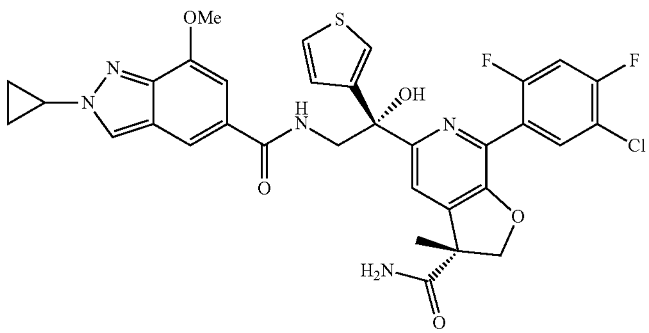 [SMILES: COc1cc(C(=O)NC[C@@](O)(c2ccsc2)c2cc3c(c(-c4cc(Cl)c(F)cc4F)n2)OC[C@]3(C)C(N)=O)cc2cn(C3CC3)nc12] | 680.34 |
| 174 | 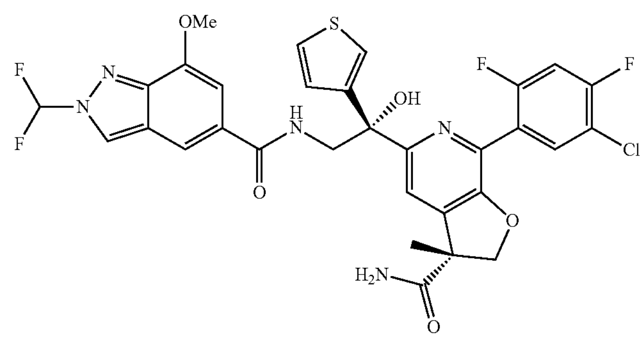 [SMILES: COc1cc(C(=O)NC[C@@](O)(c2ccsc2)c2cc3c(c(-c4cc(Cl)c(F)cc4F)n2)OC[C@]3(C)C(N)=O)cc2cn(C(F)F)nc12] | 690.15 |
| 175 | 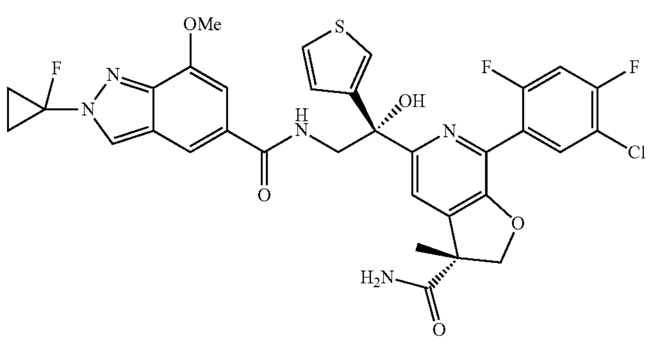 [SMILES: COc1cc(C(=O)NC[C@@](O)(c2ccsc2)c2cc3c(c(-c4cc(Cl)c(F)cc4F)n2)OC[C@]3(C)C(N)=O)cc2cn(C3(F)CC3)nc12] | 698.20 |

TABLE 3-continued

| Example | Structure | MS+ m/z |
|---|---|---|
| 176 | 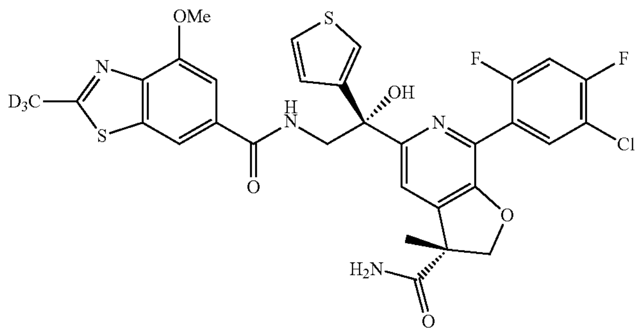 [SMILES: [2H]C([2H])([2H])c1nc2c(OC)cc(C(=O)NC[C@@](O)(c3ccsc3)c3cc4c(c(-c5cc(Cl)c(F)cc5F)n3)OC[C@]4(C)C(N)=O)cc2s1] | 674.20 |
| 177 | 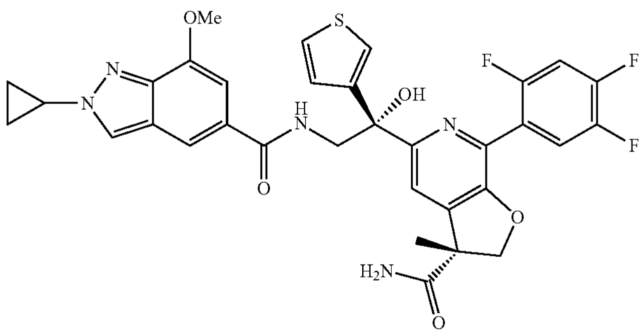 [SMILES: COc1cc(C(=O)NC[C@@](O)(c2ccsc2)c2cc3c(c(-c4cc(F)c(F)cc4F)n2)OC[C@]3(C)C(N)=O)cc2cn(C3CC3)nc12] | 664.20 |
| 178 | 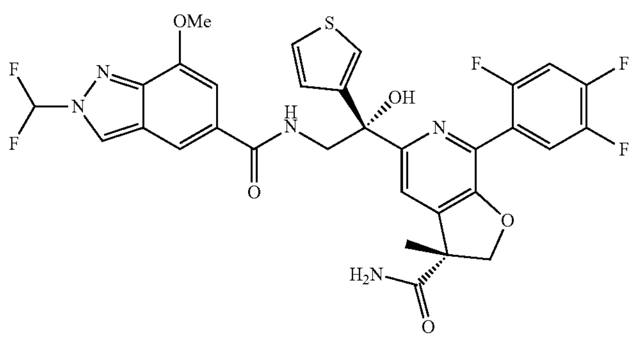 [SMILES: COc1cc(C(=O)NC[C@@](O)(c2ccsc2)c2cc3c(c(-c4cc(F)c(F)cc4F)n2)OC[C@]3(C)C(N)=O)cc2cn(C(F)F)nc12] | 674.20 |
| 179 | 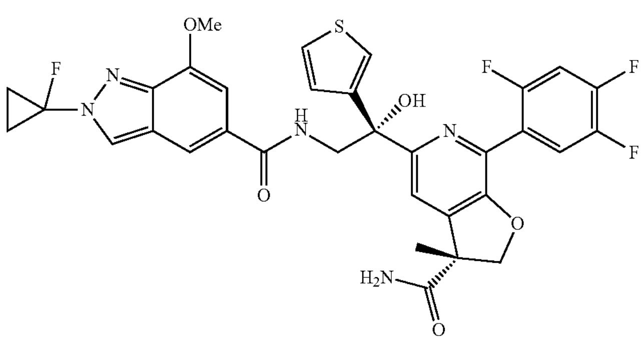 [SMILES: COc1cc(C(=O)NC[C@@](O)(c2ccsc2)c2cc3c(c(-c4cc(F)c(F)cc4F)n2)OC[C@]3(C)C(N)=O)cc2cn(C3(F)CC3)nc12] | 682.20 |

TABLE 3-continued

| Example | Structure | MS+ m/z |
|---|---|---|
| 180 | 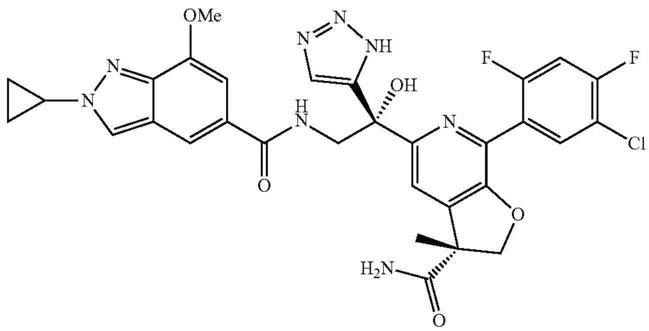 [SMILES: COc1cc(C(=O)NC[C@](O)(c2cc3c(c(-c4cc(Cl)c(F)cc4F)n2)OC[C@]3(C)C(N)=O)c2cnn[nH]2)cc2cn(C3CC3)nc12] | 665.20 |
| 181 | 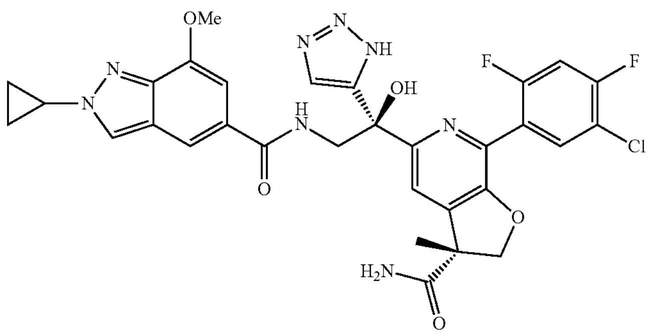 [SMILES: COc1cc(C(=O)NC[C@@](O)(c2cc3c(c(-c4cc(Cl)c(F)cc4F)n2)OC[C@]3(C)C(N)=O)c2cnn[nH]2)cc2cn(C3CC3)nc12] | 665.20 |
| 182 | 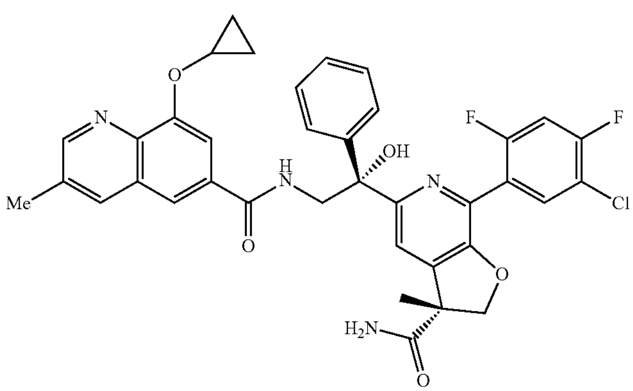 [SMILES: Cc1cnc2c(OC3CC3)cc(C(=O)NC[C@@](O)(c3ccccc3)c3cc4c(c(-c5cc(Cl)c(F)cc5F)n3)OC[C@]4(C)C(N)=O)cc2c1] | 685.20 |
| 183 | 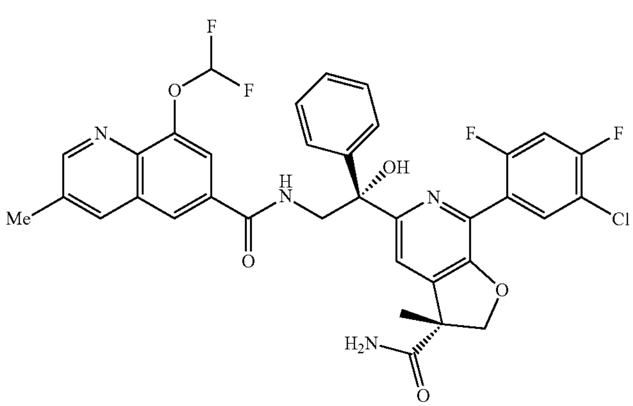 [SMILES: Cc1cnc2c(OC(F)F)cc(C(=O)NC[C@@](O)(c3ccccc3)c3cc4c(c(-c5cc(Cl)c(F)cc5F)n3)OC[C@]4(C)C(N)=O)cc2c1] | 695.20 |

TABLE 3-continued
| Example | Structure | MS+ m/z |
|---|---|---|
| 184 | 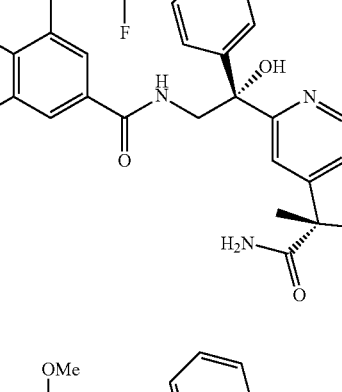 | 702.90 |
| 185 | 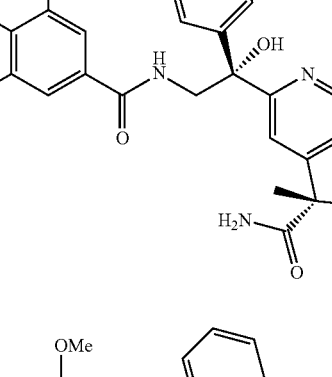 | 723.20 |
| 186 | 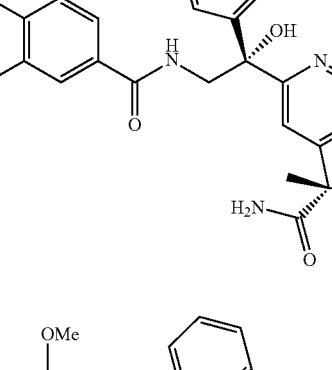 | 696.20 |
| 187 | 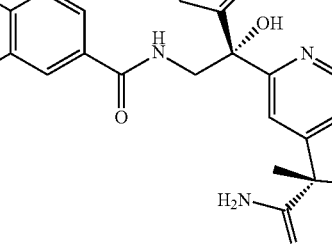 | 679.20 |

TABLE 3-continued

| Example | Structure | MS+ m/z |
|---|---|---|
| 188 | 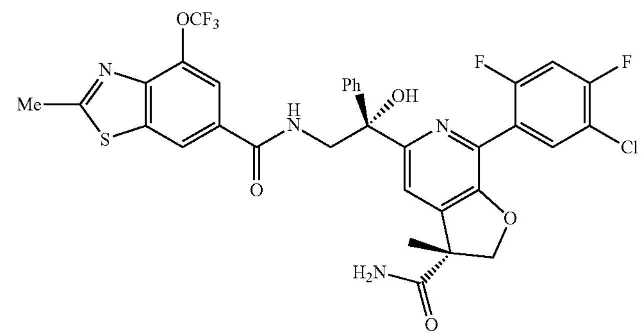 [SMILES: Cc1nc2c(OC(F)(F)F)cc(C(=O)NC[C@@](O)(c3ccccc3)c3cc4c(c(-c5cc(Cl)c(F)cc5F)n3)OC[C@]4(C)C(N)=O)cc2s1] | 719.28 |
| 189 | 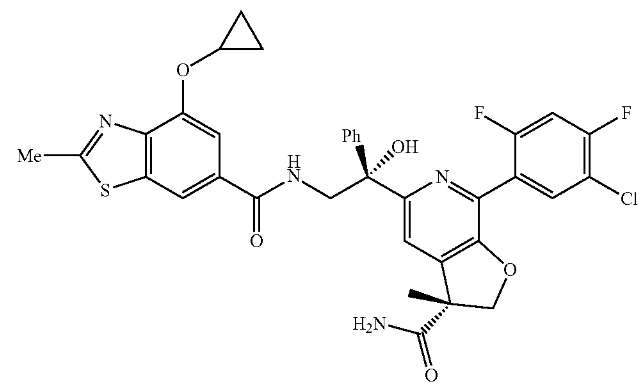 [SMILES: Cc1nc2c(OC3CC3)cc(C(=O)NC[C@@](O)(c3ccccc3)c3cc4c(c(-c5cc(Cl)c(F)cc5F)n3)OC[C@]4(C)C(N)=O)cc2s1] | 691.35 |
| 190 | 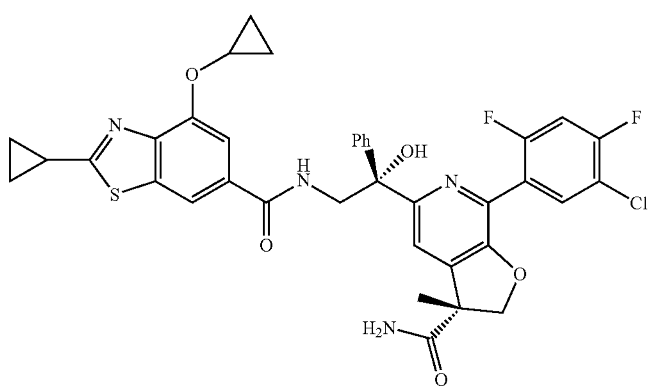 [SMILES: C[C@]1(C(N)=O)COc2c1cc([C@@](O)(CNC(=O)c1cc(OC3CC3)c3nc(C4CC4)sc3c1)c1ccccc1)nc2-c1cc(Cl)c(F)cc1F] | 717.40 |
| 191 | 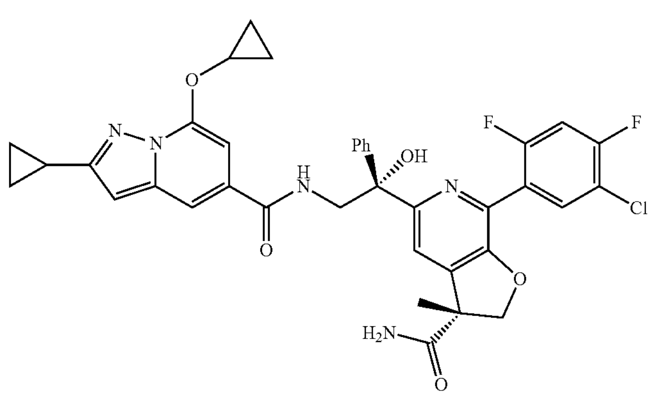 [SMILES: C[C@]1(C(N)=O)COc2c1cc([C@@](O)(CNC(=O)c1cc(OC3CC3)n3nc(C4CC4)cc3c1)c1ccccc1)nc2-c1cc(Cl)c(F)cc1F] | 700.41 |

TABLE 3-continued

| Example | Structure | MS+ m/z |
|---|---|---|
| 192 | 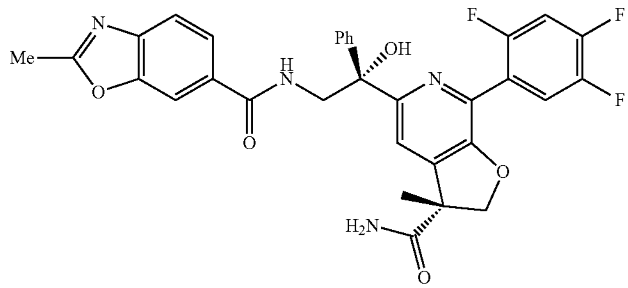 [SMILES: Cc1nc2ccc(C(=O)NC[C@@](O)(c3ccccc3)c3cc4c(c(-c5cc(F)c(F)cc5F)n3)OC[C@]4(C)C(N)=O)cc2o1] | 603.20 |
| 193 | 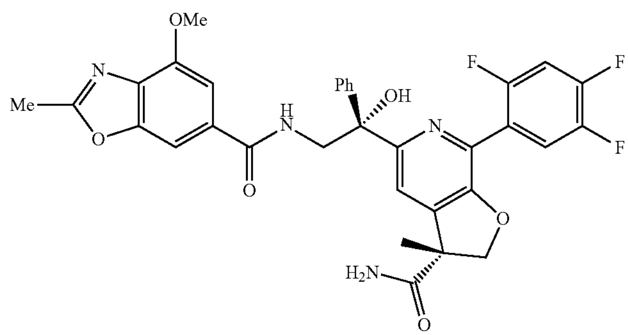 [SMILES: COc1cc(C(=O)NC[C@@](O)(c2ccccc2)c2cc3c(c(-c4cc(F)c(F)cc4F)n2)OC[C@]3(C)C(N)=O)cc2oc(C)nc12] | 633.20 |
| 194 | 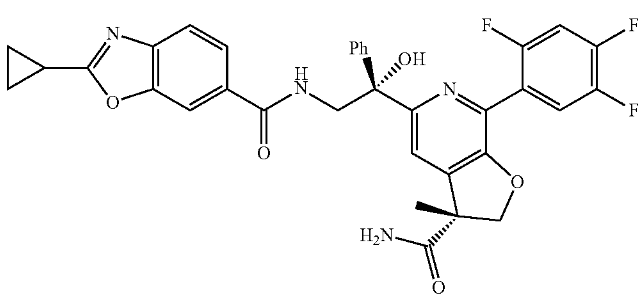 [SMILES: C[C@]1(C(N)=O)COc2c1cc([C@@](O)(CNC(=O)c1ccc3nc(C4CC4)oc3c1)c1ccccc1)nc2-c1cc(F)c(F)cc1F] | 629.20 |
| 195 | 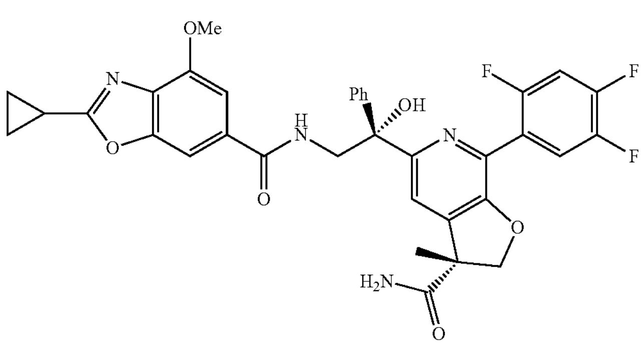 [SMILES: COc1cc(C(=O)NC[C@@](O)(c2ccccc2)c2cc3c(c(-c4cc(F)c(F)cc4F)n2)OC[C@]3(C)C(N)=O)cc2oc(C3CC3)nc12] | 659.20 |

TABLE 3-continued

| Example | Structure | MS+ m/z |
|---|---|---|
| 196 | 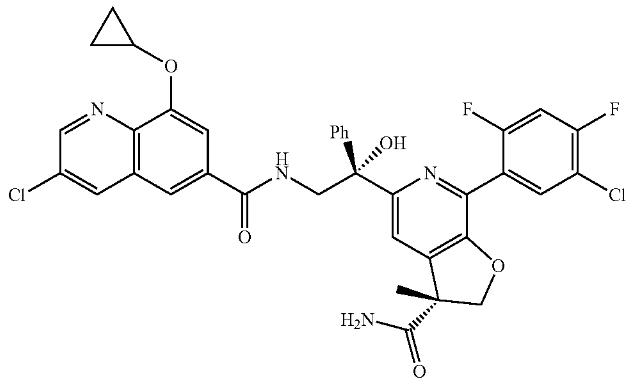 [SMILES: C[C@]1(C(N)=O)COc2c1cc([C@@](O)(CNC(=O)c1cc(OC3CC3)c3ncc(Cl)cc3c1)c1ccccc1)nc2-c1cc(Cl)c(F)cc1F] | 705.20 |
| 197 | 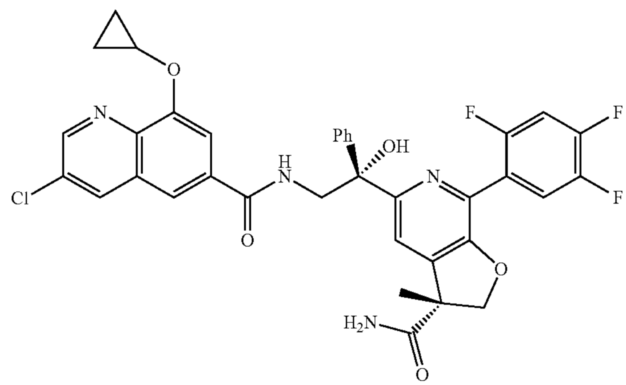 [SMILES: C[C@]1(C(N)=O)COc2c1cc([C@@](O)(CNC(=O)c1cc(OC3CC3)c3ncc(Cl)cc3c1)c1ccccc1)nc2-c1cc(F)c(F)cc1F] | 689.20 |
| 198 | 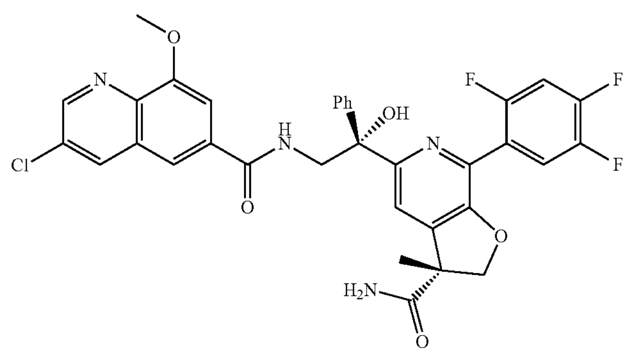 [SMILES: COc1cc(C(=O)NC[C@@](O)(c2ccccc2)c2cc3c(c(-c4cc(F)c(F)cc4F)n2)OC[C@]3(C)C(N)=O)cc2cc(Cl)cnc12] | 663.20 |
| 199 | 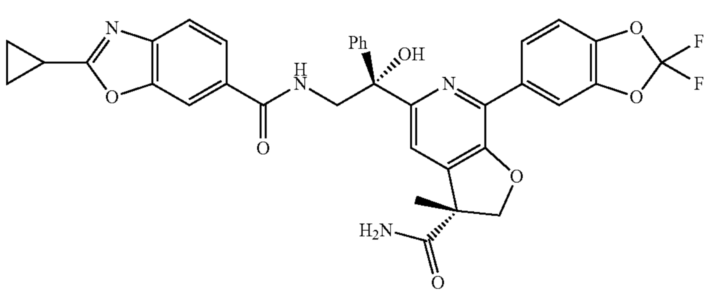 [SMILES: C[C@]1(C(N)=O)COc2c1cc([C@@](O)(CNC(=O)c1ccc3nc(C4CC4)oc3c1)c1ccccc1)nc2-c1ccc2c(c1)OC(F)(F)O2] | 655.20 |

TABLE 3-continued

| Example | Structure | MS+ m/z |
|---|---|---|
| 200 | 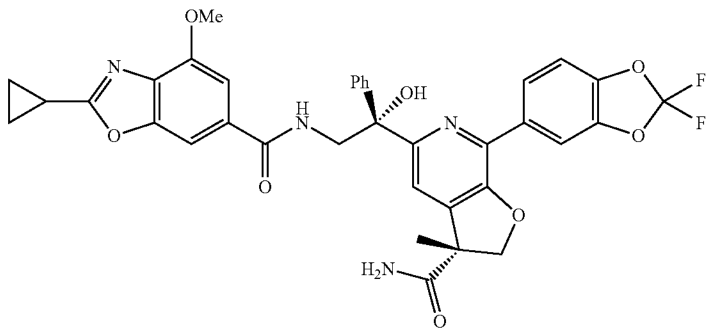 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2oc(C3CC3)nc12] | 685.20 |
| 201 | 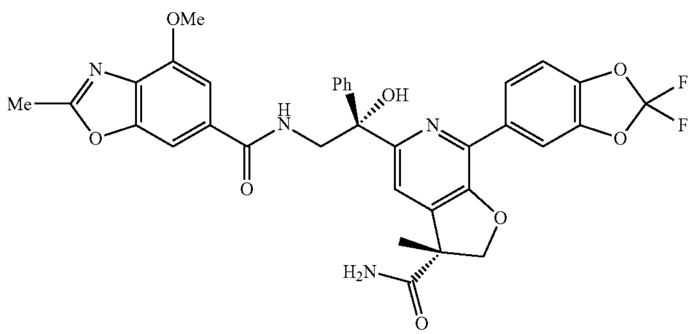 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2oc(C)nc12] | 659.20 |
| 202 | 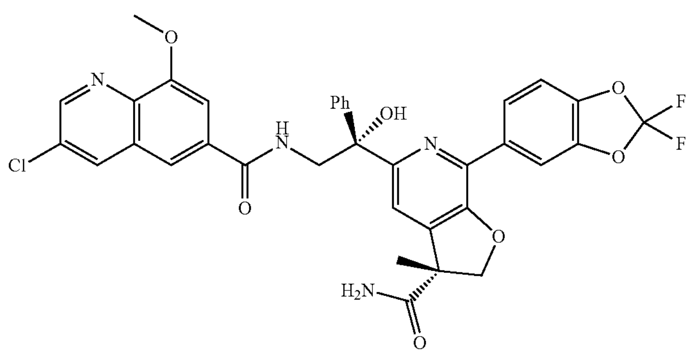 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2cc(Cl)cnc12] | 689.20 |
| 203 | 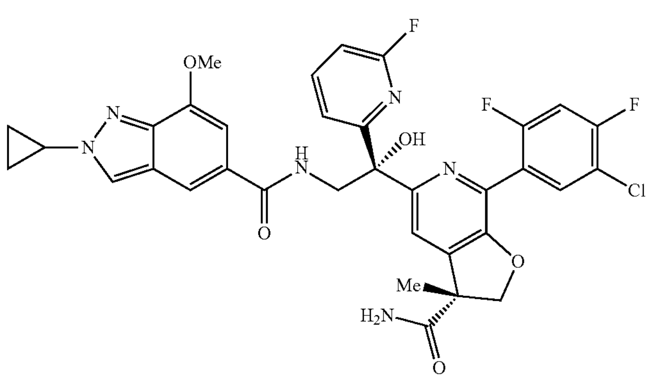 [SMILES: COc1cc(C(=O)NC[C@@](O)(c2cccc(F)n2)c2cc3c(c(-c4cc(Cl)c(F)cc4F)n2)OC[C@]3(C)C(N)=O)cc2cn(C3CC3)nc12] | 693.20 |

TABLE 3-continued

| Example | Structure | MS⁺ m/z |
|---|---|---|
| 204 | 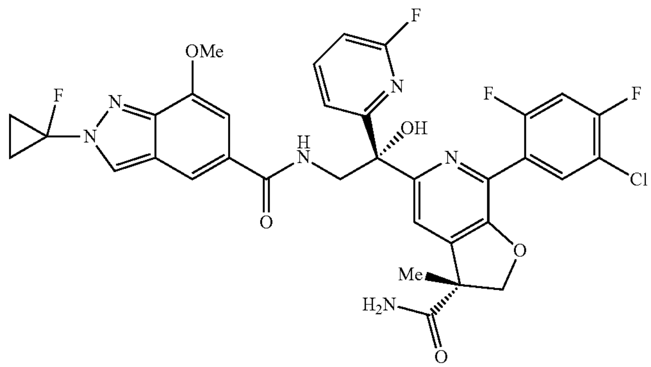 [SMILES: COc1cc(C(=O)NC[C@@](O)(c2cccc(F)n2)c2cc3c(c(-c4cc(Cl)c(F)cc4F)n2)OC[C@]3(C)C(N)=O)cc2cn(C3(F)CC3)nc12] | 711.20 |
| 205 | 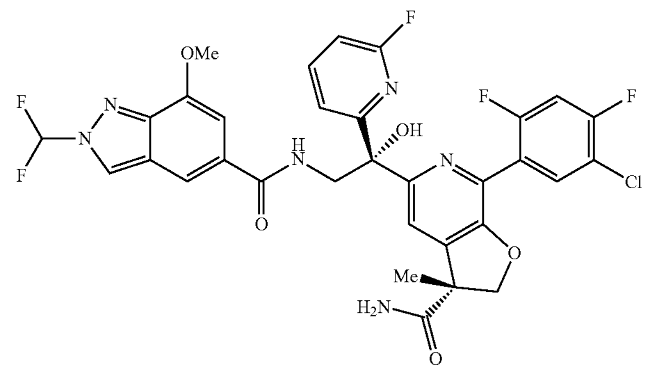 [SMILES: COc1cc(C(=O)NC[C@@](O)(c2cccc(F)n2)c2cc3c(c(-c4cc(Cl)c(F)cc4F)n2)OC[C@]3(C)C(N)=O)cc2cn(C(F)F)nc12] | 703.20 |
| 206 | 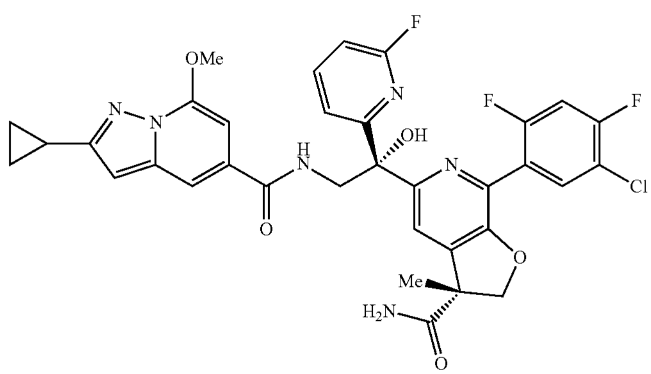 [SMILES: COc1cc(C(=O)NC[C@@](O)(c2cccc(F)n2)c2cc3c(c(-c4cc(Cl)c(F)cc4F)n2)OC[C@]3(C)C(N)=O)cc2cc(C3CC3)nn12] | 693.20 |
| 210 | 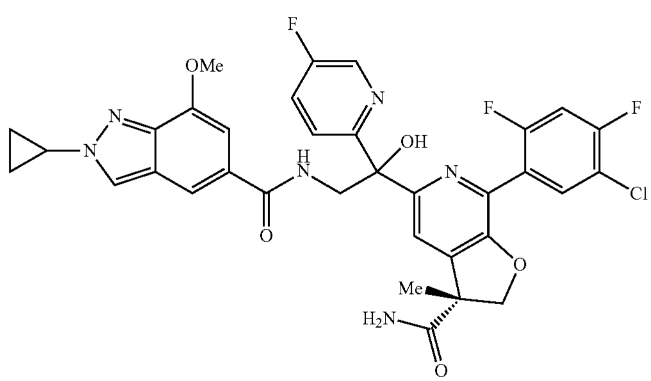 [SMILES: COc1cc(C(=O)NCC(O)(c2ccc(F)cn2)c2cc3c(c(-c4cc(Cl)c(F)cc4F)n2)OC[C@]3(C)C(N)=O)cc2cn(C3CC3)nc12] | 693.20 |

TABLE 3-continued

| Example | Structure | MS+ m/z |
|---------|-----------|---------|
| 213 | 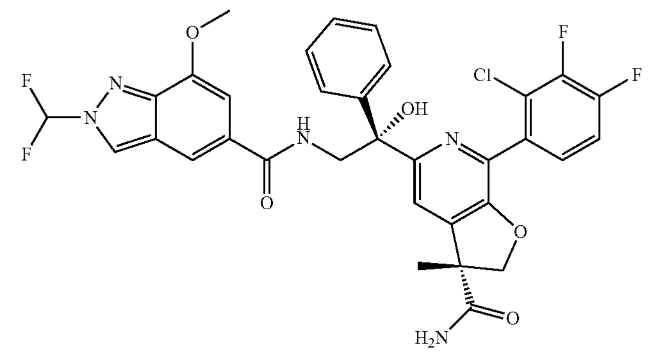 [SMILES: COc1cc(C(=O)NC[C@@](O)(c2ccccc2)c2cc3c(c(-c4ccc(F)c(F)c4Cl)n2)OC[C@]3(C)C(N)=O)cc2cn(C(F)F)nc12] | 684.15 |
| 216 | 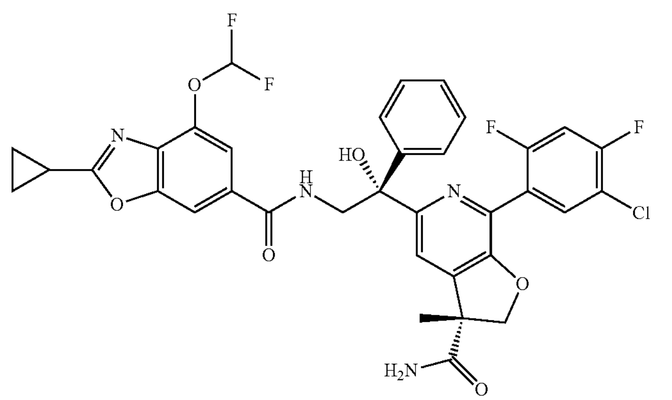 [SMILES: C[C@]1(C(N)=O)COc2c1cc([C@@](O)(CNC(=O)c1cc(OC(F)F)c3nc(C4CC4)oc3c1)c1ccccc1)nc2-c1cc(Cl)c(F)cc1F] | 711.15 |
| 217 | 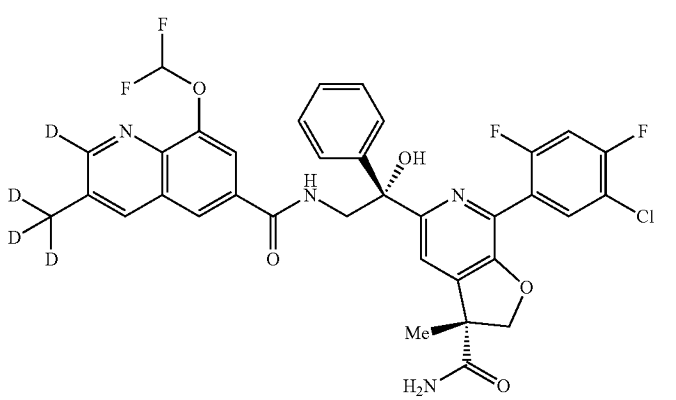 [SMILES: [2H]c1nc2c(OC(F)F)cc(C(=O)NC[C@@](O)(c3ccccc3)c3cc4c(c(-c5cc(Cl)c(F)cc5F)n3)OC[C@]4(C)C(N)=O)cc2cc1C([2H])([2H])[2H]] | 699.18 |
| 219 | 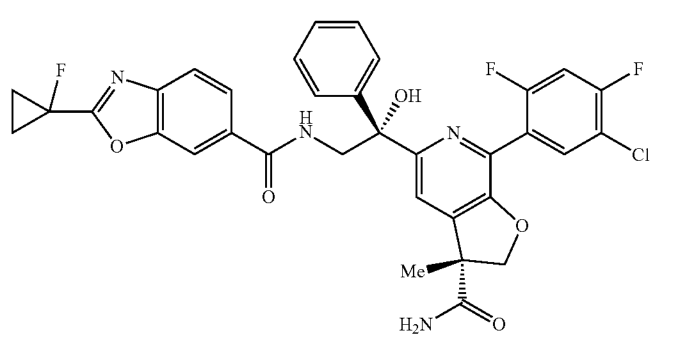 [SMILES: C[C@]1(C(N)=O)COc2c1cc([C@@](O)(CNC(=O)c1ccc3nc(C4(F)CC4)oc3c1)c1ccccc1)nc2-c1cc(Cl)c(F)cc1F] | 663.15 |

TABLE 3-continued

| Example | Structure | MS+ m/z |
|---------|-----------|---------|
| 220 | 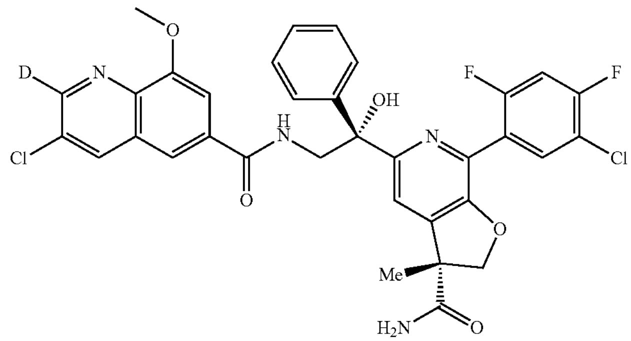 [SMILES: [2H]c1nc2c(OC)cc(C(=O)NC[C@@](O)(c3ccccc3)c3cc4c(c(-c5cc(Cl)c(F)cc5F)n3)OC[C@]4(C)C(N)=O)cc2cc1Cl] | 680.13 |
| 221 | 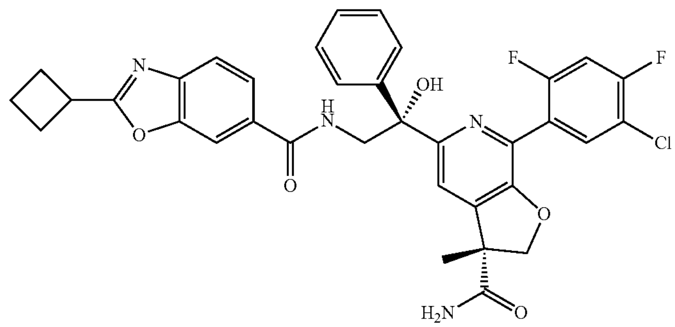 [SMILES: C[C@]1(C(N)=O)COc2c1cc([C@@](O)(CNC(=O)c1ccc3nc(C4CCC4)oc3c1)c1ccccc1)nc2-c1cc(Cl)c(F)cc1F] | 659.17 |
| 222 | 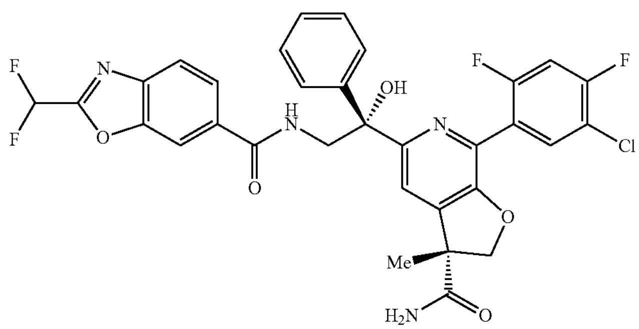 [SMILES: C[C@]1(C(N)=O)COc2c1cc([C@@](O)(CNC(=O)c1ccc3nc(C(F)F)oc3c1)c1ccccc1)nc2-c1cc(Cl)c(F)cc1F] | 655.12 |
| 223 | 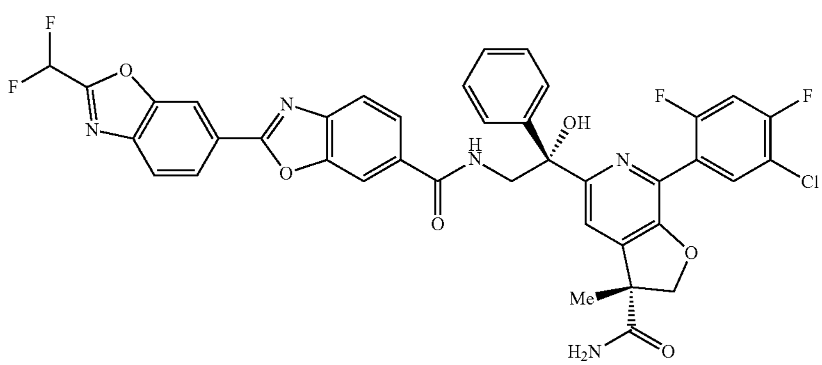 [SMILES: C[C@]1(C(N)=O)COc2c1cc([C@@](O)(CNC(=O)c1ccc3nc(-c4ccc5nc(C(F)F)oc5c4)oc3c1)c1ccccc1)nc2-c1cc(Cl)c(F)cc1F] | 772.15 |

TABLE 3-continued

| Example | Structure | MS+ m/z |
|---|---|---|
| 224 | 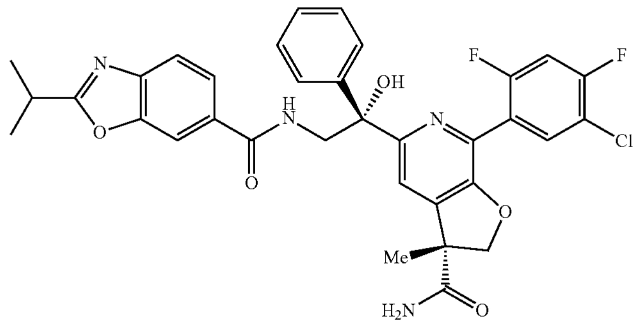 [SMILES: CC(C)c1nc2ccc(C(=O)NC[C@@](O)(c3ccccc3)c3cc4c(c(-c5cc(Cl)c(F)cc5F)n3)OC[C@]4(C)C(N)=O)cc2o1] | 647.17 |
| 227 | 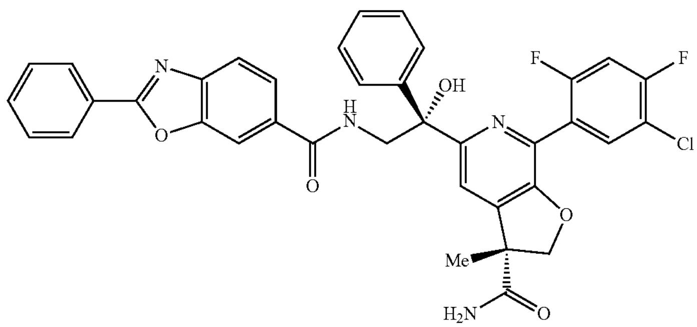 [SMILES: C[C@]1(C(N)=O)COc2c1cc([C@@](O)(CNC(=O)c1ccc3nc(-c4ccccc4)oc3c1)c1ccccc1)nc2-c1cc(Cl)c(F)cc1F] | 681.16 |
| 228 | 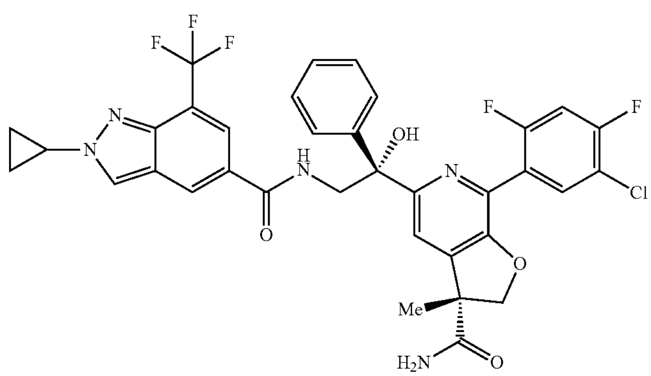 [SMILES: C[C@]1(C(N)=O)COc2c1cc([C@@](O)(CNC(=O)c1cc(C(F)(F)F)c3nn(C4CC4)cc3c1)c1ccccc1)nc2-c1cc(Cl)c(F)cc1F] | 712.16 |
| 229 | 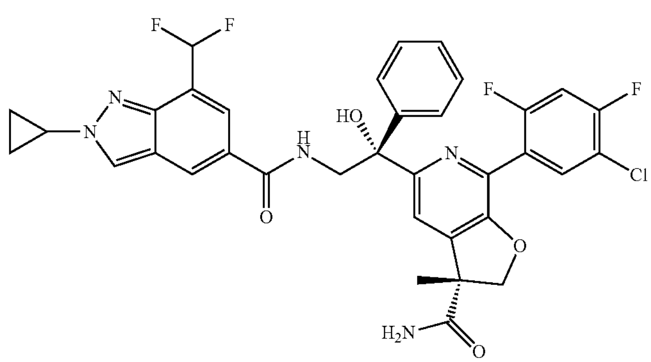 [SMILES: C[C@]1(C(N)=O)COc2c1cc([C@@](O)(CNC(=O)c1cc(C(F)F)c3nn(C4CC4)cc3c1)c1ccccc1)nc2-c1cc(Cl)c(F)cc1F] | 694.17 |

TABLE 3-continued

| Example | Structure | MS+ m/z |
|---|---|---|
| 230 | 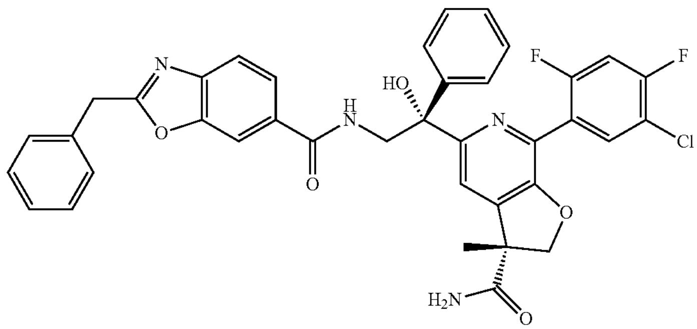 [SMILES: C[C@]1(C(N)=O)COc2c1cc([C@@](O)(CNC(=O)c1ccc3nc(Cc4ccccc4)oc3c1)c1ccccc1)nc2-c1cc(Cl)c(F)cc1F] | 695.17 |
| 231 | 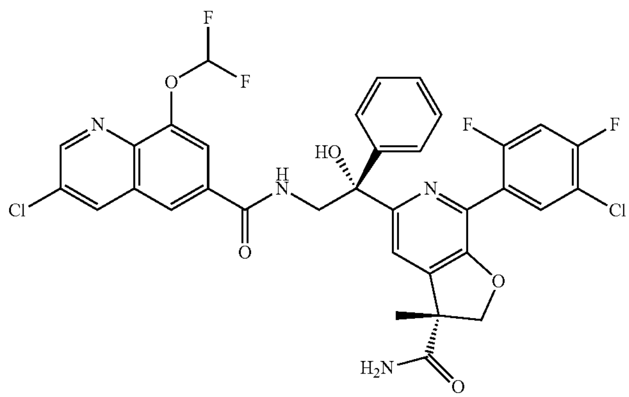 [SMILES: C[C@]1(C(N)=O)COc2c1cc([C@@](O)(CNC(=O)c1cc(OC(F)F)c3ncc(Cl)cc3c1)c1ccccc1)nc2-c1cc(Cl)c(F)cc1F] | 715.16 |
| 232 | 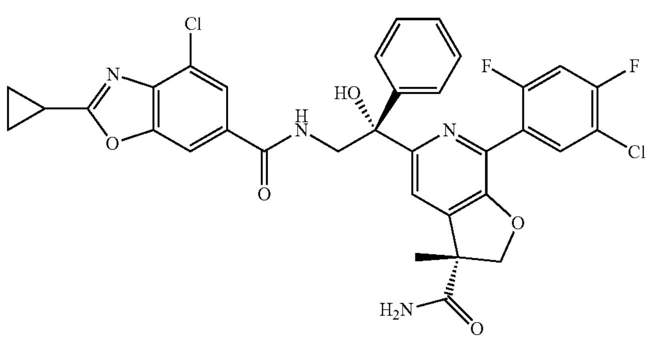 [SMILES: C[C@]1(C(N)=O)COc2c1cc([C@@](O)(CNC(=O)c1cc(Cl)c3nc(C4CC4)oc3c1)c1ccccc1)nc2-c1cc(Cl)c(F)cc1F] | 679.12 |
| 233 | 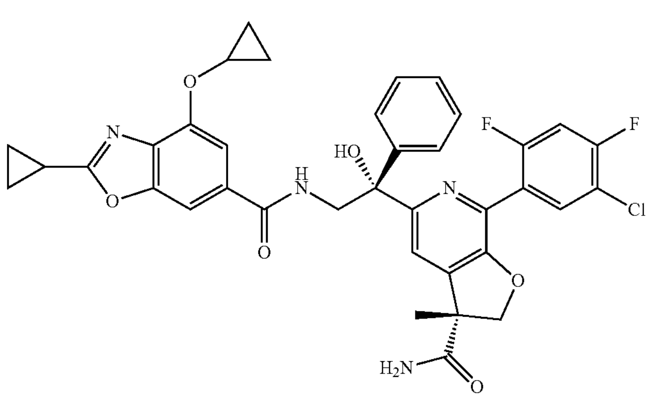 [SMILES: C[C@]1(C(N)=O)COc2c1cc([C@@](O)(CNC(=O)c1cc(OC3CC3)c3nc(C4CC4)oc3c1)c1ccccc1)nc2-c1cc(Cl)c(F)cc1F] | 701.19 |

TABLE 3-continued

| Example | Structure | MS+ m/z |
|---------|-----------|---------|
| 234 | 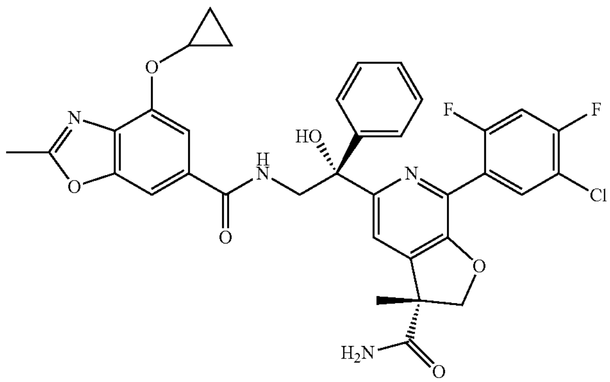 [SMILES: Cc1nc2c(OC3CC3)cc(C(=O)NC[C@@](O)(c3ccccc3)c3cc4c(c(-c5cc(Cl)c(F)cc5F)n3)OC[C@]4(C)C(N)=O)cc2o1] | 675.17 |
| 237 | 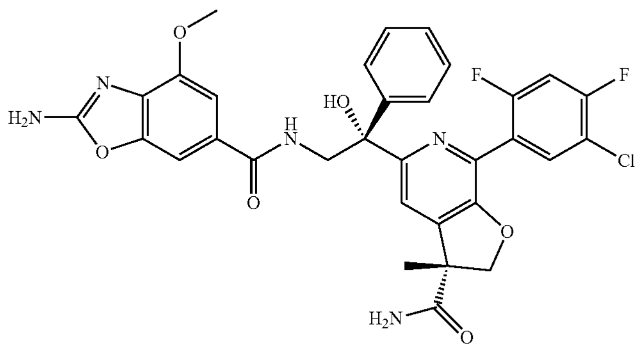 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(N)nc12] | 650.14 |
| 241 | 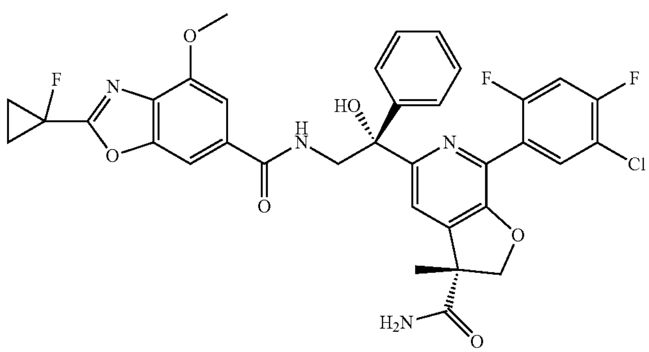 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C3(F)CC3)nc12] | 693.16 |
| 242 | 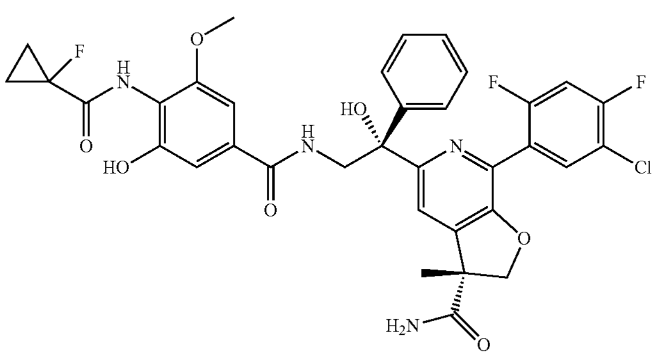 [SMILES: COc1cc(C(=O)NC[C@@](O)(c2ccccc2)c2cc3c(c(-c4cc(Cl)c(F)cc4F)n2)OC[C@]3(C)C(N)=O)cc(O)c1NC(=O)C1(F)CC1] | 711.17 |

TABLE 3-continued
| Example | Structure | MS+ m/z |
|---|---|---|
| 243 | 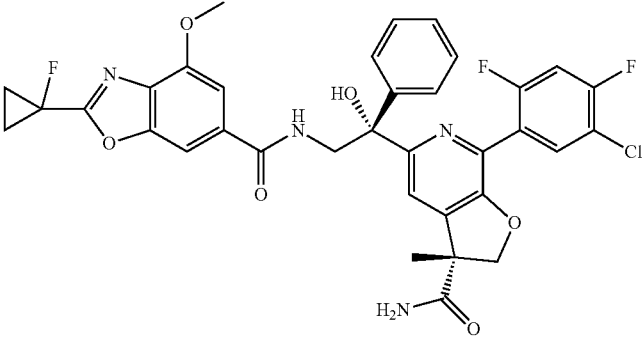 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C3(F)CC3)nc12] | 693.16 |
| 244 | 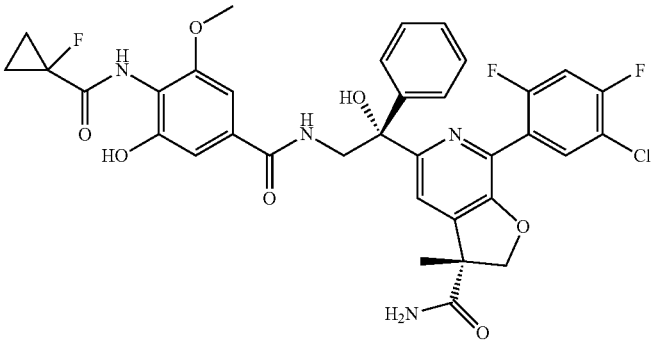 [SMILES: COc1cc(C(=O)NC[C@@](O)(c2ccccc2)c2cc3c(c(-c4cc(Cl)c(F)cc4F)n2)OC[C@]3(C)C(N)=O)cc(O)c1NC(=O)C1(F)CC1] | 711.17 |
| 251 | 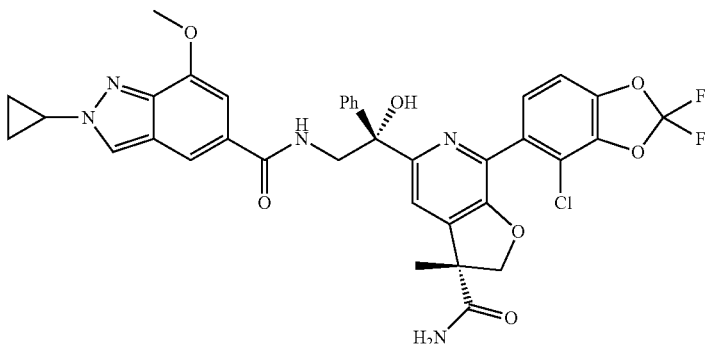 | 718.30 |
| 252 | 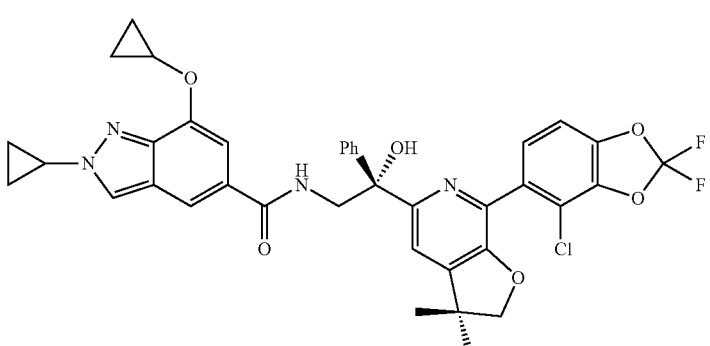 | 744.26 |

TABLE 3-continued

| Example | Structure | MS+ m/z |
|---|---|---|
| 253 | 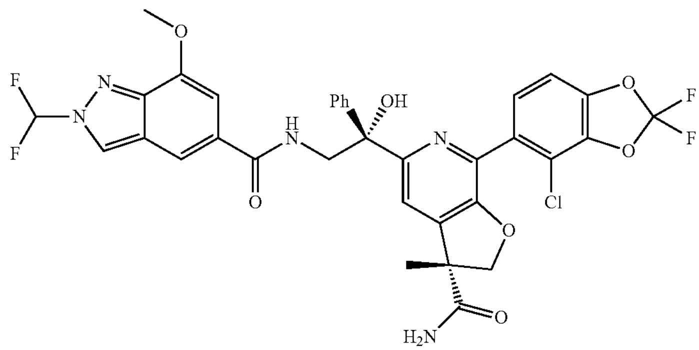 [SMILES: COc1cc(C(=O)NC[C@@](O)(c2ccccc2)c2cc3c(c(-c4ccc5c(c4Cl)OC(F)(F)O5)n2)OC[C@]3(C)C(N)=O)cc2cn(C(F)F)nc12] | 728.25 |
| 254 | 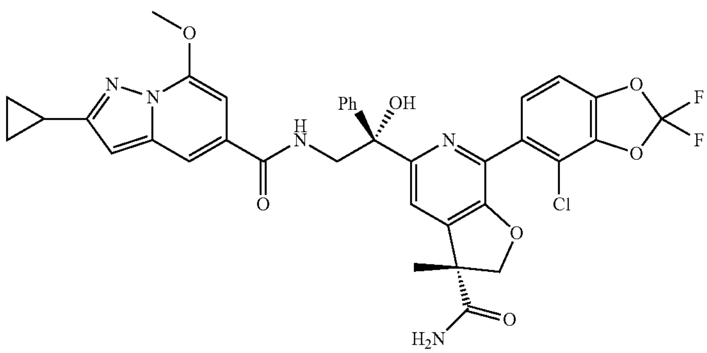 [SMILES: COc1cc(C(=O)NC[C@@](O)(c2ccccc2)c2cc3c(c(-c4ccc5c(c4Cl)OC(F)(F)O5)n2)OC[C@]3(C)C(N)=O)cc2cc(C3CC3)nn12] | 718.25 |
| 255 | 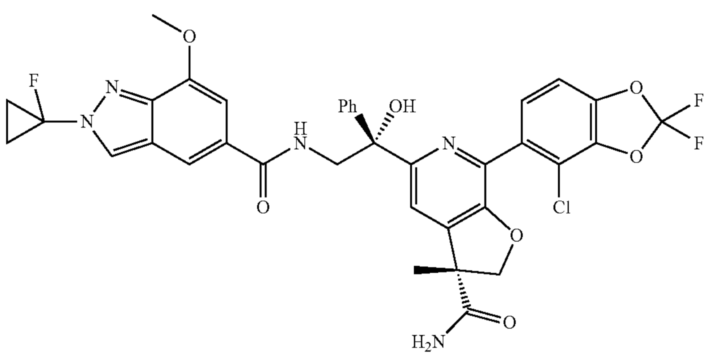 [SMILES: COc1cc(C(=O)NC[C@@](O)(c2ccccc2)c2cc3c(c(-c4ccc5c(c4Cl)OC(F)(F)O5)n2)OC[C@]3(C)C(N)=O)cc2cn(C3(F)CC3)nc12] | 736.29 |
| 256 | 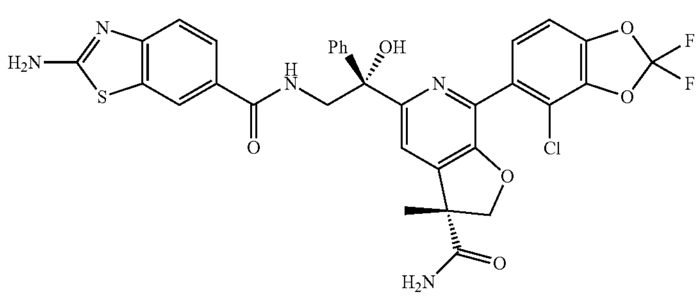 [SMILES: C[C@]1(C(N)=O)COc2c1cc([C@@](O)(CNC(=O)c1ccc3nc(N)sc3c1)c1ccccc1)nc2-c1ccc2c(c1Cl)OC(F)(F)O2] | 680.13 |

TABLE 3-continued

| Example | Structure | MS+ m/z |
|---|---|---|
| 257 | 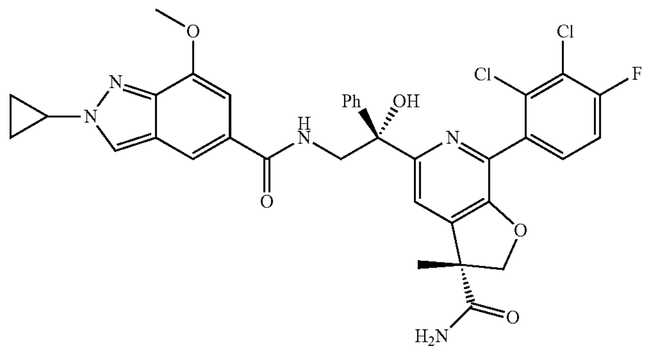 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cn(C3CC3)nc12] | 690.22 |
| 258 | 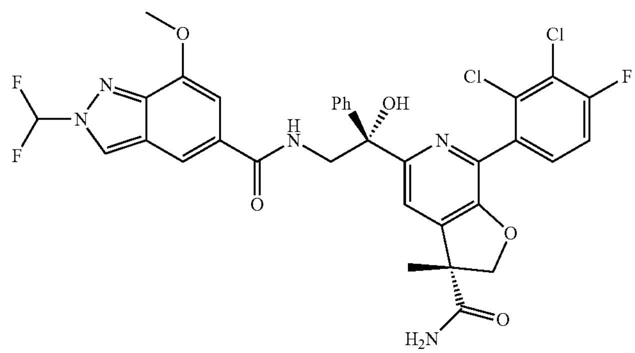 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cn(C(F)F)nc12] | 700.15 |
| 259 | 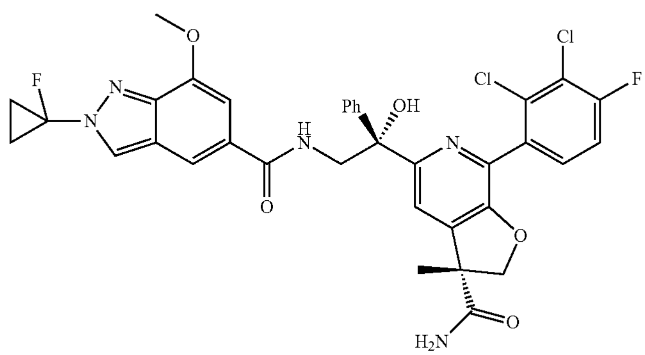 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cn(C3(F)CC3)nc12] | 708.27 |
| 260 | 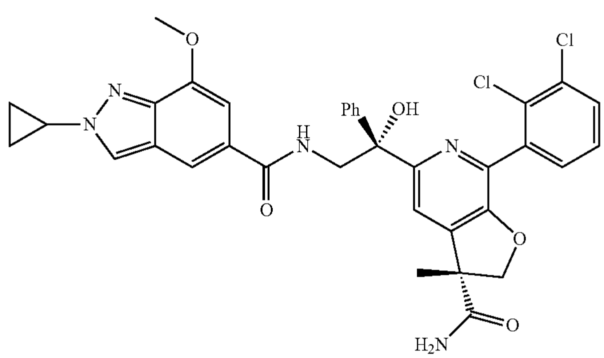 [SMILES: COc1cc(C(=O)NC[C@@](O)(c2ccccc2)c2cc3c(c(-c4cccc(Cl)c4Cl)n2)OC[C@]3(C)C(N)=O)cc2cn(C3CC3)nc12] | 672.17 |

TABLE 3-continued

| Example | Structure | MS+ m/z |
|---|---|---|
| 261 | 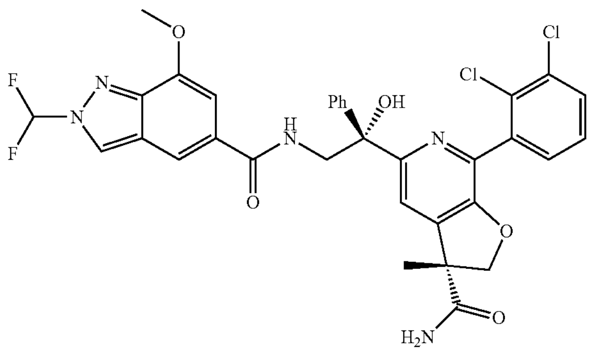 [SMILES: COc1cc(C(=O)NC[C@@](O)(c2ccccc2)c2cc3c(c(-c4cccc(Cl)c4Cl)n2)OC[C@]3(C)C(N)=O)cc2cn(C(F)F)nc12] | 682.25 |
| 262 | 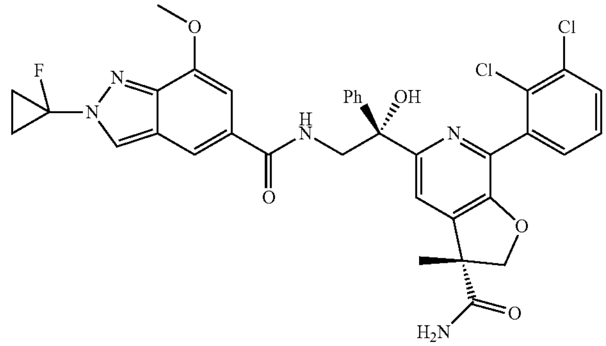 [SMILES: COc1cc(C(=O)NC[C@@](O)(c2ccccc2)c2cc3c(c(-c4cccc(Cl)c4Cl)n2)OC[C@]3(C)C(N)=O)cc2cn(C3(F)CC3)nc12] | 690.26 |
| 263 | 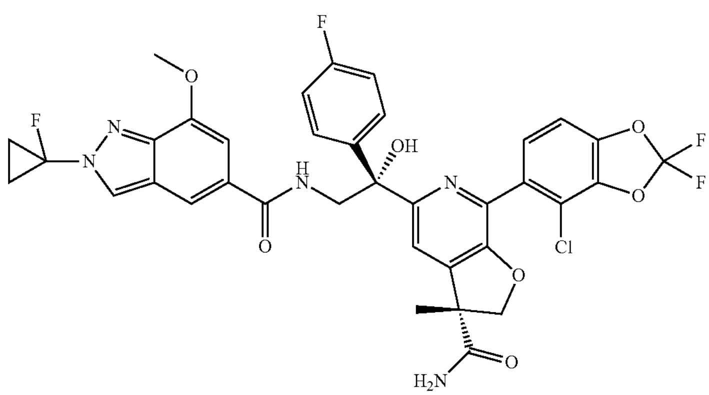 [SMILES: COc1cc(C(=O)NC[C@@](O)(c2ccc(F)cc2)c2cc3c(c(-c4ccc5c(c4Cl)OC(F)(F)O5)n2)OC[C@]3(C)C(N)=O)cc2cn(C3(F)CC3)nc12] | 754.31 |
| 264 | 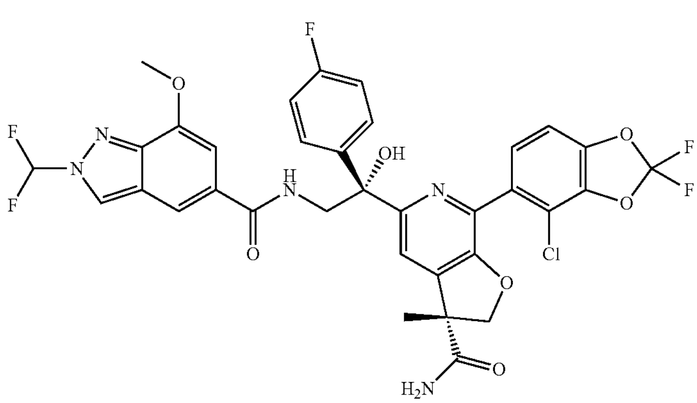 [SMILES: COc1cc(C(=O)NC[C@@](O)(c2ccc(F)cc2)c2cc3c(c(-c4ccc5c(c4Cl)OC(F)(F)O5)n2)OC[C@]3(C)C(N)=O)cc2cn(C(F)F)nc12] | 746.24 |

TABLE 3-continued
| Example | Structure | MS+ m/z |
|---|---|---|
| 265 | 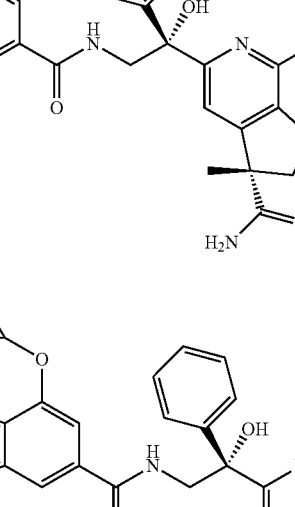 | 772.35 |
| 266 | 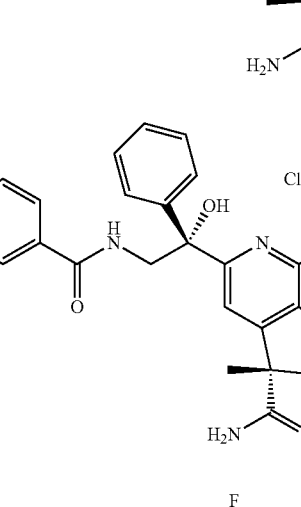 | 716.55 |
| 267 | 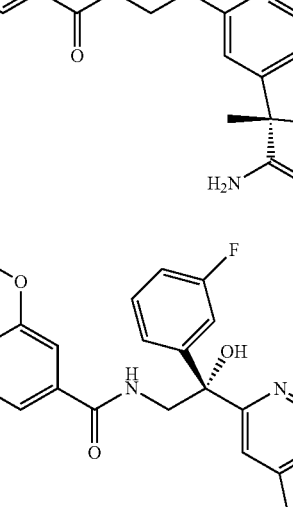 | 635.38 |
| 268 | 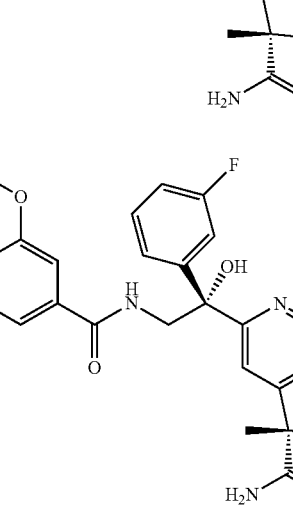 | 708.48 |

TABLE 3-continued
| Example | Structure | MS+ m/z |
|---|---|---|
| 269 | 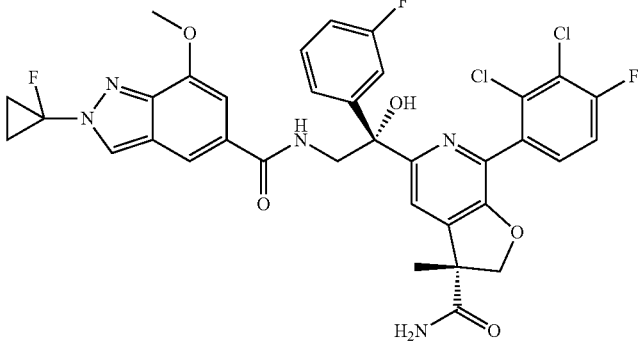 | 726.45 |
| 270 | 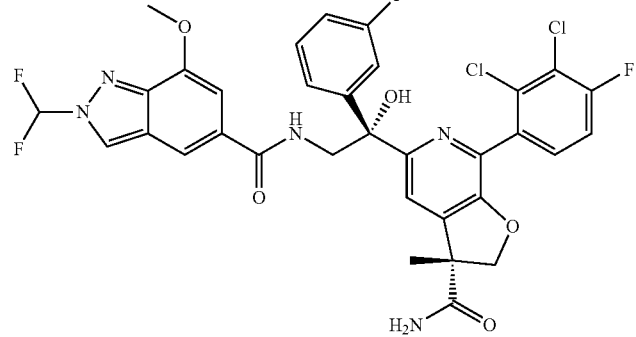 | 718.52 |
| 271 | 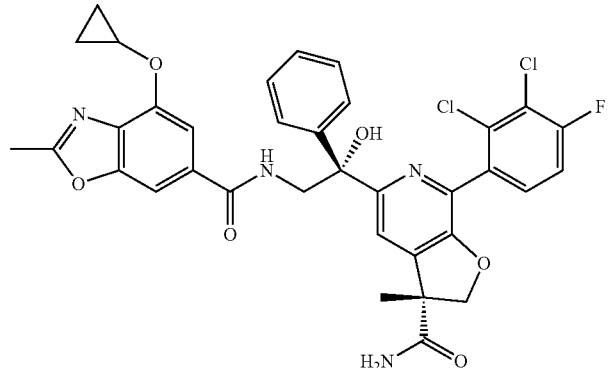 | 691.49 |
| 272 | 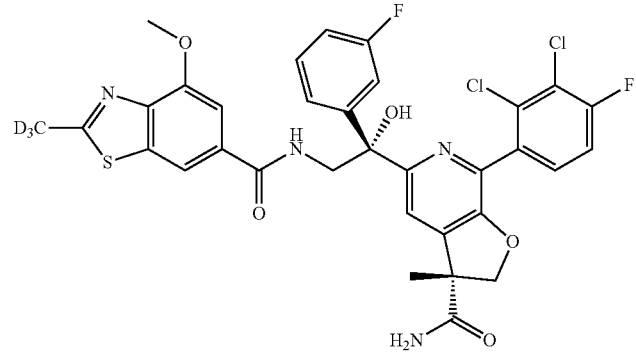 [SMILES: [2H]C([2H])([2H])c1nc2c(OC)cc(C(=O)NC[C@@](O)(c3cccc(F)c3)c3cc4c(c(-c5ccc(F)c(Cl)c5Cl)n3)OC[C@]4(C)C(N)=O)cc2s1] | 702.24 |

TABLE 3-continued

| Example | Structure | MS+ m/z |
|---------|-----------|---------|
| 273 | 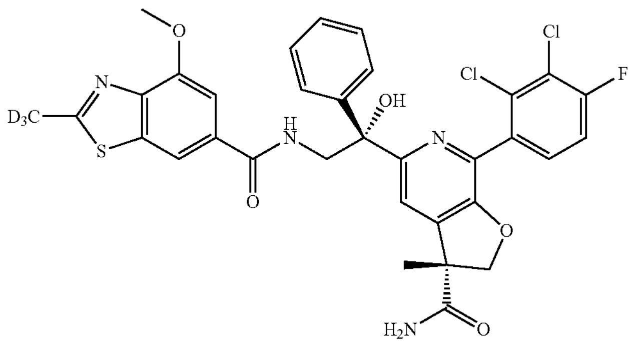 [SMILES: [2H]C([2H])([2H])c1nc2c(OC)cc(C(=O)NC[C@@](O)(c3ccccc3)c3cc4c(c(-c5ccc(F)c(Cl)c5Cl)n3)OC[C@]4(C)C(N)=O)cc2s1] | 684.39 |
| 274 | 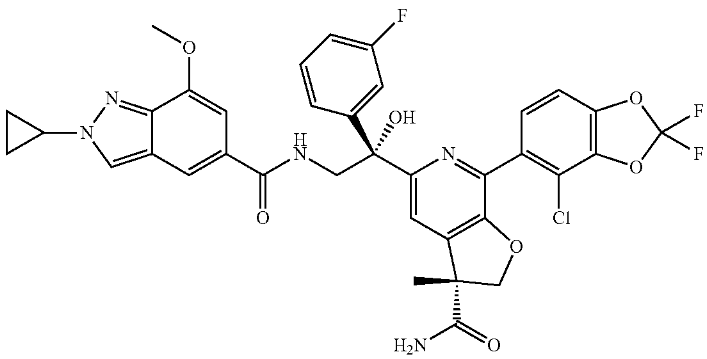 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2cn(C3CC3)nc12] | 736.57 |
| 275 | 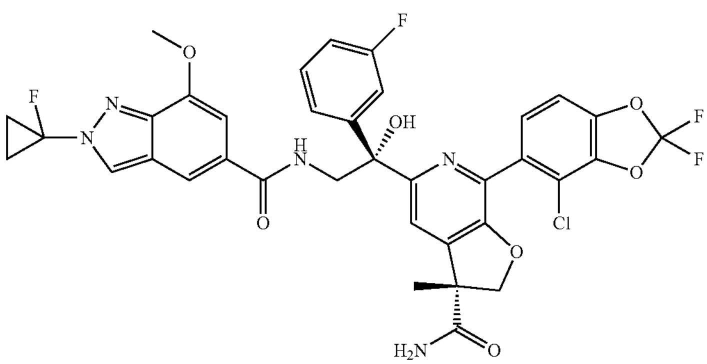 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2cn(C3(F)CC3)nc12] | 754.64 |
| 276 | 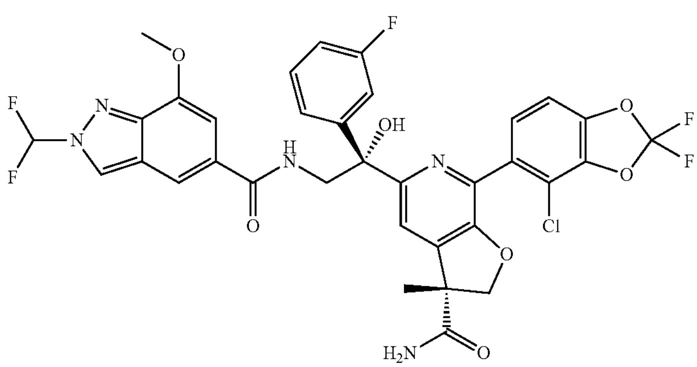 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2cn(C(F)F)nc12] | 746.50 |

TABLE 3-continued

| Example | Structure | MS+ m/z |
|---|---|---|
| 277 | 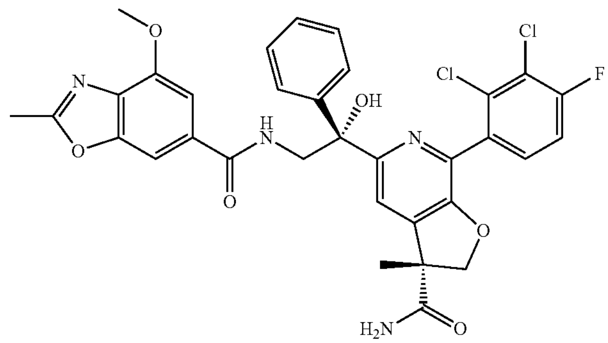 [SMILES: COc1cc(C(=O)NC[C@@](O)(c2ccccc2)c2cc3c(c(-c4ccc(F)c(Cl)c4Cl)n2)OC[C@]3(C)C(N)=O)cc2oc(C)nc12] | 665.45 |
| 278 | 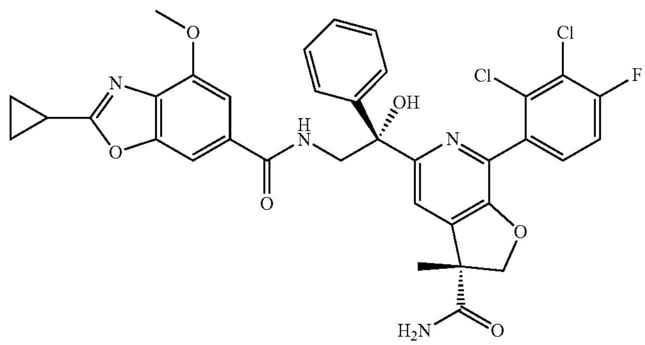 [SMILES: COc1cc(C(=O)NC[C@@](O)(c2ccccc2)c2cc3c(c(-c4ccc(F)c(Cl)c4Cl)n2)OC[C@]3(C)C(N)=O)cc2oc(C3CC3)nc12] | 691.35 |
| 279 | 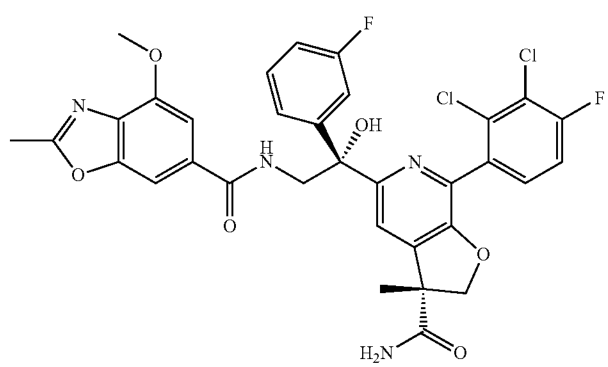 [SMILES: COc1cc(C(=O)NC[C@@](O)(c2cccc(F)c2)c2cc3c(c(-c4ccc(F)c(Cl)c4Cl)n2)OC[C@]3(C)C(N)=O)cc2oc(C)nc12] | 683.47 |
| 280 | 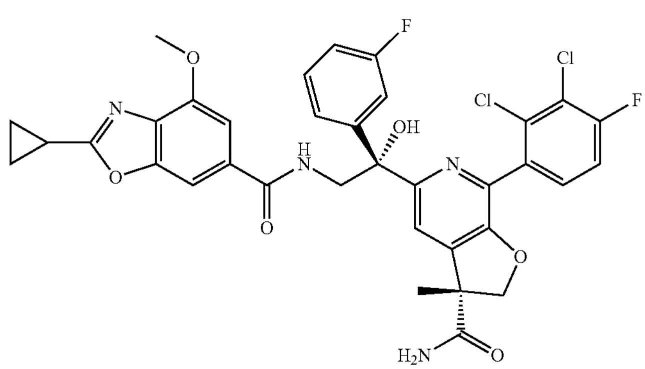 [SMILES: COc1cc(C(=O)NC[C@@](O)(c2cccc(F)c2)c2cc3c(c(-c4ccc(F)c(Cl)c4Cl)n2)OC[C@]3(C)C(N)=O)cc2oc(C3CC3)nc12] | 709.45 |

TABLE 3-continued

| Example | Structure | MS+ m/z |
|---------|-----------|---------|
| 281 | 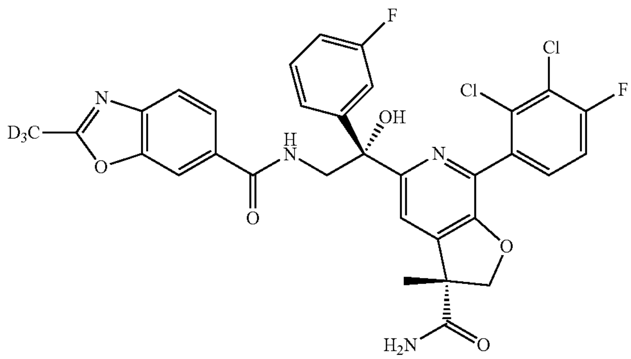 [SMILES: Cc1nc2ccc(C(=O)NC[C@@](O)(c3cccc(F)c3)c3cc4c(c(-c5ccc(F)c(Cl)c5Cl)n3)OC[C@]4(C)C(N)=O)cc2o1] | 656.29 |
| 282 | 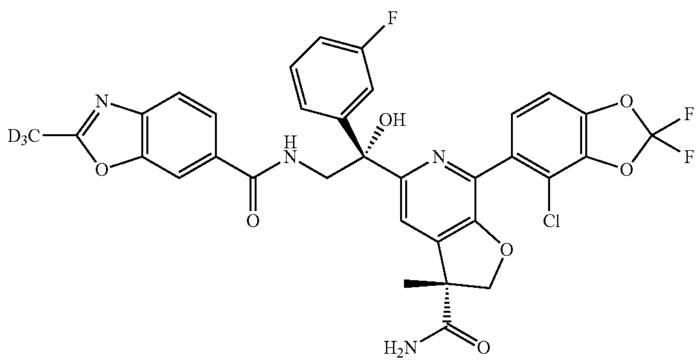 [SMILES: Cc1nc2ccc(C(=O)NC[C@@](O)(c3cccc(F)c3)c3cc4c(c(-c5ccc6c(c5Cl)OC(F)(F)O6)n3)OC[C@]4(C)C(N)=O)cc2o1] | 684.44 |
| 283 | 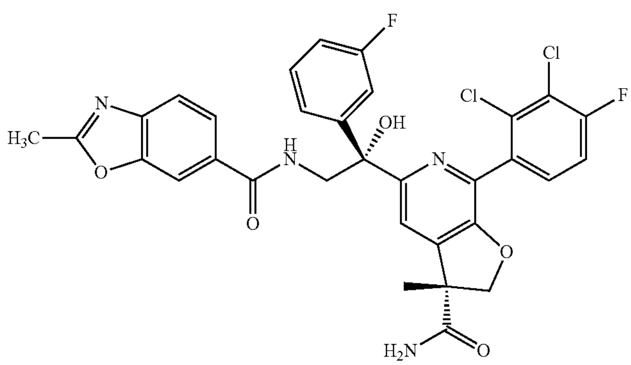 | 653.37 |
| 284 | 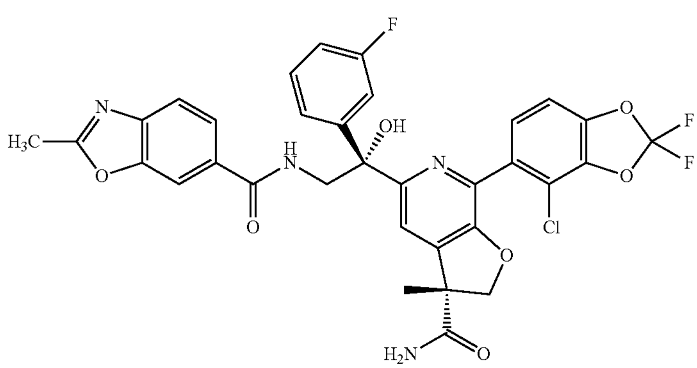 | 681.44 |

TABLE 3-continued

| Example | Structure | MS+ m/z |
|---------|-----------|---------|
| 285 | 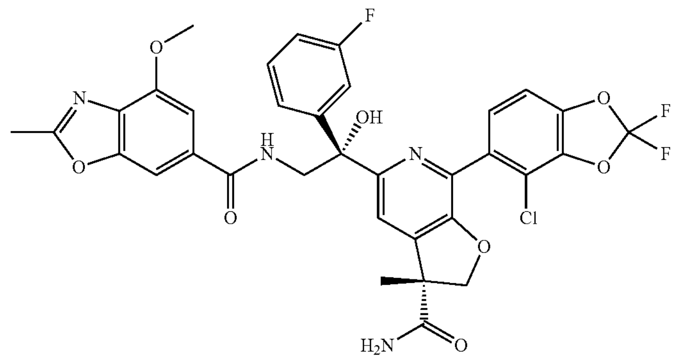 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2oc(C)nc12] | 711.61 |
| 286 | 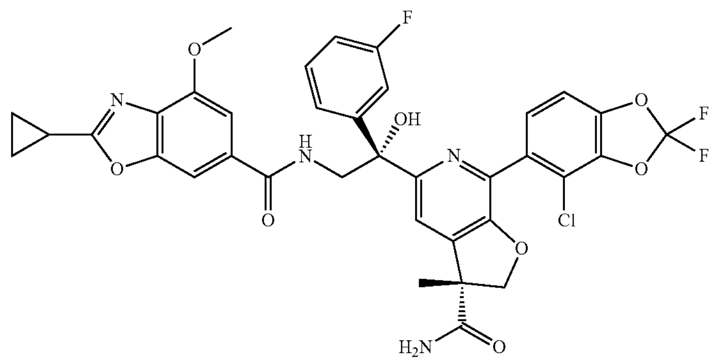 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2oc(C3CC3)nc12] | 737.54 |
| 287 | 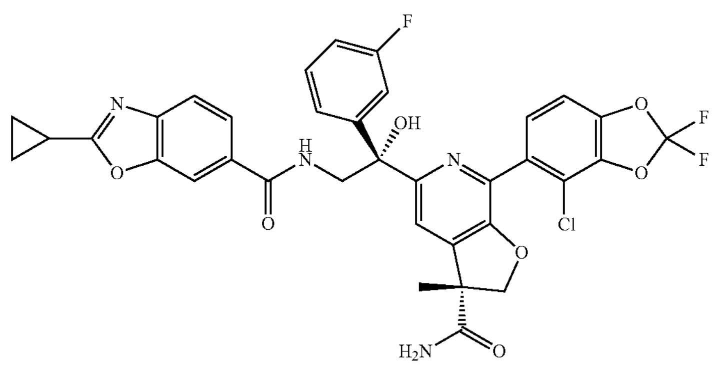 [SMILES: C[C@]1(C(N)=O)COc2c1cc([C@@](O)(CNC(=O)c1ccc3nc(C4CC4)oc3c1)c1cccc(F)c1)nc2-c1ccc2c(c1Cl)OC(F)(F)O2] | 707.54 |
| 288 | 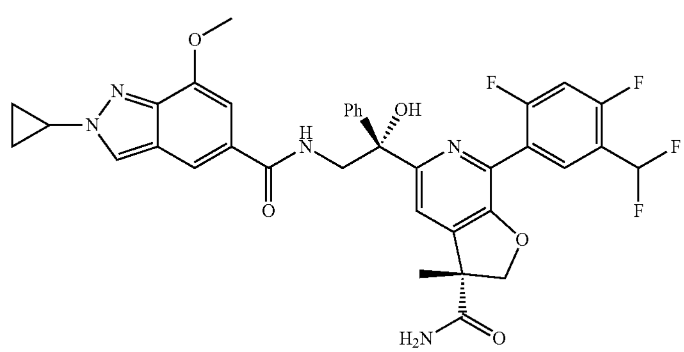 [SMILES: COc1cc(C(=O)NC[C@@](O)(c2ccccc2)c2cc3c(c(-c4cc(C(F)F)c(F)cc4F)n2)OC[C@]3(C)C(N)=O)cc2cn(C3CC3)nc12] | 690.52 |

TABLE 3-continued

| Example | Structure | MS+ m/z |
|---|---|---|
| 289 | 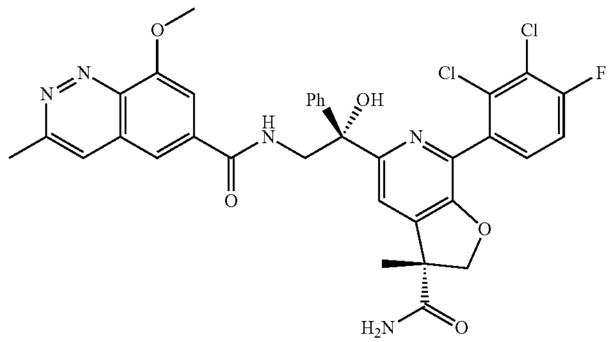 | 676.43 |
| 290 | 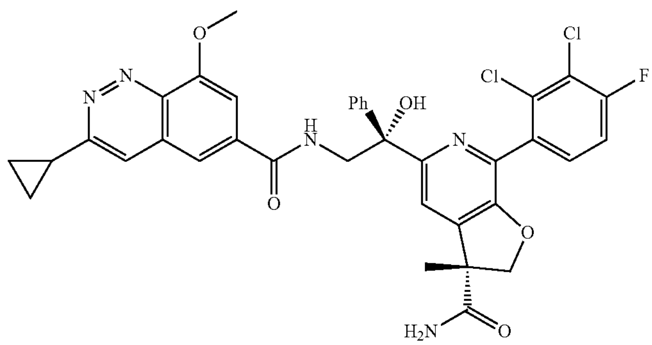 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cc(C3CC3)nnc12] | 702.49 |
| 291 | 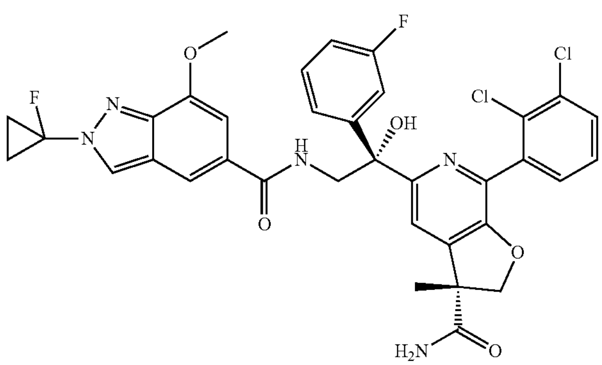 [SMILES: COc1cc(C(=O)NC[C@@](O)(c2cccc(F)c2)c2cc3c(c(-c4cccc(Cl)c4Cl)n2)OC[C@]3(C)C(N)=O)cc2cn(C3(F)CC3)nc12] | 708.39 |
| 292 | 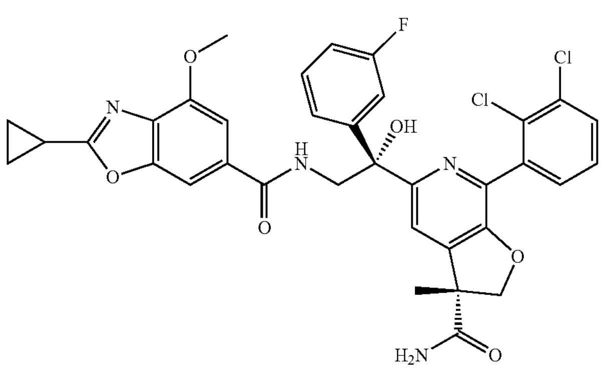 [SMILES: COc1cc(C(=O)NC[C@@](O)(c2cccc(F)c2)c2cc3c(c(-c4cccc(Cl)c4Cl)n2)OC[C@]3(C)C(N)=O)cc2oc(C3CC3)nc12] | 691.54 |

TABLE 3-continued
| Example | Structure | MS+ m/z |
|---|---|---|
| 293 | 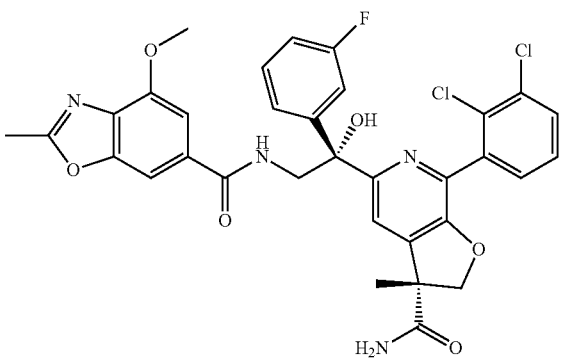 [SMILES: COc1cc(C(=O)NC[C@@](O)(c2cccc(F)c2)c2cc3c(c(-c4cccc(Cl)c4Cl)n2)OC[C@]3(C)C(N)=O)cc2oc(C)nc12] | 665.45 |
| 294 | 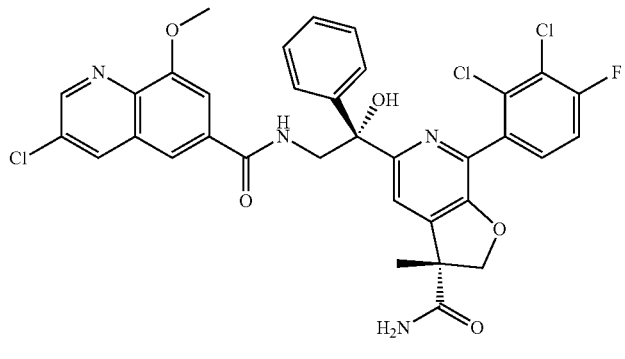 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cc(Cl)cnc12] | 695.30 |
| 295 | 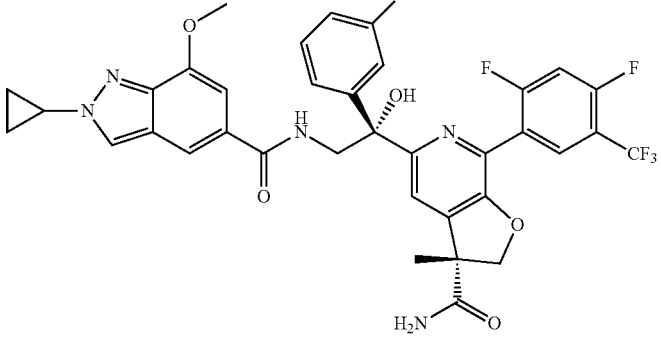 | 725.85 |
| 296 | 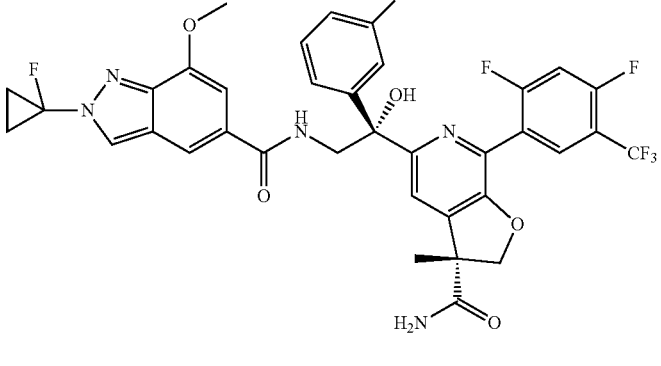 | 743.89 |

TABLE 3-continued
| Example | Structure | MS⁺ m/z |
|---|---|---|
| 297 | 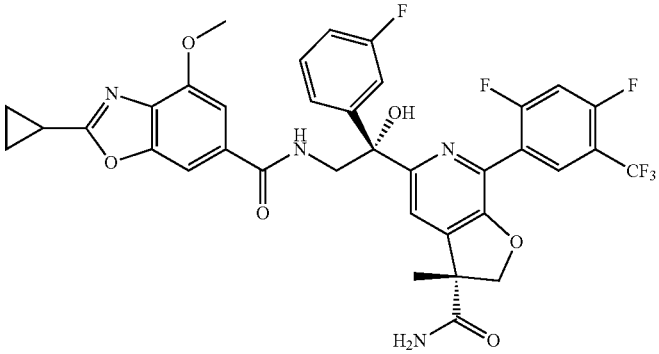 [SMILES: COc1cc(C(=O)NC[C@@](O)(c2cccc(F)c2)c2cc3c(c(-c4cc(C(F)(F)F)c(F)cc4F)n2)OC[C@]3(C)C(N)=O)cc2oc(C3CC3)nc12] | 726.85 |
| 298 | 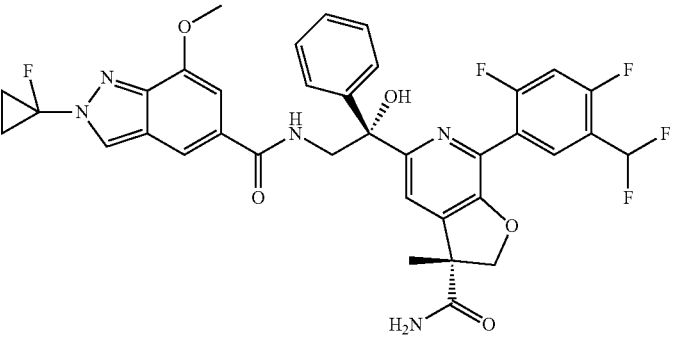 [SMILES: COc1cc(C(=O)NC[C@@](O)(c2ccccc2)c2cc3c(c(-c4cc(C(F)F)c(F)cc4F)n2)OC[C@]3(C)C(N)=O)cc2cn(C3(F)CC3)nc12] | 707.76 |
| 299 | 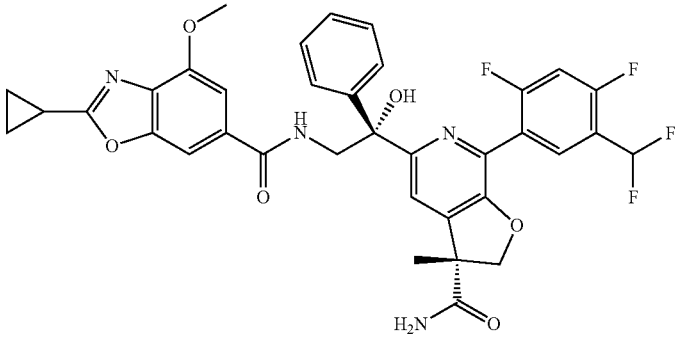 [SMILES: COc1cc(C(=O)NC[C@@](O)(c2ccccc2)c2cc3c(c(-c4cc(C(F)F)c(F)cc4F)n2)OC[C@]3(C)C(N)=O)cc2oc(C3CC3)nc12] | 690.86 |
| 300 | 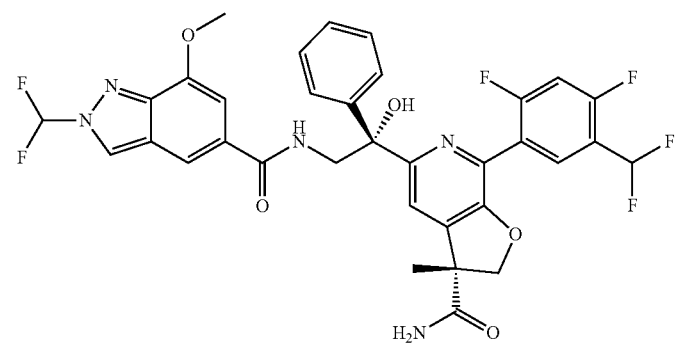 [SMILES: COc1cc(C(=O)NC[C@@](O)(c2ccccc2)c2cc3c(c(-c4cc(C(F)F)c(F)cc4F)n2)OC[C@]3(C)C(N)=O)cc2cn(C(F)F)nc12] | 700.28 |

TABLE 3-continued

| Example | Structure | MS+ m/z |
|---|---|---|
| 301 | 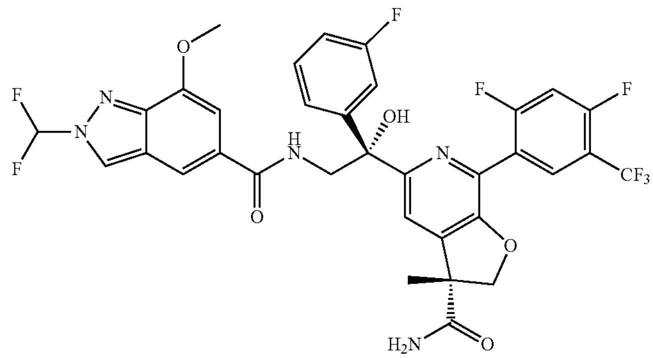 [SMILES: COc1cc(C(=O)NC[C@@](O)(c2cccc(F)c2)c2cc3c(c(-c4cc(C(F)(F)F)c(F)cc4F)n2)OC[C@]3(C)C(N)=O)cc2cn(C(F)F)nc12] | 736.17 |
| 302 | 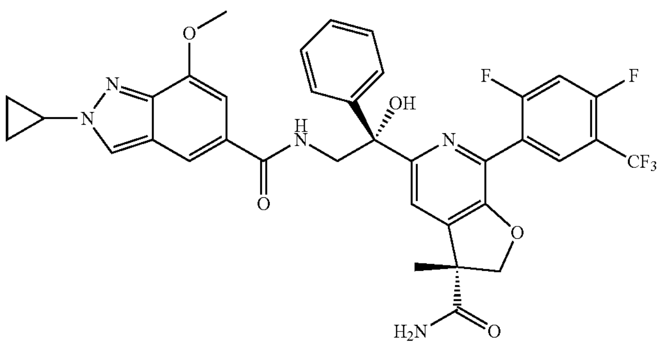 [SMILES: COc1cc(C(=O)NC[C@@](O)(c2ccccc2)c2cc3c(c(-c4cc(C(F)(F)F)c(F)cc4F)n2)OC[C@]3(C)C(N)=O)cc2cn(C3CC3)nc12] | 709.47 |
| 303 | 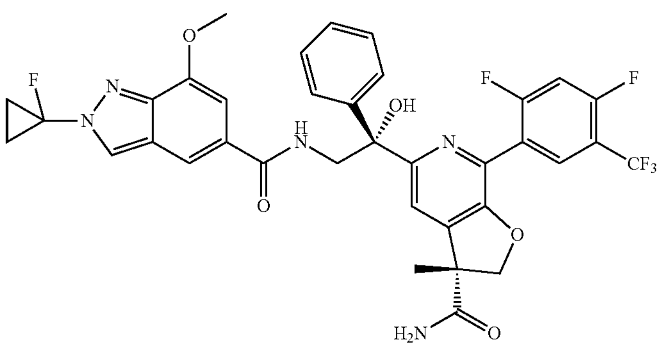 | 727.42 |
| 304 | 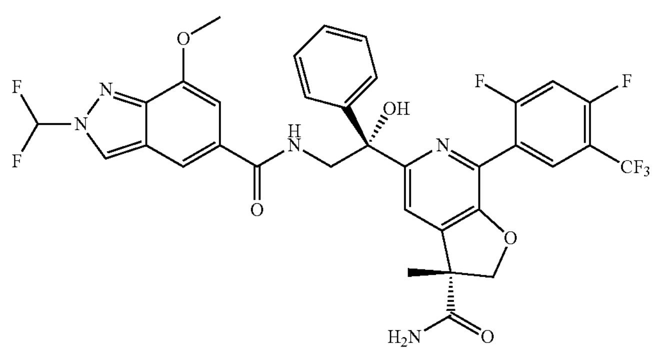 [SMILES: COc1cc(C(=O)NC[C@@](O)(c2ccccc2)c2cc3c(c(-c4cc(C(F)(F)F)c(F)cc4F)n2)OC[C@]3(C)C(N)=O)cc2cn(C(F)F)nc12] | 719.40 |

TABLE 3-continued

| Example | Structure | MS+ m/z |
|---|---|---|
| 305 | 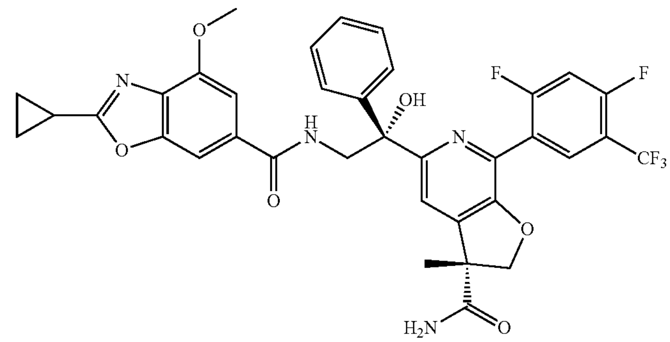 [SMILES: COc1cc(C(=O)NC[C@@](O)(c2ccccc2)c2cc3c(c(-c4cc(C(F)(F)F)c(F)cc4F)n2)OC[C@]3(C)C(N)=O)cc2oc(C3CC3)nc12] | 710.42 |
| 307 | 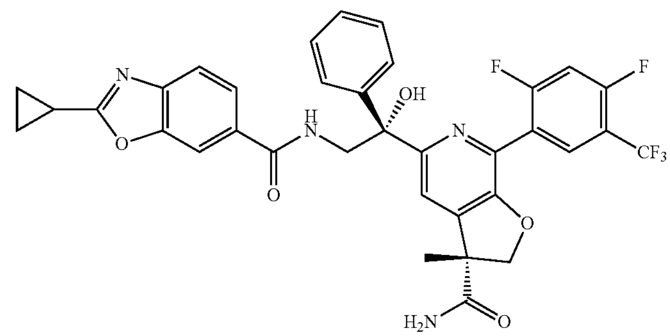 [SMILES: C[C@]1(C(N)=O)COc2c1cc([C@@](O)(CNC(=O)c1ccc3nc(C4CC4)oc3c1)c1ccccc1)nc2-c1cc(C(F)(F)F)c(F)cc1F] | 680.42 |
| 308 | 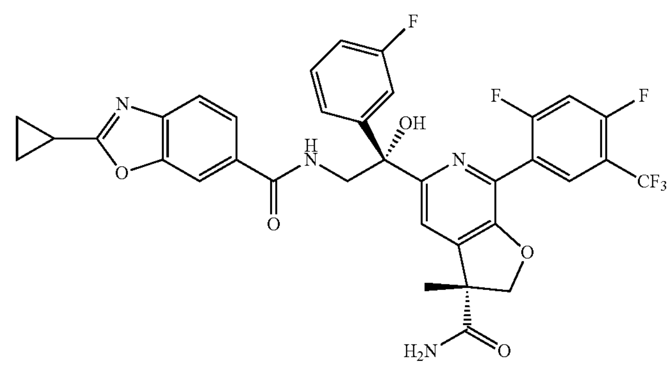 [SMILES: C[C@]1(C(N)=O)COc2c1cc([C@@](O)(CNC(=O)c1ccc3nc(C4CC4)oc3c1)c1cccc(F)c1)nc2-c1cc(C(F)(F)F)c(F)cc1F] | 698.43 |
| 311 | 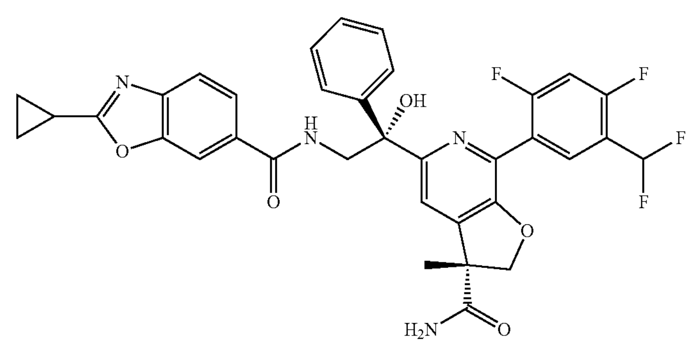 [SMILES: C[C@]1(C(N)=O)COc2c1cc([C@@](O)(CNC(=O)c1ccc3nc(C4CC4)oc3c1)c1ccccc1)nc2-c1cc(C(F)F)c(F)cc1F] | 662.38 |

TABLE 3-continued
| Example | Structure | MS+ m/z |
|---|---|---|
| 312 | 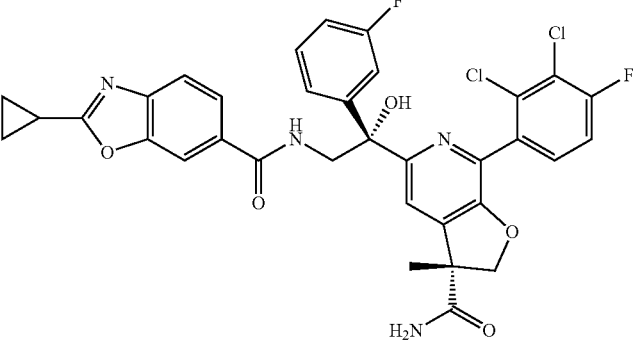 | 680.22 |
| 313 | 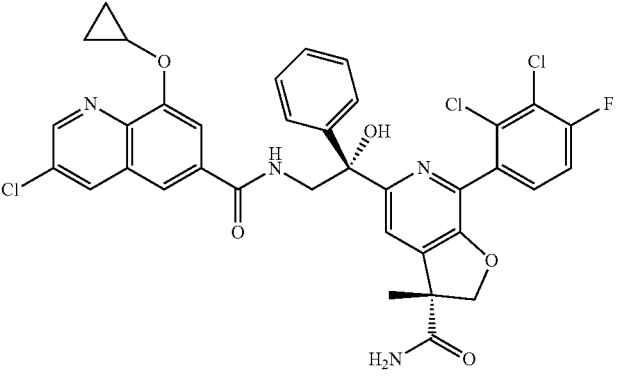 [SMILES: C[C@]1(C(N)=O)COc2c1cc([C@@](O)(CNC(=O)c1cc(OC3CC3)c3ncc(Cl)cc3c1)c1ccccc1)nc2-c1ccc(F)c(Cl)c1Cl] | 722.13 |
| 314 | 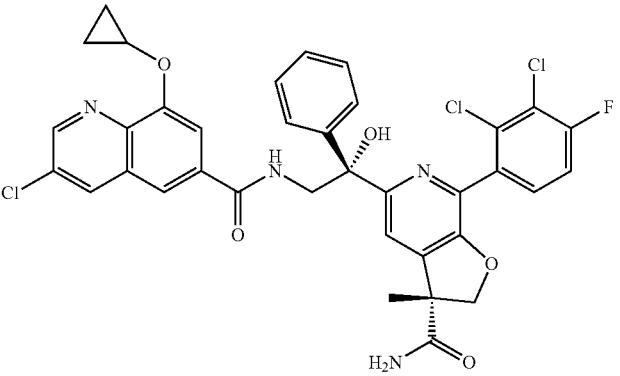 [SMILES: C[C@]1(C(N)=O)COc2c1cc([C@@](O)(CNC(=O)c1cc(OC3CC3)c3ncc(Cl)cc3c1)c1ccccc1)nc2-c1ccc(F)c(Cl)c1Cl] | 714.29 |
| 315 | 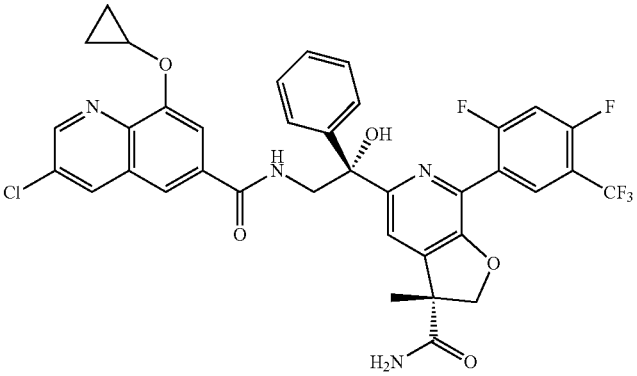 [SMILES: C[C@]1(C(N)=O)COc2c1cc([C@@](O)(CNC(=O)c1cc(OC3CC3)c3ncc(Cl)cc3c1)c1ccccc1)nc2-c1cc(C(F)(F)F)c(F)cc1F] | 740.39 |

TABLE 3-continued

| Example | Structure | MS+ m/z |
|---|---|---|
| 331 | 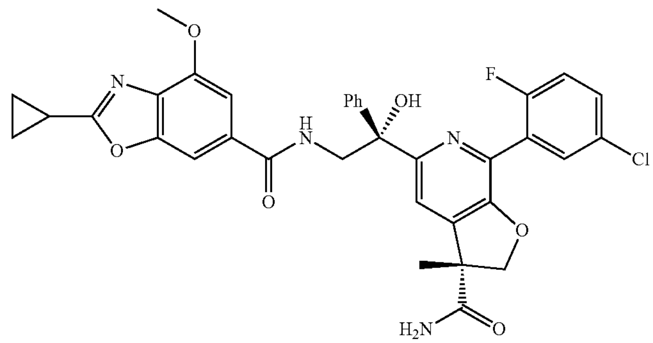 | 657.42 |
| 332 | 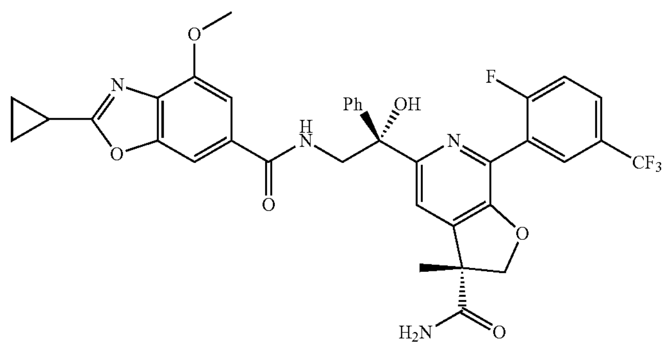 | 691.21 |
| 333 | 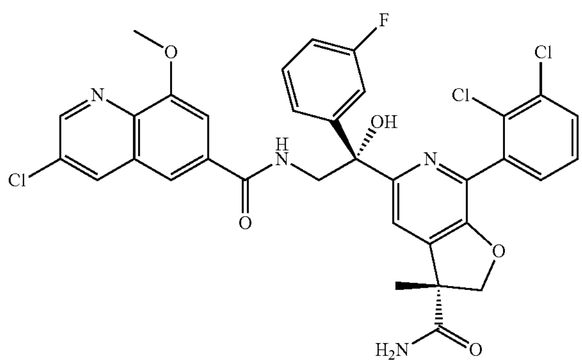 [SMILES: COc1cc(C(=O)NC[C@@](O)(c2cccc(F)c2)c2cc3c(c(-c4cccc(Cl)c4Cl)n2)OC[C@]3(C)C(N)=O)cc2cc(Cl)cnc12] | 697.06 |
| 334 | 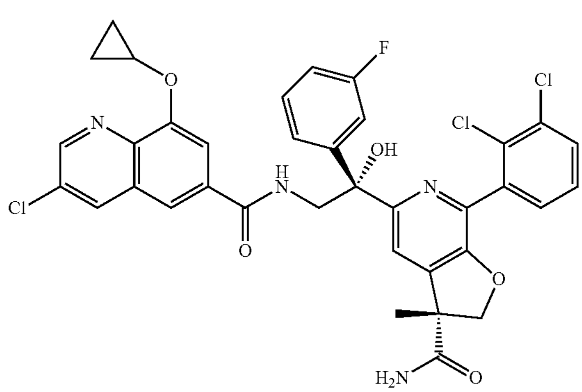 [SMILES: C[C@]1(C(N)=O)COc2c1cc([C@@](O)(CNC(=O)c1cc(OC3CC3)c3ncc(Cl)cc3c1)c1cccc(F)c1)nc2-c1cccc(Cl)c1Cl] | 721.18 |

TABLE 3-continued

| Example | Structure | MS+ m/z |
|---|---|---|
| 335 | 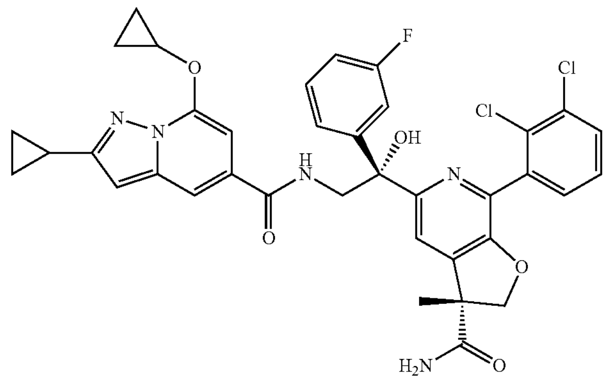 [SMILES: C[C@]1(C(N)=O)COc2c1cc([C@@](O)(CNC(=O)c1cc(OC3CC3)n3nc(C4CC4)cc3c1)c1cccc(F)c1)nc2-c1cccc(Cl)c1Cl] | 716.31 |
| 336 | 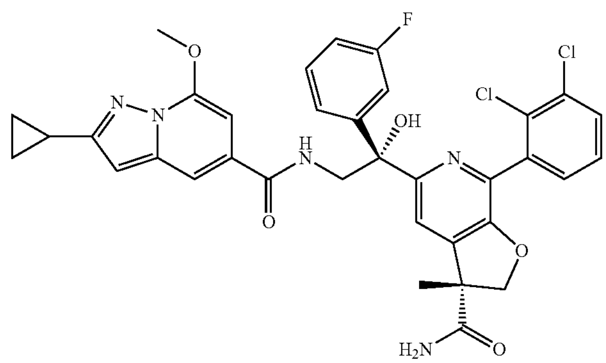 [SMILES: COc1cc(C(=O)NC[C@@](O)(c2cccc(F)c2)c2cc3c(c(-c4cccc(Cl)c4Cl)n2)OC[C@]3(C)C(N)=O)cc2cc(C3CC3)nn12] | 690.10 |
| 337 | 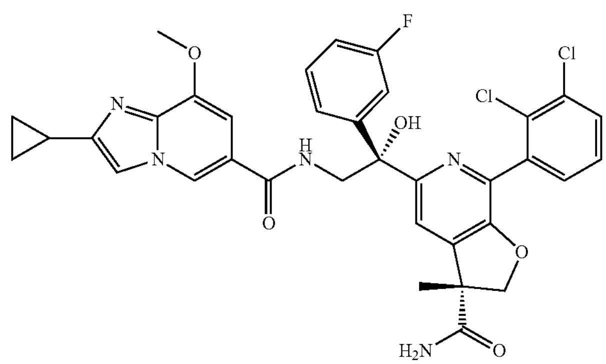 [SMILES: COc1cc(C(=O)NC[C@@](O)(c2cccc(F)c2)c2cc3c(c(-c4cccc(Cl)c4Cl)n2)OC[C@]3(C)C(N)=O)cn2cc(C3CC3)nc12] | 690.10 |
| 339 | 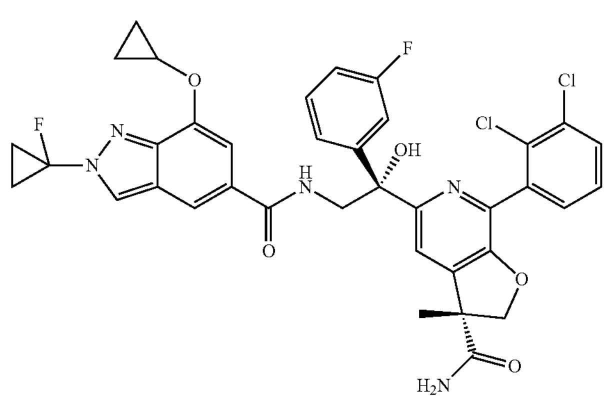 [SMILES: C[C@]1(C(N)=O)COc2c1cc([C@@](O)(CNC(=O)c1cc(OC3CC3)c3nn(C4(F)CC4)cc3c1)c1cccc(F)c1)nc2-c1cccc(Cl)c1Cl] | 735.18 |

TABLE 3-continued

| Example | Structure | MS+ m/z |
|---|---|---|
| 340 | 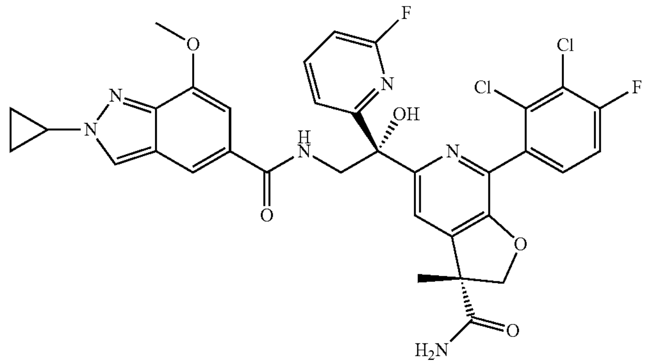 [SMILES: COc1cc(C(=O)NC[C@@](O)(c2cccc(F)n2)c2cc3c(c(-c4ccc(F)c(Cl)c4Cl)n2)OC[C@]3(C)C(N)=O)cc2cn(C3CC3)nc12] | 710.16 |
| 342 | 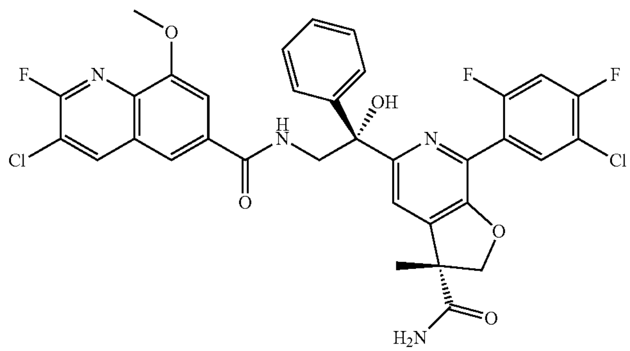 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)c(F)nc12] | 697.24 |

The following Table 4 contains examples that were prepared using methods similar to Example 47. The majority of the compounds were purified by prep-HPLC (ACN/H$_2$O, 20-90%, 25 min), and some were purified by automated column chromatography (silica gel). Some examples were unseparable by prep-HPLC and reported as a mixture of diastereomers.

TABLE 4

| Example | Structure | MS+ m/z |
|---|---|---|
| 361 | 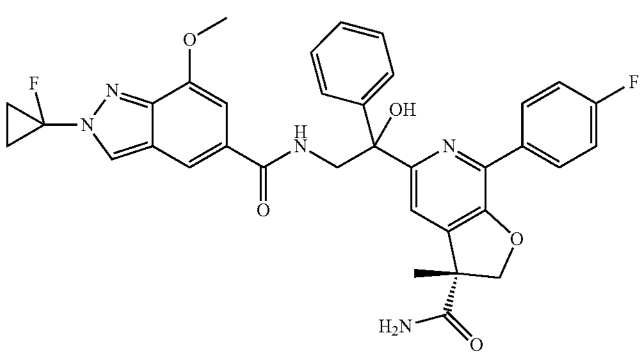 [SMILES: COc1cc(C(=O)NCC(O)(c2ccccc2)c2cc3c(c(-c4ccc(F)cc4)n2)OC[C@]3(C)C(N)=O)cc2cn(C3(F)CC3)nc12] | 640.20 |

TABLE 4-continued

| Example | Structure | MS+ m/z |
|---|---|---|
| 362 | 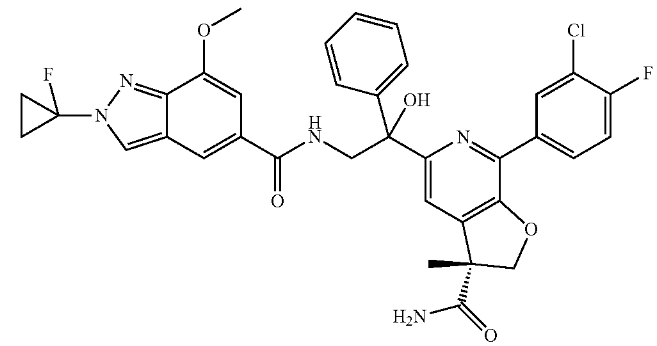 [SMILES: COc1cc(C(=O)NCC(O)(c2ccccc2)c2cc3c(c(-c4ccc(F)c(Cl)c4)n2)OC[C@]3(C)C(N)=O)cc2cn(C3(F)CC3)nc12] | 674.20 |
| 363 | 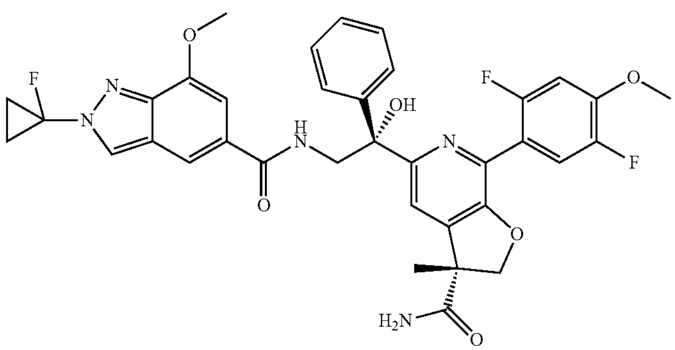 [SMILES: COc1cc(F)c(-c2nc([C@@](O)(CNC(=O)c3cc(OC)c4nn(C5(F)CC5)cc4c3)c3ccccc3)cc3c2OC[C@]3(C)C(N)=O)cc1F] | 688.20 |
| 364 | 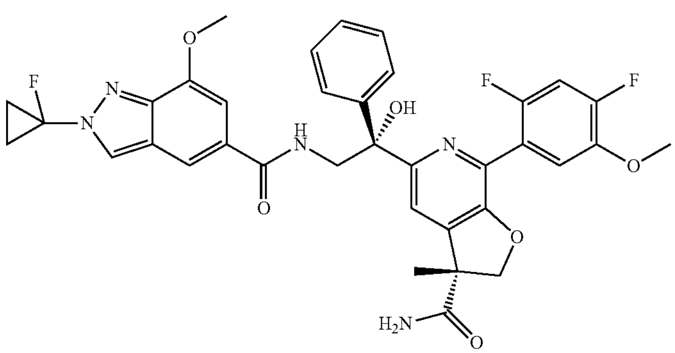 [SMILES: COc1cc(-c2nc([C@@](O)(CNC(=O)c3cc(OC)c4nn(C5(F)CC5)cc4c3)c3ccccc3)cc3c2OC[C@]3(C)C(N)=O)c(F)cc1F] | 688.20 |
| 365 | 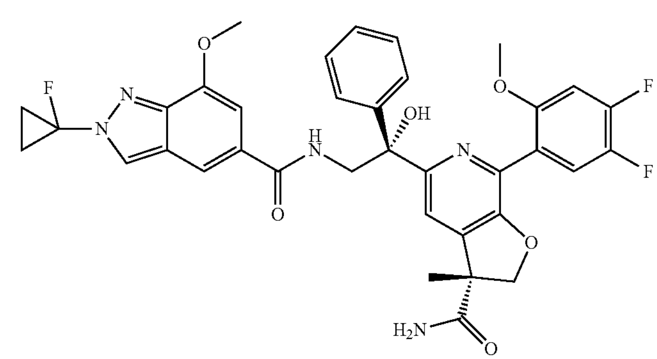 [SMILES: COc1cc(F)c(F)cc1-c1nc([C@@](O)(CNC(=O)c2cc(OC)c3nn(C4(F)CC4)cc3c2)c2ccccc2)cc2c1OC[C@]2(C)C(N)=O] | 688.20 |

TABLE 4-continued

| Example | Structure | MS+ m/z |
|---|---|---|
| 366 | 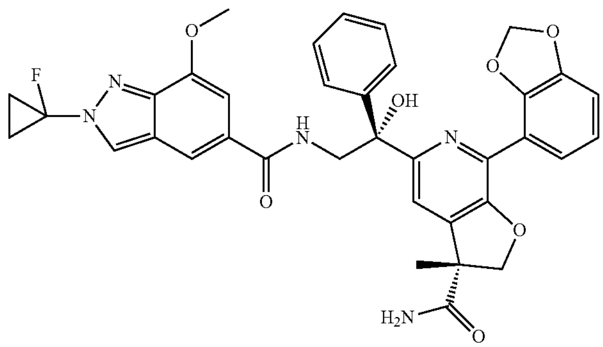 [SMILES: COc1cc(C(=O)NC[C@@](O)(c2ccccc2)c2cc3c(c(-c4cccc5c4OCO5)n2)OC[C@]3(C)C(N)=O)cc2cn(C3(F)CC3)nc12] | 666.40 |
| 367 | 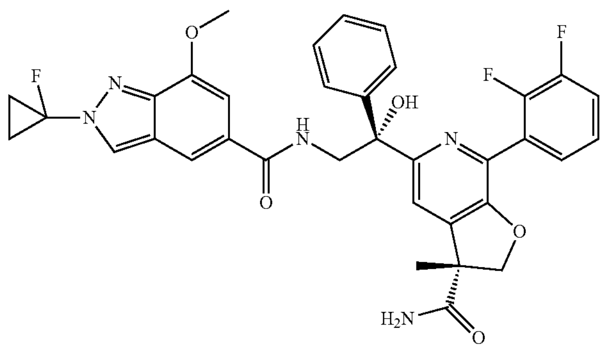 [SMILES: COc1cc(C(=O)NC[C@@](O)(c2ccccc2)c2cc3c(c(-c4cccc(F)c4F)n2)OC[C@]3(C)C(N)=O)cc2cn(C3(F)CC3)nc12] | 658.37 |
| 368 | 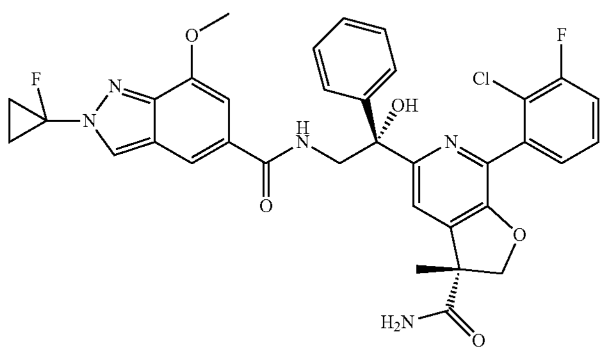 [SMILES: COc1cc(C(=O)NC[C@@](O)(c2ccccc2)c2cc3c(c(-c4cccc(F)c4Cl)n2)OC[C@]3(C)C(N)=O)cc2cn(C3(F)CC3)nc12] | 674.36 |
| 369 | 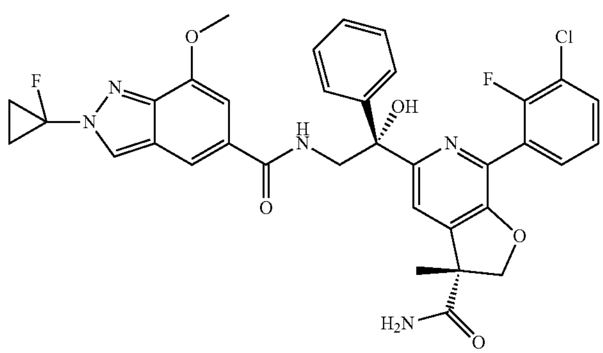 | 674.34 |

TABLE 4-continued

| Example | Structure | MS+ m/z |
|---|---|---|
| 370 | 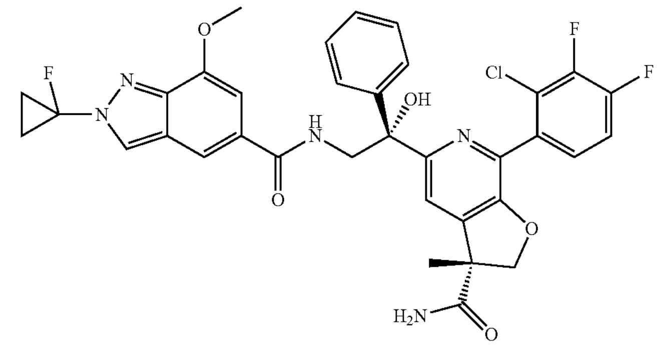 [SMILES: COc1cc(C(=O)NC[C@@](O)(c2ccccc2)c2cc3c(c(-c4ccc(F)c(F)c4Cl)n2)OC[C@]3(C)C(N)=O)cc2cn(C3(F)CC3)nc12] | 692.35 |
| 371 | 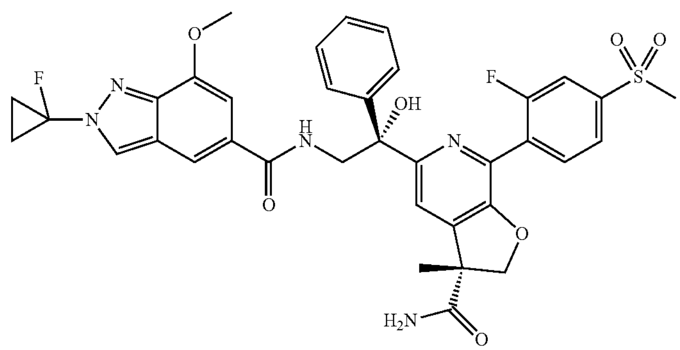 [SMILES: COc1cc(C(=O)NC[C@@](O)(c2ccccc2)c2cc3c(c(-c4ccc(S(C)(=O)=O)cc4F)n2)OC[C@]3(C)C(N)=O)cc2cn(C3(F)CC3)nc12] | 718.20 |
| 372 | 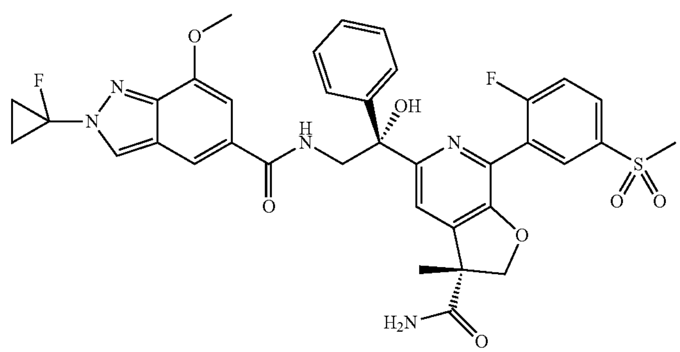 [SMILES: COc1cc(C(=O)NC[C@@](O)(c2ccccc2)c2cc3c(c(-c4cc(S(C)(=O)=O)ccc4F)n2)OC[C@]3(C)C(N)=O)cc2cn(C3(F)CC3)nc12] | 718.39 |
| 373 | 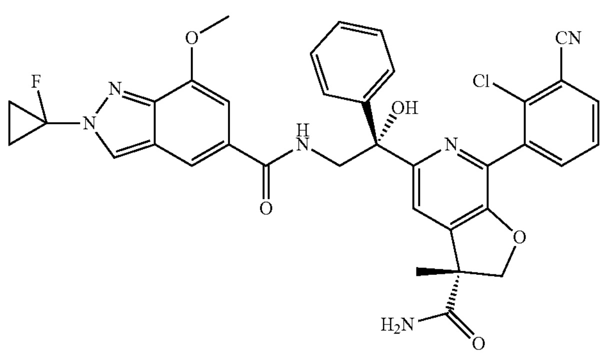 | 640.20 |

TABLE 4-continued

| Example | Structure | MS+ m/z |
|---|---|---|
| 374 | 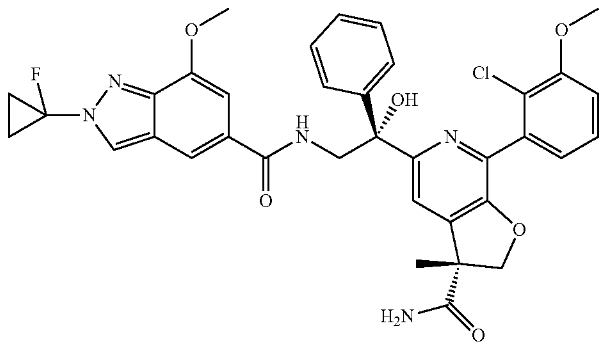 [SMILES: COc1cccc(-c2nc([C@@](O)(CNC(=O)c3cc(OC)c4nn(C5(F)CC5)cc4c3)c3ccccc3)cc3c2OC[C@]3(C)C(N)=O)c1Cl] | 686.21 |
| 375 | 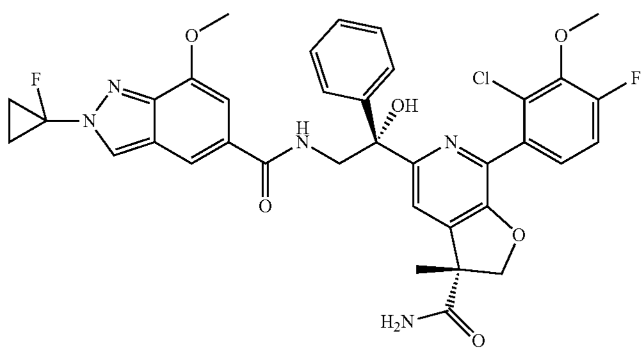 [SMILES: COc1c(F)ccc(-c2nc([C@@](O)(CNC(=O)c3cc(OC)c4nn(C5(F)CC5)cc4c3)c3ccccc3)cc3c2OC[C@]3(C)C(N)=O)c1Cl] | 704.19 |
| 397 | 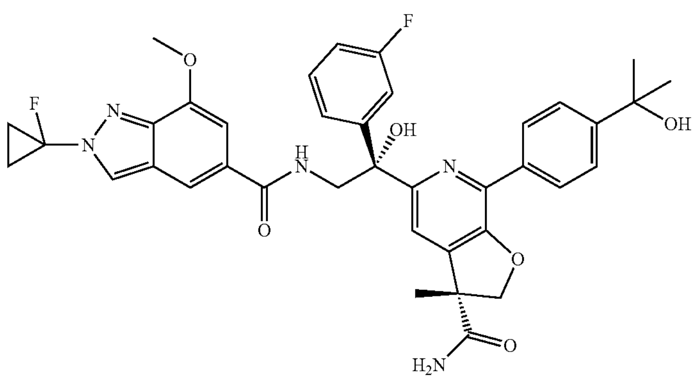 [SMILES: COc1cc(C(=O)NC[C@@](O)(c2cccc(F)c2)c2cc3c(c(-c4ccc(C(C)(C)O)cc4)n2)OC[C@]3(C)C(N)=O)cc2cn(C3(F)CC3)nc12] | 698.43 |
| 398 | 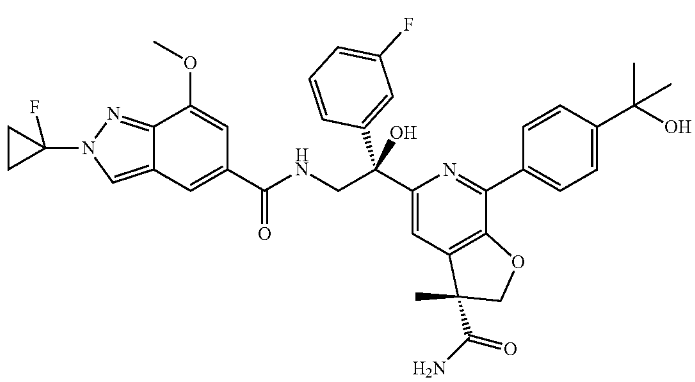 [SMILES: COc1cc(C(=O)NC[C@](O)(c2cccc(F)c2)c2cc3c(c(-c4ccc(C(C)(C)O)cc4)n2)OC[C@]3(C)C(N)=O)cc2cn(C3(F)CC3)nc12] | 698.43 |

TABLE 4-continued

| Example | Structure | MS⁺ m/z |
|---|---|---|
| 399 | 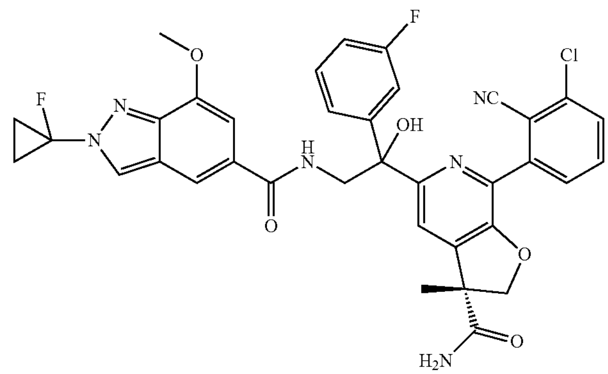 [SMILES: COc1cc(C(=O)NCC(O)(c2cccc(F)c2)c2cc3c(c(-c4cccc(Cl)c4C#N)n2)OC[C@]3(C)C(N)=O)cc2cn(C3(F)CC3)nc12] | 699.27 |
| 400 | 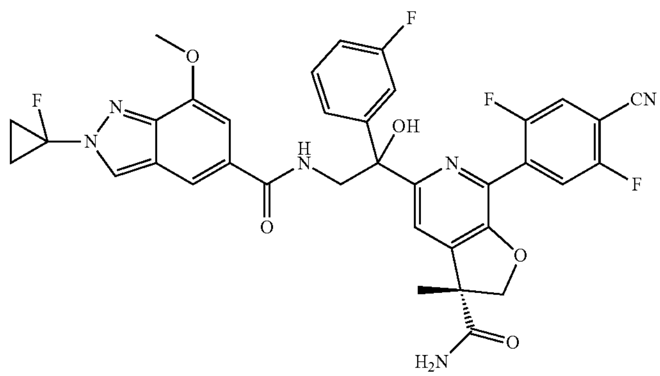 [SMILES: COc1cc(C(=O)NCC(O)(c2cccc(F)c2)c2cc3c(c(-c4cc(F)c(C#N)cc4F)n2)OC[C@]3(C)C(N)=O)cc2cn(C3(F)CC3)nc12] | 710.16 |
| 405 | 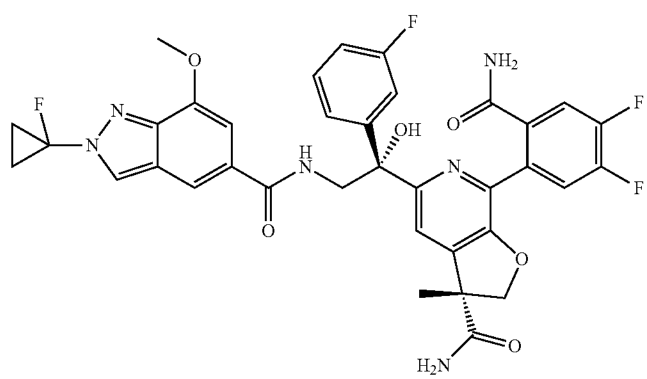 [SMILES: COc1cc(C(=O)NC[C@@](O)(c2cccc(F)c2)c2cc3c(c(-c4cc(F)c(F)cc4C(N)=O)n2)OC[C@]3(C)C(N)=O)cc2cn(C3(F)CC3)nc12] | 719.46 |
| 406 | 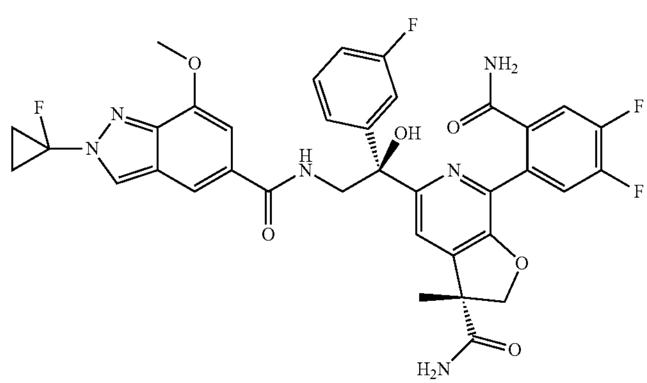 [SMILES: COc1cc(C(=O)NC[C@](O)(c2cccc(F)c2)c2cc3c(c(-c4cc(F)c(F)cc4C(N)=O)n2)OC[C@]3(C)C(N)=O)cc2cn(C3(F)CC3)nc12] | 719.46 |

Intermediate 59

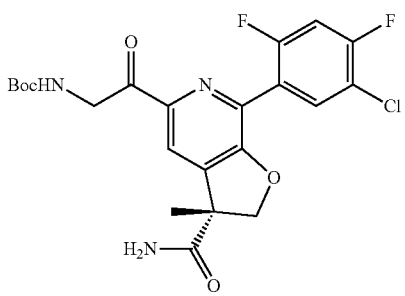 [SMILES: CC(C)(C)OC(=O)NCC(=O)c1cc2c(c(-c3cc(Cl)c(F)cc3F)n1)OC[C@]2(C)C(N)=O]

Intermediate 59 Step a

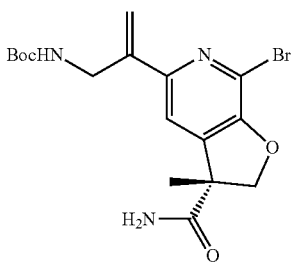 [SMILES: C=C(CNC(=O)OC(C)(C)C)c1cc2c(c(Br)n1)OC[C@]2(C)C(N)=O]

A solution of CAN-7-bromo-5-iodo-3-methyl-2,3-dihydrofuro[2,3-c]pyridine-3-carboxamide (2 g, 5.22 mmol), Pd(dppf)Cl$_2$CH$_2$Cl$_2$ (0.43 g, 0.52 mmol) and K$_2$CO$_3$ (1.44 g, 10.44 mmol) and tert-butyl N-[2-(4,4,5,5-tetramethyl-1,3,2-dioxaborolan-2-yl)prop-2-en-1-yl]carbamate (1.48 g, 5.22 mmol) in dioxane (16 mL), H$_2$O (4 mL) was stirred for 2 h at 80° C. under nitrogen atmosphere. The resulting mixture was extracted, concentrated and purified by silica gel column chromatography to afford the desired compound (1.9 g, 88%) as a yellow oil. ESI-MS m/z: 413.90 [M+H]$^+$.

Intermediate 59 Step b

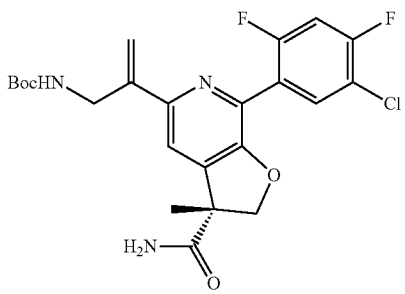 [SMILES: C=C(CNC(=O)OC(C)(C)C)c1cc2c(c(-c3cc(Cl)c(F)cc3F)n1)OC[C@]2(C)C(N)=O]

A solution of the compound from step a (1.9 g, 4.61 mmol), Pd(dppf)Cl$_2$CH$_2$Cl$_2$ (375 mg, 0.46 mmol) and K$_2$CO$_3$ (1.27 g, 9.22 mmol) and 2-(5-chloro-2,4-difluorophenyl)-4,4,5,5-tetramethyl-1,3,2-dioxaborolane (1.90 g, 6.92 mmol) in dioxane (18 mL) and H$_2$O (2 mL) was stirred for 2 h at 80° C. under nitrogen atmosphere. The resulting mixture was extracted, concentrated and purified by silica gel column chromatography to afford the desired compound (1.8 g, 81%) as a yellow solid. ESI-MS m/z: 480.10 [M+H]$^+$.

Intermediate 59 Step c

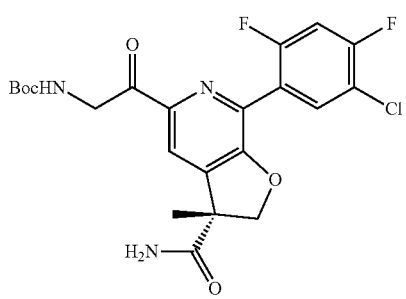 [SMILES: CC(C)(C)OC(=O)NCC(=O)c1cc2c(c(-c3cc(Cl)c(F)cc3F)n1)OC[C@]2(C)C(N)=O]

A solution of the compound from step b (2 g, 4.16 mmol), K$_2$OsO$_4$·2H$_2$O (0.06 g, 0.17 mmol), NMO (1.37 g, 11.67 mmol) and H$_2$O (20 mL) in acetone (20 mL) was stirred for overnight at room temperature. The resulting mixture was extracted, concentrated and dissolved in H$_2$O (20 mL) and acetone (20 mL). NaIO4 (4.01 g, 18.75 mmol) was added. The resulting mixture was stirred for additional 4 h at room temperature. The resulting mixture was extracted, concentrated and purified by silica gel column chromatography to afford the desired compound (1.7 g, 84%) as a yellow solid. ESI-MS m/z: 482.00 [M+H]$^+$.

Example 463

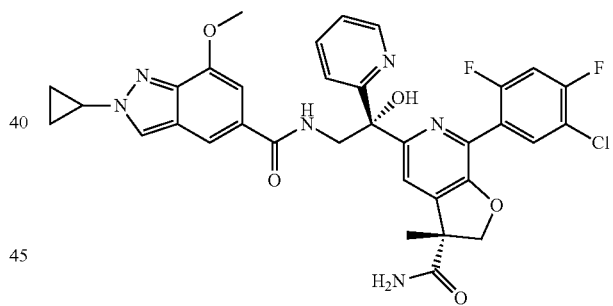

Example 463 Step a

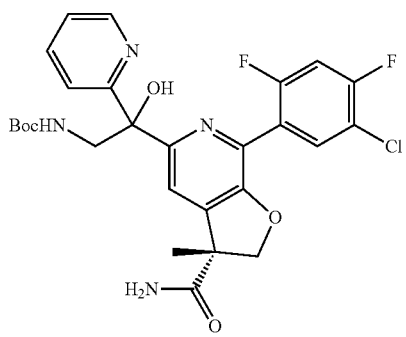 [SMILES: CC(C)(C)OC(=O)NCC(O)(c1ccccn1)c1cc2c(c(-c3cc(Cl)c(F)cc3F)n1)OC[C@]2(C)C(N)=O]

A solution of 2-bromopyridine (373 mg, 2.36 mmol), n-BuLi (151 mg, 2.36 mmol) in THF (3 mL) was stirred for 15 min at −78° C. under nitrogen atmosphere. Intermediate 59 (190 mg, 0.39 mmol) was added dropwise at −78° C. The resulting mixture was stirred for additional 30 min at −78° C. The residue was quenched, extracted, concentrated, and purified by reversed-phase flash chromatography to afford the desired compound (100 mg, 45%) as a yellow crude solid. ESI-MS m/z: 561.05 [M+H]⁺.

Example 463 Step b

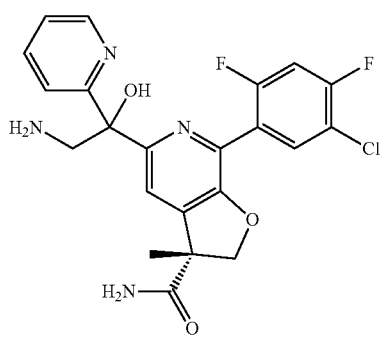 [SMILES: C[C@]1(C(N)=O)COc2c1cc(C(O)(CN)c1ccccn1)nc2-c1cc(Cl)c(F)cc1F]

A solution of the compound from step a (100 mg, 0.18 mmol), HCl in 1,4-dioxane (2 mL) and DCM (2 mL) was stirred for 1 h at room temperature. The mixture was basified, extracted, concentrated and purified by reversed-phase flash chromatography to afford the desired compound (50 mg, 60%) as a white solid. ESI-MS m/z: 460.95 [M+H]⁺.

Example 463 Step c

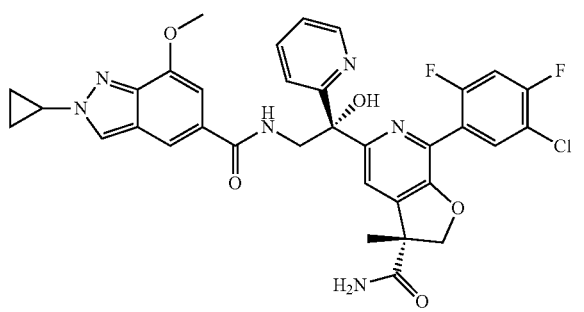 [SMILES: COc1cc(C(=O)NC[C@@](O)(c2ccccn2)c2cc3c(c(-c4cc(Cl)c(F)cc4F)n2)OC[C@]3(C)C(N)=O)cc2cn(C3CC3)nc12]

A solution of the compound from step b (50 mg, 0.11 mmol), HATU (61 mg, 0.16 mmol) and DIPEA (42 mg, 0.32 mmol) and 2-cyclopropyl-7-methoxy-2H-indazole-5-carboxylic acid (25 mg, 0.11 mmol) in DMF (1 mL) was stirred for 1 h at room temperature. The resulting mixture was extracted, concentrated and purified by prep-HPLC to afford the desired compound (3.5 mg, 17%) as a white solid. ESI-MS m/z: 675.20 [M+H]⁺.

Intermediate 60

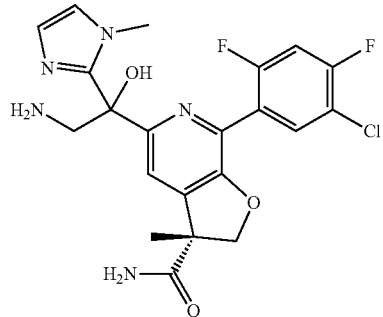 [SMILES: Cn1ccnc1C(O)(CN)c1cc2c(c(-c3cc(Cl)c(F)cc3F)n1)OC[C@]2(C)C(N)=O]

The following intermediate was prepared in an analogous sequence to Example 463 step b to afford the title compound (110 mg, 64%). ESI-MS m/z: 463.95 [M+H]⁺.

Intermediate 61

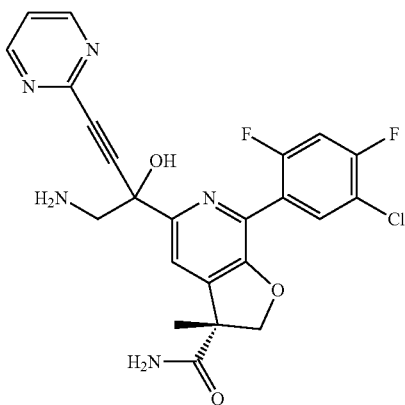 [SMILES: C[C@]1(C(N)=O)COc2c1cc(C(O)(C#Cc1ncccn1)CN)nc2-c1cc(Cl)c(F)cc1F]

The following intermediate was prepared in an analogous sequence to Example 463 step b to afford the title compound (63 mg) ESI-MS m/z: 486.15 [M+H]⁺.

The following Table 7 contains examples that were prepared with the similar method to Example 463. The majority of compounds were purified by prep-HPLC (ACN/H₂O, 20-90%, 25 min), and some were purified by automated column chromatography (silica gel).

TABLE 7

| Example | Structure | MS+ m/z |
|---------|-----------|---------|
| 464 | 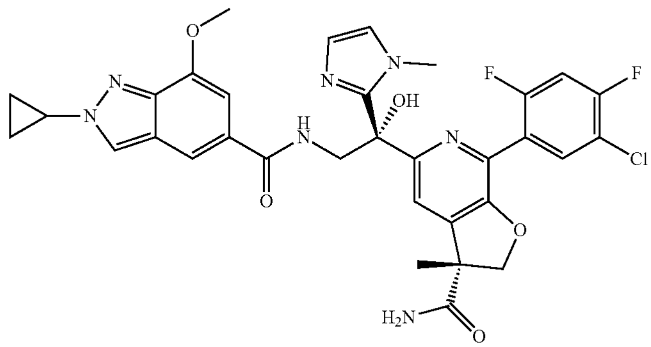 [SMILES: COc1cc(C(=O)NC[C@](O)(c2cc3c(c(-c4cc(Cl)c(F)cc4F)n2)OC[C@]3(C)C(N)=O)c2nccn2C)cc2cn(C3CC3)nc12] | 678.20 |
| 466 | 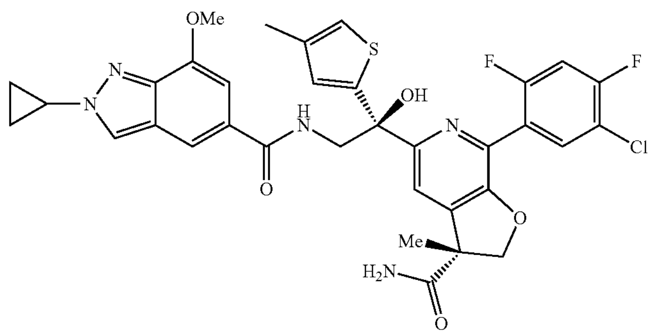 [SMILES: COc1cc(C(=O)NC[C@@](O)(c2cc3c(c(-c4cc(Cl)c(F)cc4F)n2)OC[C@]3(C)C(N)=O)c2cc(C)cs2)cc2cn(C3CC3)nc12] | 694.20 |
| 467 | 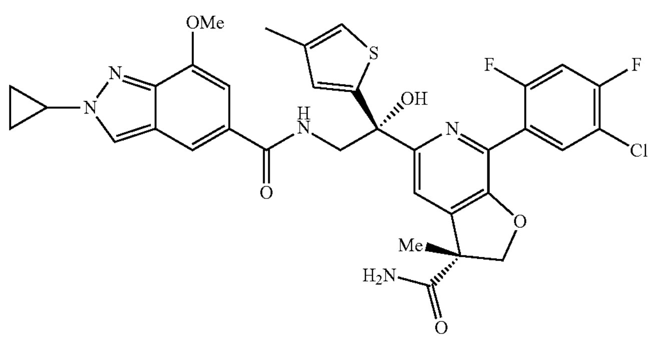 [SMILES: COc1cc(C(=O)NC[C@](O)(c2cc3c(c(-c4cc(Cl)c(F)cc4F)n2)OC[C@]3(C)C(N)=O)c2cc(C)cs2)cc2cn(C3CC3)nc12] | 694.20 |
| 468 | 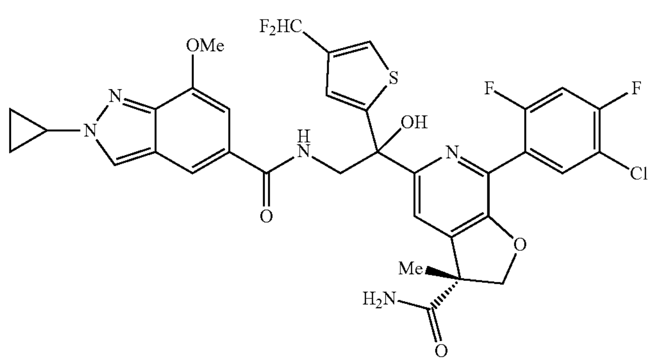 [SMILES: COc1cc(C(=O)NCC(O)(c2cc3c(c(-c4cc(Cl)c(F)cc4F)n2)OC[C@]3(C)C(N)=O)c2cc(C(F)F)cs2)cc2cn(C3CC3)nc12] | 730.20 |

TABLE 7-continued

| Example | Structure | MS+ m/z |
|---|---|---|
| 469 | 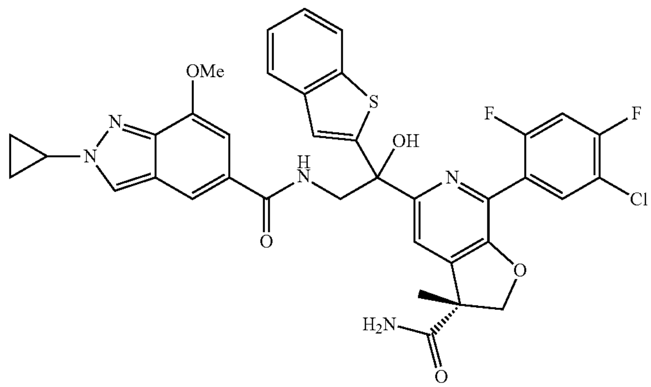 [SMILES: COc1cc(C(=O)NCC(O)(c2cc3c(c(-c4cc(Cl)c(F)cc4F)n2)OC[C@]3(C)C(N)=O)c2cc3ccccc3s2)cc2cn(C3CC3)nc12] | 730.20 |
| 470 | 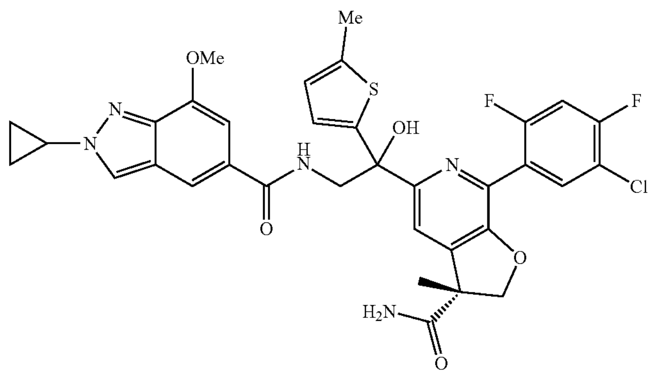 [SMILES: COc1cc(C(=O)NCC(O)(c2cc3c(c(-c4cc(Cl)c(F)cc4F)n2)OC[C@]3(C)C(N)=O)c2ccc(C)s2)cc2cn(C3CC3)nc12] | 694.20 |
| 471 | 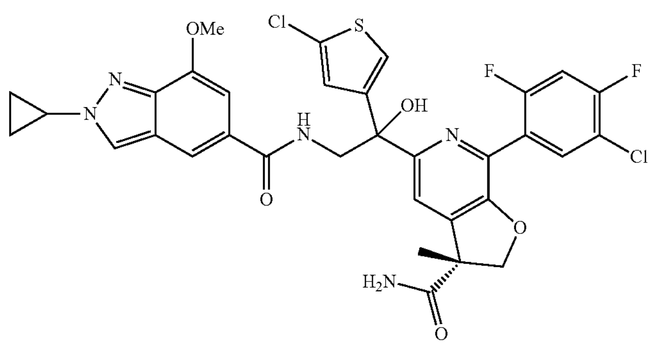 [SMILES: COc1cc(C(=O)NCC(O)(c2csc(Cl)c2)c2cc3c(c(-c4cc(Cl)c(F)cc4F)n2)OC[C@]3(C)C(N)=O)cc2cn(C3CC3)nc12] | 713.63 |
| 472 | 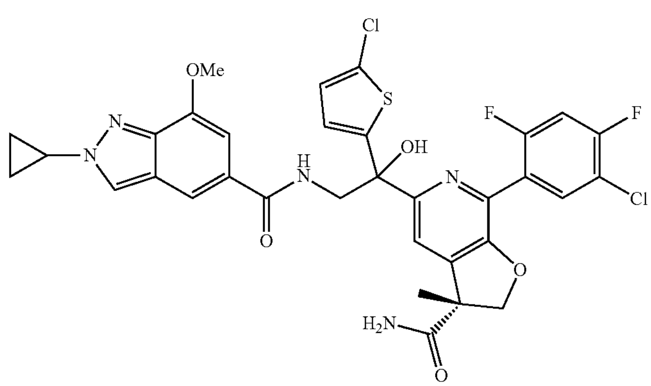 [SMILES: COc1cc(C(=O)NCC(O)(c2cc3c(c(-c4cc(Cl)c(F)cc4F)n2)OC[C@]3(C)C(N)=O)c2ccc(Cl)s2)cc2cn(C3CC3)nc12] | 714.20 |

TABLE 7-continued

| Example | Structure | MS+ m/z |
|---|---|---|
| 474 | 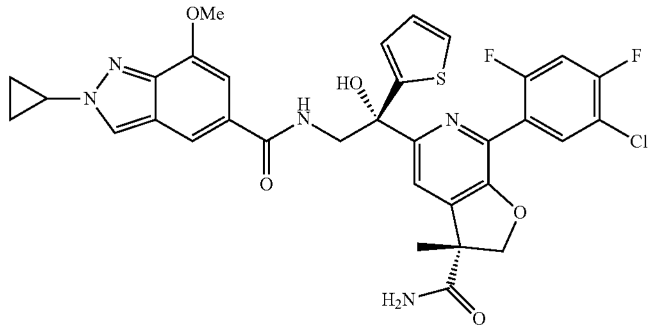 [SMILES: COc1cc(C(=O)NC[C@](O)(c2cc3c(c(-c4cc(Cl)c(F)cc4F)n2)OC[C@]3(C)C(N)=O)c2cccs2)cc2cn(C3CC3)nc12] | 680.14 |
| 475 | 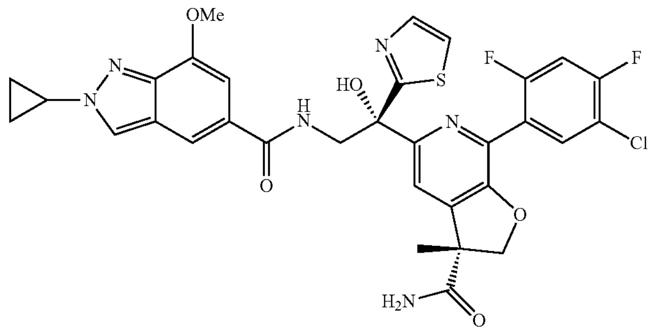 [SMILES: COc1cc(C(=O)NC[C@](O)(c2cc3c(c(-c4cc(Cl)c(F)cc4F)n2)OC[C@]3(C)C(N)=O)c2nccs2)cc2cn(C3CC3)nc12] | 681.14 |

Intermediate 62

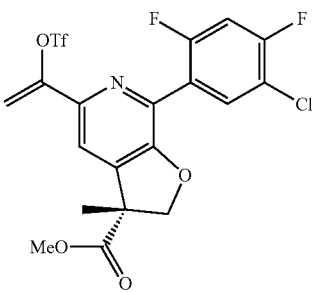 [SMILES: C=C(OS(=O)(=O)C(F)(F)F)c1cc2c(c(-c3cc(Cl)c(F)cc3F)n1)OC[C@]2(C)C(=O)OC]

Intermediate 62 Step a

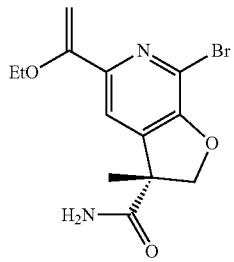 [SMILES: C=C(OCC)c1cc2c(c(Br)n1)OC[C@]2(C)C(N)=O]

To a stirred solution of CAN-7-bromo-5-iodo-3-methyl-2,3-dihydrofuro[2,3-c]pyridine-3-carboxamide (4 g, 10.44 mmol) and tributyl(1-ethoxyethenyl)stannane (3.96 g, 10.97 mmol) in toluene was added Pd(dppf)Cl$_2$CH$_2$Cl$_2$ (851 mg, 1.04 mmol) dropwise at 110° C. under nitrogen atmosphere for 2 hours. The resulting mixture was extracted with EA. The combined organic layers were concentrated under reduced pressure. The residue was purified by silica gel column chromatography, eluted with PE/EA (1:1) to afford the desired compound (2.1 g, 67%) as a brown solid. ESI-MS m/z: 327.00 [M+H]+.

Intermediate 62 Step b

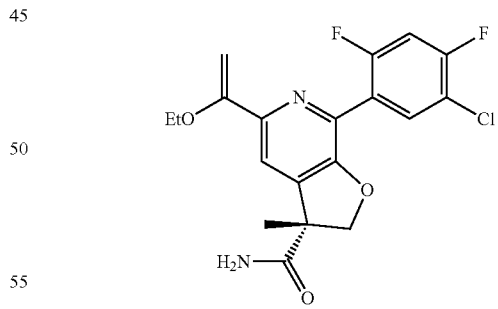

To a stirred solution of the compound from step a (4.7 g, 14.37 mmol) and 2-(5-chloro-2,4-difluorophenyl)-4,4,5,5-tetramethyl-1,3,2-dioxaborolane (3.94 g, 14.37 mmol) in dioxane (40 mL), H$_2$O (10 mL) were added Pd(dppf)Cl$_2$CH$_2$Cl$_2$ (1.17 g, 1.44 mmol) and K$_2$CO$_3$ (3.97 g, 28.73 mmol). The resulting mixture was stirred for 2 hours at 80° C. under nitrogen atmosphere. The reaction was monitored by LCMS. The resulting mixture was extracted with EA. The combined organic layers were concentrated under reduced pressure. The residue was purified by silica gel column chromatography, eluted with PE/EA (5:1) to afford the desired compound (4 g, 71%) as a yellow oil. ESI-MS m/z: 395.05 [M+H]⁺.

Intermediate 62 Step c

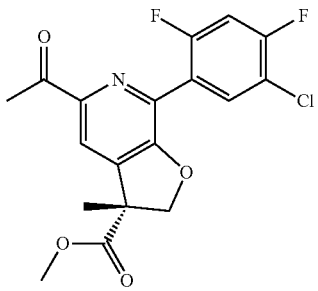 [SMILES: COC(=O)[C@@]1(C)COc2c1cc(C(C)=O)nc2-c1cc(Cl)c(F)cc1F]

To a stirred solution of the compound from step b (6 g, 16.36 mmol) and HCl (33 mL) in MeOH (20 mL) at 50° C. under nitrogen atmosphere for 2 hours. The resulting mixture was concentrated under reduced pressure. The mixture was acidified to pH 7 with saturated NaHCO₃(aq.). The resulting mixture was extracted with CH₂Cl₂ (3×30 mL). The combined organic layers were washed with brine (1×10 mL), dried over anhydrous Na₂SO₄. After filtration, the filtrate was concentrated under reduced pressure. The residue was purified by silica gel column chromatography, eluted with PE/EA (5:1) to afford the desired compound (4 g, 64%) as a yellow oil. ESI-MS m/z: 381.90 [M+H]⁺.

Intermediate 62 Step d

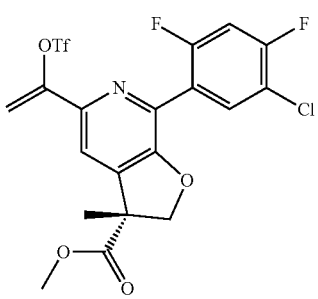 [SMILES: C=C(OS(=O)(=O)C(F)(F)F)c1cc2c(c(-c3cc(Cl)c(F)cc3F)n1)OC[C@]2(C)C(=O)OC]

The compound from step c (4 g, 10.48 mmol) was dissolved in DCM (50 mL) at 0° C. 2,6-di-tert-butyl-4-methylpyridine (2.58 g, 12.57 mmol) and Tf₂O (4.43 g, 15.72 mmol) were added. The reaction mixture was warmed to r.t. and allowed to stir at r.t. for 16 h. The reaction was monitored by LCMS. The resulting mixture was extracted with EtOAc. The combined organic layers were concentrated under reduced pressure. The residue was purified by silica gel column chromatography, eluted with PE/EA (5:1) to afford the titled compound (4 g, 74%) as a yellow oil. ESI-MS m/z: 514.00 [M+H]⁺.

Intermediate 63

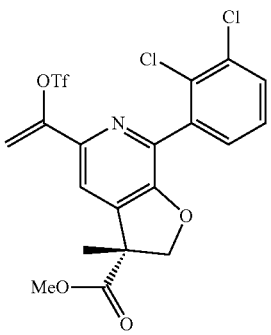 [SMILES: C=C(OS(=O)(=O)C(F)(F)F)c1cc2c(c(-c3cccc(Cl)c3Cl)n1)OC[C@]2(C)C(=O)OC]

The following intermediate was prepared in an analogous fashion to Intermediate 62 to afford the desired compound (1.7 g, 65%). ESI-MS m/z: 512.00 [M+H]⁺.

Intermediate 64

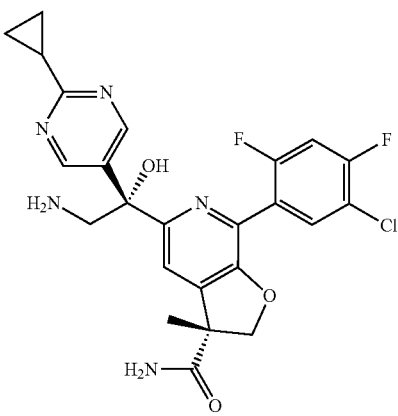 [SMILES: C[C@]1(C(N)=O)COc2c1cc([C@@](O)(CN)c1cnc(C3CC3)nc1)nc2-c1cc(Cl)c(F)cc1F]

Intermediate 64 Step a

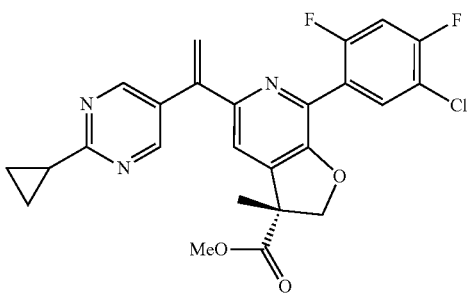 [SMILES: C=C(c1cnc(C2CC2)nc1)c1cc2c(c(-c3cc(Cl)c(F)cc3F)n1)OC[C@]2(C)C(=O)OC]

To a stirred solution of Intermediate 62 (200 mg, 0.39 mmol) and 2-cyclopropylpyrimidin-5-ylboronic acid (64 mg, 0.39 mmol) in 1,4-dioxane/H₂O (9:1) were added K₂CO₃ (108 mg, 0.78 mmol) and Pd(dppf)Cl₂CH₂Cl₂ (32 mg, 0.04 mmol), the resulting mixture was stirred for 2 hours at 85° C. under nitrogen atmosphere. The residue was purified by reversed-phase flash chromatography to afford the desired compound (130 mg, 69%) as a yellow oil. ESI-MS m/z: 484.30 [M+H]⁺.

Intermediate 64 Step b

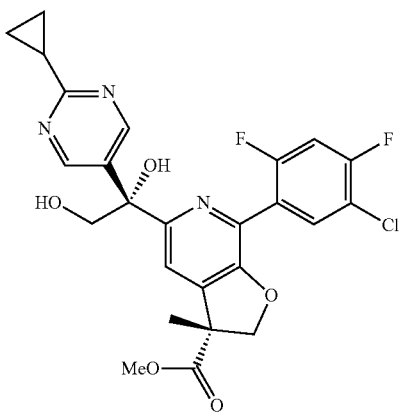 [SMILES: COC(=O)[C@@]1(C)COc2c1cc([C@@](O)(CO)c1cnc(C3CC3)nc1)nc2-c1cc(Cl)c(F)cc1F]

To a stirred solution of the compound from step a (240 mg, 0.50 mmol) and methanesulfonamide (47 mg, 0.50 mmol) in t-BuOH/H$_2$O were added ADMIX-0 (1.16 g, 1.49 mmol), the resulting mixture was stirred for overnight at room temperature. The mixture was extracted with EtOAc (3×10 mL). The residue was purified by reversed-phase flash chromatography to afford the desired compound (115 mg, 45%) as a yellow oil. ESI-MS m/z: 518.15 [M+H]$^+$.

Intermediate 64 Steps c & d

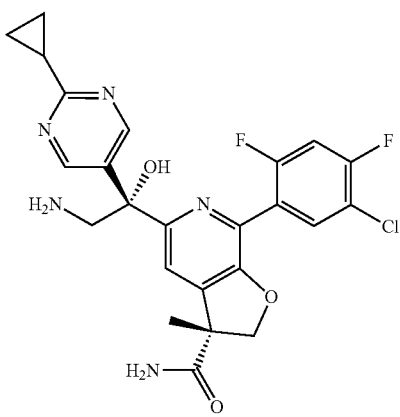 [SMILES: C[C@]1(C(N)=O)COc2c1cc([C@@](O)(CN)c1cnc(C3CC3)nc1)nc2-c1cc(Cl)c(F)cc1F]

To a stirred solution of the compound from step b (100 mg, 0.20 mmol) and TsCl(64 mg, 0.33 mmol) in DCM were added TEA (67 mg, 0.67 mmol) and DMAP (27 mg, 0.22 mmol) at room temperature under nitrogen atmosphere and stirred for 2 hours. The resulting mixture was acidified to pH 3 with HCl (1 M aq.), the resulting mixture was extracted with DCM, the combined organic layers were concentrated under reduced pressure. The residue was purified by Prep-TLC (PE/EA 1:1) to afford the desired compound (80 mg, 62%) as a yellow solid. ESI-MS m/z: 672.25 [M+H]$^+$.

A solution of the compound from step c (80 mg, 0.12 mmol) and NH$_3$(g) in MeOH (10 mL) was stirred for overnight at 40° C. The reaction was monitored by LCMS. The resulting mixture was concentrated under reduced pressure. The residue was purified by Prep-TLC (CH$_2$Cl$_2$/NH$_3$ in MeOH 12:1) to afford methyl the titled compound (60 mg, 130%) as a yellow solid. ESI-MS m/z: 502.25 [M+H]$^+$.

Intermediate 65

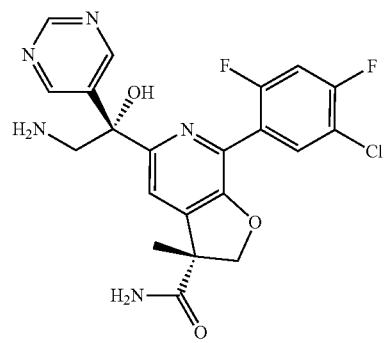 [SMILES: C[C@]1(C(N)=O)COc2c1cc([C@@](O)(CN)c1cncnc1)nc2-c1cc(Cl)c(F)cc1F]

The following intermediate was prepared in an analogous sequence to Intermediate 64 to afford the title compound (110 mg, 64%). ESI-MS m/z: 444.00 [M+H]$^+$.

Intermediate 66

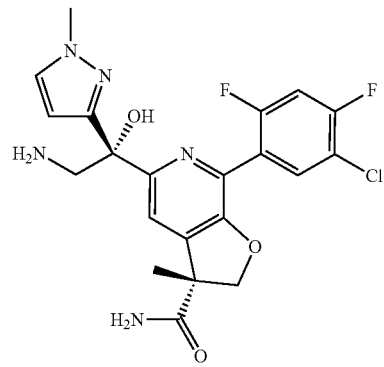 [SMILES: Cn1ccc([C@](O)(CN)c2cc3c(c(-c4cc(Cl)c(F)cc4F)n2)OC[C@]3(C)C(N)=O)n1]

The following intermediate was prepared in an analogous sequence to Intermediate 64 to afford the title compound.

Intermediate 67

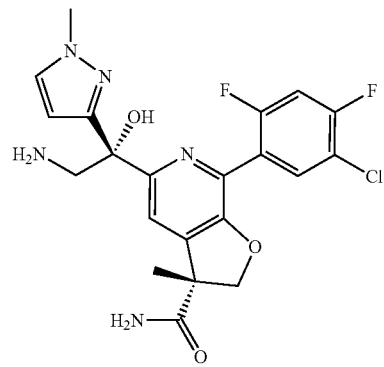 [SMILES: Cn1ccc([C@](O)(CN)c2cc3c(c(-c4cc(Cl)c(F)cc4F)n2)OC[C@]3(C)C(N)=O)n1]

The following intermediate was prepared in an analogous sequence to Intermediate 64 to afford the title compound.

Intermediate 68

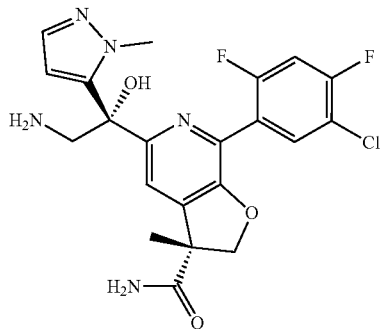 [SMILES: Cn1nccc1[C@](O)(CN)c1cc2c(c(-c3cc(Cl)c(F)cc3F)n1)OC[C@]2(C)C(N)=O]

The following intermediate was prepared in an analogous sequence to Intermediate 64 to afford the title compound.

Intermediate 69

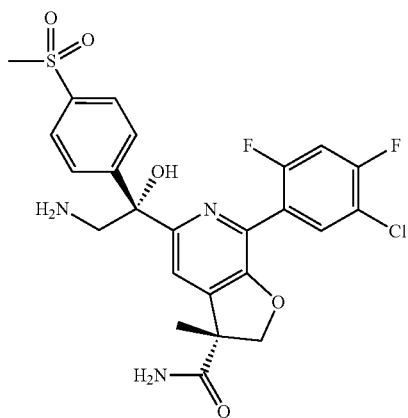 [SMILES: C[C@]1(C(N)=O)COc2c1cc([C@@](O)(CN)c1ccc(S(C)(=O)=O)cc1)nc2-c1cc(Cl)c(F)cc1F]

The following intermediate was prepared in an analogous sequence to Intermediate 64 to afford the title compound (50.2 mg, 41%) as a white solid. ESI-MS m/z: 538.15 [M+H]$^+$.

Intermediate 70

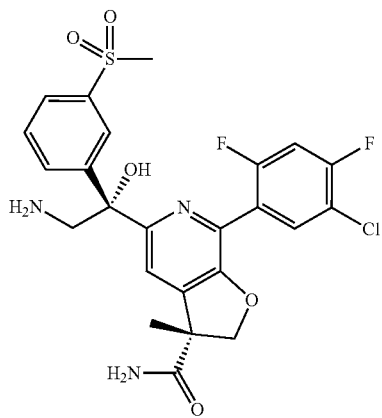 [SMILES: C[C@]1(C(N)=O)COc2c1cc([C@@](O)(CN)c1cccc(S(C)(=O)=O)c1)nc2-c1cc(Cl)c(F)cc1F]

The following intermediate was prepared in an analogous sequence to Intermediate 64 to afford the title compound.

Intermediate 71

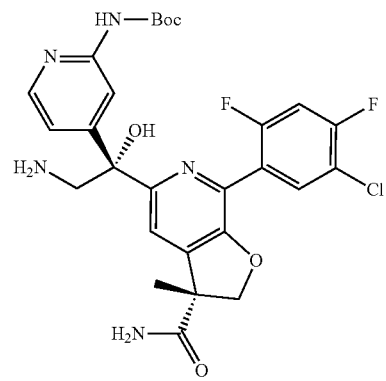 [SMILES: CC(C)(C)OC(=O)Nc1cc([C@](O)(CN)c2cc3c(c(-c4cc(Cl)c(F)cc4F)n2)OC[C@]3(C)C(N)=O)ccn1]

The following intermediate was prepared in an analogous sequence to Intermediate 64 to afford the title compound (70 mg, 75%) as a white solid. ESI-MS m/z: 576.25 [M+H]$^+$. After subsequent amide coupling, the final compound was isolated after Boc deprotection with HCl in dioxane. See table below.

Intermediate 72

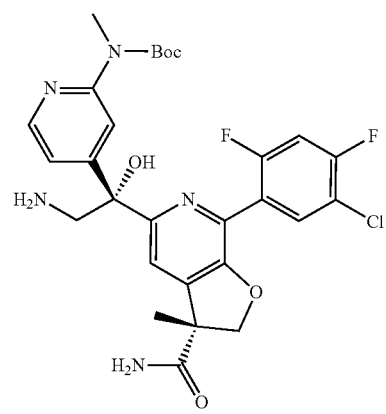 [SMILES: CN(C(=O)OC(C)(C)C)c1cc([C@](O)(CN)c2cc3c(c(-c4cc(Cl)c(F)cc4F)n2)OC[C@]3(C)C(N)=O)ccn1]

The following intermediate was prepared in an analogous sequence to Intermediate 64 to afford the title compound (80 mg, 65%) as a white solid. ESI-MS m/z: 590.00 [M+H]$^+$. After subsequent amide coupling, the final compound was isolated after Boc deprotection with HCl in dioxane. See table below.

Intermediate 73

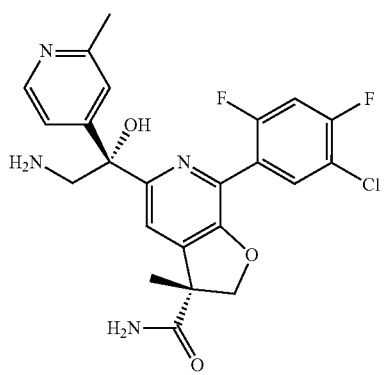 [SMILES: Cc1cc([C@](O)(CN)c2cc3c(c(-c4cc(Cl)c(F)cc4F)n2)OC[C@]3(C)C(N)=O)ccn1]

The following intermediate was prepared in an analogous sequence to Intermediate 64 to afford the title compound (27 mg, 42%) as a white solid. ESI-MS m/z: 474.95 [M+H]⁺.

Intermediate 74

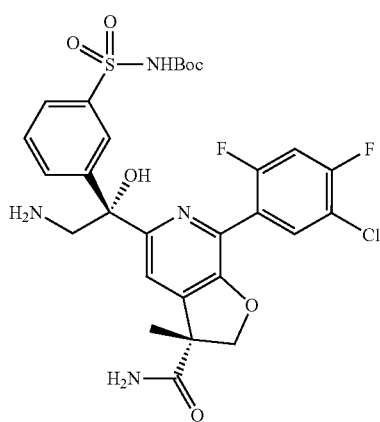 [SMILES: CC(C)(C)OC(=O)NS(=O)(=O)c1cccc([C@](O)(CN)c2cc3c(c(-c4cc(Cl)c(F)cc4F)n2)OC[C@]3(C)C(N)=O)c1]

The following intermediate was prepared in an analogous sequence to Intermediate 64 to afford the title compound (70 mg) as a white solid. ESI-MS m/z: 639.00 [M+H]⁺. After subsequent amide coupling, the final compound was isolated after Boc deprotection with HCl in dioxane. See table below.

Intermediate 75

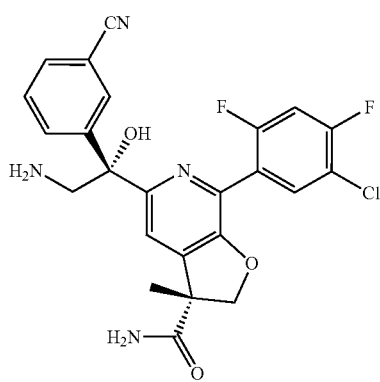 [SMILES: C[C@]1(C(N)=O)COc2c1cc([C@@](O)(CN)c1cccc(C#N)c1)nc2-c1cc(Cl)c(F)cc1F]

The following intermediate was prepared in an analogous sequence to Intermediate 64 to afford the title compound (70 mg, 71%) as a yellow solid. ESI-MS m/z: 484.95 [M+H]⁺.

Intermediate 76

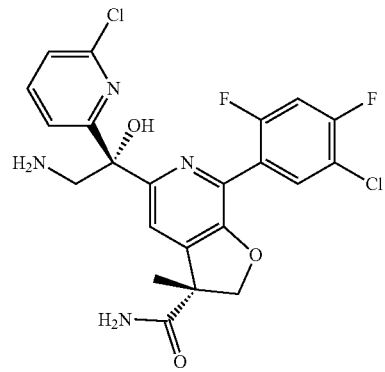 [SMILES: C[C@]1(C(N)=O)COc2c1cc([C@@](O)(CN)c1cccc(Cl)n1)nc2-c1cc(Cl)c(F)cc1F]

The following intermediate was prepared in an analogous sequence to Intermediate 64 to afford the title compound (30 mg, 81%) as a yellow solid. ESI-MS m/z: 495.00 [M+H]⁺.

Intermediate 77

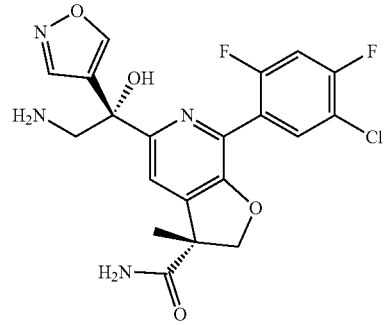 [SMILES: C[C@]1(C(N)=O)COc2c1cc([C@@](O)(CN)c1cnoc1)nc2-c1cc(Cl)c(F)cc1F]

The following intermediate was prepared in an analogous sequence to Intermediate 64 to afford the title compound (22 mg) as a yellow solid. ESI-MS m/z: 451.05 [M+H]⁺.

Intermediate 78

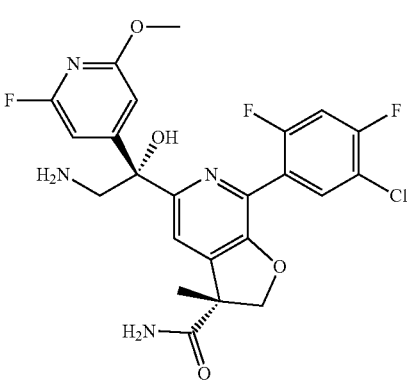 [SMILES: COc1cc([C@](O)(CN)c2cc3c(c(-c4cc(Cl)c(F)cc4F)n2)OC[C@]3(C)C(N)=O)cc(F)n1]

The following intermediate was prepared in an analogous sequence to Intermediate 64 to afford the title compound (59.4 mg, 69%) as a yellow solid. ESI-MS m/z: 509.10 [M+H]⁺.

Intermediate 79

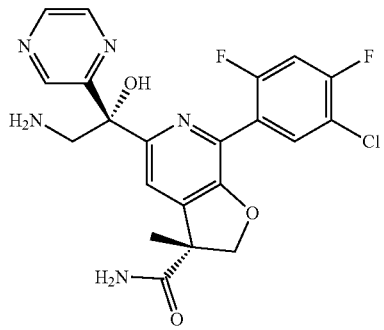 [SMILES: C[C@]1(C(N)=O)COc2c1cc([C@@](O)(CN)c1cnccn1)nc2-c1cc(Cl)c(F)cc1F]

Intermediate 79 Step a

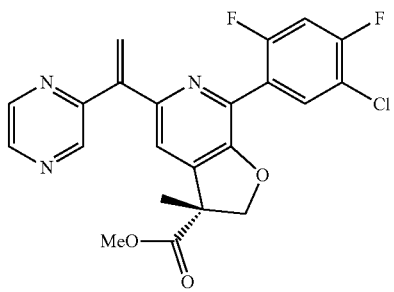 [SMILES: C=C(c1cnccn1)c1cc2c(c(-c3cc(Cl)c(F)cc3F)n1)OC[C@]2(C)C(=O)OC]

A solution of the compound A3-1036 (280 mg, 0.55 mmol), Pd(dppf)Cl₂ (40 mg, 0.06 mmol), CuCl(54 mg, 0.55 mmol) and Cs₂CO₃ (355 mg, 1.09 mmol) in DMF (10 mL) was stirred for 2 hr at 90° C. under N₂ atmosphere. The residue was purified by silica gel column chromatography, eluted with PE/EA to afford the desired product (70 mg, 29%) as a yellow oil. ESI-MS m/z: 444.00 [M+H]⁺.

Intermediate 79 Steps b, c, d, & e

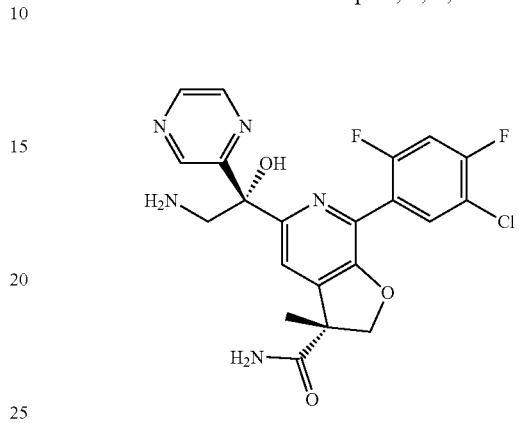

The following intermediate was prepared in an analogous sequence to Intermediate 64 to afford the title compound (15 mg, 68%) as a yellow solid. ESI-MS m/z: 462.00 [M+H]⁺.

The following Table 8 contains examples that were prepared with the similar method to Example 1. The majority of compounds were purified by prep-HPLC (ACN/H₂O, 20-90%, 25 min), and some were purified by automated column chromatography (silica gel). The amine starting materials were prepared according to Intermediates 62-80 and aryl acid amide coupling partners were prepared according to Intermediates 1-58, or by analogous procedures with slight modifications according to procedures found in U.S. Pat. No. 11,572,367.

TABLE 8

| Example | Structure | MS⁺ m/z |
|---|---|---|
| 478 | 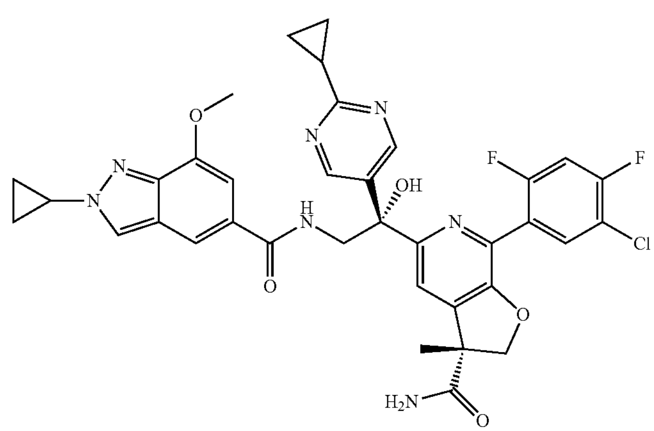 [SMILES: COc1cc(C(=O)NC[C@@](O)(c2cnc(C3CC3)nc2)c2cc3c(c(-c4cc(Cl)c(F)cc4F)n2)OC[C@]3(C)C(N)=O)cc2cn(C3CC3)nc12] | 716.30 |

TABLE 8-continued

| Example | Structure | MS+ m/z |
|---|---|---|
| 479 | 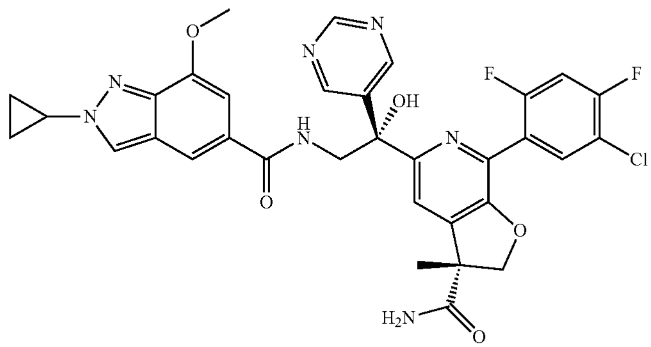 | 676.00 |
| 480 | 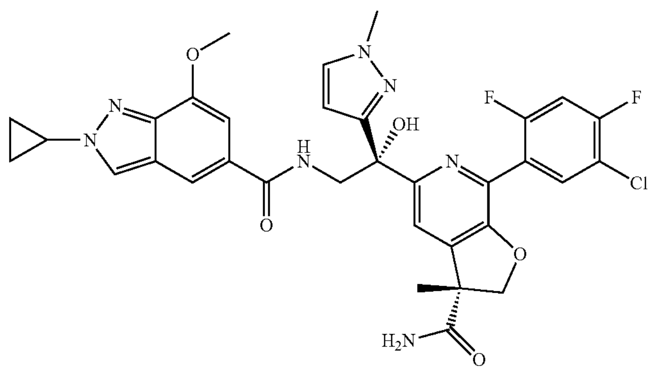 [SMILES: COc1cc(C(=O)NC[C@](O)(c2cc3c(c(-c4cc(Cl)c(F)cc4F)n2)OC[C@]3(C)C(N)=O)c2ccn(C)n2)cc2cn(C3CC3)nc12] | 678.00 |
| 481 | 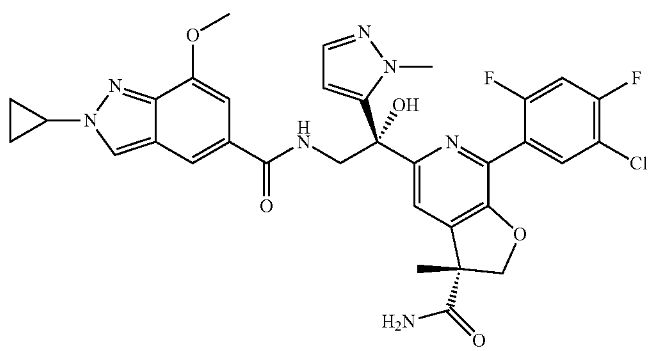 [SMILES: COc1cc(C(=O)NC[C@](O)(c2cc3c(c(-c4cc(Cl)c(F)cc4F)n2)OC[C@]3(C)C(N)=O)c2ccnn2C)cc2cn(C3CC3)nc12] | 678.25 |
| 482 | 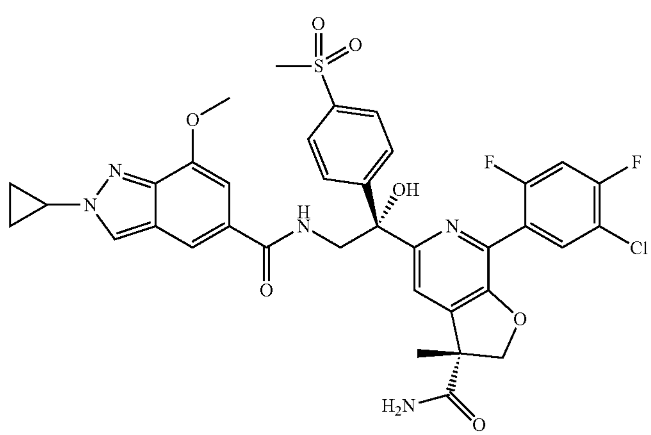 [SMILES: COc1cc(C(=O)NC[C@@](O)(c2ccc(S(C)(=O)=O)cc2)c2cc3c(c(-c4cc(Cl)c(F)cc4F)n2)OC[C@]3(C)C(N)=O)cc2cn(C3CC3)nc12] | 752.20 |

TABLE 8-continued

| Example | Structure | MS+ m/z |
|---------|-----------|---------|
| 483 | 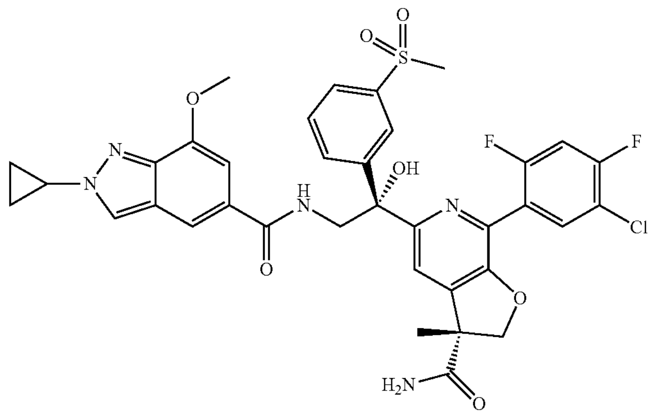 [SMILES: COc1cc(C(=O)NC[C@@](O)(c2cccc(S(C)(=O)=O)c2)c2cc3c(c(-c4cc(Cl)c(F)cc4F)n2)OC[C@]3(C)C(N)=O)cc2cn(C3CC3)nc12] | 752.00 |
| 484 | 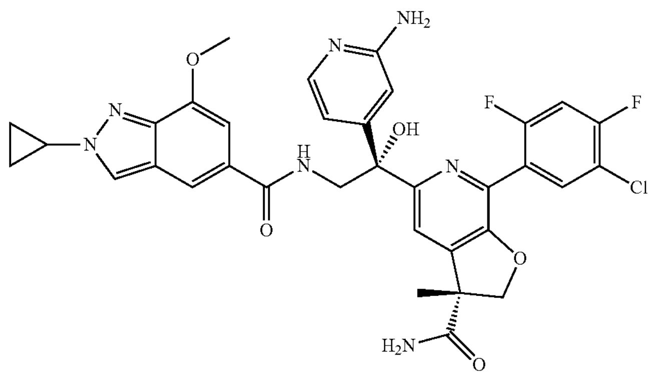 [SMILES: COc1cc(C(=O)NC[C@@](O)(c2ccnc(N)c2)c2cc3c(c(-c4cc(Cl)c(F)cc4F)n2)OC[C@]3(C)C(N)=O)cc2cn(C3CC3)nc12] | 690.00 |
| 485 | 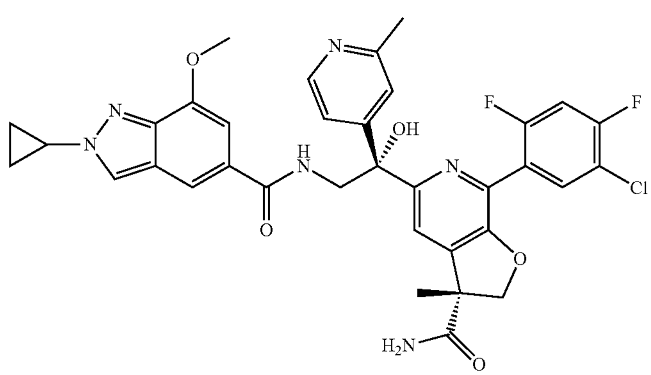 [SMILES: COc1cc(C(=O)NC[C@@](O)(c2ccnc(C)c2)c2cc3c(c(-c4cc(Cl)c(F)cc4F)n2)OC[C@]3(C)C(N)=O)cc2cn(C3CC3)nc12] | 689.15 |
| 486 | 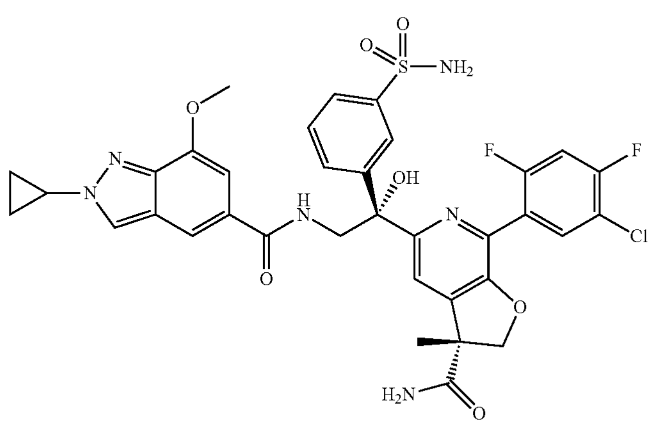 [SMILES: COc1cc(C(=O)NC[C@@](O)(c2cccc(S(N)(=O)=O)c2)c2cc3c(c(-c4cc(Cl)c(F)cc4F)n2)OC[C@]3(C)C(N)=O)cc2cn(C3CC3)nc12] | 753.20 |

TABLE 8-continued
| Example | Structure | MS+ m/z |
|---|---|---|
| 487 | 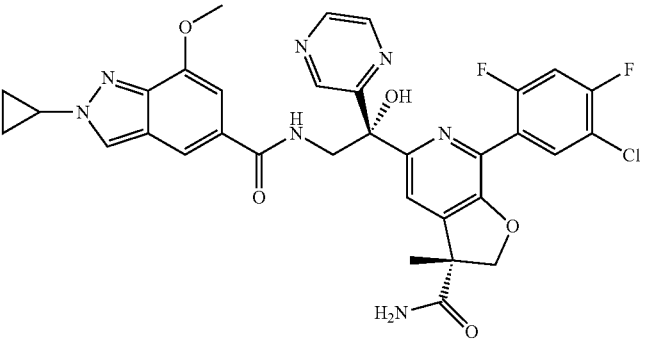 [SMILES: COc1cc(C(=O)NC[C@@](O)(c2cnccn2)c2cc3c(c(-c4cc(Cl)c(F)cc4F)n2)OC[C@]3(C)C(N)=O)cc2cn(C3CC3)nc12] | 676.00 |
| 488 | 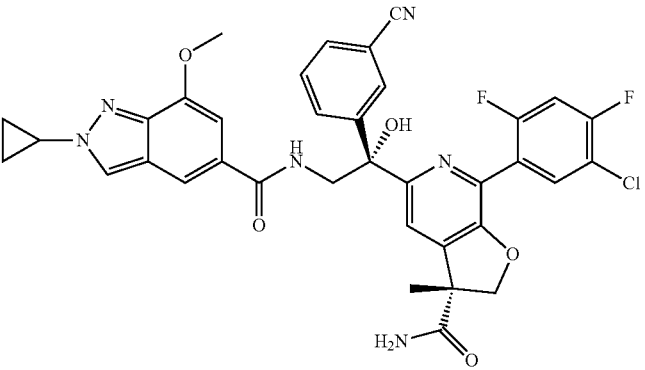 [SMILES: COc1cc(C(=O)NC[C@@](O)(c2cccc(C#N)c2)c2cc3c(c(-c4cc(Cl)c(F)cc4F)n2)OC[C@]3(C)C(N)=O)cc2cn(C3CC3)nc12] | 699.20 |
| 489 | 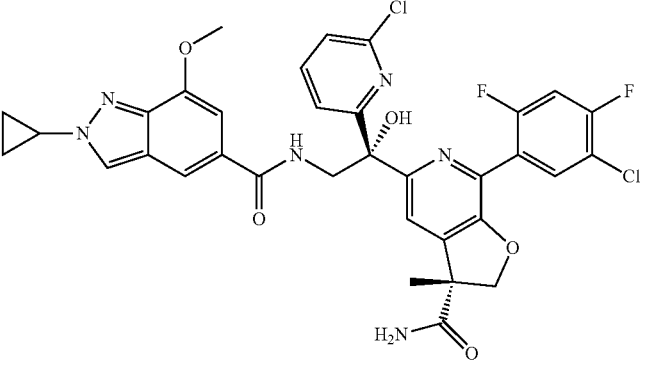 | 709.00 |
| 490 | 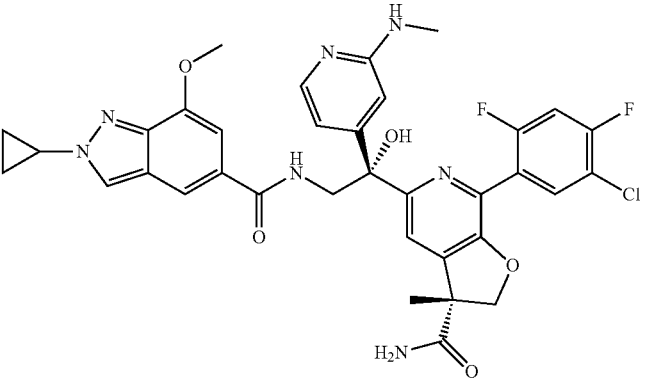 [SMILES: CNc1cc([C@](O)(CNC(=O)c2cc(OC)c3nn(C4CC4)cc3c2)c2cc3c(c(-c4cc(Cl)c(F)cc4F)n2)OC[C@]3(C)C(N)=O)ccn1] | 704.00 |

TABLE 8-continued
| Example | Structure | MS+ m/z |
|---|---|---|
| 491 | 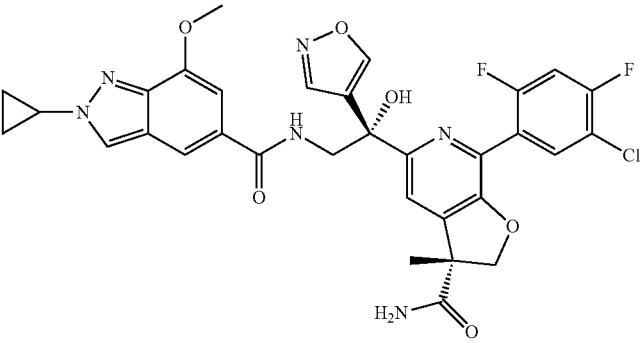 [SMILES: COc1cc(C(=O)NC[C@@](O)(c2cnoc2)c2cc3c(c(-c4cc(Cl)c(F)cc4F)n2)OC[C@]3(C)C(N)=O)cc2cn(C3CC3)nc12] | 665.20 |
| 492 | 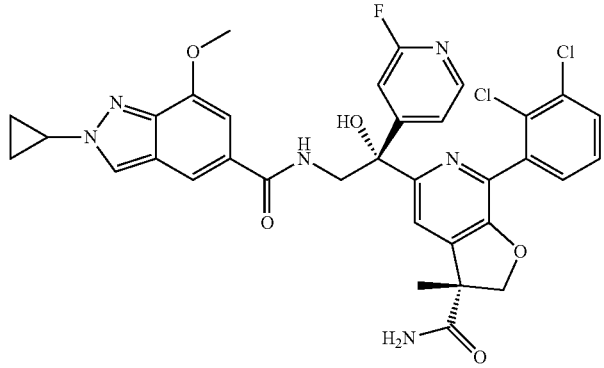 [SMILES: COc1cc(C(=O)NC[C@@](O)(c2ccnc(F)c2)c2cc3c(c(-c4cccc(Cl)c4Cl)n2)OC[C@]3(C)C(N)=O)cc2cn(C3CC3)nc12] | 691.15 |
| 493 | 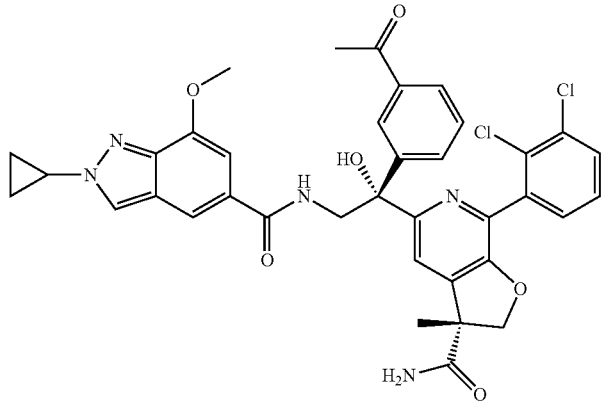 [SMILES: COc1cc(C(=O)NC[C@@](O)(c2cccc(C(C)=O)c2)c2cc3c(c(-c4cccc(Cl)c4Cl)n2)OC[C@]3(C)C(N)=O)cc2cn(C3CC3)nc12] | 714.18 |
| 494 | 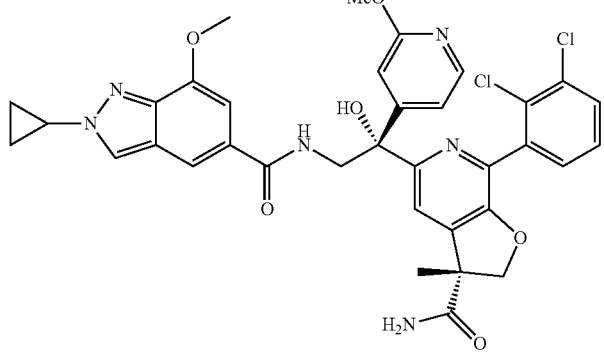 | 703.17 |

TABLE 8-continued

| Example | Structure | MS+ m/z |
|---|---|---|
| 495 | 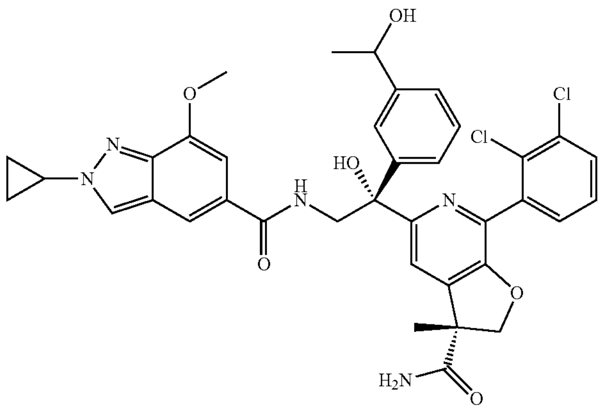 [SMILES: COc1cc(C(=O)NC[C@@](O)(c2cccc(C(C)O)c2)c2cc3c(c(-c4cccc(Cl)c4Cl)n2)OC[C@]3(C)C(N)=O)cc2cn(C3CC3)nc12] | 716.19 |
| 496 | 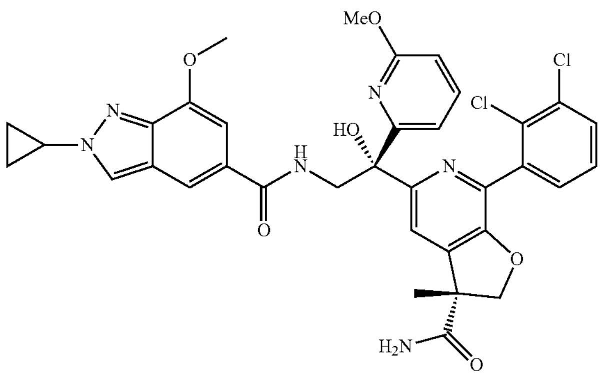 [SMILES: COc1cccc([C@](O)(CNC(=O)c2cc(OC)c3nn(C4CC4)cc3c2)c2cc3c(c(-c4cccc(Cl)c4Cl)n2)OC[C@]3(C)C(N)=O)n1] | 703.17 |
| 497 | 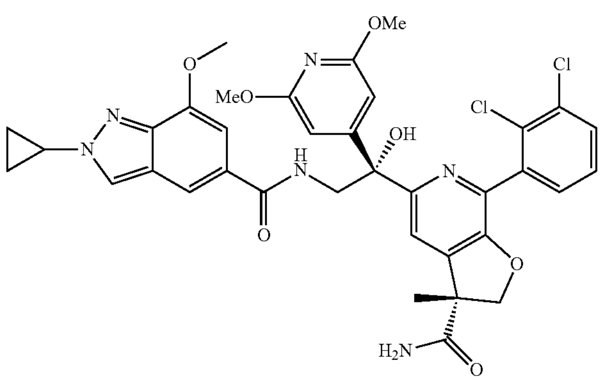 [SMILES: COc1cc([C@](O)(CNC(=O)c2cc(OC)c3nn(C4CC4)cc3c2)c2cc3c(c(-c4cccc(Cl)c4Cl)n2)OC[C@]3(C)C(N)=O)cc(OC)n1] | 733.18 |
| 498 | 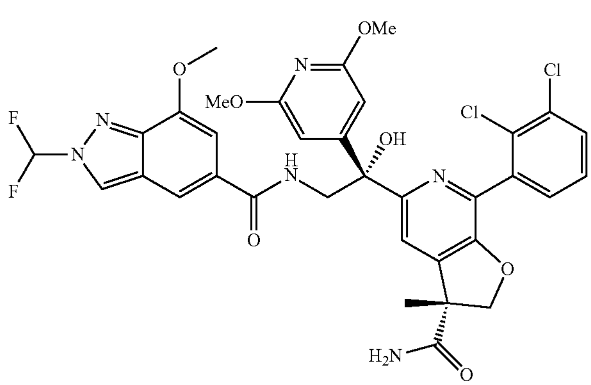 [SMILES: COc1cc([C@](O)(CNC(=O)c2cc(OC)c3nn(C(F)F)cc3c2)c2cc3c(c(-c4cccc(Cl)c4Cl)n2)OC[C@]3(C)C(N)=O)cc(OC)n1] | 743.15 |

TABLE 8-continued
| Example | Structure | MS+ m/z |
|---|---|---|
| 499 | 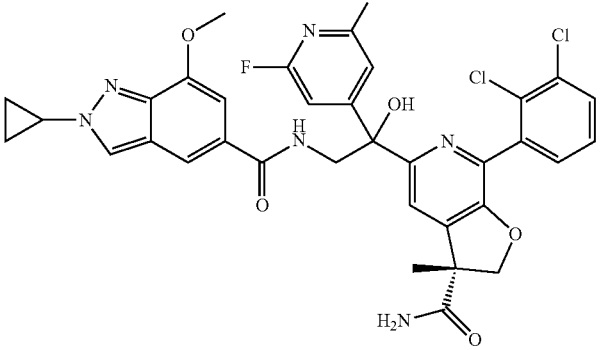 | 709.14 |
| 500 | 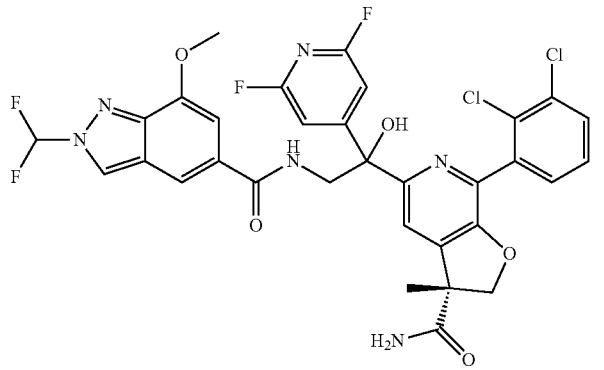 [SMILES: COc1cc(C(=O)NCC(O)(c2cc(F)nc(F)c2)c2cc3c(c(-c4cccc(Cl)c4Cl)n2)OC[C@]3(C)C(N)=O)cc2cn(C(F)F)nc12] | 719.11 |
| 501 | 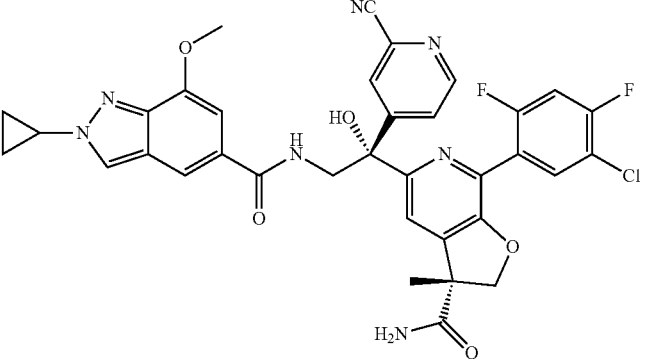 [SMILES: COc1cc(C(=O)NC[C@@](O)(c2ccnc(C#N)c2)c2cc3c(c(-c4cc(Cl)c(F)cc4F)n2)OC[C@]3(C)C(N)=O)cc2cn(C3CC3)nc12] | 700.18 |
| 502 | 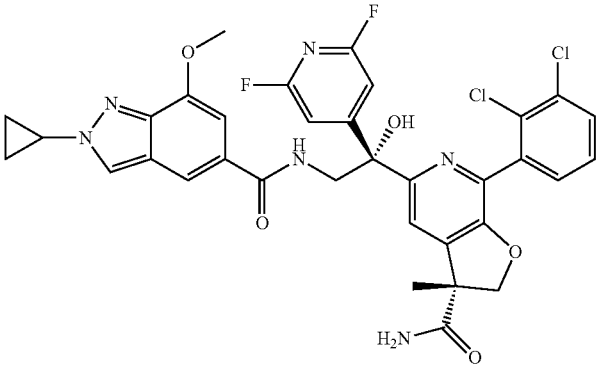 [SMILES: COc1cc(C(=O)NC[C@@](O)(c2cc(F)nc(F)c2)c2cc3c(c(-c4cccc(Cl)c4Cl)n2)OC[C@]3(C)C(N)=O)cc2cn(C3CC3)nc12] | 709.53 |

TABLE 8-continued

| Example | Structure | MS+ m/z |
|---|---|---|
| 503 | 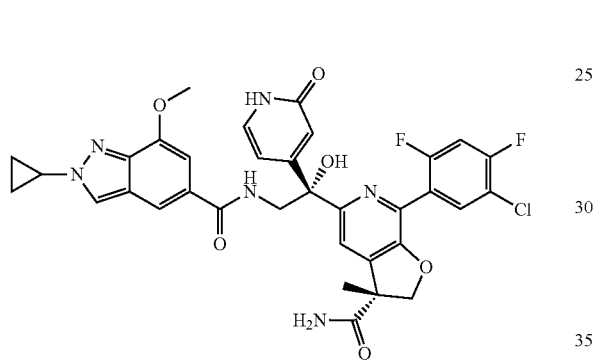 | 723.20 |

Example 504

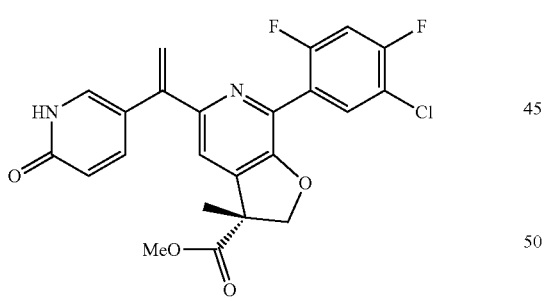

Example 504 Step a

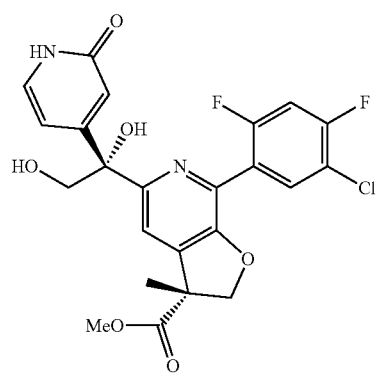 [SMILES: COC(=O)[C@@]1(C)COc2c1cc([C@@](O)(CO)c1cc[nH]c(=O)c1)nc2-c1cc(Cl)c(F)cc1F]

To a stirred solution of Intermediate 62 (300 mg, 0.58 mmol) and 4-(4,4,5,5-tetramethyl-1,3,2-dioxaborolan-2-yl)-1H-pyridin-2-one (129 mg, 0.58 mmol) in 1,4-dioxane/H$_2$O were added K$_2$CO$_3$ (161 mg, 1.17 mmol) and Pd(dppf)Cl$_2$CH$_2$Cl$_2$ (47 mg, 0.06 mmol) and the reaction was stirred at 85° C. under nitrogen atmosphere for 2 h. The residue was purified by reversed-phase flash chromatography to afford the desired product (105 mg, 39%) as a yellow solid. ESI-MS m/z: 459.00 [M+H]+.

Example 504 Step b

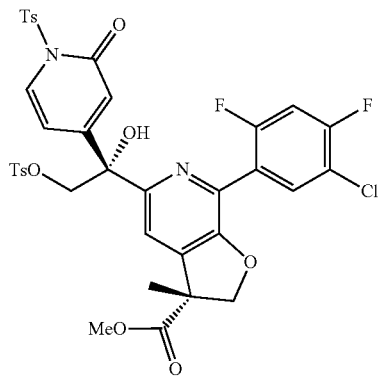 [SMILES: COC(=O)[C@@]1(C)COc2c1cc([C@@](O)(COS(=O)(=O)c1ccc(C)cc1)c1ccn(S(=O)(=O)c3ccc(C)cc3)c(=O)c1)nc2-c1cc(Cl)c(F)cc1F]

A mixture of methyl the compound from step a (100 mg, 0.22 mmol), methanesulfonamide (20 mg, 0.22 mmol) and ADMIX-0 (509 mg, 0.65 mmol) in tBuOH (3 mL), H$_2$O (3 mL) was stirred for overnight at room temperature. The reaction was monitored by LCMS. The resulting mixture was extracted with EA. The combined organic layers were concentrated under reduced pressure.

The residue was purified by Prep-TLC (EA) to afford the desired product (70 mg, 65%) as a yellow-brown oil. ESI-MS m/z: 493.15 [M+H]+.

Example 504 Step c

A mixture of the compound from step b (70 mg, 0.14 mmol), TsCl(40 mg, 0.21 mmol), DMAP (17 mg, 0.14 mmol) and TEA (43 mg, 0.43 mmol) in DCM (3 mL) was stirred for 2 hours at room temperature. The reaction was monitored by LCMS. The mixture was acidified to pH 4 with HCl (1 M aq.). The resulting mixture was extracted with $CH_2C_2$. The combined organic layers were concentrated under reduced pressure. The residue was purified by Prep-TLC (PE/EA 1:1) to afford the desired product (60 mg, 52.73%) as a yellow solid. ESI-MS m/z: 800.95 $[M+H]^+$.

Example 504 Step d

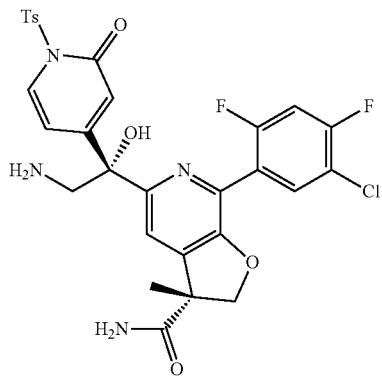 [SMILES: Cc1ccc(S(=O)(=O)n2ccc([C@](O)(CN)c3cc4c(c(-c5cc(Cl)c(F)cc5F)n3)OC[C@]4(C)C(N)=O)cc2=O)cc1]

A mixture of the compound from step c (60 mg, 0.07 mmol) and $NH_3(g)$ in MeOH (3 mL) was stirred overnight at 40° C. The reaction was monitored by LCMS. The resulting mixture was concentrated under reduced pressure. The residue was purified by Prep-TLC ($CH_2C_{2/7}$ M $NH_3$ in MeOH) to afford the desired product (20 mg, 42.3%) as a white solid. ESI-MS m/z: 631.15 $[M+H]^+$.

Example 504 Step e

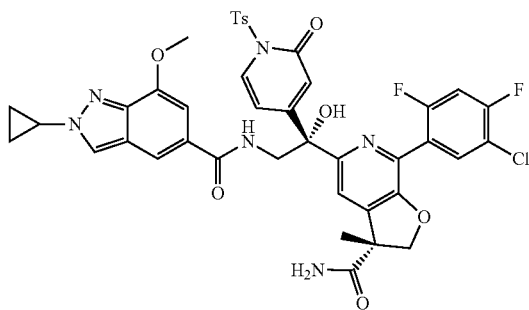 [SMILES: COc1cc(C(=O)NC[C@@](O)(c2ccn(S(=O)(=O)c3ccc(C)cc3)c(=O)c2)c2cc3c(c(-c4cc(Cl)c(F)cc4F)n2)OC[C@]3(C)C(N)=O)cc2cn(C3CC3)nc12]

A mixture of the compound from step d (25 mg, 0.04 mmol), 2-cyclopropyl-7-methoxy-2H-indazole-5-carboxylic acid (9 mg, 0.04 mmol), HATU (15 mg, 0.04 mmol) and DIEA (10 mg, 0.08 mmol) in DMF (1 mL) was stirred for 1 h at room temperature. The reaction was monitored by LCMS. The residue was purified by reversed-phase flash chromatography to afford the desired product (20 mg, 59%) as a yellow solid. ESI-MS m/z: 845.05 $[M+H]^+$.

Example 504 Step f

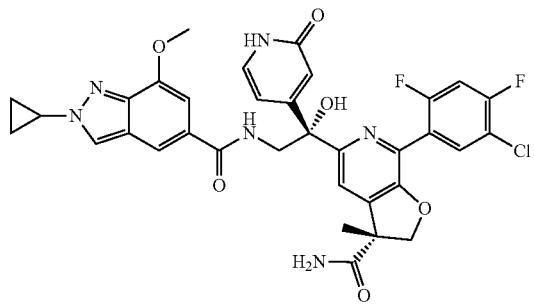 [SMILES: COc1cc(C(=O)NC[C@@](O)(c2cc[nH]c(=O)c2)c2cc3c(c(-c4cc(Cl)c(F)cc4F)n2)OC[C@]3(C)C(N)=O)cc2cn(C3CC3)nc12]

To a stirred mixture of the compound from step e (20 mg, 0.02 mmol) and MeOH (2 mL) were added LiOH (5 mg, 0.24 mmol) in $H_2O$ (0.5 mL) dropwise at room temperature. The reaction was monitored by LCMS. The resulting mixture was concentrated under vacuum. The residue was purified by Prep-TLC ($CH_2C_{12/7}$ M $NH_3MeOH$ 10:1) to afford the desired product (6.7 mg, 38%) as a white solid. ESI-MS m/z: 691.20 $[M+H]^+$.

Example 505

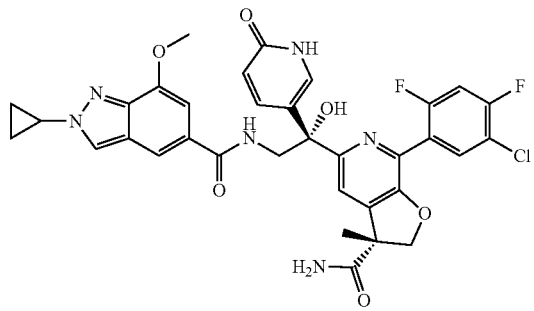 [SMILES: COc1cc(C(=O)NC[C@@](O)(c2ccc(=O)[nH]c2)c2cc3c(c(-c4cc(Cl)c(F)cc4F)n2)OC[C@]3(C)C(N)=O)cc2cn(C3CC3)nc12]

The following example was prepared in an analogous sequence to Example 504. The residue was purified by reversed-phase flash chromatography to afford the titled compound (6.4 mg, 31%) as a white solid. ESI-MS m/z: 691.20 $[M+H]^+$.

Assays

Methods for RSV-A Assay Hep-2 cells, (originally derived from tumors grown in irradiated-cortisonised weanling rats that had been injected with epidermoid carcinoma tissue from the larynx of a 56 year old male, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days. Viral stock titers were also quantified by a plaque forming unit assay, as described elsewhere.

Following extensive parameter testing, the final assay is run as follows: Hep-2 cells are seeded into the inner 60 wells of a 96-well plate at 8,000 cells per well in a volume of 50

μL using Growth Media (DMEM without phenol red, 1% L-Glut, 1% Penn/Strep, 1% nonessential amino acids, 10% heat-inactivated FBS). 2-fold serial dilutions of control and test compounds are added to the wells in duplicate in a total volume of 25 μL. Viral stock is then added to the wells at a multiplicity of infection (MOI) of 0.1 in a volume of 25 μL, bringing the total volume of each well to 100 μL. The MOI is calculated using the PFU/mL, or $TCID_{50}$ if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 μL of growth media containing an equal quantity of sucrose as those wells receiving the viral stock in order to keep consistent in media and volume conditions. The outer wells of the plate are filled with 125 μL of moat media (DMEM, 1% Penn/Strep) to act as a thermal and evaporative moat around the test wells. Following a 5-day incubation period, the plates are read using ATPlite (50 uL added per well), which quantifies the amount of ATP (a measure of cell health) present in each well. Assay plates are read using the Envision luminometer. These data are used to calculate the $EC_{50}$ each compound (Table 10). $EC_{50}$ ranges are as follows: A<0.2 μM; B>0.2 μM.

TABLE 10

Summary of Activities for RSV-A

| COMPOUND | HUMAN RSV-A ("LONG" STRAIN) $EC_{50}$ | COMPOUND | HUMAN RSV-A ("LONG" STRAIN) $EC_{50}$ |
| --- | --- | --- | --- |
| 1 | A | 2 | A |
| 3 | A | 4 | A |
| 5 | A | 6 | A |
| 7 | A | 9 | A |
| 10 | A | 11 | A |
| 12 | A | 13 | A |
| 14 | A | 15 | A |
| 16 | A | 17 | A |
| 18 | A | 19 | A |
| 20 | A | 21 | A |
| 22 | A | 23 | A |
| 24 | A | 25 | A |
| 26 | A | 27 | A |
| 28 | A | 29 | A |
| 30 | A | 31 | A |
| 32 | A | 33 | A |
| 34 | A | 35 | A |
| 36 | A | 37 | A |
| 38 | A | 39 | A |
| 40 | A | 41 | A |
| 42 | A | 43 | A |
| 44 | A | 45 | A |
| 46 | A | 47 | A |
| 48 | A | 49 | A |
| 50 | A | 51 | A |
| 52 | A | 53 | A |
| 54 | A | 55 | A |
| 56 | A | 58 | A |
| 59 | A | 60 | A |
| 61 | A | 62 | A |
| 63 | A | 64 | A |
| 65 | A | 66 | A |
| 67 | A | 69 | A |
| 70 | A | 71 | A |
| 72 | A | 80 | A |
| 86 | A | 87 | A |
| 88 | A | 89 | A |
| 90 | A | 95 | A |
| 96 | A | 97 | A |

TABLE 10-continued

Summary of Activities for RSV-A

| COMPOUND | HUMAN RSV-A ("LONG" STRAIN) $EC_{50}$ | COMPOUND | HUMAN RSV-A ("LONG" STRAIN) $EC_{50}$ |
| --- | --- | --- | --- |
| 98 | A | 99 | A |
| 100 | A | 101 | A |
| 109 | A | 110 | A |
| 113 | A | 115 | A |
| 117 | A | | |
| 130 | A | 131 | A |
| 132 | A | 133 | A |
| 134 | A | 135 | A |
| 136 | A | 137 | A |
| 138 | A | 139 | A |
| 140 | A | 141 | A |
| 142 | A | 143 | A |
| 144 | A | 145 | A |
| 146 | A | 147 | A |
| 148 | A | 149 | A |
| 152 | A | 153 | B |
| 154 | A | 155 | A |
| 156 | A | 157 | A |
| 158 | A | 159 | A |
| 160 | A | 161 | A |
| 162 | A | 163 | A |
| 164 | A | 165 | A |
| 166 | A | 167 | A |
| 168 | A | 169 | A |
| 170 | A | 171 | A |
| 172 | A | 173 | A |
| 174 | A | 175 | A |
| 176 | A | 177 | A |
| 178 | A | 179 | A |
| 180 | A | 181 | B |
| 182 | A | 183 | A |
| | | 185 | A |
| 186 | A | 187 | A |
| 192 | A | 193 | A |
| | | 195 | A |
| 196 | A | 197 | A |
| 198 | A | | |
| | | 203 | A |
| 204 | A | 205 | A |
| 206 | A | 213 | A |
| 217 | A | 219 | A |
| 220 | A | 237 | A |
| 241 | A | 243 | A |
| | | 251 | A |
| 252 | A | 253 | A |
| 254 | A | 255 | A |
| 256 | A | 257 | A |
| 258 | A | 259 | A |
| 260 | A | 261 | A |
| 262 | A | 263 | A |
| 264 | A | 265 | A |
| 266 | A | 267 | A |
| 268 | A | 269 | A |
| 270 | A | 271 | A |
| 272 | A | 273 | A |
| 274 | A | 275 | A |
| 276 | A | 277 | A |
| 278 | A | 279 | A |
| 280 | A | 281 | A |
| 282 | A | 283 | A |
| 284 | A | 285 | A |
| 286 | A | 287 | A |
| 288 | A | 289 | A |
| 290 | A | 291 | A |
| 292 | A | 293 | A |
| 294 | A | 295 | A |
| 296 | A | 297 | A |
| 298 | A | 299 | A |
| 300 | A | 301 | A |
| 302 | A | 303 | A |
| 304 | A | 305 | A |
| 307 | A | 308 | A |
| | | 313 | A |

TABLE 10-continued

Summary of Activities for RSV-A

| COMPOUND | HUMAN RSV-A ("LONG" STRAIN) $EC_{50}$ | COMPOUND | HUMAN RSV-A ("LONG" STRAIN) $EC_{50}$ |
|---|---|---|---|
| 336 | A | 337 | A |
|  |  | 339 | A |
| 340 | A | 342 | A |
| 363 | A | 364 | A |
| 366 | A |  |  |
| 368 | A | 369 | A |
| 370 | A | 371 | A |
| 373 | A | 397 | B |
| 398 | B | 405 | B |
| 406 | B | 463 | A |
| 464 | B | 467 | A |
| 468 | A | 469 | A |
| 470 | A | 471 | A |
| 472 | A |  |  |
| 474 | A | 475 | A |
| 482 | A | 483 | A |
| 484 | A | 485 | A |
| 486 | A | 487 | A |
| 488 | A | 489 | A |
|  |  | 493 | A |
| 496 | A | 497 | A |
| 498 | A | 499 | A |
| 500 | A | 501 | A |
| 504 | A | 505 | A |

Methods for HMPV Antiviral Assay

Method 1:

In vitro HMPV antiviral activity was evaluated using the clinical isolate A2 strain TN 94-49 (obtained from Dr. John Williams, Vanderbilt University, Tennessee) and LLC-IVK2 cells (ATCC #CCL-7), an immortalized kidney epithelial cell line from *Macaca mulatta*.

Compounds were resuspended in dimethyl sulfoxide (DMSO) at 10 mM, serially diluted and added to a 384-well source plate. Subsequently, the compounds were diluted and transferred onto 384-well assay plates using the Echo-650 automated liquid handling system (Beckman Coulter, Indiana). The test compounds were assessed in duplicate at a top concentration of 2 µM followed by 2.5-fold serial dilutions to give a total of 10 concentration points. DMSO control wells were also included on the assay plates and were either infected or not, acting as positive and negative controls.

A2 TN 94-49 virus infections were performed in-suspension with LLC-MK2 cells. The cells were washed twice with PBS and removed from the cell-culture flask with 0.25% trypsin-EDTA (Thermo Fisher Scientific, MA). The trypsin-EDTA was inactivated by resuspending in 2% fetal bovine serum (FBS) and OptiMEM (ThermoFisher Scientific, MA) containing 1% penicillin-streptomycin. Cells were pelleted by centrifuging for 5 minutes at 800 rpm, the supernatant was removed, and cells were re-suspended and washed in PBS plus 100 µg/mL $CaCl_2$). This step was performed twice. Cells were then re-suspended in serum-free (SF)-OptiMEM containing 4 µg/mL TPCK-Trypsin (Sigma Aldrich, MO), 1% penicillin-streptomycin (ThermoFisher Scientific, MA) and 100 µg/mL $CaCl_2$). Cells were counted and seeded at a density of 5,000 cells/well, 12.5 µL/well.

Virus infections were done at a multiplicity of infection (MOI) of 0.005 with 12.5 µL added per well. Virus infections were performed in infection media which contained SF-OptiMEM, 100 µg/mL $CaCl_2$) and 1% penicillin-streptomycin. HMPV viral stocks are suspended in infection media+5% glycerol, thus an equal volume of infection media+5% glycerol was added to uninfected wells to equalize the final % glycerol across all wells of the assay plate. The final concentration of TPCK-trypsin was 2 µg/mL. The assay plates were incubated at 37° C., 5% $CO_2$ for 7 days.

After 7 days incubation, 12.5 µL of ATP-Lite (PerkinElmer, MA) was added to each well and the raw luminescence values were determined using the Envision 2104 (Perkin Elmer, MA). The average of the raw luminescence values for the cells and virus only positive control wells was subtracted from all conditions tested and the percent cell health was determined by dividing these values by the average of the cells only negative control wells. $EC_{50}$ values were then calculated by non-linear regression using a four-parameter curve logistic equation. The curve fit model employed was XLFit Dose Response One Site Model 200:

$y=(A+(B/(1+((x/C)^\wedge D))))$, where $A$ is the minimum $y$ value, $B$ is the maximum $y$ value, $C$ is the log $EC_{50}$value, and $D$ is the slope factor.

Method 2:

In Vitro HMPV Antiviral Activity was Evaluated Using the Clinical Isolate A2 Strain TN 94-49

In vitro HMPV antiviral activity was evaluated using the clinical isolate A2 strain TN 94-49 (obtained from Dr. John Williams, Vanderbilt University, Tennessee) and LLC-MK2 cells (Millipore Sigma CB_85062804), an immortalized kidney epithelial cell line from *Macaca mulatta*.

Compounds were resuspended in dimethyl sulfoxide (DMSO) at 10 mM, serially diluted and added to a 384-well source plate. Subsequently, the compounds were diluted and transferred onto 384-well assay plates using the Echo-650 automated liquid handling system (Beckman Coulter, Indiana). The test compounds were assessed in duplicate at a top concentration of 200 nM followed by 2.5-fold serial dilutions to give a total of 10 concentration points. DMSO control wells were also included on the assay plates and were either infected or not, acting as positive and negative controls.

A2 TN 94-49 virus infections were performed in-suspension with LLC-MK2 cells. The cells were washed twice with PBS and removed from the cell-culture flask with 0.25% trypsin-EDTA (Thermo Fisher Scientific, MA). The trypsin-EDTA was inactivated by resuspending in 2% fetal bovine serum (FBS) and OptiMEM (ThermoFisher Scientific, MA) containing 1% antibiotic-antimycotic. Cells were pelleted by centrifuging for 5 minutes at 800 rpm, the supernatant was removed, and cells were re-suspended and washed in PBS plus 100 µg/mL $CaCl_2$). This step was performed twice. Cells were then re-suspended in serum-free (SF)-OptiMEM containing 4 µg/mL TPCK-Trypsin (Sigma Aldrich, MO), 1% antibiotic-antimycotic (ThermoFisher Scientific, MA), 100 µg/mL $CaCl_2$), and 4 µM of CP-100-356, a P-glycoprotein inhibitor. Cells were counted and seeded at a density of 5,000 cells/well, 12.5 µL/well. Virus infections were done at a multiplicity of infection (MOI) of 0.16 with 12.5 µL added per well. Virus infections were performed in infection media which contained SF-OptiMEM, 100 µg/mL $CaCl_2$) and 1% antibiotic-antimycotic. HMPV viral stocks are suspended in infection media+5% glycerol, thus an equal volume of infection media+5% glycerol was added to uninfected wells to equalize the final % glycerol across all wells of the assay plate. The final concentration of TPCK-trypsin was 2 µg/mL. The final concentration of CP-100-356 was 2 µM. The assay plates were incubated at 37° C., 5% $CO_2$ for 7 days.

After 7 days incubation, 12.5 μL of ATP-Lite (PerkinElmer, MA) was added to each well and the raw luminescence values were determined using the Envision 2104 (Perkin Elmer, MA).

The average of the raw luminescence values for the cells and virus only positive control wells was subtracted from all conditions tested and the percent cell health was determined by dividing these values by the average of the cells only negative control wells. $EC_{50}$ values were then calculated by non-linear regression using a four-parameter curve logistic equation. The curve fit model employed was XLFit Dose Response One Site Model 200:

$y=(A+(B/(1+((x/C)\hat{\ }D))))$, where $A$ is the minimum $y$ value, $B$ is the maximum $y$ value, $C$ is the log $EC_{50}$ value, and $D$ is the slope factor.

These data are used to calculate the $EC_{50}$ for each compound (Table 11).

Method 1 $EC_{50}$ ranges are as follows: A<0.5 μM; B>0.5 μM. Method 2 $EC_{50}$ ranges are as follows: A<0.2 μM; B>0.2 μM.

TABLE 11

Summary of Activities for hMPV A2 TN/94-49

| Compound | Method 1 hMPV $EC_{50}$ | Method 2 hMPV $EC_{50}$ | Compound | Method 1 hMPV $EC_{50}$ | Method 2 hMPV $EC_{50}$ |
|---|---|---|---|---|---|
| 1 | B | — | 2 | A | — |
| 3 | A | A | 4 | A | A |
| 5 | A | A | 6 | A | — |
| 7 | A | — | 9 | A | — |
| 10 | A | — | 11 | B | — |
| 12 | A | A | 13 | A | — |
| 14 | A | A | 15 | A | — |
| 16 | A | — | 17 | A | — |
| 18 | A | A | 19 | A | A |
| 20 | B | — | 21 | A | A |
| 22 | A | A | 23 | A | A |
| 24 | A | — | 25 | A | — |
| 26 | B | — | 27 | A | — |
| 28 | A | — | 29 | A | — |
| 30 | A | — | 31 | A | — |
| 32 | A | — | 33 | B | A |
| 34 | A | A | 35 | A | — |
| 36 | B | — | 37 | B | A |
| 38 | B | A | 39 | A | — |
| 40 | A | — | 41 | A | A |
| 42 | A | — | 43 | A | A |
| 44 | A | — | 45 | A | — |
| 46 | B | — | 47 | B | — |
| 48 | B | — | 49 | B | — |
| 50 | B | A | 51 | B | — |
| 52 | B | — | 53 | A | — |
| 54 | B | — | 55 | B | — |
| 56 | B | — | 58 | B | — |
| 59 | A | — | 60 | A | — |
| 61 | A | — | 62 | B | — |
| 63 | B | — | 64 | B | — |
| 65 | A | A | 66 | A | A |
| 67 | B | — | 69 | A | A |
| 70 | A | A | 71 | B | B |
| 72 | B | — | 79 | A | — |
| 80 | A | — | 81 | A | — |
| 82 | B | — | 83 | A | — |
| 84 | A | — | 85 | A | A |
| 86 | A | — | 87 | A | — |
| 88 | A | A | 89 | A | A |
| 90 | A | A | 93 | — | B |
| 94 | — | B | 95 | — | A |
| 96 | — | A | 97 | — | A |
| 98 | — | A | 99 | — | A |
| 100 | — | A | 101 | — | A |
| 102 | — | B | 109 | — | A |
| 110 | — | A | 113 | — | A |
| 115 | — | A | 117 | — | B |
| 118 | — | A | | | |
| 130 | B | B | 131 | A | A |
| 132 | A | A | 133 | A | A |
| 134 | A | — | 135 | B | — |
| 136 | A | — | 137 | A | — |
| 138 | A | — | 139 | — | B |
| 140 | A | A | 141 | A | — |
| 142 | A | — | 143 | A | — |
| 144 | A | A | 145 | A | A |
| 146 | A | A | 147 | A | A |
| 148 | A | — | 149 | A | — |
| 152 | — | A | 153 | — | B |
| 154 | — | A | 155 | A | — |
| 156 | A | — | 157 | A | A |
| 158 | A | A | 159 | A | — |
| 160 | A | A | 161 | A | — |
| 162 | A | A | 163 | A | — |
| 164 | A | — | 165 | A | A |
| 166 | A | A | 167 | A | — |
| 168 | A | — | 169 | A | — |
| 170 | A | A | 171 | A | A |
| 172 | A | A | 173 | A | — |
| 174 | A | — | 175 | A | — |
| 176 | A | — | 177 | A | — |
| 178 | A | — | 179 | A | A |
| 180 | B | — | 181 | B | — |
| 182 | A | A | 183 | A | A |
| 184 | B | A | 185 | A | A |
| 186 | B | A | 187 | A | A |
| 188 | — | B | 189 | — | A |
| 190 | — | B | 191 | — | A |
| 192 | — | A | 193 | — | A |
| 194 | — | A | 195 | — | A |
| 196 | — | A | 197 | — | A |
| 198 | — | A | 199 | — | B |
| 200 | — | A | 201 | — | A |
| 202 | — | A | 203 | — | A |
| 204 | — | A | 205 | — | A |
| 206 | — | A | | | |
| 210 | — | A | 213 | A | A |
| 216 | — | A | 217 | A | — |
| | | | 219 | — | A |
| 220 | — | A | 221 | — | B |
| 222 | — | B | 223 | — | B |
| 224 | — | B | 227 | — | B |
| 228 | — | A | 229 | — | A |
| 230 | — | B | 231 | — | A |
| 232 | — | A | 233 | — | A |
| 234 | — | A | 237 | — | A |
| | | | | B | 241 | — | A |
| 242 | — | B | 243 | — | A |
| 244 | — | B | 251 | A | — |
| 252 | A | — | 253 | A | — |
| 254 | A | — | 255 | A | — |
| 256 | A | — | 257 | A | — |
| 258 | A | A | 259 | A | A |
| 260 | A | A | 261 | A | — |
| 262 | A | A | 263 | A | A |
| 264 | A | A | 265 | A | A |
| 266 | A | A | 267 | A | — |
| 268 | A | A | 269 | A | A |
| 270 | A | A | 271 | A | A |
| 272 | A | — | 273 | A | — |
| 274 | A | — | 275 | A | A |
| 276 | A | A | 277 | A | A |
| 278 | A | A | 279 | A | — |
| 280 | A | A | 281 | A | A |
| 282 | A | A | 283 | A | — |
| 284 | A | — | 285 | — | A |
| 286 | — | A | 287 | A | A |
| 288 | A | — | 289 | A | A |
| 290 | A | A | 291 | A | A |
| 292 | A | A | 293 | A | A |

TABLE 11-continued

Summary of Activities for hMPV A2 TN/94-49

| Compound | Method 1 hMPV $EC_{50}$ | Method 2 hMPV $EC_{50}$ | Compound | Method 1 hMPV $EC_{50}$ | Method 2 hMPV $EC_{50}$ |
|---|---|---|---|---|---|
| 294 | A | A | 295 | A | A |
| 296 | A | A | 297 | A | A |
| 298 | A | A | 299 | A | A |
| 300 | — | A | 301 | — | A |
| 302 | — | A | 303 | — | A |
| 304 | — | A | 305 | — | A |
| 307 | — | B | 308 | — | B |
| | | | 311 | — | A |
| 312 | — | A | 313 | — | A |
| 314 | — | A | 315 | — | A |
| | | | 331 | — | A |
| 332 | — | A | 333 | — | A |
| 334 | — | A | 335 | — | A |
| 336 | — | A | 337 | — | A |
| 339 | — | A | 340 | — | A |
| 342 | — | B | 361 | — | B |
| 362 | — | A | 363 | — | B |
| 364 | — | B | 365 | — | A |
| 366 | — | B | 367 | — | A |
| 368 | — | A | 369 | — | A |
| 370 | — | A | 371 | — | B |
| 372 | — | B | 373 | — | A |
| 374 | — | A | 375 | — | A |
| | | | 397 | — | B |
| 398 | — | B | 399 | — | B |
| 400 | — | B | 405 | — | B |
| 406 | — | B | | | |
| 463 | A | A | 464 | — | B |
| 466 | B | — | 467 | A | — |
| 468 | B | A | 469 | B | — |
| 470 | A | A | 471 | A | — |
| 472 | — | B | | | |
| 474 | A | A | 475 | A | A |
| 478 | — | A | 479 | — | A |
| 480 | — | A | 481 | — | A |
| 482 | — | B | 483 | — | A |
| 484 | — | A | 485 | — | A |
| 486 | — | B | 487 | — | A |
| 488 | — | A | 489 | — | A |
| 490 | — | A | 491 | — | A |
| 492 | — | A | 493 | — | A |
| 494 | — | A | 495 | — | B |
| 496 | — | A | 497 | — | A |
| 498 | — | A | 499 | — | A |
| 500 | — | A | 501 | — | A |
| 502 | — | — | 503 | — | A |
| 504 | — | B | 505 | — | B |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (I):

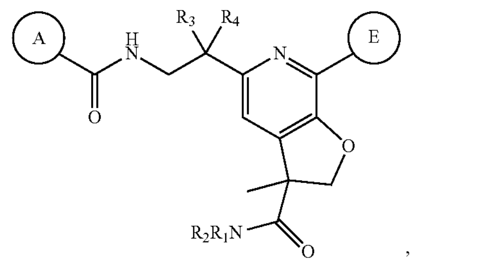

(I)

, or a pharmaceutically acceptable salt thereof, wherein:

A is selected from the group consisting of:
1) Optionally substituted aryl; and
2) Optionally substituted heteroaryl;

E is selected from the group consisting of:
1) Optionally substituted aryl; and
2) Optionally substituted heteroaryl;

$R_1$ and $R_2$ are each independently selected from the group consisting of:
1) Hydrogen;
2) Optionally substituted —$C_1$-$C_8$ alkyl;
3) optionally substituted —$C_3$-$C_8$ cycloalkyl;
4) Optionally substituted 3- to 8-membered heterocycloalkyl;
5) Optionally substituted aryl;
6) Optionally substituted arylalkyl;
7) Optionally substituted heteroaryl; and
8) Optionally substituted heteroarylalkyl;

alternatively, Rand $R_2$ are taken together with the nitrogen atom to which they are attached to form an optionally substituted 3- to 8-membered heterocyclic ring;

$R_3$ is hydroxy or fluorine; and $R_4$ is selected from the group consisting of:
1) Optionally substituted aryl;
2) Optionally substituted arylalkyl;
3) optionally substituted heteroaryl; and
4) Optionally substituted heteroarylalkyl.

2. The compound of claim 1, wherein $R_4$ selected from the groups set forth below:

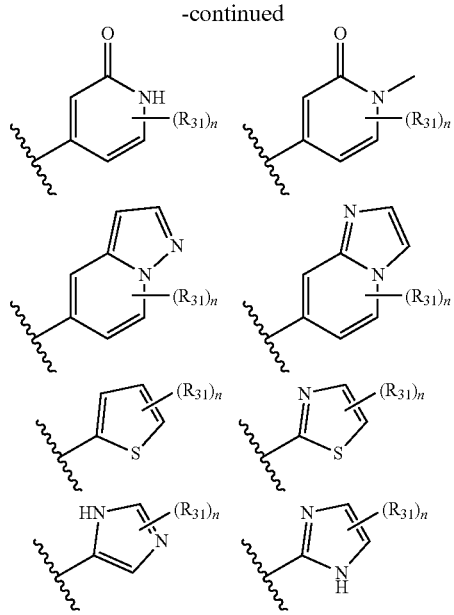

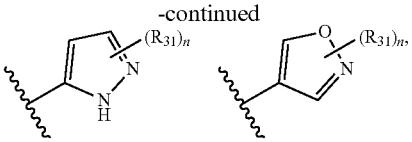

wherein R$_{31}$ is halogen, —CN, —OR$_{33}$, —CO$_2$R$_{33}$, —SO$_2$R$_{33}$, —SO$_2$NR$_{33}$R$_{34}$, —NR$_{33}$R$_{34}$, optionally substituted —C$_1$-C$_6$ alkyl, optionally substituted —C$_2$-C$_6$ alkenyl, or optionally substituted —C$_3$-C$_8$ cycloalkyl; n is 0, 1 or 2; R$_{33}$ and R$_{34}$ are each independently selected from the group consisting of hydrogen, optionally substituted —C$_1$-C$_6$ alkyl, optionally substituted —C$_2$-C$_6$ alkenyl, optionally substituted —C$_3$-C$_8$ cycloalkyl, optionally substituted 3- to 8-membered heterocycloalkyl, optionally substituted aryl, and optionally substituted heteroaryl.

3. A compound selected from the compounds set forth in the table below, or a pharmaceutically acceptable salt thereof,

| Compound | Structure |
|---|---|
| 9 | 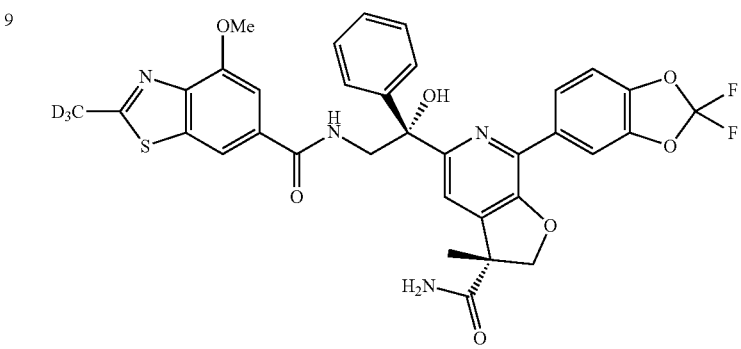 |
| 12 | 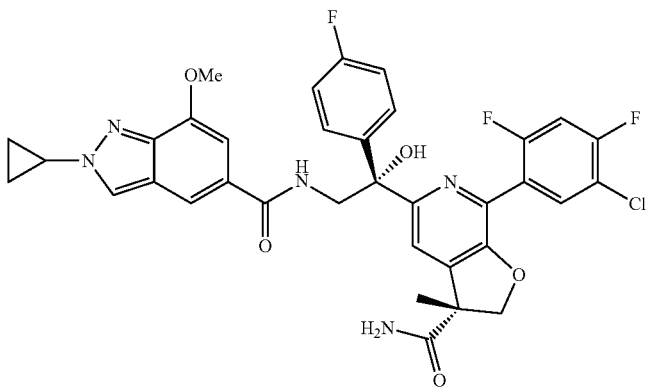 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cn(C3CC3)nc12] |

| Compound | Structure |
|---|---|
| 13 | 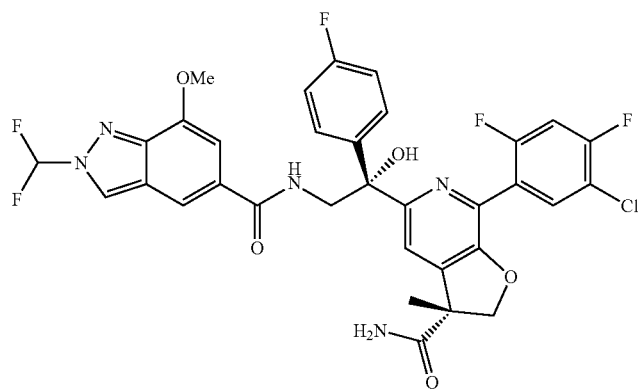 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cn(C(F)F)nc12] |
| 14 | 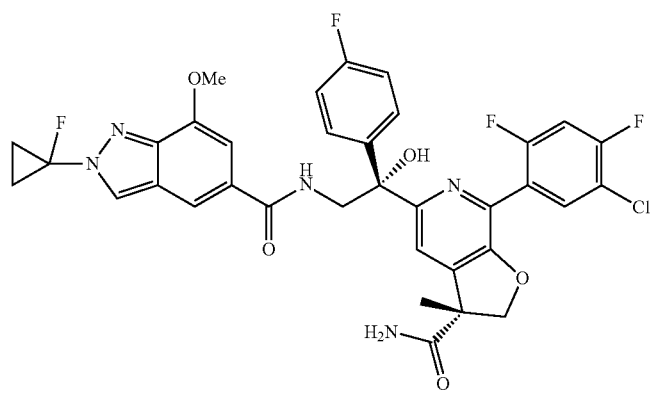 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cn(C3(F)CC3)nc12] |
| 15 | 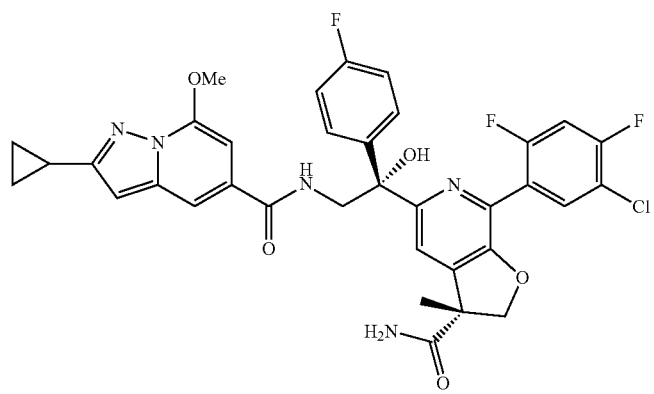 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cc(C3CC3)nn12] |
| 16 | 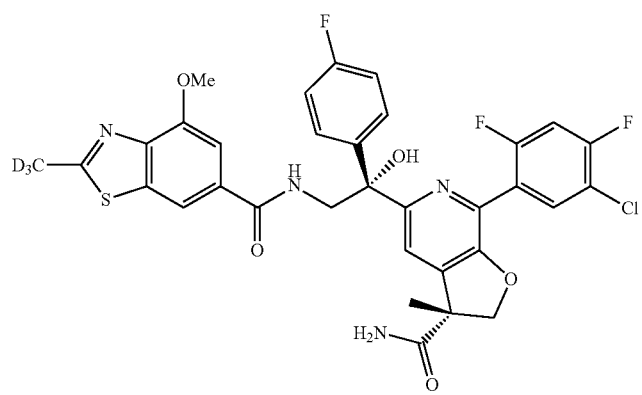 [SMILES: [2H]C([2H])([2H])c1nc2c(OC)cc(C(=O)NC[C@@](O)(c3ccc(F)cc3)c3cc4c(c(-c5cc(Cl)c(F)cc5F)n3)OC[C@]4(C)C(N)=O)cc2s1] |

| Compound | Structure |
|---|---|
| 17 | 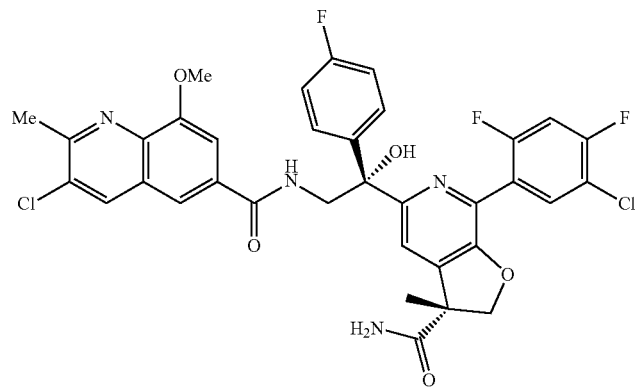 [SMILES: COc1cc(C(=O)NC[C@@](O)(c2ccc(F)cc2)c2cc3c(c(-c4cc(Cl)c(F)cc4F)n2)OC[C@]3(C)C(N)=O)cc2cc(Cl)c(C)nc12] |
| 18 | 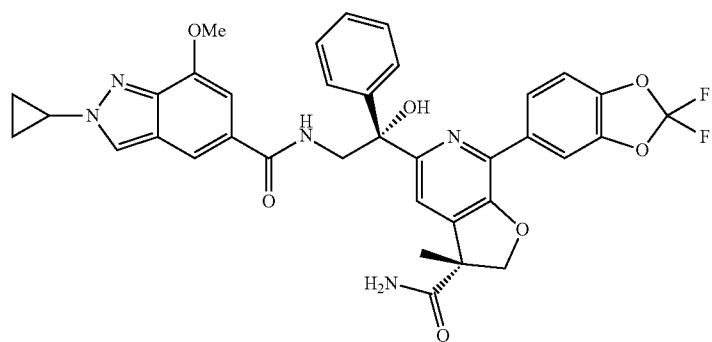 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2cn(C3CC3)nc12] |
| 19 | 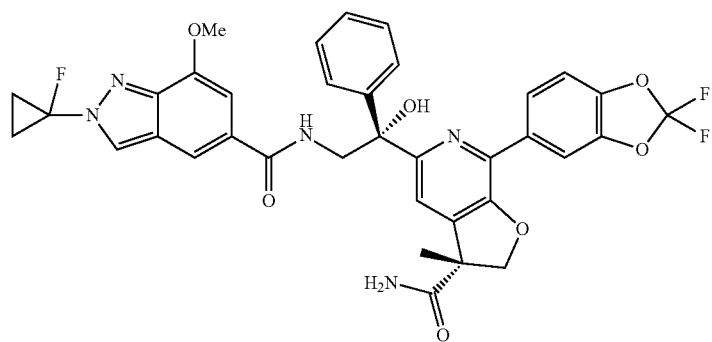 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2cn(C3(F)CC3)nc12] |
| 25 | 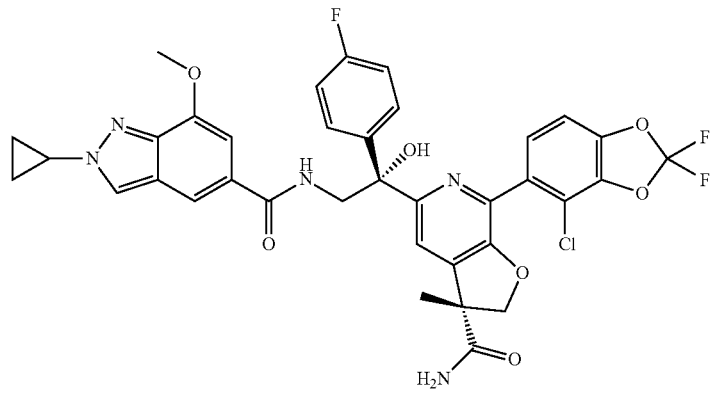 [SMILES: COc1cc(C(=O)NC[C@@](O)(c2ccc(F)cc2)c2cc3c(c(-c4ccc5c(c4Cl)OC(F)(F)O5)n2)OC[C@]3(C)C(N)=O)cc2cn(C3CC3)nc12] |

-continued
| Compound | Structure |
|---|---|
| 26 | 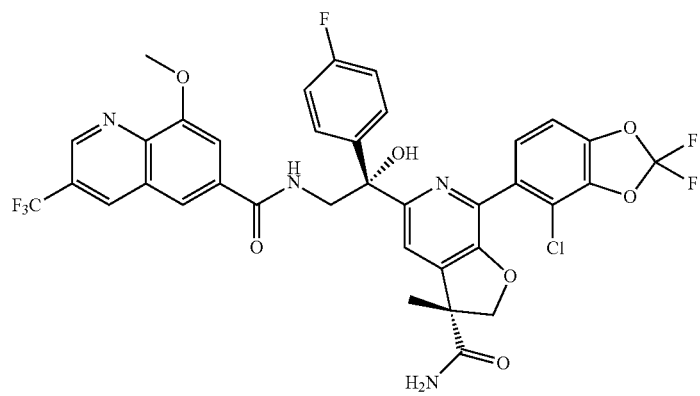 [SMILES: COc1cc(C(=O)NC[C@@](O)(c2ccc(F)cc2)c2cc3c(c(-c4ccc5c(c4Cl)OC(F)(F)O5)n2)OC[C@]3(C)C(N)=O)cc2cc(C(F)(F)F)cnc12] |
| 41 | 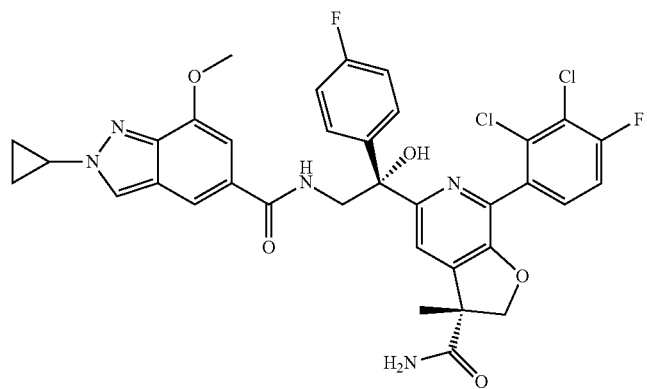 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cn(C3CC3)nc12] |
| 42 | 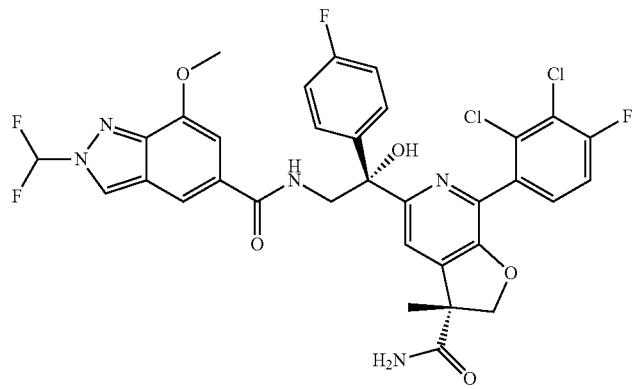 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cn(C(F)F)nc12] |
| 43 | 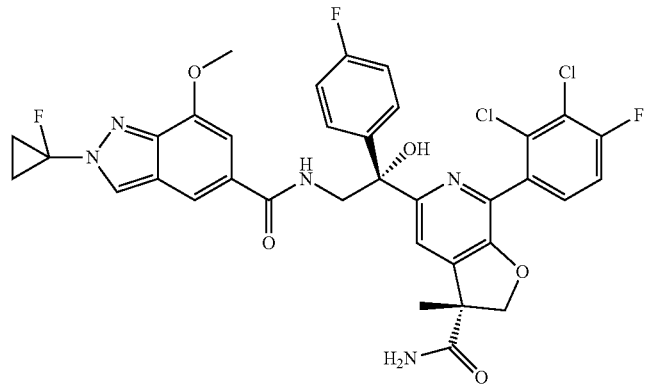 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cn(C3(F)CC3)nc12] |

| Compound | Structure |
|---|---|
| 44 | 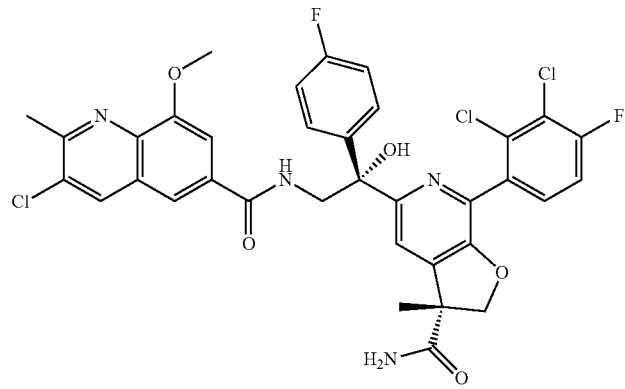 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cc(Cl)c(C)nc12] |
| 45 | 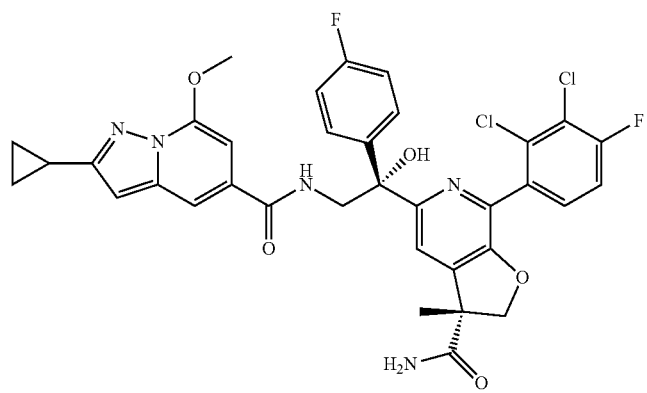 [SMILES: COc1cc(C(=O)NC[C@@](O)(c2ccc(F)cc2)c2cc3c(c(-c4ccc(F)c(Cl)c4Cl)n2)OC[C@]3(C)C(N)=O)cc2cc(C3CC3)nn12] |
| 79 | 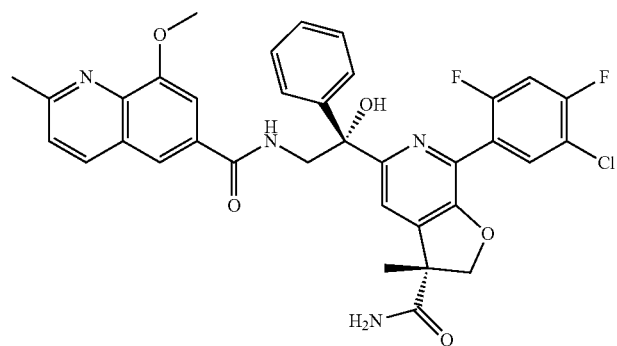 [SMILES: COc1cc(C(=O)NC[C@@](O)(c2ccccc2)c2cc3c(c(-c4cc(Cl)c(F)cc4F)n2)OC[C@]3(C)C(N)=O)cc2ccc(C)nc12] |
| 80 | 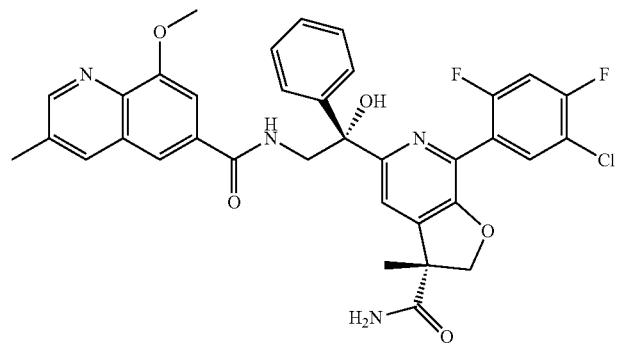 |

| Compound | Structure |
|---|---|
| 81 | 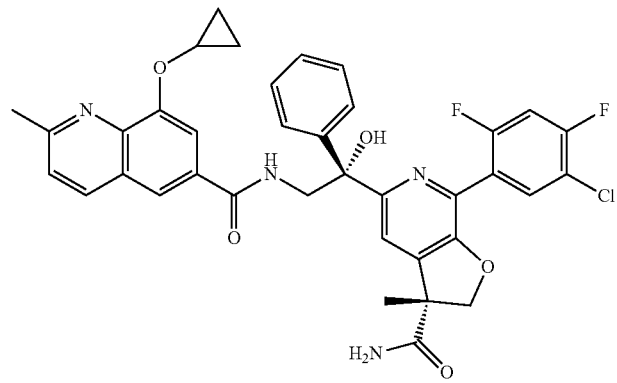 [SMILES: Cc1ccc2cc(C(=O)NC[C@@](O)(c3ccccc3)c3cc4c(c(-c5cc(Cl)c(F)cc5F)n3)OC[C@]4(C)C(N)=O)cc(OC3CC3)c2n1] |
| 82 | 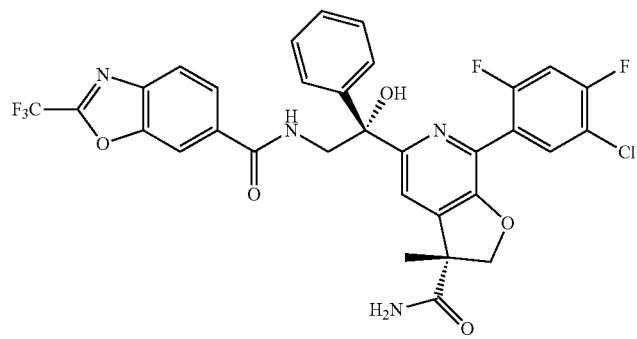 [SMILES: C[C@]1(C(N)=O)COc2c1cc([C@@](O)(CNC(=O)c1ccc3nc(C(F)(F)F)oc3c1)c1ccccc1)nc2-c1cc(Cl)c(F)cc1F] |
| 83 | 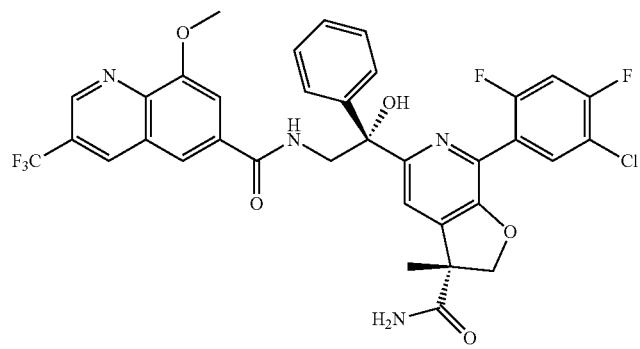 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C(F)(F)F)cnc12] |
| 84 | 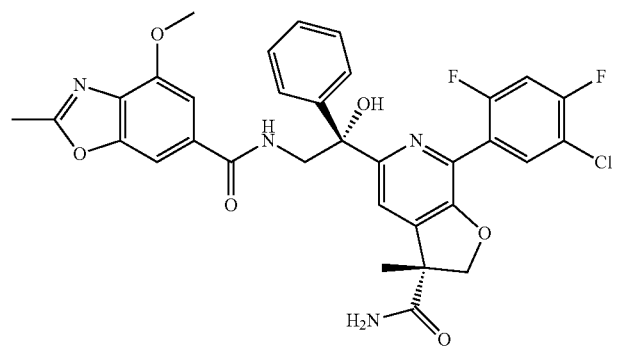 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C)nc12] |

| Compound | Structure |
|---|---|
| 85 | 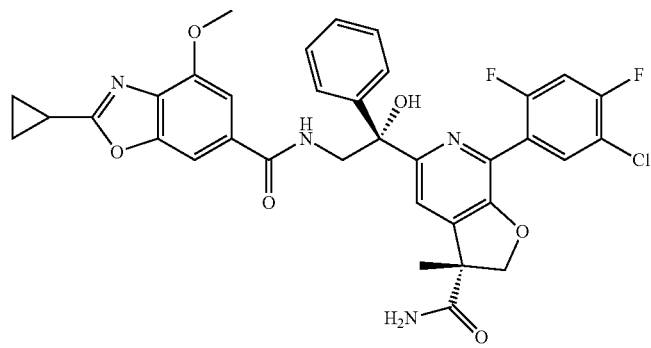 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C3CC3)nc12] |
| 86 | 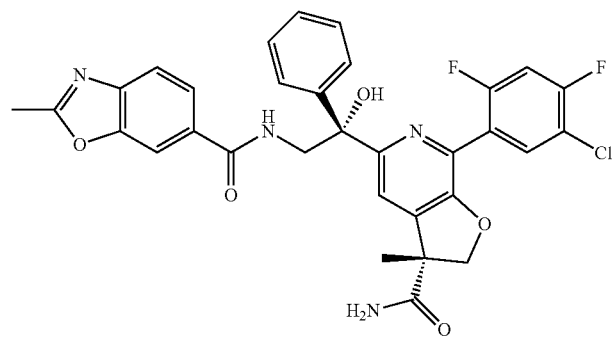 [SMILES: Cc1nc2ccc(C(=O)NC[C@@](O)(c3ccccc3)c3cc4c(c(-c5cc(Cl)c(F)cc5F)n3)OC[C@]4(C)C(N)=O)cc2o1] |
| 87 | 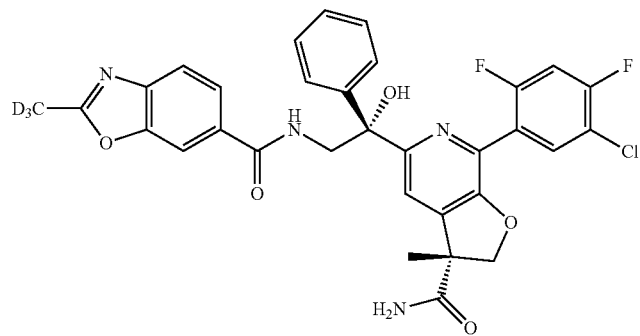 [SMILES: [2H]C([2H])([2H])c1nc2ccc(C(=O)NC[C@@](O)(c3ccccc3)c3cc4c(c(-c5cc(Cl)c(F)cc5F)n3)OC[C@]4(C)C(N)=O)cc2o1] |
| 88 | 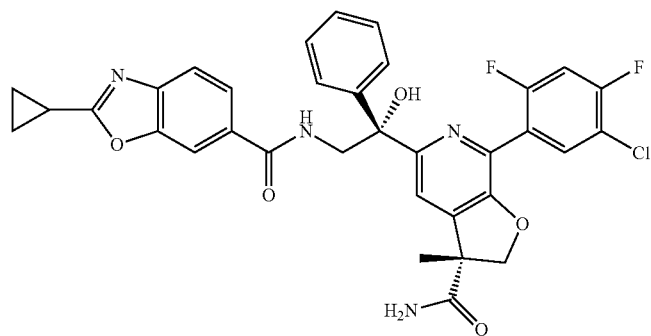 [SMILES: C[C@]1(C(N)=O)COc2c1cc([C@@](O)(CNC(=O)c1ccc3nc(C4CC4)oc3c1)c1ccccc1)nc2-c1cc(Cl)c(F)cc1F] |

| Compound | Structure |
|---|---|
| 89 | 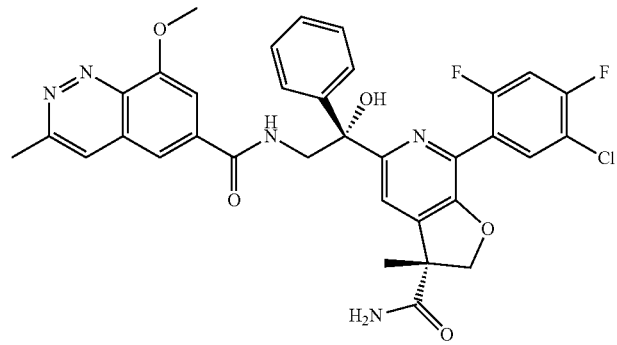 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C)nnc12] |
| 90 | 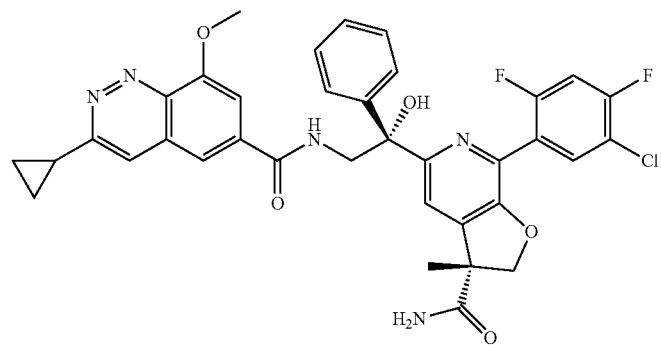 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C3CC3)nnc12] |
| 93 | 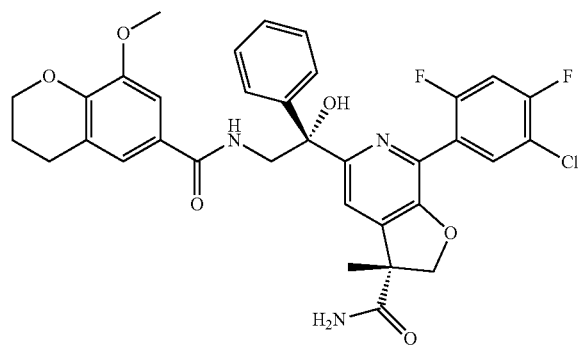 [SMILES: COc1cc(C(=O)NC[C@@](O)(c2ccccc2)c2cc3c(c(-c4cc(Cl)c(F)cc4F)n2)OC[C@]3(C)C(N)=O)cc2c1OCCC2] |
| 94 | 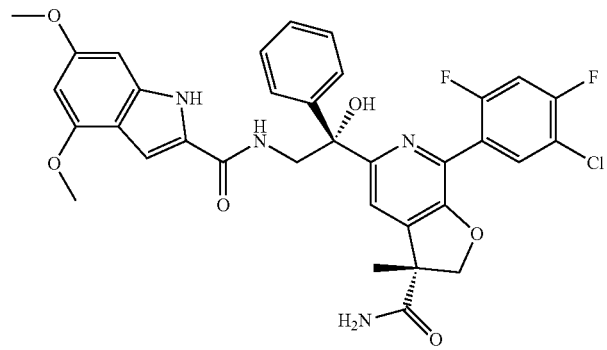 [SMILES: COc1cc(OC)c2cc(C(=O)NC[C@@](O)(c3ccccc3)c3cc4c(c(-c5cc(Cl)c(F)cc5F)n3)OC[C@]4(C)C(N)=O)[nH]c2c1] |

| Compound | Structure |
|---|---|
| 95 | 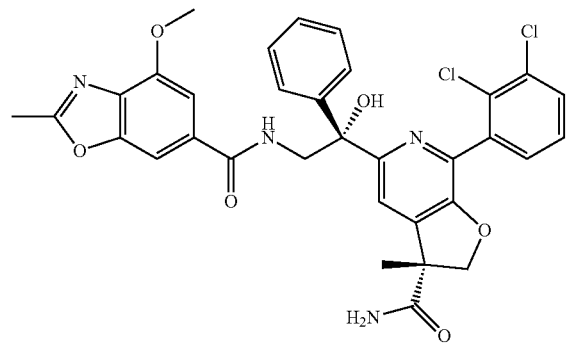 [SMILES: COc1cc(C(=O)NC[C@@](O)(c2ccccc2)c2cc3c(c(-c4cccc(Cl)c4Cl)n2)OC[C@]3(C)C(N)=O)cc2oc(C)nc12] |
| 96 | 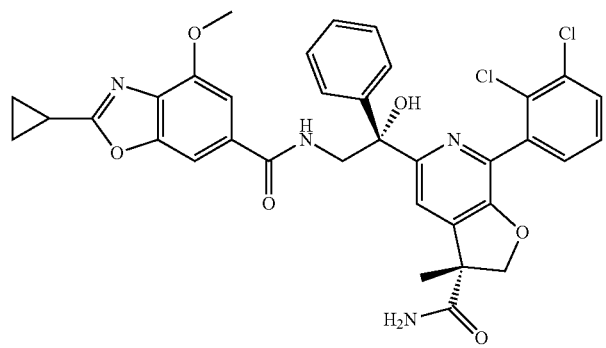 |
| 97 | 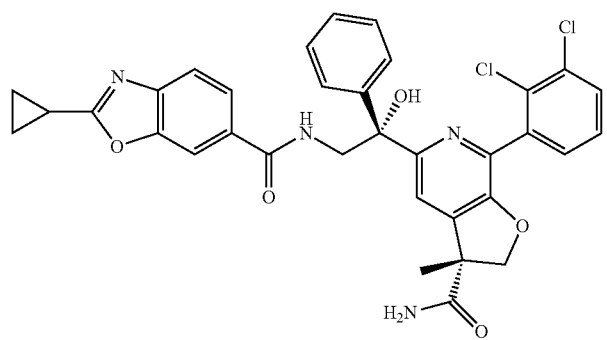 |
| 98 | 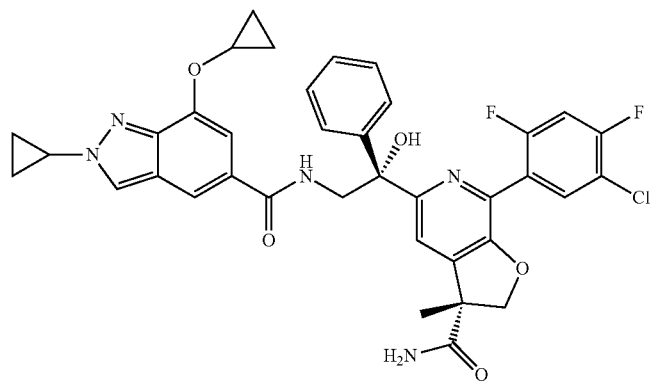 |

| Compound | Structure |
|---|---|
| 99 | 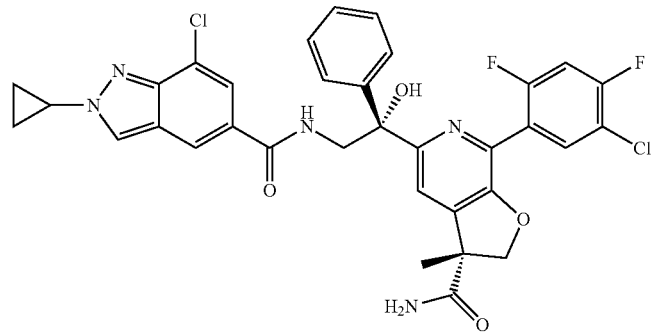 |
| 100 | 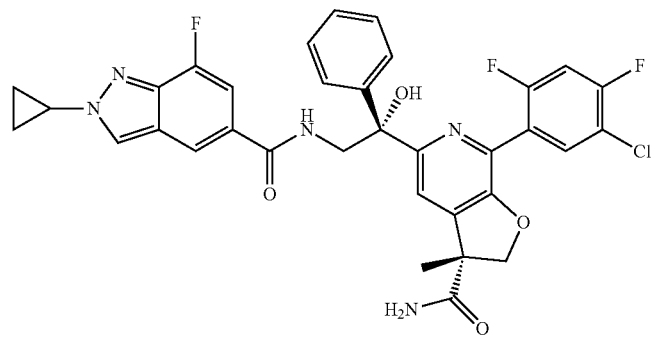 |
| 101 | 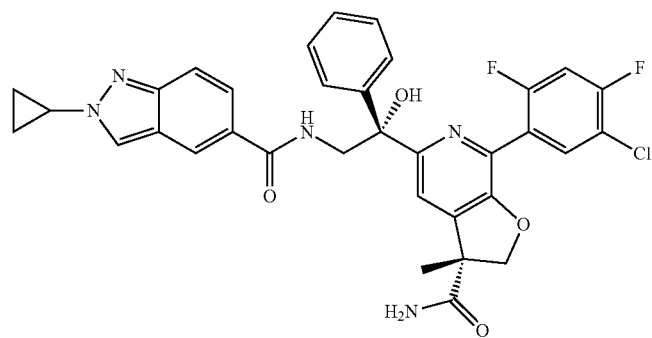 |
| 102 | 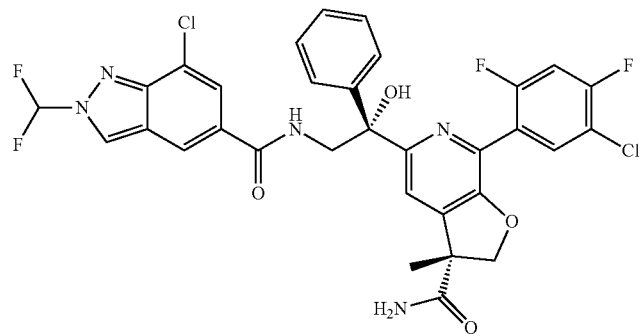 |

| Compound | Structure |
|---|---|
| 109 | 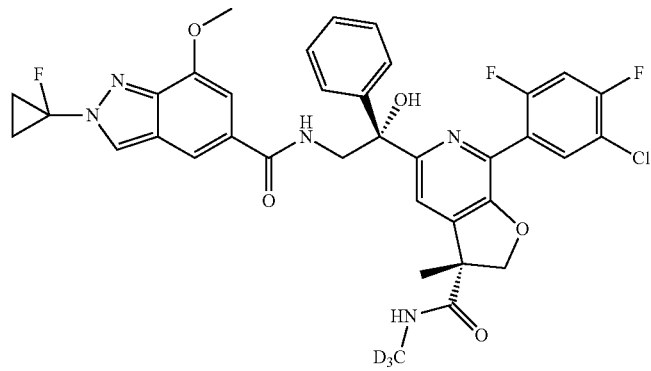 |
| 110 | 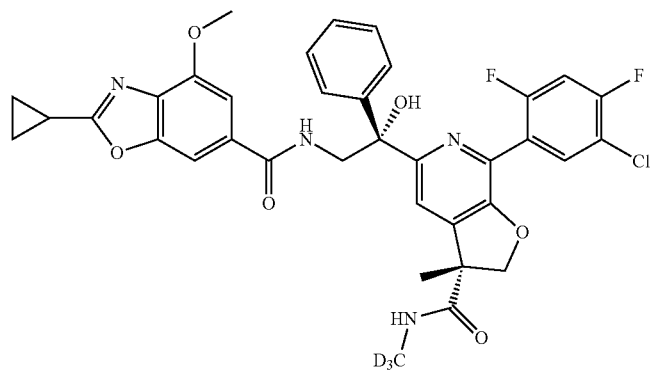 |
| 113 | 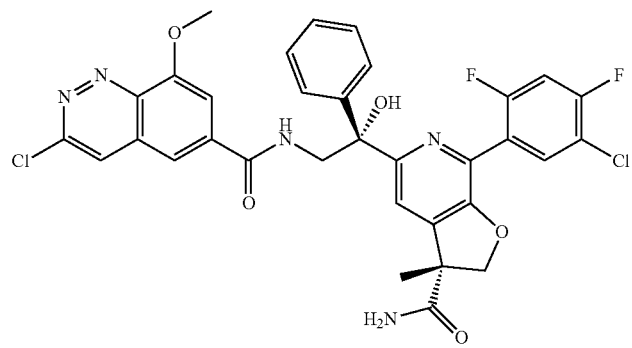 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)nnc12] |
| 115 | 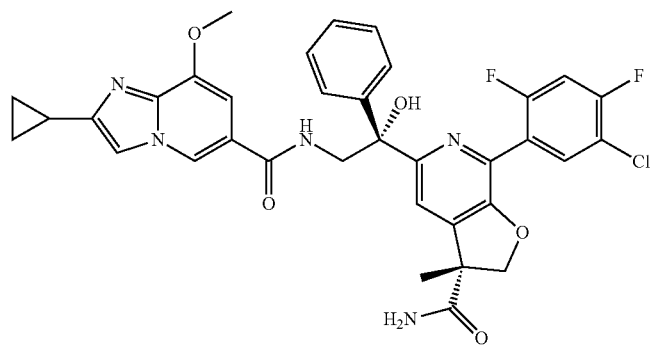 |

| Compound | Structure |
|---|---|
| 117 | 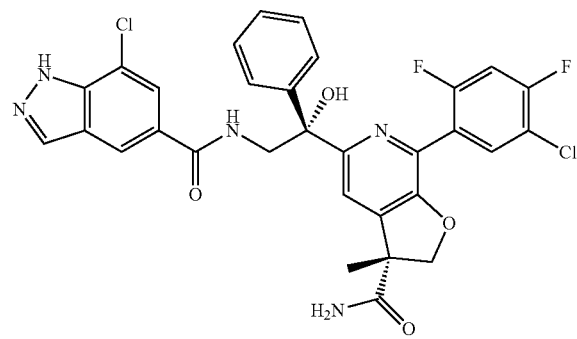 [SMILES: C[C@]1(C(N)=O)COc2c1cc([C@@](O)(CNC(=O)c1cc(Cl)c3[nH]ncc3c1)c1ccccc1)nc2-c1cc(Cl)c(F)cc1F] |
| 118 | 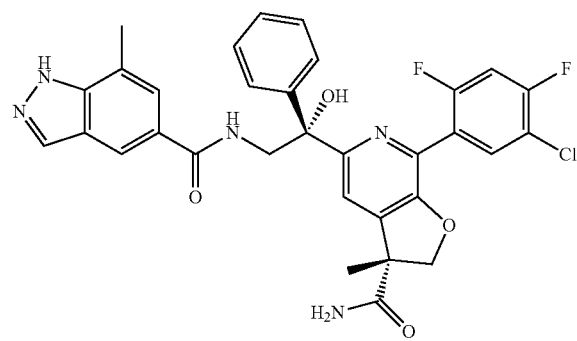 [SMILES: Cc1cc(C(=O)NC[C@@](O)(c2ccccc2)c2cc3c(c(-c4cc(Cl)c(F)cc4F)n2)OC[C@]3(C)C(N)=O)cc2cn[nH]c12] |
| 130 | 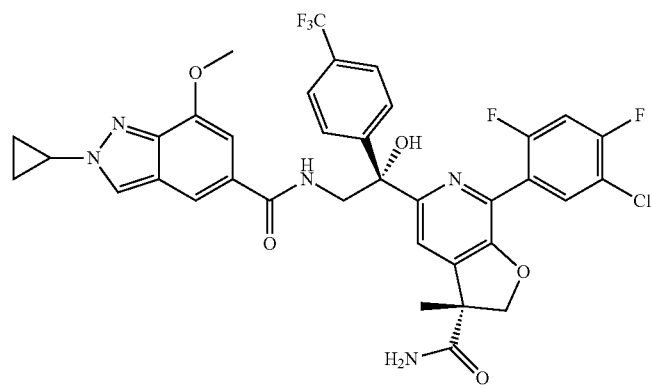 |
| 131 | 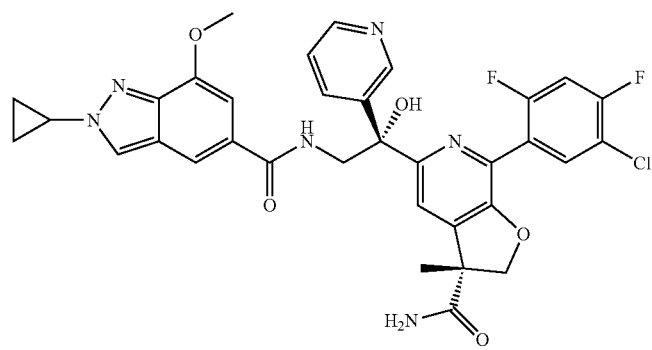 |

| Compound | Structure |
|---|---|
| 132 | 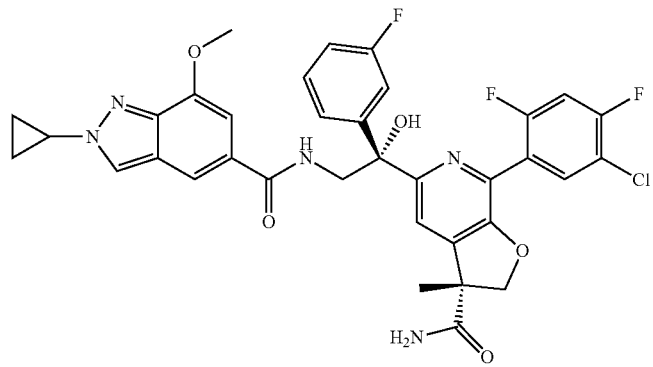 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cn(C3CC3)nc12] |
| 237 | 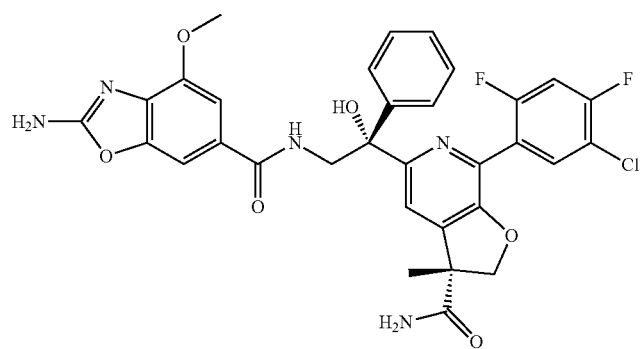 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(N)nc12] |
| 133 | 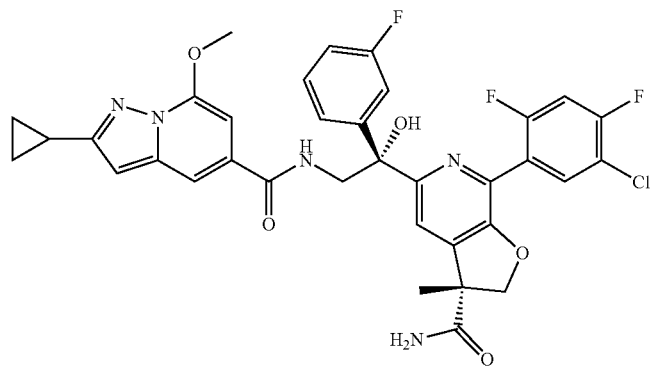 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cc(C3CC3)nn12] |
| 134 | 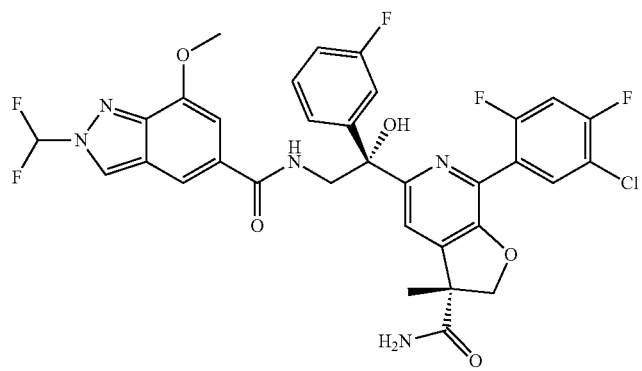 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cn(C(F)F)nc12] |

| Compound | Structure |
|---|---|
| 135 | 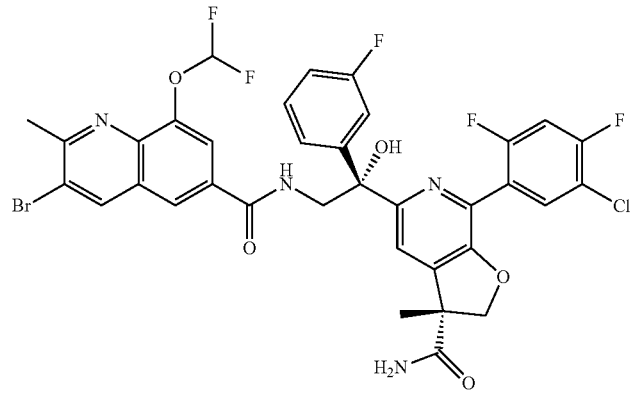 [SMILES: Cc1nc2c(OC(F)F)cc(C(=O)NC[C@@](O)(c3cccc(F)c3)c3cc4c(c(-c5cc(Cl)c(F)cc5F)n3)OC[C@]4(C)C(N)=O)cc2cc1Br] |
| 136 | 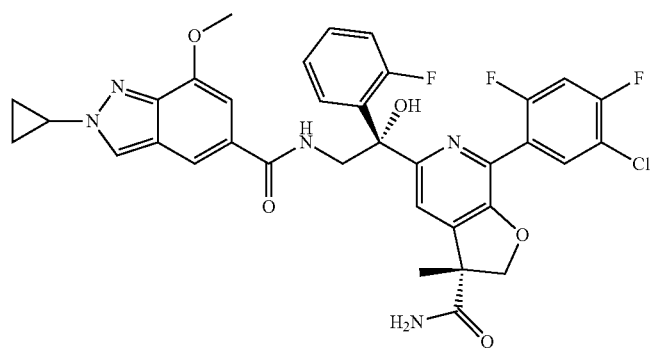 [SMILES: COc1cc(C(=O)NC[C@](O)(c2cc3c(c(-c4cc(Cl)c(F)cc4F)n2)OC[C@]3(C)C(N)=O)c2ccccc2F)cc2cn(C3CC3)nc12] |
| 137 | 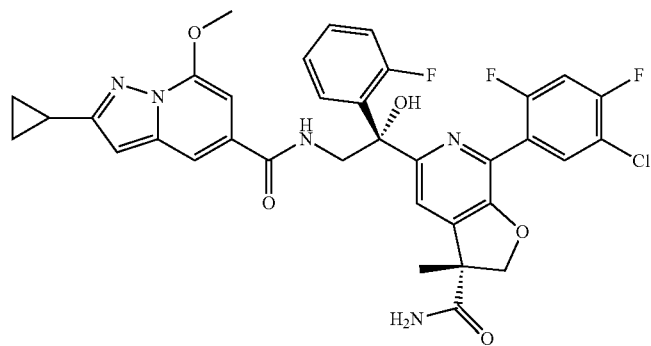 [SMILES: COc1cc(C(=O)NC[C@](O)(c2cc3c(c(-c4cc(Cl)c(F)cc4F)n2)OC[C@]3(C)C(N)=O)c2ccccc2F)cc2cc(C3CC3)nn12] |
| 138 | 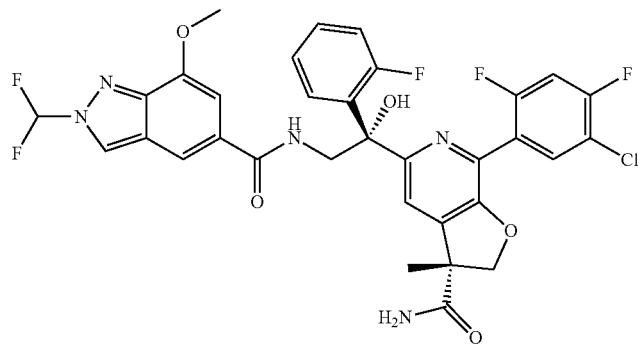 [SMILES: COc1cc(C(=O)NC[C@](O)(c2cc3c(c(-c4cc(Cl)c(F)cc4F)n2)OC[C@]3(C)C(N)=O)c2ccccc2F)cc2cn(C(F)F)nc12] |

| Compound | Structure |
|---|---|
| 139 | 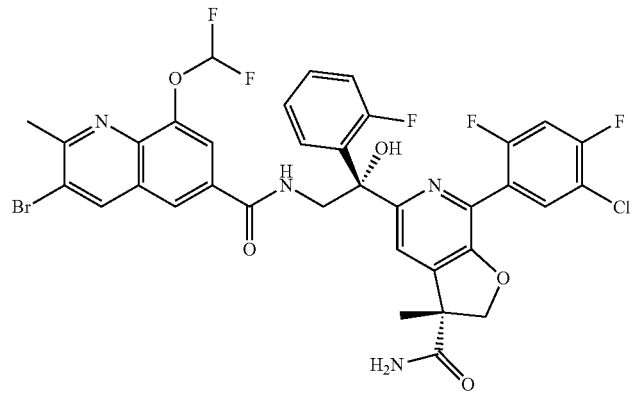 [SMILES: Cc1nc2c(OC(F)F)cc(C(=O)NC[C@](O)(c3cc4c(c(-c5cc(Cl)c(F)cc5F)n3)OC[C@]4(C)C(N)=O)c3ccccc3F)cc2cc1Br] |
| 140 | 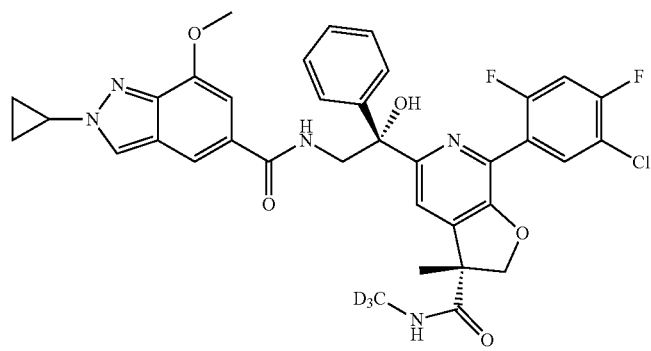 [SMILES: [2H]C([2H])([2H])NC(=O)[C@@]1(C)COc2c1cc([C@@](O)(CNC(=O)c1cc(OC)c3nn(C4CC4)cc3c1)c1ccccc1)nc2-c1cc(Cl)c(F)cc1F] |
| 141 | 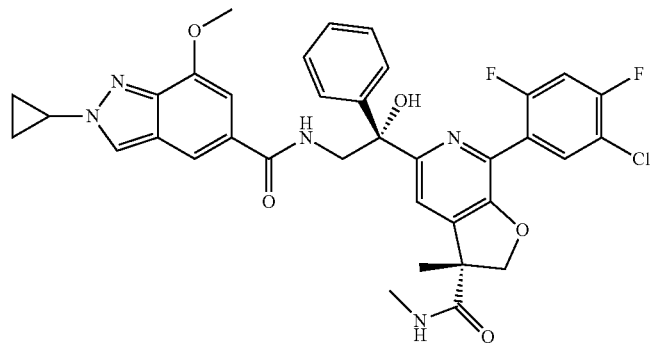 [SMILES: CNC(=O)[C@@]1(C)COc2c1cc([C@@](O)(CNC(=O)c1cc(OC)c3nn(C4CC4)cc3c1)c1ccccc1)nc2-c1cc(Cl)c(F)cc1F] |
| 142 | 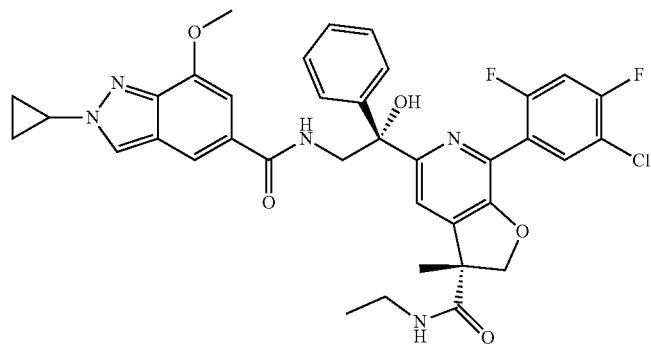 [SMILES: CCNC(=O)[C@@]1(C)COc2c1cc([C@@](O)(CNC(=O)c1cc(OC)c3nn(C4CC4)cc3c1)c1ccccc1)nc2-c1cc(Cl)c(F)cc1F] |

| Compound | Structure |
|---|---|
| 143 | 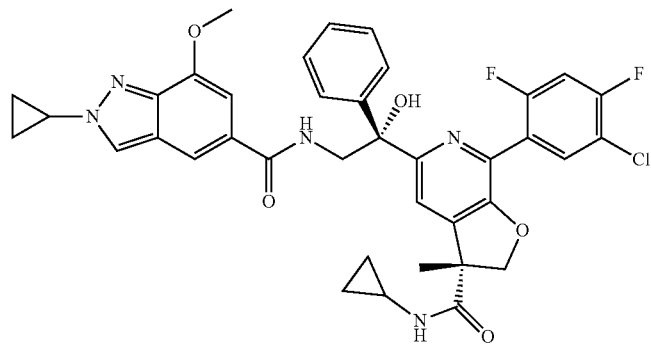 [SMILES: COc1cc(C(=O)NC[C@@](O)(c2ccccc2)c2cc3c(c(-c4cc(Cl)c(F)cc4F)n2)OC[C@]3(C)C(=O)NC2CC2)cc2cn(C3CC3)nc12] |
| 144 | 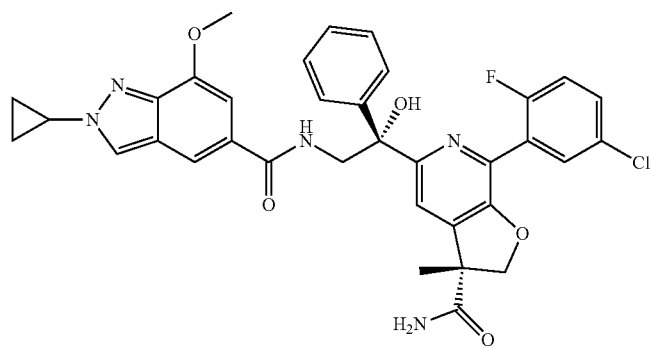 [SMILES: COc1cc(C(=O)NC[C@@](O)(c2ccccc2)c2cc3c(c(-c4cc(Cl)ccc4F)n2)OC[C@]3(C)C(N)=O)cc2cn(C3CC3)nc12] |
| 145 | 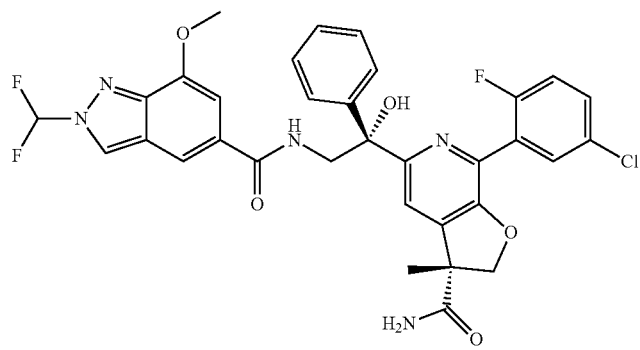 [SMILES: COc1cc(C(=O)NC[C@@](O)(c2ccccc2)c2cc3c(c(-c4cc(Cl)ccc4F)n2)OC[C@]3(C)C(N)=O)cc2cn(C(F)F)nc12] |
| 146 | 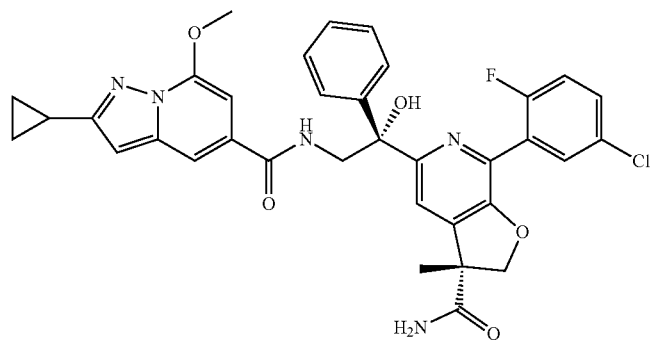 [SMILES: COc1cc(C(=O)NC[C@@](O)(c2ccccc2)c2cc3c(c(-c4cc(Cl)ccc4F)n2)OC[C@]3(C)C(N)=O)cc2cc(C3CC3)nn12] |

| Compound | Structure |
|---|---|
| 147 | 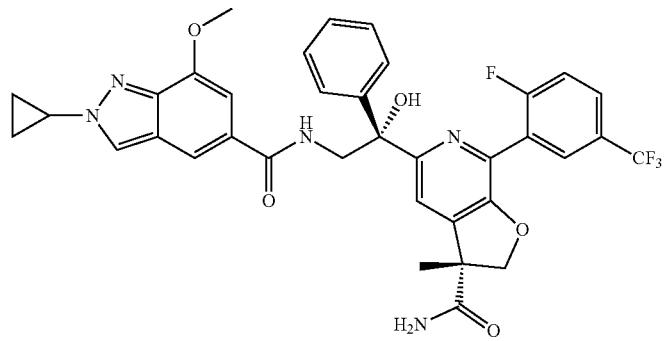 [SMILES: COc1cc(C(=O)NC[C@@](O)(c2ccccc2)c2cc3c(c(-c4cc(C(F)(F)F)ccc4F)n2)OC[C@]3(C)C(N)=O)cc2cn(C3CC3)nc12] |
| 148 | 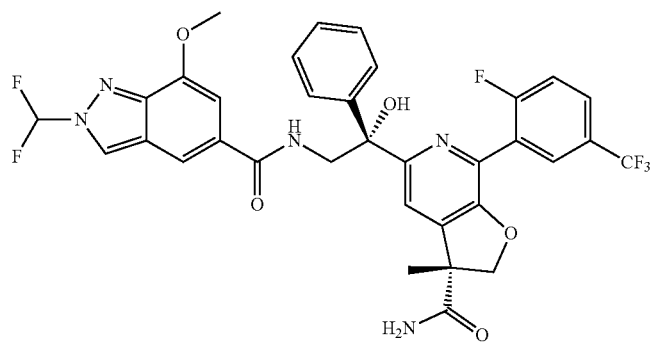 [SMILES: COc1cc(C(=O)NC[C@@](O)(c2ccccc2)c2cc3c(c(-c4cc(C(F)(F)F)ccc4F)n2)OC[C@]3(C)C(N)=O)cc2cn(C(F)F)nc12] |
| 149 | 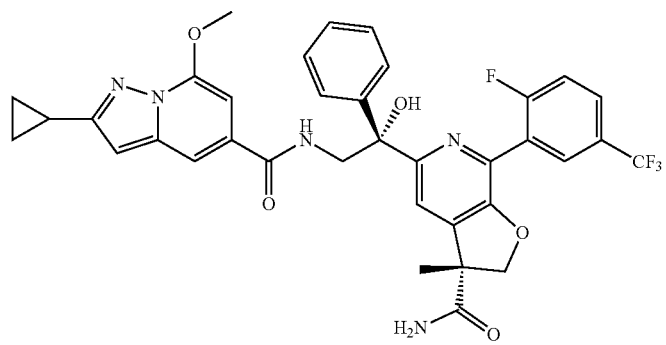 [SMILES: COc1cc(C(=O)NC[C@@](O)(c2ccccc2)c2cc3c(c(-c4cc(C(F)(F)F)ccc4F)n2)OC[C@]3(C)C(N)=O)cc2cc(C3CC3)nn12] |
| 152 | 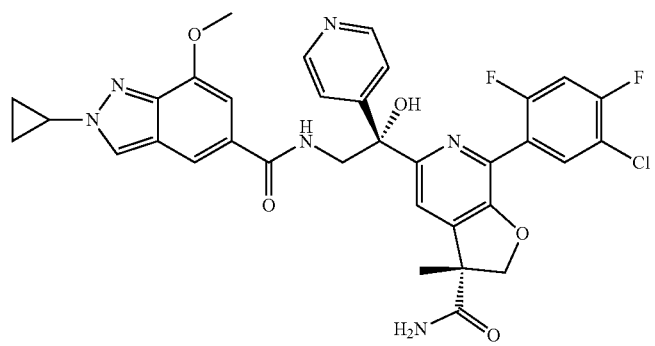 [SMILES: COc1cc(C(=O)NC[C@@](O)(c2ccncc2)c2cc3c(c(-c4cc(Cl)c(F)cc4F)n2)OC[C@]3(C)C(N)=O)cc2cn(C3CC3)nc12] |

| Compound | Structure |
|---|---|
| 153 | 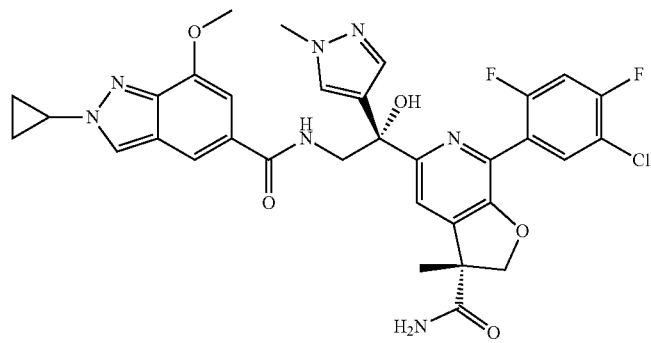 [SMILES: COc1cc(C(=O)NC[C@@](O)(c2cnn(C)c2)c2cc3c(c(-c4cc(Cl)c(F)cc4F)n2)OC[C@]3(C)C(N)=O)cc2cn(C3CC3)nc12] |
| 154 | 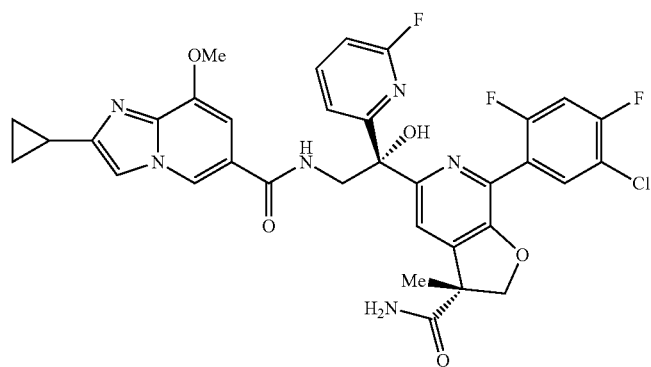 [SMILES: COc1cc(C(=O)NC[C@@](O)(c2cccc(F)n2)c2cc3c(c(-c4cc(Cl)c(F)cc4F)n2)OC[C@]3(C)C(N)=O)cn2cc(C3CC3)nc12] |
| 155 | 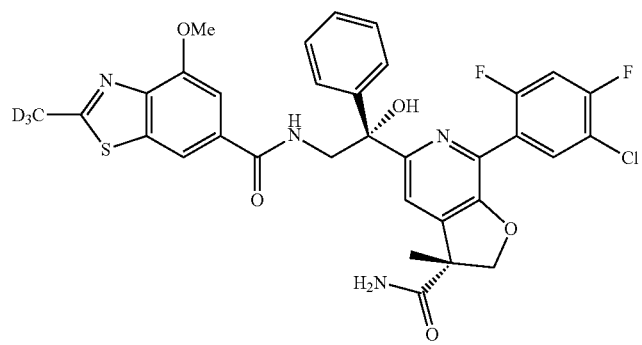 [SMILES: [2H]C([2H])([2H])c1nc2c(OC)cc(C(=O)NC[C@@](O)(c3ccccc3)c3cc4c(c(-c5cc(Cl)c(F)cc5F)n3)OC[C@]4(C)C(N)=O)cc2s1] |
| 156 | 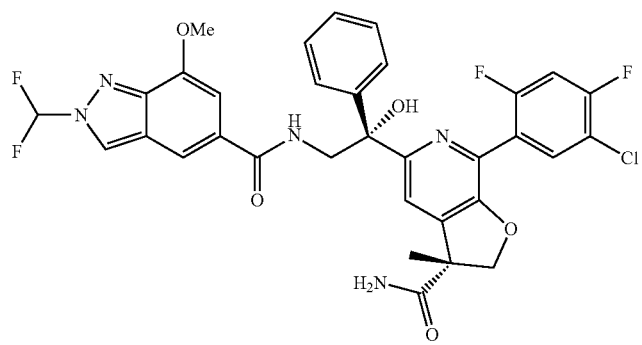 [SMILES: COc1cc(C(=O)NC[C@@](O)(c2ccccc2)c2cc3c(c(-c4cc(Cl)c(F)cc4F)n2)OC[C@]3(C)C(N)=O)cc2cn(C(F)F)nc12] |

| Compound | Structure |
|---|---|
| 157 | 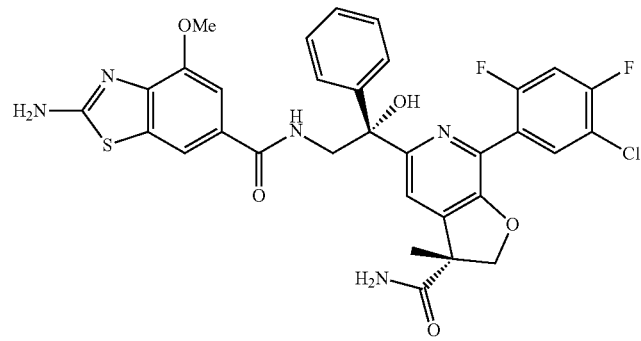 [SMILES: COc1cc(C(=O)NC[C@@](O)(c2ccccc2)c2cc3c(c(-c4cc(Cl)c(F)cc4F)n2)OC[C@]3(C)C(N)=O)cc2sc(N)nc12] |
| 158 | 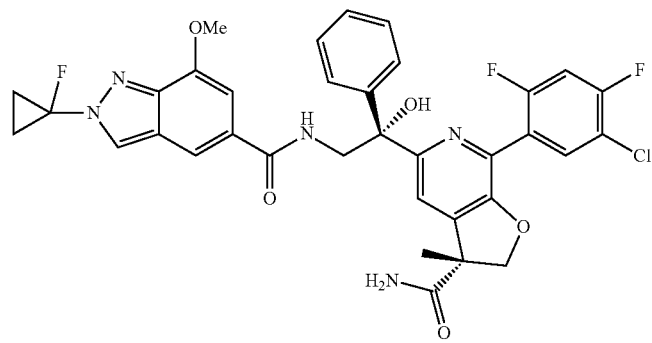 [SMILES: COc1cc(C(=O)NC[C@@](O)(c2ccccc2)c2cc3c(c(-c4cc(Cl)c(F)cc4F)n2)OC[C@]3(C)C(N)=O)cc2cn(C3(F)CC3)nc12] |
| 159 | 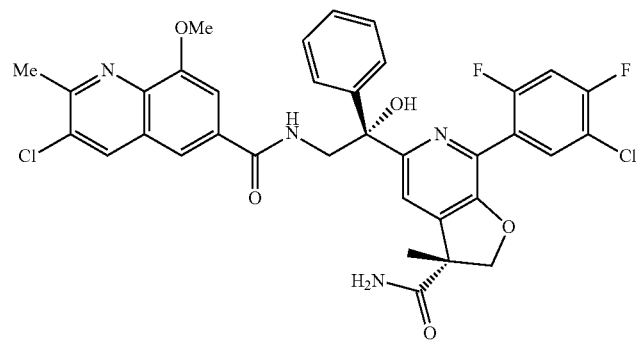 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)c(C)nc12] |
| 160 | 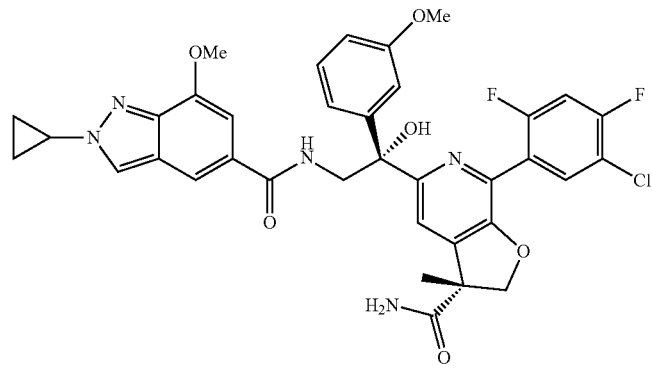 [SMILES: COc1cccc([C@](O)(CNC(=O)c2cc(OC)c3nn(C4CC4)cc3c2)c2cc3c(c(-c4cc(Cl)c(F)cc4F)n2)OC[C@]3(C)C(N)=O)c1] |

-continued
| Compound | Structure |
|---|---|
| 161 | 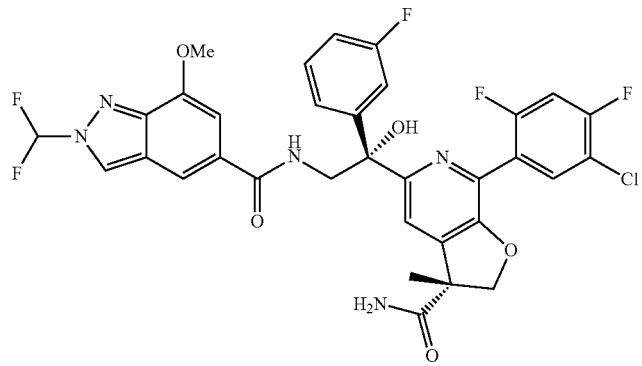 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cn(C(F)F)nc12] |
| 162 | 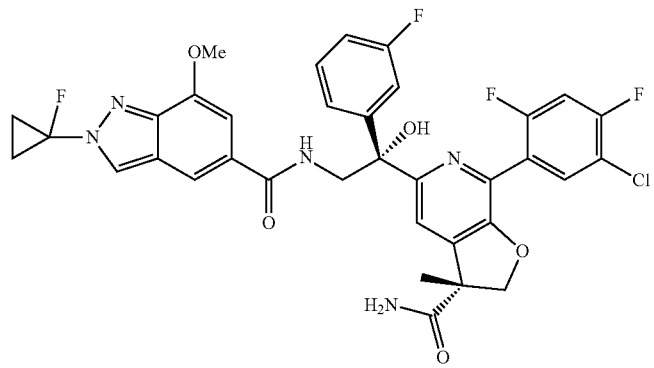 [SMILES: COc1cc(C(=O)NC[C@@](O)(c2cccc(F)c2)c2cc3c(c(-c4cc(Cl)c(F)cc4F)n2)OC[C@]3(C)C(N)=O)cc2cn(C3(F)CC3)nc12] |
| 163 | 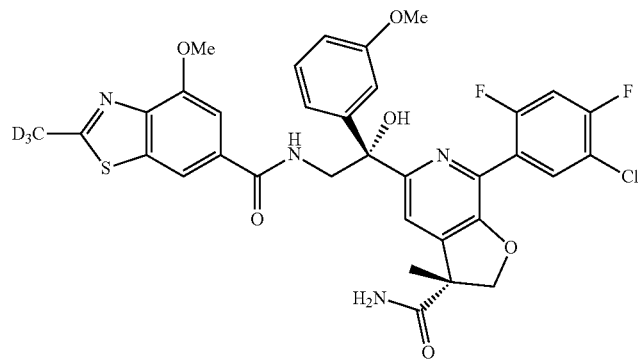 [SMILES: [2H]C([2H])([2H])c1nc2c(OC)cc(C(=O)NC[C@@](O)(c3cccc(OC)c3)c3cc4c(c(-c5cc(Cl)c(F)cc5F)n3)OC[C@]4(C)C(N)=O)cc2s1] |
| 164 | 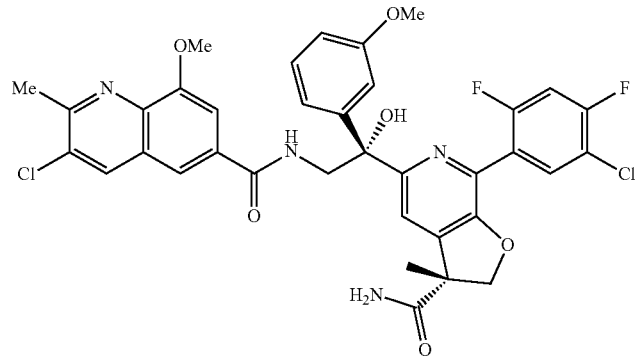 [SMILES: COc1cccc([C@](O)(CNC(=O)c2cc(OC)c3nc(C)c(Cl)cc3c2)c2cc3c(c(-c4cc(Cl)c(F)cc4F)n2)OC[C@]3(C)C(N)=O)c1] |

| Compound | Structure |
|---|---|
| 165 | 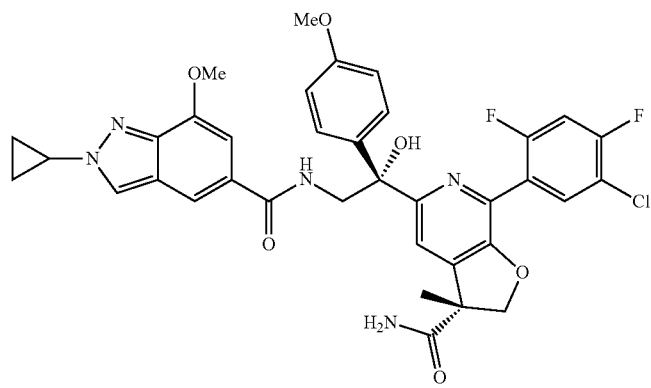 [SMILES: COc1ccc([C@](O)(CNC(=O)c2cc(OC)c3nn(C4CC4)cc3c2)c2cc3c(c(-c4cc(Cl)c(F)cc4F)n2)OC[C@]3(C)C(N)=O)cc1] |
| 166 | 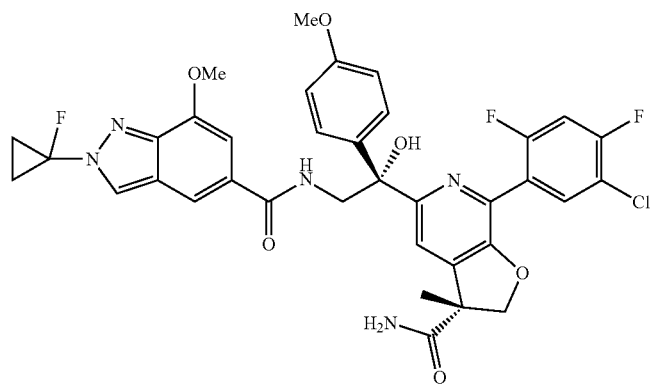 [SMILES: COc1ccc([C@](O)(CNC(=O)c2cc(OC)c3nn(C4(F)CC4)cc3c2)c2cc3c(c(-c4cc(Cl)c(F)cc4F)n2)OC[C@]3(C)C(N)=O)cc1] |
| 167 | 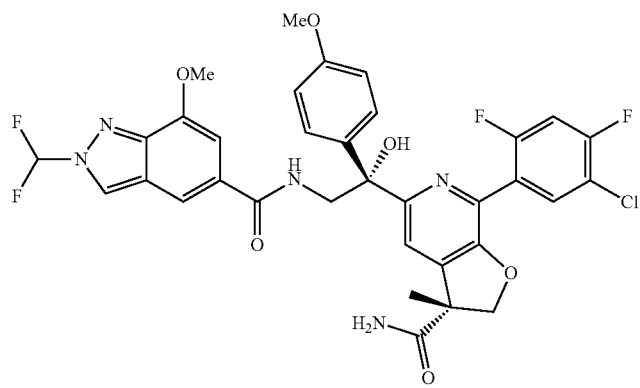 [SMILES: COc1ccc([C@](O)(CNC(=O)c2cc(OC)c3nn(C(F)F)cc3c2)c2cc3c(c(-c4cc(Cl)c(F)cc4F)n2)OC[C@]3(C)C(N)=O)cc1] |
| 168 | 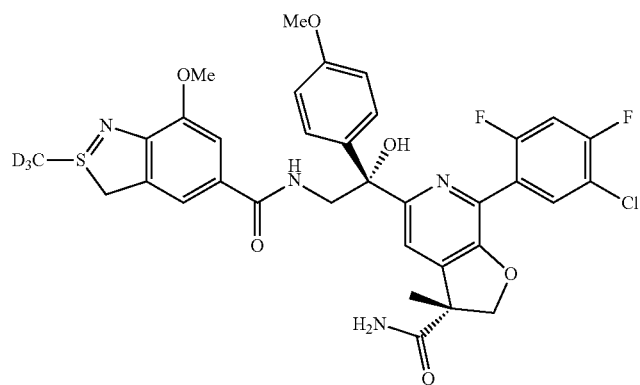 [SMILES: [2H]C([2H])([2H])S1=Nc2c(cc(C(=O)NC[C@@](O)(c3ccc(OC)cc3)c3cc4c(c(-c5cc(Cl)c(F)cc5F)n3)OC[C@]4(C)C(N)=O)cc2OC)C1] |

| Compound | Structure |
|---|---|
| 169 | 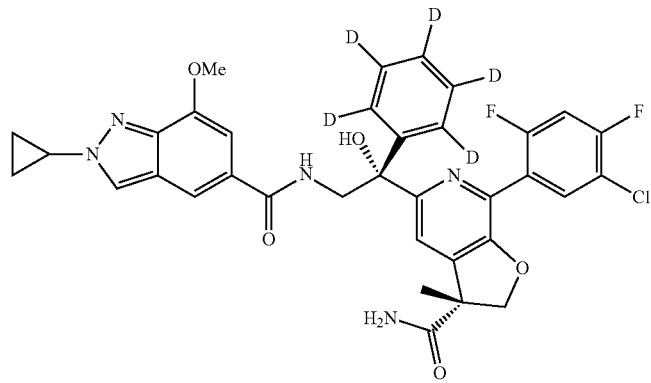 [SMILES: [2H]c1c([2H])c([2H])c([C@](O)(CNC(=O)c2cc(OC)c3nn(C4CC4)cc3c2)c2cc3c(c(-c4cc(Cl)c(F)cc4F)n2)OC[C@]3(C)C(N)=O)c([2H])c1[2H]] |
| 170 | 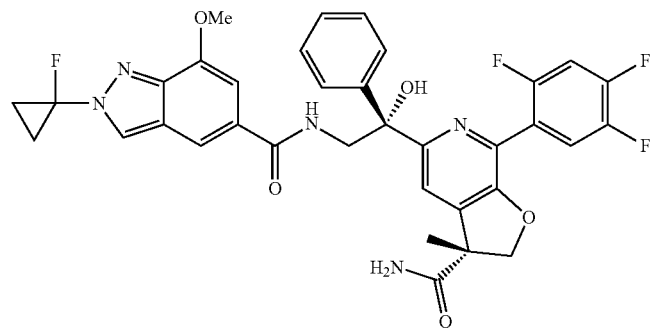 [SMILES: COc1cc(C(=O)NC[C@@](O)(c2ccccc2)c2cc3c(c(-c4cc(F)c(F)cc4F)n2)OC[C@]3(C)C(N)=O)cc2cn(C3(F)CC3)nc12] |
| 171 | 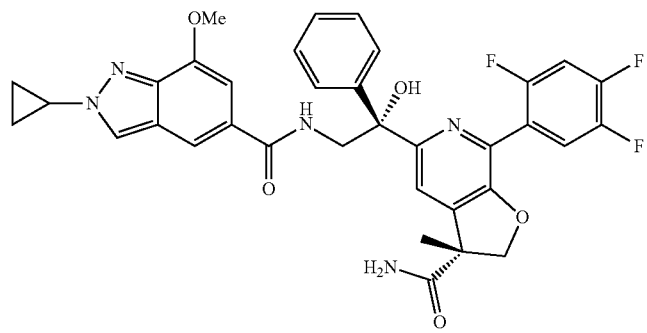 [SMILES: COc1cc(C(=O)NC[C@@](O)(c2ccccc2)c2cc3c(c(-c4cc(F)c(F)cc4F)n2)OC[C@]3(C)C(N)=O)cc2cn(C3CC3)nc12] |
| 172 | 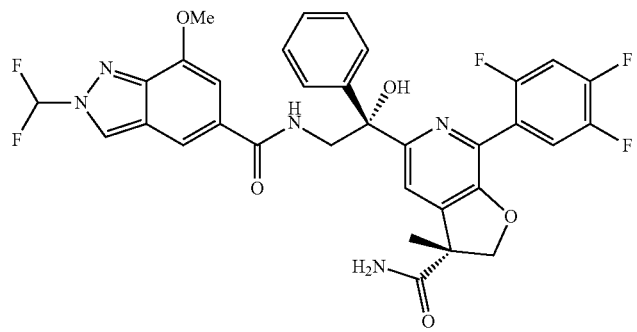 [SMILES: COc1cc(C(=O)NC[C@@](O)(c2ccccc2)c2cc3c(c(-c4cc(F)c(F)cc4F)n2)OC[C@]3(C)C(N)=O)cc2cn(C(F)F)nc12] |

-continued
| Compound | Structure |
|---|---|
| 173 | 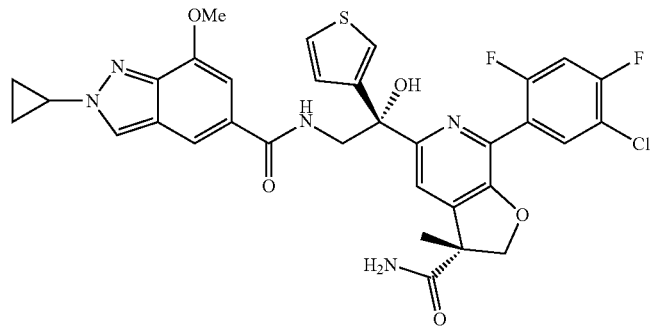 [SMILES: COc1cc(C(=O)NC[C@@](O)(c2ccsc2)c2cc3c(c(-c4cc(Cl)c(F)cc4F)n2)OC[C@]3(C)C(N)=O)cc2cn(C3CC3)nc12] |
| 174 | 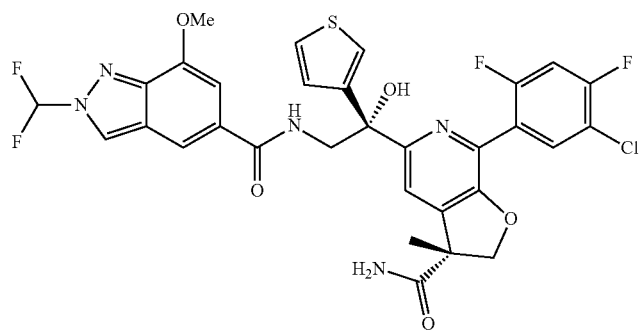 [SMILES: COc1cc(C(=O)NC[C@@](O)(c2ccsc2)c2cc3c(c(-c4cc(Cl)c(F)cc4F)n2)OC[C@]3(C)C(N)=O)cc2cn(C(F)F)nc12] |
| 175 | 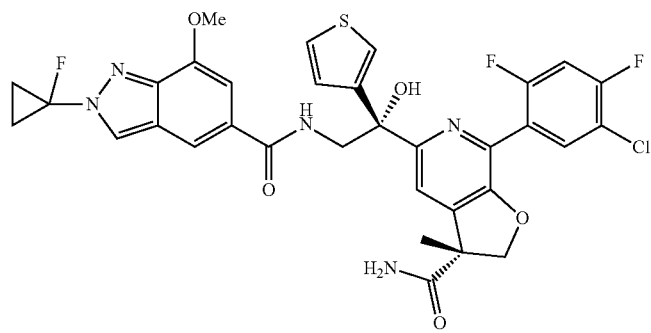 [SMILES: COc1cc(C(=O)NC[C@@](O)(c2ccsc2)c2cc3c(c(-c4cc(Cl)c(F)cc4F)n2)OC[C@]3(C)C(N)=O)cc2cn(C3(F)CC3)nc12] |
| 176 | 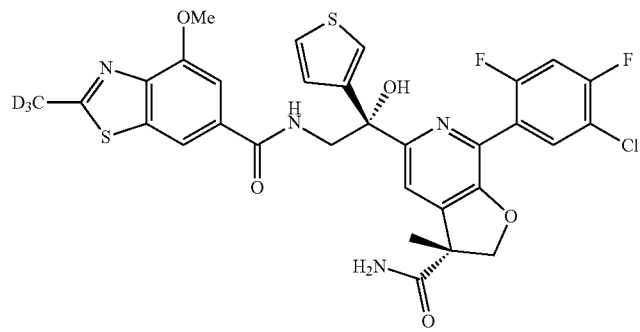 [SMILES: [2H]C([2H])([2H])c1nc2c(OC)cc(C(=O)NC[C@@](O)(c3ccsc3)c3cc4c(c(-c5cc(Cl)c(F)cc5F)n3)OC[C@]4(C)C(N)=O)cc2s1] |

| Compound | Structure |
|---|---|
| 177 | 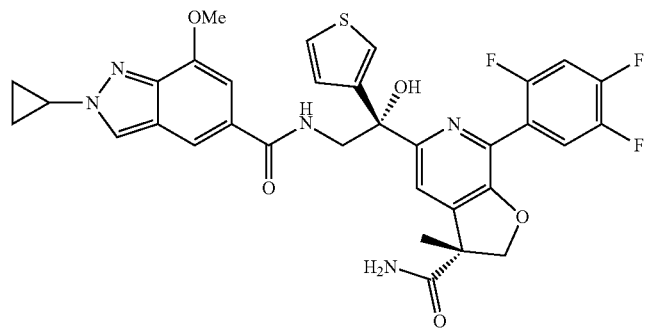 [SMILES: COc1cc(C(=O)NC[C@@](O)(c2ccsc2)c2cc3c(c(-c4cc(F)c(F)cc4F)n2)OC[C@]3(C)C(N)=O)cc2cn(C3CC3)nc12] |
| 178 | 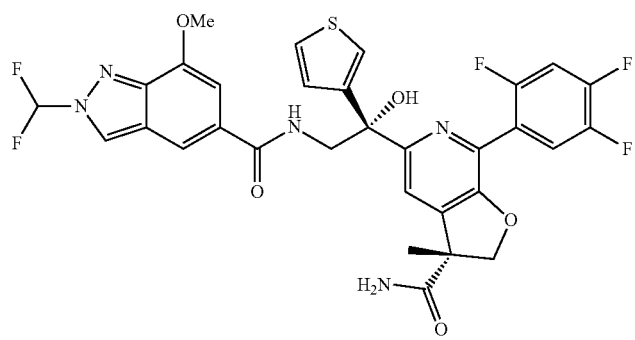 |
| 179 | 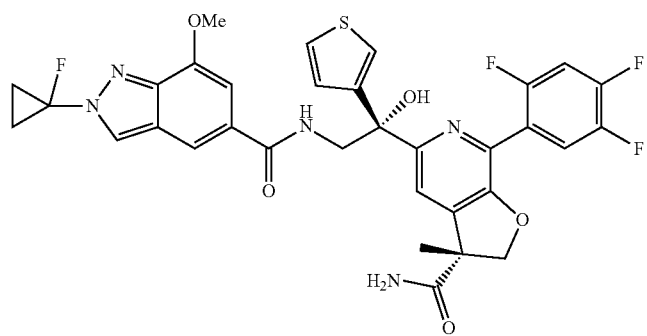 |
| 180 | 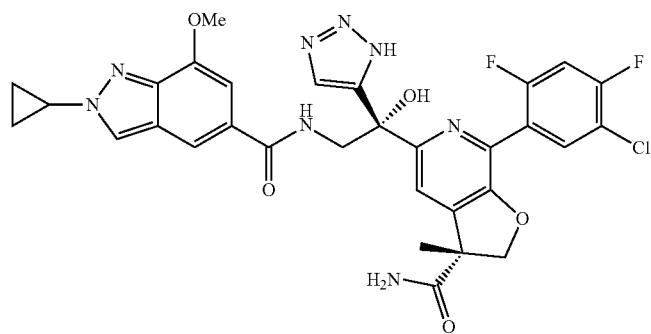 |

| Compound | Structure |
|---|---|
| 181 | 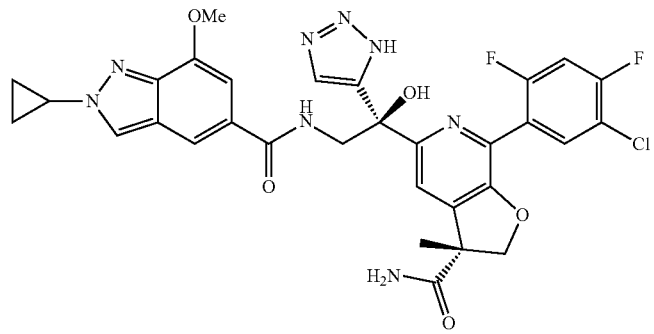 |
| 182 | 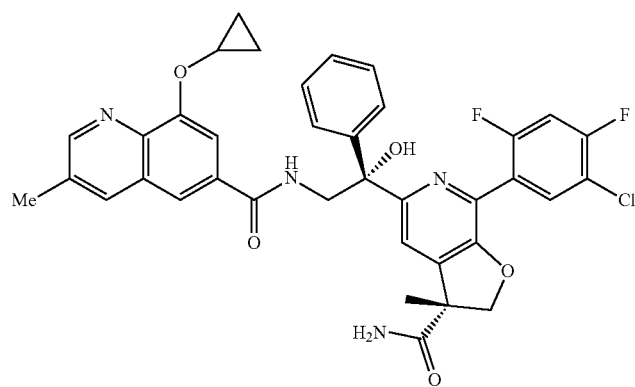 [SMILES: Cc1cnc2c(OC3CC3)cc(C(=O)NC[C@@](O)(c3ccccc3)c3cc4c(c(-c5cc(Cl)c(F)cc5F)n3)OC[C@]4(C)C(N)=O)cc2c1] |
| 183 | 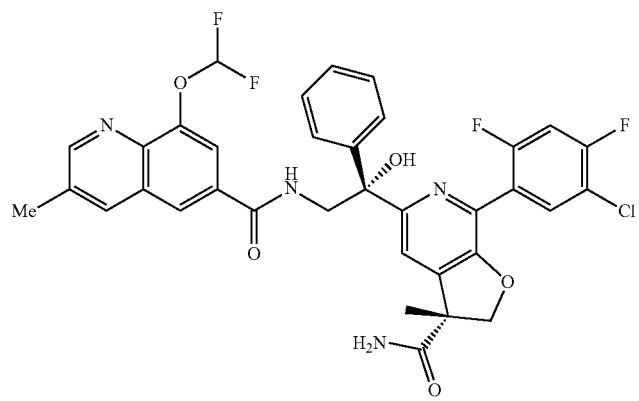 [SMILES: Cc1cnc2c(OC(F)F)cc(C(=O)NC[C@@](O)(c3ccccc3)c3cc4c(c(-c5cc(Cl)c(F)cc5F)n3)OC[C@]4(C)C(N)=O)cc2c1] |
| 184 | 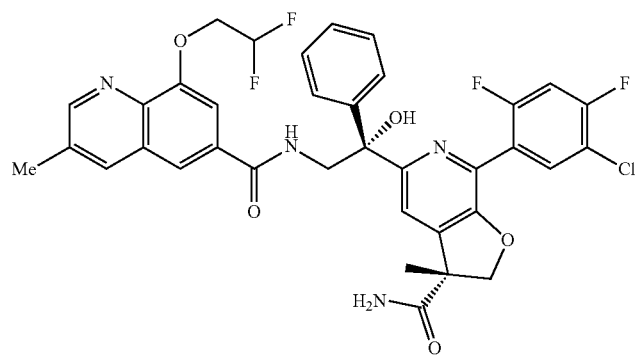 [SMILES: Cc1cnc2c(OCC(F)F)cc(C(=O)NC[C@@](O)(c3ccccc3)c3cc4c(c(-c5cc(Cl)c(F)cc5F)n3)OC[C@]4(C)C(N)=O)cc2c1] |

| Compound | Structure |
|---|---|
| 185 | 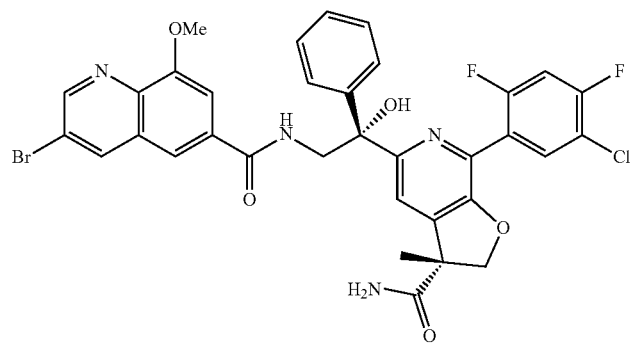 |
| 186 | 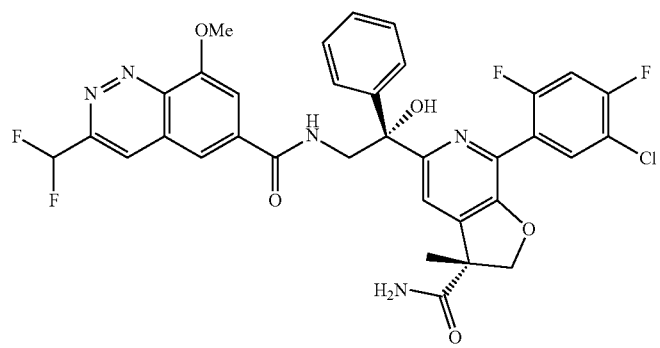 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(C(F)F)nnc12] |
| 187 | 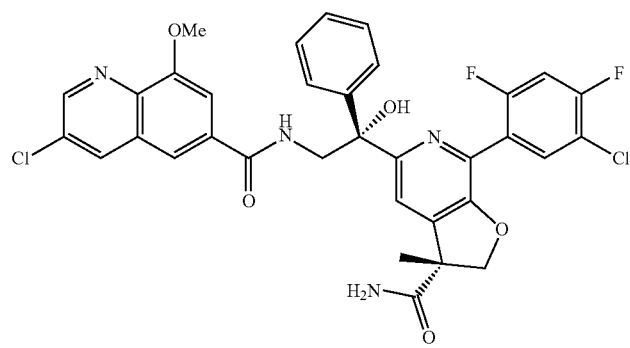 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)cnc12] |
| 188 | 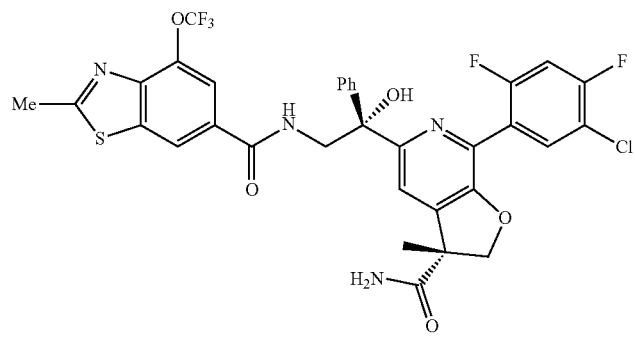 |

-continued
| Compound | Structure |
|---|---|
| 189 | 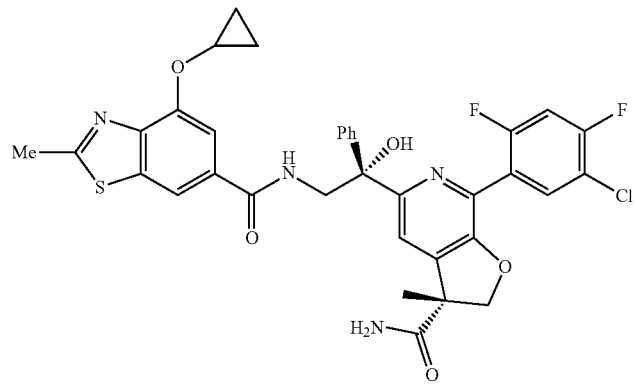 |
| 190 | 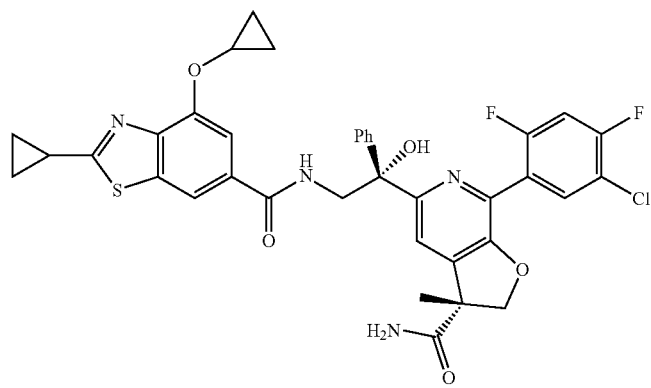 |
| 191 | 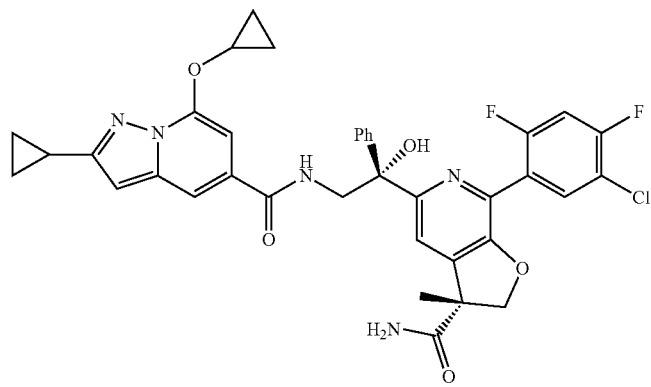 |
| 192 | 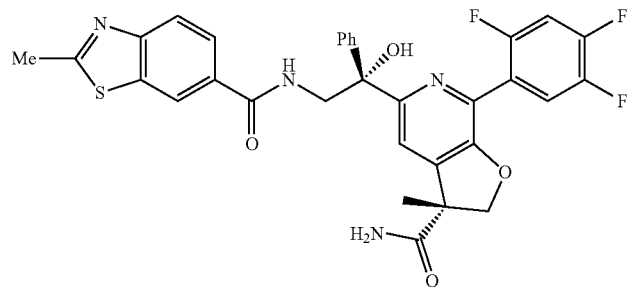 |

| Compound | Structure |
|---|---|
| 193 | 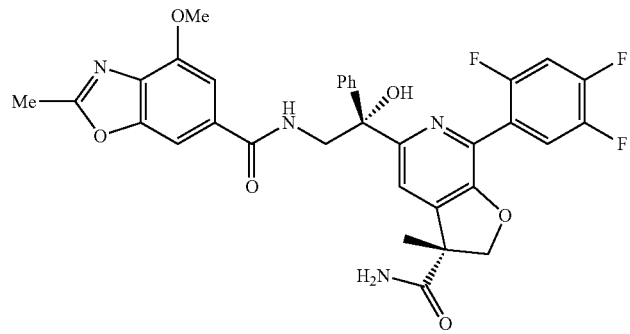 |
| 194 | 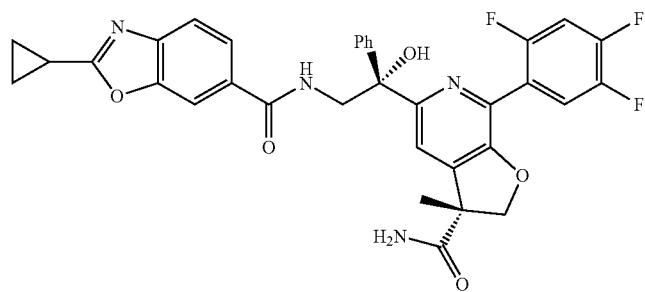 |
| 195 | 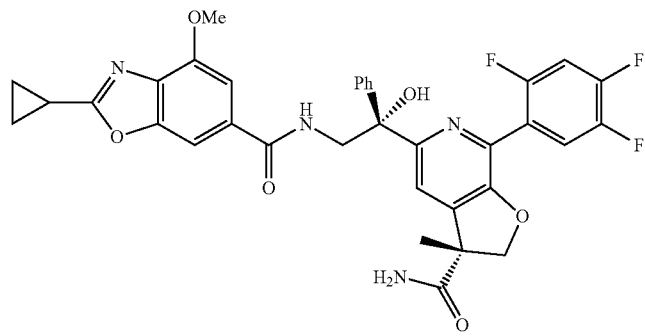 |
| 196 | 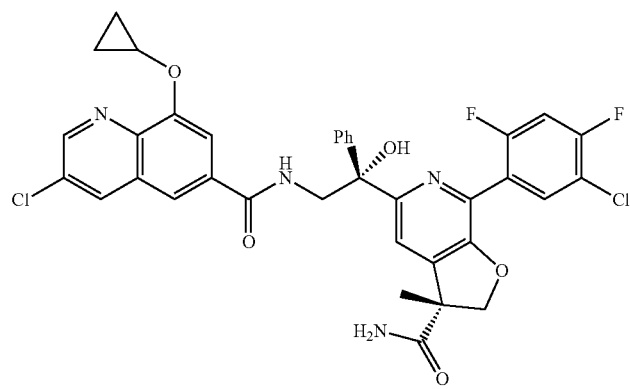 [SMILES: C[C@]1(C(N)=O)COc2c1cc([C@@](O)(CNC(=O)c1cc(OC3CC3)c3ncc(Cl)cc3c1)c1ccccc1)nc2-c1cc(Cl)c(F)cc1F] |

-continued
| Compound | Structure |
|---|---|
| 197 | 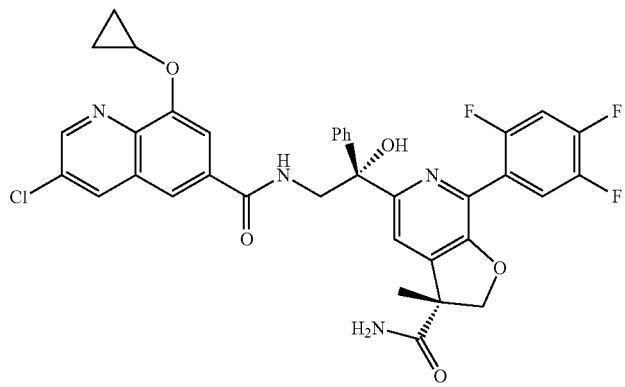 [SMILES: C[C@]1(C(N)=O)COc2c1cc([C@@](O)(CNC(=O)c1cc(OC3CC3)c3ncc(Cl)cc3c1)c1ccccc1)nc2-c1cc(F)c(F)cc1F] |
| 198 | 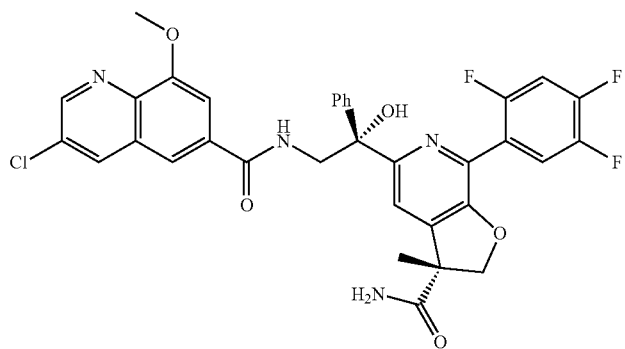 [SMILES: COc1cc(C(=O)NC[C@@](O)(c2ccccc2)c2cc3c(c(-c4cc(F)c(F)cc4F)n2)OC[C@]3(C)C(N)=O)cc2cc(Cl)cnc12] |
| 199 | 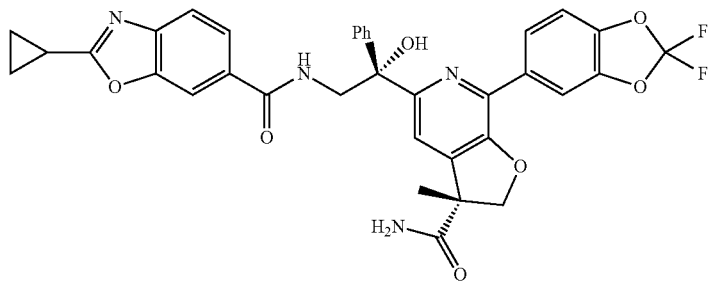 |
| 200 | 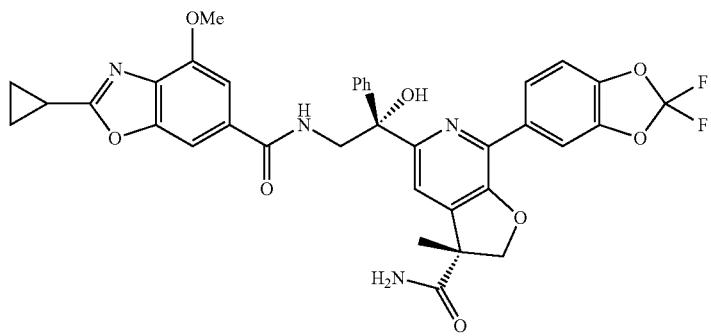 |

| Compound | Structure |
|---|---|
| 201 | 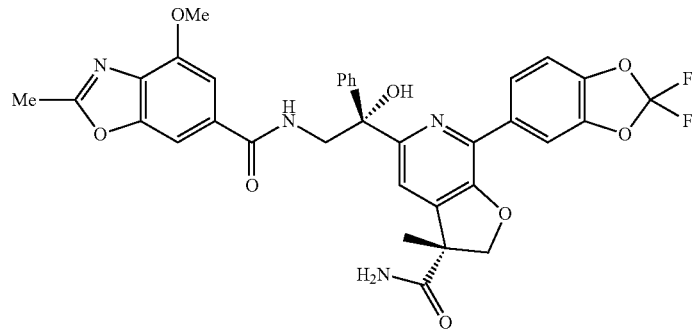 |
| 202 | 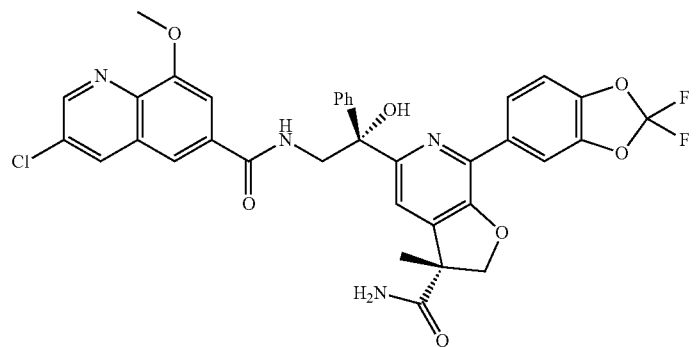 [SMILES: COc1cc(C(=O)NC[C@@](O)(c2ccccc2)c2cc3c(c(-c4ccc5c(c4)OC(F)(F)O5)n2)OC[C@]3(C)C(N)=O)cc2cc(Cl)cnc12] |
| 203 | 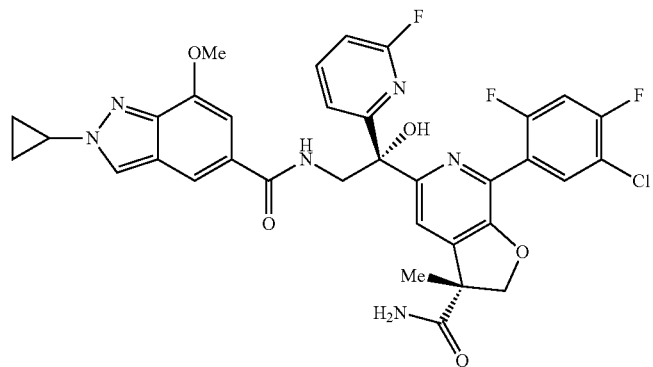 |
| 204 | 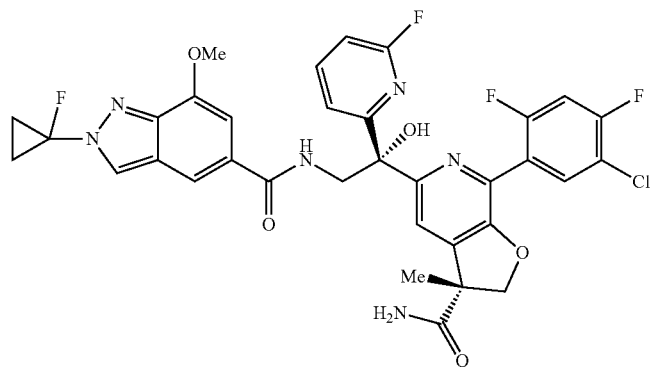 |

| Compound | Structure |
|---|---|
| 205 | 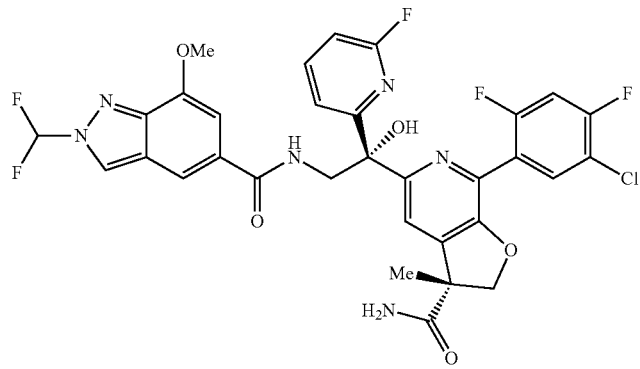 |
| 206 | 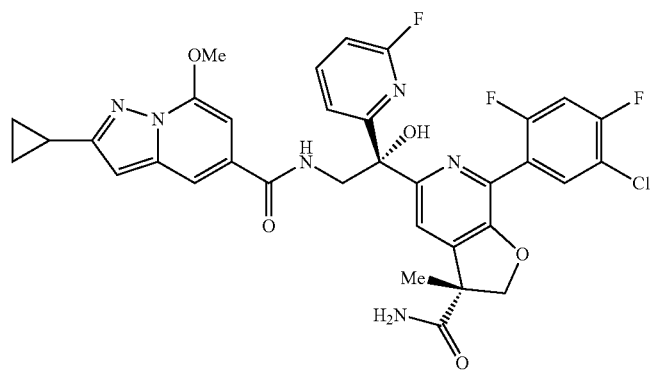 |
| 210 | 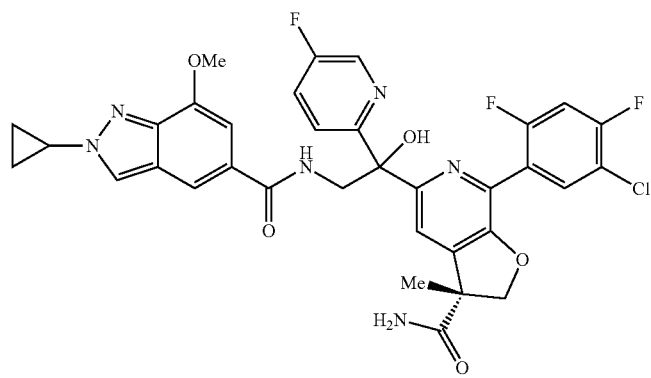 |
| 213 | 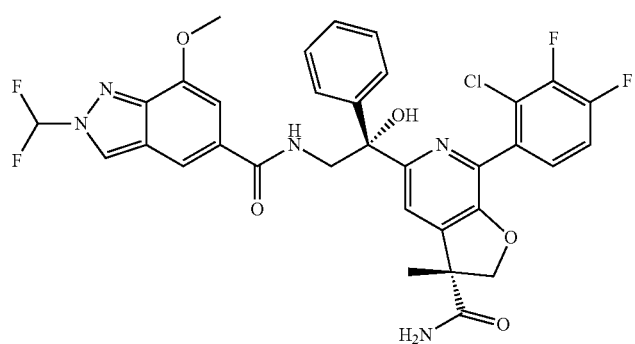 [SMILES: COc1cc(C(=O)NC[C@@](O)(c2ccccc2)c2cc3c(c(-c4ccc(F)c(F)c4Cl)n2)OC[C@]3(C)C(N)=O)cc2cn(C(F)F)nc12] |

-continued
| Compound | Structure |
|---|---|
| 216 | 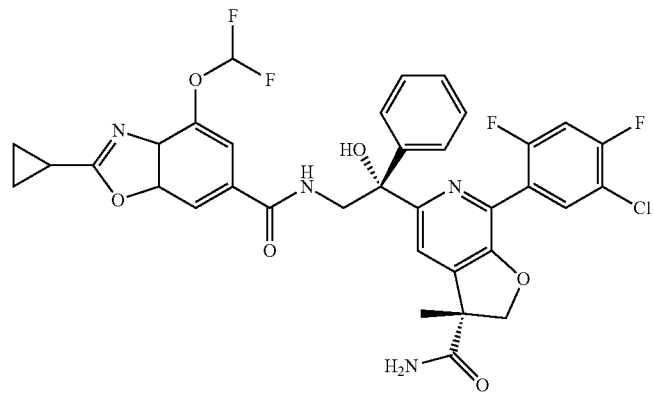 [SMILES: C[C@]1(C(N)=O)COc2c1cc([C@@](O)(CNC(=O)C1=CC3OC(C4CC4)=NC3C(OC(F)F)=C1)c1ccccc1)nc2-c1cc(Cl)c(F)cc1F] |
| 217 | 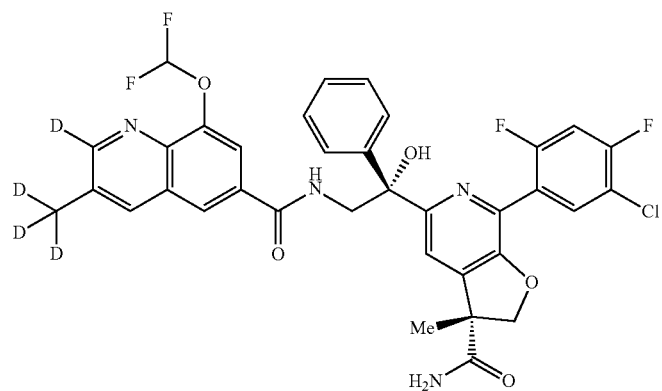 [SMILES: [2H]c1nc2c(OC(F)F)cc(C(=O)NC[C@@](O)(c3ccccc3)c3cc4c(c(-c5cc(Cl)c(F)cc5F)n3)OC[C@]4(C)C(N)=O)cc2cc1C([2H])([2H])[2H]] |
| 219 | 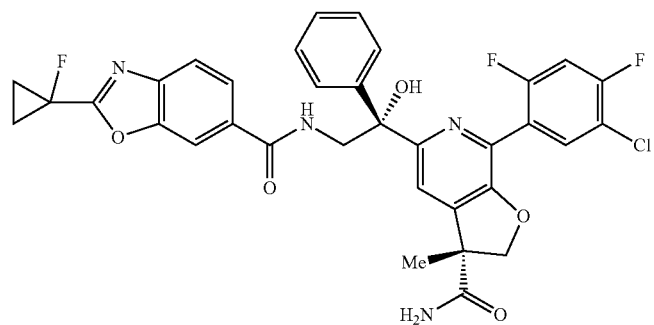 [SMILES: C[C@]1(C(N)=O)COc2c1cc([C@@](O)(CNC(=O)c1ccc3nc(C4(F)CC4)oc3c1)c1ccccc1)nc2-c1cc(Cl)c(F)cc1F] |
| 220 | 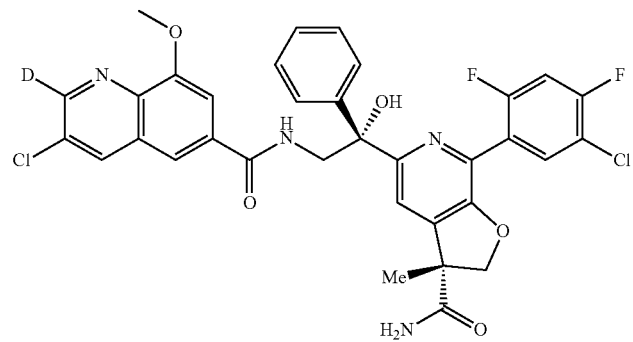 [SMILES: [2H]c1nc2c(OC)cc(C(=O)NC[C@@](O)(c3ccccc3)c3cc4c(c(-c5cc(Cl)c(F)cc5F)n3)OC[C@]4(C)C(N)=O)cc2cc1Cl] |

| Compound | Structure |
|---|---|
| 221 | 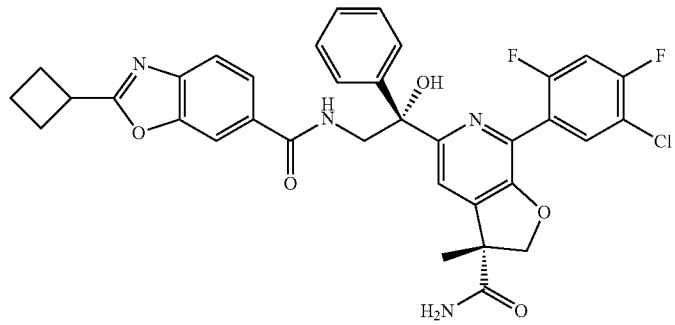 [SMILES: C[C@]1(C(N)=O)COc2c1cc([C@@](O)(CNC(=O)c1ccc3nc(C4CCC4)oc3c1)c1ccccc1)nc2-c1cc(Cl)c(F)cc1F] |
| 222 | 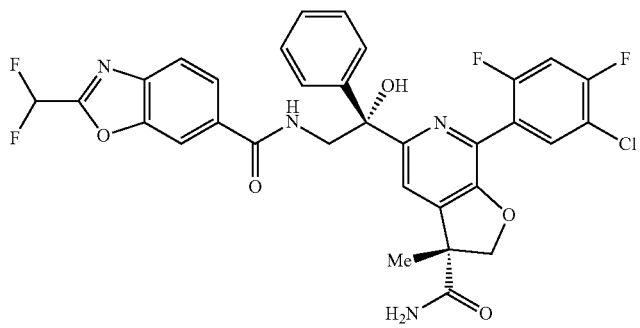 [SMILES: C[C@]1(C(N)=O)COc2c1cc([C@@](O)(CNC(=O)c1ccc3nc(C(F)F)oc3c1)c1ccccc1)nc2-c1cc(Cl)c(F)cc1F] |
| 223 | 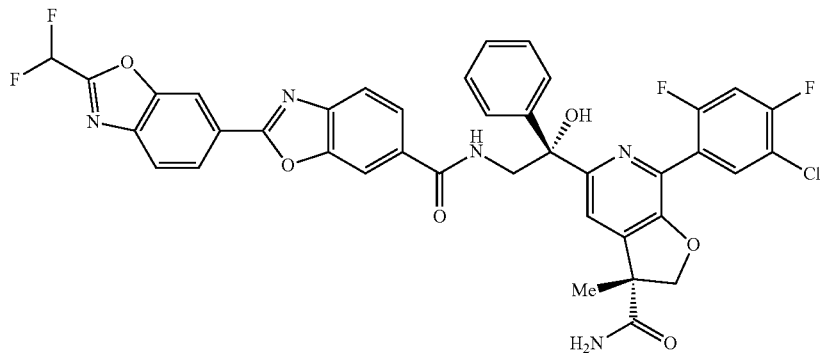 [SMILES: C[C@]1(C(N)=O)COc2c1cc([C@@](O)(CNC(=O)c1ccc3nc(-c4ccc5nc(C(F)F)oc5c4)oc3c1)c1ccccc1)nc2-c1cc(Cl)c(F)cc1F] |
| 224 | 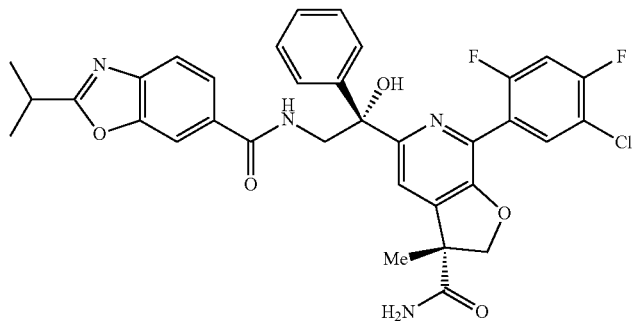 [SMILES: CC(C)c1nc2ccc(C(=O)NC[C@@](O)(c3ccccc3)c3cc4c(c(-c5cc(Cl)c(F)cc5F)n3)OC[C@]4(C)C(N)=O)cc2o1] |

| Compound | Structure |
|---|---|
| 227 | 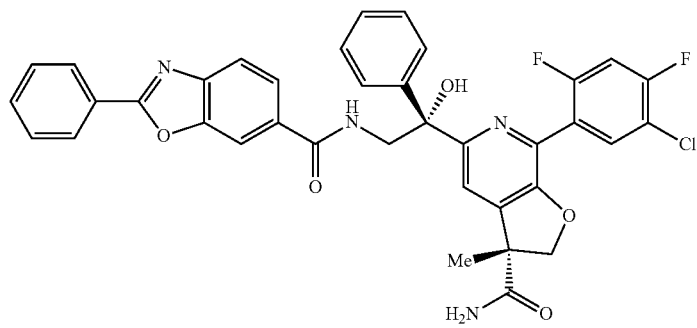 [SMILES: C[C@]1(C(N)=O)COc2c1cc([C@@](O)(CNC(=O)c1ccc3nc(-c4ccccc4)oc3c1)c1ccccc1)nc2-c1cc(Cl)c(F)cc1F] |
| 228 | 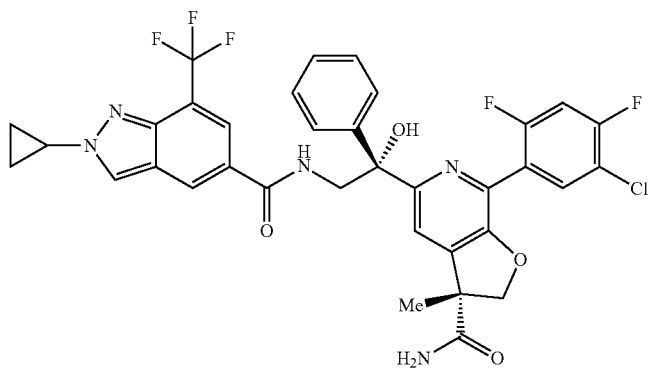 [SMILES: C[C@]1(C(N)=O)COc2c1cc([C@@](O)(CNC(=O)c1cc(C(F)(F)F)c3nn(C4CC4)cc3c1)c1ccccc1)nc2-c1cc(Cl)c(F)cc1F] |
| 229 | 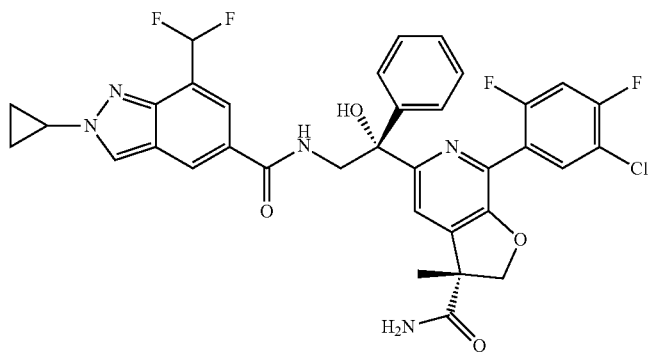 [SMILES: C[C@]1(C(N)=O)COc2c1cc([C@@](O)(CNC(=O)c1cc(C(F)F)c3nn(C4CC4)cc3c1)c1ccccc1)nc2-c1cc(Cl)c(F)cc1F] |
| 230 | 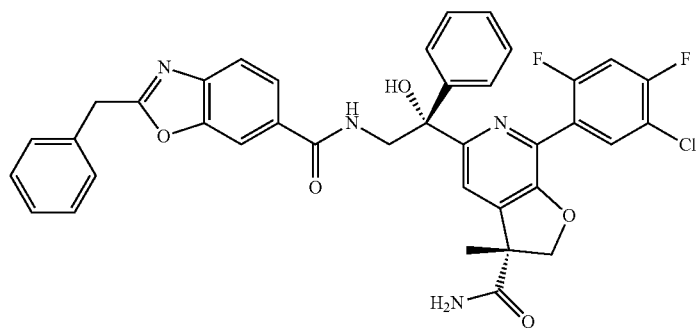 [SMILES: C[C@]1(C(N)=O)COc2c1cc([C@@](O)(CNC(=O)c1ccc3nc(Cc4ccccc4)oc3c1)c1ccccc1)nc2-c1cc(Cl)c(F)cc1F] |

| Compound | Structure |
|---|---|
| 231 | 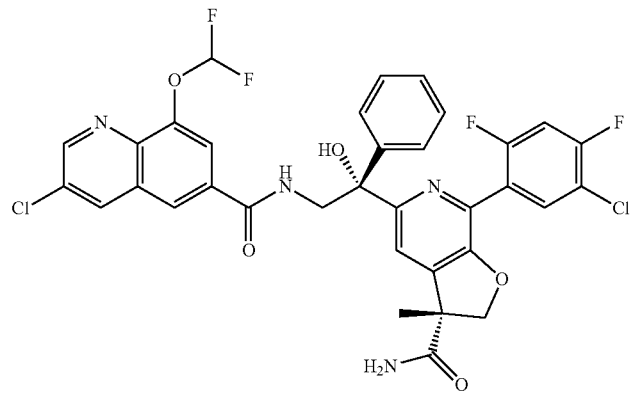 [SMILES: C[C@]1(C(N)=O)COc2c1cc([C@@](O)(CNC(=O)c1cc(OC(F)F)c3ncc(Cl)cc3c1)c1ccccc1)nc2-c1cc(Cl)c(F)cc1F] |
| 232 | 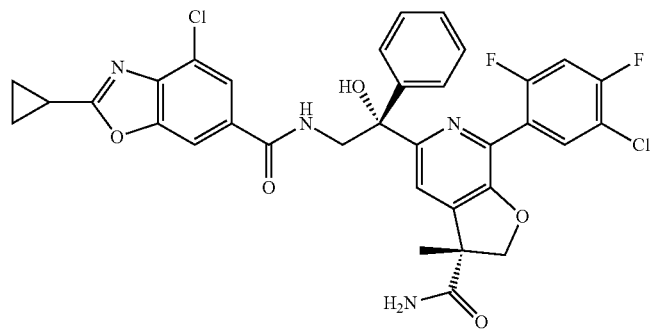 [SMILES: C[C@]1(C(N)=O)COc2c1cc([C@@](O)(CNC(=O)c1cc(Cl)c3nc(C4CC4)oc3c1)c1ccccc1)nc2-c1cc(Cl)c(F)cc1F] |
| 233 | 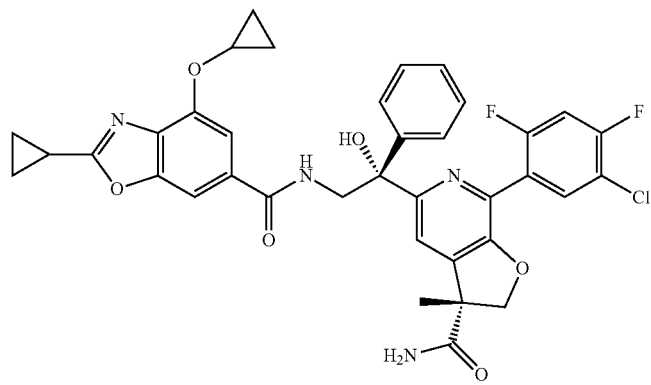 [SMILES: C[C@]1(C(N)=O)COc2c1cc([C@@](O)(CNC(=O)c1cc(OC3CC3)c3nc(C4CC4)oc3c1)c1ccccc1)nc2-c1cc(Cl)c(F)cc1F] |
| 234 | 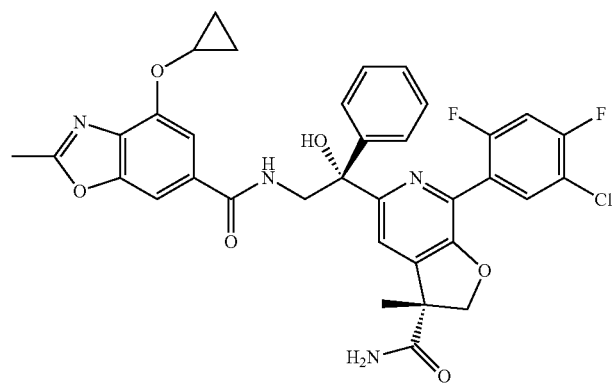 [SMILES: Cc1nc2c(OC3CC3)cc(C(=O)NC[C@@](O)(c3ccccc3)c3cc4c(c(-c5cc(Cl)c(F)cc5F)n3)OC[C@]4(C)C(N)=O)cc2o1] |

| Compound | Structure |
|---|---|
| 241 | 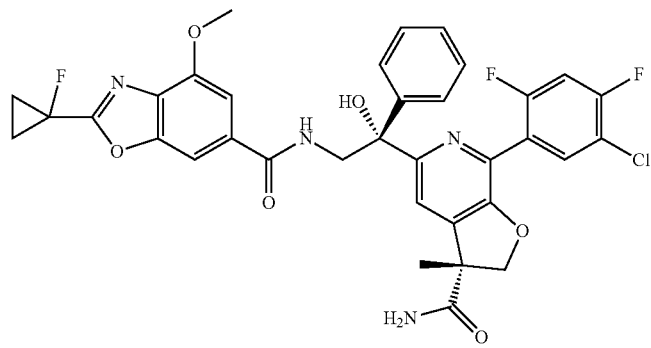 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C3(F)CC3)nc12] |
| 242 | 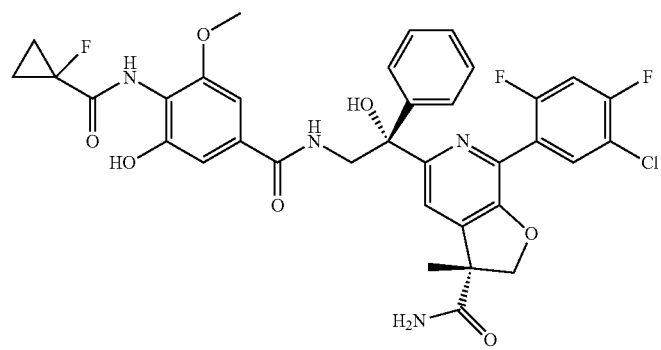 [SMILES: COc1cc(C(=O)NC[C@@](O)(c2ccccc2)c2cc3c(c(-c4cc(Cl)c(F)cc4F)n2)OC[C@]3(C)C(N)=O)cc(O)c1NC(=O)C1(F)CC1] |
| 243 | 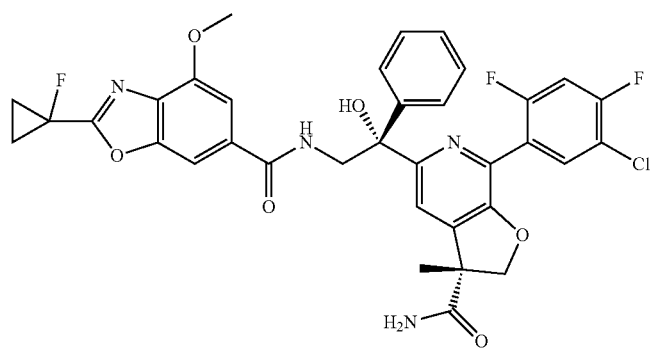 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C3(F)CC3)nc12] |
| 244 | 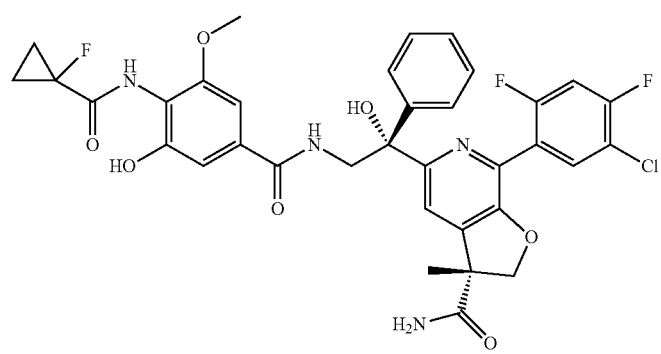 [SMILES: COc1cc(C(=O)NC[C@@](O)(c2ccccc2)c2cc3c(c(-c4cc(Cl)c(F)cc4F)n2)OC[C@]3(C)C(N)=O)cc(O)c1NC(=O)C1(F)CC1] |

-continued
| Compound | Structure |
|---|---|
| 251 | 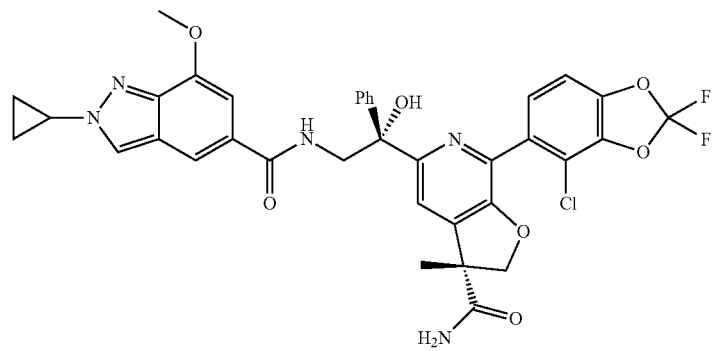 [SMILES: COc1cc(C(=O)NC[C@@](O)(c2ccccc2)c2cc3c(c(-c4ccc5c(c4Cl)OC(F)(F)O5)n2)OC[C@]3(C)C(N)=O)cc2cn(C3CC3)nc12] |
| 252 | 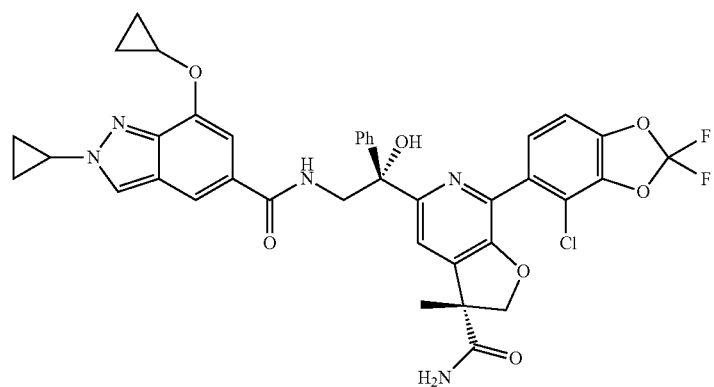 [SMILES: C[C@]1(C(N)=O)COc2c1cc([C@@](O)(CNC(=O)c1cc(OC3CC3)c3nn(C4CC4)cc3c1)c1ccccc1)nc2-c1ccc2c(c1Cl)OC(F)(F)O2] |
| 253 | 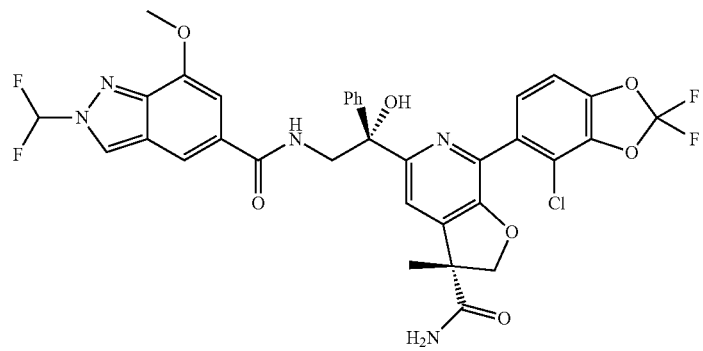 [SMILES: COc1cc(C(=O)NC[C@@](O)(c2ccccc2)c2cc3c(c(-c4ccc5c(c4Cl)OC(F)(F)O5)n2)OC[C@]3(C)C(N)=O)cc2cn(C(F)F)nc12] |
| 254 | 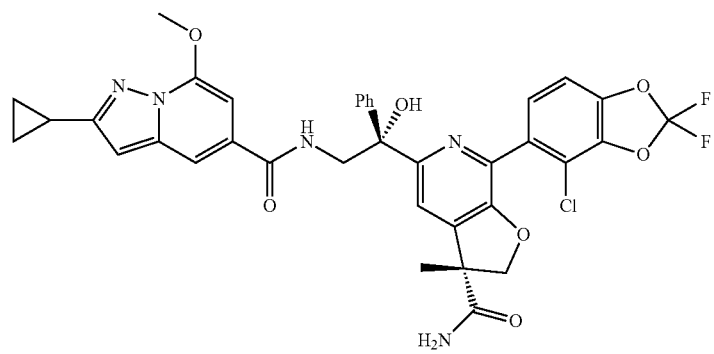 [SMILES: COc1cc(C(=O)NC[C@@](O)(c2ccccc2)c2cc3c(c(-c4ccc5c(c4Cl)OC(F)(F)O5)n2)OC[C@]3(C)C(N)=O)cc2cc(C3CC3)nn12] |

-continued
| Compound | Structure |
|---|---|
| 255 | 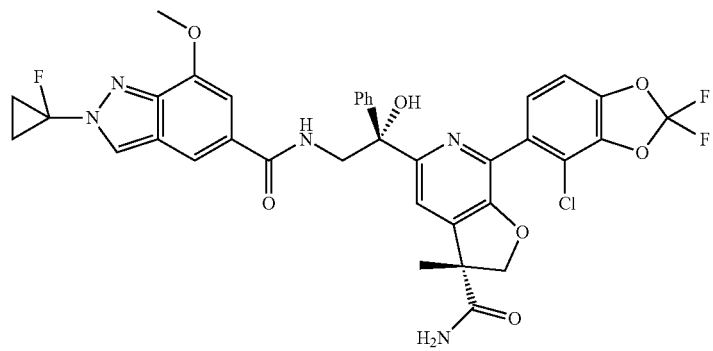 |
| 256 | 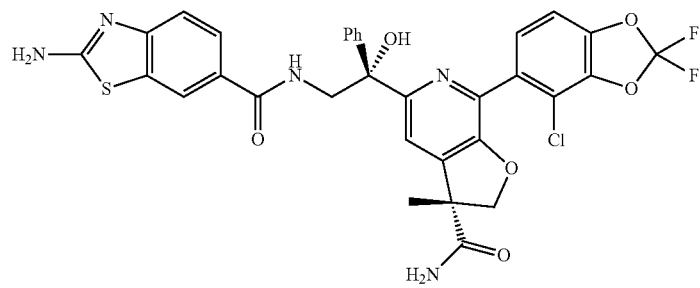 [SMILES: C[C@]1(C(N)=O)COc2c1cc([C@@](O)(CNC(=O)c1ccc3nc(N)sc3c1)c1ccccc1)nc2-c1ccc2c(c1Cl)OC(F)(F)O2] |
| 257 | 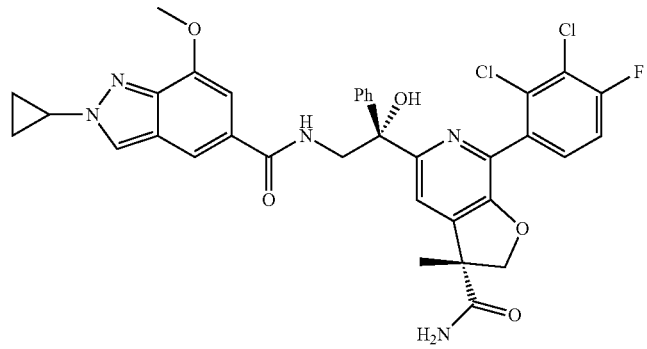 |
| 258 | 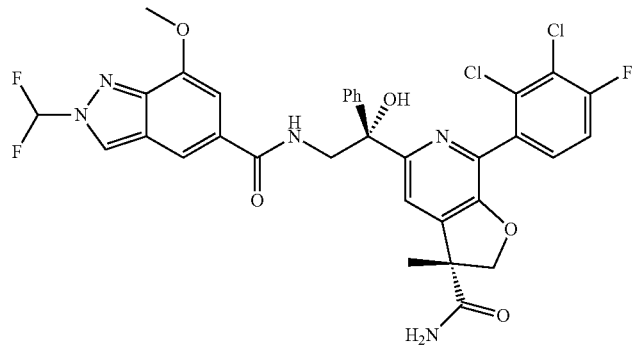 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cn(C(F)F)nc12] |

| Compound | Structure |
|---|---|
| 259 | 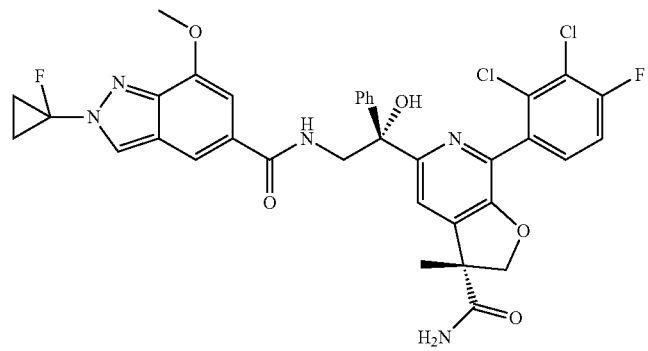 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cn(C3(F)CC3)nc12] |
| 260 | 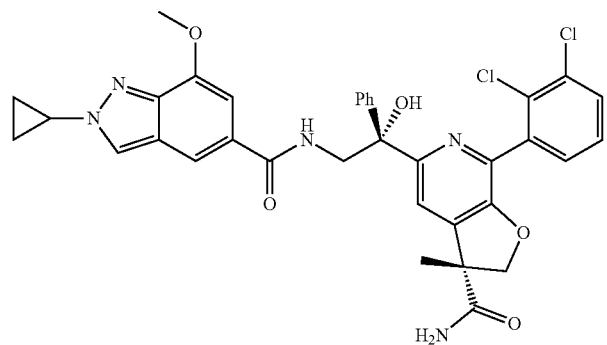 |
| 261 | 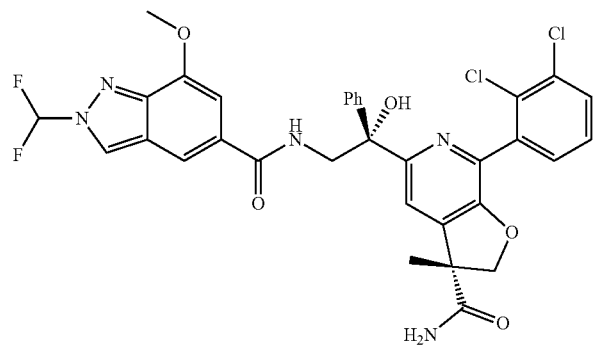 |
| 262 | 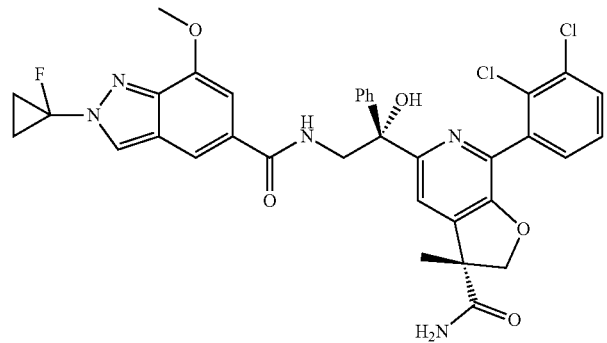 |

| Compound | Structure |
|---|---|
| 263 | 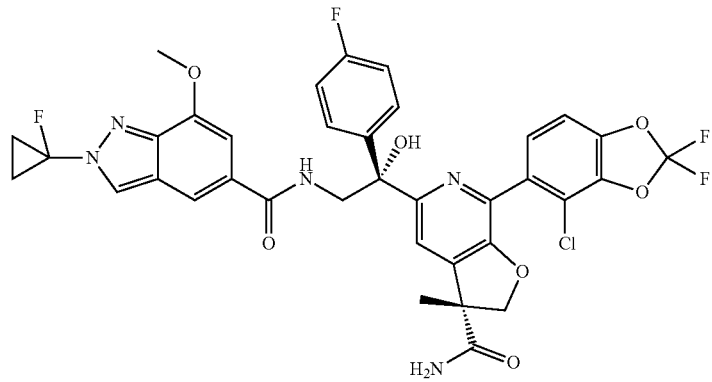 |
| 264 | 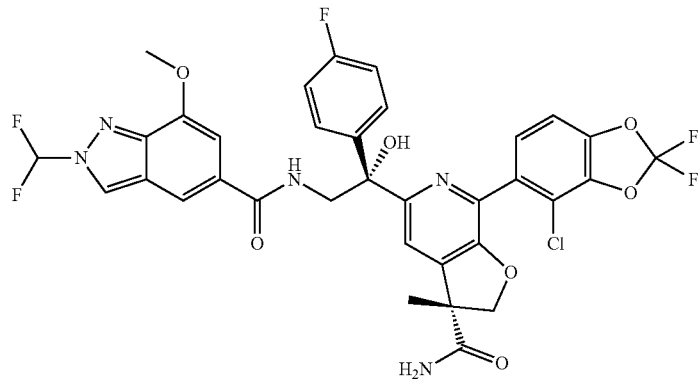 |
| 265 | 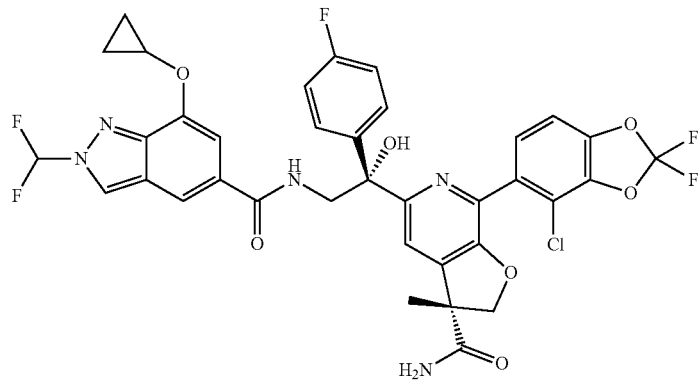 |
| 266 | 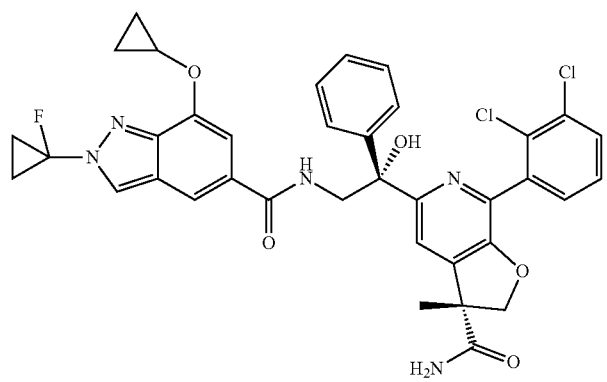 |

| Compound | Structure |
|---|---|
| 267 | 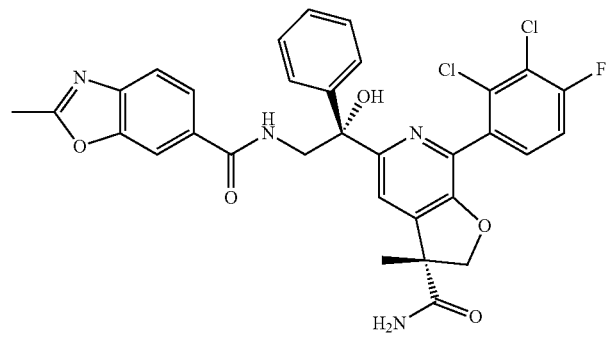 |
| 268 | 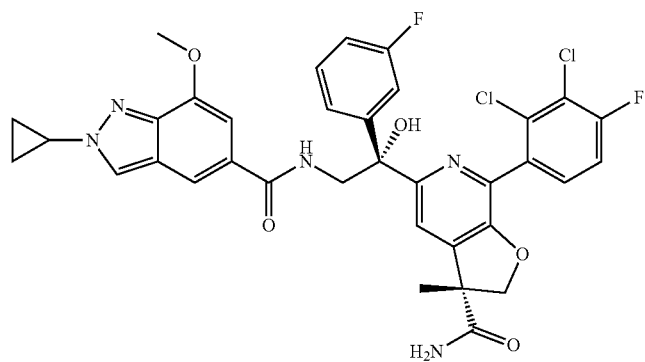 |
| 269 | 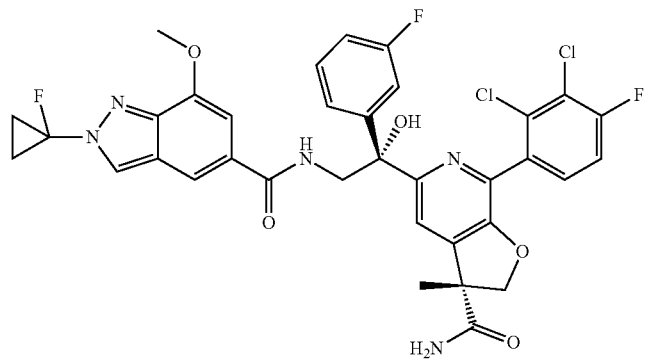 |
| 270 | 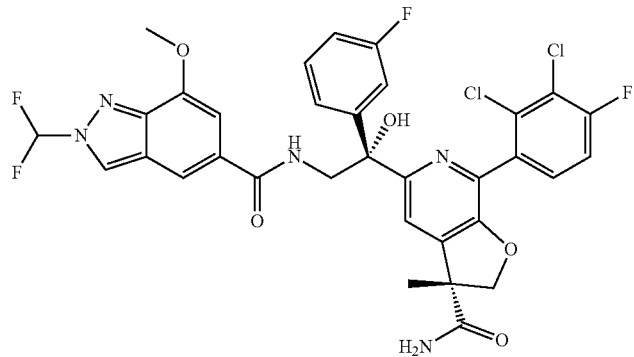 |

| Compound | Structure |
|---|---|
| 271 | 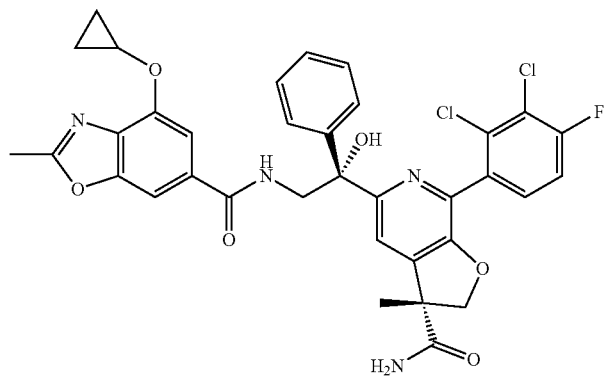 |
| 272 | 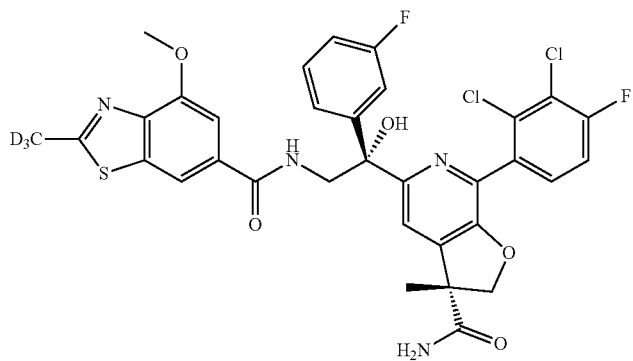 |
| 273 | 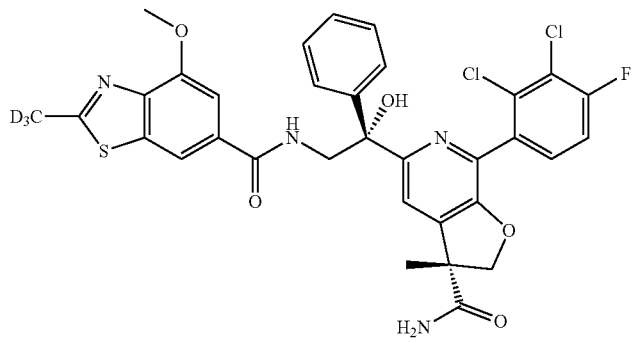 |
| 274 | 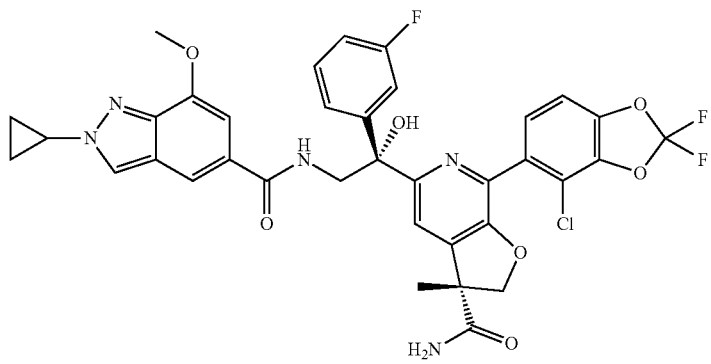 |

| Compound | Structure |
|---|---|
| 275 | 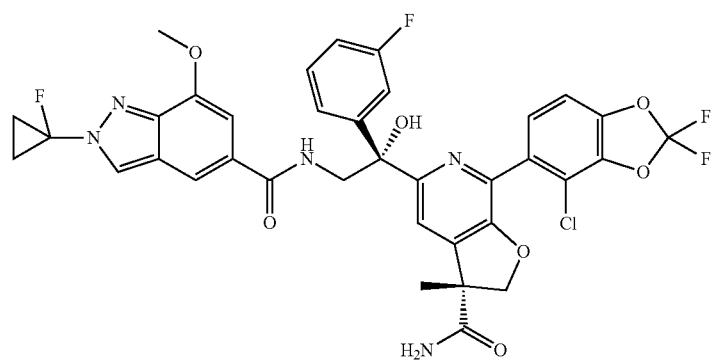 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2cn(C3(F)CC3)nc12] |
| 276 | 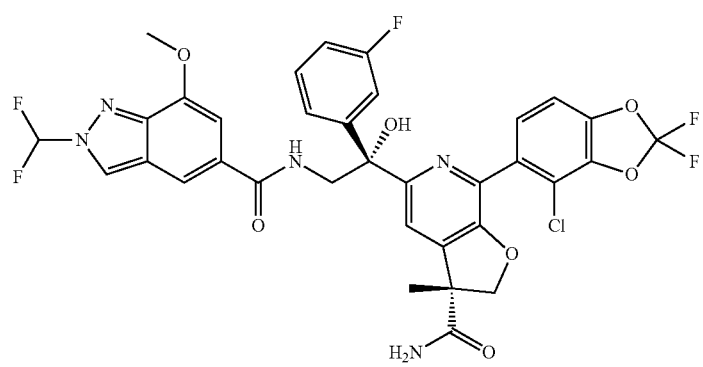 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2cn(C(F)F)nc12] |
| 277 | 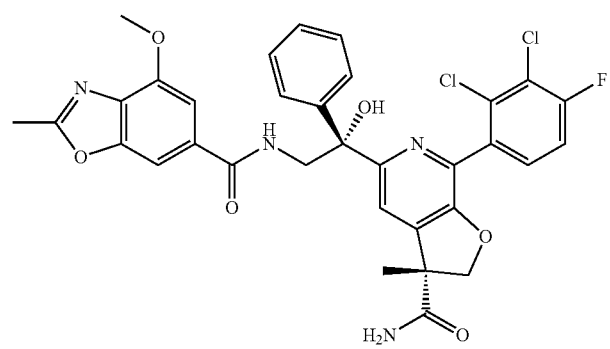 [SMILES: COc1cc(C(=O)NC[C@@](O)(c2ccccc2)c2cc3c(c(-c4ccc(F)c(Cl)c4Cl)n2)OC[C@]3(C)C(N)=O)cc2oc(C)nc12] |
| 278 | 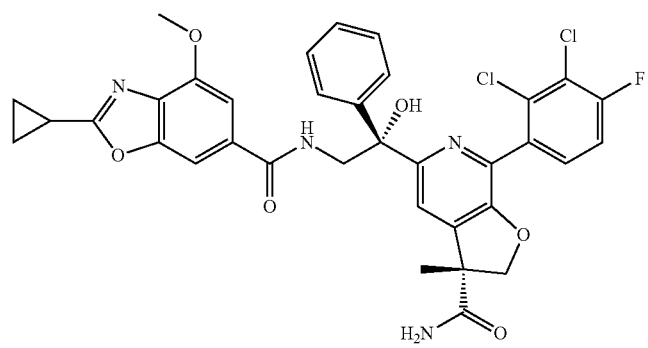 [SMILES: COc1cc(C(=O)NC[C@@](O)(c2ccccc2)c2cc3c(c(-c4ccc(F)c(Cl)c4Cl)n2)OC[C@]3(C)C(N)=O)cc2oc(C3CC3)nc12] |

| Compound | Structure |
|---|---|
| 279 | 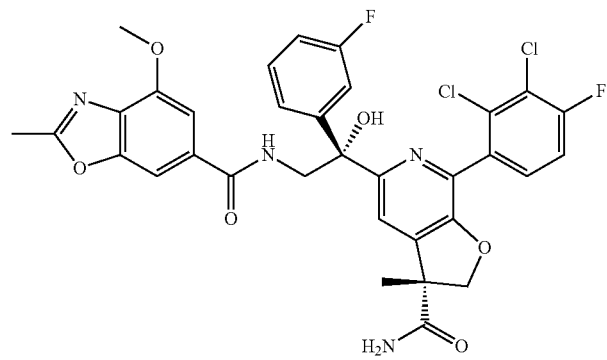 [SMILES: COc1cc(C(=O)NC[C@@](O)(c2cccc(F)c2)c2cc3c(c(-c4ccc(F)c(Cl)c4Cl)n2)OC[C@]3(C)C(N)=O)cc2oc(C)nc12] |
| 280 | 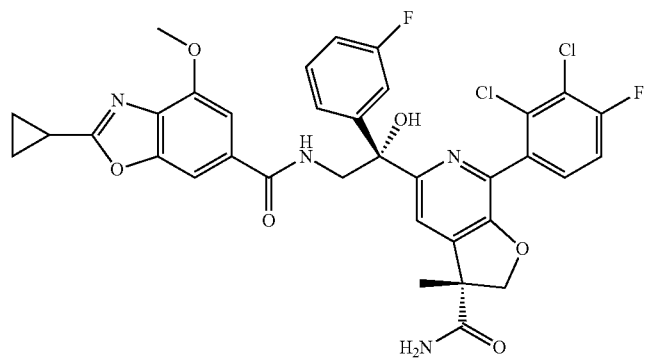 [SMILES: COc1cc(C(=O)NC[C@@](O)(c2cccc(F)c2)c2cc3c(c(-c4ccc(F)c(Cl)c4Cl)n2)OC[C@]3(C)C(N)=O)cc2oc(C3CC3)nc12] |
| 281 | 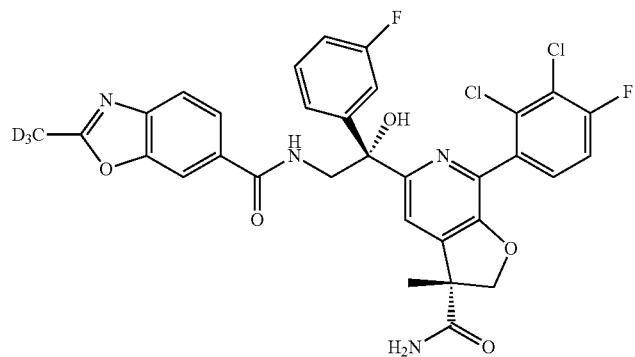 [SMILES: Cc1nc2ccc(C(=O)NC[C@@](O)(c3cccc(F)c3)c3cc4c(c(-c5ccc(F)c(Cl)c5Cl)n3)OC[C@]4(C)C(N)=O)cc2o1] |
| 282 | 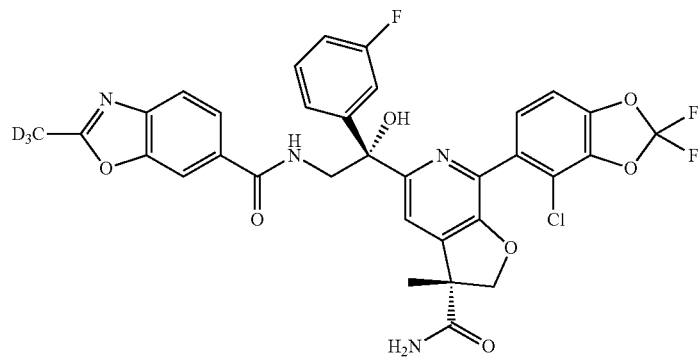 |

| Compound | Structure |
|---|---|
| 283 | 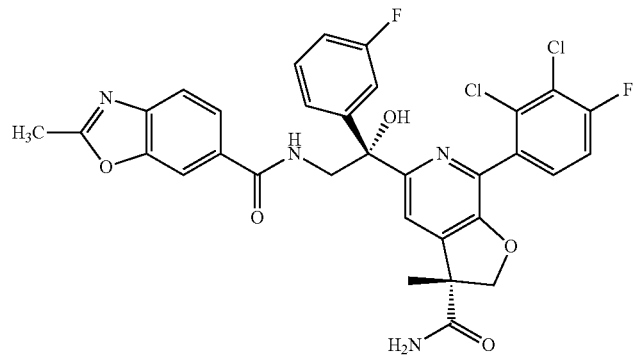 |
| 284 | 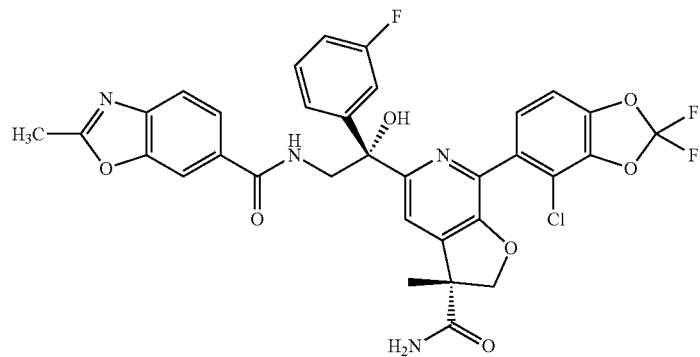 |
| 285 | 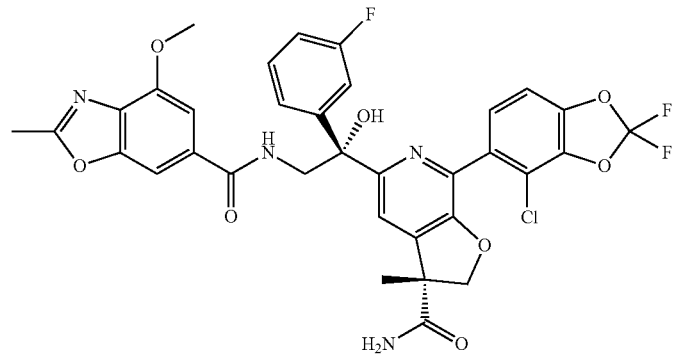 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2oc(C)nc12] |
| 286 | 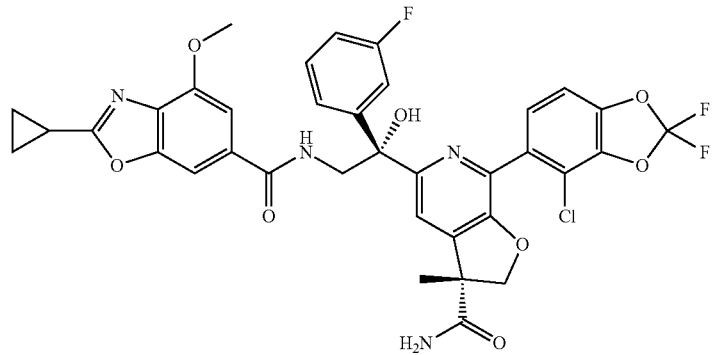 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2oc(C3CC3)nc12] |

| Compound | Structure |
|---|---|
| 287 | 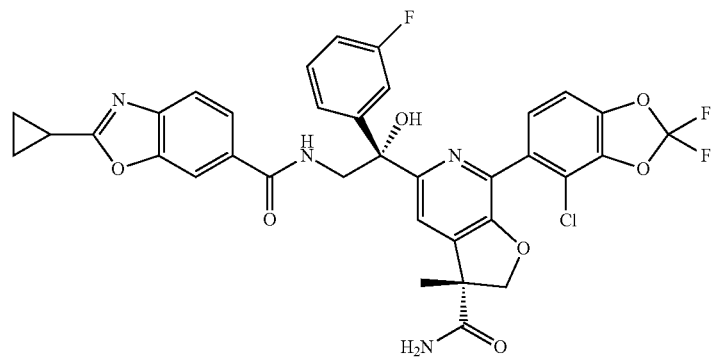 [SMILES: C[C@]1(C(N)=O)COc2c1cc([C@@](O)(CNC(=O)c1ccc3nc(C4CC4)oc3c1)c1cccc(F)c1)nc2-c1ccc2c(c1Cl)OC(F)(F)O2] |
| 288 | 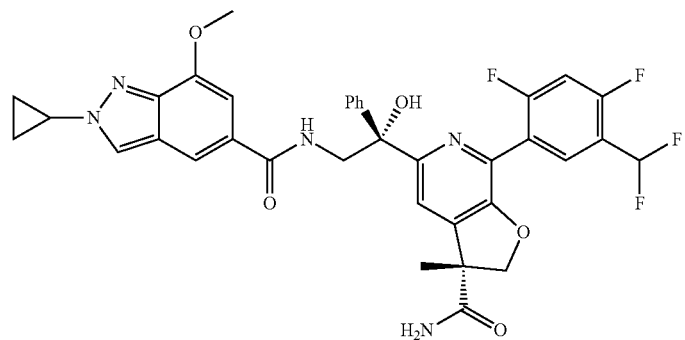 |
| 289 | 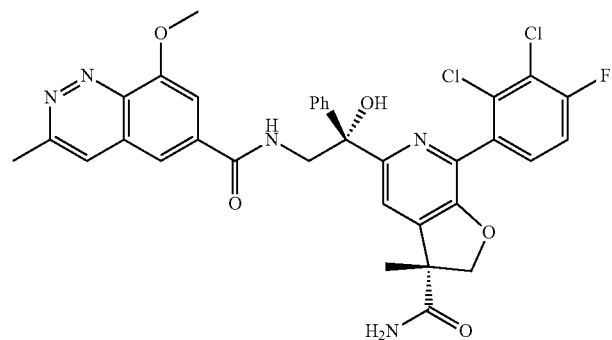 |
| 290 | 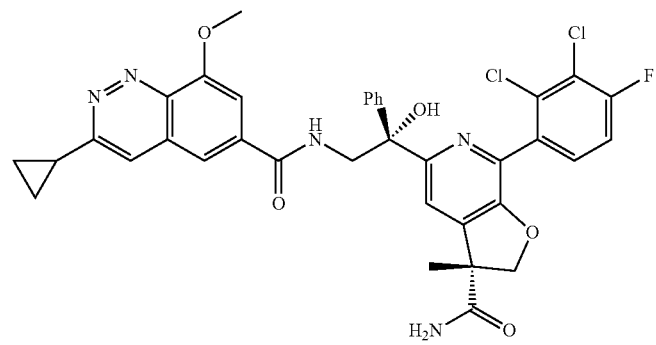 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cc(C3CC3)nnc12] |

| Compound | Structure |
|---|---|
| 291 | 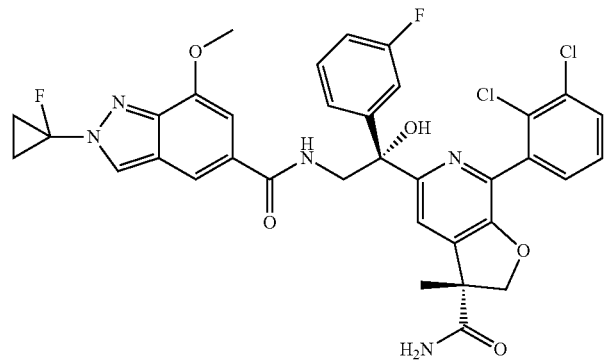 [SMILES: COc1cc(C(=O)NC[C@@](O)(c2cccc(F)c2)c2cc3c(c(-c4cccc(Cl)c4Cl)n2)OC[C@]3(C)C(N)=O)cc2cn(C3(F)CC3)nc12] |
| 292 | 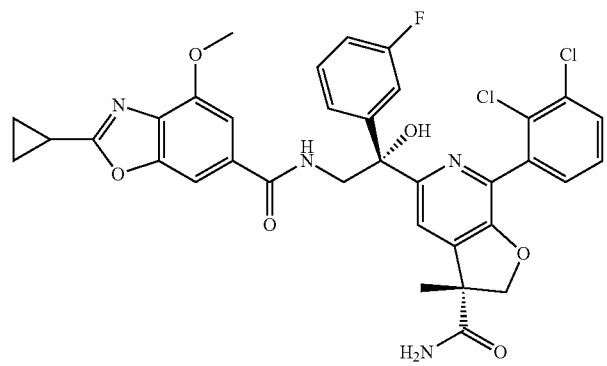 [SMILES: COc1cc(C(=O)NC[C@@](O)(c2cccc(F)c2)c2cc3c(c(-c4cccc(Cl)c4Cl)n2)OC[C@]3(C)C(N)=O)cc2oc(C3CC3)nc12] |
| 293 | 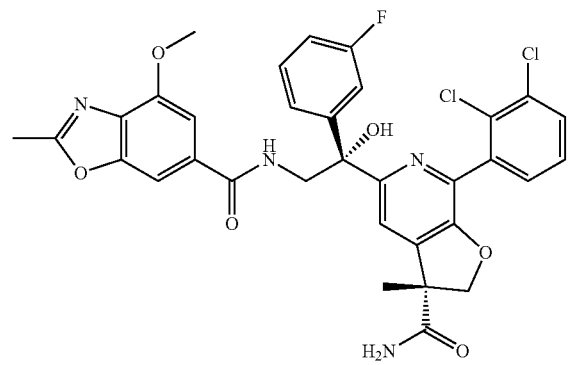 [SMILES: COc1cc(C(=O)NC[C@@](O)(c2cccc(F)c2)c2cc3c(c(-c4cccc(Cl)c4Cl)n2)OC[C@]3(C)C(N)=O)cc2oc(C)nc12] |
| 294 | 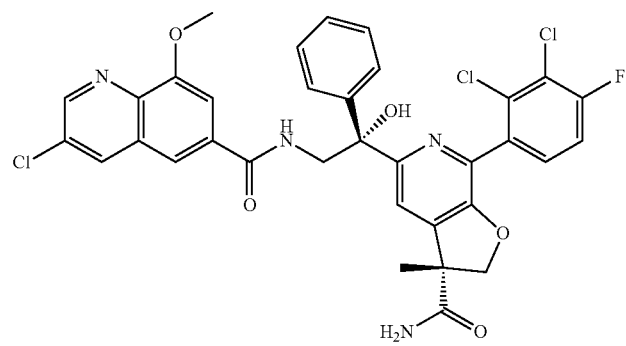 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cc(Cl)cnc12] |

| Compound | Structure |
|---|---|
| 295 | 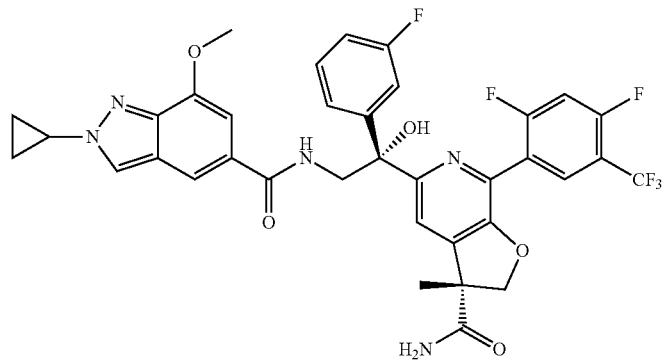 [SMILES: COc1cc(C(=O)NC[C@@](O)(c2cccc(F)c2)c2cc3c(c(-c4cc(C(F)(F)F)c(F)cc4F)n2)OC[C@]3(C)C(N)=O)cc2cn(C3CC3)nc12] |
| 296 | 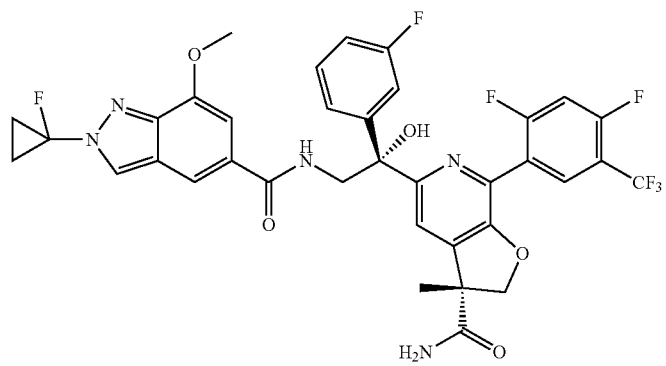 [SMILES: COc1cc(C(=O)NC[C@@](O)(c2cccc(F)c2)c2cc3c(c(-c4cc(C(F)(F)F)c(F)cc4F)n2)OC[C@]3(C)C(N)=O)cc2cn(C3(F)CC3)nc12] |
| 297 | 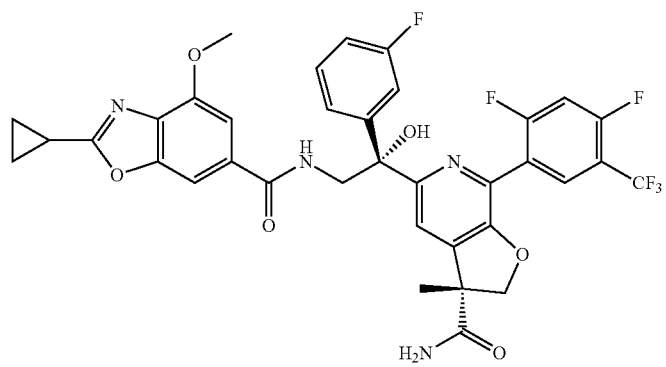 [SMILES: COc1cc(C(=O)NC[C@@](O)(c2cccc(F)c2)c2cc3c(c(-c4cc(C(F)(F)F)c(F)cc4F)n2)OC[C@]3(C)C(N)=O)cc2oc(C3CC3)nc12] |
| 298 | 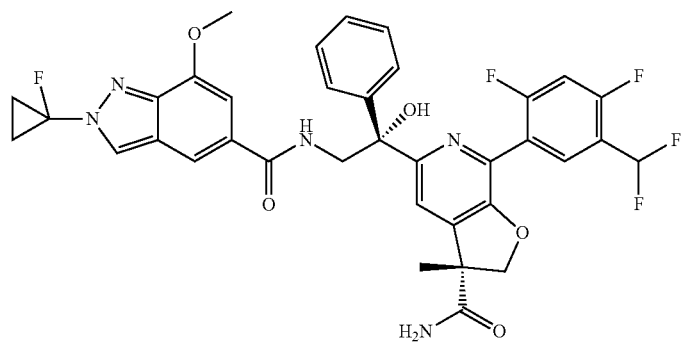 [SMILES: COc1cc(C(=O)NC[C@@](O)(c2ccccc2)c2cc3c(c(-c4cc(C(F)F)c(F)cc4F)n2)OC[C@]3(C)C(N)=O)cc2cn(C3(F)CC3)nc12] |

| Compound | Structure |
|---|---|
| 299 | 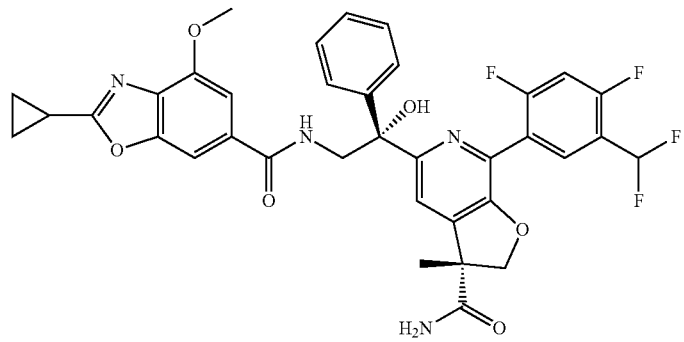 [SMILES: COc1cc(C(=O)NC[C@@](O)(c2ccccc2)c2cc3c(c(-c4cc(C(F)F)c(F)cc4F)n2)OC[C@]3(C)C(N)=O)cc2oc(C3CC3)nc12] |
| 300 | 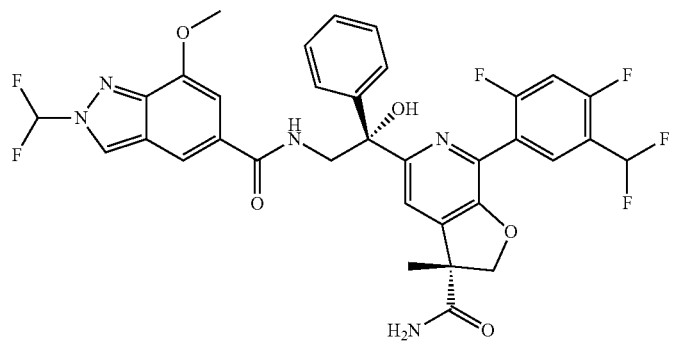 [SMILES: COc1cc(C(=O)NC[C@@](O)(c2ccccc2)c2cc3c(c(-c4cc(C(F)F)c(F)cc4F)n2)OC[C@]3(C)C(N)=O)cc2cn(C(F)F)nc12] |
| 301 | 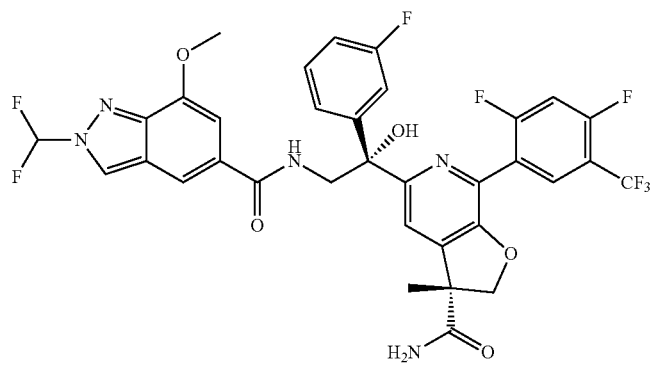 [SMILES: COc1cc(C(=O)NC[C@@](O)(c2cccc(F)c2)c2cc3c(c(-c4cc(C(F)(F)F)c(F)cc4F)n2)OC[C@]3(C)C(N)=O)cc2cn(C(F)F)nc12] |
| 302 | 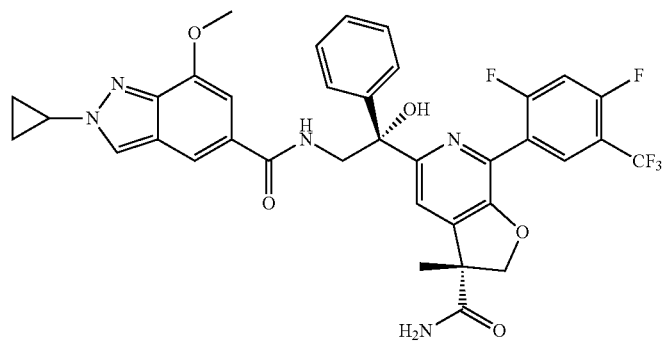 [SMILES: COc1cc(C(=O)NC[C@@](O)(c2ccccc2)c2cc3c(c(-c4cc(C(F)(F)F)c(F)cc4F)n2)OC[C@]3(C)C(N)=O)cc2cn(C3CC3)nc12] |

-continued
| Compound | Structure |
|---|---|
| 303 | 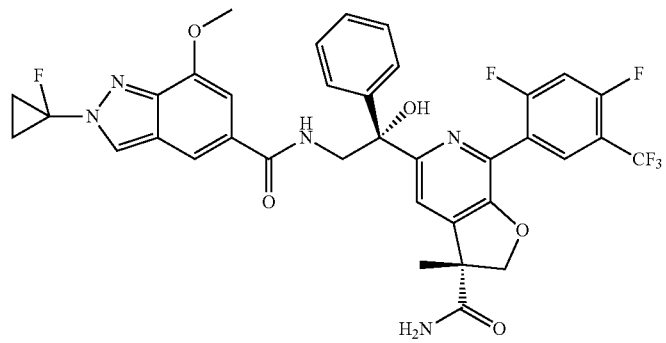 [SMILES: COc1cc(C(=O)NC[C@@](O)(c2ccccc2)c2cc3c(c(-c4cc(C(F)(F)F)c(F)cc4F)n2)OC[C@]3(C)C(N)=O)cc2cn(C3(F)CC3)nc12] |
| 304 | 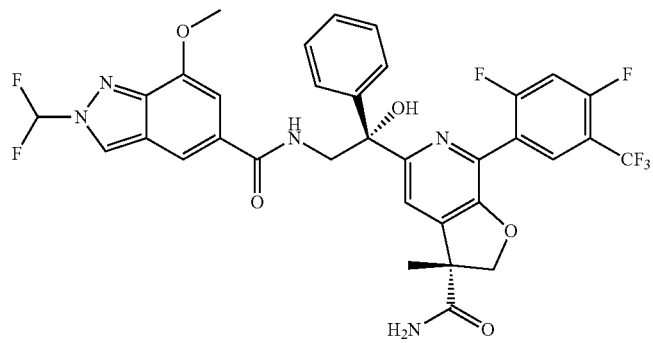 [SMILES: COc1cc(C(=O)NC[C@@](O)(c2ccccc2)c2cc3c(c(-c4cc(C(F)(F)F)c(F)cc4F)n2)OC[C@]3(C)C(N)=O)cc2cn(C(F)F)nc12] |
| 307 | 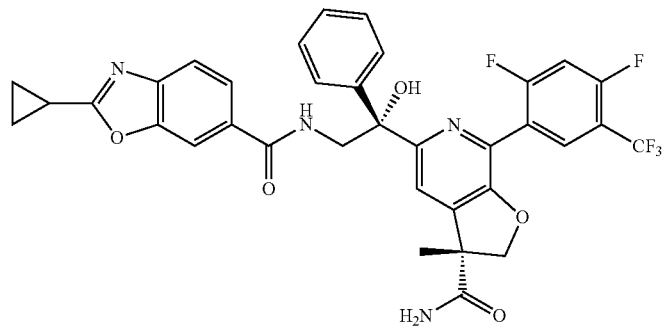 [SMILES: C[C@]1(C(N)=O)COc2c1cc([C@@](O)(CNC(=O)c1ccc3nc(C4CC4)oc3c1)c1ccccc1)nc2-c1cc(C(F)(F)F)c(F)cc1F] |
| 308 | 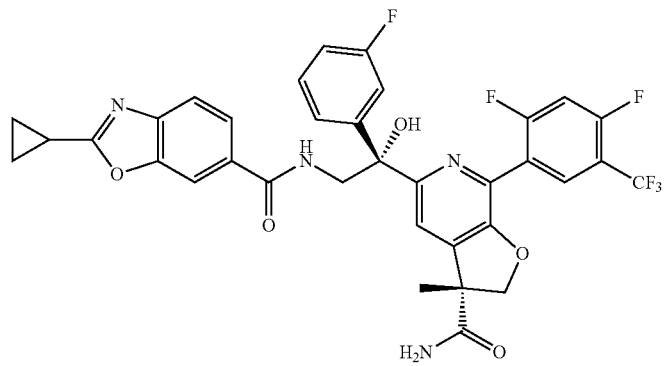 [SMILES: C[C@]1(C(N)=O)COc2c1cc([C@@](O)(CNC(=O)c1ccc3nc(C4CC4)oc3c1)c1cccc(F)c1)nc2-c1cc(C(F)(F)F)c(F)cc1F] |

| Compound | Structure |
|---|---|
| 311 | 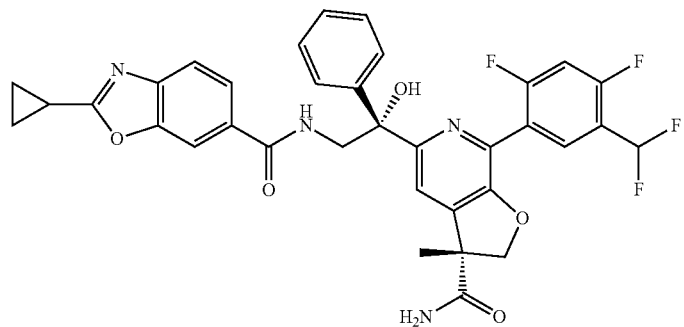 [SMILES: C[C@]1(C(N)=O)COc2c1cc([C@@](O)(CNC(=O)c1ccc3nc(C4CC4)oc3c1)c1ccccc1)nc2-c1cc(C(F)F)c(F)cc1F] |
| 312 | 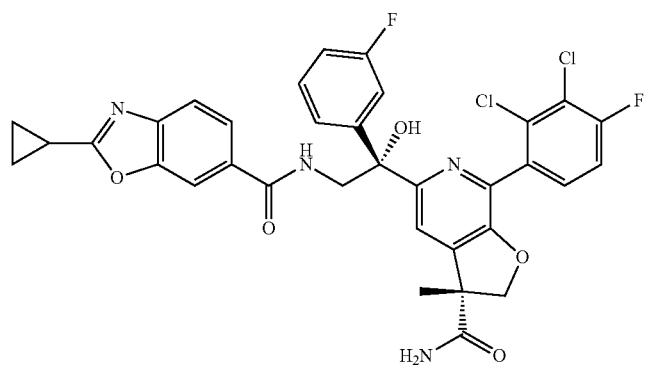 [SMILES: C[C@]1(C(N)=O)COc2c1cc([C@@](O)(CNC(=O)c1ccc3nc(C4CC4)oc3c1)c1cccc(F)c1)nc2-c1ccc(F)c(Cl)c1Cl] |
| 313 | 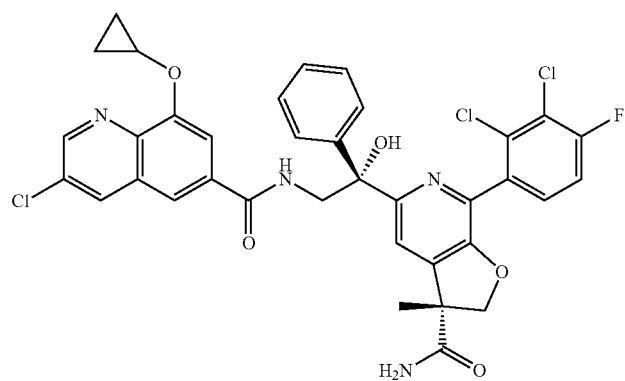 [SMILES: C[C@]1(C(N)=O)COc2c1cc([C@@](O)(CNC(=O)c1cc(OC3CC3)c3ncc(Cl)cc3c1)c1ccccc1)nc2-c1ccc(F)c(Cl)c1Cl] |
| 314 | 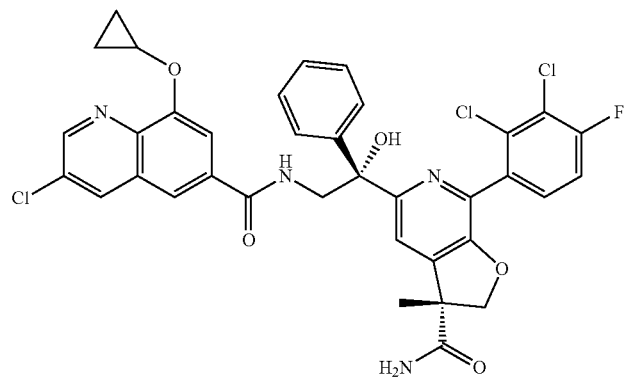 [SMILES: C[C@]1(C(N)=O)COc2c1cc([C@@](O)(CNC(=O)c1cc(OC3CC3)c3ncc(Cl)cc3c1)c1ccccc1)nc2-c1ccc(F)c(Cl)c1Cl] |

| Compound | Structure |
|---|---|
| 315 | 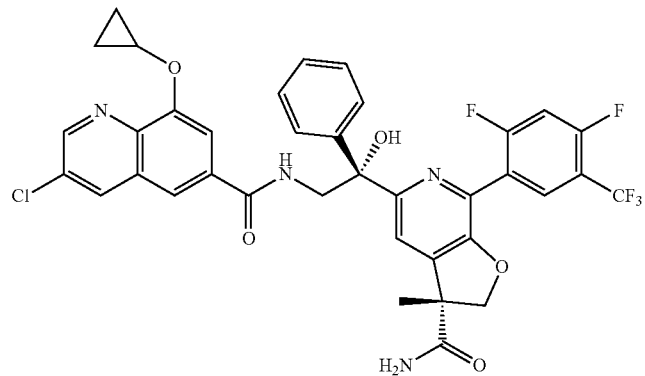 [SMILES: C[C@]1(C(N)=O)COc2c1cc([C@@](O)(CNC(=O)c1cc(OC3CC3)c3ncc(Cl)cc3c1)c1ccccc1)nc2-c1cc(C(F)(F)F)c(F)cc1F] |
| 305 | 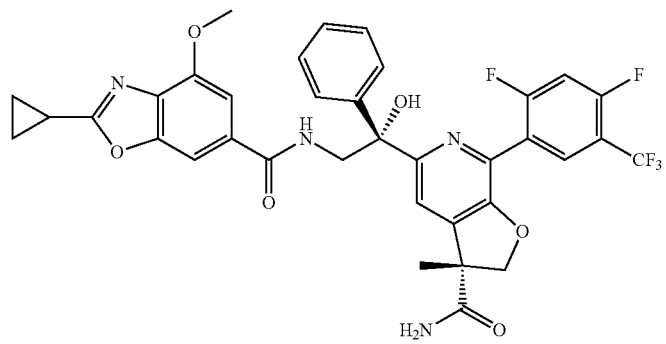 [SMILES: COc1cc(C(=O)NC[C@@](O)(c2ccccc2)c2cc3c(c(-c4cc(C(F)(F)F)c(F)cc4F)n2)OC[C@]3(C)C(N)=O)cc2oc(C3CC3)nc12] |
| 331 | 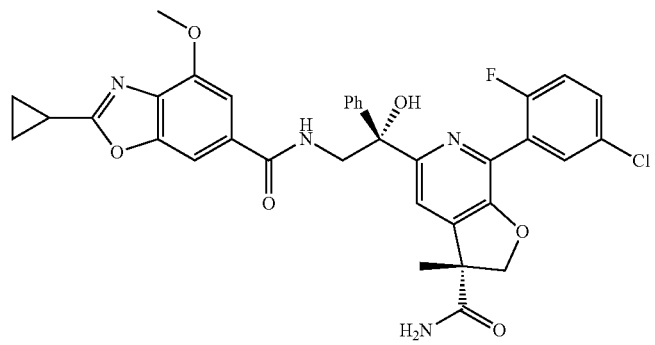 |
| 332 | 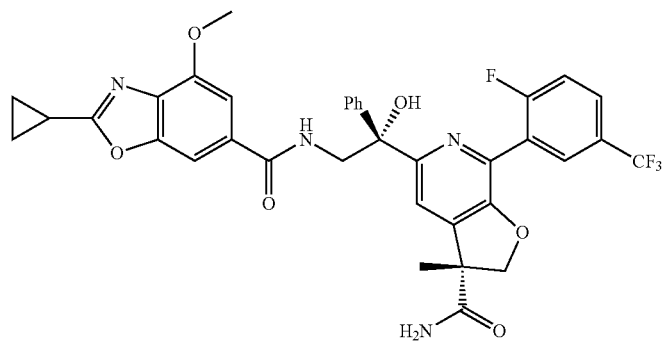 |

| Compound | Structure |
|---|---|
| 333 | 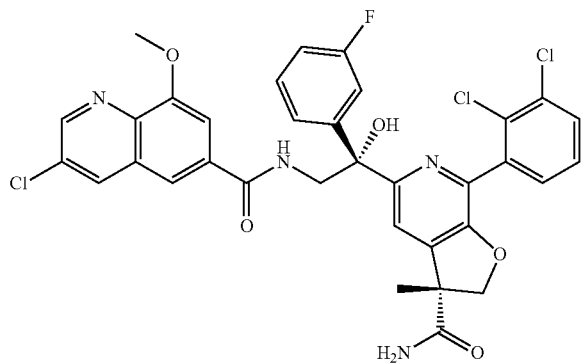 [SMILES: COc1cc(C(=O)NC[C@@](O)(c2cccc(F)c2)c2cc3c(c(-c4cccc(Cl)c4Cl)n2)OC[C@]3(C)C(N)=O)cc2cc(Cl)cnc12] |
| 334 | 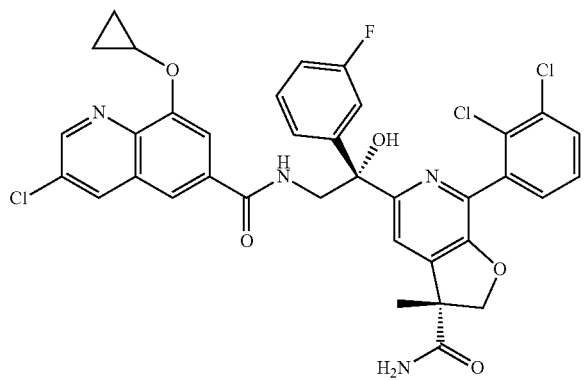 [SMILES: C[C@]1(C(N)=O)COc2c1cc([C@@](O)(CNC(=O)c1cc(OC3CC3)c3ncc(Cl)cc3c1)c1cccc(F)c1)nc2-c1cccc(Cl)c1Cl] |
| 335 | 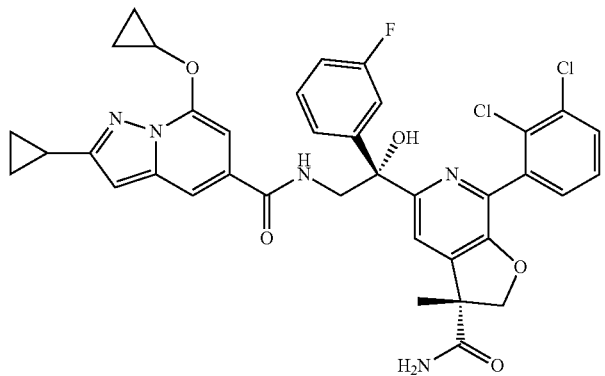 [SMILES: C[C@]1(C(N)=O)COc2c1cc([C@@](O)(CNC(=O)c1cc(OC3CC3)n3nc(C4CC4)cc3c1)c1cccc(F)c1)nc2-c1cccc(Cl)c1Cl] |
| 336 | 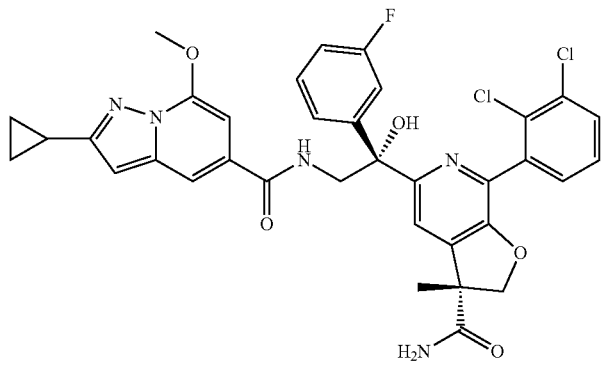 [SMILES: COc1cc(C(=O)NC[C@@](O)(c2cccc(F)c2)c2cc3c(c(-c4cccc(Cl)c4Cl)n2)OC[C@]3(C)C(N)=O)cc2cc(C3CC3)nn12] |

-continued
| Compound | Structure |
|---|---|
| 337 | 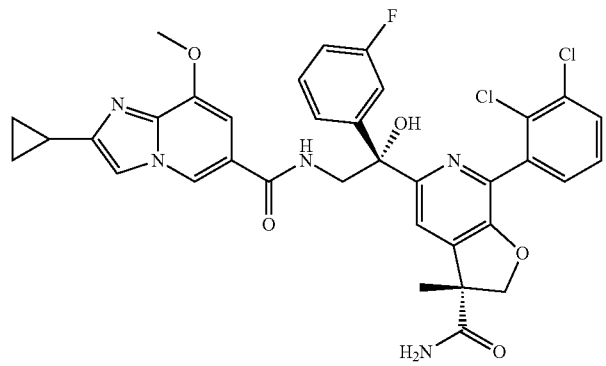 [SMILES: COc1cc(C(=O)NC[C@@](O)(c2cccc(F)c2)c2cc3c(c(-c4cccc(Cl)c4Cl)n2)OC[C@]3(C)C(N)=O)cn2cc(C3CC3)nc12] |
| 339 | 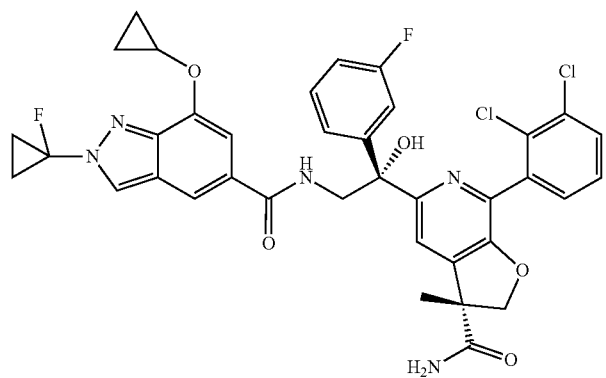 |
| 340 | 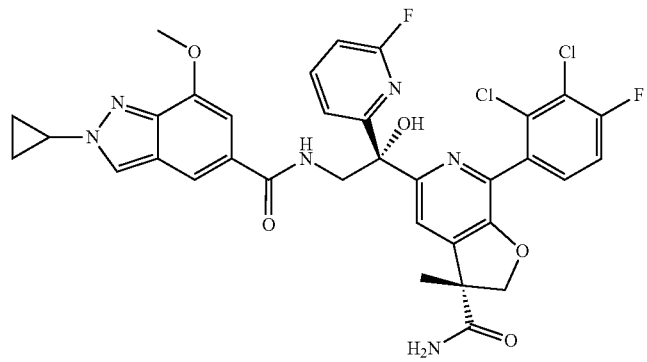 |
| 342 | 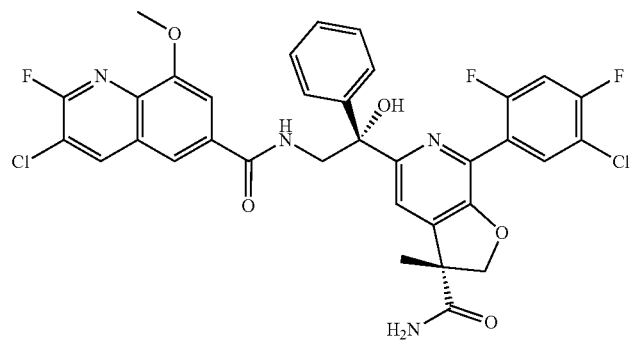 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)c(F)nc12] |

| Compound | Structure |
|---|---|
| 361 | 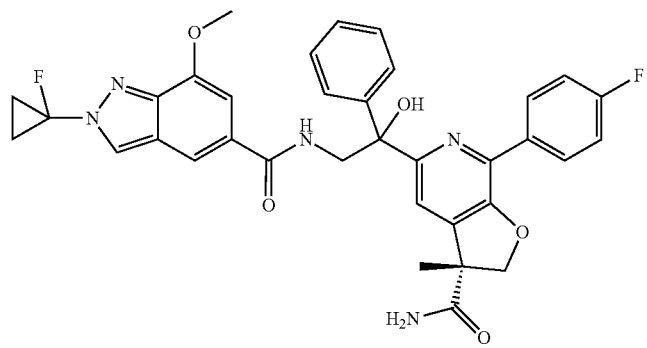 |
| 362 | 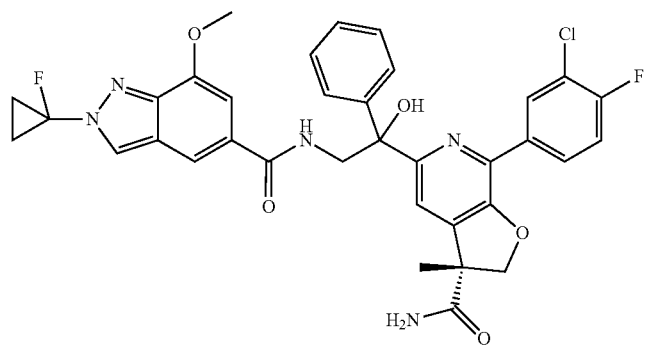 |
| 363 | 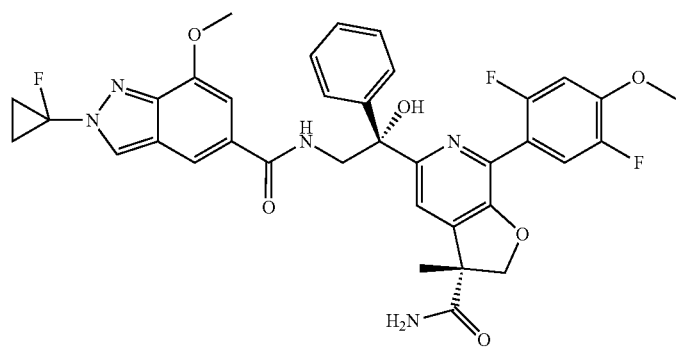 |
| 364 | 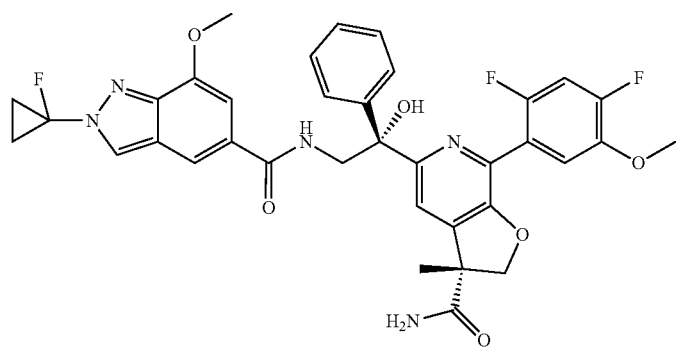 |

| Compound | Structure |
|---|---|
| 365 | 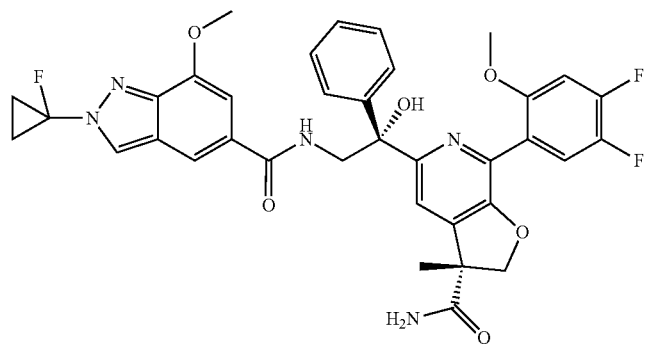 |
| 366 | 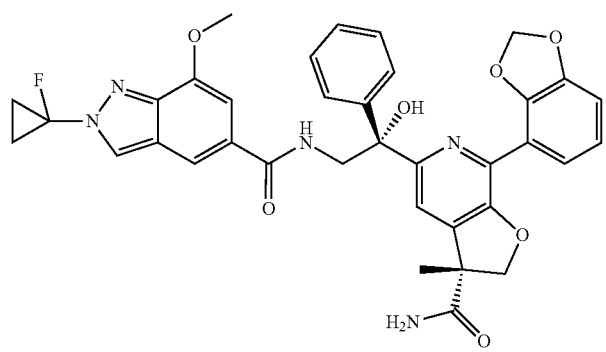 |
| 367 | 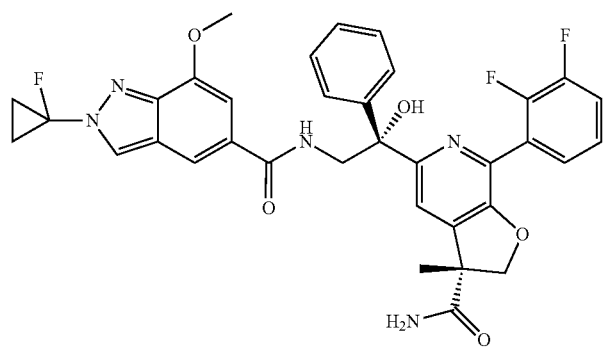 |
| 368 | 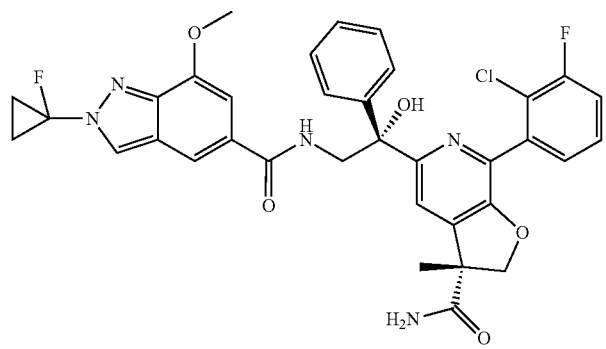 |

| Compound | Structure |
|---|---|
| 369 | 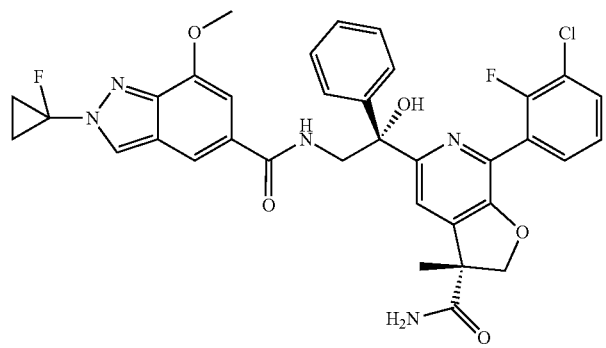 |
| 370 | 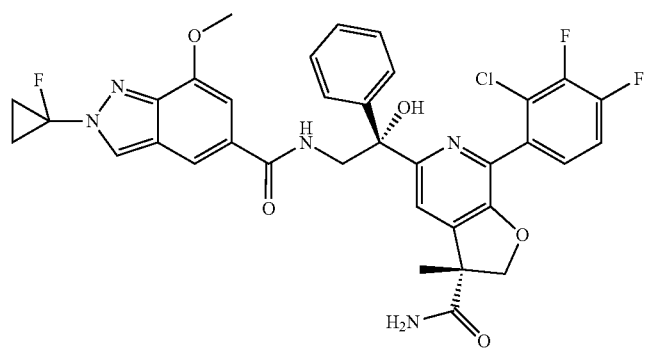 |
| 371 | 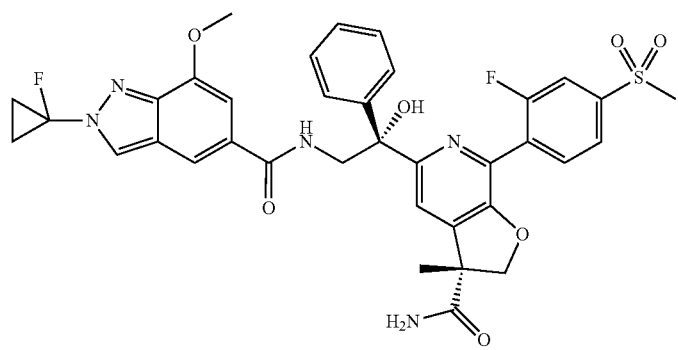 |
| 372 | 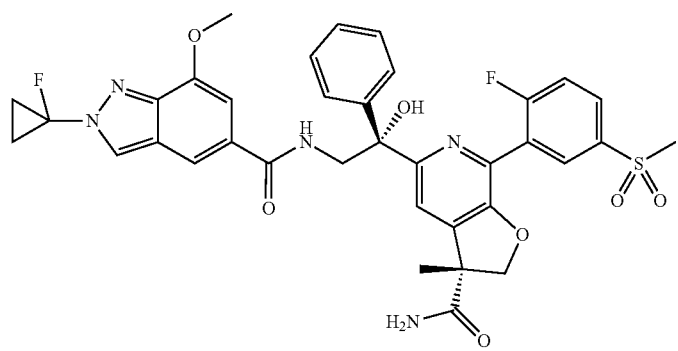 |

| Compound | Structure |
|---|---|
| 373 | 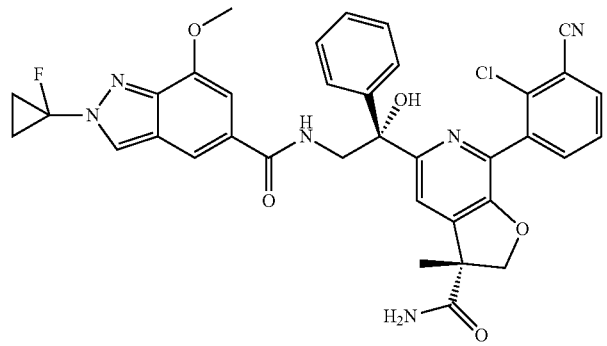 |
| 374 | 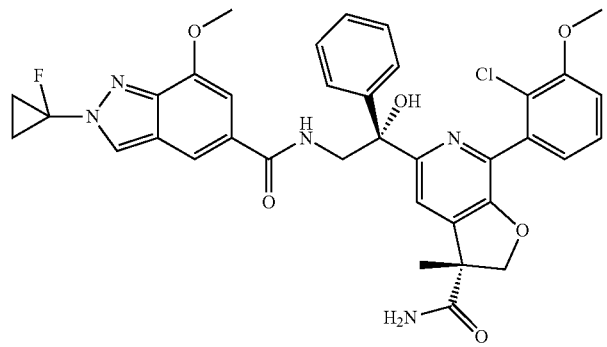 |
| 375 | 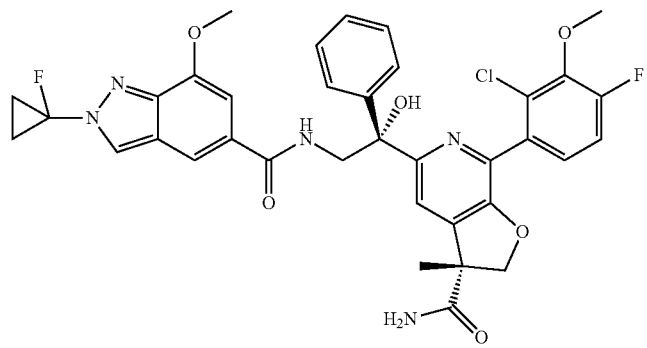 |
| 466 | 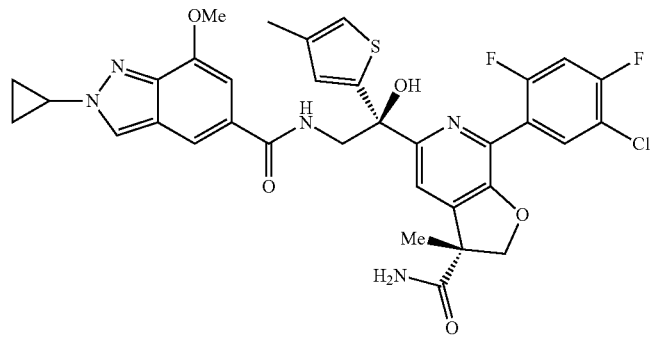 |

| Compound | Structure |
|---|---|
| 397 | 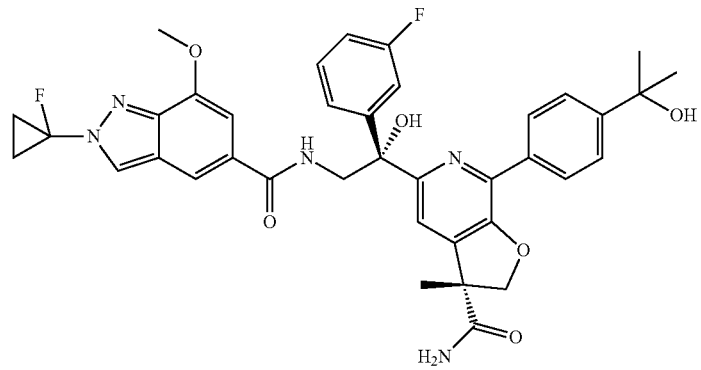 |
| 398 | 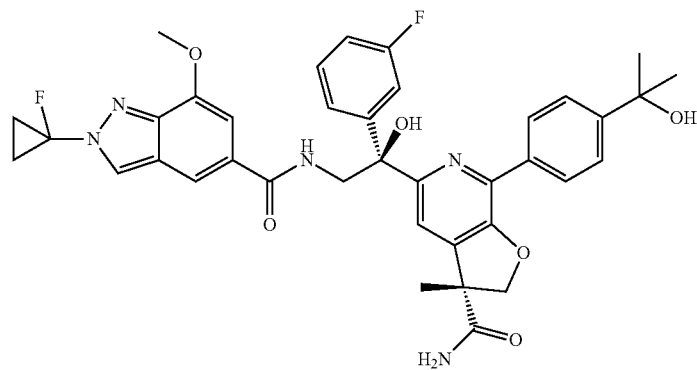 |
| 399 | 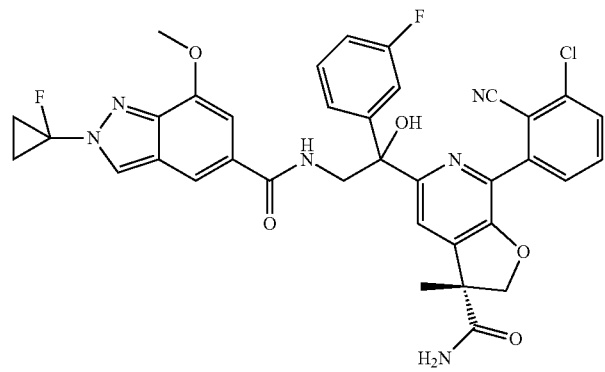 |
| 400 | 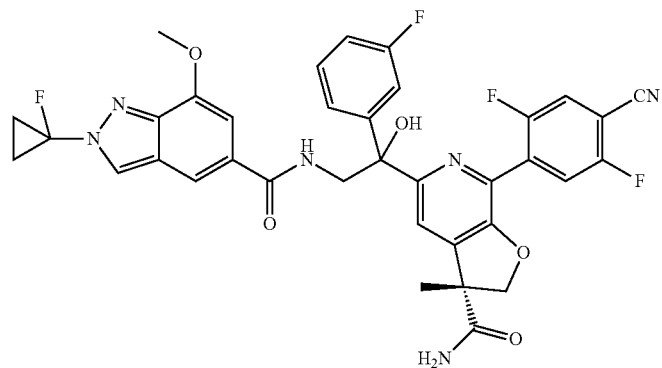 |

| Compound | Structure |
|---|---|
| 405 | 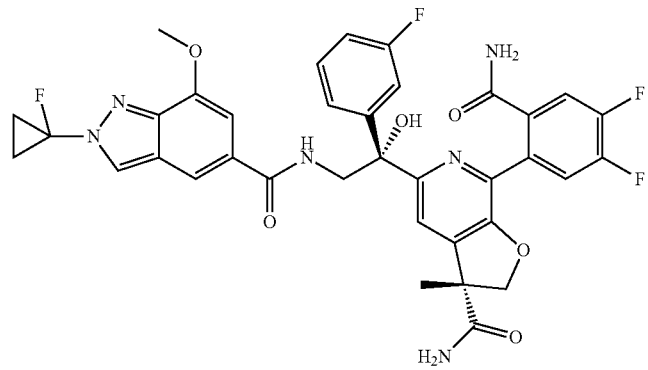 |
| 406 | 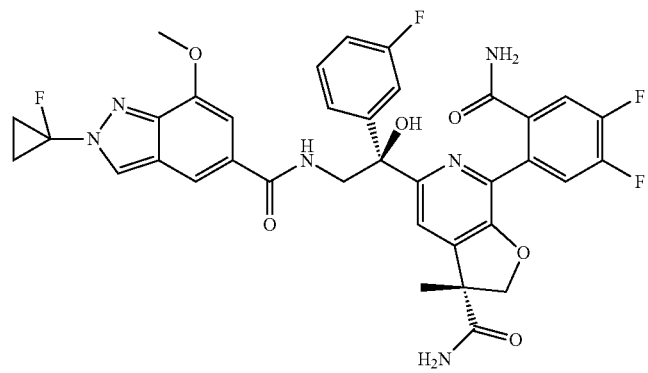 |
| 463 | 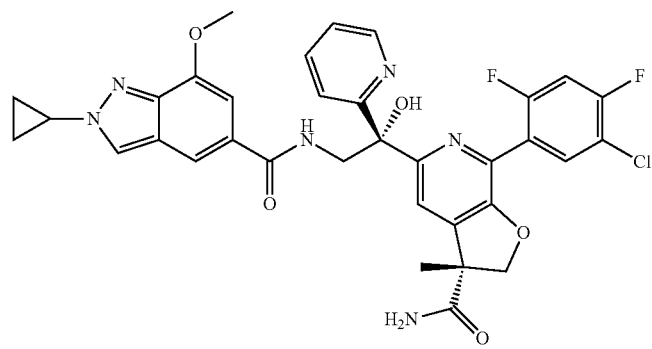 |
| 464 | 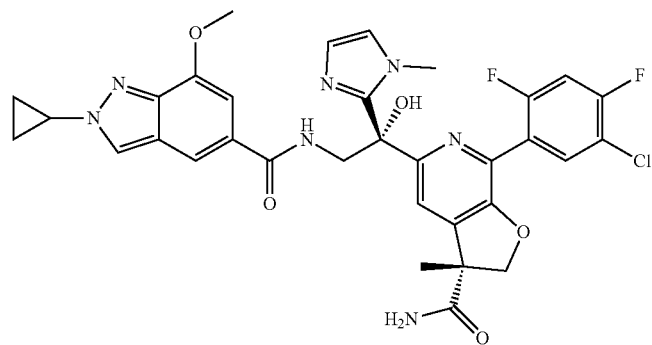 |

| Compound | Structure |
|---|---|
| 467 | 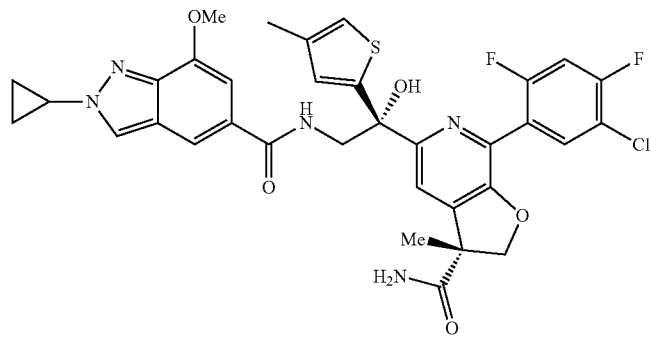 |
| 468 | 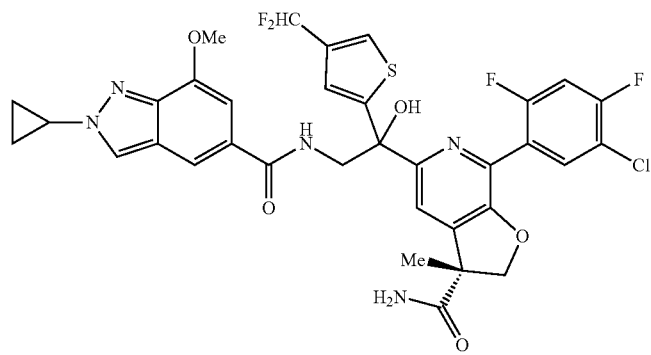 |
| 469 | 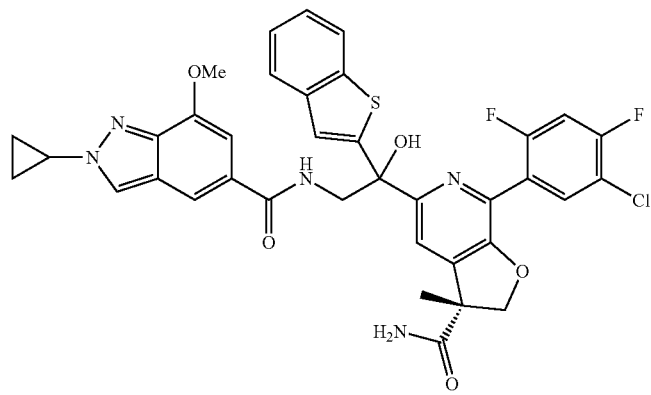 |
| 470 | 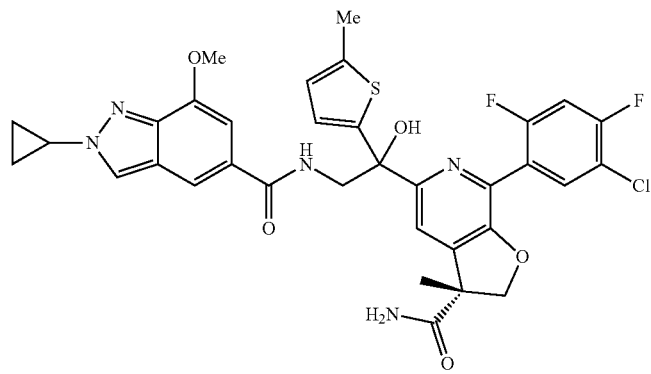 |

| Compound | Structure |
|---|---|
| 471 | 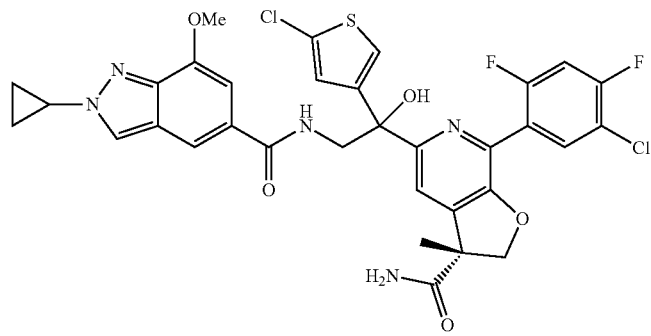 |
| 472 | 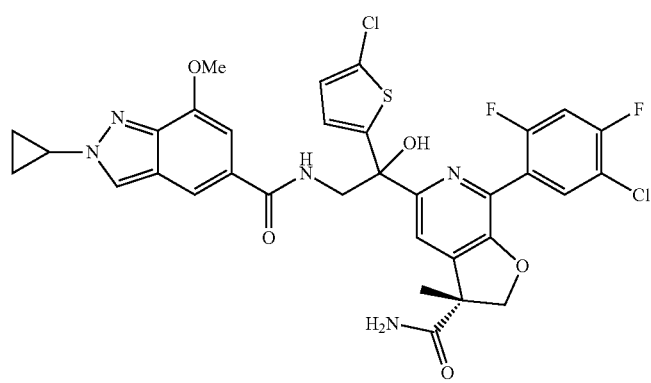 |
| 474 | 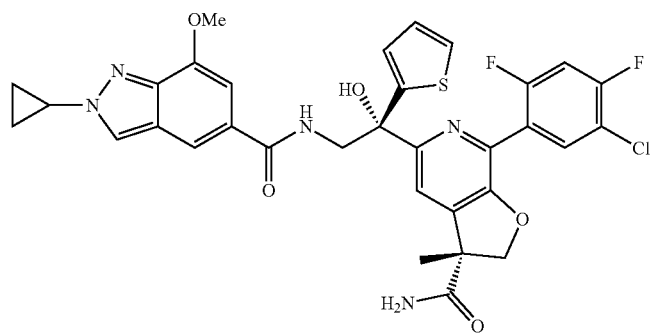 |
| 475 | 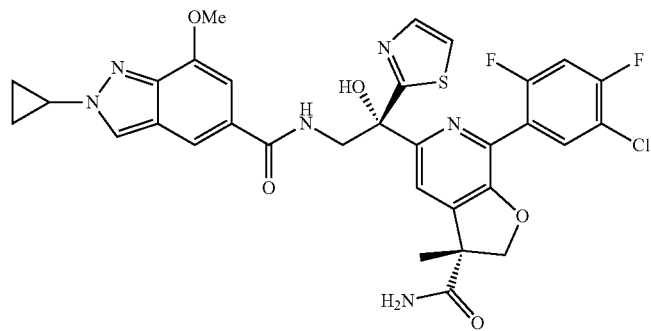 |

| Compound | Structure |
|---|---|
| 478 | 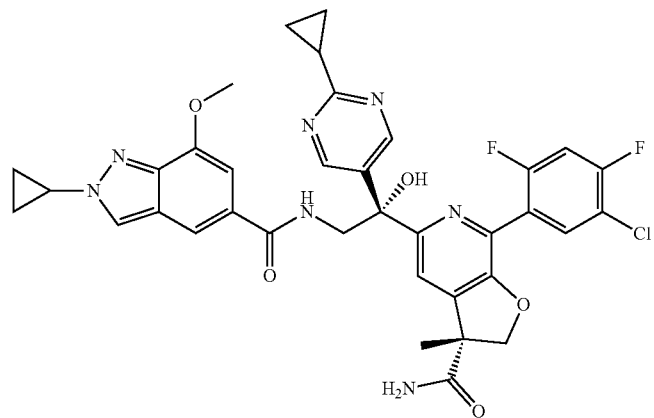 |
| 479 | 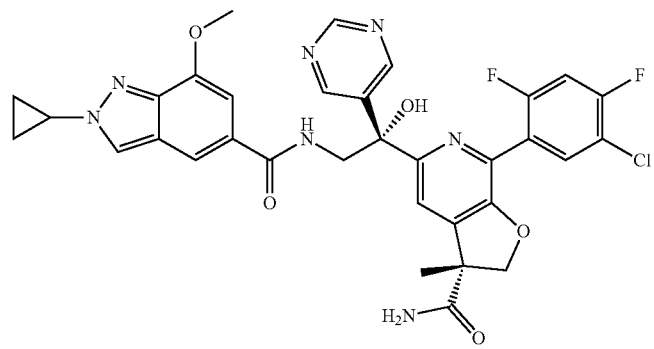 |
| 480 | 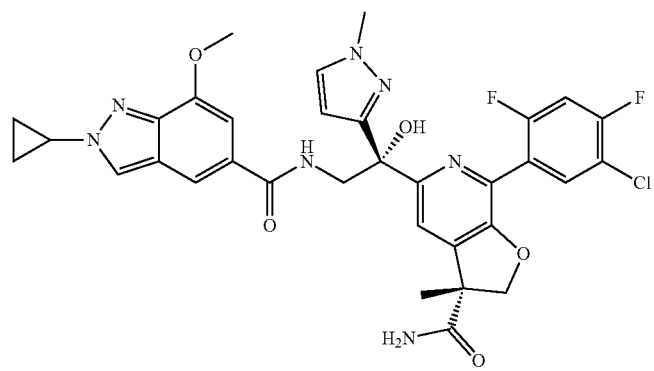 |
| 481 | 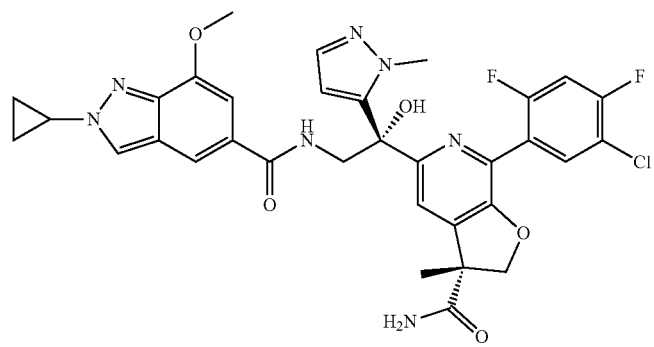 |

| Compound | Structure |
|---|---|
| 482 | 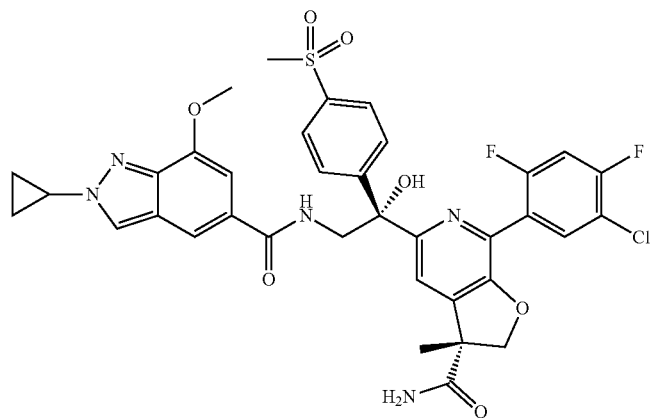 |
| 483 | 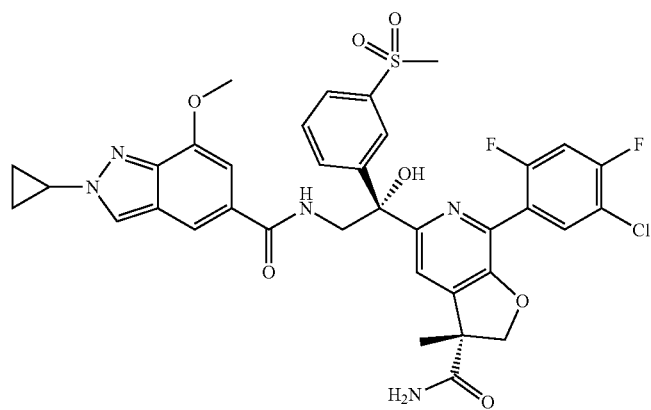 |
| 484 | 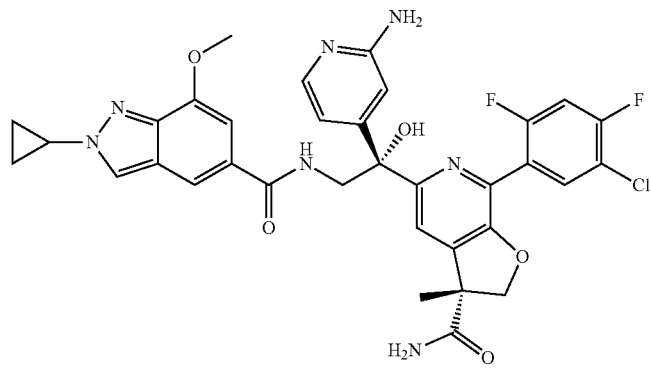 |
| 485 | 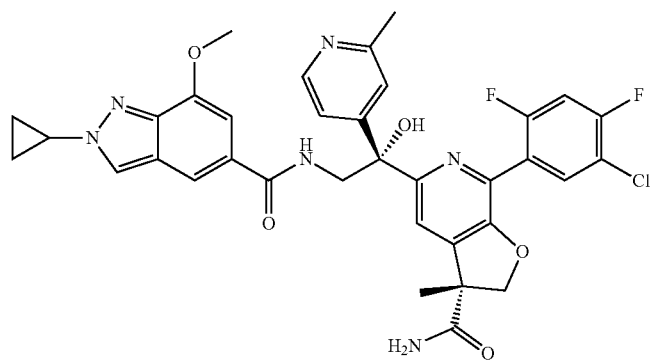 |

| Compound | Structure |
|---|---|
| 486 | 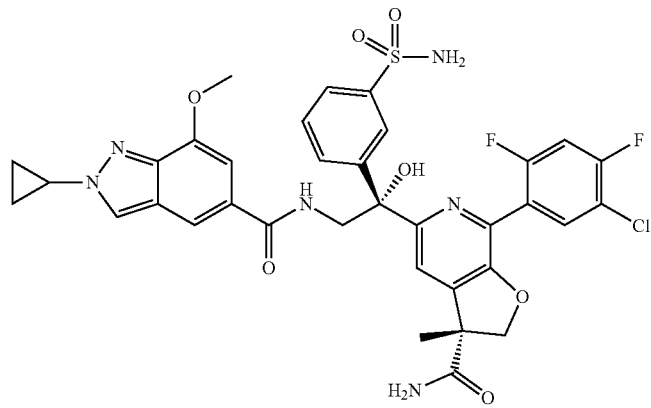 |
| 487 | 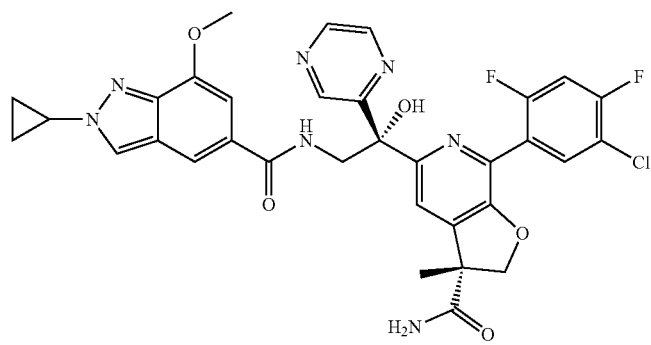 [SMILES: COc1cc(C(=O)NC[C@@](O)(c2cnccn2)c2cc3c(c(-c4cc(Cl)c(F)cc4F)n2)OC[C@]3(C)C(N)=O)cc2cn(C3CC3)nc12] |
| 488 | 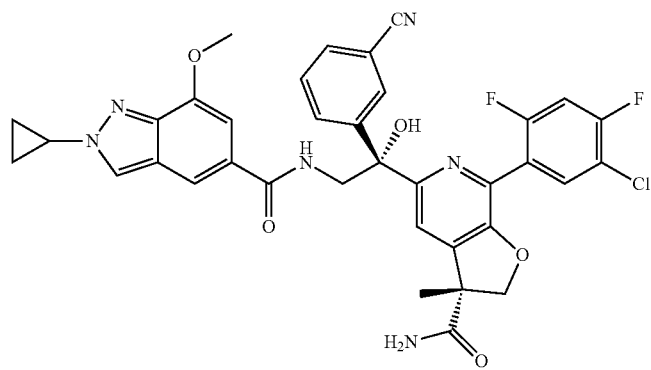 [SMILES: COc1cc(C(=O)NC[C@@](O)(c2cccc(C#N)c2)c2cc3c(c(-c4cc(Cl)c(F)cc4F)n2)OC[C@]3(C)C(N)=O)cc2cn(C3CC3)nc12] |
| 489 | 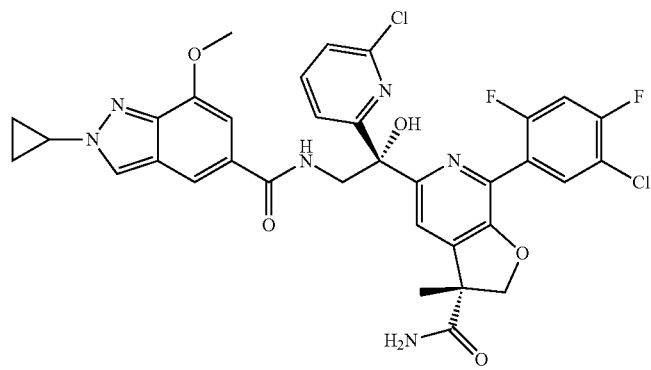 [SMILES: COc1cc(C(=O)NC[C@@](O)(c2cccc(Cl)n2)c2cc3c(c(-c4cc(Cl)c(F)cc4F)n2)OC[C@]3(C)C(N)=O)cc2cn(C3CC3)nc12] |

| Compound | Structure |
|---|---|
| 490 | 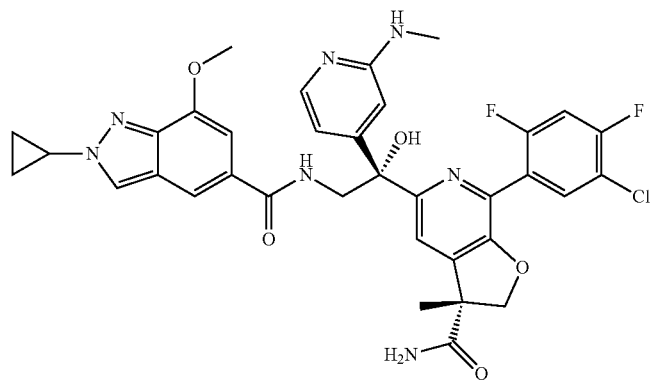 [SMILES: CNc1cc([C@](O)(CNC(=O)c2cc(OC)c3nn(C4CC4)cc3c2)c2cc3c(c(-c4cc(Cl)c(F)cc4F)n2)OC[C@]3(C)C(N)=O)ccn1] |
| 491 | 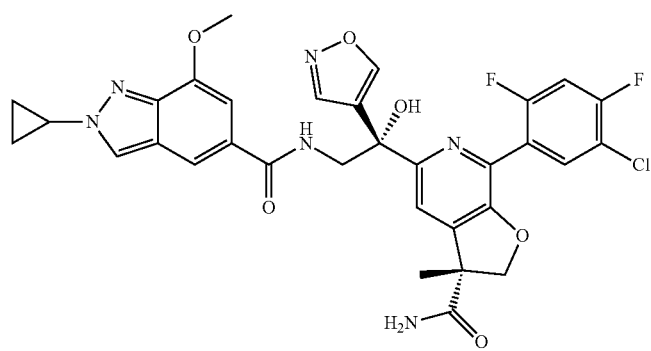 [SMILES: COc1cc(C(=O)NC[C@@](O)(c2cnoc2)c2cc3c(c(-c4cc(Cl)c(F)cc4F)n2)OC[C@]3(C)C(N)=O)cc2cn(C3CC3)nc12] |
| 492 | 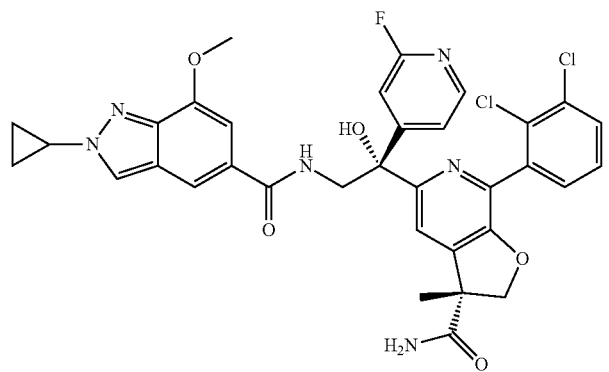 [SMILES: COc1cc(C(=O)NC[C@@](O)(c2ccnc(F)c2)c2cc3c(c(-c4cccc(Cl)c4Cl)n2)OC[C@]3(C)C(N)=O)cc2cn(C3CC3)nc12] |
| 493 | 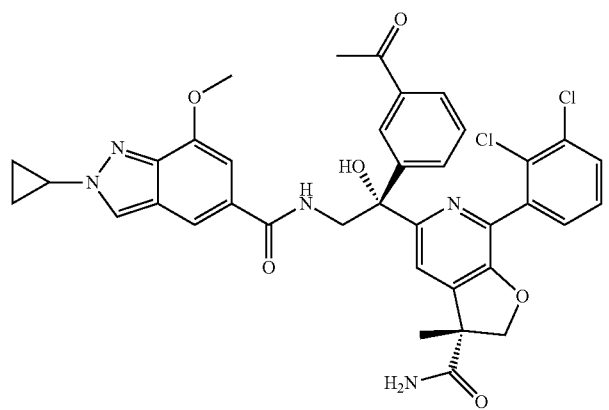 [SMILES: COc1cc(C(=O)NC[C@@](O)(c2cccc(C(C)=O)c2)c2cc3c(c(-c4cccc(Cl)c4Cl)n2)OC[C@]3(C)C(N)=O)cc2cn(C3CC3)nc12] |

| Compound | Structure |
|---|---|
| 494 | 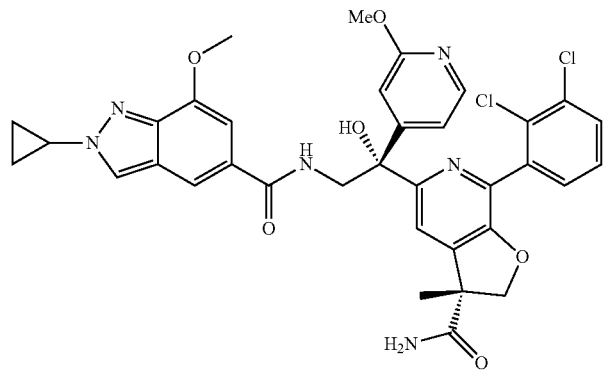 [SMILES: COc1cc([C@](O)(CNC(=O)c2cc(OC)c3nn(C4CC4)cc3c2)c2cc3c(c(-c4cccc(Cl)c4Cl)n2)OC[C@]3(C)C(N)=O)ccn1] |
| 495 | 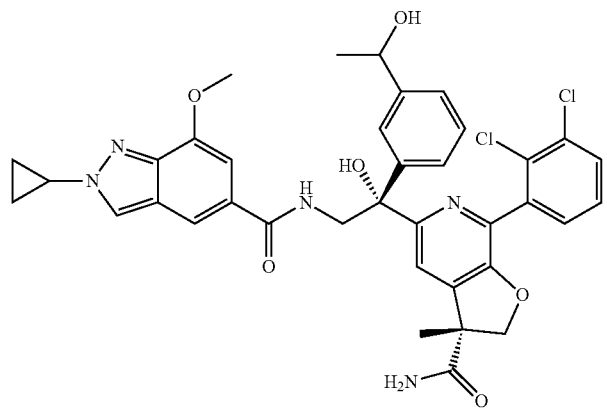 [SMILES: COc1cc(C(=O)NC[C@@](O)(c2cccc(C(C)O)c2)c2cc3c(c(-c4cccc(Cl)c4Cl)n2)OC[C@]3(C)C(N)=O)cc2cn(C3CC3)nc12] |
| 496 | 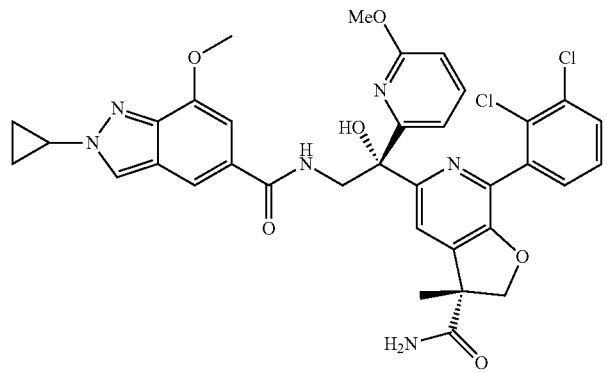 [SMILES: COc1cccc([C@](O)(CNC(=O)c2cc(OC)c3nn(C4CC4)cc3c2)c2cc3c(c(-c4cccc(Cl)c4Cl)n2)OC[C@]3(C)C(N)=O)n1] |
| 497 | 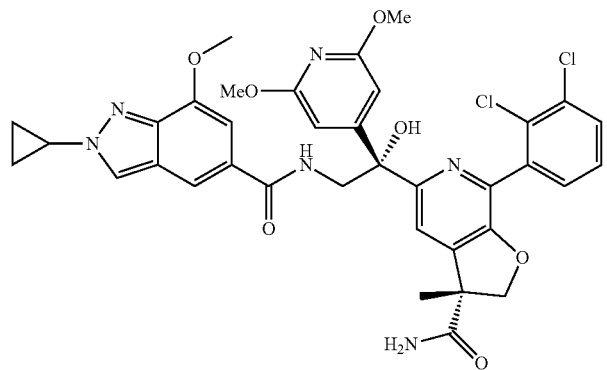 [SMILES: COc1cc([C@](O)(CNC(=O)c2cc(OC)c3nn(C4CC4)cc3c2)c2cc3c(c(-c4cccc(Cl)c4Cl)n2)OC[C@]3(C)C(N)=O)cc(OC)n1] |

| Compound | Structure |
|---|---|
| 498 | 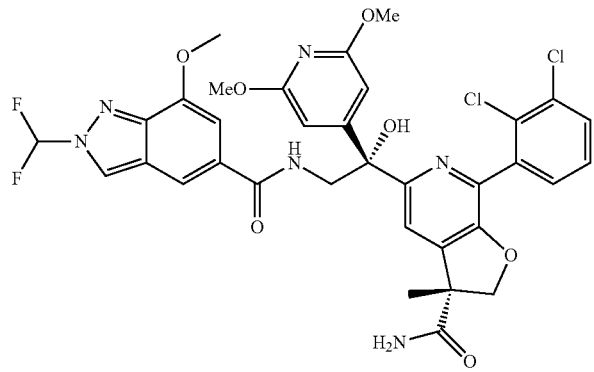 [SMILES: COc1cc([C@](O)(CNC(=O)c2cc(OC)c3nn(C(F)F)cc3c2)c2cc3c(c(-c4cccc(Cl)c4Cl)n2)OC[C@]3(C)C(N)=O)cc(OC)n1] |
| 499 | 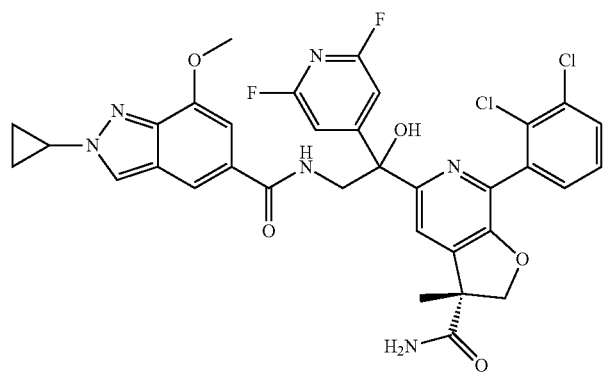 [SMILES: COc1cc(C(=O)NCC(O)(c2cc(F)nc(F)c2)c2cc3c(c(-c4cccc(Cl)c4Cl)n2)OC[C@]3(C)C(N)=O)cc2cn(C3CC3)nc12] |
| 500 | 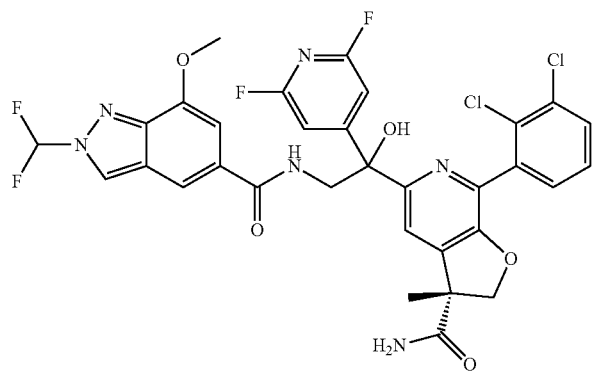 [SMILES: COc1cc(C(=O)NCC(O)(c2cc(F)nc(F)c2)c2cc3c(c(-c4cccc(Cl)c4Cl)n2)OC[C@]3(C)C(N)=O)cc2cn(C(F)F)nc12] |
| 501 | 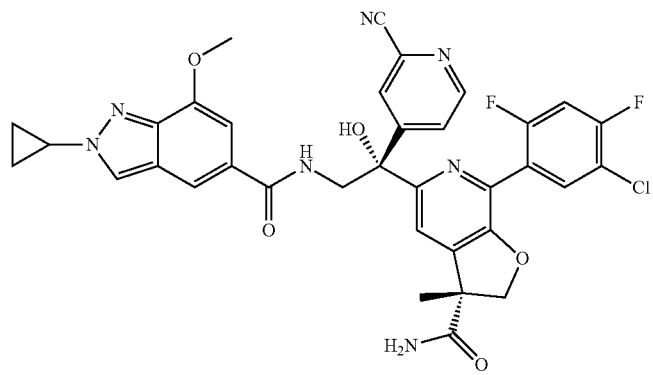 [SMILES: COc1cc(C(=O)NC[C@@](O)(c2ccnc(C#N)c2)c2cc3c(c(-c4cc(Cl)c(F)cc4F)n2)OC[C@]3(C)C(N)=O)cc2cn(C3CC3)nc12] |

| Compound | Structure |
|---|---|
| 502 | 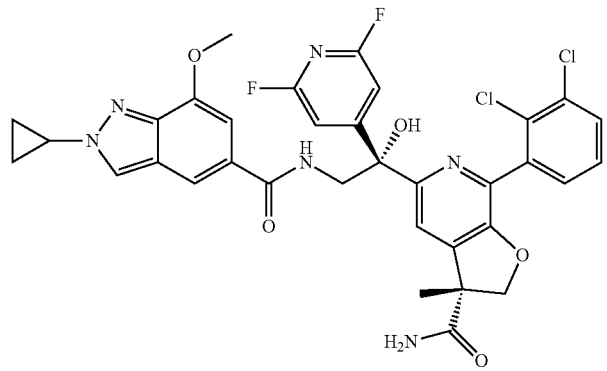 [SMILES: COc1cc(C(=O)NC[C@@](O)(c2cc(F)nc(F)c2)c2cc3c(c(-c4cccc(Cl)c4Cl)n2)OC[C@]3(C)C(N)=O)cc2cn(C3CC3)nc12] |
4. The compound of claim 3, selected from the compounds set forth in the table below, or a pharmaceutically acceptable salt thereof:
| Example # | Structure |
|---|---|
| 85 | 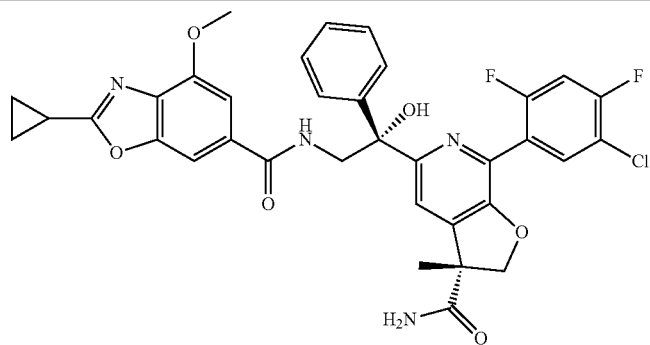 [SMILES: COc1cc(C(=O)NC[C@@](O)(c2ccccc2)c2cc3c(c(-c4cc(Cl)c(F)cc4F)n2)OC[C@]3(C)C(N)=O)cc2oc(C3CC3)nc12] |
| 155 | 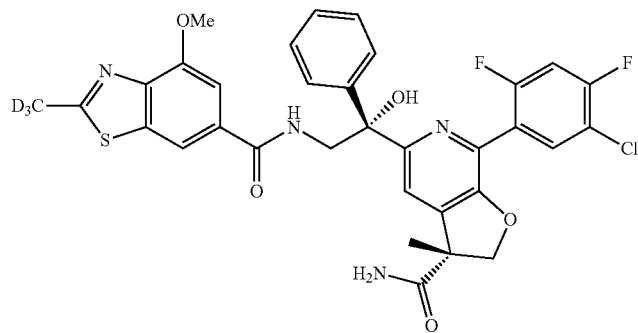 [SMILES: [2H]C([2H])([2H])c1nc2c(OC)cc(C(=O)NC[C@@](O)(c3ccccc3)c3cc4c(c(-c5cc(Cl)c(F)cc5F)n3)OC[C@]4(C)C(N)=O)cc2s1] |
| 170 | 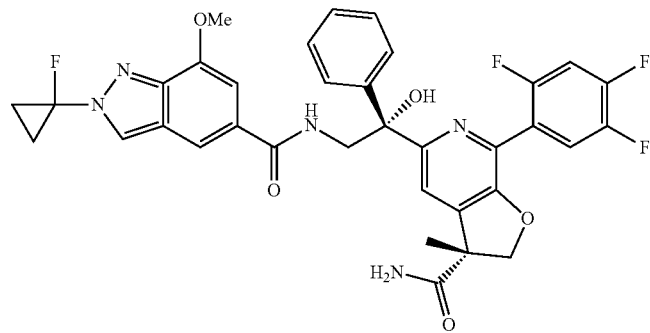 |

| Example # | Structure |
|---|---|
| 187 | 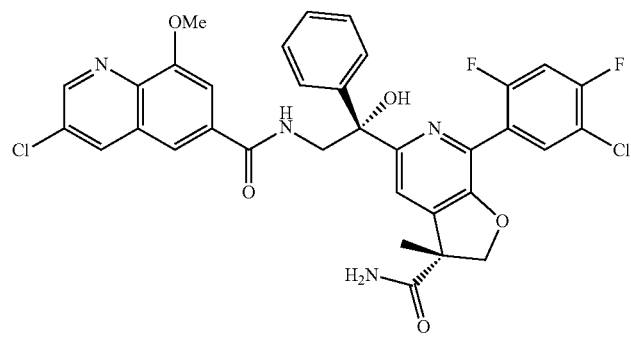 [SMILES: COc1cc(C(=O)NC[C@@](O)(c2ccccc2)c2cc3c(c(-c4cc(Cl)c(F)cc4F)n2)OC[C@]3(C)C(N)=O)cc2cc(Cl)cnc12] |
| 258 | 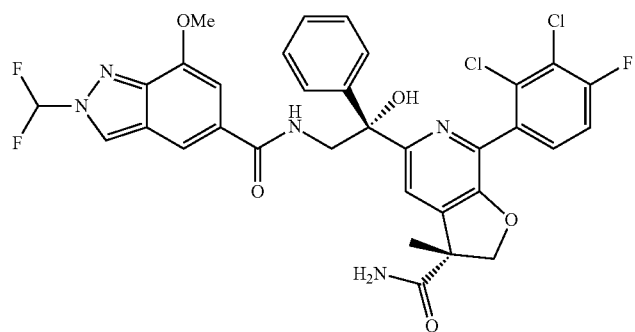 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cn(C(F)F)nc12] |
| 259 | 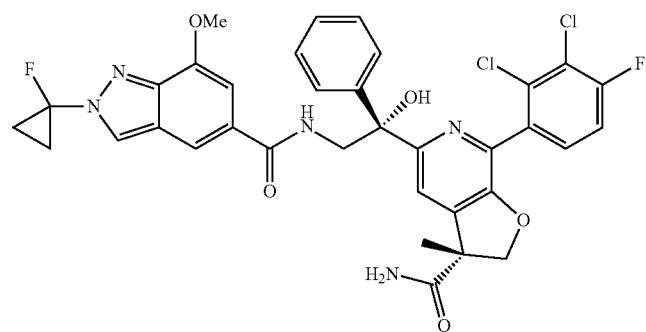 [SMILES: COc1cc(C(=O)NC[C@@](O)(c2ccccc2)c2cc3c(c(-c4ccc(F)c(Cl)c4Cl)n2)OC[C@]3(C)C(N)=O)cc2cn(C3(F)CC3)nc12] |
| 262 | 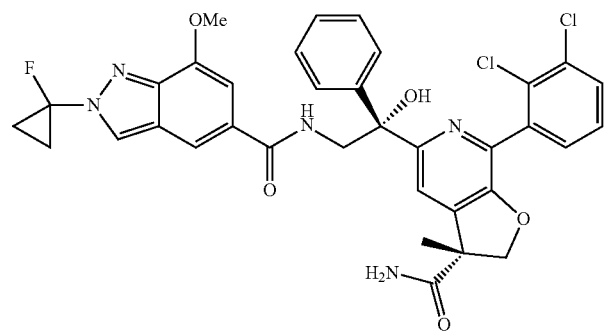 [SMILES: COc1cc(C(=O)NC[C@@](O)(c2ccccc2)c2cc3c(c(-c4cccc(Cl)c4Cl)n2)OC[C@]3(C)C(N)=O)cc2cn(C3(F)CC3)nc12] |

| Example # | Structure |
|---|---|
| 266 | 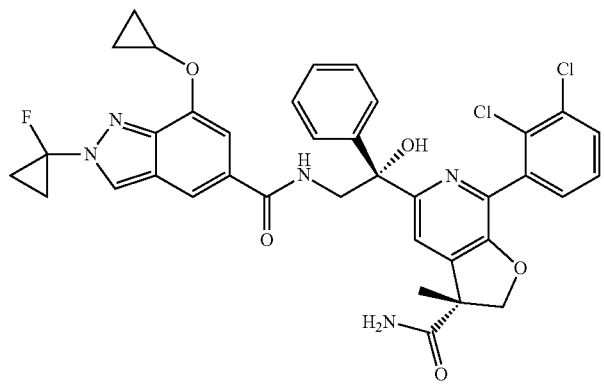 [SMILES: C[C@]1(C(N)=O)COc2c1cc([C@@](O)(CNC(=O)c1cc(OC3CC3)c3nn(C4(F)CC4)cc3c1)c1ccccc1)nc2-c1cccc(Cl)c1Cl] |
| 269 | 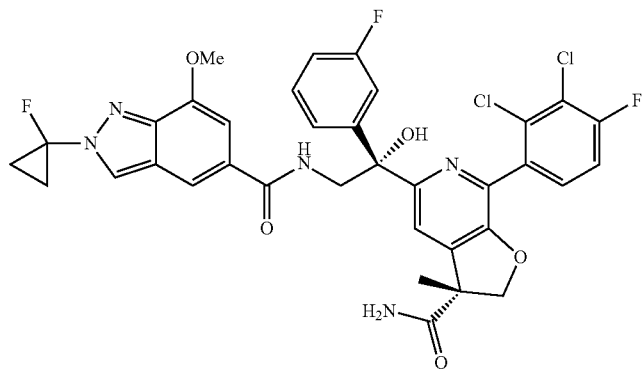 [SMILES: COc1cc(C(=O)NC[C@@](O)(c2cccc(F)c2)c2cc3c(c(-c4ccc(F)c(Cl)c4Cl)n2)OC[C@]3(C)C(N)=O)cc2cn(C3(F)CC3)nc12] |
| 275 | 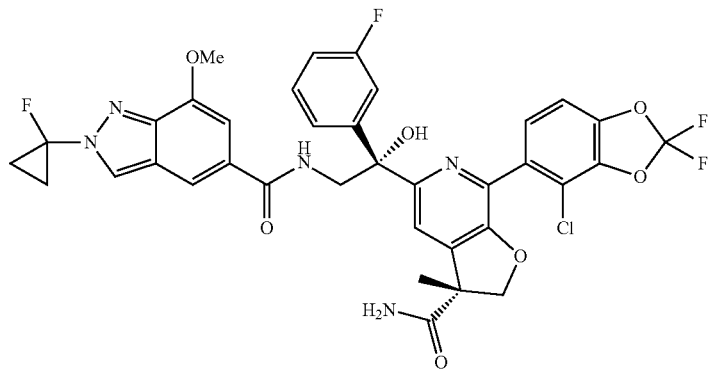 [SMILES: COc1cc(C(=O)NC[C@@](O)(c2cccc(F)c2)c2cc3c(c(-c4ccc5c(c4Cl)OC(F)(F)O5)n2)OC[C@]3(C)C(N)=O)cc2cn(C3(F)CC3)nc12] |
| 277 | 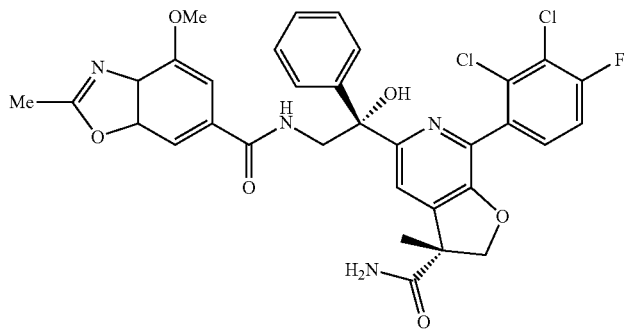 [SMILES: COC1=CC(C(=O)NC[C@@](O)(c2ccccc2)c2cc3c(c(-c4ccc(F)c(Cl)c4Cl)n2)OC[C@]3(C)C(N)=O)=CC2OC(C)=NC12] |

| Example # | Structure |
|---|---|
| 280 | 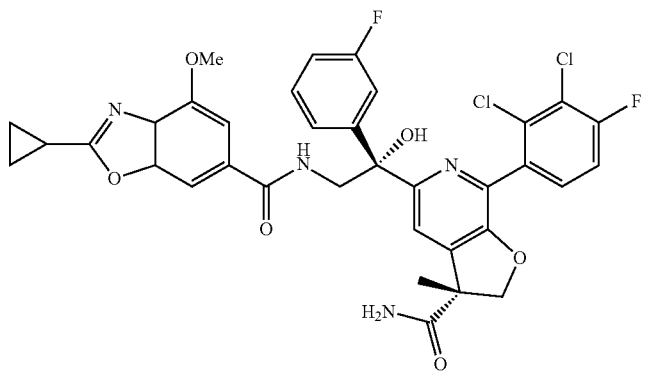 [SMILES: COC1=CC(C(=O)NC[C@@](O)(c2cccc(F)c2)c2cc3c(c(-c4ccc(F)c(Cl)c4Cl)n2)OC[C@]3(C)C(N)=O)=CC2OC(C3CC3)=NC12] |
| 286 | 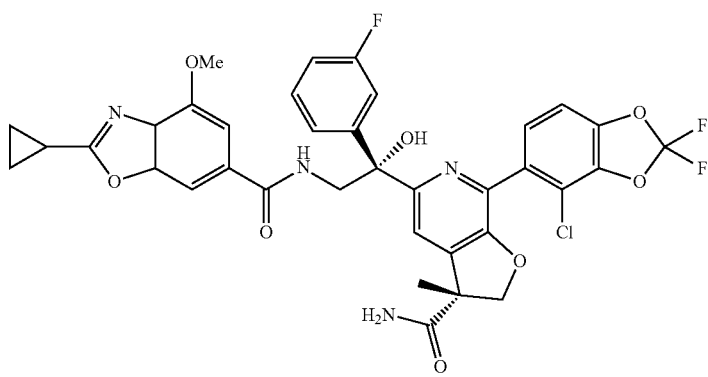 [SMILES: COC1=CC(C(=O)NC[C@@](O)(c2cccc(F)c2)c2cc3c(c(-c4ccc5c(c4Cl)OC(F)(F)O5)n2)OC[C@]3(C)C(N)=O)=CC2OC(C3CC3)=NC12] |
| 291 | 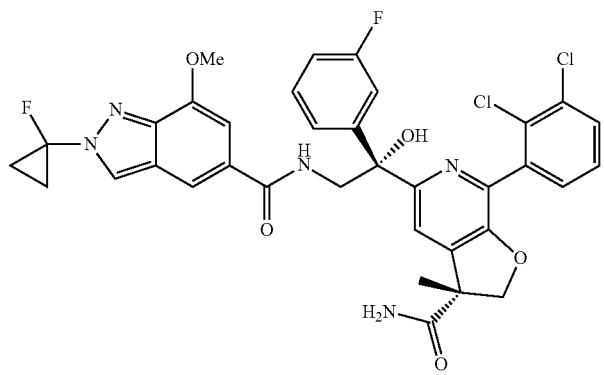 [SMILES: COc1cc(C(=O)NC[C@@](O)(c2cccc(F)c2)c2cc3c(c(-c4cccc(Cl)c4Cl)n2)OC[C@]3(C)C(N)=O)cc2cn(C3(F)CC3)nc12] |

5. A pharmaceutical composition comprising a compound according to claim 1, or a pharmaceutically acceptable salt thereof, and a pharmaceutically acceptable carrier, diluent or excipient.

6. A method of treating or preventing an RSV infection in a subject in need thereof, comprising administering to the subject a therapeutically effective amount of a compound or a combination of compounds of claim 1.

7. The method of claim 6, further comprising the step of administering to the subject an additional anti-RSV agent.

8. The method of claim 6, further comprising administering to the subject a steroid anti-inflammatory compound.

9. A method of treating an RSV infection and influenza in a subject in need thereof, comprising administering to the subject a therapeutically effective amount of a compound of claim 1 and a therapeutically effective amount of an anti-influenza agent.

10. The method of claim 7, wherein the compound and the additional anti-RSV agent are co-formulated.

11. The method of claim 7, wherein the compound and the additional anti-RSV agent are co-administered.

12. The method of claim 7, wherein administering the compound allows for administering of the additional anti-RSV agent at a lower dose or frequency as compared to the administering of the additional anti-RSV agent alone that is required to achieve similar results in prophylactically treating an RSV infection in a subject in need thereof.

13. A method of treating or preventing an HMPV infection in a subject in need thereof, comprising administering to the subject a therapeutically effective amount of a compound or a combination of compounds of claim 1.

14. The method of claim 13, further comprising the step of administering to the subject an additional anti-HMPV agent.

15. The method of claim 14, wherein the compound and the additional anti-HMPV agent are co-formulated.

16. The method of claim 14, wherein the compound and the additional anti-HMPV agent are co-administered.

\* \* \* \* \*

UNITED STATES PATENT AND TRADEMARK OFFICE
CERTIFICATE OF CORRECTION

Page 1 of 3

PATENT NO. : 12,358,921 B2
APPLICATION NO. : 18/131405
DATED : July 15, 2025
INVENTOR(S) : Adam Szymaniak et al.

It is certified that error appears in the above-identified patent and that said Letters Patent is hereby corrected as shown below:

In the Claims

<u>At Column 308</u>
Claim 1, Line 33 delete "Rand" and insert -- $R_1$ and --.

Signed and Sealed this
Twenty-eighth Day of October, 2025

John A. Squires
*Director of the United States Patent and Trademark Office*

CERTIFICATE OF CORRECTION (continued)
U.S. Pat. No. 12,358,921 B2

Page 2 of 3

At Columns 347 and 348

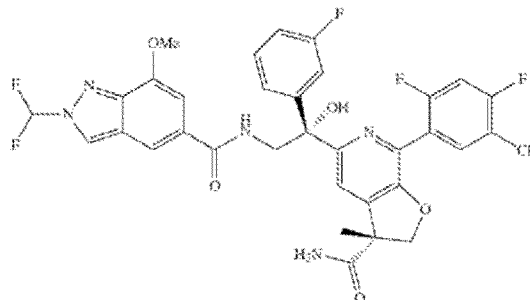

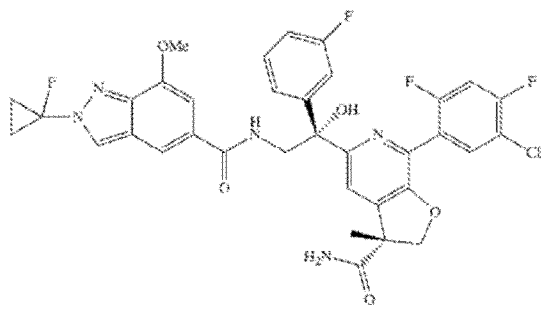

Claim 3, structures 161 and 162 delete " 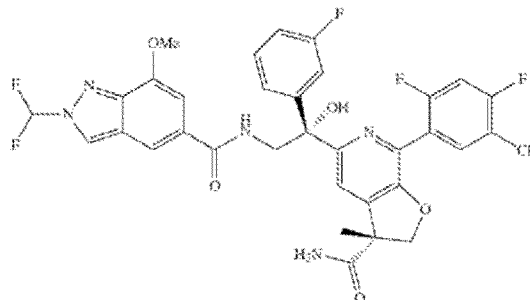 " and insert

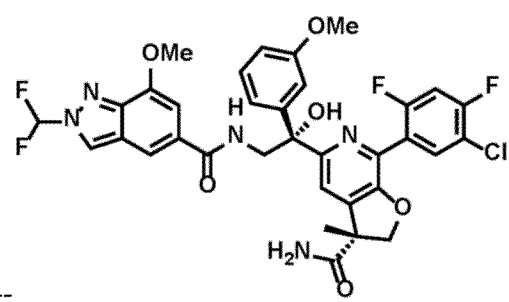 -- and -- 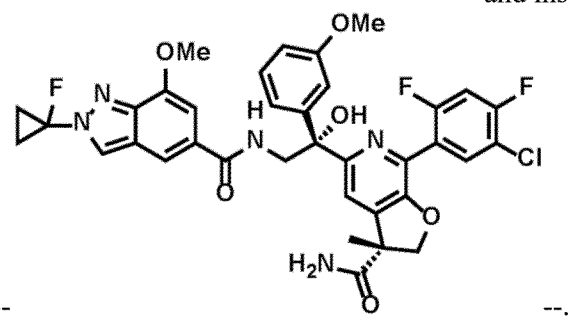 --.

At Column 349

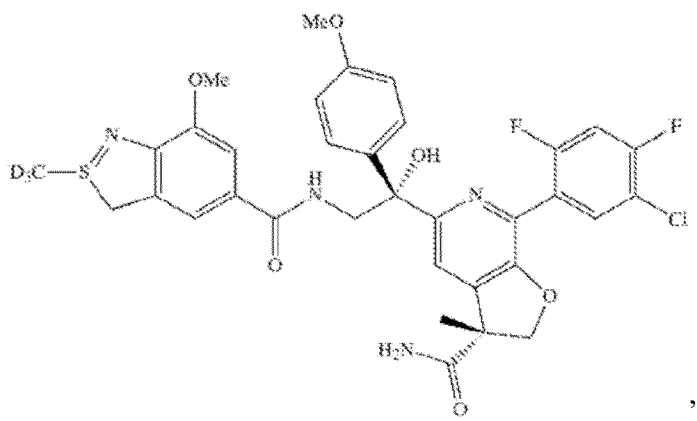

Claim 3, structure 168 delete " 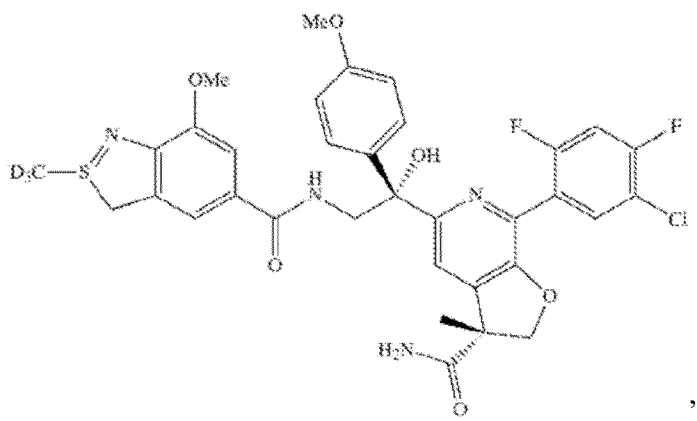 " and

CERTIFICATE OF CORRECTION (continued)
U.S. Pat. No. 12,358,921 B2 insert -- 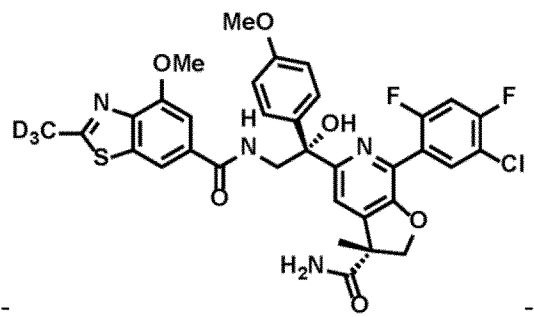 --.